(12) United States Patent
Jaskula-Ranga et al.

(10) Patent No.: US 11,766,488 B2
(45) Date of Patent: Sep. 26, 2023

(54) COMPOSITIONS AND METHODS COMPRISING IMPROVEMENTS OF CRISPR GUIDE RNAS USING THE H1 PROMOTER

(71) Applicant: The Johns Hopkins University, Baltimore, MD (US)

(72) Inventors: Vinod Jaskula-Ranga, Cambridge, MA (US); Donald Zack, Baltimore, MD (US); Derek Welsbie, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 74 days.

(21) Appl. No.: 16/315,458

(22) PCT Filed: Jul. 5, 2017

(86) PCT No.: PCT/US2017/040707
§ 371 (c)(1),
(2) Date: Jan. 4, 2019

(87) PCT Pub. No.: WO2018/009534
PCT Pub. Date: Jan. 11, 2018

(65) Prior Publication Data
US 2019/0314521 A1   Oct. 17, 2019

Related U.S. Application Data

(60) Provisional application No. 62/358,335, filed on Jul. 5, 2016.

(51) Int. Cl.
*A61K 48/00* (2006.01)
*A61K 9/00* (2006.01)
*C12N 15/86* (2006.01)

(52) U.S. Cl.
CPC .......... *A61K 48/005* (2013.01); *A61K 9/0014* (2013.01); *A61K 9/0019* (2013.01); *C12N 15/86* (2013.01); *C12N 2310/20* (2017.05); *C12N 2330/51* (2013.01); *C12N 2710/10344* (2013.01); *C12N 2750/14143* (2013.01)

(58) Field of Classification Search
None
See application file for complete search history.

(56) References Cited

U.S. PATENT DOCUMENTS

| | | | |
|---|---|---|---|
| 4,186,183 A | 1/1980 | Steck et al. | |
| 4,198,626 A | 4/1980 | Rauscher | |
| 4,217,344 A | 8/1980 | Vanlerberghe et al. | |
| 4,235,871 A | 11/1980 | Papahadjopoulos et al. | |
| 4,261,975 A | 4/1981 | Fullerton et al. | |
| 4,485,054 A | 11/1984 | Mezei et al. | |
| 4,501,728 A | 2/1985 | Geho et al. | |
| 4,774,085 A | 9/1988 | Fidler | |
| 4,797,368 A | 1/1989 | Carter et al. | |
| 4,837,028 A | 6/1989 | Allen | |
| 4,873,316 A | 10/1989 | Meade et al. | |
| 4,897,355 A | 1/1990 | Eppstein et al. | |
| 4,931,777 A | 6/1990 | Chiang | |
| 4,946,787 A | 8/1990 | Eppstein et al. | |
| 5,049,386 A | 9/1991 | Eppstein et al. | |
| 5,112,319 A | 5/1992 | Lai | |
| 5,173,414 A | 12/1992 | Lebkowski et al. | |
| 6,121,555 A | 9/2000 | Nowosielski et al. | |
| 9,938,521 B2 * | 4/2018 | Maeder ................. | C12N 15/86 |
| 2002/0139203 A1 | 10/2002 | Chimura et al. | |
| 2003/0144239 A1 | 7/2003 | Agami et al. | |
| 2006/0065448 A1 | 3/2006 | Hudson | |
| 2006/0238346 A1 | 10/2006 | Teller | |
| 2007/0106177 A1 | 5/2007 | Hama | |
| 2011/0059502 A1 | 3/2011 | Chalasani | |
| 2012/0111280 A1 | 5/2012 | Shin et al. | |
| 2012/0299731 A1 | 11/2012 | Triener | |
| 2015/0251894 A1 | 9/2015 | Lake et al. | |
| 2015/0283265 A1 | 10/2015 | Peyman | |
| 2017/0049545 A1 | 2/2017 | Carton | |

FOREIGN PATENT DOCUMENTS

| | | |
|---|---|---|
| CN | 104531632 A | 4/2015 |
| CN | 204440762 U | 7/2015 |
| EP | 2982758 A1 | 2/2016 |
| WO | WO-1991/016024 A1 | 10/1991 |
| WO | WO-1991/017424 A1 | 11/1991 |
| WO | WO-1993/024641 A2 | 12/1993 |
| WO | WO-2014/197748 A2 | 12/2014 |
| WO | WO-2015/148670 A1 | 10/2015 |
| WO | WO-2015/195621 A1 | 12/2015 |
| WO | WO-2016/054225 A1 | 4/2016 |
| WO | WO-2016/069282 A1 | 5/2016 |
| WO | WO-2016/073990 A2 | 5/2016 |
| WO | WO-2016/106244 A1 | 6/2016 |
| WO | WO-2016/210271 A1 | 12/2016 |

OTHER PUBLICATIONS

Li, et al. (2015) "Harnessing Type I and Type III CRISPR-Cas systems for genome editing", Nucleic Acids Research, 44(4): article e34, 12 pages. (Year: 2015).*

(Continued)

*Primary Examiner* — Robert M Kelly
(74) *Attorney, Agent, or Firm* — Foley Hoag LLP

(57) ABSTRACT

The presently disclosed subject matter provides compositions and methods comprising improvements of a CRISPR system (e.g. CRISPR associated (Cas) 9 (CRISPR-Cas9, non-Cas9 CRISPR systems). Such compositions may comprise modifications to the H1 promoter region, addition of 5'UTR modifications, different orthologous sequences of the H1 promoter, novel compact bidirectional promoter sequences with both pol II and pol III activity, addition of Kozak consensus sequences, termination sequences, addition of conditional pol II/pol III bidirectional promoter expression, addition of a donor template sequence for correcting mutations, or combinations thereof. Other aspects of the invention relate to modifications to Cas9 through post-transcriptional cell-cycle regulation fusions, engineered partial target sites such that the nuclease can bind without DNA cleavage, auto-regulation sites, and N-terminal modifications to modulate half-life.

19 Claims, 77 Drawing Sheets

Specification includes a Sequence Listing.

(56) References Cited

OTHER PUBLICATIONS

Adhya et al., "Location, function, and nucleotide sequence of a promoter for bacteriophage T3 RNA polymerase," PNAS 78(1):147-151 (1981).

Ahmad et al., "Antibody-mediated specific binding and cytotoxicity of liposome-entrapped doxorubicin to lung cancer cells in vitro," Cancer Res 52(17):4817-4820 (1992).

Amann et al., "Tightly regulated tac promoter vectors useful for the expression of unfused and fused proteins in *Escherichia coli*," Gene, 69(2):301-315 (1988).

Ame et al., "A bidirectional promoter connects the poly(ADP-ribose) polymerase 2 (PARP-2) gene to the gene for RNase P RNA. structure and expression of the mouse PARP-2 gene," J Biol Chem 276(14):11092-11099 (2001).

Anderson et al., "Human gene therapy," Sci 256(5058):808-813 (1992).

Bachmair et al., "In vivo half-life of a protein is a function of its amino-terminal residue," Sci 234(4773):179-186 (1986).

Baer et al., "Structure and transcription of a human gene for H1 RNA, the RNA component of human RNase P," Nucleic Acids Res 18(1): 97-103 (1990).

Baldari et al., "A novel leader peptide which allows efficient secretion of a fragment of human interleukin 1β in *Saccharomyces cerevisiae*," EMBO J 6(1): 229-234 (1987).

Banerji et al., "A lymphocyte-specific cellular enhancer is located downstream of the joining region in immunoglobulin heavy chain genes," Cell 33(3):729-40 (1983).

Barrangou et al., "CRISPR provides acquired resistance against viruses in prokaryotes," Sci 315(5819):1709-12(2007).

Behr et al., "Gene Transfer with Synthetic Cationic Amphiphiles: Prospects for Gene Therapy," Bioconjugate Chem, 5(5):382-389 (1994).

Beltran et al., "Gene therapy rescues photoreceptor blindness in dogs and paves the way for treating human X-linked retinitis pigmentosa," PNAS 109(6): 2132-2137 (2012).

Bhaya et al., "CRISPR-Cas systems in bacteria and archaea: versatile small RNAs for adaptive defense and regulation," Annu Rev Genet 45:273-97 (2011).

Boch et al., "Breaking the code of DNA binding specificity of TAL-type III effectors," Sci 326(5959):1509-12(2009).

Bolotin et al., "Clustered regularly interspaced short palindrome repeats (CRISPRs) have spacers of extrachromosomal origin," Microbiol 151(Pt8):2551-61 (2005).

Boshart et al., "A very strong enhancer is located upstream of an immediate early gene of human cytomegalovirus," Cell 41(2):521-30 (1985).

Brouns et al., "Small CRISPR RNAs guide antiviral defense in prokaryotes," Sci 321 (5891):960-4 (2008).

Buchschacher et al., "Human immunodeficiency virus vectors for inducible expression of foreign genes," J Virol, 66(5): 2731-2739 (1992).

Byrne et al., "Multiplex gene regulation: a two-tiered approach to transgene regulation in transgenic mice," PNAS 86(14): 5473-5477 (1989).

Camper et al., "Postnatal repression of the α-fetoprotein gene is enhancer independent," Genes Dev 3(4):537-46 (1989).

Cho et al., "Targeted genome engineering in human cells with the Cas9 RNA-guided endonuclease," Nat Biotechnol 31(3):230-2 (2013).

Christian et al., "Targeting DNA double-strand breaks with TAL effector nucleases," Genetics, 186(2):757-61 (2010).

Cong et al., "Multiplex Genome Engineering Using CRISPR/Cas Systems," Sci 339:819-823 (2013).

Courtney et al., "CRISPR/Cas9 DNA cleavage at SNP-derived PAM enables both in vitro and in vivo KRT12 mutation-specific targeting," Gene Ther, 23:108-112 (2016).

Crystal et al., "Transfer of Genes to Humans: Early Lessons and Obstacles to Success," Sci 270(5235):404-410(1995).

Dalkara et al., "In vivo-directed evolution of a new adeno-associated virus for therapeutic outer retinal gene delivery from the vitreous," Sci Transl Med 5(189):189ra76 (2013).

Dalkdara et al., "Gene therapy for inherited retinal degenerations," C R Biol 337(3):185-92 (2014).

Day et al., "Advances in AAV vector development for gene therapy in the retina," Adv Exp Med Biol 801:687-93 (2014).

De Bleser et al., "A distance difference matrix approach to identifying transcription factors that regulate differential gene expression," Genome Biol 8(5):R83 (2007).

Deveau et al., CRISPR/Cas system and its role in phage-bacteria interactions. Annu Rev Microbiol 64:475-93 (2010).

Dillon et al., "Regulating gene expression in gene therapy," Trends Biotechnol, 11:167-175 (1993).

Dinculescu et al., "Adeno-associated virus-vectored gene therapy for retinal disease," Hum Gene Ther 16(6):649-63 (2005).

Ding et al., "Enhanced efficiency of human pluripotent stem cell genome editing through replacing TALENs with CRISPRs," Cell Stem Cell 12(4):393-4 (2013).

Doudna et al., "Genome editing. The new frontier of genome engineering with CRISPR-Cas9," Sci 346(6213):1258096 (2014).

Dryja et al., "A point mutation of the rhodopsin gene in one form of retinitis pigmentosa," Nature 343(6256):364-366 (1990).

Dryja et al., "Mutations within the Rhodopsin Gene in Patients with Autosomal Dominant Retinitis Pigmentosa," N Engl J Med 323:1302-1307 (1990).

Edlund et al., "Cell-specific expression of the rat insulin gene: evidence for role of two distinct 5' flanking elements," Science, 230(4728):912-916 (1985).

Extended European Search Report for EP Application No. EP 17824801 dated Jun. 5, 2020.

Ford et al., "Characterization of a Trimeric Complex Containing Oct-1, SNAPc, and DNA," J Biol Chem 272(25): 16048-55 (1997).

Ford et al., "The Oct-1 POU domain activates snRNA gene transcription by contacting a region in the SNAPc largest subunit that bears sequence similarities to the Oct-1 coactivator OBF-1," Genes Dev, 12(22):3528-3540 (1998).

Gao et al., "Cationic liposome-mediated gene transfer," Gene Ther, 2(10):710-22 (1995).

Gearing et al., "CRISPR 101: Multiplex expressions of gRNAs," Addgene's Blog, 1-11 (2016).

Gibson et al., "Enzymatic assembly of DNA molecules up to several hundred kilobases," Nature Methods 6:343-345 (2009).

Groenen et al., "Nature of DNA polymorphism in the direct repeat cluster of *Mycobacterium tuberculosis*; application for strain differentiation by a novel typing method," Mol Microbiol 10(5):1057-65 (1993).

Gutschner et al., "Post-translational Regulation of Cas9 during G1 Enhances Homology-Directed Repair," Cell Rep 14(6):1555-1566 (2016).

Hermonat et al., "Use of adeno-associated virus as a mammalian DNA cloning vector: transduction of neomycin resistance into mammalian tissue culture cells," PNAS 81(20): 6466-6470 (1984).

Hoe et al., "Rapid molecular genetic subtyping of serotype M1 group A *Streptococcus* strains." Emerg Infect Dis, 5(2):254-263 (1999).

Horvath et al., "CRISPR/Cas, the immune system of bacteria and archaea," Sci 327(5962):167-70 (2010).

Hou et al., "Efficient genome engineering in human pluripotent stem cells using Cas9 from Neisseria meningitidis," PNAS 110(39):15644-9 (2013).

Hovde et al., "Activator recruitment by the general transcription machinery: X-ray structural analysis of the Oct-1 POU domain/human U1 octamer/SNAP190 peptide ternary complex," Genes Dev 16(21):2772-7 (2002).

Hsu et al., "Development and applications of CRISPR-Cas9 for genome engineering," Cell 157(6):1262-78 (2014).

Hwang et al., "Efficient genome editing in zebrafish using a CRISPR-Cas system," Nat Biotechnol 31(3):227-9 (2013).

International Search Report and Written Opinion for International Application No. PCT/US2017/040707 dated Oct. 19, 2017.

(56) References Cited

OTHER PUBLICATIONS

Ishino et al., "Nucleotide sequence of the iap gene, responsible for alkaline phosphatase isozyme conversion in *Escherichia coli*, and identification of the gene product," J Bacteriol, 169(12):5429-5433 (1987).
Jain et al., "Ocular MECP2 Protein Expression in Patients With and Without Rett Syndrome," Pediatr Neurol 43(1):35-40 (2010).
Jansen et al., "Identification of genes that are associated with DNA repeats in prokaryotes," Mol Microbiol 43(6):1565-75 (2002).
Jinek et al., "A Programmable Dual-RNA—Guided DNA Endonuclease in Adaptive Bacterial Immunity," Sci 337:816-821 (2012).
Jinek et al., "RNA-programmed genome editing in human cells," Elife, 2:e00471 (2013).
Johann et al., "GLVR1, a receptor for gibbon ape leukemia virus, is homologous to a phosphate permease of Neurospora crassa and is expressed at high levels in the brain and thymus," J Virol 66(3):1635-40 (1992).
Kabadi et al., "Multiplex CRISPR/Cas9-based genome engineering from a single lentiviral vector," Nucleic Acids Research, 42(19):e147 (2014).
Kaufman et al., "Translational efficiency of polycistronic mRNAs and their utilization to express heterologous genes in mammalian cells," EMBO J 6(1):187-93 (1987).
Kessel et al., "Murine developmental control genes," Sci 249(4967): 374-379 (1990).
Kotin et al., "Prospects for the use of adeno-associated virus as a vector for human gene therapy," Hum Gene Ther, 5(7):793-801 (1994).
Kotterman et al., "Antibody Neutralization Poses a Barrier to Intravitreal Adeno-Associated Viral Vector Gene Delivery to Non-Human Primates," Gene Ther 22(2): 116-126 (2015).
Kremer et al., "Adenovirus and adeno-associated virus mediated gene transfer," Br Med Bull, 51(1):31-44(1995).
Kunkel et al., "The distal elements, OCT and SPH, stimulate the formation of preinitiation complexes on a human U6 snRNA gene promoter in vitro," Nucleic Acids Res 26(6): 1536-154 (1998).
Kurjan et al., "Structure of a yeast pheromone gene (MF alpha): a putative alpha-factor precursor contains four tandem copies of mature alpha-factor," Cell 30(3):933-43 (1982).
Liang, et al., "Rhodopsin Signaling and Organization in Heterozygote Rhodopsin Knockout Mice," J Biol Chem 279(46): 48189-48196 (2004).
Makarova, et al., "Evolution and classification of the CRISPR-Cas systems," Nat Rev Microbiol 9(6):467-77 (2011).
Mali et al., "RNA-Guided Human Genome Engineering via Cas9," Sci 339:823-826 (2013).
Mancuso et al., "Gene therapy for red-green colour blindness in adult primates," Nat 461(7265):784-7 (2009).
Marraffini et al., "CRISPR interference: RNA-directed adaptive immunity in bacteria and archaea," Nat Rev Genet 11(3):181-90 (2010).
Masepohl et al., "Long tandemly repeated repetitive (LTRR) sequences in the filamentous cyanobacterium Anabaena sp. PCC 7120," Biochim Biophys Acta, 1307(1):26-30 (1996).
Matthess, et al., "Conditional inhibition of cancer cell proliferation by tetracycline-responsive, H1 promoter-driven silencing of PLK1," Oncogene 24(18):2973-80 (2005).
Mcivor et al., "New insights into repeat instability: role of RNA-DNA hybrids," RNA Biol, 7(5):551-8 (2010).
Mefferd et al., "Expression of CRISPR/Cas single guide RNAs using small tRNA promoters," RNA, 21(9): 1683-1689 (2015).
Melton et al., "Efficient in vitro synthesis of biologically active RNA and RNA hybridization probes from plasmids containing a bacteriophage SP6 promoter," Nucleic Acids Res,12(18): 7035-7056 (1984).
Miller et al., "A tale nuclease architecture for efficient genome editing," Nat Biotechnol, 29(2):143-8 (2011).
Miller et al., "An improved zinc-finger nuclease architecture for highly specific genome editing," Nat Biotechnol, 25(7):778-85 (2007).

Miller et al., "Construction and properties of retrovirus packaging cells based on gibbon ape leukemia virus," J Virol 65(5):2220-4 (1991).
Miller et al., "Human gene therapy comes of age," Nat 357(6378):455-60 (1992).
Mitani et al., "Delivering therapeutic genes—matching approach and application," Trends Biotechnol 11(5):162-6 (1993).
Mittal et al., "The Oct-1 POU-specific domain can stimulate small nuclear RNA gene transcription by stabilizing the basal transcription complex SNAPc," Mol Cell Biol, 16(5):1955-1965 (1996).
Mojica et al., "Intervening sequences of regularly spaced prokaryotic repeats derive from foreign genetic elements," J Mol Evol 60(2):174-82 (2005).
Mojica et al., "Long stretches of short tandem repeats are present in the largest replicons of the Archaea Haloferax mediterranei and Haloferax volcanii and could be involved in replicon partitioning," Mol Microbiol, 17(1):85-93 (1995).
Moscou et al., "A simple cipher governs DNA recognition by TAL effectors," Sci 326(5959):1501 (2009).
Mowat et al., "Tyrosine capsid-mutant AAV vectors for gene delivery to the canine retina from asubretinal or intravitreal approach," Gene Ther 21(1):96-105 (2014).
Murphy et al., "Oct-1 and Oct-2 potentiate functional interactions of a transcription factor with the proximal sequence element of small nuclear RNA genes," Mol Cell Biol 12(7): 3247-3261 (1992).
Muzyczka et al., "Adeno-associated virus (AAV) vectors: will they work?" J Clin Invest, 94(4): 1351 (1994).
Myslinksi et al., "An unusually compact external promoter for RNA polymerase III transcription of the human H1RNA gene," Nucleic Acids Res 29(12): 2502-2509 (2001).
Nabel et al., "Direct gene transfer for immunotherapy and immunization," Trends Biotechnol 11(5):211-5(1993).
Nakamura et al., "Codon usage tabulated from international DNA sequence databases: status for the year 2000," Nucleic Acids Res, 28(1):292 (2000).
Nakata et al., "Unusual nucleotide arrangement with repeated sequences in the *Escherichia coli* K-12 chromosome," J Bacteriol, 171(6):3553-3556 (1989).
Nemudryi et al., "TALEN and CRISPR/Cas genome editing systems: tools of discovery," Acta Naturae 6(3): 19-40 (22) (2014).
O'Hare et al., "Transformation of mouse fibroblasts to methotrexate resistance by a recombinant plasmid expressing a prokaryotic dihydrofolate reductase," PNAS 78(3):1527-31 (1981).
Partial Supplementary European Search Report for EP 17824801 dated Jan. 24, 2020.
Petrs-Silva et al., "Novel properties of tyrosine-mutant AAV2 vectors in the mouse retina," Mol Ther 19(2):293-301 (2011).
Pinkert et al., "An albumin enhancer located 10 kb upstream functions along with its promoter to direct efficient, liver-specific expression in transgenic mice," Genes Dev 1 (3):268-76 (1987).
Pleiss et al., "T7 RNA polymerase produces 5' end heterogeneity during in vitro transcription from certain templates," RNA, 4:1313-1317 (1998).
Porteus et al., "Chimeric nucleases stimulate gene targeting in human cells," Sci 300(5620):763 (2003).
Queen et al., "Immunoglobulin Gene Transcription Is Activated by Downstream Sequence Elements," Cell 33(3):741-8 (1983).
Ranganathan et al., "Expansion of the CRISPR-Cas9 genome targeting space through the use of H1 promoter-expressed guide RNAs," Nat Commun 5:4516 (2014).
Remy et al., "Gene Transfer with a Series of Lipophilic DNA-Binding Molecules," Bioconjugate Chem, 5(6):647-654 (1994).
Reyon et al., "FLASH assembly of TALENs for high-throughput genome editing," Nat Biotechnol, 30(5):460-5 (2012).
Sakaue-Sawano, et al., "Visualizing spatiotemporal dynamics of multicellular cell-cycle progression," Cell 132(3):487-98 (2008).
Samulski et al., "Helper-free stocks of recombinant adeno-associated viruses: normal integration does not require viral gene expression," J Virol, 63(9): 3822-3828 (1989).
Sander et al., "Selection-free zinc-finger-nuclease engineering by context-dependent assembly (CoDA)," Nat Methods, 8(1):67-9 (2011).

(56) References Cited

OTHER PUBLICATIONS

Schultz et al., "Expression and secretion in yeast of a 400-kda envelope glycoprotein derived from epstein-barr virus," Gene 54:113-123 (1987).
Seed et al., "An LFA-3 cDNA encodes a phospholipid-linked membrane protein homologous to its receptor CD2," Nat 329(6142):840-2 (1987).
Senis et al., "CRISPR/Cas9-mediated genome engineering: An Adeno-associated viral (AAV) vector toolbox," Biotechnology Journal, 9:1402-1412 (2014).
Sluch et al., "Differentiation of human ESCs to retinal ganglion cells using a CRISPR engineered reporter cell line," Sci Rep, 5:16595 (2015).
Smith et al., "Single-step purification of polypeptides expressed in *Escherichia coli* as fusions with glutathione S-transferase," Gene 67(1):31-40 (1988).
Sommerfelt et al., "Receptor interference groups of 20 retroviruses plating on human cells," Virol 176(1):58-69 (1990).
Song et al., "DNA methylation reader MECP2: cell type- and differentiation stage-specific protein distribution," Epigenetics Chromatin 7:17 (2014).
Swiech et al., "In vivo interrogation of gene function in the mammalian brain using CRISPR-Cas9," Nat Biotechnol 33(1):102-6 (2015).
Takebe et al., "SRα promoter: an efficient and versatile mammalian cDNA expression system composed of the simian virus 40 early promoter and the R-U5 segment of human T-cell leukemia virus type 1 long terminal repeat," Mol Cell Biol, 8(1): 466-472 (1988).
Tasaki et al., "The N-end rule pathway," Annu Rev Biochem 81:261-89 (2012).
Translation of CN 20440762 U (2015).
Tratschin et al., "A human parvovirus, adeno-associated virus, as a eucaryotic vector: transient expression and encapsidation of the procaryotic gene for chloramphenicol acetyltransferase," Mol Cell Biol, 4(10): 2072-2081 (1984).
Tratschin et al., "Adeno-associated virus vector for high-frequency integration, expression, and rescue of genes in mammalian cells," Mol Cell Biol, 5(11):3251-3260 (1985).
Van Embden et al., "Genetic variation and evolutionary origin of the direct repeat locus of *Mycobacterium tuberculosis* complex bacteria," J Bacteriol 182(9):2393-401 (2000).
Varshavsky et al., "The N-end rule pathway and regulation by proteolysis," Protein Sci 20(8):1298-345 (2011).
Wellensiek et al., "Genome-wide profiling of human cap-independent translation-enhancing elements," Nat Methods 10(8):747-50 (2013).
West et al., "Gene expression in adeno-associated virus vectors: the effects of chimeric mRNA structure, helper virus, and adenovirus VA1 RNA," Virol 160(1):38-47 (1987).
Wiedenheft et al., "RNA-guided genetic silencing systems in bacteria and archaea," Nat 482(7385):331-8 (2012).
Willett et al., "Immunology of AAV-mediated gene transfer in the eye," Front Immunol 4: 261 (2013).
Wilson et al., "Formation of infectious hybrid virions with gibbon ape leukemia virus and human T-cell leukemia virus retroviral envelope glycoproteins and the gag and pol proteins of Moloney murine leukemia virus," J Virol 63(5):2374-8 (1989).
Winoto et al., "A novel, inducible and T cell-specific enhancer located at the 3' end of the T cell receptor α locus," EMBO J, 8(3):729-733 (1989).
Wood et al., "Targeted genome editing across species using ZFNs and TALENs," Sci 333(6040):307 (2011).
Yu et al., "Progress towards gene therapy for HIV infection," Gene Ther, 1(1):13-26 (1994).
Zhang et al., "Efficient construction of sequence-specific TAL effectors for modulating mammalian transcription," Nat Biotechnol, 29(2):149-53 (2011).

\* cited by examiner

5'UTR and Translational Enhancers

| | |
|---|---|
| Strong Kozak | 9bp |
| Beta-Globin 5'UTR | 50bp |
| 6.947* | 91bp |
| 6.967* | 75bp |

9nt Kozak sequence: GCCGCCACC
6nt Kozak sequence: GCCACC

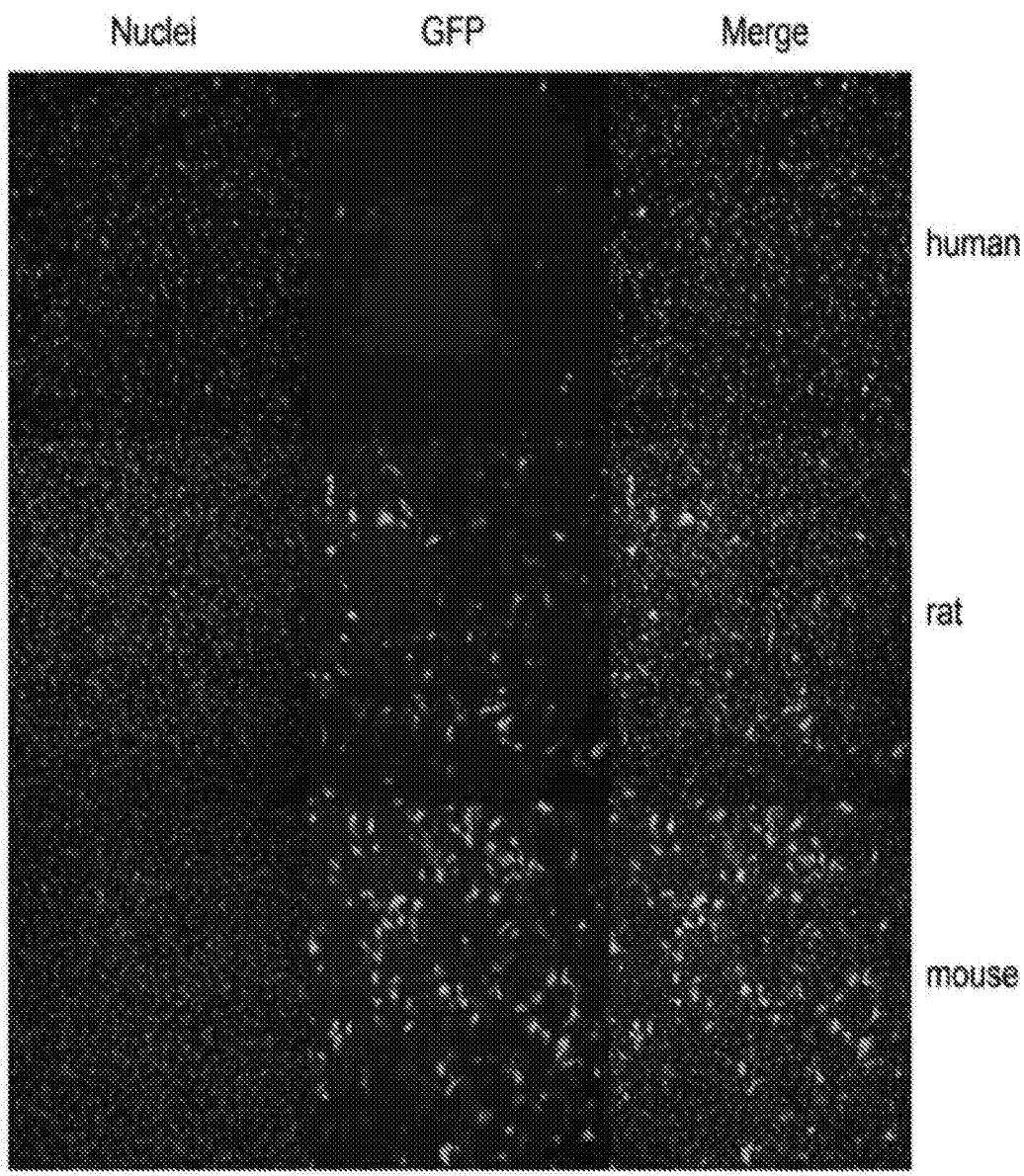

```
>mus_musculus/1-254
TTCAG-CATCTAGACCG---GCCGCCACTCTATAAGGCTCGAAAAGA-CGAATAAATTTTCGGTTAGGCTGAATTTCCCAC-AA
AGCACCAGCG------CGTAATTT-GCATG-CGCT---------CTACCCCAGGC---------------------TCCT---
GTCCTTCAAGCGCG---GTGCTA------GACAAG------A------AGC-----CGGGCAA-CGGATGATGACGTC
>rattus_norvegicus/1-254
AGCAGAG-TGTGAAGACCT--GCCGGCACATATAAGACTCCAAAAG-ACAGTGAATTAACACTTACCGTTCCCAC-AA
AGCACACAGCG------TGTAATTT-GCATG-CGCT---------CTAGCCCAGGC---------------------TCCA---
GTCCTTCAAGCGCT------GCTCCG------GACCAG------A------AGC---CCGGC-GCATC-CCGGCAA-AGGGTGATGACGTC
>dipodomys_ordii/1-254
AGGAA-ACACTTCGCTGAGGCAGACTTTATAAGGCTCGAGAGTTTATAAGGCTCGAAAGAAACTTATATCGTGATTTCCCAC-AA
CACCACTGCGTCATGCAAATAACAGGGTACGGCGTTC-CAT---GTACCCTTAAGG-----TTTTTTCTAGGCGCGGTAC-
GC----TCTGCGTATT-CAGCCACGTGACCCT------G------AGC-----CAGT-GGTTG-TTGGGAGCACGTGTGGACCTG-
TGGCGTTTGGATTCC
>ictidomys_tridecemlineatus/1-254
GAAAG-CGGACTCCGCACAGCAGAGTTTATAAGGCTCCCATTCTCGGTCATGGTAACTACCCAC-AA
CACCACCGGATATGCAAATATAGCAGAGCGTGTCTTC-CCG---CGCGCCCCTGGTCGTCCTC----GGCGGCCGGC
GC----GCTGGGTGGGCGGAACTGTGACAGA-----G-----ACC---CTGC-GATTC-CTGGGAGCCTGGCTGGATGACATC
AGTGTCTAACCTCC
>cavia_porcellus/1-254
GAGAA-AGAAAGCCTCAAACCTAGCCACAGATTTATAAGGCTCCCATATATTTTTGGTTATGGTGACTTCCCAC-AA
TGCATAGCCGATATGTAGATATTGC-CAGGAGTACATTGC-CAGG-----TTCTGGGTCCTGTCAGCTCTTCTAGGACG---CGC
GC-----GCTCGCAGGTTTCCAGCCTGTG----G-----CAGC-AATTC-C--GGGAATGAATTGATGACGTC
AGCGGTTTGAATTCC
>ochotona_princeps/1-254
GGGGG-AAGCTGGGCTCGGATCAGCGCCTTTATAAAGCTCCCAAGACATTCTGTTACCGGTGGCTTCCCAC-AG
TACACAGCGGACATGCAAAT------AGCTTGCCAAT------GAATTCGCGGACCGCTTCCCGGACGCGGCAGGC
GC-----GC-CGGACCTGTCCCCCTGGACGC-----G-----CGG-----TCGC-GGTTC-CCCGGCAGCTGGCTGATGA------
---CGTTCGGTCTCC
>oryctolagus_cuniculus/1-254
GGGGA-GAGGTGGATCCGAACAGACTTTATAAAGCTCCCAAGGCATCTTCCCCTTACGGTAGCTTCCCAC-AA
GACATAGCGACATGCAAATT---TCTTG-AAGT---------ATGCTTCAGACGC-GCTTCCGCCACAGCGCAAGC
GC------GCTGTGTGCTGACGC----G------GGGAAC------GGTTC-CCGGGTTC-CCCGGAGCCGGGTTGGATGACGTT
------AGATCTCC
```

FIG. 5(cont.)

```
>callithrix_jacchus/1-254
GAGGA-AAGGTAGTCCCACAGAGACAACTTATAAGAATTCCCATACCCTAAGACATTCACGATTATGGTGACTTCCCAG-AA
GACACAGCGACATGCAAATATTGCCACAGTGCAGGTGCGTGTTCG-CCT----GTCCCTCACAGTCGTCTTCCTGCCAGGGCGCACGC
GC----GCTGGGT-TTCCGGCCACTGACGCT----G-----TCGC--GATTC--CTTGGAGCGGGGTTGATGACGTC
AGCGGTTCGAATTCC >chlorocebus_sabaeus/1-254
CGGGA-ACGGTGGTCCCTACACAGACTTATAAGAACTTATAAGAGACATTCACGGTTATGGTGACTTCCCAG-AA
CACATAGCGGACATGCAAATATGCCAGGGCGGTCACACC--CCT-----CTCCCTCACAGTCATCTTCCTGCCAGGGCCACGG
GC----GCTGGGGTGTTCCGCCTAGTGACACT----G-----GGC--CCGC--GATTC--CTTGGAGCGGGGTTGATGACGTC
AGCGGTTCGAATTCC >macaca_mulatta/1-254
CGGGA-AGGGTGGTCCCACAGAACTTATAAGAGATTCCCATACTCCAAAGACATTCACGGTTATGGTGACTTCCCAG-AA
CACACAGCGGACATGCAAATATTGGGGCGGTCACACC--CCT----GTCCCTCACAGTCATCTTCCCCAGGGCGCACGC
GC----GCTGGGGTGTTCCCCGCCTAGTGACACT----G-----GGC--CCGC--GATTC--CTTGGAGCGGGGTTGATGACGTC
AGCGGTTCGAATTCC >papio_anubis/1-254
CGGGGA-AAGGTGGTCCCTACCACAGAACTTATAAGAGATTCCCATACTCCAAAGACATTCACGGTTATGGTGACTTCCCAG-AA
GACACAGCGGACATGCAAATATTGTAGGGCGTCACACCCCT----G-----CCGC--GATTC--CTTGGAGCGGGGTTGATGACGTC
AGCGGTTCGAATTCC >gorilla_gorilla/1-254
CGGAA-ACGGGTGGTCCCACACAGAACTTATAAGAGACTCCCATATCCAAAGACATTTCACGGTTATGGTGACTTCCCAG-AA
CACATAGCGACATGCAAATATGCCAGGGCGGTCACTCC--CCA-----G----GGC--CCGC--GATTC--CTTGGAGCGGGGTTGATGACGTC
AGCGGTTCGAATTCC >homo_sapiens/1-254
CGGGAA-AAGGTGGTCCCATACAGAACTTATAAGAGATCCCAATCCCAAAGACATTCACGGTTATGGTGATTCCCAG-AA
CACATAGCGACATGCAAATATGCCAGGGGCGCACTCC--CCT-----GTCCCTCACAGCCATCTTCCCAGGGGCGCACGC
GC----GCTGGGGTGTTCCGCATGTGACACT----G-----GGC--CCGC--GATTC--CTTGGAGCCGGGGTTGATGACGTC
AGCGGTTCGAATTCC >pan_troglodytes/1-254
CGGGA-ACGGGTGGGCCACAGAGAACTTATAAGAACTTATGGTGATTCCCAG-AA
CACATAGCGACATGCAAATATGCCAGGGCGGCACTCC--CCT-----GTCCCTCACTCCATCTTCCTGCCAGGGCGCACGGC
GC----GCTGGGGTGTTCCCGCCTAGTGACACT----G-----GGC--CCGC--GATTC--CTTGGAGCGGGGTTGATGACGTC
AGCGGTTCGAATTCC
```

FIG. 5(cont.)

```
>pongo_abelii/1-254
GAGAA-AGGGTGGTCCCGTCCAGAACTTATAAGATTCCCATACCCAAGACACATTTCACGTTTATGGTGACTTCCAG-AA
TGCATAGCGACATGCAAATATGCAGGGCGTCACTCC--CCT----GTCCCTCACGCCATCTTCCTGCCAGGGCGCCGC
GC-----GCTG-GTGTTCCCGGCTACTGACACT----G-----CCAC--GATTC--CTTGGAGCGGGGTTGATGACGTC
AGCGGCTCGTATTCC >nomascus_leucogenys/1-254
CGGGA--AAAGTAGT-------AGACCTTATATAAGATTCCCAAACACATTTCCGTTTATGGTGACTTCCAG-AA
GACATAGCGGACATGCAAATATGCAGGGCGCCACTCC--CCT----GTCCCTCACGCCATCTCCTGCCAGGGCGCACGC
GC-----GCTCCGTGTTCCCGGCTACTGACACT----C-----CCGC--GATTC--CTTGGAGCGGGTGATGACGTC
AGCGGTTCGAATTCC >tarsius_syrichta/1-254
CCGGAG-AGGGTGGGTCCACACAGAGCTTATAAGGTTCACAAGT--AAAGATATTTCACGGGTGACTTCCCAC-AA
TACACTCCGACACATGCAAATATAGCCGGGCGTCCCTCC--CCG----ATCCCGGAGAGCCACTCCTACCCAGTGCCACGC
GC-----GCTCCGTGTTCGGTCCTAGGTCGCT----G-----CCGG--GGTTC--CTGGGAGCGGG-TGGTGACGTC
AGCGGCCCAGCTTC >otolemur_garnettii/1-254
CCCTA-AAGGCGGCCGCATGCAGAGACATTTATAAGGTTCCCAAACACAGAGACACATTCATTATGGTGACTTCCAG-AA
TGCACAGAGGCCATGCAAATATGCTAGGACGCGCTCCC--CCG----CTACCTTAAGGTCGTCAACTAACCAGTGCGCGGC
GC-----ACTGCGCGTTCCCCGCGGGTGACTCA----A-----TGC-----CCGC--GTTTG-GTGGGAGCTAGTTGGTGACCTC
AGTTCTGGAGGCTC >tupaia_belangeri/1-254
CGGGG-AAGCTCGGGTCCGGTCCACTGAGTTCTTATAAGGTTTCCAGTCCTAGAGCGATTTACCCATTCCGGTGATTCCCAG-CA
TCCGTAGCTACATGCAAATAGCCGGGGCGCGTCTCT--CAG----GTCCCTCCCGCCCCTCTCACTGT---ACGTACCC
GC----GT--------CCTAGGGACGCC----G-----CGG----CCGG--GGTTC--CC-----------GGACGTC
AGCGGTTCCGACCGCA >ailuropoda_melanoleuca/1-254
AGGGA-AAGCCCGGCCACCGAGGCCTGGGCGGATTTATAAGGCCTTCCATATCTAAAGGCATTCACAGTCATGGTGACTTCCCAC-AA
TACATAGCAACATGCAAATATCGTGGAGAGTACCGCC--CCT----GTCCCTGTACGCGGCTTC---TAAAGACGCACGC
GC-----GCTCTGTGTTCCCGGCCCTGTCGACTCT----A-----GGGC-----AATTC--CTGGACAGTGTT-CTGAGCGGG
AACGTTCAGGCTTC >mustela_putorius_furo/1-254
GGGAA-AGGGTGGACCCACCGAGACATTTATAAGACATTTACAGTTATGGTGACTTCCCAC-AA
CGCGTAGCAACATGCAAATATCGTGGAGAGTACCGCC--CCT----GTCCCATGCACGCGTCTTCTCAGCAGCACGCACGC
GC-----GCT--GTGTTCCGGCCCCTGTGACTCC----A-----GGGT--ATTT-CCAGGGGCGGGTTGCTGACAGG
AACGTTCAGGCTTC
```

FIG. 5(cont.)

```
>canis_familiaris/1-254
GC-----AGGGGCAGCCCCTCTC--GCXGCCTTATAAGTGCCG--CCCCGCACGGCCCTTCTCGCTCTACGGCGGACTCCCAT-AA
CACACAGCAGCCATGCAAATACCCGCGGGGAGCCCCGCC--CCGCCCCGGCA------CCCGCCCTCGGAGCGGCGACGCATGC
GGGCTCT--CCGTTCCCGCCTTCGGCCGGCCGGCC----GGGGC-GAGCGGGCGGAGCGGCGGCTC--CGGGCGGGG
GACGAGCGGCGGCC >felis_catus/1-254
GGGAA-AGGGCTGGCCCCGGCCGGCCCAGCACTCC-CCATACCCTAAAGACACATTCTCAGTTATGCGTGATTCCCAC--AA
CACACAGCAACAACGCAAATACCCAGCGGTGTACGGCC--CCT-------GTCCTTTGTAGACGTCCTCCCAGGACGCACGGC
GC----OCT--GTATCCCCCCTTGTCGTGACTCT---A------GGGC-GATTC-CTGGGAGAGCGGTTGATGACGTC
CAAGTTCTGGCTTC >equus_caballus/1-254
GGGGG-AAAACAGCCCATGCGCTGCATAAGACTCACAGATCTAAAGCCATTCACGAATAGGCGTGACTTCCCAC--AA
TACACAGCAGCATGCAAACATAGCCACGGGGCGGTGCCTTT--CCT---GTACCCTGTGGGCA---TCTCCTCCTGGACGCACGC
GC----GCCGGGTGTTCCCGGCCGTGTGACTCT---A-----AAGC-GCTTC-CTGGGACAGAGTTGATGACGTG
AGCCATTCGGGCTCC >myotis_lucifugus/1-254
GGGAGG-AGGGAGG--CGTAGAGGATATATAAGGGCCCCCCTTATGTCGTAGTCGACTTCCTTTACGGTTACGGTGACTTCCCAC--AA
CGGATAGCGGACATGCAAAT--TTGACGGGCGGCAAAT--GTCCCT--GCGGGCAACTTCTCGCCAGAACGCGCGC
GC----GCTGCCGTGTTCCCGGCCTTTTGACTCC----A-----GCC-GAATC-CTGGGAGGAGCAGGGTGACGGTCG
AACAGTCAGGCTCG >pteropus_vampyrus/1-254
GGGAG-AAAAATTCTCACGCACAGAATATATAAGGATCTCGAAGACATTTACGATTACGGCGATTCCCAC--AA
CCGAG-ACACCGGACACGCAAATAGCCACACTTATAATGTGCTCATATCCTAGAGAGCCACTTTTCCGGTTACGGTGACTTCTCAAAAA
CACATACCGACATGCAAATGTAGCGCATGCCTCC--CC------GTCCCTGTGCCAGCTTCCGCCAGAACCCACGC
GC----CGTGCGGTGTTCCCGGCCTTGTG--GAGTC---A----AGT----A-GGGAGGAGATTGATGACGGTC
AGCTCACCCGGCTCC >bos_taurus/1-254
CGGCAA-ACACCGGACATGCACGCAAATAGCCACACTTATAATGTGCTCATATCCTAGAGAGCCACTTTTCCGGTTACGGTGACTTCTCAAAAA
GACAGTCGGACATGCAAATGCCGATTACAGTGCGTCCGTCC--CC------TGGTAGTTGTACGCTACAGACGCACCACGC
GC----ACTACCG--GTTCCCGCCTATAGACT------G------CGC--GATTC-CTGGGAGCCGACTGATGACGTC
AGCGGTTCGGGGATCC >ovis_aries/1-254
CGGCGA-ACAATGCCGGCAAGCGGCAAACAGCCATTTATAATGAGCCACACTTACGGTTGACTTCCAC--AA
GACAGTCCGGGACATGCAAATAGCGATTACAGTGCCGTCC--CC------G------CGC--GATTC-CA-GGAGCGGCTAGGACGACACGC
GC----ACTACG--GTCCCGCGCTTAGACT-----G------CGC-----TGGC-GATTC-CA-GAAGCCGACTGATGACGTC
AGCCGTTCGGGGCTCC >tursiops_truncatus/1-254
GCCGA-AAACCGGACGCTTCACAGCCACACATTTATAAGCCTCAAGTGCTAACTACATTGTCCGGTTACATTCCGGC--AC
CACATACGCAACATGCAAATACCACGCCTCCAGCGGAGCGGCACTCCGGAGCGGCACTCGGAGCGGACTGATGACGTC
AGCCGTTCGGGGCTCC
CAACTCCTCCCGCTCGGGACGGCACGC
```

FIG. 5(cont.)

```
GC------GCTACGGTGCTCCCGGCCTTTG--ACT-----G------CGGC---GATAC--TTGGGAGAGGGTGATGACGTC
AGCGTTCTGGCTCC
>vicugna_pacos/1-254
GGGAA-AGGGTGGGCTCACGGCAGCCTTTATAAGACTCCCAAACTTAAAGACATTTCTCGGTTATGGCGACTTCCCAC--AA
GACATAGCGACATGCAAATACTGCAGGGCGCG---AC--CCG---GTCCTGTGCCAGCCATCTTCGGCTCGGACGCACGGC
GC------GCTGCGGTGTTCCCGGCCCTGTG--ACT-----G------CGGC--GATTA--CTGGGAGAGGAATTGATGACGTC
AACGTTCGGGTTCC
>sus_scrofa/1-254
GTAGGAAAACTGCT-TCTGTGAGCACTTATAAAACTCCCATAAGTAGAGAGATTCATAGTTATGGTCGATTCCCAT--AA
GACATTGCGACATGCAAATATTGTGGCCGTTCGTCC--CC------GTCCCGGTGCAGGCACGTTCGCTCCAGGACGCACGC
GC------AATACATGTTCCCGGCCTTGAGACT------G------CGGC-----CGGCAGATTC--CTAGGAAGTGGTTGATGACGTC
GATGTTAGGGATCC
>erinaceus_europaeus/1-254
GCCTA-AACCGGCTCCTTTCGACACTTATAAGGACTTATATCTTAGGACATTTTTTGTTAGGGTAACTTCCCAC--GA
TGCATAGCCGATATGGTAAATAT---GGCGCCGCA------GTCTCTCCCTAGGCGTCTCC---CCAGGACGCAGGC
GC------ACTGCTGTTCCCGGCGT--TAACATT---------GC-TGATT-CTGGAGACTGCTGATGACGTC
AGCGTTCCAGTCTAC
>choloepus_hoffmanni/1-254
AGAAA-AAAATAGT-TTATGCTGGATTTATAGATTCCCAAATCTACAGTTCACAGTACGGTCATTCCCAC--TA
CACACGCGCGATATGCAAATATAGCGGAA------GT---GTTCCTGACG-----CGTGGGTAAGCGCGCGC
GC------GCTGCAGAGTTCCCGGCCCTGTGCT---------G------GGC---TGGCA--GATGC--CTGAGAACTGGCTGATGACGGC
AACGTTCGGGCTCC
>dasypus_novemcinctus/1-254
AAAGC-GATAGTTTTTAAACTGGACTTATAAGGCACCCATATCTACGTATATTCATGGGTGCATTCCCAC--AA
CACATAGCCACCAAATCCAAATATTGCGAGGGCGCTG------AGGCGTGGTC------GGGCGGCAAGC
GC------GCTCCGACTTCGGCCCTTCGGCCCT---------A------GGC-----CCCA--GATTC--CTGGAGCGTGATGATGACGTC
GACGTTCGGATACC
>laxodonta_africana/1-254
GGGAA-CCAACAAATTCGT--CAGGATTTATAAGACTCTCAGAGCTCGTAGACATTTCACACGTTAGGCGCCATGTCCCAC--AA
TACATACACACGATATGCAAATATCTAGGAGGGCCAGCCCT--CCC----CGTCCCGGTCGTCCATCTTCCGGCTAGGCGACGC
CC------GCTGCGGTGTTCCCGGCCCTGTG--ACC-----A------AGGC--GATTC--CTGAGAACCGGCTTGGTGGTGACGTC
AGTGTTCTGGCTCC
>procavia_capensis/1-254
AGGGT-AAATCGGCGCGAGAATCGGCCTGCTCAGCATTTAAAAGAATCCCAAAATGTGGTCGCCATTTTACGCTTAGGGTGATATCCCAC--AA
GACACCAGCCACATGCAAATATCGTGAGTGCTCTCTGTTTC--CCT---GTCCCA-CGAGGGCGTCCCTCCGCTGGGGCGCACGC
GC------CGTGTGTGTGCCGCCCCCCGGTTGTG------T------TTC----CCGGC--GATTC--CAAAGAACTGGTTGATAACGTT
AGAACTTCCGGCTGC
```

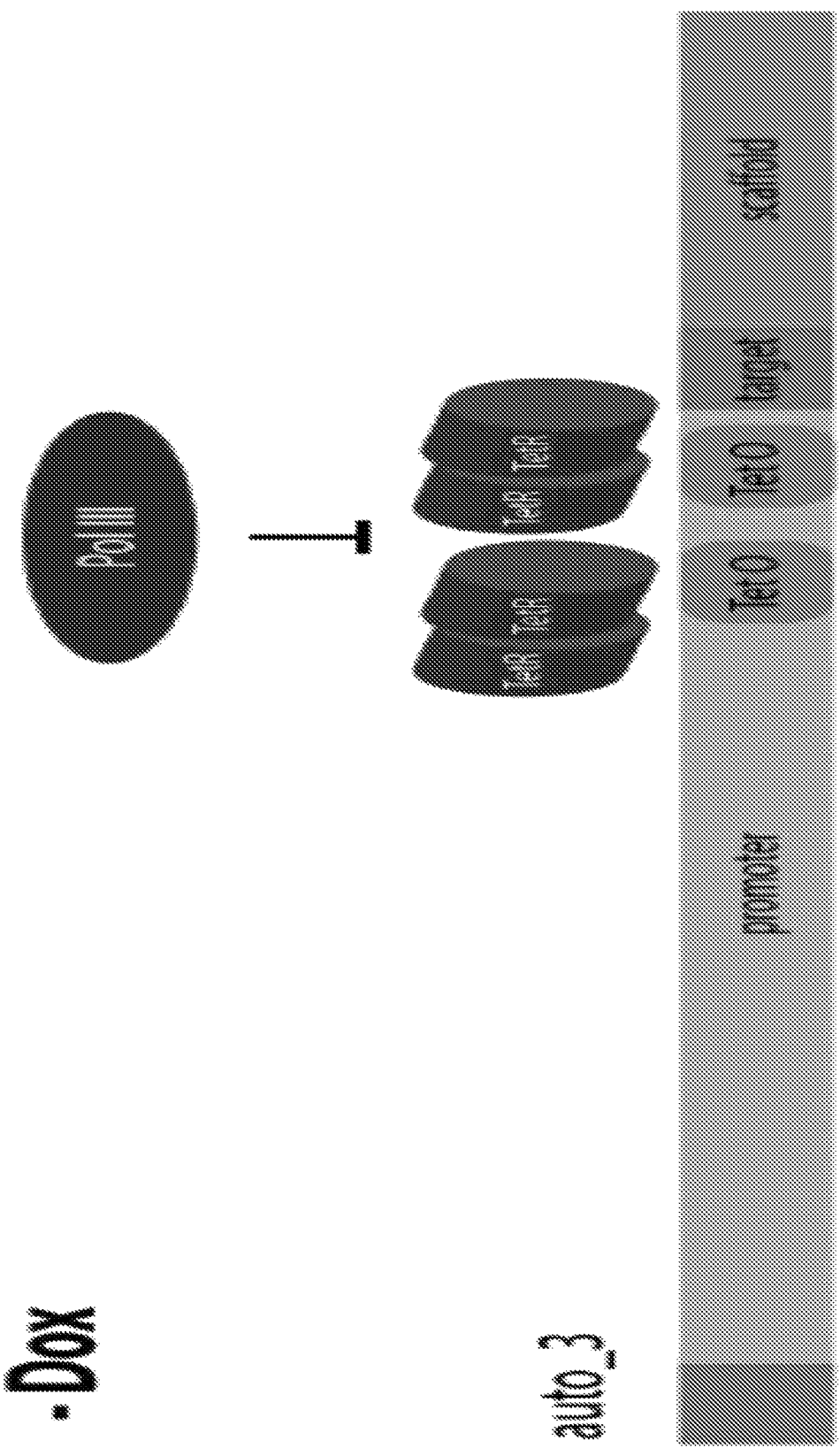

+ Dox

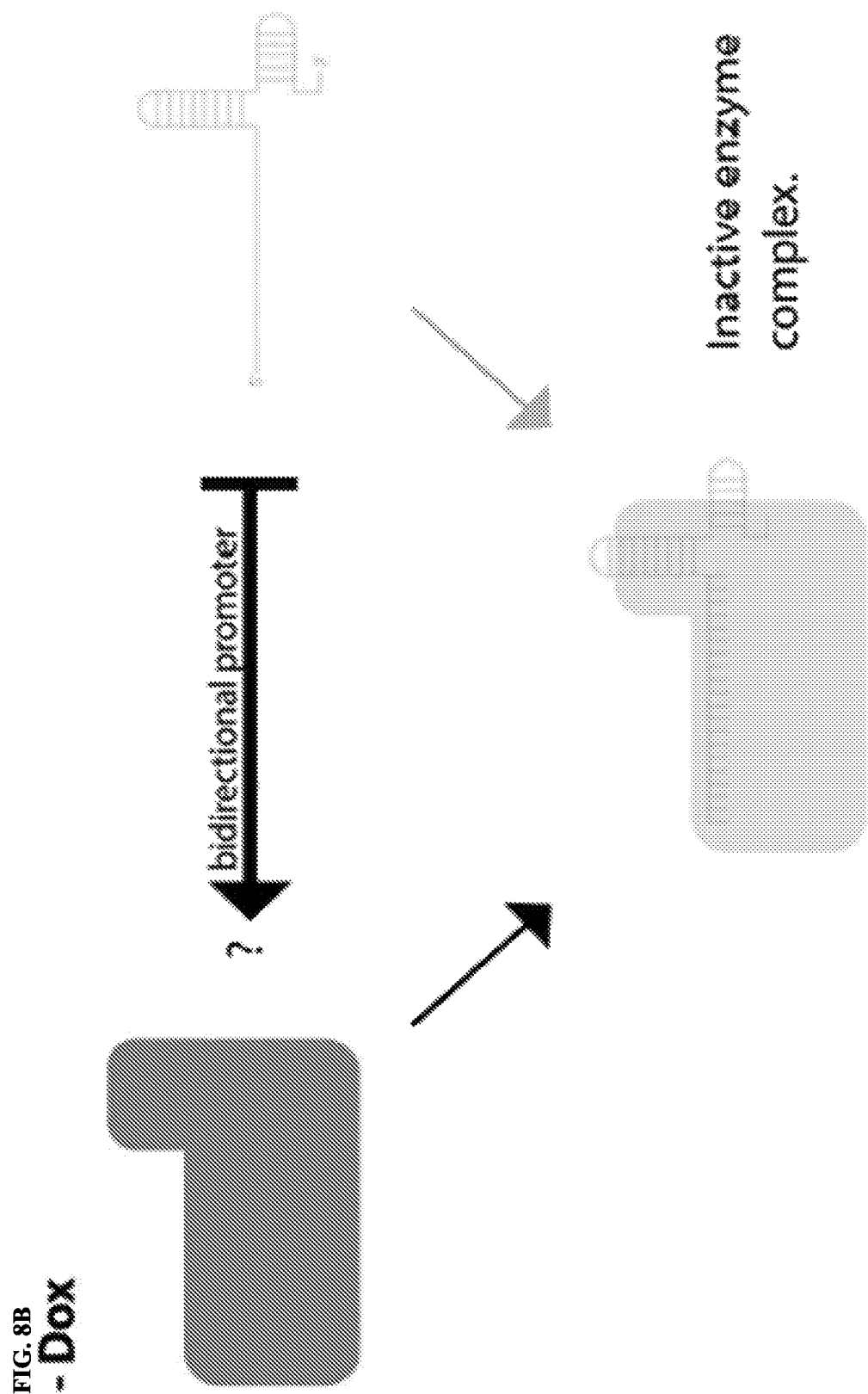

FIG. 10B

Left homology (300bp)-ACGGGTGTGGTAGGTACCACAGTACTACTGGCTGA-Right Homology (300bp)

P2a

ACGGGTGTGGTAGGTACCACAGTACTACTGGCTGA
TGCCCACACCATGGTGTCATGATGATGACCGACT

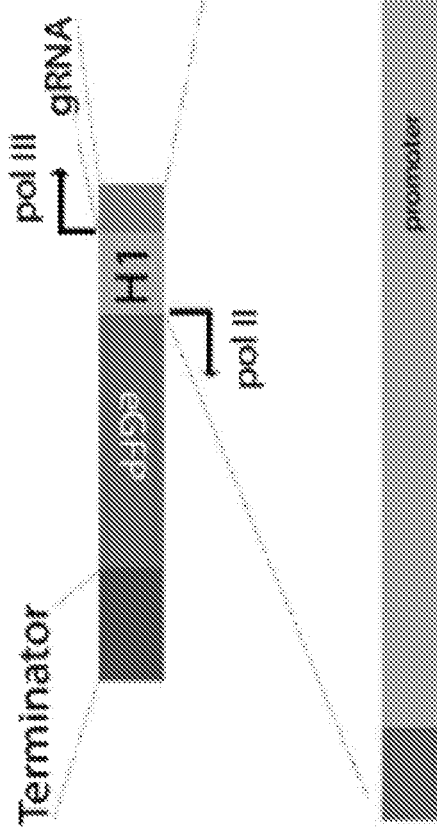
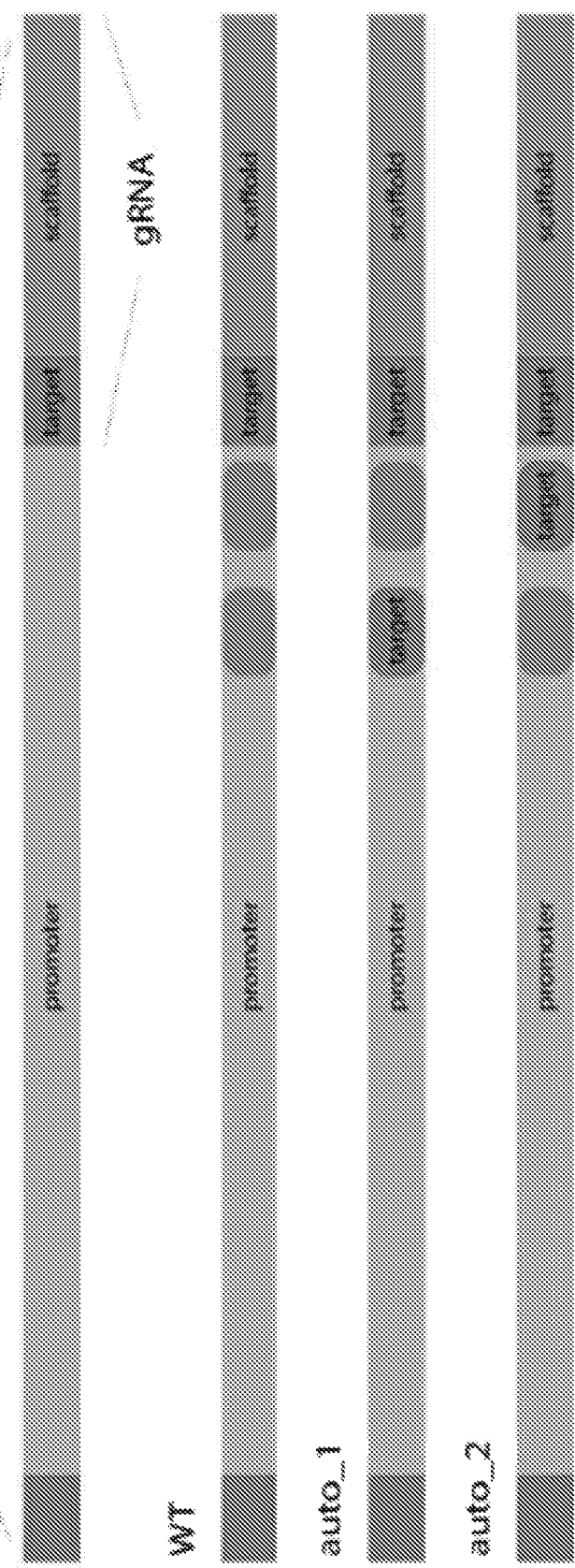
FIG. 15

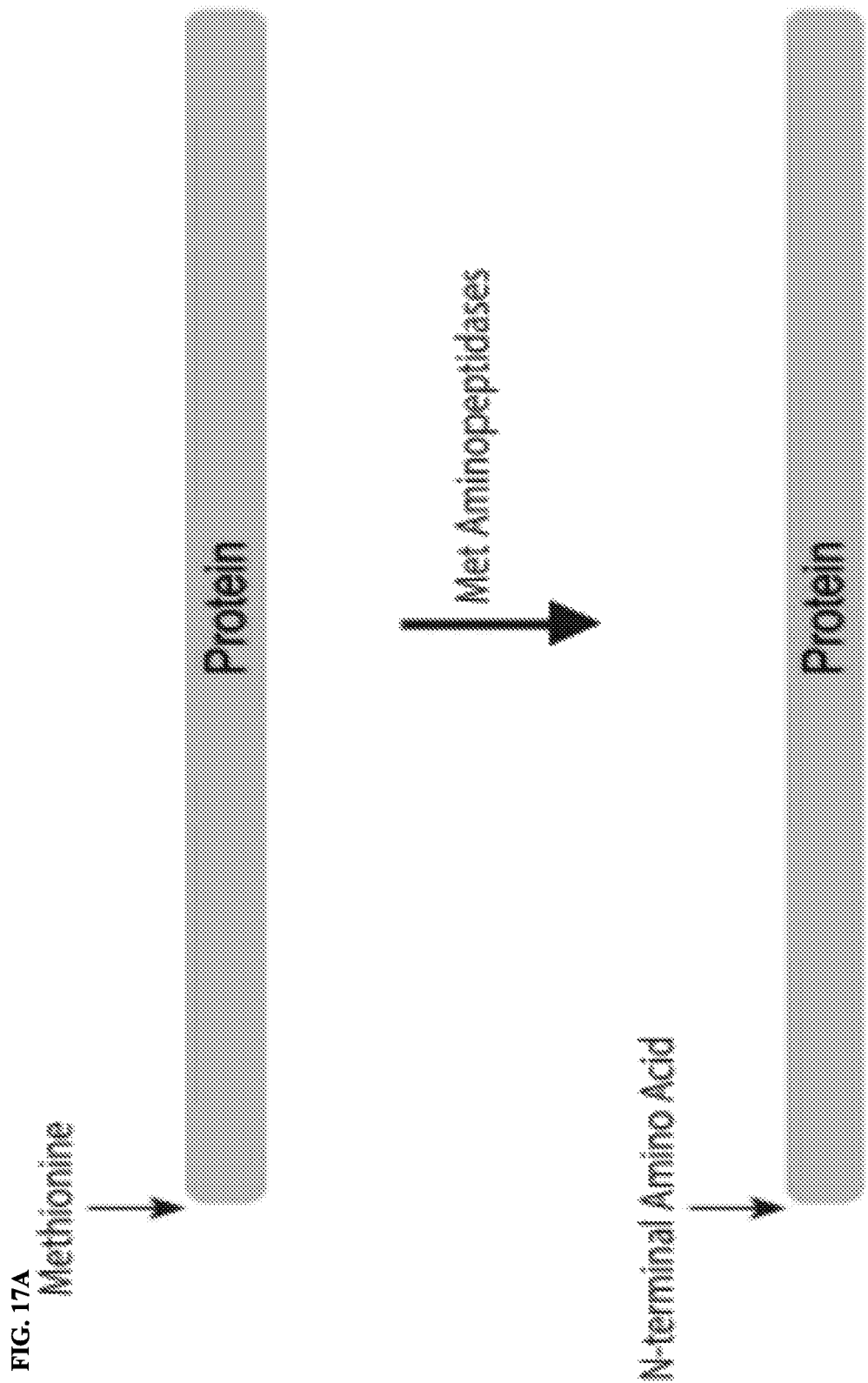

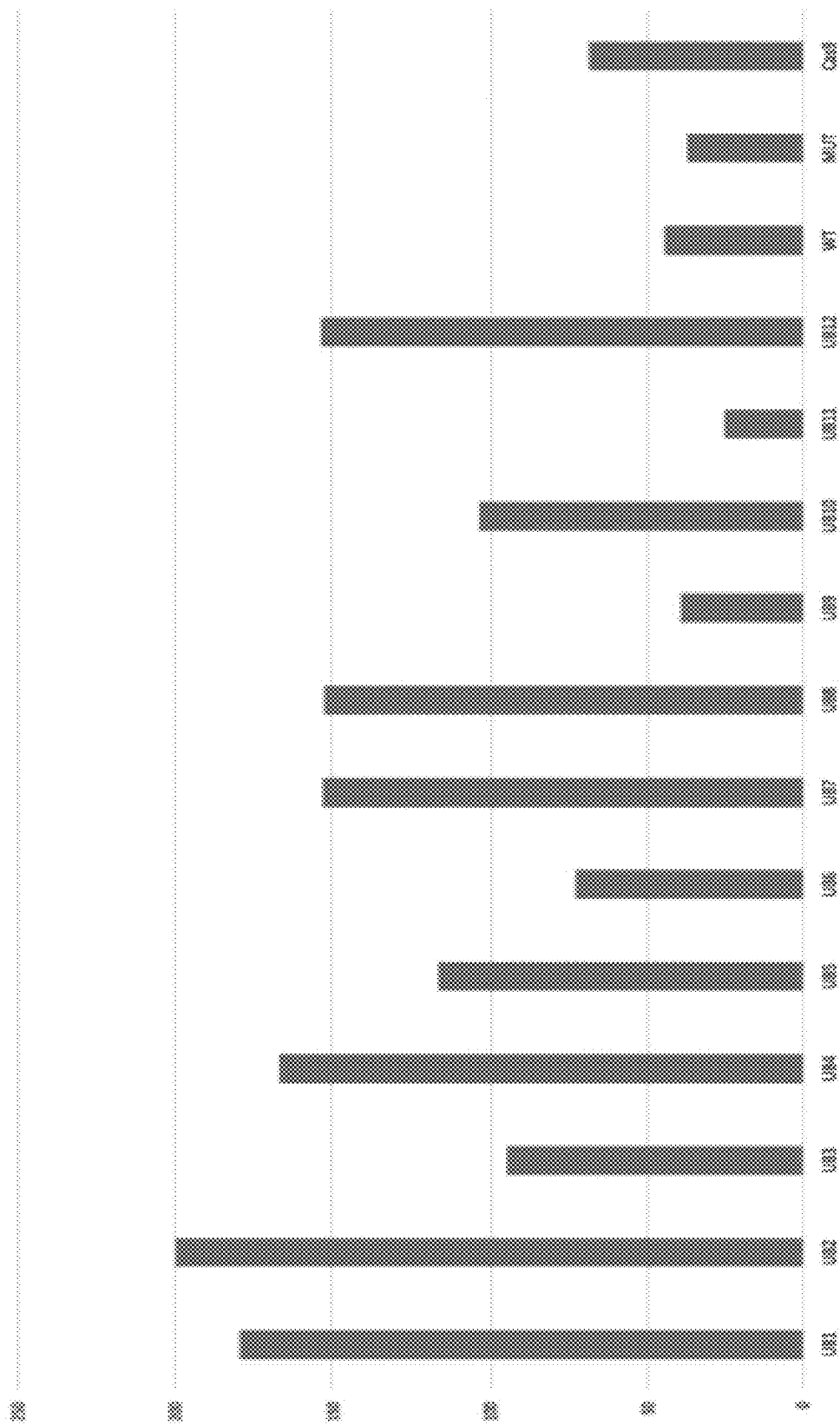

FIG. 22B
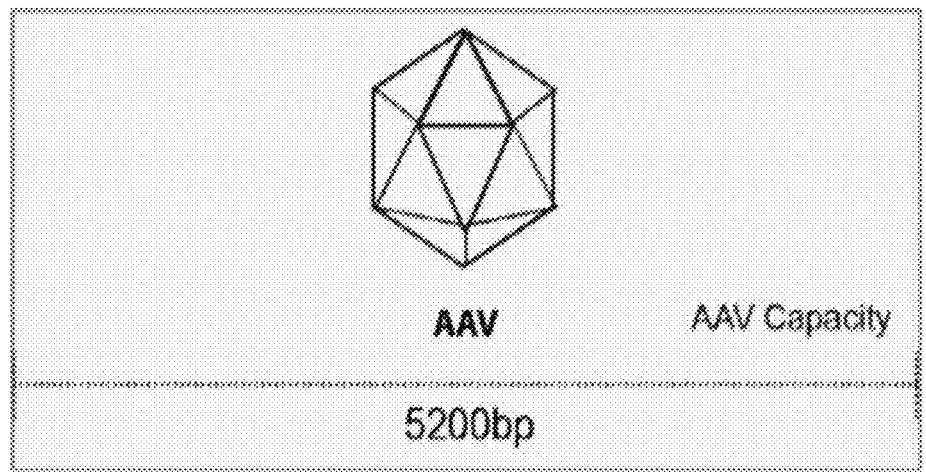
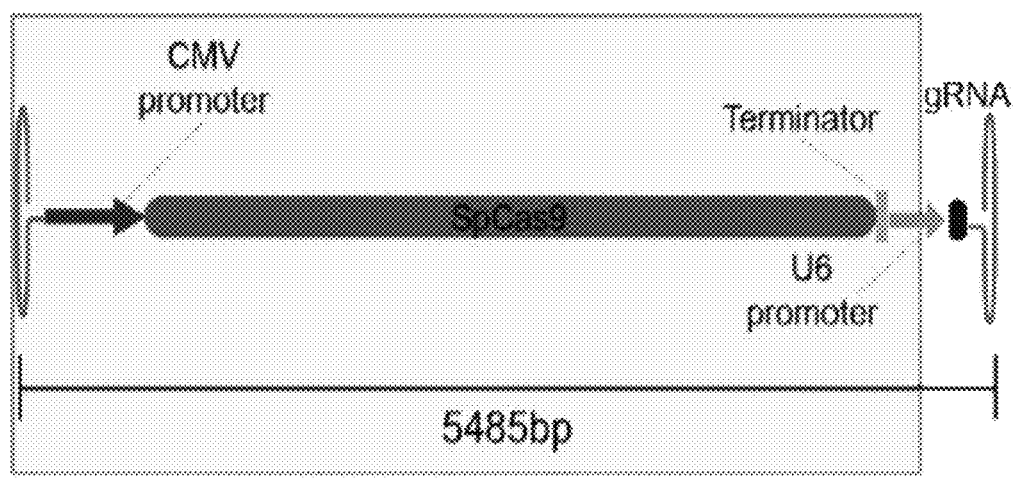
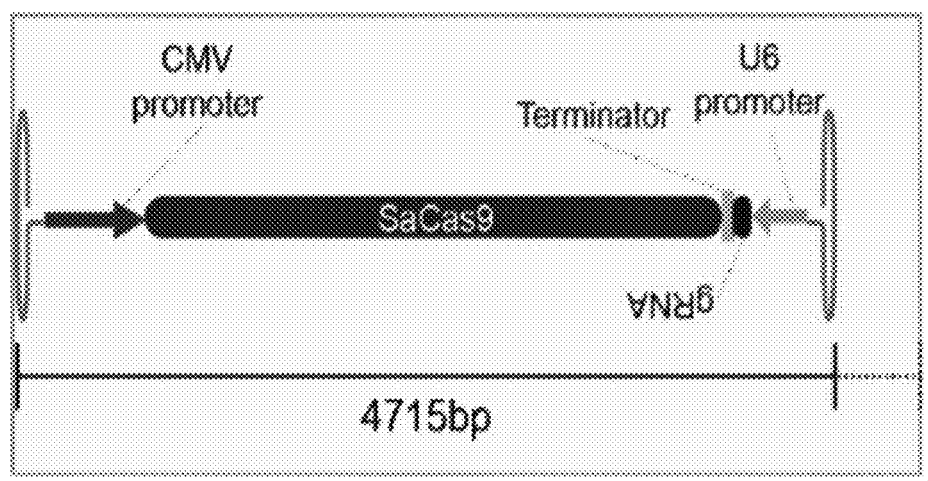

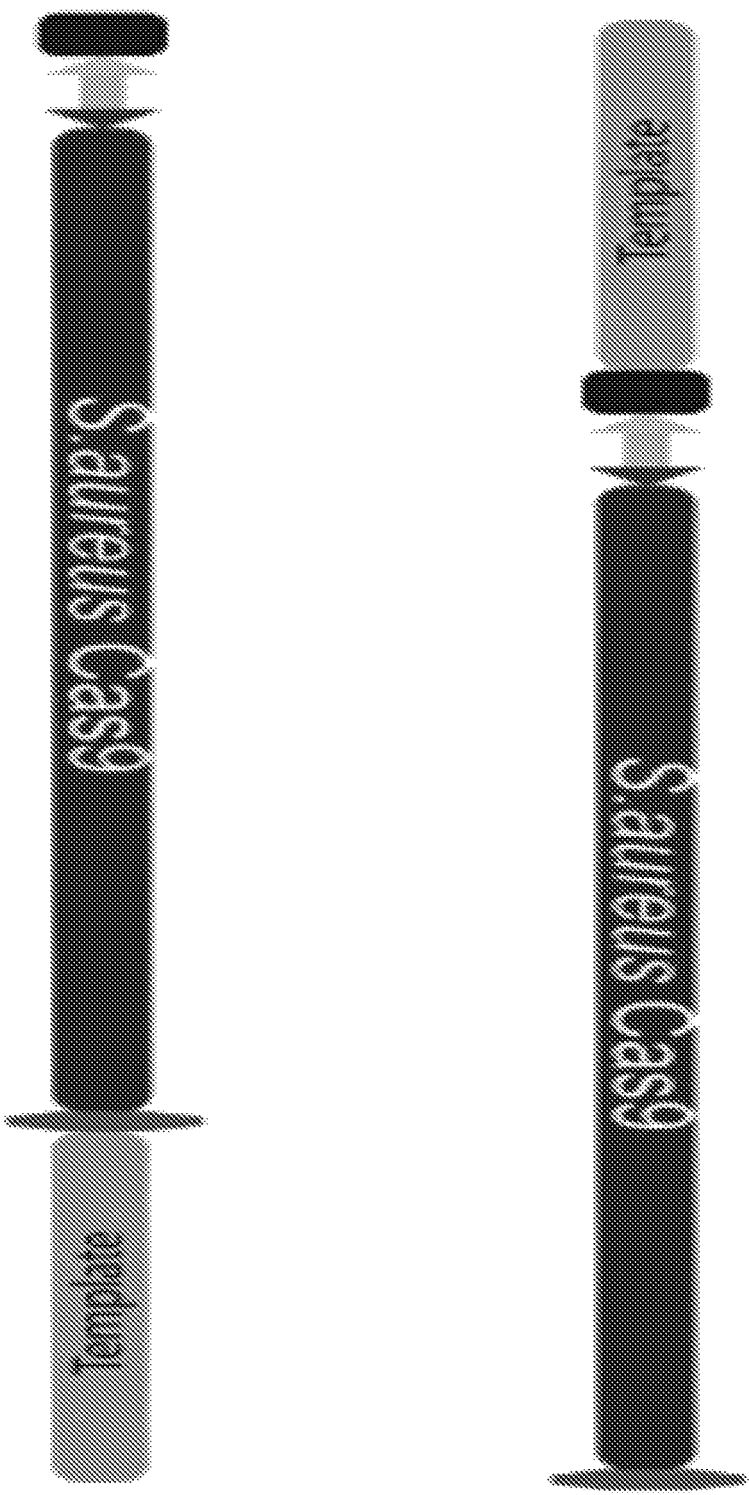
FIG. 24A Some Potential Configurations:

RPE65 example: rd12 with SaCas9 nickase 1000 example with SpCas9

| ncRNA gene | Protein gene | Distance |
|---|---|---|
| RPPH1 | PARP2 | 230bp |
| SRP | RPS29 | 233bp |
| 7sk1 | GSTA4 | 239bp |
| SNAR-G1 | CGB1 | 308bp |
| SNAR | CGB2 | 308bp |
| RMRP | CCDC107 | 361bp |
| tRNA(Lys) | ALOXE3 | 376bp |
| RNU6-9 | MED16 | 412bp |
| tRNA(Gly) | DPP9 | 484bp |
| SNORD13 | C8orf41 | 847bp |

SEQUENCE LISTING

```
<160> NUMBER OF SEQ ID NOS: 147

<210> SEQ ID NO 1
<211> LENGTH: 9
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1 gccgccacc                                                                 9

<210> SEQ ID NO 2
<211> LENGTH: 6
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2 gccacc                                                                    6

<210> SEQ ID NO 3
<211> LENGTH: 398
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
ggtggcggcg atagcttttc aggctttctg gagtccactc ggaggcctgg agccgcacaa        60
agcgccaggt cagcggtccc ggctgggtga gaccagcagg cggctctagc gcgcgggagc       120
tgggcgaggc tccgggacga cctcaccaat ggagactgca gtatttagca tgccccaccc       180
atctgcaagg cattctggat agtgtcaaaa cagccggaaa tcaagtccgt ttatctcaaa       240
ctttagcatt tgggaataa atgatatttg ctatgctggt taaattagat tttagttaaa       300
tttcctgctg aagctctagt acgataagca acttgaccta agtgtaaagt tgagacttcc       360
ttcaggttta tatagcttgt gcgccgcttg ggtacctc                               398

<210> SEQ ID NO 4
<211> LENGTH: 248
<212> TYPE: DNA
<213> ORGANISM: Homo sapiens

<400> SEQUENCE: 4
ggtggcggca gtatttagca tgccccaccc atctgcaagg cattctggat agtgtcaaaa        60
cagccggaaa tcaagtccgt ttatctcaaa ctttagcatt tgggaataa atgatatttg       120 ctatgctggt taaattagat tttagttaaa tttcctgctg aagctctagt acgataagca       180
acttgaccta agtgtaaagt tgagacttcc ttcaggttta tatagcttgt gcgccgcttg       240
ggtacctc                                                                248
```

<210> SEQ ID NO 5
<211> LENGTH: 289
<212> TYPE: DNA
<213> ORGANISM: Homo sapiens

<400> SEQUENCE: 5

```
ggtgtctgtt tgaggttgct agtgaacaca gttgtgtcag aagcaaatgt agtatttagc        60
atgccccacc catctgcaag gcattctgga tagtgtcaaa acagccggaa atcaagtccg       120
tttatctcaa actttagcat tttgggaata aatgatattt gctatgctgg ttaaattaga       180
ttttagttaa atttcctgct gaagctctag tacgataagc aacttgacct aagtgtaaag       240
ttgagacttc cttcaggttt atatagcttg tgcgccgctt gggtacctc                   289
```

<210> SEQ ID NO 6
<211> LENGTH: 350
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6

```
ggtggcggcc tcgtatggga ccgcaccgga cacgggcgcc tgggccagga gcagagccgg        60
gccgtagaat agacatggcc gtcgggggcg gggcttcgga aggtttaacc aatccaaact       120
gttgtatttt gcatagcccc aaagcatttt ggttaacagt aaaaacatcc taaatttaag       180
tattttaatt taaacttaga acgaagcgag tataaaaagg attatttaac cctaaaacgg       240
attcaggatt tgttataata tcaagtacag tcggctacat aaggtcacca catgtgtaaa       300
gttacaaaat tctatggcct tatataccta ccaagagcct gcttactctc                  350
```

<210> SEQ ID NO 7
<211> LENGTH: 289
<212> TYPE: DNA
<213> ORGANISM: Mus musculus

<400> SEQUENCE: 7

```
ggtggcggca gacatggccg tcgggggcgg ggcttcggaa ggtttaacca atccaaactg        60
ttgtattttg catagcccca aagcattttg gttaacagta aaaacatcct aaatttaagt       120
attttaattt aaacttagaa cgaagcgagt ataaaaagga ttatttaacc ctaaaacgga       180
ttcaggattt gttataatat caagtacagt cggctacata aggtcaccac atgtgtaaag       240
ttacaaaatt ctatggcctt atatacctac caagagcctg cttactctc                   289
```

<210> SEQ ID NO 8
<211> LENGTH: 330
<212> TYPE: DNA
<213> ORGANISM: Mus musculus

<400> SEQUENCE: 8

```
ggtgtctgtt tgaggttgct agtgaacaca gttgtgtcag aagcaaatgt agacatggcc        60
gtcgggggcg gggcttcgga aggtttaacc aatccaaact gttgtatttt gcatagcccc       120
aaagcatttt ggttaacagt aaaaacatcc taaatttaag tattttaatt taaacttaga       180
acgaagcgag tataaaaagg attatttaac cctaaaacgg attcaggatt tgttataata       240
tcaagtacag tcggctacat aaggtcacca catgtgtaaa gttacaaaat tctatggcct       300
tatataccta ccaagagcct gcttactctc                                        330
```

<210> SEQ ID NO 9
<211> LENGTH: 20
<212> TYPE: DNA
<213> ORGANISM: Mus musculus

<400> SEQUENCE: 9
gaagaaggtt cgagatctca                                                    20

<210> SEQ ID NO 10
<211> LENGTH: 23
<212> TYPE: DNA
<213> ORGANISM: Mus musculus

<400> SEQUENCE: 10
gaagaaggtt cgagatctca agg                                                23

<210> SEQ ID NO 11
<211> LENGTH: 19
<212> TYPE: DNA
<213> ORGANISM: Unknown
<220> FEATURE:
<223> OTHER INFORMATION: Description of Unknown:
      TetO site sequence

<400> SEQUENCE: 11
tccctatcag tgatagaga                                                     19

<210> SEQ ID NO 12
<211> LENGTH: 230
<212> TYPE: DNA
<213> ORGANISM: Unknown
<220> FEATURE:
<223> OTHER INFORMATION: Description of Unknown:
      H1 wildtype sequence

<400> SEQUENCE: 12
ggaattcgaa cgctgacgtc atcaacccgc tccaaggaat cgcgggccca gtgtcactag        60
gcgggaacac ccagcgcgcg tgcgccctgg caggaagatg gctgtgaggg acaggggagt       120
ggcgccctgc aatatttgca tgtcgctatg tgttctggga aatcaccata aacgtgaaat       180
gtctttggat ttgggaatct tataagttct gtatgagacc acttttttccc                 230

<210> SEQ ID NO 13
<211> LENGTH: 230
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
ggaattcgaa cgctgacgtc atcaacccgc tccaaggaat cgcgggccca gtgtcactag        60
gcgggaacac ccagcgcgcg tgcgccctgg caggaagatg gctgtgaggg acaggggagt       120
ggcgccctgc aatatttgca tgtcgctatg tgttctggga aatcaccata aacgtgaaat       180
ccctatcagt gatagagact tataagttcc ctatcagtga tagagatccc                  230

<210> SEQ ID NO 14
<211> LENGTH: 215
<212> TYPE: PRT
<213> ORGANISM: Unknown
<220> FEATURE:
<223> OTHER INFORMATION: Description of Unknown:
      TetR sequence

<400> SEQUENCE: 14

```
Met Ser Arg Leu Asp Lys Ser Lys Val Ile Asn Ser Ala Leu Glu Leu
1               5                   10                  15

Leu Asn Glu Val Gly Ile Glu Gly Leu Thr Thr Arg Lys Leu Ala Gln
            20                  25                  30

Lys Leu Gly Val Glu Gln Pro Thr Leu Tyr Trp His Val Lys Asn Lys
        35                  40                  45

Arg Ala Leu Leu Asp Ala Leu Ala Ile Glu Met Leu Asp Arg His His
    50                  55                  60

Thr His Phe Cys Pro Leu Glu Gly Ser Trp Gln Asp Phe Leu Arg
65                  70                  75                  80

Asn Asn Ala Lys Ser Phe Arg Cys Ala Leu Leu Ser His Arg Asp Gly
                85                  90                  95

Ala Lys Val His Leu Gly Thr Arg Pro Thr Glu Lys Gln Tyr Glu Thr
            100                 105                 110

Leu Glu Asn Gln Leu Ala Phe Leu Cys Gln Gln Gly Phe Ser Leu Glu
        115                 120                 125

Asn Ala Leu Tyr Ala Leu Ser Ala Val Gly His Phe Thr Leu Gly Cys
    130                 135                 140

Val Leu Glu Asp Gln Glu His Gln Val Ala Lys Glu Glu Arg Glu Thr
145                 150                 155                 160

Pro Thr Thr Asp Ser Met Pro Pro Leu Leu Arg Gln Ala Ile Glu Leu
                165                 170                 175

Phe Asp His Gln Gly Ala Glu Pro Ala Phe Leu Phe Gly Leu Glu Leu
            180                 185                 190

Ile Ile Cys Gly Leu Glu Lys Gln Leu Lys Cys Glu Ser Gly Ser Ala
        195                 200                 205

Tyr Ser Gly Ser Arg Glu Phe
    210                 215
```

<210> SEQ ID NO 15
<211> LENGTH: 126
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 15

```
cagaaggccc taacttctac gtgcccttct ccaatgcgac gggtgtggta cgcagcccct      60
gaattcaccc acagtactac ctggctgagc catggcagtt ctccatgctg ccgcctaca     120
tgtttc                                                                126
```

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 16

```
tggagccctg agtggctgag                                                  20
```

<210> SEQ ID NO 17
<211> LENGTH: 25
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 17
ccacctagga ccatgaagag gtcag                                              25

<210> SEQ ID NO 18
<211> LENGTH: 91
<212> TYPE: PRT
<213> ORGANISM: Homo sapiens

<400> SEQUENCE: 18
```

Pro Ser Pro Ala Arg Pro Ala Leu Arg Ala Pro Ala Ser Ala Thr Ser
1               5                   10                  15

Gly Ser Arg Lys Arg Ala Arg Pro Pro Ala Ala Pro Gly Arg Asp Gln
            20                  25                  30

Ala Arg Pro Pro Ala Arg Arg Leu Arg Leu Ser Val Asp Glu Val
        35                  40                  45

Ser Ser Pro Ser Thr Pro Glu Ala Pro Asp Ile Pro Ala Cys Pro Ser
    50                  55                  60

Pro Gly Gln Lys Ile Lys Lys Ser Thr Pro Ala Ala Gly Gln Pro Pro
65                  70                  75                  80

His Leu Thr Ser Ala Gln Asp Gln Asp Thr Ile
                85                  90

```
<210> SEQ ID NO 19
<211> LENGTH: 110
<212> TYPE: PRT
<213> ORGANISM: Homo sapiens

<400> SEQUENCE: 19
```

Met Asn Pro Ser Met Lys Gln Lys Gln Glu Glu Ile Lys Glu Asn Ile
1               5                   10                  15

Lys Asn Ser Ser Val Pro Arg Arg Thr Leu Lys Met Ile Gln Pro Ser
            20                  25                  30

Ala Ser Gly Ser Leu Val Gly Arg Glu Asn Glu Leu Ser Ala Gly Leu
        35                  40                  45

Ser Lys Arg Lys His Arg Asn Asp His Leu Thr Ser Thr Thr Ser Ser
    50                  55                  60

Pro Gly Val Ile Val Pro Glu Ser Ser Glu Asn Lys Asn Leu Gly Gly
65                  70                  75                  80

Val Thr Gln Glu Ser Phe Asp Leu Met Ile Lys Glu Asn Pro Ser Ser
                85                  90                  95

Gln Tyr Trp Lys Glu Val Ala Glu Lys Arg Arg Lys Ala Leu
            100                 105                 110

```
<210> SEQ ID NO 20
<211> LENGTH: 1486
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20
```

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe

-continued

```
                20                  25                  30
Lys Val Leu Gly Asn Thr Asp Arg His Ser Ile Lys Lys Asn Leu Ile
            35                  40                  45
Gly Ala Leu Leu Phe Asp Ser Gly Glu Thr Ala Glu Ala Thr Arg Leu
        50                  55                  60
Lys Arg Thr Ala Arg Arg Tyr Thr Arg Arg Lys Asn Arg Ile Cys
65                  70                  75                  80
Tyr Leu Gln Glu Ile Phe Ser Asn Glu Met Ala Lys Val Asp Asp Ser
                85                  90                  95
Phe Phe His Arg Leu Glu Glu Ser Phe Leu Val Glu Glu Asp Lys Lys
                100                 105                 110
His Glu Arg His Pro Ile Phe Gly Asn Ile Val Asp Glu Val Ala Tyr
            115                 120                 125
His Glu Lys Tyr Pro Thr Ile Tyr His Leu Arg Lys Lys Leu Val Asp
        130                 135                 140
Ser Thr Asp Lys Ala Asp Leu Arg Leu Ile Tyr Leu Ala Leu Ala His
145                 150                 155                 160
Met Ile Lys Phe Arg Gly His Phe Leu Ile Glu Gly Asp Leu Asn Pro
                165                 170                 175
Asp Asn Ser Asp Val Asp Lys Leu Phe Ile Gln Leu Val Gln Thr Tyr
                180                 185                 190
Asn Gln Leu Phe Glu Glu Asn Pro Ile Asn Ala Ser Gly Val Asp Ala
            195                 200                 205
Lys Ala Ile Leu Ser Ala Arg Leu Ser Lys Ser Arg Arg Leu Glu Asn
        210                 215                 220
Leu Ile Ala Gln Leu Pro Gly Glu Lys Lys Asn Gly Leu Phe Gly Asn
225                 230                 235                 240
Leu Ile Ala Leu Ser Leu Gly Leu Thr Pro Asn Phe Lys Ser Asn Phe
                245                 250                 255
Asp Leu Ala Glu Asp Ala Lys Leu Gln Leu Ser Lys Asp Thr Tyr Asp
                260                 265                 270
Asp Asp Leu Asp Asn Leu Leu Ala Gln Ile Gly Asp Gln Tyr Ala Asp
            275                 280                 285
Leu Phe Leu Ala Ala Lys Asn Leu Ser Asp Ala Ile Leu Leu Ser Asp
        290                 295                 300
Ile Leu Arg Val Asn Thr Glu Ile Thr Lys Ala Pro Leu Ser Ala Ser
305                 310                 315                 320
Met Ile Lys Arg Tyr Asp Glu His His Gln Asp Leu Thr Leu Leu Lys
                325                 330                 335
Ala Leu Val Arg Gln Gln Leu Pro Glu Lys Tyr Lys Glu Ile Phe Phe
                340                 345                 350
Asp Gln Ser Lys Asn Gly Tyr Ala Gly Tyr Ile Asp Gly Gly Ala Ser
            355                 360                 365
Gln Glu Glu Phe Tyr Lys Phe Ile Lys Pro Ile Leu Glu Lys Met Asp
        370                 375                 380
Gly Thr Glu Glu Leu Leu Val Lys Leu Asn Arg Glu Asp Leu Leu Arg
385                 390                 395                 400
Lys Gln Arg Thr Phe Asp Asn Gly Ser Ile Pro His Gln Ile His Leu
                405                 410                 415
Gly Glu Leu His Ala Ile Leu Arg Arg Gln Glu Asp Phe Tyr Pro Phe
                420                 425                 430
Leu Lys Asp Asn Arg Glu Lys Ile Glu Lys Ile Leu Thr Phe Arg Ile
            435                 440                 445
```

```
Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
    850                 855                 860
```

```
Gly Lys Ser Asp Asn Val Pro Ser Glu Glu Val Val Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
        995                 1000                1005

Val Tyr Gly Asp Tyr Lys Val Tyr Asp Val Arg Lys Met Ile Ala
    1010                1015                1020

Lys Ser Glu Gln Glu Ile Gly Lys Ala Thr Ala Lys Tyr Phe Phe
    1025                1030                1035

Tyr Ser Asn Ile Met Asn Phe Phe Lys Thr Glu Ile Thr Leu Ala
    1040                1045                1050

Asn Gly Glu Ile Arg Lys Arg Pro Leu Ile Glu Thr Asn Gly Glu
    1055                1060                1065

Thr Gly Glu Ile Val Trp Asp Lys Gly Arg Asp Phe Ala Thr Val
    1070                1075                1080

Arg Lys Val Leu Ser Met Pro Gln Val Asn Ile Val Lys Lys Thr
    1085                1090                1095

Glu Val Gln Thr Gly Gly Phe Ser Lys Glu Ser Ile Leu Pro Lys
    1100                1105                1110

Arg Asn Ser Asp Lys Leu Ile Ala Arg Lys Lys Asp Trp Asp Pro
    1115                1120                1125

Lys Lys Tyr Gly Gly Phe Asp Ser Pro Thr Val Ala Tyr Ser Val
    1130                1135                1140

Leu Val Val Ala Lys Val Glu Lys Gly Lys Ser Lys Lys Leu Lys
    1145                1150                1155

Ser Val Lys Glu Leu Leu Gly Ile Thr Ile Met Glu Arg Ser Ser
    1160                1165                1170

Phe Glu Lys Asn Pro Ile Asp Phe Leu Glu Ala Lys Gly Tyr Lys
    1175                1180                1185

Glu Val Lys Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
```

```
                1265                1270                1275

Arg Val Ile Leu Ala Asp Ala Asn Leu Asp Lys Val Leu Ser Ala
        1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
1340                1345                1350

Gly Leu Tyr Glu Thr Arg Ile Asp Leu Ser Gln Leu Gly Gly Asp
    1355                1360                1365

Ser Arg Ala Asp Pro Lys Lys Lys Arg Lys Val Arg Gly Gly Gly
1370                1375                1380

Gly Ser Gly Gly Gly Gly Ser Gly Gly Gly Gly Ser Pro Ser Pro
    1385                1390                1395

Ala Arg Pro Ala Leu Arg Ala Pro Ala Ser Ala Thr Ser Gly Ser
1400                1405                1410

Arg Lys Arg Ala Arg Pro Pro Ala Ala Pro Gly Arg Asp Gln Ala
    1415                1420                1425

Arg Pro Pro Ala Arg Arg Arg Leu Arg Leu Ser Val Asp Glu Val
1430                1435                1440

Ser Ser Pro Ser Thr Pro Glu Ala Pro Asp Ile Pro Ala Cys Pro
    1445                1450                1455

Ser Pro Gly Gln Lys Ile Lys Lys Ser Thr Pro Ala Ala Gly Gln
    1460                1465                1470

Pro Pro His Leu Thr Ser Ala Gln Asp Gln Asp Thr Ile
1475                1480                1485

<210> SEQ ID NO 21
<211> LENGTH: 1505
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125
```

```
His Glu Lys Tyr Pro Thr Ile Tyr His Leu Arg Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
```

```
            545                 550                 555                 560
       Val Lys Gln Leu Lys Glu Asp Tyr Phe Lys Ile Glu Cys Phe Asp
                       565                 570                 575
       Ser Val Glu Ile Ser Gly Val Glu Asp Arg Phe Asn Ala Ser Leu Gly
                       580                 585                 590
       Thr Tyr His Asp Leu Leu Lys Ile Ile Lys Asp Lys Asp Phe Leu Asp
                       595                 600                 605
       Asn Glu Glu Asn Glu Asp Ile Leu Glu Asp Ile Val Leu Thr Leu Thr
                       610                 615                 620
       Leu Phe Glu Asp Arg Glu Met Ile Glu Glu Arg Leu Lys Thr Tyr Ala
       625                 630                 635                 640
       His Leu Phe Asp Asp Lys Val Met Lys Gln Leu Lys Arg Arg Arg Tyr
                       645                 650                 655
       Thr Gly Trp Gly Arg Leu Ser Arg Lys Leu Ile Asn Gly Ile Arg Asp
                       660                 665                 670
       Lys Gln Ser Gly Lys Thr Ile Leu Asp Phe Leu Lys Ser Asp Gly Phe
                       675                 680                 685
       Ala Asn Arg Asn Phe Met Gln Leu Ile His Asp Asp Ser Leu Thr Phe
       690                 695                 700
       Lys Glu Asp Ile Gln Lys Ala Gln Val Ser Gly Gln Gly Asp Ser Leu
       705                 710                 715                 720
       His Glu His Ile Ala Asn Leu Ala Gly Ser Pro Ala Ile Lys Lys Gly
                       725                 730                 735
       Ile Leu Gln Thr Val Lys Val Val Asp Glu Leu Val Lys Val Met Gly
                       740                 745                 750
       Arg His Lys Pro Glu Asn Ile Val Ile Glu Met Ala Arg Glu Asn Gln
                       755                 760                 765
       Thr Thr Gln Lys Gly Gln Lys Asn Ser Arg Glu Arg Met Lys Arg Ile
       770                 775                 780
       Glu Glu Gly Ile Lys Glu Leu Gly Ser Gln Ile Leu Lys Glu His Pro
       785                 790                 795                 800
       Val Glu Asn Thr Gln Leu Gln Asn Glu Lys Leu Tyr Leu Tyr Tyr Leu
                       805                 810                 815
       Gln Asn Gly Arg Asp Met Tyr Val Asp Gln Glu Leu Asp Ile Asn Arg
                       820                 825                 830
       Leu Ser Asp Tyr Asp Val Asp His Ile Val Pro Gln Ser Phe Leu Lys
                       835                 840                 845
       Asp Asp Ser Ile Asp Asn Lys Val Leu Thr Arg Ser Asp Lys Asn Arg
       850                 855                 860
       Gly Lys Ser Asp Asn Val Pro Ser Glu Glu Val Val Lys Lys Met Lys
       865                 870                 875                 880
       Asn Tyr Trp Arg Gln Leu Leu Asn Ala Lys Leu Ile Thr Gln Arg Lys
                       885                 890                 895
       Phe Asp Asn Leu Thr Lys Ala Glu Arg Gly Gly Leu Ser Glu Leu Asp
                       900                 905                 910
       Lys Ala Gly Phe Ile Lys Arg Gln Leu Val Glu Thr Arg Gln Ile Thr
                       915                 920                 925
       Lys His Val Ala Gln Ile Leu Asp Ser Arg Met Asn Thr Lys Tyr Asp
                       930                 935                 940
       Glu Asn Asp Lys Leu Ile Arg Glu Val Lys Val Ile Thr Leu Lys Ser
       945                 950                 955                 960
       Lys Leu Val Ser Asp Phe Arg Lys Asp Phe Gln Phe Tyr Lys Val Arg
                       965                 970                 975
```

-continued

Glu Ile Asn Asn Tyr His His Ala His Asp Ala Tyr Leu Asn Ala Val
                      980                 985                 990

Val Gly Thr Ala Leu Ile Lys Lys  Tyr Pro Lys Leu Glu  Ser Glu Phe
            995                 1000                1005

Val Tyr Gly Asp Tyr Lys Val  Tyr Asp Val Arg Lys  Met Ile Ala
    1010                1015                1020

Lys Ser Glu Gln Glu Ile Gly  Lys Ala Thr Ala Lys  Tyr Phe Phe
    1025                1030                1035

Tyr Ser Asn Ile Met Asn Phe  Phe Lys Thr Glu Ile  Thr Leu Ala
    1040                1045                1050

Asn Gly Glu Ile Arg Lys Arg  Pro Leu Ile Glu Thr  Asn Gly Glu
    1055                1060                1065

Thr Gly Glu Ile Val Trp Asp  Lys Gly Arg Asp Phe  Ala Thr Val
    1070                1075                1080

Arg Lys Val Leu Ser Met Pro  Gln Val Asn Ile Val  Lys Lys Thr
    1085                1090                1095

Glu Val Gln Thr Gly Gly Phe  Ser Lys Glu Ser Ile  Leu Pro Lys
    1100                1105                1110

Arg Asn Ser Asp Lys Leu Ile  Ala Arg Lys Lys Asp  Trp Asp Pro
    1115                1120                1125

Lys Lys Tyr Gly Gly Phe Asp  Ser Pro Thr Val Ala  Tyr Ser Val
    1130                1135                1140

Leu Val Val Ala Lys Val Glu  Lys Gly Lys Ser Lys  Lys Leu Lys
    1145                1150                1155

Ser Val Lys Glu Leu Leu Gly  Ile Thr Ile Met Glu  Arg Ser Ser
    1160                1165                1170

Phe Glu Lys Asn Pro Ile Asp  Phe Leu Glu Ala Lys  Gly Tyr Lys
    1175                1180                1185

Glu Val Lys Lys Asp Leu Ile  Ile Lys Leu Pro Lys  Tyr Ser Leu
    1190                1195                1200

Phe Glu Leu Glu Asn Gly Arg  Lys Arg Met Leu Ala  Ser Ala Gly
    1205                1210                1215

Glu Leu Gln Lys Gly Asn Glu  Leu Ala Leu Pro Ser  Lys Tyr Val
    1220                1225                1230

Asn Phe Leu Tyr Leu Ala Ser  His Tyr Glu Lys Leu  Lys Gly Ser
    1235                1240                1245

Pro Glu Asp Asn Glu Gln Lys  Gln Leu Phe Val Glu  Gln His Lys
    1250                1255                1260

His Tyr Leu Asp Glu Ile Ile  Glu Gln Ile Ser Glu  Phe Ser Lys
    1265                1270                1275

Arg Val Ile Leu Ala Asp Ala  Asn Leu Asp Lys Val  Leu Ser Ala
    1280                1285                1290

Tyr Asn Lys His Arg Asp Lys  Pro Ile Arg Glu Gln  Ala Glu Asn
    1295                1300                1305

Ile Ile His Leu Phe Thr Leu  Thr Asn Leu Gly Ala  Pro Ala Ala
    1310                1315                1320

Phe Lys Tyr Phe Asp Thr Thr  Ile Asp Arg Lys Arg  Tyr Thr Ser
    1325                1330                1335

Thr Lys Glu Val Leu Asp Ala  Thr Leu Ile His Gln  Ser Ile Thr
    1340                1345                1350

Gly Leu Tyr Glu Thr Arg Ile  Asp Leu Ser Gln Leu  Gly Gly Asp
    1355                1360                1365

```
Ser Arg Ala Asp Pro Lys Lys Lys Arg Lys Val Arg Gly Gly Gly
    1370                1375                1380

Gly Ser Gly Gly Gly Ser Gly Gly Gly Gly Ser Met Asn Pro
    1385                1390                1395

Ser Met Lys Gln Lys Gln Glu Glu Ile Lys Glu Asn Ile Lys Asn
    1400                1405                1410

Ser Ser Val Pro Arg Arg Thr Leu Lys Met Ile Gln Pro Ser Ala
    1415                1420                1425

Ser Gly Ser Leu Val Gly Arg Glu Asn Glu Leu Ser Ala Gly Leu
    1430                1435                1440

Ser Lys Arg Lys His Arg Asn Asp His Leu Thr Ser Thr Thr Ser
    1445                1450                1455

Ser Pro Gly Val Ile Val Pro Glu Ser Ser Glu Asn Lys Asn Leu
    1460                1465                1470

Gly Gly Val Thr Gln Glu Ser Phe Asp Leu Met Ile Lys Glu Asn
    1475                1480                1485

Pro Ser Ser Gln Tyr Trp Lys Glu Val Ala Glu Lys Arg Arg Lys
    1490                1495                1500

Ala Leu
    1505

<210> SEQ ID NO 22
<211> LENGTH: 1486
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Met Pro Ser Pro Ala Arg Pro Ala Leu Arg Ala Pro Ala Ser Ala Thr
1               5                   10                  15

Ser Gly Ser Arg Lys Arg Ala Arg Pro Pro Ala Pro Gly Arg Asp
            20                  25                  30

Gln Ala Arg Pro Pro Ala Arg Arg Leu Arg Leu Ser Val Asp Glu
        35                  40                  45

Val Ser Ser Pro Ser Thr Pro Glu Ala Pro Asp Ile Pro Ala Cys Pro
    50                  55                  60

Ser Pro Gly Gln Lys Ile Lys Lys Ser Thr Pro Ala Ala Gly Gln Pro
65                  70                  75                  80

Pro His Leu Thr Ser Ala Gln Asp Gln Asp Thr Ile Gly Gly Gly Gly
                85                  90                  95

Ser Gly Gly Gly Gly Ser Gly Gly Gly Gly Ser Asp Lys Lys Tyr Ser
            100                 105                 110

Ile Gly Leu Asp Ile Gly Thr Asn Ser Val Gly Trp Ala Val Ile Thr
        115                 120                 125

Asp Glu Tyr Lys Val Pro Ser Lys Lys Phe Lys Val Leu Gly Asn Thr
    130                 135                 140

Asp Arg His Ser Ile Lys Lys Asn Leu Ile Gly Ala Leu Leu Phe Asp
145                 150                 155                 160

Ser Gly Glu Thr Ala Glu Ala Thr Arg Leu Lys Arg Thr Ala Arg Arg
                165                 170                 175

Arg Tyr Thr Arg Arg Lys Asn Arg Ile Cys Tyr Leu Gln Glu Ile Phe
            180                 185                 190

Ser Asn Glu Met Ala Lys Val Asp Asp Ser Phe Phe His Arg Leu Glu
        195                 200                 205
```

Glu Ser Phe Leu Val Glu Glu Asp Lys Lys His Glu Arg His Pro Ile
    210                 215                 220

Phe Gly Asn Ile Val Asp Glu Val Ala Tyr His Glu Lys Tyr Pro Thr
225                 230                 235                 240

Ile Tyr His Leu Arg Lys Lys Leu Val Asp Ser Thr Asp Lys Ala Asp
            245                 250                 255

Leu Arg Leu Ile Tyr Leu Ala Leu Ala His Met Ile Lys Phe Arg Gly
        260                 265                 270

His Phe Leu Ile Glu Gly Asp Leu Asn Pro Asp Asn Ser Asp Val Asp
    275                 280                 285

Lys Leu Phe Ile Gln Leu Val Gln Thr Tyr Asn Gln Leu Phe Glu Glu
290                 295                 300

Asn Pro Ile Asn Ala Ser Gly Val Asp Ala Lys Ala Ile Leu Ser Ala
305                 310                 315                 320

Arg Leu Ser Lys Ser Arg Arg Leu Glu Asn Leu Ile Ala Gln Leu Pro
            325                 330                 335

Gly Glu Lys Lys Asn Gly Leu Phe Gly Asn Leu Ile Ala Leu Ser Leu
        340                 345                 350

Gly Leu Thr Pro Asn Phe Lys Ser Asn Phe Asp Leu Ala Glu Asp Ala
    355                 360                 365

Lys Leu Gln Leu Ser Lys Asp Thr Tyr Asp Asp Asp Leu Asp Asn Leu
370                 375                 380

Leu Ala Gln Ile Gly Asp Gln Tyr Ala Asp Leu Phe Leu Ala Ala Lys
385                 390                 395                 400

Asn Leu Ser Asp Ala Ile Leu Leu Ser Asp Ile Leu Arg Val Asn Thr
            405                 410                 415

Glu Ile Thr Lys Ala Pro Leu Ser Ala Ser Met Ile Lys Arg Tyr Asp
        420                 425                 430

Glu His His Gln Asp Leu Thr Leu Leu Lys Ala Leu Val Arg Gln Gln
    435                 440                 445

Leu Pro Glu Lys Tyr Lys Glu Ile Phe Phe Asp Gln Ser Lys Asn Gly
450                 455                 460

Tyr Ala Gly Tyr Ile Asp Gly Gly Ala Ser Gln Glu Glu Phe Tyr Lys
465                 470                 475                 480

Phe Ile Lys Pro Ile Leu Glu Lys Met Asp Gly Thr Glu Glu Leu Leu
            485                 490                 495

Val Lys Leu Asn Arg Glu Asp Leu Leu Arg Lys Gln Arg Thr Phe Asp
        500                 505                 510

Asn Gly Ser Ile Pro His Gln Ile His Leu Gly Glu Leu His Ala Ile
    515                 520                 525

Leu Arg Arg Gln Glu Asp Phe Tyr Pro Phe Leu Lys Asp Asn Arg Glu
530                 535                 540

Lys Ile Glu Lys Ile Leu Thr Phe Arg Ile Pro Tyr Tyr Val Gly Pro
545                 550                 555                 560

Leu Ala Arg Gly Asn Ser Arg Phe Ala Trp Met Thr Arg Lys Ser Glu
            565                 570                 575

Glu Thr Ile Thr Pro Trp Asn Phe Glu Glu Val Val Asp Lys Gly Ala
        580                 585                 590

Ser Ala Gln Ser Phe Ile Glu Arg Met Thr Asn Phe Asp Lys Asn Leu
    595                 600                 605

Pro Asn Glu Lys Val Leu Pro Lys His Ser Leu Leu Tyr Glu Tyr Phe
610                 615                 620

-continued

Thr Val Tyr Asn Glu Leu Thr Lys Val Lys Tyr Val Thr Glu Gly Met
625                 630                 635                 640

Arg Lys Pro Ala Phe Leu Ser Gly Glu Gln Lys Lys Ala Ile Val Asp
            645                 650                 655

Leu Leu Phe Lys Thr Asn Arg Lys Val Thr Val Lys Gln Leu Lys Glu
            660                 665                 670

Asp Tyr Phe Lys Lys Ile Glu Cys Phe Asp Ser Val Glu Ile Ser Gly
            675                 680                 685

Val Glu Asp Arg Phe Asn Ala Ser Leu Gly Thr Tyr His Asp Leu Leu
        690                 695                 700

Lys Ile Ile Lys Asp Lys Asp Phe Leu Asp Asn Glu Glu Asn Glu Asp
705                 710                 715                 720

Ile Leu Glu Asp Ile Val Leu Thr Leu Thr Leu Phe Glu Asp Arg Glu
                725                 730                 735

Met Ile Glu Glu Arg Leu Lys Thr Tyr Ala His Leu Phe Asp Asp Lys
            740                 745                 750

Val Met Lys Gln Leu Lys Arg Arg Arg Tyr Thr Gly Trp Gly Arg Leu
            755                 760                 765

Ser Arg Lys Leu Ile Asn Gly Ile Arg Asp Lys Gln Ser Gly Lys Thr
770                 775                 780

Ile Leu Asp Phe Leu Lys Ser Asp Gly Phe Ala Asn Arg Asn Phe Met
785                 790                 795                 800

Gln Leu Ile His Asp Asp Ser Leu Thr Phe Lys Glu Asp Ile Gln Lys
            805                 810                 815

Ala Gln Val Ser Gly Gln Gly Asp Ser Leu His Glu His Ile Ala Asn
            820                 825                 830

Leu Ala Gly Ser Pro Ala Ile Lys Lys Gly Ile Leu Gln Thr Val Lys
            835                 840                 845

Val Val Asp Glu Leu Val Lys Val Met Gly Arg His Lys Pro Glu Asn
850                 855                 860

Ile Val Ile Glu Met Ala Arg Glu Asn Gln Thr Thr Gln Lys Gly Gln
865                 870                 875                 880

Lys Asn Ser Arg Glu Arg Met Lys Arg Ile Glu Glu Gly Ile Lys Glu
            885                 890                 895

Leu Gly Ser Gln Ile Leu Lys Glu His Pro Val Glu Asn Thr Gln Leu
            900                 905                 910

Gln Asn Glu Lys Leu Tyr Leu Tyr Tyr Leu Gln Asn Gly Arg Asp Met
            915                 920                 925

Tyr Val Asp Gln Glu Leu Asp Ile Asn Arg Leu Ser Asp Tyr Asp Val
        930                 935                 940

Asp His Ile Val Pro Gln Ser Phe Leu Lys Asp Asp Ser Ile Asp Asn
945                 950                 955                 960

Lys Val Leu Thr Arg Ser Asp Lys Asn Arg Gly Lys Ser Asp Asn Val
                965                 970                 975

Pro Ser Glu Glu Val Val Lys Lys Met Lys Asn Tyr Trp Arg Gln Leu
            980                 985                 990

Leu Asn Ala Lys Leu Ile Thr Gln Arg Lys Phe Asp Asn Leu Thr Lys
            995                 1000                1005

Ala Glu Arg Gly Gly Leu Ser Glu Leu Asp Lys Ala Gly Phe Ile
        1010                1015                1020

Lys Arg Gln Leu Val Glu Thr Arg Gln Ile Thr Lys His Val Ala
    1025                1030                1035

Gln Ile Leu Asp Ser Arg Met Asn Thr Lys Tyr Asp Glu Asn Asp

```
                1040                1045                1050
Lys Leu Ile Arg Glu Val Lys Val Ile Thr Leu Lys Ser Lys Leu
    1055                1060                1065

Val Ser Asp Phe Arg Lys Asp Phe Gln Phe Tyr Lys Val Arg Glu
    1070                1075                1080

Ile Asn Asn Tyr His His Ala His Asp Ala Tyr Leu Asn Ala Val
    1085                1090                1095

Val Gly Thr Ala Leu Ile Lys Lys Tyr Pro Lys Leu Glu Ser Glu
    1100                1105                1110

Phe Val Tyr Gly Asp Tyr Lys Val Tyr Asp Val Arg Lys Met Ile
    1115                1120                1125

Ala Lys Ser Glu Gln Glu Ile Gly Lys Ala Thr Ala Lys Tyr Phe
    1130                1135                1140

Phe Tyr Ser Asn Ile Met Asn Phe Phe Lys Thr Glu Ile Thr Leu
    1145                1150                1155

Ala Asn Gly Glu Ile Arg Lys Arg Pro Leu Ile Glu Thr Asn Gly
    1160                1165                1170

Glu Thr Gly Glu Ile Val Trp Asp Lys Gly Arg Asp Phe Ala Thr
    1175                1180                1185

Val Arg Lys Val Leu Ser Met Pro Gln Val Asn Ile Val Lys Lys
    1190                1195                1200

Thr Glu Val Gln Thr Gly Gly Phe Ser Lys Glu Ser Ile Leu Pro
    1205                1210                1215

Lys Arg Asn Ser Asp Lys Leu Ile Ala Arg Lys Lys Asp Trp Asp
    1220                1225                1230

Pro Lys Lys Tyr Gly Gly Phe Asp Ser Pro Thr Val Ala Tyr Ser
    1235                1240                1245

Val Leu Val Val Ala Lys Val Glu Lys Gly Lys Ser Lys Lys Leu
    1250                1255                1260

Lys Ser Val Lys Glu Leu Leu Gly Ile Thr Ile Met Glu Arg Ser
    1265                1270                1275

Ser Phe Glu Lys Asn Pro Ile Asp Phe Leu Glu Ala Lys Gly Tyr
    1280                1285                1290

Lys Glu Val Lys Lys Asp Leu Ile Ile Lys Leu Pro Lys Tyr Ser
    1295                1300                1305

Leu Phe Glu Leu Glu Asn Gly Arg Lys Arg Met Leu Ala Ser Ala
    1310                1315                1320

Gly Glu Leu Gln Lys Gly Asn Glu Leu Ala Leu Pro Ser Lys Tyr
    1325                1330                1335

Val Asn Phe Leu Tyr Leu Ala Ser His Tyr Glu Lys Leu Lys Gly
    1340                1345                1350

Ser Pro Glu Asp Asn Glu Gln Lys Gln Leu Phe Val Glu Gln His
    1355                1360                1365

Lys His Tyr Leu Asp Glu Ile Ile Glu Gln Ile Ser Glu Phe Ser
    1370                1375                1380

Lys Arg Val Ile Leu Ala Asp Ala Asn Leu Asp Lys Val Leu Ser
    1385                1390                1395

Ala Tyr Asn Lys His Arg Asp Lys Pro Ile Arg Glu Gln Ala Glu
    1400                1405                1410

Asn Ile Ile His Leu Phe Thr Leu Thr Asn Leu Gly Ala Pro Ala
    1415                1420                1425

Ala Phe Lys Tyr Phe Asp Thr Thr Ile Asp Arg Lys Arg Tyr Thr
    1430                1435                1440
```

```
Ser Thr Lys Glu Val Leu Asp Ala Thr Leu Ile His Gln Ser Ile
    1445            1450                1455
Thr Gly Leu Tyr Glu Thr Arg Ile Asp Leu Ser Gln Leu Gly Gly
        1460            1465            1470
Asp Ser Arg Ala Asp Pro Lys Lys Lys Arg Lys Val Arg
    1475            1480            1485
```

<210> SEQ ID NO 23
<211> LENGTH: 1504
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

```
Met Asn Pro Ser Met Lys Gln Lys Gln Glu Glu Ile Lys Glu Asn Ile
1               5                   10                  15
Lys Asn Ser Ser Val Pro Arg Arg Thr Leu Lys Met Ile Gln Pro Ser
            20                  25                  30
Ala Ser Gly Ser Leu Val Gly Arg Glu Asn Glu Leu Ser Ala Gly Leu
        35                  40                  45
Ser Lys Arg Lys His Arg Asn Asp His Leu Thr Ser Thr Thr Ser Ser
    50                  55                  60
Pro Gly Val Ile Val Pro Glu Ser Ser Glu Asn Lys Asn Leu Gly Gly
65                  70                  75                  80
Val Thr Gln Glu Ser Phe Asp Leu Met Ile Lys Glu Asn Pro Ser Ser
                85                  90                  95
Gln Tyr Trp Lys Glu Val Ala Glu Lys Arg Arg Lys Ala Leu Gly Gly
            100                 105                 110
Gly Gly Ser Gly Gly Gly Ser Gly Gly Gly Ser Asp Lys Lys
        115                 120                 125
Tyr Ser Ile Gly Leu Asp Ile Gly Thr Asn Ser Val Gly Trp Ala Val
    130                 135                 140
Ile Thr Asp Glu Tyr Lys Val Pro Ser Lys Lys Phe Lys Val Leu Gly
145                 150                 155                 160
Asn Thr Asp Arg His Ser Ile Lys Lys Asn Leu Ile Gly Ala Leu Leu
                165                 170                 175
Phe Asp Ser Gly Glu Thr Ala Glu Ala Thr Arg Leu Lys Arg Thr Ala
            180                 185                 190
Arg Arg Arg Tyr Thr Arg Arg Lys Asn Arg Ile Cys Tyr Leu Gln Glu
        195                 200                 205
Ile Phe Ser Asn Glu Met Ala Lys Val Asp Asp Ser Phe Phe His Arg
    210                 215                 220
Leu Glu Glu Ser Phe Leu Val Glu Glu Asp Lys Lys His Glu Arg His
225                 230                 235                 240
Pro Ile Phe Gly Asn Ile Val Asp Glu Val Ala Tyr His Glu Lys Tyr
                245                 250                 255
Pro Thr Ile Tyr His Leu Arg Lys Lys Leu Val Asp Ser Thr Asp Lys
            260                 265                 270
Ala Asp Leu Arg Leu Ile Tyr Leu Ala Leu Ala His Met Ile Lys Phe
        275                 280                 285
Arg Gly His Phe Leu Ile Glu Gly Asp Leu Asn Pro Asp Asn Ser Asp
    290                 295                 300
Val Asp Lys Leu Phe Ile Gln Leu Val Gln Thr Tyr Asn Gln Leu Phe
```

```
                305                 310                 315                 320
        Glu Glu Asn Pro Ile Asn Ala Ser Gly Val Asp Ala Lys Ala Ile Leu
                        325                 330                 335

Ser Ala Arg Leu Ser Lys Ser Arg Arg Leu Glu Asn Leu Ile Ala Gln
                        340                 345                 350

Leu Pro Gly Glu Lys Lys Asn Gly Leu Phe Gly Asn Leu Ile Ala Leu
                        355                 360                 365

Ser Leu Gly Leu Thr Pro Asn Phe Lys Ser Asn Phe Asp Leu Ala Glu
                370                 375                 380

Asp Ala Lys Leu Gln Leu Ser Lys Asp Thr Tyr Asp Asp Leu Asp
        385                 390                 395                 400

Asn Leu Leu Ala Gln Ile Gly Asp Gln Tyr Ala Asp Leu Phe Leu Ala
                        405                 410                 415

Ala Lys Asn Leu Ser Asp Ala Ile Leu Leu Ser Asp Ile Leu Arg Val
                        420                 425                 430

Asn Thr Glu Ile Thr Lys Ala Pro Leu Ser Ala Ser Met Ile Lys Arg
                        435                 440                 445

Tyr Asp Glu His His Gln Asp Leu Thr Leu Leu Lys Ala Leu Val Arg
        450                 455                 460

Gln Gln Leu Pro Glu Lys Tyr Lys Glu Ile Phe Phe Asp Gln Ser Lys
        465                 470                 475                 480

Asn Gly Tyr Ala Gly Tyr Ile Asp Gly Gly Ala Ser Gln Glu Glu Phe
                        485                 490                 495

Tyr Lys Phe Ile Lys Pro Ile Leu Glu Lys Met Asp Gly Thr Glu Glu
                        500                 505                 510

Leu Leu Val Lys Leu Asn Arg Glu Asp Leu Leu Arg Lys Gln Arg Thr
                        515                 520                 525

Phe Asp Asn Gly Ser Ile Pro His Gln Ile His Leu Gly Glu Leu His
                        530                 535                 540

Ala Ile Leu Arg Arg Gln Glu Asp Phe Tyr Pro Phe Leu Lys Asp Asn
        545                 550                 555                 560

Arg Glu Lys Ile Glu Lys Ile Leu Thr Phe Arg Ile Pro Tyr Tyr Val
                        565                 570                 575

Gly Pro Leu Ala Arg Gly Asn Ser Arg Phe Ala Trp Met Thr Arg Lys
                        580                 585                 590

Ser Glu Glu Thr Ile Thr Pro Trp Asn Phe Glu Glu Val Val Asp Lys
                        595                 600                 605

Gly Ala Ser Ala Gln Ser Phe Ile Glu Arg Met Thr Asn Phe Asp Lys
                        610                 615                 620

Asn Leu Pro Asn Glu Lys Val Leu Pro Lys His Ser Leu Leu Tyr Glu
        625                 630                 635                 640

Tyr Phe Thr Val Tyr Asn Glu Leu Thr Lys Val Lys Tyr Val Thr Glu
                        645                 650                 655

Gly Met Arg Lys Pro Ala Phe Leu Ser Gly Glu Gln Lys Lys Ala Ile
                        660                 665                 670

Val Asp Leu Leu Phe Lys Thr Asn Arg Lys Val Thr Val Lys Gln Leu
                        675                 680                 685

Lys Glu Asp Tyr Phe Lys Lys Ile Glu Cys Phe Asp Ser Val Glu Ile
        690                 695                 700

Ser Gly Val Glu Asp Arg Phe Asn Ala Ser Leu Gly Thr Tyr His Asp
        705                 710                 715                 720

Leu Leu Lys Ile Ile Lys Asp Lys Asp Phe Leu Asp Asn Glu Glu Asn
                        725                 730                 735
```

```
Glu Asp Ile Leu Glu Asp Ile Val Leu Thr Leu Thr Leu Phe Glu Asp
            740                 745                 750

Arg Glu Met Ile Glu Arg Leu Lys Thr Tyr Ala His Leu Phe Asp
            755                 760                 765

Asp Lys Val Met Lys Gln Leu Lys Arg Arg Tyr Thr Gly Trp Gly
    770                 775                 780

Arg Leu Ser Arg Lys Leu Ile Asn Gly Ile Arg Asp Lys Gln Ser Gly
785                 790                 795                 800

Lys Thr Ile Leu Asp Phe Leu Lys Ser Asp Gly Phe Ala Asn Arg Asn
                805                 810                 815

Phe Met Gln Leu Ile His Asp Asp Ser Leu Thr Phe Lys Glu Asp Ile
                820                 825                 830

Gln Lys Ala Gln Val Ser Gly Gln Gly Asp Ser Leu His Glu His Ile
            835                 840                 845

Ala Asn Leu Ala Gly Ser Pro Ala Ile Lys Lys Gly Ile Leu Gln Thr
850                 855                 860

Val Lys Val Val Asp Glu Leu Val Lys Val Met Gly Arg His Lys Pro
865                 870                 875                 880

Glu Asn Ile Val Ile Glu Met Ala Arg Glu Asn Gln Thr Thr Gln Lys
                885                 890                 895

Gly Gln Lys Asn Ser Arg Glu Arg Met Lys Arg Ile Glu Glu Gly Ile
            900                 905                 910

Lys Glu Leu Gly Ser Gln Ile Leu Lys Glu His Pro Val Glu Asn Thr
            915                 920                 925

Gln Leu Gln Asn Glu Lys Leu Tyr Leu Tyr Tyr Leu Gln Asn Gly Arg
            930                 935                 940

Asp Met Tyr Val Asp Gln Glu Leu Asp Ile Asn Arg Leu Ser Asp Tyr
945                 950                 955                 960

Asp Val Asp His Ile Val Pro Gln Ser Phe Leu Lys Asp Asp Ser Ile
                965                 970                 975

Asp Asn Lys Val Leu Thr Arg Ser Asp Lys Asn Arg Gly Lys Ser Asp
                980                 985                 990

Asn Val Pro Ser Glu Glu Val Val Lys Lys Met Lys Asn Tyr Trp Arg
            995                 1000                1005

Gln Leu Leu Asn Ala Lys Leu Ile Thr Gln Arg Lys Phe Asp Asn
    1010                1015                1020

Leu Thr Lys Ala Glu Arg Gly Gly Leu Ser Glu Leu Asp Lys Ala
    1025                1030                1035

Gly Phe Ile Lys Arg Gln Leu Val Glu Thr Arg Gln Ile Thr Lys
    1040                1045                1050

His Val Ala Gln Ile Leu Asp Ser Arg Met Asn Thr Lys Tyr Asp
    1055                1060                1065

Glu Asn Asp Lys Leu Ile Arg Glu Val Lys Val Ile Thr Leu Lys
    1070                1075                1080

Ser Lys Leu Val Ser Asp Phe Arg Lys Asp Phe Gln Phe Tyr Lys
    1085                1090                1095

Val Arg Glu Ile Asn Asn Tyr His His Ala His Asp Ala Tyr Leu
    1100                1105                1110

Asn Ala Val Val Gly Thr Ala Leu Ile Lys Lys Tyr Pro Lys Leu
    1115                1120                1125

Glu Ser Glu Phe Val Tyr Gly Asp Tyr Lys Val Tyr Asp Val Arg
    1130                1135                1140
```

| | | | | | | | | | | |
|---|---|---|---|---|---|---|---|---|---|---|
|Lys|Met|Ile|Ala|Lys|Ser|Glu|Gln|Glu|Ile|Gly|Lys|Ala|Thr|Ala|
| |1145| | | |1150| | | |1155| | | | | |
|Lys|Tyr|Phe|Phe|Tyr|Ser|Asn|Ile|Met|Asn|Phe|Phe|Lys|Thr|Glu|
| |1160| | | |1165| | | |1170| | | | | |
|Ile|Thr|Leu|Ala|Asn|Gly|Glu|Ile|Arg|Lys|Arg|Pro|Leu|Ile|Glu|
| |1175| | | |1180| | | |1185| | | | | |
|Thr|Asn|Gly|Glu|Thr|Gly|Glu|Ile|Val|Trp|Asp|Lys|Gly|Arg|Asp|
| |1190| | | |1195| | | |1200| | | | | |
|Phe|Ala|Thr|Val|Arg|Lys|Val|Leu|Ser|Met|Pro|Gln|Val|Asn|Ile|
| |1205| | | |1210| | | |1215| | | | | |
|Val|Lys|Lys|Thr|Glu|Val|Gln|Thr|Gly|Gly|Phe|Ser|Lys|Glu|Ser|
| |1220| | | |1225| | | |1230| | | | | |
|Ile|Leu|Pro|Lys|Arg|Asn|Ser|Asp|Lys|Leu|Ile|Ala|Arg|Lys|Lys|
| |1235| | | |1240| | | |1245| | | | | |
|Asp|Trp|Asp|Pro|Lys|Lys|Tyr|Gly|Gly|Phe|Asp|Ser|Pro|Thr|Val|
| |1250| | | |1255| | | |1260| | | | | |
|Ala|Tyr|Ser|Val|Leu|Val|Val|Ala|Lys|Val|Glu|Lys|Gly|Lys|Ser|
| |1265| | | |1270| | | |1275| | | | | |
|Lys|Lys|Leu|Lys|Ser|Val|Lys|Glu|Leu|Leu|Gly|Ile|Thr|Ile|Met|
| |1280| | | |1285| | | |1290| | | | | |
|Glu|Arg|Ser|Ser|Phe|Glu|Lys|Asn|Pro|Ile|Asp|Phe|Leu|Glu|Ala|
| |1295| | | |1300| | | |1305| | | | | |
|Lys|Gly|Tyr|Lys|Glu|Val|Lys|Lys|Asp|Leu|Ile|Ile|Lys|Leu|Pro|
| |1310| | | |1315| | | |1320| | | | | |
|Lys|Tyr|Ser|Leu|Phe|Glu|Leu|Glu|Asn|Gly|Arg|Lys|Arg|Met|Leu|
| |1325| | | |1330| | | |1335| | | | | |
|Ala|Ser|Ala|Gly|Glu|Leu|Gln|Lys|Gly|Asn|Glu|Leu|Ala|Leu|Pro|
| |1340| | | |1345| | | |1350| | | | | |
|Ser|Lys|Tyr|Val|Asn|Phe|Leu|Tyr|Leu|Ala|Ser|His|Tyr|Glu|Lys|
| |1355| | | |1360| | | |1365| | | | | |
|Leu|Lys|Gly|Ser|Pro|Glu|Asp|Asn|Glu|Gln|Lys|Gln|Leu|Phe|Val|
| |1370| | | |1375| | | |1380| | | | | |
|Glu|Gln|His|Lys|His|Tyr|Leu|Asp|Glu|Ile|Ile|Glu|Gln|Ile|Ser|
| |1385| | | |1390| | | |1395| | | | | |
|Glu|Phe|Ser|Lys|Arg|Val|Ile|Leu|Ala|Asp|Ala|Asn|Leu|Asp|Lys|
| |1400| | | |1405| | | |1410| | | | | |
|Val|Leu|Ser|Ala|Tyr|Asn|Lys|His|Arg|Asp|Lys|Pro|Ile|Arg|Glu|
| |1415| | | |1420| | | |1425| | | | | |
|Gln|Ala|Glu|Asn|Ile|Ile|His|Leu|Phe|Thr|Leu|Thr|Asn|Leu|Gly|
| |1430| | | |1435| | | |1440| | | | | |
|Ala|Pro|Ala|Ala|Phe|Lys|Tyr|Phe|Asp|Thr|Thr|Ile|Asp|Arg|Lys|
| |1445| | | |1450| | | |1455| | | | | |
|Arg|Tyr|Thr|Ser|Thr|Lys|Glu|Val|Leu|Asp|Ala|Thr|Leu|Ile|His|
| |1460| | | |1465| | | |1470| | | | | |
|Gln|Ser|Ile|Thr|Gly|Leu|Tyr|Glu|Thr|Arg|Ile|Asp|Leu|Ser|Gln|
| |1475| | | |1480| | | |1485| | | | | |
|Leu|Gly|Gly|Asp|Ser|Arg|Ala|Asp|Pro|Lys|Lys|Lys|Arg|Lys|Val|
| |1490| | | |1495| | | |1500| | | | | |
|Arg| | | | | | | | | | | | | | |

```
<210> SEQ ID NO 24
<211> LENGTH: 4458
<212> TYPE: DNA
<213> ORGANISM: Artificial Sequence
```

<220> FEATURE:
<223> OTHER INFORMATION: Description of Artificial Sequence: Synthetic polynucleotide

<400> SEQUENCE: 24

| | | | | | |
|---|---|---|---|---|---|
| atggacaaga | agtactccat | tgggctcgat | atcggcacaa | acagcgtcgg ctgggccgtc | 60 |
| attacggacg | agtacaaggt | gccgagcaaa | aaattcaaag | ttctgggcaa taccgatcgc | 120 |
| cacagcataa | agaagaacct | cattggcgcc | ctcctgttcg | actccgggga gacggccgaa | 180 |
| gccacgcggc | tcaaaagaac | agcacggcgc | agatatcccc | gcagaaagaa tcggatctgc | 240 |
| tacctgcagg | agatctttag | taatgagatg | gctaaggtgg | atgactcttt cttccatagg | 300 |
| ctggaggagt | ccttttttggt | ggaggaggat | aaaaagcacg | agcgccaccc aatctttggc | 360 |
| aatatcgtgg | acgaggtggc | gtaccatgaa | agtacccaa | ccatatatca tctgaggaag | 420 |
| aagcttgtag | acagtactga | taaggctgac | ttgcggttga | tctatctcgc gctggcgcat | 480 |
| atgatcaaat | tcggggaca | cttcctcatc | gaggggacc | tgaacccaga caacagcgat | 540 |
| gtcgacaaac | tctttatcca | actggttcag | acttacaatc | agcttttcga agagaacccg | 600 |
| atcaacgcat | ccggagttga | cgccaaagca | atcctgagcg | ctaggctgtc caaatcccgg | 660 |
| cggctcgaaa | acctcatcgc | acagctccct | ggggagaaga | gaacggcct gtttggtaat | 720 |
| cttatcgccc | tgtcactcgg | gctgaccccc | aactttaaat | ctaacttcga cctggccgaa | 780 |
| gatgccaagc | ttcaactgag | caaagacacc | tacgatgatg | atctcgacaa tctgctggcc | 840 |
| cagatcggcg | accagtacgc | agacctttttt | ttggcggcaa | agaacctgtc agacgccatt | 900 |
| ctgctgagtg | atattctgcg | agtgaacacg | gagatcacca | agctccgct gagcgctagt | 960 |
| atgatcaagc | gctatgatga | gcaccaccaa | gacttgactt | tgctgaaggc ccttgtcaga | 1020 |
| cagcaactgc | ctgagaagta | caaggaaatt | ttcttcgatc | agtctaaaaa tggctacgcc | 1080 |
| ggatacattg | acggcggagc | aagccaggag | gaattttaca | aatttattaa gcccatcttg | 1140 |
| gaaaaaatgg | acggcaccga | ggagctgctg | gtaaagctta | cagagaaga tctgttgcgc | 1200 |
| aaacagcgca | ctttcgacaa | tggaagcatc | ccccaccaga | ttcacctggg cgaactgcac | 1260 |
| gctatcctca | gcggcaaga | ggatttctac | ccctttttga | aagataacag ggaaaagatt | 1320 |
| gagaaaatcc | tcacatttcg | gatacccctac | tatgtaggcc | ccctcgcccg gggaaattcc | 1380 |
| agattcgcgt | ggatgactcg | caaatcagaa | gagaccatca | ctcccctggaa cttcgaggaa | 1440 |
| gtcgtggata | aggggggcctc | tgcccagtcc | ttcatcgaaa | ggatgactaa ctttgataaa | 1500 |
| aatctgccta | acgaaaaggt | gcttcctaaa | cactctctgc | tgtacgagta cttcacagtt | 1560 |
| tataacgagc | tcaccaaggt | caaatacgtc | acagaaggga | tgagaaagcc agcattcctg | 1620 |
| tctggagagc | agaagaaagc | tatcgtggac | ctcctcttca | agacgaaccg gaaagttacc | 1680 |
| gtgaaacagc | tcaaagaaga | ctatttcaaa | aagattgaat | gtttcgactc tgttgaaatc | 1740 |
| agcggagtgg | aggatcgctt | caacgcatcc | ctgggaacgt | atcacgatct cctgaaaatc | 1800 |
| attaaagaca | aggacttcct | ggacaatgag | gagaacgagg | acattcttga ggacattgtc | 1860 |
| ctcacccctta | cgttgttttga | agataggag | atgattgaag | aacgcttgaa aacttacgct | 1920 |
| catctcttcg | acgacaaagt | catgaaacag | ctcaagaggc | gccgatatac aggatggggg | 1980 |
| cggctgtcaa | gaaaactgat | caatgggatc | cgagacaagc | agagtggaaa gacaatcctg | 2040 |
| gattttctta | agtccgatgg | atttgccaac | cggaacttca | tgcagttgat ccatgatgac | 2100 |
| tctctcacct | ttaaggagga | catccagaaa | gcacaagttt | ctggccaggg ggacagtctt | 2160 |
| cacgagcaca | tcgctaatct | tgcaggtagc | ccagctatca | aaaagggaat actgcagacc | 2220 |

```
gttaaggtcg tggatgaact cgtcaaagta atgggaaggc ataagcccga gaatatcgtt    2280
atcgagatgg cccgagagaa ccaaactacc cagaagggac agaagaacag tagggaaagg    2340
atgaagagga ttgaagaggg tataaaagaa ctggggtccc aaatccttaa ggaacaccca    2400
gttgaaaaca cccagcttca gaatgagaag ctctacctgt actacctgca gaacggcagg    2460
gacatgtacg tggatcagga actggacatc aatcggctct ccgactacga cgtggatcat    2520
atcgtgcccc agtcttttct caaagatgat tctattgata ataaagtgtt gacaagatcc    2580
gataaaaata gagggaagag tgataacgtc ccctcagaag aagttgtcaa gaaaatgaaa    2640
aattattggc ggcagctgct gaacgccaaa ctgatcacac aacggaagtt cgataatctg    2700
actaaggctg aacgaggtgg cctgtctgag ttggataaag ccggcttcat caaaaggcag    2760
cttgttgaga cacgccagat caccaagcac gtggcccaaa ttctcgattc acgcatgaac    2820
accaagtacg atgaaaatga caaactgatt cgagaggtga agttattac tctgaagtct    2880 aagctggtct cagatttcag aaaggacttt cagttttata aggtgagaga gatcaacaat    2940
taccaccatg cgcatgatgc ctacctgaat gcagtggtag gcactgcact tatcaaaaaa    3000
tatcccaagc ttgaatctga atttgtttac ggagactata agtgtacga tgttaggaaa    3060 atgatcgcaa agtctgagca ggaaataggc aaggccaccg ctaagtactt cttttacagc    3120
aatattatga attttttcaa gaccgagatt acactggcca atggagagat tcggaagcga    3180
ccacttatcg aaacaaacgg agaaacagga gaaatcgtgt gggacaaggg tagggatttc    3240
gcgacagtcc ggaaggtcct gtccatgccg caggtgaaca tcgttaaaaa gaccgaagta    3300
cagaccggag gcttctccaa ggaaagtatc ctcccgaaaa ggaacagcga caagctgatc    3360
gcacgcaaaa aagattggga ccccaagaaa tacggcggat cgattctcc tacagtcgct    3420 tacagtgtac tggttgtggc caaagtggag aaagggaagt ctaaaaaact caaaagcgtc    3480
aaggaactgc tgggcatcac aatcatggag cgatcaagct cgaaaaaaaa ccccatcgac    3540
tttctcgagg cgaaaggata taagaggtc aaaaaagacc tcatcattaa gcttcccaag    3600
tactctctct ttgagcttga aaacggccgg aaacgaatgc tcgctagtgc gggcgagctg    3660
cagaaaggta acgagctggc actgcccttct aaatacgtta atttcttgta tctggccagc    3720
cactatgaaa agctcaaagg gtctcccgaa gataatgagc agaagcagct gttcgtggaa    3780
caacacaaac actaccttga tgagatcatc gagcaaataa gcgaattctc caaaagagtg    3840
atcctcgccg acgctaacct cgataaggtg ctttctgctt acaataagca cagggataag    3900
cccatcaggg agcaggcaga aaacattatc cacttgttta ctctgaccaa cttgggcgcg    3960
cctgcagcct tcaagtactt cgacaccacc atagacagaa agcggtacac ctctacaaag    4020
gaggtcctgg acgccacact gattcatcag tcaattacgg ggctctatga aacaagaatc    4080
gacctctctc agctcggtgg agacagcagg gctgacccca agaagaagag gaaggtgagg    4140
ggaggcggag atctggcgg aggcggaagt ggcggagggg cagcccatc tcctgccaga    4200 cctgctctga gagcccctgc ctctgccaca agcggcagca gaaagagagc cagacctcct    4260
gccgcccctg gcagagatca ggctagacct ccagctcggc ggagactgag actgagcgtg    4320
gacgaggtgt ccagccctag cacacctgag gcccctgata tccccgcctg tcctagcccc    4380
ggccagaaga tcaagaagtc caccctgcc gccggacagc ctcctcatct gacatctgcc    4440
caggaccagg acaccatc                                                  4458

<210> SEQ ID NO 25
```

```
<211> LENGTH: 4515
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25
```

| | | | | |
|---|---|---|---|---|
| atggacaaga | agtactccat | tgggctcgat | atcggcacaa | acagcgtcgg | ctgggccgtc | 60 |
| attacggacg | agtacaaggt | gccgagcaaa | aaattcaaag | ttctgggcaa | taccgatcgc | 120 |
| cacagcataa | agaagaacct | cattggcgcc | ctcctgttcg | actccgggga | gacggccgaa | 180 |
| gccacgcggc | tcaaaagaac | agcacggcgc | agatatatccc | gcagaaagaa | tcggatctgc | 240 |
| tacctgcagg | agatctttag | taatgagatg | gctaaggtgg | atgactcttt | cttccatagg | 300 |
| ctggaggagt | cctttttggt | ggaggaggat | aaaaagcacg | agcgccaccc | aatctttggc | 360 |
| aatatcgtgg | acgaggtggc | gtaccatgaa | aagtacccaa | ccatatatca | tctgaggaag | 420 |
| aagcttgtag | acagtactga | taaggctgac | ttgcggttga | tctatctcgc | gctggcgcat | 480 |
| atgatcaaat | tcggggaca | cttcctcatc | gagggggacc | tgaacccaga | caacagcgat | 540 |
| gtcgacaaac | tctttatcca | actggttcag | acttacaatc | agcttttcga | agagaacccg | 600 |
| atcaacgcat | ccggagttga | cgccaaagca | atcctgagcg | ctaggctgtc | caaatcccgg | 660 |
| cggctcgaaa | acctcatcgc | acagctccct | ggggagaaga | agaacggcct | gtttggtaat | 720 |
| cttatcgccc | tgtcactcgg | gctgacccc | aactttaaat | ctaacttcga | cctggccgaa | 780 |
| gatgccaagc | ttcaactgag | caaagacacc | tacgatgatg | atctcgacaa | tctgctggcc | 840 |
| cagatcggcg | accagtacgc | agacctttt | ttggcggcaa | agaacctgtc | agacgccatt | 900 |
| ctgctgagtg | atattctgcg | agtgaacacg | gagatcacca | aagctccgct | gagcgctagt | 960 |
| atgatcaagc | gctatgatga | gcaccaccaa | gacttgactt | tgctgaaggc | ccttgtcaga | 1020 |
| cagcaactgc | ctgagaagta | caaggaaatt | ttcttcgatc | agtctaaaaa | tggctacgcc | 1080 |
| ggatacattg | acggcggagc | aagccaggag | gaattttaca | aatttattaa | gcccatcttg | 1140 |
| gaaaaaatgg | acggcaccga | ggagctgctg | gtaaagctta | acagagaaga | tctgttgcgc | 1200 |
| aaacagcgca | ctttcgacaa | tggaagcatc | ccccaccaga | ttcacctggg | cgaactgcac | 1260 |
| gctatcctca | ggcggcaaga | ggatttctac | ccctttttga | agataacag | ggaaaagatt | 1320 |
| gagaaaatcc | tcacatttcg | ataccctac | tatgtaggcc | ccctcgcccg | ggaaaattcc | 1380 |
| agattcgcgt | ggatgactcg | caaatcagaa | gagaccatca | ctccctggaa | cttcgaggaa | 1440 |
| gtcgtggata | aggggggcctc | tgcccagtcc | ttcatcgaaa | ggatgactaa | ctttgataaa | 1500 |
| aatctgccta | acgaaaaggt | gcttcctaaa | cactctctgc | tgtacgagta | cttcacagtt | 1560 |
| tataacgagc | tcaccaaggt | caaatacgtc | acagaaggga | tgagaaagcc | agcattcctg | 1620 |
| tctggagagc | agaagaaagc | tatcgtggac | ctcctcttca | agacgaaccg | gaaagttacc | 1680 |
| gtgaaacagc | tcaaagaaga | ctatttcaaa | aagattgaat | gtttcgactc | tgttgaaatc | 1740 |
| agcggagtgg | aggatcgctt | caacgcatcc | ctgggaacgt | atcacgatct | cctgaaaatc | 1800 |
| attaaagaca | aggacttcct | ggacaatgag | gagaacgagg | acattcttga | ggacattgtc | 1860 |
| ctcacccta | cgttgtttga | agataggag | atgattgaag | aacgcttgaa | aacttacgct | 1920 |
| catctcttcg | acgacaaagt | catgaaacag | ctcaagaggc | gccgatatac | aggatggggg | 1980 |
| cggctgtcaa | gaaaactgat | caatgggatc | cgagacaagc | agagtggaaa | gacaatcctg | 2040 |
| gatttttctta | agtccgatgg | atttgccaac | cggaacttca | tgcagttgat | ccatgatgac | 2100 |

```
tctctcacct ttaaggagga catccagaaa gcacaagttt ctggccaggg ggacagtctt    2160
cacgagcaca tcgctaatct tgcaggtagc ccagctatca aaagggaat  actgcagacc    2220 gttaaggtcg tggatgaact cgtcaaagta atgggaaggc ataagcccga gaatatcgtt    2280
atcgagatgg cccgagagaa ccaaactacc cagaagggac agaagaacag tagggaaagg    2340
atgaagagga ttgaagaggg tataaaagaa ctggggtccc aaatccttaa ggaacaccca    2400
gttgaaaaca cccagcttca gaatgagaag ctctacctgt actacctgca gaacggcagg    2460
gacatgtacg tggatcagga actggacatc aatcggctct ccgactacga cgtggatcat    2520
atcgtgcccc agtctttcct caaagatgat tctattgata taaagtgtt  gacaagatcc    2580 gataaaaata gagggaagag tgataacgtc ccctcagaag aagttgtcaa gaaaatgaaa    2640
aattattggc ggcagctgct gaacgccaaa ctgatcacac aacggaagtt cgataatctg    2700
actaaggctg aacgaggtgg cctgtctgag ttggataaag ccggcttcat caaaaggcag    2760
cttgttgaga cacgccagat caccaagcac gtggcccaaa ttctcgattc acgcatgaac    2820
accaagtacg atgaaaatga caaactgatt cgagaggtga agttattac  tctgaagtct    2880 aagctggtct cagatttcag aaaggacttt cagttttata aggtgagaga gatcaacaat    2940
taccaccatg cgcatgatgc ctacctgaat gcagtggtag gcactgcact tatcaaaaaa    3000
tatcccaagc ttgaatctga atttgtttac ggagactata agtgtacga  tgttaggaaa    3060 atgatcgcaa agtctgagca ggaaataggc aaggccaccg ctaagtactt cttttacagc    3120
aatattatga attttttcaa gaccgagatt acactggcca atggagagat tcggaagcga    3180
ccacttatcg aaacaaacgg agaaacagga gaaatcgtgt gggacaaggg tagggatttc    3240
gcgacagtcc ggaaggtcct gtccatgccg caggtgaaca tcgttaaaaa gaccgaagta    3300
cagaccggag gcttctccaa ggaaagtatc ctcccgaaaa ggaacagcga caagctgatc    3360
gcacgcaaaa aagattggga ccccaagaaa tacggcggat tcgattctcc tacagtcgct    3420
tacagtgtac tggttgtggc caaagtggag aaagggaagt ctaaaaaact caaaagcgtc    3480
aaggaactgc tgggcatcac aatcatggag cgatcaagct tcgaaaaaaa ccccatcgac    3540
tttctcgagg cgaaaggata taagaggtc  aaaaagagacc tcatcattaa gcttcccaag    3600
tactctctct ttgagcttga aaacggccgg aaacgaatgc tcgctagtgc gggcgagctg    3660
cagaaaggta acgagctggc actgccctct aaatacgtta atttcttgta tctggccagc    3720
cactatgaaa agctcaaagg gtctcccgaa gataatgagc agaagcagct gttcgtggaa    3780
caacacaaac actaccttga tgagatcatc gagcaaataa gcgaattctc caaaagagtg    3840
atcctcgccg acgctaacct cgataaggtg ctttctgctt acaataagca cagggataag    3900
cccatcaggg agcaggcaga aaacattatc cacttgttta ctctgaccaa cttgggcgcg    3960
cctgcagcct tcaagtactt cgacaccacc atagacagaa agcggtacac ctctacaaag    4020
gaggtcctgg acgccacact gattcatcag tcaattacgg ggctctatga aacaagaatc    4080
gacctctctc agctcggtgg agacagcagg gctgacccca agaagaagag gaaggtgagg    4140
ggaggcggag gatctggcgg aggcggaagt ggcggagggg gcagcatgaa ccctagcatg    4200
aagcagaagc aggaagagat caaagagaac atcaagaaca gcagcgtgcc cagacggacc    4260
ctgaagatga tccagcctag cgccagcggc agcctcgtgg gcagagagaa tgaactgtct    4320
gccggcctga caagcggaa  gcacagaaac gaccacctga ccagcaccac cagcagccct    4380
ggcgtgatcg tgcctgagag cagcgagaac aagaacctgg gcggcgtgac ccaggaatcc    4440
ttcgacctga tgatcaaaga aaaccccagc agccagtatt ggaaagaggt ggccgagaag    4500
```

<210> SEQ ID NO 26
<211> LENGTH: 4458
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 26

```
cggcggaagg ccctg                                              4515 atgccatctc ctgccagacc tgctctgaga gccectgcct ctgccacaag cggcagcaga    60
aagagagcca gacctcctgc cgcccctggc agagatcagg ctagacctcc agctcggcgg   120
agactgagac tgagcgtgga cgaggtgtcc agccctagca cacctgaggc ccctgatatc   180
cccgcctgtc ctagccctgg ccagaagatc aagaagtcca ccctgccgc cggacagcct   240
cctcatctga catctgccca ggaccaggac accatcggag gcggaggatc tggcggaggc   300
ggaagtggcg gaggggcag cgacaagaag tactccattg gctcgatat cggcacaaac    360
agcgtcggct gggccgtcat tacggacgag tacaaggtgc cgagcaaaaa attcaaagtt   420
ctgggcaata ccgatcgcca cagcataaag aagaacctca ttggcgccct cctgttcgac   480
tccggggaga cggccgaagc cacgcggctc aaaagaacag cacggcgcag atatacccgc   540
agaaagaatc ggatctgcta cctgcaggag atctttagta atgagatggc taaggtggat   600
gactctttct ccataggct ggaggagtcc tttttggtgg aggaggataa aaagcacgag    660
cgccacccaa tctttggcaa tatcgtggac gaggtggcgt accatgaaaa gtacccaacc   720
atatatcatc tgaggaagaa gcttgtagac agtactgata ggctgactt gcggttgatc    780
tatctcgcgc tggcgcatat gatcaaattt cggggacact ccctcatcga ggggacctg    840
aacccagaca acagcgatgt cgacaaactc tttatccaac tggttcagac ttacaatcag    900
cttttcgaag agaacccgat caacgcatcc ggagttgacg ccaaagcaat cctgagcgct    960
aggctgtcca atcccggcg gctcgaaaac ctcatcgcac agctccctgg ggagaagaag   1020
aacggcctgt ttggtaatct tatcgccctg tcactcgggc tgacccccaa ctttaaatct   1080
aacttcgacc tggccgaaga tgccaagctt caactgagca agacaccta cgatgatgat   1140
ctcgacaatc tgctggccca gatcggcgac cagtacgcag accttttttt ggcggcaaag   1200
aacctgtcag acgccattct gctgagtgat attctgcgag tgaacacgga gatcaccaaa   1260
gctccgctga cgctagtat gatcaagcgc tatgatgagc accaccaaga cttgactttg   1320
ctgaaggccc ttgtcagaca gcaactgcct gagaagtaca aggaaatttt cttcgatcag   1380
tctaaaaatg gctacgccgg atacattgac ggcggagcaa gccaggagga attttacaaa   1440
tttattaagc ccatcttgga aaaaatggac ggcaccgagg agctgctggt aaagcttaac   1500
agagaagatc tgttgcgcaa acagcgcact ttcgacaatg gaagcatccc caccagatt   1560
cacctgggcg aactgcacgc tatcctcagg cggcaagagg atttctaccc cttttttgaaa   1620
gataacaggg aaaagattga gaaatcctc acatttcgga taccctacta tgtaggcccc   1680
ctcgcccggg gaaattccag attcgcgtgg atgactcgca atcagaaga gaccatcact   1740
ccctggaact tcgaggaagt cgtggataag ggggcctctg cccagtcctt catcgaaagg   1800
atgactaact tgataaaaaa tctgcctaac gaaaaggtgc ttcctaaaca ctctctgctg   1860
tacgagtact tcacagttta taacgagctc accaaggtca aatacgtcac agaagggatg   1920
agaaagccag cattcctgtc tggagagcag aagaaagcta tcgtggacct cctcttcaag   1980
```

```
acgaaccgga aagttaccgt gaaacagctc aaagaagact atttcaaaaa gattgaatgt    2040
ttcgactctg ttgaaatcag cggagtggag gatcgcttca acgcatccct gggaacgtat    2100
cacgatctcc tgaaaatcat taaagacaag gacttcctgg acaatgagga gaacgaggac    2160
attcttgagg acattgtcct caccttacg ttgtttgaag ataggagat gattgaagaa    2220 cgcttgaaaa cttacgctca tctcttcgac gacaaagtca tgaaacagct caagaggcgc    2280
cgatatacag gatggggcg gctgtcaaga aaactgatca atgggatccg agacaagcag    2340
agtggaaaga caatcctgga ttttcttaag tccgatggat ttgccaaccg gaacttcatg    2400
cagttgatcc atgatgactc tctcaccttt aaggaggaca tccagaaagc acaagtttct    2460 ggccagggg acagtcttca cgagcacatc gctaatcttg caggtagccc agctatcaaa    2520
aagggaatac tgcagaccgt taaggtcgtg gatgaactcg tcaaagtaat gggaaggcat    2580
aagcccgaga atatcgttat cgagatggcc cgagagaacc aaaactaccc gaagggacag    2640
aagaacagta gggaaaggat gaagaggatt gaagagggta taaaagaact ggggtcccaa    2700
atccttaagg aacacccagt tgaaaacacc cagcttcaga atgagaagct ctacctgtac    2760
tacctgcaga acggcaggga catgtacgtg atcaggaac tggacatcaa tcggctctcc    2820
gactacgacg tggatcatat cgtgccccag tcttttctca aagatgattc tattgataat    2880
aaagtgttga caagatccga taaaaataga gggaagagtg ataacgtccc ctcagaagaa    2940
gttgtcaaga aaatgaaaaa ttattggcgg cagctgctga acgccaaact gatcacacaa    3000
cggaagttcg ataatctgac taaggctgaa cgaggtggcc tgtctgagtt ggataaagcc    3060
ggcttcatca aaaggcagct tgttgagaca cgccagatca ccaagcacgt ggcccaaatt    3120
ctcgattcac gcatgaacac caagtacgat gaaaatgaca aactgattcg agaggtgaaa    3180
gttattactc tgaagtctaa gctggtctca gatttcagaa aggactttca gttttataag    3240
gtgagagaga tcaacaatta ccaccatgcg catgatgcct acctgaatgc agtggtaggc    3300
actgcactta tcaaaaaata tcccaagctt gaatctgaat ttgtttacgg agactataaa    3360
gtgtacgatg ttaggaaaat gatcgcaaag tctgagcagg aaataggcaa ggccaccgct    3420
aagtacttct tttacagcaa tattatgaat ttttcaaga ccgagattac actggccaat    3480
ggagagattc ggaagcgacc acttatcgaa acaaacggag aaacaggaga atcgtgtgg    3540 gacaagggta gggatttcgc gacagtccgg aaggtcctgt ccatgccgca ggtgaacatc    3600
gttaaaaaga ccgaagtaca gaccggaggc ttctccaagg aaagtatcct cccgaaaagg    3660
aacagcgaca agctgatcgc acgcaaaaaa gattgggacc caagaaaata cggcggattc    3720
gattctccta cagtcgctta cagtgtactg gttgtggcca agtggagaa agggaagtct    3780 aaaaactca aaagcgtcaa ggaactgctg ggcatcacaa tcatggagcg atcaagcttc    3840
gaaaaaaacc ccatcgactt tctcgaggcg aaaggatata agaggtcaa aaaagacctc    3900 atcattaagc ttcccaagta ctctctcttt gagcttgaaa acggccggaa acgaatgctc    3960
gctagtgcgg gcgagctgca gaaaggtaac gagctggcac tgccctctaa atacgttaat    4020
ttcttgtatc tggccagcca ctatgaaaag ctcaaagggt ctcccgaaga taatgagcag    4080
aagcagctgt tcgtggaaca acacaaacac tacctgatg agatcatcga gcaaataagc    4140
gaattctcca aaagagtgat cctcgccgac gctaacctcg ataaggtgct ttctgcttac    4200
aataagcaca gggataagcc catcagggag caggcagaaa acattatcca cttgtttact    4260
ctgaccaact tgggcgcgcc tgcagccttc aagtacttcg acaccaccat agacagaaag    4320
```

-continued

| | |
|---|---|
| cggtacacct ctacaaagga ggtcctggac gccacactga ttcatcagtc aattacgggg | 4380 |
| ctctatgaaa caagaatcga cctctctcag ctcggtggag acagcagggc tgaccccaag | 4440 |
| aagaagagga aggtgagg | 4458 |

<210> SEQ ID NO 27
<211> LENGTH: 4512
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27

| | |
|---|---|
| atgaacccta gcatgaagca aagcaggaa gagatcaaag agaacatcaa gaacagcagc | 60 |
| gtgcccagac ggaccctgaa gatgatccag cctagcgcca gcggcagcct cgtgggcaga | 120 |
| gagaatgaac tgtctgccgg cctgagcaag cggaagcaca gaaacgacca cctgaccagc | 180 |
| accaccagca gccctggcgt gatcgtgcct gagagcagcg agaacaagaa cctgggcggc | 240 |
| gtgacccagg aatccttcga cctgatgatc aaagaaaacc ccagcagcca gtattggaaa | 300 |
| gaggtggccg agaagcggcg gaaggccctg gaggcggag atctggcgg aggcggaagt | 360 |
| ggcggagggg gcagcgacaa gaagtactcc attgggctcg atatcggcac aaacagcgtc | 420 |
| ggctgggccg tcattacgga cgagtacaag gtgccgagca aaaaattcaa agttctgggc | 480 |
| aataccgatc gccacagcat aaagaagaac ctcattggcg ccctcctgtt cgactccggg | 540 |
| gagacggccg aagccacgcg gctcaaaaga acagcacggc gcagatatac ccgcagaaag | 600 |
| aatcggatct gctacctgca ggagatcttt agtaatgaga tggctaaggt ggatgactct | 660 |
| ttcttccata ggctggagga gtccttttg gtggaggagg ataaaaagca cgagcgccac | 720 |
| ccaatctttg caatatcgt ggacgaggtg gcgtaccatg aaaagtaccc aaccatatat | 780 |
| catctgagga gaagcttgt agacagtact gataaggctg acttgcggtt gatctatctc | 840 |
| gcgctggcgc atatgatcaa atttcgggga cacttcctca tcgagggga cctgaaccca | 900 |
| gacaacagcg atgtcgacaa actctttatc caactggttc agacttacaa tcagcttttc | 960 |
| gaagagaacc cgatcaacgc atccggagtt gacgccaaag caatcctgag cgctaggctg | 1020 |
| tccaaatccc ggcggctcga aaacctcatc gcacagctcc ctggggagaa gaagaacggc | 1080 |
| ctgtttggta tcttatcgc cctgtcactc gggctgaccc ccaactttaa atctaacttc | 1140 |
| gacctggccg aagatgccaa gcttcaactg agcaaagaca cctacgatga tgatctcgac | 1200 |
| aatctgctgg cccagatcgg cgaccagtac gcagaccttt ttttggcggc aaagaacctg | 1260 |
| tcagacgcca ttctgctgag tgatattctg cgagtgaaca cggagatcac caaagctccg | 1320 |
| ctgagcgcta gtatgatcaa gcgctatgat gagcaccacc aagacttgac tttgctgaag | 1380 |
| gcccttgtca gacagcaact gcctgagaag tacaaggaaa ttttcttcga tcagtctaaa | 1440 |
| aatggctacg ccggatacat tgacggcgga gcaagccagg aggaattta caaatttatt | 1500 |
| aagcccatct tggaaaaaat ggacggcacc gaggagctgc tggtaaagct aacagagaa | 1560 |
| gatctgttgc gcaaacagcg cacttttgac aatggaagca tcccccacca gattcacctg | 1620 |
| ggcgaactgc acgctatcct caggcggcaa gaggatttct accccttttt gaaagataac | 1680 |
| agggaaaaga ttgagaaaat cctcacattt cggataccct actatgtagg cccctcgcc | 1740 |
| cggggaaatt ccagattcgc gtggatgact cgcaaatcag aagagaccat cactccctgg | 1800 |
| aacttcgagg aagtcgtgga taagggggcc tctgcccagt ccttcatcga aaggatgact | 1860 |

```
aactttgata aaaatctgcc taacgaaaag gtgcttccta acactctct gctgtacgag    1920 tacttcacag tttataacga gctcaccaag gtcaaatacg tcacagaagg gatgagaaag    1980
ccagcattcc tgtctggaga gcagaagaaa gctatcgtgg acctcctctt caagacgaac    2040
cggaaagtta ccgtgaaaca gctcaaagaa gactatttca aaaagattga atgtttcgac    2100
tctgttgaaa tcagcggagt ggaggatcgc ttcaacgcat ccctgggaac gtatcacgat    2160
ctcctgaaaa tcattaaaga caaggacttc ctggacaatg aggagaacga ggacattctt    2220
gaggacattg tcctcaccct tacgttgttt gaagataggg agatgattga agaacgcttg    2280
aaaacttacg ctcatctctt cgacgacaaa gtcatgaaac agctcaagag cgccgatat    2340 acaggatggg ggcggctgtc aagaaaactg atcaatggga tccgagacaa gcagagtgga    2400
aagacaatcc tggattttct taagtccgat ggatttgcca accggaactt catgcagttg    2460
atccatgatg actctctcac ctttaaggag gacatccaga aagcacaagt ttctggccag    2520
ggggacagtc ttcacgagca catcgctaat cttgcaggta gcccagctat caaaaaggga    2580
atactgcaga ccgttaaggt cgtggatgaa ctcgtcaaaa taatgggaag gcataagccc    2640
gagaatatcg ttatcgagat ggcccgagag aaccaaacta cccagaaggg acagaagaac    2700
agtagggaaa ggatgaagag gattgaagag ggtataaaag aactggggtc ccaaatcctt    2760
aaggaacacc cagttgaaaa cacccagctt cagaatgaga gctctacct gtactacctg    2820 cagaacggca gggacatgta cgtggatcag gaactggaca tcaatcggct ctccgactac    2880
gacgtggatc atatcgtgcc ccagtctttt ctcaaagatg attctattga taataaagtg    2940
ttgacaagat ccgataaaaa tagagggaag agtgataacg tcccctcaga agaagttgtc    3000
aagaaaatga aaaattattg gcggcagctg ctgaacgcca aactgatcac acaacggaag    3060
ttcgataatc tgactaaggc tgaacgaggt ggcctgtctg agttggataa agccggcttc    3120 atcaaaggc agcttgttga cacgccag atcaccaagc acgtggccca aattctcgat    3180
tcacgcatga acaccaagta cgatgaaaat gacaaactga ttcgagaggt gaaagttatt    3240
actctgaagt ctaagctggt ctcagatttc agaaaggact ttcagtttta taggtgagaa    3300
gagatcaaca attaccacca tgcgcatgat gcctacctga atgcagtggt aggcactgca    3360
cttatcaaaa aatatcccaa gcttgaatct gaatttgttt acggagacta taaagtgtac    3420
gatgttagga aaatgatcgc aaagtctgag caggaaatag caaggccac cgctaagtac    3480 ttcttttaca gcaatattat gaatttttc aagaccgaga ttacactggc caatggagag    3540
attcggaagc gaccacttat cgaaacaaac ggagaaacag gagaaatcgt gtgggacaag    3600
ggtagggatt tcgcgacagt ccggaaggtc ctgtccatgc cgcaggtgaa catcgttaaa    3660
aagaccgaag tacagaccgg aggcttctcc aaggaaagta tcctcccgaa aaggaacagc    3720
gacaagctga tcgcacgcaa aaaagattgg gaccccaaga atacggcgg attcgattct    3780 cctacagtcg cttacagtgt actggttgtg gccaaagtgg agaaagggaa gtctaaaaaa    3840
ctcaaaagcg tcaaggaact gctgggcatc acaatcatga gcgatcaag cttcgaaaaa    3900 aacccccatcg actttctcga ggcgaaagga tataagagg tcaaaaaaga cctcatcatt    3960
aagcttccca gtactctctc ttttgagctt gaaaacggcc ggaaacgaat gctcgctagt    4020
gcgggcgagc tgcagaaagg taacgagctg gcactgccct ctaaatacgt taatttcttg    4080
tatctggcca gccactatga aaagctcaaa gggtctcccg aagataatga gcagaagcag    4140
ctgttcgtgg aacaacacaa acactacctt gatgagatca tcgagcaaat aagcgaattc    4200
tccaaaagag tgatcctcgc cgacgctaac ctcgataagg tgctttctgc ttacaataag    4260
```

-continued

| | |
|---|---|
| cacagggata agcccatcag ggagcaggca gaaaacatta tccacttgtt tactctgacc | 4320 |
| aacttgggcg cgcctgcagc cttcaagtac ttcgacacca ccatagacag aaagcggtac | 4380 |
| acctctacaa aggaggtcct ggacgccaca ctgattcatc agtcaattac ggggctctat | 4440 |
| gaaacaagaa tcgacctctc tcagctcggt ggagacagca gggctgaccc caagaagaag | 4500 |
| aggaaggtga gg | 4512 |

<210> SEQ ID NO 28
<211> LENGTH: 20
<212> TYPE: DNA
<213> ORGANISM: Mus musculus

<400> SEQUENCE: 28

| | |
|---|---|
| gaagaaggtt cgagatctca | 20 |

<210> SEQ ID NO 29
<211> LENGTH: 23
<212> TYPE: DNA
<213> ORGANISM: Mus musculus

<400> SEQUENCE: 29

| | |
|---|---|
| gaagaaggtt cgagatctca agg | 23 |

<210> SEQ ID NO 30
<211> LENGTH: 19
<212> TYPE: DNA
<213> ORGANISM: Unknown
<220> FEATURE:
<223> OTHER INFORMATION: Description of Unknown:
    Auto1 site sequence

<400> SEQUENCE: 30

| | |
|---|---|
| gttcgagatc tcagggaat | 19 |

<210> SEQ ID NO 31
<211> LENGTH: 19
<212> TYPE: DNA
<213> ORGANISM: Unknown
<220> FEATURE:
<223> OTHER INFORMATION: Description of Unknown:
    Auto2 site sequence

<400> SEQUENCE: 31

| | |
|---|---|
| gttcgagatc tcagggttt | 19 |

<210> SEQ ID NO 32
<211> LENGTH: 230
<212> TYPE: DNA
<213> ORGANISM: Unknown
<220> FEATURE:
<223> OTHER INFORMATION: Description of Unknown:
    H1 wildtype sequence

<400> SEQUENCE: 32

| | |
|---|---|
| ggaattcgaa cgctgacgtc atcaacccgc tccaaggaat cgcgggccca gtgtcactag | 60 |
| gcgggaacac ccagcgcgcg tgcgccctgg caggaagatg gctgtgaggg acaggggagt | 120 |
| ggcgccctgc aatatttgca tgtcgctatg tgttctggga aatcaccata aacgtgaaat | 180 |
| gtctttggat ttgggaatct tataagttct gtatgagacc actttttccc | 230 |

<210> SEQ ID NO 33
<211> LENGTH: 230

```
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33
ggaattcgaa cgctgacgtc atcaacccgc tccaaggaat cgcgggccca gtgtcactag     60
gcgggaacac ccagcgcgcg tgcgccctgg caggaagatg gctgtgaggg acaggggagt    120
ggcgccctgc aatatttgca tgtcgctatg tgttctggga aatcaccata aacgtgaaag    180
ttcgagatct cagggaatct tataagttct gtatgagacc acttttttccc              230

<210> SEQ ID NO 34
<211> LENGTH: 230
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34
ggaattcgaa cgctgacgtc atcaacccgc tccaaggaat cgcgggccca gtgtcactag     60
gcgggaacac ccagcgcgcg tgcgccctgg caggaagatg gctgtgaggg acaggggagt    120
ggcgccctgc aatatttgca tgtcgctatg tgttctggga aatcaccata aacgtgaaat    180
gtctttggat ttgggaatct tataagtgtt cgagatctca gggttttccc               230

<210> SEQ ID NO 35
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 36
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gly Ser Gly Glu Gly Arg Gly Ser Leu Leu Thr Cys Gly Asp Val Glu
1               5                   10                  15

Glu Asn Pro Gly Pro
            20

<210> SEQ ID NO 37
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37
```

```
Gly Ser Gly Gln Cys Thr Asn Tyr Ala Leu Leu Lys Leu Ala Gly Asp
1               5                   10                  15

Val Glu Ser Asn Pro Gly Pro
            20
```

<210> SEQ ID NO 38
<211> LENGTH: 25
<212> TYPE: PRT
<213> ORGANISM: Artificial Sequence
<220> FEATURE:
<223> OTHER INFORMATION: Description of Artificial Sequence: Synthetic peptide

<400> SEQUENCE: 38

```
Gly Ser Gly Val Lys Gln Thr Leu Asn Phe Asp Leu Leu Lys Leu Ala
1               5                   10                  15

Gly Asp Val Glu Ser Asn Pro Gly Pro
            20                  25
```

<210> SEQ ID NO 39
<211> LENGTH: 1455
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 39

```
Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly Val Asp Lys Lys
65                  70                  75                  80

Tyr Ser Ile Gly Leu Asp Ile Gly Thr Asn Ser Val Gly Trp Ala Val
                85                  90                  95

Ile Thr Asp Glu Tyr Lys Val Pro Ser Lys Lys Phe Lys Val Leu Gly
            100                 105                 110

Asn Thr Asp Arg His Ser Ile Lys Lys Asn Leu Ile Gly Ala Leu Leu
        115                 120                 125

Phe Asp Ser Gly Glu Thr Ala Glu Ala Thr Arg Leu Lys Arg Thr Ala
    130                 135                 140

Arg Arg Arg Tyr Thr Arg Arg Lys Asn Arg Ile Cys Tyr Leu Gln Glu
145                 150                 155                 160

Ile Phe Ser Asn Glu Met Ala Lys Val Asp Asp Ser Phe Phe His Arg
                165                 170                 175

Leu Glu Glu Ser Phe Leu Val Glu Glu Asp Lys Lys His Glu Arg His
            180                 185                 190

Pro Ile Phe Gly Asn Ile Val Asp Glu Val Ala Tyr His Glu Lys Tyr
        195                 200                 205

Pro Thr Ile Tyr His Leu Arg Lys Lys Leu Val Asp Ser Thr Asp Lys
    210                 215                 220

Ala Asp Leu Arg Leu Ile Tyr Leu Ala Leu Ala His Met Ile Lys Phe
225                 230                 235                 240
```

```
Arg Gly His Phe Leu Ile Glu Gly Asp Leu Asn Pro Asp Asn Ser Asp
                245                 250                 255

Val Asp Lys Leu Phe Ile Gln Leu Val Gln Thr Tyr Asn Gln Leu Phe
            260                 265                 270

Glu Glu Asn Pro Ile Asn Ala Ser Gly Val Asp Ala Lys Ala Ile Leu
        275                 280                 285

Ser Ala Arg Leu Ser Lys Ser Arg Arg Leu Glu Asn Leu Ile Ala Gln
    290                 295                 300

Leu Pro Gly Glu Lys Lys Asn Gly Leu Phe Gly Asn Leu Ile Ala Leu
305                 310                 315                 320

Ser Leu Gly Leu Thr Pro Asn Phe Lys Ser Asn Phe Asp Leu Ala Glu
                325                 330                 335

Asp Ala Lys Leu Gln Leu Ser Lys Asp Thr Tyr Asp Asp Asp Leu Asp
            340                 345                 350

Asn Leu Leu Ala Gln Ile Gly Asp Gln Tyr Ala Asp Leu Phe Leu Ala
        355                 360                 365

Ala Lys Asn Leu Ser Asp Ala Ile Leu Leu Ser Asp Ile Leu Arg Val
    370                 375                 380

Asn Thr Glu Ile Thr Lys Ala Pro Leu Ser Ala Ser Met Ile Lys Arg
385                 390                 395                 400

Tyr Asp Glu His His Gln Asp Leu Thr Leu Leu Lys Ala Leu Val Arg
                405                 410                 415

Gln Gln Leu Pro Glu Lys Tyr Lys Glu Ile Phe Phe Asp Gln Ser Lys
            420                 425                 430

Asn Gly Tyr Ala Gly Tyr Ile Asp Gly Gly Ala Ser Gln Glu Glu Phe
        435                 440                 445

Tyr Lys Phe Ile Lys Pro Ile Leu Glu Lys Met Asp Gly Thr Glu Glu
    450                 455                 460

Leu Leu Val Lys Leu Asn Arg Glu Asp Leu Leu Arg Lys Gln Arg Thr
465                 470                 475                 480

Phe Asp Asn Gly Ser Ile Pro His Gln Ile His Leu Gly Glu Leu His
                485                 490                 495

Ala Ile Leu Arg Arg Gln Glu Asp Phe Tyr Pro Phe Leu Lys Asp Asn
            500                 505                 510

Arg Glu Lys Ile Glu Lys Ile Leu Thr Phe Arg Ile Pro Tyr Tyr Val
        515                 520                 525

Gly Pro Leu Ala Arg Gly Asn Ser Arg Phe Ala Trp Met Thr Arg Lys
    530                 535                 540

Ser Glu Glu Thr Ile Thr Pro Trp Asn Phe Glu Val Val Asp Lys
545                 550                 555                 560

Gly Ala Ser Ala Gln Ser Phe Ile Glu Arg Met Thr Asn Phe Asp Lys
                565                 570                 575

Asn Leu Pro Asn Glu Lys Val Leu Pro Lys His Ser Leu Leu Tyr Glu
            580                 585                 590

Tyr Phe Thr Val Tyr Asn Glu Leu Thr Lys Val Lys Tyr Val Thr Glu
        595                 600                 605

Gly Met Arg Lys Pro Ala Phe Leu Ser Gly Glu Gln Lys Lys Ala Ile
    610                 615                 620

Val Asp Leu Leu Phe Lys Thr Asn Arg Lys Val Thr Val Lys Gln Leu
625                 630                 635                 640

Lys Glu Asp Tyr Phe Lys Lys Ile Glu Cys Phe Asp Ser Val Glu Ile
                645                 650                 655
```

```
Ser Gly Val Glu Asp Arg Phe Asn Ala Ser Leu Gly Thr Tyr His Asp
            660                 665                 670

Leu Leu Lys Ile Ile Lys Asp Lys Asp Phe Leu Asp Asn Glu Glu Asn
675                 680                 685

Glu Asp Ile Leu Glu Asp Ile Val Leu Thr Leu Thr Leu Phe Glu Asp
    690                 695                 700

Arg Glu Met Ile Glu Glu Arg Leu Lys Thr Tyr Ala His Leu Phe Asp
705                 710                 715                 720

Asp Lys Val Met Lys Gln Leu Lys Arg Arg Tyr Thr Gly Trp Gly
                725                 730                 735

Arg Leu Ser Arg Lys Leu Ile Asn Gly Ile Arg Asp Lys Gln Ser Gly
            740                 745                 750

Lys Thr Ile Leu Asp Phe Leu Lys Ser Asp Gly Phe Ala Asn Arg Asn
            755                 760                 765

Phe Met Gln Leu Ile His Asp Asp Ser Leu Thr Phe Lys Glu Asp Ile
770                 775                 780

Gln Lys Ala Gln Val Ser Gly Gln Gly Asp Ser Leu His Glu His Ile
785                 790                 795                 800

Ala Asn Leu Ala Gly Ser Pro Ala Ile Lys Lys Gly Ile Leu Gln Thr
            805                 810                 815

Val Lys Val Val Asp Glu Leu Val Lys Val Met Gly Arg His Lys Pro
            820                 825                 830

Glu Asn Ile Val Ile Glu Met Ala Arg Glu Asn Gln Thr Thr Gln Lys
            835                 840                 845

Gly Gln Lys Asn Ser Arg Glu Arg Met Lys Arg Ile Glu Glu Gly Ile
850                 855                 860

Lys Glu Leu Gly Ser Gln Ile Leu Lys Glu His Pro Val Glu Asn Thr
865                 870                 875                 880

Gln Leu Gln Asn Glu Lys Leu Tyr Leu Tyr Tyr Leu Gln Asn Gly Arg
            885                 890                 895

Asp Met Tyr Val Asp Gln Glu Leu Asp Ile Asn Arg Leu Ser Asp Tyr
            900                 905                 910

Asp Val Asp His Ile Val Pro Gln Ser Phe Leu Lys Asp Asp Ser Ile
            915                 920                 925

Asp Asn Lys Val Leu Thr Arg Ser Asp Lys Asn Arg Gly Lys Ser Asp
930                 935                 940

Asn Val Pro Ser Glu Glu Val Val Lys Lys Met Lys Asn Tyr Trp Arg
945                 950                 955                 960

Gln Leu Leu Asn Ala Lys Leu Ile Thr Gln Arg Lys Phe Asp Asn Leu
            965                 970                 975

Thr Lys Ala Glu Arg Gly Gly Leu Ser Glu Leu Asp Lys Ala Gly Phe
            980                 985                 990

Ile Lys Arg Gln Leu Val Glu Thr Arg Gln Ile Thr Lys His Val Ala
            995                 1000                1005

Gln Ile Leu Asp Ser Arg Met Asn Thr Lys Tyr Asp Glu Asn Asp
        1010                1015                1020

Lys Leu Ile Arg Glu Val Lys Val Ile Thr Leu Lys Ser Lys Leu
        1025                1030                1035

Val Ser Asp Phe Arg Lys Asp Phe Gln Phe Tyr Lys Val Arg Glu
        1040                1045                1050

Ile Asn Asn Tyr His His Ala His Asp Ala Tyr Leu Asn Ala Val
        1055                1060                1065

Val Gly Thr Ala Leu Ile Lys Lys Tyr Pro Lys Leu Glu Ser Glu
```

|  |  |  | 1070 |  |  | 1075 |  |  | 1080 |
|---|---|---|---|---|---|---|---|---|---|

Phe Val Tyr Gly Asp Tyr Lys Val Tyr Asp Val Arg Lys Met Ile
1085              1090              1095

Ala Lys Ser Glu Gln Glu Ile Gly Lys Ala Thr Ala Lys Tyr Phe
1100              1105              1110

Phe Tyr Ser Asn Ile Met Asn Phe Phe Lys Thr Glu Ile Thr Leu
1115              1120              1125

Ala Asn Gly Glu Ile Arg Lys Arg Pro Leu Ile Glu Thr Asn Gly
1130              1135              1140

Glu Thr Gly Glu Ile Val Trp Asp Lys Gly Arg Asp Phe Ala Thr
1145              1150              1155

Val Arg Lys Val Leu Ser Met Pro Gln Val Asn Ile Val Lys Lys
1160              1165              1170

Thr Glu Val Gln Thr Gly Gly Phe Ser Lys Glu Ser Ile Leu Pro
1175              1180              1185

Lys Arg Asn Ser Asp Lys Leu Ile Ala Arg Lys Lys Asp Trp Asp
1190              1195              1200

Pro Lys Lys Tyr Gly Gly Phe Asp Ser Pro Thr Val Ala Tyr Ser
1205              1210              1215

Val Leu Val Val Ala Lys Val Glu Lys Gly Lys Ser Lys Lys Leu
1220              1225              1230

Lys Ser Val Lys Glu Leu Leu Gly Ile Thr Ile Met Glu Arg Ser
1235              1240              1245

Ser Phe Glu Lys Asn Pro Ile Asp Phe Leu Glu Ala Lys Gly Tyr
1250              1255              1260

Lys Glu Val Lys Lys Asp Leu Ile Ile Lys Leu Pro Lys Tyr Ser
1265              1270              1275

Leu Phe Glu Leu Glu Asn Gly Arg Lys Arg Met Leu Ala Ser Ala
1280              1285              1290

Gly Glu Leu Gln Lys Gly Asn Glu Leu Ala Leu Pro Ser Lys Tyr
1295              1300              1305

Val Asn Phe Leu Tyr Leu Ala Ser His Tyr Glu Lys Leu Lys Gly
1310              1315              1320

Ser Pro Glu Asp Asn Glu Gln Lys Gln Leu Phe Val Glu Gln His
1325              1330              1335

Lys His Tyr Leu Asp Glu Ile Ile Glu Gln Ile Ser Glu Phe Ser
1340              1345              1350

Lys Arg Val Ile Leu Ala Asp Ala Asn Leu Asp Lys Val Leu Ser
1355              1360              1365

Ala Tyr Asn Lys His Arg Asp Lys Pro Ile Arg Glu Gln Ala Glu
1370              1375              1380

Asn Ile Ile His Leu Phe Thr Leu Thr Asn Leu Gly Ala Pro Ala
1385              1390              1395

Ala Phe Lys Tyr Phe Asp Thr Thr Ile Asp Arg Lys Arg Tyr Thr
1400              1405              1410

Ser Thr Lys Glu Val Leu Asp Ala Thr Leu Ile His Gln Ser Ile
1415              1420              1425

Thr Gly Leu Tyr Glu Thr Arg Ile Asp Leu Ser Gln Leu Gly Gly
1430              1435              1440

Asp Ser Arg Ala Asp Pro Lys Lys Lys Arg Lys Val
1445              1450              1455

<210> SEQ ID NO 40

```
<211> LENGTH: 1455
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly Met Asp Lys Lys
65                  70                  75                  80

Tyr Ser Ile Gly Leu Asp Ile Gly Thr Asn Ser Val Gly Trp Ala Val
                85                  90                  95

Ile Thr Asp Glu Tyr Lys Val Pro Ser Lys Lys Phe Lys Val Leu Gly
            100                 105                 110

Asn Thr Asp Arg His Ser Ile Lys Lys Asn Leu Ile Gly Ala Leu Leu
        115                 120                 125

Phe Asp Ser Gly Glu Thr Ala Glu Ala Thr Arg Leu Lys Arg Thr Ala
    130                 135                 140

Arg Arg Arg Tyr Thr Arg Arg Lys Asn Arg Ile Cys Tyr Leu Gln Glu
145                 150                 155                 160

Ile Phe Ser Asn Glu Met Ala Lys Val Asp Asp Ser Phe Phe His Arg
                165                 170                 175

Leu Glu Glu Ser Phe Leu Val Glu Glu Asp Lys Lys His Glu Arg His
            180                 185                 190

Pro Ile Phe Gly Asn Ile Val Asp Glu Val Ala Tyr His Glu Lys Tyr
        195                 200                 205

Pro Thr Ile Tyr His Leu Arg Lys Lys Leu Val Asp Ser Thr Asp Lys
    210                 215                 220

Ala Asp Leu Arg Leu Ile Tyr Leu Ala Leu Ala His Met Ile Lys Phe
225                 230                 235                 240

Arg Gly His Phe Leu Ile Glu Gly Asp Leu Asn Pro Asp Asn Ser Asp
                245                 250                 255

Val Asp Lys Leu Phe Ile Gln Leu Val Gln Thr Tyr Asn Gln Leu Phe
            260                 265                 270

Glu Glu Asn Pro Ile Asn Ala Ser Gly Val Asp Ala Lys Ala Ile Leu
        275                 280                 285

Ser Ala Arg Leu Ser Lys Ser Arg Arg Leu Glu Asn Leu Ile Ala Gln
    290                 295                 300

Leu Pro Gly Glu Lys Lys Asn Gly Leu Phe Gly Asn Leu Ile Ala Leu
305                 310                 315                 320

Ser Leu Gly Leu Thr Pro Asn Phe Lys Ser Asn Phe Asp Leu Ala Glu
                325                 330                 335

Asp Ala Lys Leu Gln Leu Ser Lys Asp Thr Tyr Asp Asp Leu Asp
            340                 345                 350

Asn Leu Leu Ala Gln Ile Gly Asp Gln Tyr Ala Asp Leu Phe Leu Ala
        355                 360                 365

Ala Lys Asn Leu Ser Asp Ala Ile Leu Leu Ser Asp Ile Leu Arg Val
```

```
            370                 375                 380
Asn Thr Glu Ile Thr Lys Ala Pro Leu Ser Ala Ser Met Ile Lys Arg
385                 390                 395                 400

Tyr Asp Glu His His Gln Asp Leu Thr Leu Leu Lys Ala Leu Val Arg
                405                 410                 415

Gln Gln Leu Pro Glu Lys Tyr Lys Glu Ile Phe Phe Asp Gln Ser Lys
                420                 425                 430

Asn Gly Tyr Ala Gly Tyr Ile Asp Gly Gly Ala Ser Gln Glu Glu Phe
            435                 440                 445

Tyr Lys Phe Ile Lys Pro Ile Leu Glu Lys Met Asp Gly Thr Glu Glu
            450                 455                 460

Leu Leu Val Lys Leu Asn Arg Glu Asp Leu Leu Arg Lys Gln Arg Thr
465                 470                 475                 480

Phe Asp Asn Gly Ser Ile Pro His Gln Ile His Leu Gly Glu Leu His
                485                 490                 495

Ala Ile Leu Arg Arg Gln Glu Asp Phe Tyr Pro Phe Leu Lys Asp Asn
                500                 505                 510

Arg Glu Lys Ile Glu Lys Ile Leu Thr Phe Arg Ile Pro Tyr Tyr Val
                515                 520                 525

Gly Pro Leu Ala Arg Gly Asn Ser Arg Phe Ala Trp Met Thr Arg Lys
                530                 535                 540

Ser Glu Glu Thr Ile Thr Pro Trp Asn Phe Glu Glu Val Val Asp Lys
545                 550                 555                 560

Gly Ala Ser Ala Gln Ser Phe Ile Glu Arg Met Thr Asn Phe Asp Lys
                565                 570                 575

Asn Leu Pro Asn Glu Lys Val Leu Pro Lys His Ser Leu Leu Tyr Glu
                580                 585                 590

Tyr Phe Thr Val Tyr Asn Glu Leu Thr Lys Val Lys Tyr Val Thr Glu
                595                 600                 605

Gly Met Arg Lys Pro Ala Phe Leu Ser Gly Glu Gln Lys Lys Ala Ile
            610                 615                 620

Val Asp Leu Leu Phe Lys Thr Asn Arg Lys Val Thr Val Lys Gln Leu
625                 630                 635                 640

Lys Glu Asp Tyr Phe Lys Lys Ile Glu Cys Phe Asp Ser Val Glu Ile
                645                 650                 655

Ser Gly Val Glu Asp Arg Phe Asn Ala Ser Leu Gly Thr Tyr His Asp
                660                 665                 670

Leu Leu Lys Ile Ile Lys Asp Lys Asp Phe Leu Asp Asn Glu Glu Asn
                675                 680                 685

Glu Asp Ile Leu Glu Asp Ile Val Leu Thr Leu Thr Leu Phe Glu Asp
            690                 695                 700

Arg Glu Met Ile Glu Glu Arg Leu Lys Thr Tyr Ala His Leu Phe Asp
705                 710                 715                 720

Asp Lys Val Met Lys Gln Leu Lys Arg Arg Arg Tyr Thr Gly Trp Gly
                725                 730                 735

Arg Leu Ser Arg Lys Leu Ile Asn Gly Ile Arg Asp Lys Gln Ser Gly
                740                 745                 750

Lys Thr Ile Leu Asp Phe Leu Lys Ser Asp Gly Phe Ala Asn Arg Asn
            755                 760                 765

Phe Met Gln Leu Ile His Asp Asp Ser Leu Thr Phe Lys Glu Asp Ile
            770                 775                 780

Gln Lys Ala Gln Val Ser Gly Gln Gly Asp Ser Leu His Glu His Ile
785                 790                 795                 800
```

```
Ala Asn Leu Ala Gly Ser Pro Ala Ile Lys Lys Gly Ile Leu Gln Thr
                805                 810                 815

Val Lys Val Val Asp Glu Leu Val Lys Val Met Gly Arg His Lys Pro
            820                 825                 830

Glu Asn Ile Val Ile Glu Met Ala Arg Glu Asn Gln Thr Thr Gln Lys
                835                 840                 845

Gly Gln Lys Asn Ser Arg Glu Arg Met Lys Arg Ile Glu Glu Gly Ile
850                 855                 860

Lys Glu Leu Gly Ser Gln Ile Leu Lys Glu His Pro Val Glu Asn Thr
865                 870                 875                 880

Gln Leu Gln Asn Glu Lys Leu Tyr Leu Tyr Tyr Leu Gln Asn Gly Arg
                885                 890                 895

Asp Met Tyr Val Asp Gln Glu Leu Asp Ile Asn Arg Leu Ser Asp Tyr
                900                 905                 910

Asp Val Asp His Ile Val Pro Gln Ser Phe Leu Lys Asp Asp Ser Ile
                915                 920                 925

Asp Asn Lys Val Leu Thr Arg Ser Asp Lys Asn Arg Gly Lys Ser Asp
                930                 935                 940

Asn Val Pro Ser Glu Glu Val Val Lys Lys Met Lys Asn Tyr Trp Arg
945                 950                 955                 960

Gln Leu Leu Asn Ala Lys Leu Ile Thr Gln Arg Lys Phe Asp Asn Leu
                965                 970                 975

Thr Lys Ala Glu Arg Gly Gly Leu Ser Glu Leu Asp Lys Ala Gly Phe
                980                 985                 990

Ile Lys Arg Gln Leu Val Glu Thr Arg Gln Ile Thr Lys His Val Ala
                995                 1000                1005

Gln Ile Leu Asp Ser Arg Met Asn Thr Lys Tyr Asp Glu Asn Asp
        1010                1015                1020

Lys Leu Ile Arg Glu Val Lys Val Ile Thr Leu Lys Ser Lys Leu
        1025                1030                1035

Val Ser Asp Phe Arg Lys Asp Phe Gln Phe Tyr Lys Val Arg Glu
        1040                1045                1050

Ile Asn Asn Tyr His His Ala His Asp Ala Tyr Leu Asn Ala Val
        1055                1060                1065

Val Gly Thr Ala Leu Ile Lys Lys Tyr Pro Lys Leu Glu Ser Glu
        1070                1075                1080

Phe Val Tyr Gly Asp Tyr Lys Val Tyr Asp Val Arg Lys Met Ile
        1085                1090                1095

Ala Lys Ser Glu Gln Glu Ile Gly Lys Ala Thr Ala Lys Tyr Phe
        1100                1105                1110

Phe Tyr Ser Asn Ile Met Asn Phe Phe Lys Thr Glu Ile Thr Leu
        1115                1120                1125

Ala Asn Gly Glu Ile Arg Lys Arg Pro Leu Ile Glu Thr Asn Gly
        1130                1135                1140

Glu Thr Gly Glu Ile Val Trp Asp Lys Gly Arg Asp Phe Ala Thr
        1145                1150                1155

Val Arg Lys Val Leu Ser Met Pro Gln Val Asn Ile Val Lys Lys
        1160                1165                1170

Thr Glu Val Gln Thr Gly Gly Phe Ser Lys Glu Ser Ile Leu Pro
        1175                1180                1185

Lys Arg Asn Ser Asp Lys Leu Ile Ala Arg Lys Lys Asp Trp Asp
        1190                1195                1200
```

```
Pro Lys Lys Tyr Gly Gly Phe Asp Ser Pro Thr Val Ala Tyr Ser
    1205                1210                1215

Val Leu Val Val Ala Lys Val Glu Lys Gly Lys Ser Lys Lys Leu
    1220                1225                1230

Lys Ser Val Lys Glu Leu Leu Gly Ile Thr Ile Met Glu Arg Ser
    1235                1240                1245

Ser Phe Glu Lys Asn Pro Ile Asp Phe Leu Glu Ala Lys Gly Tyr
    1250                1255                1260

Lys Glu Val Lys Lys Asp Leu Ile Ile Lys Leu Pro Lys Tyr Ser
    1265                1270                1275

Leu Phe Glu Leu Glu Asn Gly Arg Lys Arg Met Leu Ala Ser Ala
    1280                1285                1290

Gly Glu Leu Gln Lys Gly Asn Glu Leu Ala Leu Pro Ser Lys Tyr
    1295                1300                1305

Val Asn Phe Leu Tyr Leu Ala Ser His Tyr Glu Lys Leu Lys Gly
    1310                1315                1320

Ser Pro Glu Asp Asn Glu Gln Lys Gln Leu Phe Val Glu Gln His
    1325                1330                1335

Lys His Tyr Leu Asp Glu Ile Ile Glu Gln Ile Ser Glu Phe Ser
    1340                1345                1350

Lys Arg Val Ile Leu Ala Asp Ala Asn Leu Asp Lys Val Leu Ser
    1355                1360                1365

Ala Tyr Asn Lys His Arg Asp Lys Pro Ile Arg Glu Gln Ala Glu
    1370                1375                1380

Asn Ile Ile His Leu Phe Thr Leu Thr Asn Leu Gly Ala Pro Ala
    1385                1390                1395

Ala Phe Lys Tyr Phe Asp Thr Thr Ile Asp Arg Lys Arg Tyr Thr
    1400                1405                1410

Ser Thr Lys Glu Val Leu Asp Ala Thr Leu Ile His Gln Ser Ile
    1415                1420                1425

Thr Gly Leu Tyr Glu Thr Arg Ile Asp Leu Ser Gln Leu Gly Gly
    1430                1435                1440

Asp Ser Arg Ala Asp Pro Lys Lys Lys Arg Lys Val
    1445                1450                1455

<210> SEQ ID NO 41
<211> LENGTH: 1455
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly Asp Lys Lys
65                  70                  75                  80

Tyr Ser Ile Gly Leu Asp Ile Gly Thr Asn Ser Val Gly Trp Ala Val
                85                  90                  95
```

-continued

Ile Thr Asp Glu Tyr Lys Val Pro Ser Lys Lys Phe Lys Val Leu Gly
            100                 105                 110

Asn Thr Asp Arg His Ser Ile Lys Lys Asn Leu Ile Gly Ala Leu Leu
            115                 120                 125

Phe Asp Ser Gly Glu Thr Ala Glu Ala Thr Arg Leu Lys Arg Thr Ala
            130                 135                 140

Arg Arg Arg Tyr Thr Arg Arg Lys Asn Arg Ile Cys Tyr Leu Gln Glu
145                 150                 155                 160

Ile Phe Ser Asn Glu Met Ala Lys Val Asp Asp Ser Phe Phe His Arg
            165                 170                 175

Leu Glu Glu Ser Phe Leu Val Glu Glu Asp Lys Lys His Glu Arg His
            180                 185                 190

Pro Ile Phe Gly Asn Ile Val Asp Glu Val Ala Tyr His Glu Lys Tyr
            195                 200                 205

Pro Thr Ile Tyr His Leu Arg Lys Lys Leu Val Asp Ser Thr Asp Lys
            210                 215                 220

Ala Asp Leu Arg Leu Ile Tyr Leu Ala Leu Ala His Met Ile Lys Phe
225                 230                 235                 240

Arg Gly His Phe Leu Ile Glu Gly Asp Leu Asn Pro Asp Asn Ser Asp
            245                 250                 255

Val Asp Lys Leu Phe Ile Gln Leu Val Gln Thr Tyr Asn Gln Leu Phe
            260                 265                 270

Glu Glu Asn Pro Ile Asn Ala Ser Gly Val Asp Ala Lys Ala Ile Leu
            275                 280                 285

Ser Ala Arg Leu Ser Lys Ser Arg Arg Leu Glu Asn Leu Ile Ala Gln
            290                 295                 300

Leu Pro Gly Glu Lys Lys Asn Gly Leu Phe Gly Asn Leu Ile Ala Leu
305                 310                 315                 320

Ser Leu Gly Leu Thr Pro Asn Phe Lys Ser Asn Phe Asp Leu Ala Glu
            325                 330                 335

Asp Ala Lys Leu Gln Leu Ser Lys Asp Thr Tyr Asp Asp Asp Leu Asp
            340                 345                 350

Asn Leu Leu Ala Gln Ile Gly Asp Gln Tyr Ala Asp Leu Phe Leu Ala
            355                 360                 365

Ala Lys Asn Leu Ser Asp Ala Ile Leu Leu Ser Asp Ile Leu Arg Val
            370                 375                 380

Asn Thr Glu Ile Thr Lys Ala Pro Leu Ser Ala Ser Met Ile Lys Arg
385                 390                 395                 400

Tyr Asp Glu His His Gln Asp Leu Thr Leu Leu Lys Ala Leu Val Arg
            405                 410                 415

Gln Gln Leu Pro Glu Lys Tyr Lys Glu Ile Phe Phe Asp Gln Ser Lys
            420                 425                 430

Asn Gly Tyr Ala Gly Tyr Ile Asp Gly Gly Ala Ser Gln Glu Glu Phe
            435                 440                 445

Tyr Lys Phe Ile Lys Pro Ile Leu Glu Lys Met Asp Gly Thr Glu Glu
            450                 455                 460

Leu Leu Val Lys Leu Asn Arg Glu Asp Leu Leu Arg Lys Gln Arg Thr
465                 470                 475                 480

Phe Asp Asn Gly Ser Ile Pro His Gln Ile His Leu Gly Glu Leu His
            485                 490                 495

Ala Ile Leu Arg Arg Gln Glu Asp Phe Tyr Pro Phe Leu Lys Asp Asn
            500                 505                 510

```
Arg Glu Lys Ile Glu Lys Ile Leu Thr Phe Arg Ile Pro Tyr Tyr Val
        515                 520                 525

Gly Pro Leu Ala Arg Gly Asn Ser Arg Phe Ala Trp Met Thr Arg Lys
        530                 535                 540

Ser Glu Glu Thr Ile Thr Pro Trp Asn Phe Glu Glu Val Val Asp Lys
545                 550                 555                 560

Gly Ala Ser Ala Gln Ser Phe Ile Glu Arg Met Thr Asn Phe Asp Lys
                565                 570                 575

Asn Leu Pro Asn Glu Lys Val Leu Pro Lys His Ser Leu Leu Tyr Glu
            580                 585                 590

Tyr Phe Thr Val Tyr Asn Glu Leu Thr Lys Val Lys Tyr Val Thr Glu
            595                 600                 605

Gly Met Arg Lys Pro Ala Phe Leu Ser Gly Glu Gln Lys Lys Ala Ile
        610                 615                 620

Val Asp Leu Leu Phe Lys Thr Asn Arg Lys Val Thr Val Lys Gln Leu
625                 630                 635                 640

Lys Glu Asp Tyr Phe Lys Lys Ile Glu Cys Phe Asp Ser Val Glu Ile
                645                 650                 655

Ser Gly Val Glu Asp Arg Phe Asn Ala Ser Leu Gly Thr Tyr His Asp
            660                 665                 670

Leu Leu Lys Ile Ile Lys Asp Lys Asp Phe Leu Asp Asn Glu Glu Asn
        675                 680                 685

Glu Asp Ile Leu Glu Asp Ile Val Leu Thr Leu Thr Leu Phe Glu Asp
        690                 695                 700

Arg Glu Met Ile Glu Glu Arg Leu Lys Thr Tyr Ala His Leu Phe Asp
705                 710                 715                 720

Asp Lys Val Met Lys Gln Leu Lys Arg Arg Arg Tyr Thr Gly Trp Gly
                725                 730                 735

Arg Leu Ser Arg Lys Leu Ile Asn Gly Ile Arg Asp Lys Gln Ser Gly
            740                 745                 750

Lys Thr Ile Leu Asp Phe Leu Lys Ser Asp Gly Phe Ala Asn Arg Asn
        755                 760                 765

Phe Met Gln Leu Ile His Asp Asp Ser Leu Thr Phe Lys Glu Asp Ile
770                 775                 780

Gln Lys Ala Gln Val Ser Gly Gln Gly Asp Ser Leu His Glu His Ile
785                 790                 795                 800

Ala Asn Leu Ala Gly Ser Pro Ala Ile Lys Lys Gly Ile Leu Gln Thr
                805                 810                 815

Val Lys Val Val Asp Glu Leu Val Lys Val Met Gly Arg His Lys Pro
            820                 825                 830

Glu Asn Ile Val Ile Glu Met Ala Arg Glu Asn Gln Thr Thr Gln Lys
        835                 840                 845

Gly Gln Lys Asn Ser Arg Glu Arg Met Lys Arg Ile Glu Glu Gly Ile
        850                 855                 860

Lys Glu Leu Gly Ser Gln Ile Leu Lys Glu His Pro Val Glu Asn Thr
865                 870                 875                 880

Gln Leu Gln Asn Glu Lys Leu Tyr Leu Tyr Tyr Leu Gln Asn Gly Arg
                885                 890                 895

Asp Met Tyr Val Asp Gln Glu Leu Asp Ile Asn Arg Leu Ser Asp Tyr
            900                 905                 910

Asp Val Asp His Ile Val Pro Gln Ser Phe Leu Lys Asp Asp Ser Ile
        915                 920                 925

Asp Asn Lys Val Leu Thr Arg Ser Asp Lys Asn Arg Gly Lys Ser Asp
```

```
                930             935             940
    Asn Val Pro Ser Glu Glu Val Lys Lys Met Lys Asn Tyr Trp Arg
945                 950             955                 960
    Gln Leu Leu Asn Ala Lys Leu Ile Thr Gln Arg Lys Phe Asp Asn Leu
                965             970             975
    Thr Lys Ala Glu Arg Gly Gly Leu Ser Glu Leu Asp Lys Ala Gly Phe
                    980             985             990
    Ile Lys Arg Gln Leu Val Glu Thr Arg Gln Ile Thr Lys His Val Ala
                995             1000            1005
    Gln Ile Leu Asp Ser Arg Met Asn Thr Lys Tyr Asp Glu Asn Asp
        1010            1015            1020
    Lys Leu Ile Arg Glu Val Lys Val Ile Thr Leu Lys Ser Lys Leu
        1025            1030            1035
    Val Ser Asp Phe Arg Lys Asp Phe Gln Phe Tyr Lys Val Arg Glu
        1040            1045            1050
    Ile Asn Asn Tyr His His Ala His Asp Ala Tyr Leu Asn Ala Val
        1055            1060            1065
    Val Gly Thr Ala Leu Ile Lys Lys Tyr Pro Lys Leu Glu Ser Glu
        1070            1075            1080
    Phe Val Tyr Gly Asp Tyr Lys Val Tyr Asp Val Arg Lys Met Ile
        1085            1090            1095
    Ala Lys Ser Glu Gln Glu Ile Gly Lys Ala Thr Ala Lys Tyr Phe
        1100            1105            1110
    Phe Tyr Ser Asn Ile Met Asn Phe Phe Lys Thr Glu Ile Thr Leu
        1115            1120            1125
    Ala Asn Gly Glu Ile Arg Lys Arg Pro Leu Ile Glu Thr Asn Gly
        1130            1135            1140
    Glu Thr Gly Glu Ile Val Trp Asp Lys Gly Arg Asp Phe Ala Thr
        1145            1150            1155
    Val Arg Lys Val Leu Ser Met Pro Gln Val Asn Ile Val Lys Lys
        1160            1165            1170
    Thr Glu Val Gln Thr Gly Gly Phe Ser Lys Glu Ser Ile Leu Pro
        1175            1180            1185
    Lys Arg Asn Ser Asp Lys Leu Ile Ala Arg Lys Lys Asp Trp Asp
        1190            1195            1200
    Pro Lys Lys Tyr Gly Gly Phe Asp Ser Pro Thr Val Ala Tyr Ser
        1205            1210            1215
    Val Leu Val Val Ala Lys Val Glu Lys Gly Lys Ser Lys Lys Leu
        1220            1225            1230
    Lys Ser Val Lys Glu Leu Leu Gly Ile Thr Ile Met Glu Arg Ser
        1235            1240            1245
    Ser Phe Glu Lys Asn Pro Ile Asp Phe Leu Glu Ala Lys Gly Tyr
        1250            1255            1260
    Lys Glu Val Lys Lys Asp Leu Ile Ile Lys Leu Pro Lys Tyr Ser
        1265            1270            1275
    Leu Phe Glu Leu Glu Asn Gly Arg Lys Arg Met Leu Ala Ser Ala
        1280            1285            1290
    Gly Glu Leu Gln Lys Gly Asn Glu Leu Ala Leu Pro Ser Lys Tyr
        1295            1300            1305
    Val Asn Phe Leu Tyr Leu Ala Ser His Tyr Glu Lys Leu Lys Gly
        1310            1315            1320
    Ser Pro Glu Asp Asn Glu Gln Lys Gln Leu Phe Val Glu Gln His
        1325            1330            1335
```

```
Lys His Tyr Leu Asp Glu Ile Ile Glu Gln Ile Ser Glu Phe Ser
    1340                1345                1350

Lys Arg Val Ile Leu Ala Asp Ala Asn Leu Asp Lys Val Leu Ser
    1355                1360                1365

Ala Tyr Asn Lys His Arg Asp Lys Pro Ile Arg Glu Gln Ala Glu
    1370                1375                1380

Asn Ile Ile His Leu Phe Thr Leu Thr Asn Leu Gly Ala Pro Ala
    1385                1390                1395

Ala Phe Lys Tyr Phe Asp Thr Thr Ile Asp Arg Lys Arg Tyr Thr
    1400                1405                1410

Ser Thr Lys Glu Val Leu Asp Ala Thr Leu Ile His Gln Ser Ile
    1415                1420                1425

Thr Gly Leu Tyr Glu Thr Arg Ile Asp Leu Ser Gln Leu Gly Gly
    1430                1435                1440

Asp Ser Arg Ala Asp Pro Lys Lys Lys Arg Lys Val
    1445                1450                1455

<210> SEQ ID NO 42
<211> LENGTH: 1455
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly Pro Asp Lys Lys
65                  70                  75                  80

Tyr Ser Ile Gly Leu Asp Ile Gly Thr Asn Ser Val Gly Trp Ala Val
                85                  90                  95

Ile Thr Asp Glu Tyr Lys Val Pro Ser Lys Lys Phe Lys Val Leu Gly
            100                 105                 110

Asn Thr Asp Arg His Ser Ile Lys Lys Asn Leu Ile Gly Ala Leu Leu
        115                 120                 125

Phe Asp Ser Gly Glu Thr Ala Glu Ala Thr Arg Leu Lys Arg Thr Ala
    130                 135                 140

Arg Arg Arg Tyr Thr Arg Arg Lys Asn Arg Ile Cys Tyr Leu Gln Glu
145                 150                 155                 160

Ile Phe Ser Asn Glu Met Ala Lys Val Asp Asp Ser Phe Phe His Arg
                165                 170                 175

Leu Glu Glu Ser Phe Leu Val Glu Glu Asp Lys Lys His Glu Arg His
            180                 185                 190

Pro Ile Phe Gly Asn Ile Val Asp Glu Val Ala Tyr His Glu Lys Tyr
        195                 200                 205

Pro Thr Ile Tyr His Leu Arg Lys Lys Leu Val Asp Ser Thr Asp Lys
    210                 215                 220

Ala Asp Leu Arg Leu Ile Tyr Leu Ala Leu Ala His Met Ile Lys Phe
```

```
            225                 230                 235                 240
        Arg Gly His Phe Leu Ile Glu Gly Asp Leu Asn Pro Asp Asn Ser Asp
                        245                 250                 255

Val Asp Lys Leu Phe Ile Gln Leu Val Gln Thr Tyr Asn Gln Leu Phe
                        260                 265                 270

Glu Glu Asn Pro Ile Asn Ala Ser Gly Val Asp Ala Lys Ala Ile Leu
                        275                 280                 285

Ser Ala Arg Leu Ser Lys Ser Arg Arg Leu Glu Asn Leu Ile Ala Gln
                    290                 295                 300

Leu Pro Gly Glu Lys Lys Asn Gly Leu Phe Gly Asn Leu Ile Ala Leu
        305                 310                 315                 320

Ser Leu Gly Leu Thr Pro Asn Phe Lys Ser Asn Phe Asp Leu Ala Glu
                        325                 330                 335

Asp Ala Lys Leu Gln Leu Ser Lys Asp Thr Tyr Asp Asp Asp Leu Asp
                        340                 345                 350

Asn Leu Leu Ala Gln Ile Gly Asp Gln Tyr Ala Asp Leu Phe Leu Ala
                        355                 360                 365

Ala Lys Asn Leu Ser Asp Ala Ile Leu Leu Ser Asp Ile Leu Arg Val
                    370                 375                 380

Asn Thr Glu Ile Thr Lys Ala Pro Leu Ser Ala Ser Met Ile Lys Arg
        385                 390                 395                 400

Tyr Asp Glu His His Gln Asp Leu Thr Leu Leu Lys Ala Leu Val Arg
                        405                 410                 415

Gln Gln Leu Pro Glu Lys Tyr Lys Glu Ile Phe Phe Asp Gln Ser Lys
                        420                 425                 430

Asn Gly Tyr Ala Gly Tyr Ile Asp Gly Gly Ala Ser Gln Glu Glu Phe
                    435                 440                 445

Tyr Lys Phe Ile Lys Pro Ile Leu Glu Lys Met Asp Gly Thr Glu Glu
                    450                 455                 460

Leu Leu Val Lys Leu Asn Arg Glu Asp Leu Leu Arg Lys Gln Arg Thr
        465                 470                 475                 480

Phe Asp Asn Gly Ser Ile Pro His Gln Ile His Leu Gly Glu Leu His
                        485                 490                 495

Ala Ile Leu Arg Arg Gln Glu Asp Phe Tyr Pro Phe Leu Lys Asp Asn
                        500                 505                 510

Arg Glu Lys Ile Glu Lys Ile Leu Thr Phe Arg Ile Pro Tyr Tyr Val
                        515                 520                 525

Gly Pro Leu Ala Arg Gly Asn Ser Arg Phe Ala Trp Met Thr Arg Lys
                    530                 535                 540

Ser Glu Glu Thr Ile Thr Pro Trp Asn Phe Glu Glu Val Val Asp Lys
        545                 550                 555                 560

Gly Ala Ser Ala Gln Ser Phe Ile Glu Arg Met Thr Asn Phe Asp Lys
                        565                 570                 575

Asn Leu Pro Asn Glu Lys Val Leu Pro Lys His Ser Leu Leu Tyr Glu
                        580                 585                 590

Tyr Phe Thr Val Tyr Asn Glu Leu Thr Lys Val Lys Tyr Val Thr Glu
                        595                 600                 605

Gly Met Arg Lys Pro Ala Phe Leu Ser Gly Glu Gln Lys Lys Ala Ile
                    610                 615                 620

Val Asp Leu Leu Phe Lys Thr Asn Arg Lys Val Thr Val Lys Gln Leu
        625                 630                 635                 640

Lys Glu Asp Tyr Phe Lys Lys Ile Glu Cys Phe Asp Ser Val Glu Ile
                        645                 650                 655
```

-continued

```
Ser Gly Val Glu Asp Arg Phe Asn Ala Ser Leu Gly Thr Tyr His Asp
            660                 665                 670

Leu Leu Lys Ile Ile Lys Asp Lys Asp Phe Leu Asp Asn Glu Glu Asn
            675                 680                 685

Glu Asp Ile Leu Glu Asp Ile Val Leu Thr Leu Thr Leu Phe Glu Asp
            690                 695                 700

Arg Glu Met Ile Glu Glu Arg Leu Lys Thr Tyr Ala His Leu Phe Asp
705                 710                 715                 720

Asp Lys Val Met Lys Gln Leu Lys Arg Arg Arg Tyr Thr Gly Trp Gly
                725                 730                 735

Arg Leu Ser Arg Lys Leu Ile Asn Gly Ile Arg Asp Lys Gln Ser Gly
            740                 745                 750

Lys Thr Ile Leu Asp Phe Leu Lys Ser Asp Gly Phe Ala Asn Arg Asn
            755                 760                 765

Phe Met Gln Leu Ile His Asp Asp Ser Leu Thr Phe Lys Glu Asp Ile
            770                 775                 780

Gln Lys Ala Gln Val Ser Gly Gln Gly Asp Ser Leu His Glu His Ile
785                 790                 795                 800

Ala Asn Leu Ala Gly Ser Pro Ala Ile Lys Lys Gly Ile Leu Gln Thr
                805                 810                 815

Val Lys Val Val Asp Glu Leu Val Lys Val Met Gly Arg His Lys Pro
            820                 825                 830

Glu Asn Ile Val Ile Glu Met Ala Arg Glu Asn Gln Thr Thr Gln Lys
            835                 840                 845

Gly Gln Lys Asn Ser Arg Glu Arg Met Lys Arg Ile Glu Glu Gly Ile
            850                 855                 860

Lys Glu Leu Gly Ser Gln Ile Leu Lys Glu His Pro Val Glu Asn Thr
865                 870                 875                 880

Gln Leu Gln Asn Glu Lys Leu Tyr Leu Tyr Tyr Leu Gln Asn Gly Arg
                885                 890                 895

Asp Met Tyr Val Asp Gln Glu Leu Asp Ile Asn Arg Leu Ser Asp Tyr
            900                 905                 910

Asp Val Asp His Ile Val Pro Gln Ser Phe Leu Lys Asp Ser Ile
            915                 920                 925

Asp Asn Lys Val Leu Thr Arg Ser Asp Lys Asn Arg Gly Lys Ser Asp
            930                 935                 940

Asn Val Pro Ser Glu Glu Val Val Lys Lys Met Lys Asn Tyr Trp Arg
945                 950                 955                 960

Gln Leu Leu Asn Ala Lys Leu Ile Thr Gln Arg Lys Phe Asp Asn Leu
                965                 970                 975

Thr Lys Ala Glu Arg Gly Gly Leu Ser Glu Leu Asp Lys Ala Gly Phe
            980                 985                 990

Ile Lys Arg Gln Leu Val Glu Thr  Arg Gln Ile Thr Lys  His Val Ala
            995                 1000                1005

Gln Ile  Leu Asp Ser Arg Met  Asn Thr Lys Tyr Asp  Glu Asn Asp
        1010                1015                1020

Lys Leu  Ile Arg Glu Val Lys  Val Ile Thr Leu Lys  Ser Lys Leu
        1025                1030                1035

Val Ser  Asp Phe Arg Lys Asp  Phe Gln Phe Tyr Lys  Val Arg Glu
        1040                1045                1050

Ile Asn  Asn Tyr His His Ala  His Asp Ala Tyr Leu  Asn Ala Val
        1055                1060                1065
```

```
Val Gly Thr Ala Leu Ile Lys Lys Tyr Pro Lys Leu Glu Ser Glu
    1070                1075                1080

Phe Val Tyr Gly Asp Tyr Lys Val Tyr Asp Val Arg Lys Met Ile
    1085                1090                1095

Ala Lys Ser Glu Gln Glu Ile Gly Lys Ala Thr Ala Lys Tyr Phe
    1100                1105                1110

Phe Tyr Ser Asn Ile Met Asn Phe Phe Lys Thr Glu Ile Thr Leu
    1115                1120                1125

Ala Asn Gly Glu Ile Arg Lys Arg Pro Leu Ile Glu Thr Asn Gly
    1130                1135                1140

Glu Thr Gly Glu Ile Val Trp Asp Lys Gly Arg Asp Phe Ala Thr
    1145                1150                1155

Val Arg Lys Val Leu Ser Met Pro Gln Val Asn Ile Val Lys Lys
    1160                1165                1170

Thr Glu Val Gln Thr Gly Gly Phe Ser Lys Glu Ser Ile Leu Pro
    1175                1180                1185

Lys Arg Asn Ser Asp Lys Leu Ile Ala Arg Lys Lys Asp Trp Asp
    1190                1195                1200

Pro Lys Lys Tyr Gly Gly Phe Asp Ser Pro Thr Val Ala Tyr Ser
    1205                1210                1215

Val Leu Val Val Ala Lys Val Glu Lys Gly Lys Ser Lys Lys Leu
    1220                1225                1230

Lys Ser Val Lys Glu Leu Leu Gly Ile Thr Ile Met Glu Arg Ser
    1235                1240                1245

Ser Phe Glu Lys Asn Pro Ile Asp Phe Leu Glu Ala Lys Gly Tyr
    1250                1255                1260

Lys Glu Val Lys Lys Asp Leu Ile Ile Lys Leu Pro Lys Tyr Ser
    1265                1270                1275

Leu Phe Glu Leu Glu Asn Gly Arg Lys Arg Met Leu Ala Ser Ala
    1280                1285                1290

Gly Glu Leu Gln Lys Gly Asn Glu Leu Ala Leu Pro Ser Lys Tyr
    1295                1300                1305

Val Asn Phe Leu Tyr Leu Ala Ser His Tyr Glu Lys Leu Lys Gly
    1310                1315                1320

Ser Pro Glu Asp Asn Glu Gln Lys Gln Leu Phe Val Glu Gln His
    1325                1330                1335

Lys His Tyr Leu Asp Glu Ile Ile Glu Gln Ile Ser Glu Phe Ser
    1340                1345                1350

Lys Arg Val Ile Leu Ala Asp Ala Asn Leu Asp Lys Val Leu Ser
    1355                1360                1365

Ala Tyr Asn Lys His Arg Asp Lys Pro Ile Arg Glu Gln Ala Glu
    1370                1375                1380

Asn Ile Ile His Leu Phe Thr Leu Thr Asn Leu Gly Ala Pro Ala
    1385                1390                1395

Ala Phe Lys Tyr Phe Asp Thr Thr Ile Asp Arg Lys Arg Tyr Thr
    1400                1405                1410

Ser Thr Lys Glu Val Leu Asp Ala Thr Leu Ile His Gln Ser Ile
    1415                1420                1425

Thr Gly Leu Tyr Glu Thr Arg Ile Asp Leu Ser Gln Leu Gly Gly
    1430                1435                1440

Asp Ser Arg Ala Asp Pro Lys Lys Lys Arg Lys Val
    1445                1450                1455
```

```
<210> SEQ ID NO 43
<211> LENGTH: 1455
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly Ile Asp Lys Lys
65                  70                  75                  80

Tyr Ser Ile Gly Leu Asp Ile Gly Thr Asn Ser Val Gly Trp Ala Val
                85                  90                  95

Ile Thr Asp Glu Tyr Lys Val Pro Ser Lys Lys Phe Lys Val Leu Gly
            100                 105                 110

Asn Thr Asp Arg His Ser Ile Lys Lys Asn Leu Ile Gly Ala Leu Leu
        115                 120                 125

Phe Asp Ser Gly Glu Thr Ala Glu Ala Thr Arg Leu Lys Arg Thr Ala
    130                 135                 140

Arg Arg Arg Tyr Thr Arg Arg Lys Asn Arg Ile Cys Tyr Leu Gln Glu
145                 150                 155                 160

Ile Phe Ser Asn Glu Met Ala Lys Val Asp Asp Ser Phe Phe His Arg
                165                 170                 175

Leu Glu Glu Ser Phe Leu Val Glu Glu Asp Lys Lys His Glu Arg His
            180                 185                 190

Pro Ile Phe Gly Asn Ile Val Asp Glu Val Ala Tyr His Glu Lys Tyr
        195                 200                 205

Pro Thr Ile Tyr His Leu Arg Lys Lys Leu Val Asp Ser Thr Asp Lys
    210                 215                 220

Ala Asp Leu Arg Leu Ile Tyr Leu Ala Leu Ala His Met Ile Lys Phe
225                 230                 235                 240

Arg Gly His Phe Leu Ile Glu Gly Asp Leu Asn Pro Asp Asn Ser Asp
                245                 250                 255

Val Asp Lys Leu Phe Ile Gln Leu Val Gln Thr Tyr Asn Gln Leu Phe
            260                 265                 270

Glu Glu Asn Pro Ile Asn Ala Ser Gly Val Asp Ala Lys Ala Ile Leu
        275                 280                 285

Ser Ala Arg Leu Ser Lys Ser Arg Arg Leu Glu Asn Leu Ile Ala Gln
    290                 295                 300

Leu Pro Gly Glu Lys Lys Asn Gly Leu Phe Gly Asn Leu Ile Ala Leu
305                 310                 315                 320

Ser Leu Gly Leu Thr Pro Asn Phe Lys Ser Asn Phe Asp Leu Ala Glu
                325                 330                 335

Asp Ala Lys Leu Gln Leu Ser Lys Asp Thr Tyr Asp Asp Asp Leu Asp
            340                 345                 350

Asn Leu Leu Ala Gln Ile Gly Asp Gln Tyr Ala Asp Leu Phe Leu Ala
        355                 360                 365
```

```
Ala Lys Asn Leu Ser Asp Ala Ile Leu Leu Ser Asp Ile Leu Arg Val
    370             375                 380
Asn Thr Glu Ile Thr Lys Ala Pro Leu Ser Ala Ser Met Ile Lys Arg
385             390                 395                 400
Tyr Asp Glu His His Gln Asp Leu Thr Leu Leu Lys Ala Leu Val Arg
                405                 410                 415
Gln Gln Leu Pro Glu Lys Tyr Lys Glu Ile Phe Phe Asp Gln Ser Lys
            420                 425                 430
Asn Gly Tyr Ala Gly Tyr Ile Asp Gly Gly Ala Ser Gln Glu Glu Phe
            435                 440                 445
Tyr Lys Phe Ile Lys Pro Ile Leu Glu Lys Met Asp Gly Thr Glu Glu
    450                 455                 460
Leu Leu Val Lys Leu Asn Arg Glu Asp Leu Leu Arg Lys Gln Arg Thr
465             470                 475                 480
Phe Asp Asn Gly Ser Ile Pro His Gln Ile His Leu Gly Glu Leu His
                485                 490                 495
Ala Ile Leu Arg Arg Gln Glu Asp Phe Tyr Pro Phe Leu Lys Asp Asn
            500                 505                 510
Arg Glu Lys Ile Glu Lys Ile Leu Thr Phe Arg Ile Pro Tyr Tyr Val
            515                 520                 525
Gly Pro Leu Ala Arg Gly Asn Ser Arg Phe Ala Trp Met Thr Arg Lys
            530                 535                 540
Ser Glu Glu Thr Ile Thr Pro Trp Asn Phe Glu Val Val Asp Lys
545                 550                 555                 560
Gly Ala Ser Ala Gln Ser Phe Ile Glu Arg Met Thr Asn Phe Asp Lys
                565                 570                 575
Asn Leu Pro Asn Glu Lys Val Leu Pro Lys His Ser Leu Leu Tyr Glu
            580                 585                 590
Tyr Phe Thr Val Tyr Asn Glu Leu Thr Lys Val Lys Tyr Val Thr Glu
        595                 600                 605
Gly Met Arg Lys Pro Ala Phe Leu Ser Gly Glu Gln Lys Lys Ala Ile
    610                 615                 620
Val Asp Leu Leu Phe Lys Thr Asn Arg Lys Val Thr Val Lys Gln Leu
625             630                 635                 640
Lys Glu Asp Tyr Phe Lys Lys Ile Glu Cys Phe Asp Ser Val Glu Ile
                645                 650                 655
Ser Gly Val Glu Asp Arg Phe Asn Ala Ser Leu Gly Thr Tyr His Asp
            660                 665                 670
Leu Leu Lys Ile Ile Lys Asp Lys Asp Phe Leu Asp Asn Glu Glu Asn
            675                 680                 685
Glu Asp Ile Leu Glu Asp Ile Val Leu Thr Leu Thr Leu Phe Glu Asp
    690                 695                 700
Arg Glu Met Ile Glu Glu Arg Leu Lys Thr Tyr Ala His Leu Phe Asp
705             710                 715                 720
Asp Lys Val Met Lys Gln Leu Lys Arg Arg Tyr Thr Gly Trp Gly
                725                 730                 735
Arg Leu Ser Arg Lys Leu Ile Asn Gly Ile Arg Asp Lys Gln Ser Gly
            740                 745                 750
Lys Thr Ile Leu Asp Phe Leu Lys Ser Asp Gly Phe Ala Asn Arg Asn
            755                 760                 765
Phe Met Gln Leu Ile His Asp Asp Ser Leu Thr Phe Lys Glu Asp Ile
    770                 775                 780
Gln Lys Ala Gln Val Ser Gly Gln Gly Asp Ser Leu His Glu His Ile
```

-continued

```
785                 790                 795                 800
Ala Asn Leu Ala Gly Ser Pro Ala Ile Lys Lys Gly Ile Leu Gln Thr
                    805                 810                 815
Val Lys Val Val Asp Glu Leu Val Lys Val Met Gly Arg His Lys Pro
                    820                 825                 830
Glu Asn Ile Val Ile Glu Met Ala Arg Glu Asn Gln Thr Thr Gln Lys
                    835                 840                 845
Gly Gln Lys Asn Ser Arg Glu Arg Met Lys Arg Ile Glu Glu Gly Ile
        850                 855                 860
Lys Glu Leu Gly Ser Gln Ile Leu Lys Glu His Pro Val Glu Asn Thr
865                 870                 875                 880
Gln Leu Gln Asn Glu Lys Leu Tyr Leu Tyr Tyr Leu Gln Asn Gly Arg
                    885                 890                 895
Asp Met Tyr Val Asp Gln Glu Leu Asp Ile Asn Arg Leu Ser Asp Tyr
                    900                 905                 910
Asp Val Asp His Ile Val Pro Gln Ser Phe Leu Lys Asp Asp Ser Ile
                    915                 920                 925
Asp Asn Lys Val Leu Thr Arg Ser Asp Lys Asn Arg Gly Lys Ser Asp
930                 935                 940
Asn Val Pro Ser Glu Glu Val Val Lys Lys Met Lys Asn Tyr Trp Arg
945                 950                 955                 960
Gln Leu Leu Asn Ala Lys Leu Ile Thr Gln Arg Lys Phe Asp Asn Leu
                    965                 970                 975
Thr Lys Ala Glu Arg Gly Gly Leu Ser Glu Leu Asp Lys Ala Gly Phe
                    980                 985                 990
Ile Lys Arg Gln Leu Val Glu Thr Arg Gln Ile Thr Lys His Val Ala
                    995                 1000                1005
Gln Ile Leu Asp Ser Arg Met Asn Thr Lys Tyr Asp Glu Asn Asp
        1010                1015                1020
Lys Leu Ile Arg Glu Val Lys Val Ile Thr Leu Lys Ser Lys Leu
        1025                1030                1035
Val Ser Asp Phe Arg Lys Asp Phe Gln Phe Tyr Lys Val Arg Glu
        1040                1045                1050
Ile Asn Asn Tyr His His Ala His Asp Ala Tyr Leu Asn Ala Val
        1055                1060                1065
Val Gly Thr Ala Leu Ile Lys Lys Tyr Pro Lys Leu Glu Ser Glu
        1070                1075                1080
Phe Val Tyr Gly Asp Tyr Lys Val Tyr Asp Val Arg Lys Met Ile
        1085                1090                1095
Ala Lys Ser Glu Gln Glu Ile Gly Lys Ala Thr Ala Lys Tyr Phe
        1100                1105                1110
Phe Tyr Ser Asn Ile Met Asn Phe Phe Lys Thr Glu Ile Thr Leu
        1115                1120                1125
Ala Asn Gly Glu Ile Arg Lys Arg Pro Leu Ile Glu Thr Asn Gly
        1130                1135                1140
Glu Thr Gly Glu Ile Val Trp Asp Lys Gly Arg Asp Phe Ala Thr
        1145                1150                1155
Val Arg Lys Val Leu Ser Met Pro Gln Val Asn Ile Val Lys Lys
        1160                1165                1170
Thr Glu Val Gln Thr Gly Gly Phe Ser Lys Glu Ser Ile Leu Pro
        1175                1180                1185
Lys Arg Asn Ser Asp Lys Leu Ile Ala Arg Lys Lys Asp Trp Asp
        1190                1195                1200
```

```
Pro Lys Lys Tyr Gly Gly Phe Asp Ser Pro Thr Val Ala Tyr Ser
    1205                1210                1215

Val Leu Val Val Ala Lys Val Glu Lys Gly Lys Ser Lys Lys Leu
    1220                1225                1230

Lys Ser Val Lys Glu Leu Leu Gly Ile Thr Ile Met Glu Arg Ser
    1235                1240                1245

Ser Phe Glu Lys Asn Pro Ile Asp Phe Leu Glu Ala Lys Gly Tyr
    1250                1255                1260

Lys Glu Val Lys Lys Asp Leu Ile Ile Lys Leu Pro Lys Tyr Ser
    1265                1270                1275

Leu Phe Glu Leu Glu Asn Gly Arg Lys Arg Met Leu Ala Ser Ala
    1280                1285                1290

Gly Glu Leu Gln Lys Gly Asn Glu Leu Ala Leu Pro Ser Lys Tyr
    1295                1300                1305

Val Asn Phe Leu Tyr Leu Ala Ser His Tyr Glu Lys Leu Lys Gly
    1310                1315                1320

Ser Pro Glu Asp Asn Glu Gln Lys Gln Leu Phe Val Glu Gln His
    1325                1330                1335

Lys His Tyr Leu Asp Glu Ile Ile Glu Gln Ile Ser Glu Phe Ser
    1340                1345                1350

Lys Arg Val Ile Leu Ala Asp Ala Asn Leu Asp Lys Val Leu Ser
    1355                1360                1365

Ala Tyr Asn Lys His Arg Asp Lys Pro Ile Arg Glu Gln Ala Glu
    1370                1375                1380

Asn Ile Ile His Leu Phe Thr Leu Thr Asn Leu Gly Ala Pro Ala
    1385                1390                1395

Ala Phe Lys Tyr Phe Asp Thr Thr Ile Asp Arg Lys Arg Tyr Thr
    1400                1405                1410

Ser Thr Lys Glu Val Leu Asp Ala Thr Leu Ile His Gln Ser Ile
    1415                1420                1425

Thr Gly Leu Tyr Glu Thr Arg Ile Asp Leu Ser Gln Leu Gly Gly
    1430                1435                1440

Asp Ser Arg Ala Asp Pro Lys Lys Lys Arg Lys Val
    1445                1450                1455

<210> SEQ ID NO 44
<211> LENGTH: 1455
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly Thr Asp Lys Lys
65                  70                  75                  80

Tyr Ser Ile Gly Leu Asp Ile Gly Thr Asn Ser Val Gly Trp Ala Val
```

```
                 85                  90                  95
Ile Thr Asp Glu Tyr Lys Val Pro Ser Lys Lys Phe Lys Val Leu Gly
                100                 105                 110

Asn Thr Asp Arg His Ser Ile Lys Lys Asn Leu Ile Gly Ala Leu Leu
                115                 120                 125

Phe Asp Ser Gly Glu Thr Ala Glu Ala Thr Arg Leu Lys Arg Thr Ala
                130                 135                 140

Arg Arg Arg Tyr Thr Arg Arg Lys Asn Arg Ile Cys Tyr Leu Gln Glu
145                 150                 155                 160

Ile Phe Ser Asn Glu Met Ala Lys Val Asp Asp Ser Phe Phe His Arg
                165                 170                 175

Leu Glu Glu Ser Phe Leu Val Glu Glu Asp Lys Lys His Glu Arg His
                180                 185                 190

Pro Ile Phe Gly Asn Ile Val Asp Glu Val Ala Tyr His Glu Lys Tyr
                195                 200                 205

Pro Thr Ile Tyr His Leu Arg Lys Lys Leu Val Asp Ser Thr Asp Lys
                210                 215                 220

Ala Asp Leu Arg Leu Ile Tyr Leu Ala Leu Ala His Met Ile Lys Phe
225                 230                 235                 240

Arg Gly His Phe Leu Ile Glu Gly Asp Leu Asn Pro Asp Asn Ser Asp
                245                 250                 255

Val Asp Lys Leu Phe Ile Gln Leu Val Gln Thr Tyr Asn Gln Leu Phe
                260                 265                 270

Glu Glu Asn Pro Ile Asn Ala Ser Gly Val Asp Ala Lys Ala Ile Leu
                275                 280                 285

Ser Ala Arg Leu Ser Lys Ser Arg Arg Leu Glu Asn Leu Ile Ala Gln
                290                 295                 300

Leu Pro Gly Glu Lys Lys Asn Gly Leu Phe Gly Asn Leu Ile Ala Leu
305                 310                 315                 320

Ser Leu Gly Leu Thr Pro Asn Phe Lys Ser Asn Phe Asp Leu Ala Glu
                325                 330                 335

Asp Ala Lys Leu Gln Leu Ser Lys Asp Thr Tyr Asp Asp Asp Leu Asp
                340                 345                 350

Asn Leu Leu Ala Gln Ile Gly Asp Gln Tyr Ala Asp Leu Phe Leu Ala
                355                 360                 365

Ala Lys Asn Leu Ser Asp Ala Ile Leu Leu Ser Asp Ile Leu Arg Val
                370                 375                 380

Asn Thr Glu Ile Thr Lys Ala Pro Leu Ser Ala Ser Met Ile Lys Arg
385                 390                 395                 400

Tyr Asp Glu His His Gln Asp Leu Thr Leu Leu Lys Ala Leu Val Arg
                405                 410                 415

Gln Gln Leu Pro Glu Lys Tyr Lys Glu Ile Phe Phe Asp Gln Ser Lys
                420                 425                 430

Asn Gly Tyr Ala Gly Tyr Ile Asp Gly Gly Ala Ser Gln Glu Glu Phe
                435                 440                 445

Tyr Lys Phe Ile Lys Pro Ile Leu Glu Lys Met Asp Gly Thr Glu Glu
                450                 455                 460

Leu Leu Val Lys Leu Asn Arg Glu Asp Leu Leu Arg Lys Gln Arg Thr
465                 470                 475                 480

Phe Asp Asn Gly Ser Ile Pro His Gln Ile His Leu Gly Glu Leu His
                485                 490                 495

Ala Ile Leu Arg Arg Gln Glu Asp Phe Tyr Pro Phe Leu Lys Asp Asn
                500                 505                 510
```

```
Arg Glu Lys Ile Glu Lys Ile Leu Thr Phe Arg Ile Pro Tyr Tyr Val
            515                 520                 525

Gly Pro Leu Ala Arg Gly Asn Ser Arg Phe Ala Trp Met Thr Arg Lys
        530                 535                 540

Ser Glu Glu Thr Ile Thr Pro Trp Asn Phe Glu Glu Val Val Asp Lys
545                 550                 555                 560

Gly Ala Ser Ala Gln Ser Phe Ile Glu Arg Met Thr Asn Phe Asp Lys
                565                 570                 575

Asn Leu Pro Asn Glu Lys Val Leu Pro Lys His Ser Leu Leu Tyr Glu
            580                 585                 590

Tyr Phe Thr Val Tyr Asn Glu Leu Thr Lys Val Lys Tyr Val Thr Glu
            595                 600                 605

Gly Met Arg Lys Pro Ala Phe Leu Ser Gly Glu Gln Lys Lys Ala Ile
        610                 615                 620

Val Asp Leu Leu Phe Lys Thr Asn Arg Lys Val Thr Val Lys Gln Leu
625                 630                 635                 640

Lys Glu Asp Tyr Phe Lys Lys Ile Glu Cys Phe Asp Ser Val Glu Ile
                645                 650                 655

Ser Gly Val Glu Asp Arg Phe Asn Ala Ser Leu Gly Thr Tyr His Asp
            660                 665                 670

Leu Leu Lys Ile Ile Lys Asp Lys Asp Phe Leu Asp Asn Glu Glu Asn
        675                 680                 685

Glu Asp Ile Leu Glu Asp Ile Val Leu Thr Leu Thr Leu Phe Glu Asp
        690                 695                 700

Arg Glu Met Ile Glu Glu Arg Leu Lys Thr Tyr Ala His Leu Phe Asp
705                 710                 715                 720

Asp Lys Val Met Lys Gln Leu Lys Arg Arg Arg Tyr Thr Gly Trp Gly
                725                 730                 735

Arg Leu Ser Arg Lys Leu Ile Asn Gly Ile Arg Asp Lys Gln Ser Gly
            740                 745                 750

Lys Thr Ile Leu Asp Phe Leu Lys Ser Asp Gly Phe Ala Asn Arg Asn
        755                 760                 765

Phe Met Gln Leu Ile His Asp Asp Ser Leu Thr Phe Lys Glu Asp Ile
        770                 775                 780

Gln Lys Ala Gln Val Ser Gly Gln Gly Asp Ser Leu His Glu His Ile
785                 790                 795                 800

Ala Asn Leu Ala Gly Ser Pro Ala Ile Lys Lys Gly Ile Leu Gln Thr
                805                 810                 815

Val Lys Val Val Asp Glu Leu Val Lys Val Met Gly Arg His Lys Pro
            820                 825                 830

Glu Asn Ile Val Ile Glu Met Ala Arg Glu Asn Gln Thr Thr Gln Lys
        835                 840                 845

Gly Gln Lys Asn Ser Arg Glu Arg Met Lys Arg Ile Glu Glu Gly Ile
        850                 855                 860

Lys Glu Leu Gly Ser Gln Ile Leu Lys Glu His Pro Val Glu Asn Thr
865                 870                 875                 880

Gln Leu Gln Asn Glu Lys Leu Tyr Leu Tyr Tyr Leu Gln Asn Gly Arg
                885                 890                 895

Asp Met Tyr Val Asp Gln Glu Leu Asp Ile Asn Arg Leu Ser Asp Tyr
            900                 905                 910

Asp Val Asp His Ile Val Pro Gln Ser Phe Leu Lys Asp Ser Ile
        915                 920                 925
```

```
Asp Asn Lys Val Leu Thr Arg Ser Asp Lys Asn Arg Gly Lys Ser Asp
930                 935                 940

Asn Val Pro Ser Glu Glu Val Lys Met Lys Asn Tyr Trp Arg
945                 950                 955                 960

Gln Leu Leu Asn Ala Lys Leu Ile Thr Gln Arg Lys Phe Asp Asn Leu
                965                 970                 975

Thr Lys Ala Glu Arg Gly Gly Leu Ser Glu Leu Asp Lys Ala Gly Phe
            980                 985                 990

Ile Lys Arg Gln Leu Val Glu Thr Arg Gln Ile Thr Lys His Val Ala
            995                 1000                1005

Gln Ile Leu Asp Ser Arg Met Asn Thr Lys Tyr Asp Glu Asn Asp
    1010                1015                1020

Lys Leu Ile Arg Glu Val Lys Val Ile Thr Leu Lys Ser Lys Leu
    1025                1030                1035

Val Ser Asp Phe Arg Lys Asp Phe Gln Phe Tyr Lys Val Arg Glu
    1040                1045                1050

Ile Asn Asn Tyr His His Ala His Asp Ala Tyr Leu Asn Ala Val
    1055                1060                1065

Val Gly Thr Ala Leu Ile Lys Lys Tyr Pro Lys Leu Glu Ser Glu
    1070                1075                1080

Phe Val Tyr Gly Asp Tyr Lys Val Tyr Asp Val Arg Lys Met Ile
    1085                1090                1095

Ala Lys Ser Glu Gln Glu Ile Gly Lys Ala Thr Ala Lys Tyr Phe
    1100                1105                1110

Phe Tyr Ser Asn Ile Met Asn Phe Phe Lys Thr Glu Ile Thr Leu
    1115                1120                1125

Ala Asn Gly Glu Ile Arg Lys Arg Pro Leu Ile Glu Thr Asn Gly
    1130                1135                1140

Glu Thr Gly Glu Ile Val Trp Asp Lys Gly Arg Asp Phe Ala Thr
    1145                1150                1155

Val Arg Lys Val Leu Ser Met Pro Gln Val Asn Ile Val Lys Lys
    1160                1165                1170

Thr Glu Val Gln Thr Gly Gly Phe Ser Lys Glu Ser Ile Leu Pro
    1175                1180                1185

Lys Arg Asn Ser Asp Lys Leu Ile Ala Arg Lys Lys Asp Trp Asp
    1190                1195                1200

Pro Lys Lys Tyr Gly Gly Phe Asp Ser Pro Thr Val Ala Tyr Ser
    1205                1210                1215

Val Leu Val Val Ala Lys Val Glu Lys Gly Lys Ser Lys Lys Leu
    1220                1225                1230

Lys Ser Val Lys Glu Leu Leu Gly Ile Thr Ile Met Glu Arg Ser
    1235                1240                1245

Ser Phe Glu Lys Asn Pro Ile Asp Phe Leu Glu Ala Lys Gly Tyr
    1250                1255                1260

Lys Glu Val Lys Lys Asp Leu Ile Ile Lys Leu Pro Lys Tyr Ser
    1265                1270                1275

Leu Phe Glu Leu Glu Asn Gly Arg Lys Arg Met Leu Ala Ser Ala
    1280                1285                1290

Gly Glu Leu Gln Lys Gly Asn Glu Leu Ala Leu Pro Ser Lys Tyr
    1295                1300                1305

Val Asn Phe Leu Tyr Leu Ala Ser His Tyr Glu Lys Leu Lys Gly
    1310                1315                1320

Ser Pro Glu Asp Asn Glu Gln Lys Gln Leu Phe Val Glu Gln His
```

```
                    1325                1330                1335

Lys His  Tyr Leu Asp Glu  Ile Ile Glu Gln  Ile Ser Glu Phe Ser
         1340                1345                1350

Lys Arg  Val Ile Leu Ala  Asp Ala Asn Leu  Asp Lys Val Leu Ser
         1355                1360                1365

Ala Tyr  Asn Lys His Arg  Asp Lys Pro Ile  Arg Glu Gln Ala Glu
         1370                1375                1380

Asn Ile  Ile His Leu Phe  Thr Leu Thr Asn  Leu Gly Ala Pro Ala
         1385                1390                1395

Ala Phe  Lys Tyr Phe Asp  Thr Ile Asp Arg  Lys Arg Tyr Thr
         1400                1405                1410

Ser Thr  Lys Glu Val Leu  Asp Ala Thr Leu  Ile His Gln Ser Ile
         1415                1420                1425

Thr Gly  Leu Tyr Glu Thr  Arg Ile Asp Leu  Ser Gln Leu Gly Gly
         1430                1435                1440

Asp Ser  Arg Ala Asp Pro  Lys Lys Lys Arg  Lys Val
         1445                1450                1455

<210> SEQ ID NO 45
<211> LENGTH: 1455
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly Leu Asp Lys Lys
65                  70                  75                  80

Tyr Ser Ile Gly Leu Asp Ile Gly Thr Asn Ser Val Gly Trp Ala Val
                85                  90                  95

Ile Thr Asp Glu Tyr Lys Val Pro Ser Lys Lys Phe Lys Val Leu Gly
            100                 105                 110

Asn Thr Asp Arg His Ser Ile Lys Lys Asn Leu Ile Gly Ala Leu Leu
        115                 120                 125

Phe Asp Ser Gly Glu Thr Ala Glu Ala Thr Arg Leu Lys Arg Thr Ala
    130                 135                 140

Arg Arg Arg Tyr Thr Arg Arg Lys Asn Arg Ile Cys Tyr Leu Gln Glu
145                 150                 155                 160

Ile Phe Ser Asn Glu Met Ala Lys Val Asp Asp Ser Phe Phe His Arg
                165                 170                 175

Leu Glu Glu Ser Phe Leu Val Glu Glu Asp Lys Lys His Glu Arg His
            180                 185                 190

Pro Ile Phe Gly Asn Ile Val Asp Glu Val Ala Tyr His Glu Lys Tyr
        195                 200                 205

Pro Thr Ile Tyr His Leu Arg Lys Lys Leu Val Asp Ser Thr Asp Lys
    210                 215                 220
```

-continued

```
Ala Asp Leu Arg Leu Ile Tyr Leu Ala Leu Ala His Met Ile Lys Phe
225                 230                 235                 240

Arg Gly His Phe Leu Ile Glu Gly Asp Leu Asn Pro Asp Asn Ser Asp
            245                 250                 255

Val Asp Lys Leu Phe Ile Gln Leu Val Gln Thr Tyr Asn Gln Leu Phe
        260                 265                 270

Glu Glu Asn Pro Ile Asn Ala Ser Gly Val Asp Ala Lys Ala Ile Leu
    275                 280                 285

Ser Ala Arg Leu Ser Lys Ser Arg Arg Leu Glu Asn Leu Ile Ala Gln
290                 295                 300

Leu Pro Gly Glu Lys Lys Asn Gly Leu Phe Gly Asn Leu Ile Ala Leu
305                 310                 315                 320

Ser Leu Gly Leu Thr Pro Asn Phe Lys Ser Asn Phe Asp Leu Ala Glu
            325                 330                 335

Asp Ala Lys Leu Gln Leu Ser Lys Asp Thr Tyr Asp Asp Asp Leu Asp
        340                 345                 350

Asn Leu Leu Ala Gln Ile Gly Asp Gln Tyr Ala Asp Leu Phe Leu Ala
    355                 360                 365

Ala Lys Asn Leu Ser Asp Ala Ile Leu Leu Ser Asp Ile Leu Arg Val
370                 375                 380

Asn Thr Glu Ile Thr Lys Ala Pro Leu Ser Ala Ser Met Ile Lys Arg
385                 390                 395                 400

Tyr Asp Glu His His Gln Asp Leu Thr Leu Leu Lys Ala Leu Val Arg
            405                 410                 415

Gln Gln Leu Pro Glu Lys Tyr Lys Glu Ile Phe Phe Asp Gln Ser Lys
        420                 425                 430

Asn Gly Tyr Ala Gly Tyr Ile Asp Gly Gly Ala Ser Gln Glu Glu Phe
    435                 440                 445

Tyr Lys Phe Ile Lys Pro Ile Leu Glu Lys Met Asp Gly Thr Glu Glu
450                 455                 460

Leu Leu Val Lys Leu Asn Arg Glu Asp Leu Leu Arg Lys Gln Arg Thr
465                 470                 475                 480

Phe Asp Asn Gly Ser Ile Pro His Gln Ile His Leu Gly Glu Leu His
            485                 490                 495

Ala Ile Leu Arg Arg Gln Glu Asp Phe Tyr Pro Phe Leu Lys Asp Asn
        500                 505                 510

Arg Glu Lys Ile Glu Lys Ile Leu Thr Phe Arg Ile Pro Tyr Tyr Val
    515                 520                 525

Gly Pro Leu Ala Arg Gly Asn Ser Arg Phe Ala Trp Met Thr Arg Lys
530                 535                 540

Ser Glu Glu Thr Ile Thr Pro Trp Asn Phe Glu Glu Val Val Asp Lys
545                 550                 555                 560

Gly Ala Ser Ala Gln Ser Phe Ile Glu Arg Met Thr Asn Phe Asp Lys
            565                 570                 575

Asn Leu Pro Asn Glu Lys Val Leu Pro Lys His Ser Leu Leu Tyr Glu
        580                 585                 590

Tyr Phe Thr Val Tyr Asn Glu Leu Thr Lys Val Lys Tyr Val Thr Glu
    595                 600                 605

Gly Met Arg Lys Pro Ala Phe Leu Ser Gly Glu Gln Lys Lys Ala Ile
610                 615                 620

Val Asp Leu Leu Phe Lys Thr Asn Arg Lys Val Thr Val Lys Gln Leu
625                 630                 635                 640

Lys Glu Asp Tyr Phe Lys Lys Ile Glu Cys Phe Asp Ser Val Glu Ile
```

```
                645                 650                 655
Ser Gly Val Glu Asp Arg Phe Asn Ala Ser Leu Gly Thr Tyr His Asp
                660                 665                 670

Leu Leu Lys Ile Ile Lys Asp Lys Asp Phe Leu Asp Asn Glu Glu Asn
                675                 680                 685

Glu Asp Ile Leu Glu Asp Ile Val Leu Thr Leu Thr Leu Phe Glu Asp
        690                 695                 700

Arg Glu Met Ile Glu Glu Arg Leu Lys Thr Tyr Ala His Leu Phe Asp
705                 710                 715                 720

Asp Lys Val Met Lys Gln Leu Lys Arg Arg Arg Tyr Thr Gly Trp Gly
                725                 730                 735

Arg Leu Ser Arg Lys Leu Ile Asn Gly Ile Arg Asp Lys Gln Ser Gly
                740                 745                 750

Lys Thr Ile Leu Asp Phe Leu Lys Ser Asp Gly Phe Ala Asn Arg Asn
        755                 760                 765

Phe Met Gln Leu Ile His Asp Asp Ser Leu Thr Phe Lys Glu Asp Ile
        770                 775                 780

Gln Lys Ala Gln Val Ser Gly Gln Gly Asp Ser Leu His Glu His Ile
785                 790                 795                 800

Ala Asn Leu Ala Gly Ser Pro Ala Ile Lys Lys Gly Ile Leu Gln Thr
                805                 810                 815

Val Lys Val Val Asp Glu Leu Val Lys Val Met Gly Arg His Lys Pro
                820                 825                 830

Glu Asn Ile Val Ile Glu Met Ala Arg Glu Asn Gln Thr Thr Gln Lys
        835                 840                 845

Gly Gln Lys Asn Ser Arg Glu Arg Met Lys Arg Ile Glu Glu Gly Ile
850                 855                 860

Lys Glu Leu Gly Ser Gln Ile Leu Lys Glu His Pro Val Glu Asn Thr
865                 870                 875                 880

Gln Leu Gln Asn Glu Lys Leu Tyr Leu Tyr Tyr Leu Gln Asn Gly Arg
                885                 890                 895

Asp Met Tyr Val Asp Gln Glu Leu Asp Ile Asn Arg Leu Ser Asp Tyr
                900                 905                 910

Asp Val Asp His Ile Val Pro Gln Ser Phe Leu Lys Asp Asp Ser Ile
        915                 920                 925

Asp Asn Lys Val Leu Thr Arg Ser Asp Lys Asn Arg Gly Lys Ser Asp
        930                 935                 940

Asn Val Pro Ser Glu Glu Val Val Lys Lys Met Lys Asn Tyr Trp Arg
945                 950                 955                 960

Gln Leu Leu Asn Ala Lys Leu Ile Thr Gln Arg Lys Phe Asp Asn Leu
                965                 970                 975

Thr Lys Ala Glu Arg Gly Gly Leu Ser Glu Leu Asp Lys Ala Gly Phe
                980                 985                 990

Ile Lys Arg Gln Leu Val Glu Thr Arg Gln Ile Thr Lys His Val Ala
        995                 1000                1005

Gln Ile Leu Asp Ser Arg Met Asn Thr Lys Tyr Asp Glu Asn Asp
        1010                1015                1020

Lys Leu Ile Arg Glu Val Lys Val Ile Thr Leu Lys Ser Lys Leu
        1025                1030                1035

Val Ser Asp Phe Arg Lys Asp Phe Gln Phe Tyr Lys Val Arg Glu
        1040                1045                1050

Ile Asn Asn Tyr His His Ala His Asp Ala Tyr Leu Asn Ala Val
        1055                1060                1065
```

Val Gly Thr Ala Leu Ile Lys Lys Tyr Pro Lys Leu Glu Ser Glu
1070          1075          1080

Phe Val Tyr Gly Asp Tyr Lys Val Tyr Asp Val Arg Lys Met Ile
1085          1090          1095

Ala Lys Ser Glu Gln Glu Ile Gly Lys Ala Thr Ala Lys Tyr Phe
1100          1105          1110

Phe Tyr Ser Asn Ile Met Asn Phe Phe Lys Thr Glu Ile Thr Leu
1115          1120          1125

Ala Asn Gly Glu Ile Arg Lys Arg Pro Leu Ile Glu Thr Asn Gly
1130          1135          1140

Glu Thr Gly Glu Ile Val Trp Asp Lys Gly Arg Asp Phe Ala Thr
1145          1150          1155

Val Arg Lys Val Leu Ser Met Pro Gln Val Asn Ile Val Lys Lys
1160          1165          1170

Thr Glu Val Gln Thr Gly Gly Phe Ser Lys Glu Ser Ile Leu Pro
1175          1180          1185

Lys Arg Asn Ser Asp Lys Leu Ile Ala Arg Lys Lys Asp Trp Asp
1190          1195          1200

Pro Lys Lys Tyr Gly Gly Phe Asp Ser Pro Thr Val Ala Tyr Ser
1205          1210          1215

Val Leu Val Val Ala Lys Val Glu Lys Gly Lys Ser Lys Lys Leu
1220          1225          1230

Lys Ser Val Lys Glu Leu Leu Gly Ile Thr Ile Met Glu Arg Ser
1235          1240          1245

Ser Phe Glu Lys Asn Pro Ile Asp Phe Leu Glu Ala Lys Gly Tyr
1250          1255          1260

Lys Glu Val Lys Lys Asp Leu Ile Ile Lys Leu Pro Lys Tyr Ser
1265          1270          1275

Leu Phe Glu Leu Glu Asn Gly Arg Lys Arg Met Leu Ala Ser Ala
1280          1285          1290

Gly Glu Leu Gln Lys Gly Asn Glu Leu Ala Leu Pro Ser Lys Tyr
1295          1300          1305

Val Asn Phe Leu Tyr Leu Ala Ser His Tyr Glu Lys Leu Lys Gly
1310          1315          1320

Ser Pro Glu Asp Asn Glu Gln Lys Gln Leu Phe Val Glu Gln His
1325          1330          1335

Lys His Tyr Leu Asp Glu Ile Ile Glu Gln Ile Ser Glu Phe Ser
1340          1345          1350

Lys Arg Val Ile Leu Ala Asp Ala Asn Leu Asp Lys Val Leu Ser
1355          1360          1365

Ala Tyr Asn Lys His Arg Asp Lys Pro Ile Arg Glu Gln Ala Glu
1370          1375          1380

Asn Ile Ile His Leu Phe Thr Leu Thr Asn Leu Gly Ala Pro Ala
1385          1390          1395

Ala Phe Lys Tyr Phe Asp Thr Thr Ile Asp Arg Lys Arg Tyr Thr
1400          1405          1410

Ser Thr Lys Glu Val Leu Asp Ala Thr Leu Ile His Gln Ser Ile
1415          1420          1425

Thr Gly Leu Tyr Glu Thr Arg Ile Asp Leu Ser Gln Leu Gly Gly
1430          1435          1440

Asp Ser Arg Ala Asp Pro Lys Lys Lys Arg Lys Val
1445          1450          1455

<210> SEQ ID NO 46
<211> LENGTH: 1455
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 46

```
Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly Ala Asp Lys Lys
65                  70                  75                  80

Tyr Ser Ile Gly Leu Asp Ile Gly Thr Asn Ser Val Gly Trp Ala Val
                85                  90                  95

Ile Thr Asp Glu Tyr Lys Val Pro Ser Lys Lys Phe Lys Val Leu Gly
            100                 105                 110

Asn Thr Asp Arg His Ser Ile Lys Lys Asn Leu Ile Gly Ala Leu Leu
        115                 120                 125

Phe Asp Ser Gly Glu Thr Ala Glu Ala Thr Arg Leu Lys Arg Thr Ala
    130                 135                 140

Arg Arg Arg Tyr Thr Arg Arg Lys Asn Arg Ile Cys Tyr Leu Gln Glu
145                 150                 155                 160

Ile Phe Ser Asn Glu Met Ala Lys Val Asp Asp Ser Phe Phe His Arg
                165                 170                 175

Leu Glu Glu Ser Phe Leu Val Glu Glu Asp Lys Lys His Glu Arg His
            180                 185                 190

Pro Ile Phe Gly Asn Ile Val Asp Glu Val Ala Tyr His Glu Lys Tyr
        195                 200                 205

Pro Thr Ile Tyr His Leu Arg Lys Lys Leu Val Asp Ser Thr Asp Lys
    210                 215                 220

Ala Asp Leu Arg Leu Ile Tyr Leu Ala Leu Ala His Met Ile Lys Phe
225                 230                 235                 240

Arg Gly His Phe Leu Ile Glu Gly Asp Leu Asn Pro Asp Asn Ser Asp
                245                 250                 255

Val Asp Lys Leu Phe Ile Gln Leu Val Gln Thr Tyr Asn Gln Leu Phe
            260                 265                 270

Glu Glu Asn Pro Ile Asn Ala Ser Gly Val Asp Ala Lys Ala Ile Leu
        275                 280                 285

Ser Ala Arg Leu Ser Lys Ser Arg Arg Leu Glu Asn Leu Ile Ala Gln
    290                 295                 300

Leu Pro Gly Glu Lys Lys Asn Gly Leu Phe Gly Asn Leu Ile Ala Leu
305                 310                 315                 320

Ser Leu Gly Leu Thr Pro Asn Phe Lys Ser Asn Phe Asp Leu Ala Glu
                325                 330                 335

Asp Ala Lys Leu Gln Leu Ser Lys Asp Thr Tyr Asp Asp Asp Leu Asp
            340                 345                 350

Asn Leu Leu Ala Gln Ile Gly Asp Gln Tyr Ala Asp Leu Phe Leu Ala
        355                 360                 365
```

```
Ala Lys Asn Leu Ser Asp Ala Ile Leu Leu Ser Asp Ile Leu Arg Val
    370                 375                 380

Asn Thr Glu Ile Thr Lys Ala Pro Leu Ser Ala Ser Met Ile Lys Arg
385                 390                 395                 400

Tyr Asp Glu His His Gln Asp Leu Thr Leu Leu Lys Ala Leu Val Arg
                405                 410                 415

Gln Gln Leu Pro Glu Lys Tyr Lys Glu Ile Phe Phe Asp Gln Ser Lys
            420                 425                 430

Asn Gly Tyr Ala Gly Tyr Ile Asp Gly Gly Ala Ser Gln Glu Glu Phe
        435                 440                 445

Tyr Lys Phe Ile Lys Pro Ile Leu Glu Lys Met Asp Gly Thr Glu Glu
    450                 455                 460

Leu Leu Val Lys Leu Asn Arg Glu Asp Leu Leu Arg Lys Gln Arg Thr
465                 470                 475                 480

Phe Asp Asn Gly Ser Ile Pro His Gln Ile His Leu Gly Glu Leu His
                485                 490                 495

Ala Ile Leu Arg Arg Gln Glu Asp Phe Tyr Pro Phe Leu Lys Asp Asn
            500                 505                 510

Arg Glu Lys Ile Glu Lys Ile Leu Thr Phe Arg Ile Pro Tyr Tyr Val
        515                 520                 525

Gly Pro Leu Ala Arg Gly Asn Ser Arg Phe Ala Trp Met Thr Arg Lys
    530                 535                 540

Ser Glu Glu Thr Ile Thr Pro Trp Asn Phe Glu Val Val Asp Lys
545                 550                 555                 560

Gly Ala Ser Ala Gln Ser Phe Ile Glu Arg Met Thr Asn Phe Asp Lys
                565                 570                 575

Asn Leu Pro Asn Glu Lys Val Leu Pro Lys His Ser Leu Leu Tyr Glu
            580                 585                 590

Tyr Phe Thr Val Tyr Asn Glu Leu Thr Lys Val Lys Tyr Val Thr Glu
        595                 600                 605

Gly Met Arg Lys Pro Ala Phe Leu Ser Gly Glu Gln Lys Lys Ala Ile
    610                 615                 620

Val Asp Leu Leu Phe Lys Thr Asn Arg Lys Val Thr Val Lys Gln Leu
625                 630                 635                 640

Lys Glu Asp Tyr Phe Lys Lys Ile Glu Cys Phe Asp Ser Val Glu Ile
                645                 650                 655

Ser Gly Val Glu Asp Arg Phe Asn Ala Ser Leu Gly Thr Tyr His Asp
            660                 665                 670

Leu Leu Lys Ile Ile Lys Asp Lys Asp Phe Leu Asp Asn Glu Glu Asn
        675                 680                 685

Glu Asp Ile Leu Glu Asp Ile Val Leu Thr Leu Thr Leu Phe Glu Asp
    690                 695                 700

Arg Glu Met Ile Glu Glu Arg Leu Lys Thr Tyr Ala His Leu Phe Asp
705                 710                 715                 720

Asp Lys Val Met Lys Gln Leu Lys Arg Arg Tyr Thr Gly Trp Gly
                725                 730                 735

Arg Leu Ser Arg Lys Leu Ile Asn Gly Ile Arg Asp Lys Gln Ser Gly
            740                 745                 750

Lys Thr Ile Leu Asp Phe Leu Lys Ser Asp Gly Phe Ala Asn Arg Asn
        755                 760                 765

Phe Met Gln Leu Ile His Asp Asp Ser Leu Thr Phe Lys Glu Asp Ile
    770                 775                 780
```

```
Gln Lys Ala Gln Val Ser Gly Gln Gly Asp Ser Leu His Glu His Ile
785                 790                 795                 800

Ala Asn Leu Ala Gly Ser Pro Ala Ile Lys Lys Gly Ile Leu Gln Thr
            805                 810                 815

Val Lys Val Val Asp Glu Leu Val Lys Val Met Gly Arg His Lys Pro
            820                 825                 830

Glu Asn Ile Val Ile Glu Met Ala Arg Glu Asn Gln Thr Thr Gln Lys
        835                 840                 845

Gly Gln Lys Asn Ser Arg Glu Arg Met Lys Arg Ile Glu Glu Gly Ile
850                 855                 860

Lys Glu Leu Gly Ser Gln Ile Leu Lys Glu His Pro Val Glu Asn Thr
865                 870                 875                 880

Gln Leu Gln Asn Glu Lys Leu Tyr Leu Tyr Tyr Leu Gln Asn Gly Arg
            885                 890                 895

Asp Met Tyr Val Asp Gln Glu Leu Asp Ile Asn Arg Leu Ser Asp Tyr
            900                 905                 910

Asp Val Asp His Ile Val Pro Gln Ser Phe Leu Lys Asp Asp Ser Ile
            915                 920                 925

Asp Asn Lys Val Leu Thr Arg Ser Asp Lys Asn Arg Gly Lys Ser Asp
930                 935                 940

Asn Val Pro Ser Glu Glu Val Val Lys Lys Met Lys Asn Tyr Trp Arg
945                 950                 955                 960

Gln Leu Leu Asn Ala Lys Leu Ile Thr Gln Arg Lys Phe Asp Asn Leu
            965                 970                 975

Thr Lys Ala Glu Arg Gly Gly Leu Ser Glu Leu Asp Lys Ala Gly Phe
            980                 985                 990

Ile Lys Arg Gln Leu Val Glu Thr Arg Gln Ile Thr Lys His Val Ala
            995                 1000                1005

Gln Ile Leu Asp Ser Arg Met Asn Thr Lys Tyr Asp Glu Asn Asp
        1010                1015                1020

Lys Leu Ile Arg Glu Val Lys Val Ile Thr Leu Lys Ser Lys Leu
        1025                1030                1035

Val Ser Asp Phe Arg Lys Asp Phe Gln Phe Tyr Lys Val Arg Glu
        1040                1045                1050

Ile Asn Asn Tyr His His Ala His Asp Ala Tyr Leu Asn Ala Val
        1055                1060                1065

Val Gly Thr Ala Leu Ile Lys Lys Tyr Pro Lys Leu Glu Ser Glu
        1070                1075                1080

Phe Val Tyr Gly Asp Tyr Lys Val Tyr Asp Val Arg Lys Met Ile
        1085                1090                1095

Ala Lys Ser Glu Gln Glu Ile Gly Lys Ala Thr Ala Lys Tyr Phe
        1100                1105                1110

Phe Tyr Ser Asn Ile Met Asn Phe Phe Lys Thr Glu Ile Thr Leu
        1115                1120                1125

Ala Asn Gly Glu Ile Arg Lys Arg Pro Leu Ile Glu Thr Asn Gly
        1130                1135                1140

Glu Thr Gly Glu Ile Val Trp Asp Lys Gly Arg Asp Phe Ala Thr
        1145                1150                1155

Val Arg Lys Val Leu Ser Met Pro Gln Val Asn Ile Val Lys Lys
        1160                1165                1170

Thr Glu Val Gln Thr Gly Gly Phe Ser Lys Glu Ser Ile Leu Pro
        1175                1180                1185

Lys Arg Asn Ser Asp Lys Leu Ile Ala Arg Lys Lys Asp Trp Asp
```

```
                1190               1195               1200

Pro Lys Lys Tyr Gly Gly Phe Asp Ser Pro Thr Val Ala Tyr Ser
    1205                1210                1215

Val Leu Val Val Ala Lys Val Glu Lys Gly Lys Ser Lys Lys Leu
    1220                1225                1230

Lys Ser Val Lys Glu Leu Leu Gly Ile Thr Ile Met Glu Arg Ser
    1235                1240                1245

Ser Phe Glu Lys Asn Pro Ile Asp Phe Leu Glu Ala Lys Gly Tyr
    1250                1255                1260

Lys Glu Val Lys Lys Asp Leu Ile Ile Lys Leu Pro Lys Tyr Ser
    1265                1270                1275

Leu Phe Glu Leu Glu Asn Gly Arg Lys Arg Met Leu Ala Ser Ala
    1280                1285                1290

Gly Glu Leu Gln Lys Gly Asn Glu Leu Ala Leu Pro Ser Lys Tyr
    1295                1300                1305

Val Asn Phe Leu Tyr Leu Ala Ser His Tyr Glu Lys Leu Lys Gly
    1310                1315                1320

Ser Pro Glu Asp Asn Glu Gln Lys Gln Leu Phe Val Glu Gln His
    1325                1330                1335

Lys His Tyr Leu Asp Glu Ile Ile Glu Gln Ile Ser Glu Phe Ser
    1340                1345                1350

Lys Arg Val Ile Leu Ala Asp Ala Asn Leu Asp Lys Val Leu Ser
    1355                1360                1365

Ala Tyr Asn Lys His Arg Asp Lys Pro Ile Arg Glu Gln Ala Glu
    1370                1375                1380

Asn Ile Ile His Leu Phe Thr Leu Thr Asn Leu Gly Ala Pro Ala
    1385                1390                1395

Ala Phe Lys Tyr Phe Asp Thr Thr Ile Asp Arg Lys Arg Tyr Thr
    1400                1405                1410

Ser Thr Lys Glu Val Leu Asp Ala Thr Leu Ile His Gln Ser Ile
    1415                1420                1425

Thr Gly Leu Tyr Glu Thr Arg Ile Asp Leu Ser Gln Leu Gly Gly
    1430                1435                1440

Asp Ser Arg Ala Asp Pro Lys Lys Lys Arg Lys Val
    1445                1450                1455

<210> SEQ ID NO 47
<211> LENGTH: 1455
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
                20                  25                  30

Lys Glu Gly Ile Pro Pro Asp Gln Gln Arg Leu Ile Phe Ala Gly Lys
            35                  40                  45

Gln Leu Glu Asp Gly Arg Thr Leu Ser Asp Tyr Asn Ile Gln Lys Glu
        50                  55                  60

Ser Thr Leu His Leu Val Leu Arg Leu Arg Gly Gly His Asp Lys Lys
65                  70                  75                  80
```

```
Tyr Ser Ile Gly Leu Asp Ile Gly Thr Asn Ser Val Gly Trp Ala Val
             85                  90                  95
Ile Thr Asp Glu Tyr Lys Val Pro Ser Lys Lys Phe Lys Val Leu Gly
            100                 105                 110
Asn Thr Asp Arg His Ser Ile Lys Lys Asn Leu Ile Gly Ala Leu Leu
            115                 120                 125
Phe Asp Ser Gly Glu Thr Ala Glu Ala Thr Arg Leu Lys Arg Thr Ala
            130                 135                 140
Arg Arg Arg Tyr Thr Arg Arg Lys Asn Arg Ile Cys Tyr Leu Gln Glu
145                 150                 155                 160
Ile Phe Ser Asn Glu Met Ala Lys Val Asp Asp Ser Phe Phe His Arg
                165                 170                 175
Leu Glu Glu Ser Phe Leu Val Glu Glu Asp Lys Lys His Glu Arg His
                180                 185                 190
Pro Ile Phe Gly Asn Ile Val Asp Glu Val Ala Tyr His Glu Lys Tyr
            195                 200                 205
Pro Thr Ile Tyr His Leu Arg Lys Lys Leu Val Asp Ser Thr Asp Lys
            210                 215                 220
Ala Asp Leu Arg Leu Ile Tyr Leu Ala Leu Ala His Met Ile Lys Phe
225                 230                 235                 240
Arg Gly His Phe Leu Ile Glu Gly Asp Leu Asn Pro Asp Asn Ser Asp
                245                 250                 255
Val Asp Lys Leu Phe Ile Gln Leu Val Gln Thr Tyr Asn Gln Leu Phe
            260                 265                 270
Glu Glu Asn Pro Ile Asn Ala Ser Gly Val Asp Ala Lys Ala Ile Leu
            275                 280                 285
Ser Ala Arg Leu Ser Lys Ser Arg Arg Leu Glu Asn Leu Ile Ala Gln
            290                 295                 300
Leu Pro Gly Glu Lys Lys Asn Gly Leu Phe Gly Asn Leu Ile Ala Leu
305                 310                 315                 320
Ser Leu Gly Leu Thr Pro Asn Phe Lys Ser Asn Phe Asp Leu Ala Glu
                325                 330                 335
Asp Ala Lys Leu Gln Leu Ser Lys Asp Thr Tyr Asp Asp Asp Leu Asp
                340                 345                 350
Asn Leu Leu Ala Gln Ile Gly Asp Gln Tyr Ala Asp Leu Phe Leu Ala
            355                 360                 365
Ala Lys Asn Leu Ser Asp Ala Ile Leu Leu Ser Asp Ile Leu Arg Val
            370                 375                 380
Asn Thr Glu Ile Thr Lys Ala Pro Leu Ser Ala Ser Met Ile Lys Arg
385                 390                 395                 400
Tyr Asp Glu His His Gln Asp Leu Thr Leu Leu Lys Ala Leu Val Arg
                405                 410                 415
Gln Gln Leu Pro Glu Lys Tyr Lys Glu Ile Phe Phe Asp Gln Ser Lys
                420                 425                 430
Asn Gly Tyr Ala Gly Tyr Ile Asp Gly Gly Ala Ser Gln Glu Glu Phe
            435                 440                 445
Tyr Lys Phe Ile Lys Pro Ile Leu Glu Lys Met Asp Gly Thr Glu Glu
            450                 455                 460
Leu Leu Val Lys Leu Asn Arg Glu Asp Leu Leu Arg Lys Gln Arg Thr
465                 470                 475                 480
Phe Asp Asn Gly Ser Ile Pro His Gln Ile His Leu Gly Glu Leu His
                485                 490                 495
Ala Ile Leu Arg Arg Gln Glu Asp Phe Tyr Pro Phe Leu Lys Asp Asn
```

```
                500                 505                 510
Arg Glu Lys Ile Glu Lys Ile Leu Thr Phe Arg Ile Pro Tyr Tyr Val
            515                 520                 525

Gly Pro Leu Ala Arg Gly Asn Ser Arg Phe Ala Trp Met Thr Arg Lys
        530                 535                 540

Ser Glu Glu Thr Ile Thr Pro Trp Asn Phe Glu Val Val Asp Lys
545                 550                 555                 560

Gly Ala Ser Ala Gln Ser Phe Ile Glu Arg Met Thr Asn Phe Asp Lys
            565                 570                 575

Asn Leu Pro Asn Glu Lys Val Leu Pro Lys His Ser Leu Leu Tyr Glu
        580                 585                 590

Tyr Phe Thr Val Tyr Asn Glu Leu Thr Lys Val Lys Tyr Val Thr Glu
    595                 600                 605

Gly Met Arg Lys Pro Ala Phe Leu Ser Gly Glu Gln Lys Lys Ala Ile
        610                 615                 620

Val Asp Leu Leu Phe Lys Thr Asn Arg Lys Val Thr Val Lys Gln Leu
625                 630                 635                 640

Lys Glu Asp Tyr Phe Lys Lys Ile Glu Cys Phe Asp Ser Val Glu Ile
            645                 650                 655

Ser Gly Val Glu Asp Arg Phe Asn Ala Ser Leu Gly Thr Tyr His Asp
        660                 665                 670

Leu Leu Lys Ile Ile Lys Asp Lys Asp Phe Leu Asp Asn Glu Glu Asn
        675                 680                 685

Glu Asp Ile Leu Glu Asp Ile Val Leu Thr Leu Thr Leu Phe Glu Asp
    690                 695                 700

Arg Glu Met Ile Glu Glu Arg Leu Lys Thr Tyr Ala His Leu Phe Asp
705                 710                 715                 720

Asp Lys Val Met Lys Gln Leu Lys Arg Arg Arg Tyr Thr Gly Trp Gly
            725                 730                 735

Arg Leu Ser Arg Lys Leu Ile Asn Gly Ile Arg Asp Lys Gln Ser Gly
        740                 745                 750

Lys Thr Ile Leu Asp Phe Leu Lys Ser Asp Gly Phe Ala Asn Arg Asn
        755                 760                 765

Phe Met Gln Leu Ile His Asp Asp Ser Leu Thr Phe Lys Glu Asp Ile
    770                 775                 780

Gln Lys Ala Gln Val Ser Gly Gln Gly Asp Ser Leu His Glu His Ile
785                 790                 795                 800

Ala Asn Leu Ala Gly Ser Pro Ala Ile Lys Lys Gly Ile Leu Gln Thr
            805                 810                 815

Val Lys Val Val Asp Glu Leu Val Lys Val Met Gly Arg His Lys Pro
        820                 825                 830

Glu Asn Ile Val Ile Glu Met Ala Arg Glu Asn Gln Thr Thr Gln Lys
        835                 840                 845

Gly Gln Lys Asn Ser Arg Glu Arg Met Lys Arg Ile Glu Glu Gly Ile
    850                 855                 860

Lys Glu Leu Gly Ser Gln Ile Leu Lys Glu His Pro Val Glu Asn Thr
865                 870                 875                 880

Gln Leu Gln Asn Glu Lys Leu Tyr Leu Tyr Tyr Leu Gln Asn Gly Arg
            885                 890                 895

Asp Met Tyr Val Asp Gln Glu Leu Asp Ile Asn Arg Leu Ser Asp Tyr
        900                 905                 910

Asp Val Asp His Ile Val Pro Gln Ser Phe Leu Lys Asp Asp Ser Ile
        915                 920                 925
```

```
Asp Asn Lys Val Leu Thr Arg Ser Asp Lys Asn Arg Gly Lys Ser Asp
        930                 935                 940

Asn Val Pro Ser Glu Glu Val Val Lys Lys Met Lys Asn Tyr Trp Arg
945                 950                 955                 960

Gln Leu Leu Asn Ala Lys Leu Ile Thr Gln Arg Lys Phe Asp Asn Leu
            965                 970                 975

Thr Lys Ala Glu Arg Gly Gly Leu Ser Glu Leu Asp Lys Ala Gly Phe
                980                 985                 990

Ile Lys Arg Gln Leu Val Glu Thr Arg Gln Ile Thr Lys His Val Ala
        995                 1000                1005

Gln Ile Leu Asp Ser Arg Met Asn Thr Lys Tyr Asp Glu Asn Asp
    1010                1015                1020

Lys Leu Ile Arg Glu Val Lys Val Ile Thr Leu Lys Ser Lys Leu
    1025                1030                1035

Val Ser Asp Phe Arg Lys Asp Phe Gln Phe Tyr Lys Val Arg Glu
    1040                1045                1050

Ile Asn Asn Tyr His His Ala His Asp Ala Tyr Leu Asn Ala Val
    1055                1060                1065

Val Gly Thr Ala Leu Ile Lys Lys Tyr Pro Lys Leu Glu Ser Glu
    1070                1075                1080

Phe Val Tyr Gly Asp Tyr Lys Val Tyr Asp Val Arg Lys Met Ile
    1085                1090                1095

Ala Lys Ser Glu Gln Glu Ile Gly Lys Ala Thr Ala Lys Tyr Phe
    1100                1105                1110

Phe Tyr Ser Asn Ile Met Asn Phe Phe Lys Thr Glu Ile Thr Leu
    1115                1120                1125

Ala Asn Gly Glu Ile Arg Lys Arg Pro Leu Ile Glu Thr Asn Gly
    1130                1135                1140

Glu Thr Gly Glu Ile Val Trp Asp Lys Gly Arg Asp Phe Ala Thr
    1145                1150                1155

Val Arg Lys Val Leu Ser Met Pro Gln Val Asn Ile Val Lys Lys
    1160                1165                1170

Thr Glu Val Gln Thr Gly Gly Phe Ser Lys Glu Ser Ile Leu Pro
    1175                1180                1185

Lys Arg Asn Ser Asp Lys Leu Ile Ala Arg Lys Lys Asp Trp Asp
    1190                1195                1200

Pro Lys Lys Tyr Gly Gly Phe Asp Ser Pro Thr Val Ala Tyr Ser
    1205                1210                1215

Val Leu Val Val Ala Lys Val Glu Lys Gly Lys Ser Lys Lys Leu
    1220                1225                1230

Lys Ser Val Lys Glu Leu Leu Gly Ile Thr Ile Met Glu Arg Ser
    1235                1240                1245

Ser Phe Glu Lys Asn Pro Ile Asp Phe Leu Glu Ala Lys Gly Tyr
    1250                1255                1260

Lys Glu Val Lys Lys Asp Leu Ile Ile Lys Leu Pro Lys Tyr Ser
    1265                1270                1275

Leu Phe Glu Leu Glu Asn Gly Arg Lys Arg Met Leu Ala Ser Ala
    1280                1285                1290

Gly Glu Leu Gln Lys Gly Asn Glu Leu Ala Leu Pro Ser Lys Tyr
    1295                1300                1305

Val Asn Phe Leu Tyr Leu Ala Ser His Tyr Glu Lys Leu Lys Gly
    1310                1315                1320
```

```
Ser Pro Glu Asp Asn Glu Gln Lys Gln Leu Phe Val Glu Gln His
    1325                1330                1335

Lys His Tyr Leu Asp Glu Ile Ile Glu Gln Ile Ser Glu Phe Ser
    1340                1345                1350

Lys Arg Val Ile Leu Ala Asp Ala Asn Leu Asp Lys Val Leu Ser
    1355                1360                1365

Ala Tyr Asn Lys His Arg Asp Lys Pro Ile Arg Glu Gln Ala Glu
    1370                1375                1380

Asn Ile Ile His Leu Phe Thr Leu Thr Asn Leu Gly Ala Pro Ala
    1385                1390                1395

Ala Phe Lys Tyr Phe Asp Thr Thr Ile Asp Arg Lys Arg Tyr Thr
    1400                1405                1410

Ser Thr Lys Glu Val Leu Asp Ala Thr Leu Ile His Gln Ser Ile
    1415                1420                1425

Thr Gly Leu Tyr Glu Thr Arg Ile Asp Leu Ser Gln Leu Gly Gly
    1430                1435                1440

Asp Ser Arg Ala Asp Pro Lys Lys Lys Arg Lys Val
    1445                1450                1455

<210> SEQ ID NO 48
<211> LENGTH: 1455
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly Trp Asp Lys Lys
65                  70                  75                  80

Tyr Ser Ile Gly Leu Asp Ile Gly Thr Asn Ser Val Gly Trp Ala Val
                85                  90                  95

Ile Thr Asp Glu Tyr Lys Val Pro Ser Lys Lys Phe Lys Val Leu Gly
            100                 105                 110

Asn Thr Asp Arg His Ser Ile Lys Lys Asn Leu Ile Gly Ala Leu Leu
        115                 120                 125

Phe Asp Ser Gly Glu Thr Ala Glu Ala Thr Arg Leu Lys Arg Thr Ala
    130                 135                 140

Arg Arg Arg Tyr Thr Arg Arg Lys Asn Arg Ile Cys Tyr Leu Gln Glu
145                 150                 155                 160

Ile Phe Ser Asn Glu Met Ala Lys Val Asp Asp Ser Phe Phe His Arg
                165                 170                 175

Leu Glu Glu Ser Phe Leu Val Glu Glu Asp Lys Lys His Glu Arg His
            180                 185                 190

Pro Ile Phe Gly Asn Ile Val Asp Glu Val Ala Tyr His Glu Lys Tyr
        195                 200                 205

Pro Thr Ile Tyr His Leu Arg Lys Lys Leu Val Asp Ser Thr Asp Lys
    210                 215                 220
```

```
Ala Asp Leu Arg Leu Ile Tyr Leu Ala Leu Ala His Met Ile Lys Phe
225                 230                 235                 240

Arg Gly His Phe Leu Ile Glu Gly Asp Leu Asn Pro Asp Asn Ser Asp
            245                 250                 255

Val Asp Lys Leu Phe Ile Gln Leu Val Gln Thr Tyr Asn Gln Leu Phe
            260                 265                 270

Glu Glu Asn Pro Ile Asn Ala Ser Gly Val Asp Ala Lys Ala Ile Leu
            275                 280                 285

Ser Ala Arg Leu Ser Lys Ser Arg Arg Leu Glu Asn Leu Ile Ala Gln
290                 295                 300

Leu Pro Gly Glu Lys Lys Asn Gly Leu Phe Gly Asn Leu Ile Ala Leu
305                 310                 315                 320

Ser Leu Gly Leu Thr Pro Asn Phe Lys Ser Asn Phe Asp Leu Ala Glu
            325                 330                 335

Asp Ala Lys Leu Gln Leu Ser Lys Asp Thr Tyr Asp Asp Asp Leu Asp
            340                 345                 350

Asn Leu Leu Ala Gln Ile Gly Asp Gln Tyr Ala Asp Leu Phe Leu Ala
            355                 360                 365

Ala Lys Asn Leu Ser Asp Ala Ile Leu Leu Ser Asp Ile Leu Arg Val
370                 375                 380

Asn Thr Glu Ile Thr Lys Ala Pro Leu Ser Ala Ser Met Ile Lys Arg
385                 390                 395                 400

Tyr Asp Glu His His Gln Asp Leu Thr Leu Leu Lys Ala Leu Val Arg
            405                 410                 415

Gln Gln Leu Pro Glu Lys Tyr Lys Glu Ile Phe Phe Asp Gln Ser Lys
            420                 425                 430

Asn Gly Tyr Ala Gly Tyr Ile Asp Gly Gly Ala Ser Gln Glu Glu Phe
            435                 440                 445

Tyr Lys Phe Ile Lys Pro Ile Leu Glu Lys Met Asp Gly Thr Glu Glu
450                 455                 460

Leu Leu Val Lys Leu Asn Arg Glu Asp Leu Leu Arg Lys Gln Arg Thr
465                 470                 475                 480

Phe Asp Asn Gly Ser Ile Pro His Gln Ile His Leu Gly Glu Leu His
            485                 490                 495

Ala Ile Leu Arg Arg Gln Glu Asp Phe Tyr Pro Phe Leu Lys Asp Asn
            500                 505                 510

Arg Glu Lys Ile Glu Lys Ile Leu Thr Phe Arg Ile Pro Tyr Tyr Val
            515                 520                 525

Gly Pro Leu Ala Arg Gly Asn Ser Arg Phe Ala Trp Met Thr Arg Lys
            530                 535                 540

Ser Glu Glu Thr Ile Thr Pro Trp Asn Phe Glu Glu Val Val Asp Lys
545                 550                 555                 560

Gly Ala Ser Ala Gln Ser Phe Ile Glu Arg Met Thr Asn Phe Asp Lys
            565                 570                 575

Asn Leu Pro Asn Glu Lys Val Leu Pro Lys His Ser Leu Leu Tyr Glu
            580                 585                 590

Tyr Phe Thr Val Tyr Asn Glu Leu Thr Lys Val Lys Tyr Val Thr Glu
            595                 600                 605

Gly Met Arg Lys Pro Ala Phe Leu Ser Gly Glu Gln Lys Lys Ala Ile
            610                 615                 620

Val Asp Leu Leu Phe Lys Thr Asn Arg Lys Val Thr Val Lys Gln Leu
625                 630                 635                 640
```

-continued

```
Lys Glu Asp Tyr Phe Lys Lys Ile Glu Cys Phe Asp Ser Val Glu Ile
            645                 650                 655

Ser Gly Val Glu Asp Arg Phe Asn Ala Ser Leu Gly Thr Tyr His Asp
            660                 665                 670

Leu Leu Lys Ile Ile Lys Asp Lys Asp Phe Leu Asp Asn Glu Glu Asn
            675                 680                 685

Glu Asp Ile Leu Glu Asp Ile Val Leu Thr Leu Thr Leu Phe Glu Asp
            690                 695                 700

Arg Glu Met Ile Glu Glu Arg Leu Lys Thr Tyr Ala His Leu Phe Asp
705                 710                 715                 720

Asp Lys Val Met Lys Gln Leu Lys Arg Arg Tyr Thr Gly Trp Gly
                725                 730                 735

Arg Leu Ser Arg Lys Leu Ile Asn Gly Ile Arg Asp Lys Gln Ser Gly
            740                 745                 750

Lys Thr Ile Leu Asp Phe Leu Lys Ser Asp Gly Phe Ala Asn Arg Asn
            755                 760                 765

Phe Met Gln Leu Ile His Asp Asp Ser Leu Thr Phe Lys Glu Asp Ile
770                 775                 780

Gln Lys Ala Gln Val Ser Gly Gln Gly Asp Ser Leu His Glu His Ile
785                 790                 795                 800

Ala Asn Leu Ala Gly Ser Pro Ala Ile Lys Lys Gly Ile Leu Gln Thr
            805                 810                 815

Val Lys Val Val Asp Glu Leu Val Lys Val Met Gly Arg His Lys Pro
            820                 825                 830

Glu Asn Ile Val Ile Glu Met Ala Arg Glu Asn Gln Thr Thr Gln Lys
            835                 840                 845

Gly Gln Lys Asn Ser Arg Glu Arg Met Lys Arg Ile Glu Glu Gly Ile
850                 855                 860

Lys Glu Leu Gly Ser Gln Ile Leu Lys Glu His Pro Val Glu Asn Thr
865                 870                 875                 880

Gln Leu Gln Asn Glu Lys Leu Tyr Leu Tyr Tyr Leu Gln Asn Gly Arg
            885                 890                 895

Asp Met Tyr Val Asp Gln Glu Leu Asp Ile Asn Arg Leu Ser Asp Tyr
            900                 905                 910

Asp Val Asp His Ile Val Pro Gln Ser Phe Leu Lys Asp Asp Ser Ile
            915                 920                 925

Asp Asn Lys Val Leu Thr Arg Ser Asp Lys Asn Arg Gly Lys Ser Asp
            930                 935                 940

Asn Val Pro Ser Glu Glu Val Val Lys Lys Met Lys Asn Tyr Trp Arg
945                 950                 955                 960

Gln Leu Leu Asn Ala Lys Leu Ile Thr Gln Arg Lys Phe Asp Asn Leu
            965                 970                 975

Thr Lys Ala Glu Arg Gly Gly Leu Ser Glu Leu Asp Lys Ala Gly Phe
            980                 985                 990

Ile Lys Arg Gln Leu Val Glu Thr Arg Gln Ile Thr Lys His Val Ala
            995                 1000                1005

Gln Ile Leu Asp Ser Arg Met Asn Thr Lys Tyr Asp Glu Asn Asp
            1010                1015                1020

Lys Leu Ile Arg Glu Val Lys Val Ile Thr Leu Lys Ser Lys Leu
            1025                1030                1035

Val Ser Asp Phe Arg Lys Asp Phe Gln Phe Tyr Lys Val Arg Glu
            1040                1045                1050

Ile Asn Asn Tyr His His Ala His Asp Ala Tyr Leu Asn Ala Val
```

```
                    1055                1060                1065
Val  Gly  Thr  Ala  Leu  Ile  Lys  Lys  Tyr  Pro  Lys  Leu  Glu  Ser  Glu
                    1070                1075                1080

Phe  Val  Tyr  Gly  Asp  Tyr  Lys  Val  Tyr  Asp  Val  Arg  Lys  Met  Ile
                    1085                1090                1095

Ala  Lys  Ser  Glu  Gln  Glu  Ile  Gly  Lys  Ala  Thr  Ala  Lys  Tyr  Phe
                    1100                1105                1110

Phe  Tyr  Ser  Asn  Ile  Met  Asn  Phe  Phe  Lys  Thr  Glu  Ile  Thr  Leu
                    1115                1120                1125

Ala  Asn  Gly  Glu  Ile  Arg  Lys  Arg  Pro  Leu  Ile  Glu  Thr  Asn  Gly
                    1130                1135                1140

Glu  Thr  Gly  Glu  Ile  Val  Trp  Asp  Lys  Gly  Arg  Asp  Phe  Ala  Thr
                    1145                1150                1155

Val  Arg  Lys  Val  Leu  Ser  Met  Pro  Gln  Val  Asn  Ile  Val  Lys  Lys
                    1160                1165                1170

Thr  Glu  Val  Gln  Thr  Gly  Gly  Phe  Ser  Lys  Glu  Ser  Ile  Leu  Pro
                    1175                1180                1185

Lys  Arg  Asn  Ser  Asp  Lys  Leu  Ile  Ala  Arg  Lys  Lys  Asp  Trp  Asp
                    1190                1195                1200

Pro  Lys  Lys  Tyr  Gly  Gly  Phe  Asp  Ser  Pro  Thr  Val  Ala  Tyr  Ser
                    1205                1210                1215

Val  Leu  Val  Val  Ala  Lys  Val  Glu  Lys  Gly  Lys  Ser  Lys  Lys  Leu
                    1220                1225                1230

Lys  Ser  Val  Lys  Glu  Leu  Leu  Gly  Ile  Thr  Ile  Met  Glu  Arg  Ser
                    1235                1240                1245

Ser  Phe  Glu  Lys  Asn  Pro  Ile  Asp  Phe  Leu  Glu  Ala  Lys  Gly  Tyr
                    1250                1255                1260

Lys  Glu  Val  Lys  Lys  Asp  Leu  Ile  Ile  Lys  Leu  Pro  Lys  Tyr  Ser
                    1265                1270                1275

Leu  Phe  Glu  Leu  Glu  Asn  Gly  Arg  Lys  Arg  Met  Leu  Ala  Ser  Ala
                    1280                1285                1290

Gly  Glu  Leu  Gln  Lys  Gly  Asn  Glu  Leu  Ala  Leu  Pro  Ser  Lys  Tyr
                    1295                1300                1305

Val  Asn  Phe  Leu  Tyr  Leu  Ala  Ser  His  Tyr  Glu  Lys  Leu  Lys  Gly
                    1310                1315                1320

Ser  Pro  Glu  Asp  Asn  Glu  Gln  Lys  Gln  Leu  Phe  Val  Glu  Gln  His
                    1325                1330                1335

Lys  His  Tyr  Leu  Asp  Glu  Ile  Ile  Glu  Gln  Ile  Ser  Glu  Phe  Ser
                    1340                1345                1350

Lys  Arg  Val  Ile  Leu  Ala  Asp  Ala  Asn  Leu  Asp  Lys  Val  Leu  Ser
                    1355                1360                1365

Ala  Tyr  Asn  Lys  His  Arg  Asp  Lys  Pro  Ile  Arg  Glu  Gln  Ala  Glu
                    1370                1375                1380

Asn  Ile  Ile  His  Leu  Phe  Thr  Leu  Thr  Asn  Leu  Gly  Ala  Pro  Ala
                    1385                1390                1395

Ala  Phe  Lys  Tyr  Phe  Asp  Thr  Thr  Ile  Asp  Arg  Lys  Arg  Tyr  Thr
                    1400                1405                1410

Ser  Thr  Lys  Glu  Val  Leu  Asp  Ala  Thr  Leu  Ile  His  Gln  Ser  Ile
                    1415                1420                1425

Thr  Gly  Leu  Tyr  Glu  Thr  Arg  Ile  Asp  Leu  Ser  Gln  Leu  Gly  Gly
                    1430                1435                1440

Asp  Ser  Arg  Ala  Asp  Pro  Lys  Lys  Lys  Arg  Lys  Val
                    1445                1450                1455
```

<210> SEQ ID NO 49
<211> LENGTH: 1455
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 49

```
Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly Tyr Asp Lys Lys
65                  70                  75                  80

Tyr Ser Ile Gly Leu Asp Ile Gly Thr Asn Ser Val Gly Trp Ala Val
                85                  90                  95

Ile Thr Asp Glu Tyr Lys Val Pro Ser Lys Lys Phe Lys Val Leu Gly
            100                 105                 110

Asn Thr Asp Arg His Ser Ile Lys Lys Asn Leu Ile Gly Ala Leu Leu
        115                 120                 125

Phe Asp Ser Gly Glu Thr Ala Glu Ala Thr Arg Leu Lys Arg Thr Ala
    130                 135                 140

Arg Arg Arg Tyr Thr Arg Arg Lys Asn Arg Ile Cys Tyr Leu Gln Glu
145                 150                 155                 160

Ile Phe Ser Asn Glu Met Ala Lys Val Asp Asp Ser Phe Phe His Arg
                165                 170                 175

Leu Glu Glu Ser Phe Leu Val Glu Glu Asp Lys Lys His Glu Arg His
            180                 185                 190

Pro Ile Phe Gly Asn Ile Val Asp Glu Val Ala Tyr His Glu Lys Tyr
        195                 200                 205

Pro Thr Ile Tyr His Leu Arg Lys Lys Leu Val Asp Ser Thr Asp Lys
    210                 215                 220

Ala Asp Leu Arg Leu Ile Tyr Leu Ala Leu Ala His Met Ile Lys Phe
225                 230                 235                 240

Arg Gly His Phe Leu Ile Glu Gly Asp Leu Asn Pro Asp Asn Ser Asp
                245                 250                 255

Val Asp Lys Leu Phe Ile Gln Leu Val Gln Thr Tyr Asn Gln Leu Phe
            260                 265                 270

Glu Glu Asn Pro Ile Asn Ala Ser Gly Val Asp Ala Lys Ala Ile Leu
        275                 280                 285

Ser Ala Arg Leu Ser Lys Ser Arg Arg Leu Glu Asn Leu Ile Ala Gln
    290                 295                 300

Leu Pro Gly Glu Lys Lys Asn Gly Leu Phe Gly Asn Leu Ile Ala Leu
305                 310                 315                 320

Ser Leu Gly Leu Thr Pro Asn Phe Lys Ser Asn Phe Asp Leu Ala Glu
                325                 330                 335

Asp Ala Lys Leu Gln Leu Ser Lys Asp Thr Tyr Asp Asp Asp Leu Asp
            340                 345                 350

Asn Leu Leu Ala Gln Ile Gly Asp Gln Tyr Ala Asp Leu Phe Leu Ala
```

```
              355                 360                 365
Ala Lys Asn Leu Ser Asp Ala Ile Leu Leu Ser Asp Ile Leu Arg Val
    370                 375                 380

Asn Thr Glu Ile Thr Lys Ala Pro Leu Ser Ala Ser Met Ile Lys Arg
385                 390                 395                 400

Tyr Asp Glu His His Gln Asp Leu Thr Leu Leu Lys Ala Leu Val Arg
                405                 410                 415

Gln Gln Leu Pro Glu Lys Tyr Lys Glu Ile Phe Phe Asp Gln Ser Lys
            420                 425                 430

Asn Gly Tyr Ala Gly Tyr Ile Asp Gly Gly Ala Ser Gln Glu Glu Phe
        435                 440                 445

Tyr Lys Phe Ile Lys Pro Ile Leu Glu Lys Met Asp Gly Thr Glu Glu
    450                 455                 460

Leu Leu Val Lys Leu Asn Arg Glu Asp Leu Leu Arg Lys Gln Arg Thr
465                 470                 475                 480

Phe Asp Asn Gly Ser Ile Pro His Gln Ile His Leu Gly Glu Leu His
                485                 490                 495

Ala Ile Leu Arg Arg Gln Glu Asp Phe Tyr Pro Phe Leu Lys Asp Asn
            500                 505                 510

Arg Glu Lys Ile Glu Lys Ile Leu Thr Phe Arg Ile Pro Tyr Tyr Val
        515                 520                 525

Gly Pro Leu Ala Arg Gly Asn Ser Arg Phe Ala Trp Met Thr Arg Lys
    530                 535                 540

Ser Glu Glu Thr Ile Thr Pro Trp Asn Phe Glu Glu Val Val Asp Lys
545                 550                 555                 560

Gly Ala Ser Ala Gln Ser Phe Ile Glu Arg Met Thr Asn Phe Asp Lys
                565                 570                 575

Asn Leu Pro Asn Glu Lys Val Leu Pro Lys His Ser Leu Leu Tyr Glu
            580                 585                 590

Tyr Phe Thr Val Tyr Asn Glu Leu Thr Lys Val Lys Tyr Val Thr Glu
        595                 600                 605

Gly Met Arg Lys Pro Ala Phe Leu Ser Gly Glu Gln Lys Lys Ala Ile
    610                 615                 620

Val Asp Leu Leu Phe Lys Thr Asn Arg Lys Val Thr Val Lys Gln Leu
625                 630                 635                 640

Lys Glu Asp Tyr Phe Lys Lys Ile Glu Cys Phe Asp Ser Val Glu Ile
                645                 650                 655

Ser Gly Val Glu Asp Arg Phe Asn Ala Ser Leu Gly Thr Tyr His Asp
            660                 665                 670

Leu Leu Lys Ile Ile Lys Asp Lys Asp Phe Leu Asp Asn Glu Glu Asn
        675                 680                 685

Glu Asp Ile Leu Glu Asp Ile Val Leu Thr Leu Thr Leu Phe Glu Asp
    690                 695                 700

Arg Glu Met Ile Glu Glu Arg Leu Lys Thr Tyr Ala His Leu Phe Asp
705                 710                 715                 720

Asp Lys Val Met Lys Gln Leu Lys Arg Arg Arg Tyr Thr Gly Trp Gly
                725                 730                 735

Arg Leu Ser Arg Lys Leu Ile Asn Gly Ile Arg Asp Lys Gln Ser Gly
            740                 745                 750

Lys Thr Ile Leu Asp Phe Leu Lys Ser Asp Gly Phe Ala Asn Arg Asn
        755                 760                 765

Phe Met Gln Leu Ile His Asp Asp Ser Leu Thr Phe Lys Glu Asp Ile
    770                 775                 780
```

```
Gln Lys Ala Gln Val Ser Gly Gln Gly Asp Ser Leu His Glu His Ile
785                 790                 795                 800

Ala Asn Leu Ala Gly Ser Pro Ala Ile Lys Lys Gly Ile Leu Gln Thr
            805                 810                 815

Val Lys Val Val Asp Glu Leu Val Lys Val Met Gly Arg His Lys Pro
            820                 825                 830

Glu Asn Ile Val Ile Glu Met Ala Arg Glu Asn Gln Thr Thr Gln Lys
        835                 840                 845

Gly Gln Lys Asn Ser Arg Glu Arg Met Lys Arg Ile Glu Glu Gly Ile
        850                 855                 860

Lys Glu Leu Gly Ser Gln Ile Leu Lys Glu His Pro Val Glu Asn Thr
865                 870                 875                 880

Gln Leu Gln Asn Glu Lys Leu Tyr Leu Tyr Tyr Leu Gln Asn Gly Arg
            885                 890                 895

Asp Met Tyr Val Asp Gln Glu Leu Asp Ile Asn Arg Leu Ser Asp Tyr
            900                 905                 910

Asp Val Asp His Ile Val Pro Gln Ser Phe Leu Lys Asp Asp Ser Ile
            915                 920                 925

Asp Asn Lys Val Leu Thr Arg Ser Asp Lys Asn Arg Gly Lys Ser Asp
930                 935                 940

Asn Val Pro Ser Glu Glu Val Val Lys Lys Met Lys Asn Tyr Trp Arg
945                 950                 955                 960

Gln Leu Leu Asn Ala Lys Leu Ile Thr Gln Arg Lys Phe Asp Asn Leu
            965                 970                 975

Thr Lys Ala Glu Arg Gly Gly Leu Ser Glu Leu Asp Lys Ala Gly Phe
            980                 985                 990

Ile Lys Arg Gln Leu Val Glu Thr Arg Gln Ile Thr Lys His Val Ala
            995                 1000                1005

Gln Ile Leu Asp Ser Arg Met Asn Thr Lys Tyr Asp Glu Asn Asp
    1010                1015                1020

Lys Leu Ile Arg Glu Val Lys Val Ile Thr Leu Lys Ser Lys Leu
    1025                1030                1035

Val Ser Asp Phe Arg Lys Asp Phe Gln Phe Tyr Lys Val Arg Glu
    1040                1045                1050

Ile Asn Asn Tyr His His Ala His Asp Ala Tyr Leu Asn Ala Val
    1055                1060                1065

Val Gly Thr Ala Leu Ile Lys Lys Tyr Pro Lys Leu Glu Ser Glu
    1070                1075                1080

Phe Val Tyr Gly Asp Tyr Lys Val Tyr Asp Val Arg Lys Met Ile
    1085                1090                1095

Ala Lys Ser Glu Gln Glu Ile Gly Lys Ala Thr Ala Lys Tyr Phe
    1100                1105                1110

Phe Tyr Ser Asn Ile Met Asn Phe Phe Lys Thr Glu Ile Thr Leu
    1115                1120                1125

Ala Asn Gly Glu Ile Arg Lys Arg Pro Leu Ile Glu Thr Asn Gly
    1130                1135                1140

Glu Thr Gly Glu Ile Val Trp Asp Lys Gly Arg Asp Phe Ala Thr
    1145                1150                1155

Val Arg Lys Val Leu Ser Met Pro Gln Val Asn Ile Val Lys Lys
    1160                1165                1170

Thr Glu Val Gln Thr Gly Gly Phe Ser Lys Glu Ser Ile Leu Pro
    1175                1180                1185
```

-continued

```
Lys Arg Asn Ser Asp Lys Leu Ile Ala Arg Lys Lys Asp Trp Asp
    1190                1195                1200

Pro Lys Lys Tyr Gly Gly Phe Asp Ser Pro Thr Val Ala Tyr Ser
    1205                1210                1215

Val Leu Val Val Ala Lys Val Glu Lys Gly Lys Ser Lys Lys Leu
    1220                1225                1230

Lys Ser Val Lys Glu Leu Leu Gly Ile Thr Ile Met Glu Arg Ser
    1235                1240                1245

Ser Phe Glu Lys Asn Pro Ile Asp Phe Leu Glu Ala Lys Gly Tyr
    1250                1255                1260

Lys Glu Val Lys Lys Asp Leu Ile Ile Lys Leu Pro Lys Tyr Ser
    1265                1270                1275

Leu Phe Glu Leu Glu Asn Gly Arg Lys Arg Met Leu Ala Ser Ala
    1280                1285                1290

Gly Glu Leu Gln Lys Gly Asn Glu Leu Ala Leu Pro Ser Lys Tyr
    1295                1300                1305

Val Asn Phe Leu Tyr Leu Ala Ser His Tyr Glu Lys Leu Lys Gly
    1310                1315                1320

Ser Pro Glu Asp Asn Glu Gln Lys Gln Leu Phe Val Glu Gln His
    1325                1330                1335

Lys His Tyr Leu Asp Glu Ile Ile Glu Gln Ile Ser Glu Phe Ser
    1340                1345                1350

Lys Arg Val Ile Leu Ala Asp Ala Asn Leu Asp Lys Val Leu Ser
    1355                1360                1365

Ala Tyr Asn Lys His Arg Asp Lys Pro Ile Arg Glu Gln Ala Glu
    1370                1375                1380

Asn Ile Ile His Leu Phe Thr Leu Thr Asn Leu Gly Ala Pro Ala
    1385                1390                1395

Ala Phe Lys Tyr Phe Asp Thr Thr Ile Asp Arg Lys Arg Tyr Thr
    1400                1405                1410

Ser Thr Lys Glu Val Leu Asp Ala Thr Leu Ile His Gln Ser Ile
    1415                1420                1425

Thr Gly Leu Tyr Glu Thr Arg Ile Asp Leu Ser Gln Leu Gly Gly
    1430                1435                1440

Asp Ser Arg Ala Asp Pro Lys Lys Lys Arg Lys Val
    1445                1450                1455

<210> SEQ ID NO 50
<211> LENGTH: 1455
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
                20                  25                  30

Lys Glu Gly Ile Pro Pro Asp Gln Gln Arg Leu Ile Phe Ala Gly Lys
            35                  40                  45

Gln Leu Glu Asp Gly Arg Thr Leu Ser Asp Tyr Asn Ile Gln Lys Glu
        50                  55                  60

Ser Thr Leu His Leu Val Leu Arg Leu Arg Gly Gly Ser Asp Lys Lys
65                  70                  75                  80
```

```
Tyr Ser Ile Gly Leu Asp Ile Gly Thr Asn Ser Val Gly Trp Ala Val
                85                  90                  95

Ile Thr Asp Glu Tyr Lys Val Pro Ser Lys Lys Phe Lys Val Leu Gly
            100                 105                 110

Asn Thr Asp Arg His Ser Ile Lys Lys Asn Leu Ile Gly Ala Leu Leu
            115                 120                 125

Phe Asp Ser Gly Glu Thr Ala Glu Ala Thr Arg Leu Lys Arg Thr Ala
            130                 135                 140

Arg Arg Arg Tyr Thr Arg Arg Lys Asn Arg Ile Cys Tyr Leu Gln Glu
145                 150                 155                 160

Ile Phe Ser Asn Glu Met Ala Lys Val Asp Asp Ser Phe Phe His Arg
            165                 170                 175

Leu Glu Glu Ser Phe Leu Val Glu Glu Asp Lys Lys His Glu Arg His
            180                 185                 190

Pro Ile Phe Gly Asn Ile Val Asp Glu Val Ala Tyr His Glu Lys Tyr
            195                 200                 205

Pro Thr Ile Tyr His Leu Arg Lys Lys Leu Val Asp Ser Thr Asp Lys
            210                 215                 220

Ala Asp Leu Arg Leu Ile Tyr Leu Ala Leu Ala His Met Ile Lys Phe
225                 230                 235                 240

Arg Gly His Phe Leu Ile Glu Gly Asp Leu Asn Pro Asp Asn Ser Asp
            245                 250                 255

Val Asp Lys Leu Phe Ile Gln Leu Val Gln Thr Tyr Asn Gln Leu Phe
            260                 265                 270

Glu Glu Asn Pro Ile Asn Ala Ser Gly Val Asp Ala Lys Ala Ile Leu
            275                 280                 285

Ser Ala Arg Leu Ser Lys Ser Arg Arg Leu Glu Asn Leu Ile Ala Gln
            290                 295                 300

Leu Pro Gly Glu Lys Lys Asn Gly Leu Phe Gly Asn Leu Ile Ala Leu
305                 310                 315                 320

Ser Leu Gly Leu Thr Pro Asn Phe Lys Ser Asn Phe Asp Leu Ala Glu
            325                 330                 335

Asp Ala Lys Leu Gln Leu Ser Lys Asp Thr Tyr Asp Asp Asp Leu Asp
            340                 345                 350

Asn Leu Leu Ala Gln Ile Gly Asp Gln Tyr Ala Asp Leu Phe Leu Ala
            355                 360                 365

Ala Lys Asn Leu Ser Asp Ala Ile Leu Leu Ser Asp Ile Leu Arg Val
            370                 375                 380

Asn Thr Glu Ile Thr Lys Ala Pro Leu Ser Ala Ser Met Ile Lys Arg
385                 390                 395                 400

Tyr Asp Glu His His Gln Asp Leu Thr Leu Leu Lys Ala Leu Val Arg
            405                 410                 415

Gln Gln Leu Pro Glu Lys Tyr Lys Glu Ile Phe Phe Asp Gln Ser Lys
            420                 425                 430

Asn Gly Tyr Ala Gly Tyr Ile Asp Gly Gly Ala Ser Gln Glu Glu Phe
            435                 440                 445

Tyr Lys Phe Ile Lys Pro Ile Leu Glu Lys Met Asp Gly Thr Glu Glu
            450                 455                 460

Leu Leu Val Lys Leu Asn Arg Glu Asp Leu Leu Arg Lys Gln Arg Thr
465                 470                 475                 480

Phe Asp Asn Gly Ser Ile Pro His Gln Ile His Leu Gly Glu Leu His
            485                 490                 495
```

```
Ala Ile Leu Arg Arg Gln Glu Asp Phe Tyr Pro Phe Leu Lys Asp Asn
            500                 505                 510

Arg Glu Lys Ile Glu Lys Ile Leu Thr Phe Arg Ile Pro Tyr Tyr Val
        515                 520                 525

Gly Pro Leu Ala Arg Gly Asn Ser Arg Phe Ala Trp Met Thr Arg Lys
        530                 535                 540

Ser Glu Glu Thr Ile Thr Pro Trp Asn Phe Glu Val Val Asp Lys
545                 550                 555                 560

Gly Ala Ser Ala Gln Ser Phe Ile Glu Arg Met Thr Asn Phe Asp Lys
                565                 570                 575

Asn Leu Pro Asn Glu Lys Val Leu Pro Lys His Ser Leu Leu Tyr Glu
            580                 585                 590

Tyr Phe Thr Val Tyr Asn Glu Leu Thr Lys Val Lys Tyr Val Thr Glu
        595                 600                 605

Gly Met Arg Lys Pro Ala Phe Leu Ser Gly Glu Gln Lys Lys Ala Ile
        610                 615                 620

Val Asp Leu Leu Phe Lys Thr Asn Arg Lys Val Thr Val Lys Gln Leu
625                 630                 635                 640

Lys Glu Asp Tyr Phe Lys Lys Ile Glu Cys Phe Asp Ser Val Glu Ile
                645                 650                 655

Ser Gly Val Glu Asp Arg Phe Asn Ala Ser Leu Gly Thr Tyr His Asp
            660                 665                 670

Leu Leu Lys Ile Ile Lys Asp Lys Asp Phe Leu Asp Asn Glu Glu Asn
        675                 680                 685

Glu Asp Ile Leu Glu Asp Ile Val Leu Thr Leu Thr Leu Phe Glu Asp
        690                 695                 700

Arg Glu Met Ile Glu Glu Arg Leu Lys Thr Tyr Ala His Leu Phe Asp
705                 710                 715                 720

Asp Lys Val Met Lys Gln Leu Lys Arg Arg Arg Tyr Thr Gly Trp Gly
                725                 730                 735

Arg Leu Ser Arg Lys Leu Ile Asn Gly Ile Arg Asp Lys Gln Ser Gly
            740                 745                 750

Lys Thr Ile Leu Asp Phe Leu Lys Ser Asp Gly Phe Ala Asn Arg Asn
        755                 760                 765

Phe Met Gln Leu Ile His Asp Asp Ser Leu Thr Phe Lys Glu Asp Ile
770                 775                 780

Gln Lys Ala Gln Val Ser Gly Gln Gly Asp Ser Leu His Glu His Ile
785                 790                 795                 800

Ala Asn Leu Ala Gly Ser Pro Ala Ile Lys Lys Gly Ile Leu Gln Thr
                805                 810                 815

Val Lys Val Val Asp Glu Leu Val Lys Val Met Gly Arg His Lys Pro
            820                 825                 830

Glu Asn Ile Val Ile Glu Met Ala Arg Glu Asn Gln Thr Thr Gln Lys
        835                 840                 845

Gly Gln Lys Asn Ser Arg Glu Arg Met Lys Arg Ile Glu Glu Gly Ile
        850                 855                 860

Lys Glu Leu Gly Ser Gln Ile Leu Lys Glu His Pro Val Glu Asn Thr
865                 870                 875                 880

Gln Leu Gln Asn Glu Lys Leu Tyr Leu Tyr Tyr Leu Gln Asn Gly Arg
                885                 890                 895

Asp Met Tyr Val Asp Gln Glu Leu Asp Ile Asn Arg Leu Ser Asp Tyr
            900                 905                 910

Asp Val Asp His Ile Val Pro Gln Ser Phe Leu Lys Asp Asp Ser Ile
```

-continued

```
           915                 920                 925
Asp Asn Lys Val Leu Thr Arg Ser Asp Lys Asn Arg Gly Lys Ser Asp
  930                 935                 940

Asn Val Pro Ser Glu Glu Val Lys Lys Met Lys Asn Tyr Trp Arg
945                 950                 955                 960

Gln Leu Leu Asn Ala Lys Leu Ile Thr Gln Arg Lys Phe Asp Asn Leu
                965                 970                 975

Thr Lys Ala Glu Arg Gly Gly Leu Ser Glu Leu Asp Lys Ala Gly Phe
            980                 985                 990

Ile Lys Arg Gln Leu Val Glu Thr Arg Gln Ile Thr Lys His Val Ala
            995                 1000                1005

Gln Ile Leu Asp Ser Arg Met Asn Thr Lys Tyr Asp Glu Asn Asp
    1010                1015                1020

Lys Leu Ile Arg Glu Val Lys Val Ile Thr Leu Lys Ser Lys Leu
    1025                1030                1035

Val Ser Asp Phe Arg Lys Asp Phe Gln Phe Tyr Lys Val Arg Glu
    1040                1045                1050

Ile Asn Asn Tyr His His Ala His Asp Ala Tyr Leu Asn Ala Val
    1055                1060                1065

Val Gly Thr Ala Leu Ile Lys Lys Tyr Pro Lys Leu Glu Ser Glu
    1070                1075                1080

Phe Val Tyr Gly Asp Tyr Lys Val Tyr Asp Val Arg Lys Met Ile
    1085                1090                1095

Ala Lys Ser Glu Gln Glu Ile Gly Lys Ala Thr Ala Lys Tyr Phe
    1100                1105                1110

Phe Tyr Ser Asn Ile Met Asn Phe Phe Lys Thr Glu Ile Thr Leu
    1115                1120                1125

Ala Asn Gly Glu Ile Arg Lys Arg Pro Leu Ile Glu Thr Asn Gly
    1130                1135                1140

Glu Thr Gly Glu Ile Val Trp Asp Lys Gly Arg Asp Phe Ala Thr
    1145                1150                1155

Val Arg Lys Val Leu Ser Met Pro Gln Val Asn Ile Val Lys Lys
    1160                1165                1170

Thr Glu Val Gln Thr Gly Gly Phe Ser Lys Glu Ser Ile Leu Pro
    1175                1180                1185

Lys Arg Asn Ser Asp Lys Leu Ile Ala Arg Lys Lys Asp Trp Asp
    1190                1195                1200

Pro Lys Lys Tyr Gly Gly Phe Asp Ser Pro Thr Val Ala Tyr Ser
    1205                1210                1215

Val Leu Val Val Ala Lys Val Glu Lys Gly Lys Ser Lys Lys Leu
    1220                1225                1230

Lys Ser Val Lys Glu Leu Leu Gly Ile Thr Ile Met Glu Arg Ser
    1235                1240                1245

Ser Phe Glu Lys Asn Pro Ile Asp Phe Leu Glu Ala Lys Gly Tyr
    1250                1255                1260

Lys Glu Val Lys Lys Asp Leu Ile Ile Lys Leu Pro Lys Tyr Ser
    1265                1270                1275

Leu Phe Glu Leu Glu Asn Gly Arg Lys Arg Met Leu Ala Ser Ala
    1280                1285                1290

Gly Glu Leu Gln Lys Gly Asn Glu Leu Ala Leu Pro Ser Lys Tyr
    1295                1300                1305

Val Asn Phe Leu Tyr Leu Ala Ser His Tyr Glu Lys Leu Lys Gly
    1310                1315                1320
```

Ser Pro Glu Asp Asn Glu Gln Lys Gln Leu Phe Val Glu Gln His
    1325                1330                1335

Lys His Tyr Leu Asp Glu Ile Ile Glu Gln Ile Ser Glu Phe Ser
    1340                1345                1350

Lys Arg Val Ile Leu Ala Asp Ala Asn Leu Asp Lys Val Leu Ser
    1355                1360                1365

Ala Tyr Asn Lys His Arg Asp Lys Pro Ile Arg Glu Gln Ala Glu
    1370                1375                1380

Asn Ile Ile His Leu Phe Thr Leu Thr Asn Leu Gly Ala Pro Ala
    1385                1390                1395

Ala Phe Lys Tyr Phe Asp Thr Thr Ile Asp Arg Lys Arg Tyr Thr
    1400                1405                1410

Ser Thr Lys Glu Val Leu Asp Ala Thr Leu Ile His Gln Ser Ile
    1415                1420                1425

Thr Gly Leu Tyr Glu Thr Arg Ile Asp Leu Ser Gln Leu Gly Gly
    1430                1435                1440

Asp Ser Arg Ala Asp Pro Lys Lys Lys Arg Lys Val
    1445                1450                1455

<210> SEQ ID NO 51
<211> LENGTH: 1455
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly Asn Asp Lys Lys
65                  70                  75                  80

Tyr Ser Ile Gly Leu Asp Ile Gly Thr Asn Ser Val Gly Trp Ala Val
                85                  90                  95

Ile Thr Asp Glu Tyr Lys Val Pro Ser Lys Lys Phe Lys Val Leu Gly
            100                 105                 110

Asn Thr Asp Arg His Ser Ile Lys Lys Asn Leu Ile Gly Ala Leu Leu
        115                 120                 125

Phe Asp Ser Gly Glu Thr Ala Glu Ala Thr Arg Leu Lys Arg Thr Ala
    130                 135                 140

Arg Arg Arg Tyr Thr Arg Arg Lys Asn Arg Ile Cys Tyr Leu Gln Glu
145                 150                 155                 160

Ile Phe Ser Asn Glu Met Ala Lys Val Asp Asp Ser Phe Phe His Arg
                165                 170                 175

Leu Glu Glu Ser Phe Leu Val Glu Glu Asp Lys Lys His Glu Arg His
            180                 185                 190

Pro Ile Phe Gly Asn Ile Val Asp Glu Val Ala Tyr His Glu Lys Tyr
        195                 200                 205

Pro Thr Ile Tyr His Leu Arg Lys Lys Leu Val Asp Ser Thr Asp Lys

```
            210                 215                 220
Ala Asp Leu Arg Leu Ile Tyr Leu Ala Leu Ala His Met Ile Lys Phe
225                 230                 235                 240

Arg Gly His Phe Leu Ile Glu Gly Asp Leu Asn Pro Asp Asn Ser Asp
                245                 250                 255

Val Asp Lys Leu Phe Ile Gln Leu Val Gln Thr Tyr Asn Gln Leu Phe
                260                 265                 270

Glu Glu Asn Pro Ile Asn Ala Ser Gly Val Asp Ala Lys Ala Ile Leu
            275                 280                 285

Ser Ala Arg Leu Ser Lys Ser Arg Arg Leu Glu Asn Leu Ile Ala Gln
290                 295                 300

Leu Pro Gly Glu Lys Lys Asn Gly Leu Phe Gly Asn Leu Ile Ala Leu
305                 310                 315                 320

Ser Leu Gly Leu Thr Pro Asn Phe Lys Ser Asn Phe Asp Leu Ala Glu
                325                 330                 335

Asp Ala Lys Leu Gln Leu Ser Lys Asp Thr Tyr Asp Asp Asp Leu Asp
                340                 345                 350

Asn Leu Leu Ala Gln Ile Gly Asp Gln Tyr Ala Asp Leu Phe Leu Ala
                355                 360                 365

Ala Lys Asn Leu Ser Asp Ala Ile Leu Leu Ser Asp Ile Leu Arg Val
        370                 375                 380

Asn Thr Glu Ile Thr Lys Ala Pro Leu Ser Ala Ser Met Ile Lys Arg
385                 390                 395                 400

Tyr Asp Glu His His Gln Asp Leu Thr Leu Leu Lys Ala Leu Val Arg
                405                 410                 415

Gln Gln Leu Pro Glu Lys Tyr Lys Glu Ile Phe Phe Asp Gln Ser Lys
                420                 425                 430

Asn Gly Tyr Ala Gly Tyr Ile Asp Gly Gly Ala Ser Gln Glu Glu Phe
            435                 440                 445

Tyr Lys Phe Ile Lys Pro Ile Leu Glu Lys Met Asp Gly Thr Glu Glu
            450                 455                 460

Leu Leu Val Lys Leu Asn Arg Glu Asp Leu Leu Arg Lys Gln Arg Thr
465                 470                 475                 480

Phe Asp Asn Gly Ser Ile Pro His Gln Ile His Leu Gly Glu Leu His
                485                 490                 495

Ala Ile Leu Arg Arg Gln Glu Asp Phe Tyr Pro Phe Leu Lys Asp Asn
                500                 505                 510

Arg Glu Lys Ile Glu Lys Ile Leu Thr Phe Arg Ile Pro Tyr Tyr Val
            515                 520                 525

Gly Pro Leu Ala Arg Gly Asn Ser Arg Phe Ala Trp Met Thr Arg Lys
            530                 535                 540

Ser Glu Glu Thr Ile Thr Pro Trp Asn Phe Glu Glu Val Val Asp Lys
545                 550                 555                 560

Gly Ala Ser Ala Gln Ser Phe Ile Glu Arg Met Thr Asn Phe Asp Lys
                565                 570                 575

Asn Leu Pro Asn Glu Lys Val Leu Pro Lys His Ser Leu Leu Tyr Glu
                580                 585                 590

Tyr Phe Thr Val Tyr Asn Glu Leu Thr Lys Val Lys Tyr Val Thr Glu
            595                 600                 605

Gly Met Arg Lys Pro Ala Phe Leu Ser Gly Glu Gln Lys Lys Ala Ile
            610                 615                 620

Val Asp Leu Leu Phe Lys Thr Asn Arg Lys Val Thr Val Lys Gln Leu
625                 630                 635                 640
```

-continued

```
Lys Glu Asp Tyr Phe Lys Lys Ile Glu Cys Phe Asp Ser Val Glu Ile
            645                 650                 655

Ser Gly Val Glu Asp Arg Phe Asn Ala Ser Leu Gly Thr Tyr His Asp
        660                 665                 670

Leu Leu Lys Ile Ile Lys Asp Lys Asp Phe Leu Asp Asn Glu Glu Asn
            675                 680                 685

Glu Asp Ile Leu Glu Asp Ile Val Leu Thr Leu Thr Leu Phe Glu Asp
    690                 695                 700

Arg Glu Met Ile Glu Glu Arg Leu Lys Thr Tyr Ala His Leu Phe Asp
705                 710                 715                 720

Asp Lys Val Met Lys Gln Leu Lys Arg Arg Tyr Thr Gly Trp Gly
            725                 730                 735

Arg Leu Ser Arg Lys Leu Ile Asn Gly Ile Arg Asp Lys Gln Ser Gly
        740                 745                 750

Lys Thr Ile Leu Asp Phe Leu Lys Ser Asp Gly Phe Ala Asn Arg Asn
            755                 760                 765

Phe Met Gln Leu Ile His Asp Asp Ser Leu Thr Phe Lys Glu Asp Ile
    770                 775                 780

Gln Lys Ala Gln Val Ser Gly Gln Gly Asp Ser Leu His Glu His Ile
785                 790                 795                 800

Ala Asn Leu Ala Gly Ser Pro Ala Ile Lys Lys Gly Ile Leu Gln Thr
            805                 810                 815

Val Lys Val Val Asp Glu Leu Val Lys Val Met Gly Arg His Lys Pro
        820                 825                 830

Glu Asn Ile Val Ile Glu Met Ala Arg Glu Asn Gln Thr Thr Gln Lys
            835                 840                 845

Gly Gln Lys Asn Ser Arg Glu Arg Met Lys Arg Ile Glu Glu Gly Ile
    850                 855                 860

Lys Glu Leu Gly Ser Gln Ile Leu Lys Glu His Pro Val Glu Asn Thr
865                 870                 875                 880

Gln Leu Gln Asn Glu Lys Leu Tyr Leu Tyr Tyr Leu Gln Asn Gly Arg
            885                 890                 895

Asp Met Tyr Val Asp Gln Glu Leu Asp Ile Asn Arg Leu Ser Asp Tyr
        900                 905                 910

Asp Val Asp His Ile Val Pro Gln Ser Phe Leu Lys Asp Asp Ser Ile
            915                 920                 925

Asp Asn Lys Val Leu Thr Arg Ser Asp Lys Asn Arg Gly Lys Ser Asp
    930                 935                 940

Asn Val Pro Ser Glu Glu Val Val Lys Lys Met Lys Asn Tyr Trp Arg
945                 950                 955                 960

Gln Leu Leu Asn Ala Lys Leu Ile Thr Gln Arg Lys Phe Asp Asn Leu
            965                 970                 975

Thr Lys Ala Glu Arg Gly Gly Leu Ser Glu Leu Asp Lys Ala Gly Phe
        980                 985                 990

Ile Lys Arg Gln Leu Val Glu Thr Arg Gln Ile Thr Lys His Val Ala
            995                1000                1005

Gln Ile Leu Asp Ser Arg Met Asn Thr Lys Tyr Asp Glu Asn Asp
   1010                1015                1020

Lys Leu Ile Arg Glu Val Lys Val Ile Thr Leu Lys Ser Lys Leu
   1025                1030                1035

Val Ser Asp Phe Arg Lys Asp Phe Gln Phe Tyr Lys Val Arg Glu
   1040                1045                1050
```

```
Ile Asn Asn Tyr His His Ala His Asp Ala Tyr Leu Asn Ala Val
1055                1060                1065

Val Gly Thr Ala Leu Ile Lys Lys Tyr Pro Lys Leu Glu Ser Glu
1070                1075                1080

Phe Val Tyr Gly Asp Tyr Lys Val Tyr Asp Val Arg Lys Met Ile
1085                1090                1095

Ala Lys Ser Glu Gln Glu Ile Gly Lys Ala Thr Ala Lys Tyr Phe
1100                1105                1110

Phe Tyr Ser Asn Ile Met Asn Phe Phe Lys Thr Glu Ile Thr Leu
1115                1120                1125

Ala Asn Gly Glu Ile Arg Lys Arg Pro Leu Ile Glu Thr Asn Gly
1130                1135                1140

Glu Thr Gly Glu Ile Val Trp Asp Lys Gly Arg Asp Phe Ala Thr
1145                1150                1155

Val Arg Lys Val Leu Ser Met Pro Gln Val Asn Ile Val Lys Lys
1160                1165                1170

Thr Glu Val Gln Thr Gly Gly Phe Ser Lys Glu Ser Ile Leu Pro
1175                1180                1185

Lys Arg Asn Ser Asp Lys Leu Ile Ala Arg Lys Lys Asp Trp Asp
1190                1195                1200

Pro Lys Lys Tyr Gly Gly Phe Asp Ser Pro Thr Val Ala Tyr Ser
1205                1210                1215

Val Leu Val Val Ala Lys Val Glu Lys Gly Lys Ser Lys Lys Leu
1220                1225                1230

Lys Ser Val Lys Glu Leu Leu Gly Ile Thr Ile Met Glu Arg Ser
1235                1240                1245

Ser Phe Glu Lys Asn Pro Ile Asp Phe Leu Glu Ala Lys Gly Tyr
1250                1255                1260

Lys Glu Val Lys Lys Asp Leu Ile Ile Lys Leu Pro Lys Tyr Ser
1265                1270                1275

Leu Phe Glu Leu Glu Asn Gly Arg Lys Arg Met Leu Ala Ser Ala
1280                1285                1290

Gly Glu Leu Gln Lys Gly Asn Glu Leu Ala Leu Pro Ser Lys Tyr
1295                1300                1305

Val Asn Phe Leu Tyr Leu Ala Ser His Tyr Glu Lys Leu Lys Gly
1310                1315                1320

Ser Pro Glu Asp Asn Glu Gln Lys Gln Leu Phe Val Glu Gln His
1325                1330                1335

Lys His Tyr Leu Asp Glu Ile Ile Glu Gln Ile Ser Glu Phe Ser
1340                1345                1350

Lys Arg Val Ile Leu Ala Asp Ala Asn Leu Asp Lys Val Leu Ser
1355                1360                1365

Ala Tyr Asn Lys His Arg Asp Lys Pro Ile Arg Glu Gln Ala Glu
1370                1375                1380

Asn Ile Ile His Leu Phe Thr Leu Thr Asn Leu Gly Ala Pro Ala
1385                1390                1395

Ala Phe Lys Tyr Phe Asp Thr Thr Ile Asp Arg Lys Arg Tyr Thr
1400                1405                1410

Ser Thr Lys Glu Val Leu Asp Ala Thr Leu Ile His Gln Ser Ile
1415                1420                1425

Thr Gly Leu Tyr Glu Thr Arg Ile Asp Leu Ser Gln Leu Gly Gly
1430                1435                1440

Asp Ser Arg Ala Asp Pro Lys Lys Lys Arg Lys Val
```

<210> SEQ ID NO 52
<211> LENGTH: 1455
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 52

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly Lys Asp Lys Lys
65                  70                  75                  80

Tyr Ser Ile Gly Leu Asp Ile Gly Thr Asn Ser Val Gly Trp Ala Val
                85                  90                  95

Ile Thr Asp Glu Tyr Lys Val Pro Ser Lys Lys Phe Lys Val Leu Gly
            100                 105                 110

Asn Thr Asp Arg His Ser Ile Lys Lys Asn Leu Ile Gly Ala Leu Leu
        115                 120                 125

Phe Asp Ser Gly Glu Thr Ala Glu Ala Thr Arg Leu Lys Arg Thr Ala
    130                 135                 140

Arg Arg Arg Tyr Thr Arg Arg Lys Asn Arg Ile Cys Tyr Leu Gln Glu
145                 150                 155                 160

Ile Phe Ser Asn Glu Met Ala Lys Val Asp Asp Ser Phe Phe His Arg
                165                 170                 175

Leu Glu Glu Ser Phe Leu Val Glu Glu Asp Lys Lys His Glu Arg His
            180                 185                 190

Pro Ile Phe Gly Asn Ile Val Asp Glu Val Ala Tyr His Glu Lys Tyr
        195                 200                 205

Pro Thr Ile Tyr His Leu Arg Lys Lys Leu Val Asp Ser Thr Asp Lys
    210                 215                 220

Ala Asp Leu Arg Leu Ile Tyr Leu Ala Leu Ala His Met Ile Lys Phe
225                 230                 235                 240

Arg Gly His Phe Leu Ile Glu Gly Asp Leu Asn Pro Asp Asn Ser Asp
                245                 250                 255

Val Asp Lys Leu Phe Ile Gln Leu Val Gln Thr Tyr Asn Gln Leu Phe
            260                 265                 270

Glu Glu Asn Pro Ile Asn Ala Ser Gly Val Asp Ala Lys Ala Ile Leu
        275                 280                 285

Ser Ala Arg Leu Ser Lys Ser Arg Arg Leu Glu Asn Leu Ile Ala Gln
    290                 295                 300

Leu Pro Gly Glu Lys Lys Asn Gly Leu Phe Gly Asn Leu Ile Ala Leu
305                 310                 315                 320

Ser Leu Gly Leu Thr Pro Asn Phe Lys Ser Asn Phe Asp Leu Ala Glu
                325                 330                 335

Asp Ala Lys Leu Gln Leu Ser Lys Asp Thr Tyr Asp Asp Asp Leu Asp
            340                 345                 350

```
Asn Leu Leu Ala Gln Ile Gly Asp Gln Tyr Ala Asp Leu Phe Leu Ala
            355                 360                 365

Ala Lys Asn Leu Ser Asp Ala Ile Leu Leu Ser Asp Ile Leu Arg Val
370                 375                 380

Asn Thr Glu Ile Thr Lys Ala Pro Leu Ser Ala Ser Met Ile Lys Arg
385                 390                 395                 400

Tyr Asp Glu His His Gln Asp Leu Thr Leu Leu Lys Ala Leu Val Arg
                405                 410                 415

Gln Gln Leu Pro Glu Lys Tyr Lys Glu Ile Phe Phe Asp Gln Ser Lys
            420                 425                 430

Asn Gly Tyr Ala Gly Tyr Ile Asp Gly Gly Ala Ser Gln Glu Glu Phe
            435                 440                 445

Tyr Lys Phe Ile Lys Pro Ile Leu Glu Lys Met Asp Gly Thr Glu Glu
            450                 455                 460

Leu Leu Val Lys Leu Asn Arg Glu Asp Leu Leu Arg Lys Gln Arg Thr
465                 470                 475                 480

Phe Asp Asn Gly Ser Ile Pro His Gln Ile His Leu Gly Glu Leu His
                485                 490                 495

Ala Ile Leu Arg Arg Gln Glu Asp Phe Tyr Pro Phe Leu Lys Asp Asn
            500                 505                 510

Arg Glu Lys Ile Glu Lys Ile Leu Thr Phe Arg Ile Pro Tyr Tyr Val
            515                 520                 525

Gly Pro Leu Ala Arg Gly Asn Ser Arg Phe Ala Trp Met Thr Arg Lys
            530                 535                 540

Ser Glu Glu Thr Ile Thr Pro Trp Asn Phe Glu Glu Val Val Asp Lys
545                 550                 555                 560

Gly Ala Ser Ala Gln Ser Phe Ile Glu Arg Met Thr Asn Phe Asp Lys
                565                 570                 575

Asn Leu Pro Asn Glu Lys Val Leu Pro Lys His Ser Leu Leu Tyr Glu
            580                 585                 590

Tyr Phe Thr Val Tyr Asn Glu Leu Thr Lys Val Lys Tyr Val Thr Glu
            595                 600                 605

Gly Met Arg Lys Pro Ala Phe Leu Ser Gly Glu Gln Lys Lys Ala Ile
610                 615                 620

Val Asp Leu Leu Phe Lys Thr Asn Arg Lys Val Thr Val Lys Gln Leu
625                 630                 635                 640

Lys Glu Asp Tyr Phe Lys Lys Ile Glu Cys Phe Asp Ser Val Glu Ile
                645                 650                 655

Ser Gly Val Glu Asp Arg Phe Asn Ala Ser Leu Gly Thr Tyr His Asp
            660                 665                 670

Leu Leu Lys Ile Ile Lys Asp Lys Asp Phe Leu Asp Asn Glu Glu Asn
            675                 680                 685

Glu Asp Ile Leu Glu Asp Ile Val Leu Thr Leu Thr Leu Phe Glu Asp
            690                 695                 700

Arg Glu Met Ile Glu Glu Arg Leu Lys Thr Tyr Ala His Leu Phe Asp
705                 710                 715                 720

Asp Lys Val Met Lys Gln Leu Lys Arg Arg Tyr Thr Gly Trp Gly
                725                 730                 735

Arg Leu Ser Arg Lys Leu Ile Asn Gly Ile Arg Asp Lys Gln Ser Gly
            740                 745                 750

Lys Thr Ile Leu Asp Phe Leu Lys Ser Asp Gly Phe Ala Asn Arg Asn
            755                 760                 765

Phe Met Gln Leu Ile His Asp Asp Ser Leu Thr Phe Lys Glu Asp Ile
```

```
            770                 775                 780
Gln Lys Ala Gln Val Ser Gly Gln Gly Asp Ser Leu His Glu His Ile
785                 790                 795                 800

Ala Asn Leu Ala Gly Ser Pro Ala Ile Lys Lys Gly Ile Leu Gln Thr
                805                 810                 815

Val Lys Val Val Asp Glu Leu Val Lys Val Met Gly Arg His Lys Pro
                820                 825                 830

Glu Asn Ile Val Ile Glu Met Ala Arg Glu Asn Gln Thr Thr Gln Lys
                835                 840                 845

Gly Gln Lys Asn Ser Arg Glu Arg Met Lys Arg Ile Glu Glu Gly Ile
850                 855                 860

Lys Glu Leu Gly Ser Gln Ile Leu Lys Glu His Pro Val Glu Asn Thr
865                 870                 875                 880

Gln Leu Gln Asn Glu Lys Leu Tyr Leu Tyr Tyr Leu Gln Asn Gly Arg
                885                 890                 895

Asp Met Tyr Val Asp Gln Glu Leu Asp Ile Asn Arg Leu Ser Asp Tyr
                900                 905                 910

Asp Val Asp His Ile Val Pro Gln Ser Phe Leu Lys Asp Asp Ser Ile
                915                 920                 925

Asp Asn Lys Val Leu Thr Arg Ser Asp Lys Asn Arg Gly Lys Ser Asp
930                 935                 940

Asn Val Pro Ser Glu Glu Val Val Lys Lys Met Lys Asn Tyr Trp Arg
945                 950                 955                 960

Gln Leu Leu Asn Ala Lys Leu Ile Thr Gln Arg Lys Phe Asp Asn Leu
                965                 970                 975

Thr Lys Ala Glu Arg Gly Gly Leu Ser Glu Leu Asp Lys Ala Gly Phe
                980                 985                 990

Ile Lys Arg Gln Leu Val Glu Thr Arg Gln Ile Thr Lys His Val Ala
                995                 1000                1005

Gln Ile Leu Asp Ser Arg Met Asn Thr Lys Tyr Asp Glu Asn Asp
      1010                1015                1020

Lys Leu Ile Arg Glu Val Lys Val Ile Thr Leu Lys Ser Lys Leu
      1025                1030                1035

Val Ser Asp Phe Arg Lys Asp Phe Gln Phe Tyr Lys Val Arg Glu
      1040                1045                1050

Ile Asn Asn Tyr His His Ala His Asp Ala Tyr Leu Asn Ala Val
      1055                1060                1065

Val Gly Thr Ala Leu Ile Lys Lys Tyr Pro Lys Leu Glu Ser Glu
      1070                1075                1080

Phe Val Tyr Gly Asp Tyr Lys Val Tyr Asp Val Arg Lys Met Ile
      1085                1090                1095

Ala Lys Ser Glu Gln Glu Ile Gly Lys Ala Thr Ala Lys Tyr Phe
      1100                1105                1110

Phe Tyr Ser Asn Ile Met Asn Phe Phe Lys Thr Glu Ile Thr Leu
      1115                1120                1125

Ala Asn Gly Glu Ile Arg Lys Arg Pro Leu Ile Glu Thr Asn Gly
      1130                1135                1140

Glu Thr Gly Glu Ile Val Trp Asp Lys Gly Arg Asp Phe Ala Thr
      1145                1150                1155

Val Arg Lys Val Leu Ser Met Pro Gln Val Asn Ile Val Lys Lys
      1160                1165                1170

Thr Glu Val Gln Thr Gly Gly Phe Ser Lys Glu Ser Ile Leu Pro
      1175                1180                1185
```

Lys Arg Asn Ser Asp Lys Leu Ile Ala Arg Lys Asp Trp Asp
    1190                1195                1200

Pro Lys Lys Tyr Gly Gly Phe Asp Ser Pro Thr Val Ala Tyr Ser
    1205                1210                1215

Val Leu Val Val Ala Lys Val Glu Lys Gly Lys Ser Lys Lys Leu
    1220                1225                1230

Lys Ser Val Lys Glu Leu Leu Gly Ile Thr Ile Met Glu Arg Ser
    1235                1240                1245

Ser Phe Glu Lys Asn Pro Ile Asp Phe Leu Glu Ala Lys Gly Tyr
    1250                1255                1260

Lys Glu Val Lys Lys Asp Leu Ile Ile Lys Leu Pro Lys Tyr Ser
    1265                1270                1275

Leu Phe Glu Leu Glu Asn Gly Arg Lys Arg Met Leu Ala Ser Ala
    1280                1285                1290

Gly Glu Leu Gln Lys Gly Asn Glu Leu Ala Leu Pro Ser Lys Tyr
    1295                1300                1305

Val Asn Phe Leu Tyr Leu Ala Ser His Tyr Glu Lys Leu Lys Gly
    1310                1315                1320

Ser Pro Glu Asp Asn Glu Gln Lys Gln Leu Phe Val Glu Gln His
    1325                1330                1335

Lys His Tyr Leu Asp Glu Ile Ile Glu Gln Ile Ser Glu Phe Ser
    1340                1345                1350

Lys Arg Val Ile Leu Ala Asp Ala Asn Leu Asp Lys Val Leu Ser
    1355                1360                1365

Ala Tyr Asn Lys His Arg Asp Lys Pro Ile Arg Glu Gln Ala Glu
    1370                1375                1380

Asn Ile Ile His Leu Phe Thr Leu Thr Asn Leu Gly Ala Pro Ala
    1385                1390                1395

Ala Phe Lys Tyr Phe Asp Thr Thr Ile Asp Arg Lys Arg Tyr Thr
    1400                1405                1410

Ser Thr Lys Glu Val Leu Asp Ala Thr Leu Ile His Gln Ser Ile
    1415                1420                1425

Thr Gly Leu Tyr Glu Thr Arg Ile Asp Leu Ser Gln Leu Gly Gly
    1430                1435                1440

Asp Ser Arg Ala Asp Pro Lys Lys Lys Arg Lys Val
    1445                1450                1455

<210> SEQ ID NO 53
<211> LENGTH: 1455
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly Cys Asp Lys Lys

```
              65                  70                  75                  80
Tyr Ser Ile Gly Leu Asp Ile Gly Thr Asn Ser Val Gly Trp Ala Val
                85                  90                  95

Ile Thr Asp Glu Tyr Lys Val Pro Ser Lys Lys Phe Lys Val Leu Gly
                100                 105                 110

Asn Thr Asp Arg His Ser Ile Lys Lys Asn Leu Ile Gly Ala Leu Leu
                115                 120                 125

Phe Asp Ser Gly Glu Thr Ala Glu Ala Thr Arg Leu Lys Arg Thr Ala
                130                 135                 140

Arg Arg Arg Tyr Thr Arg Arg Lys Asn Arg Ile Cys Tyr Leu Gln Glu
145                 150                 155                 160

Ile Phe Ser Asn Glu Met Ala Lys Val Asp Asp Ser Phe Phe His Arg
                165                 170                 175

Leu Glu Glu Ser Phe Leu Val Glu Glu Asp Lys Lys His Glu Arg His
                180                 185                 190

Pro Ile Phe Gly Asn Ile Val Asp Glu Val Ala Tyr His Glu Lys Tyr
                195                 200                 205

Pro Thr Ile Tyr His Leu Arg Lys Lys Leu Val Asp Ser Thr Asp Lys
210                 215                 220

Ala Asp Leu Arg Leu Ile Tyr Leu Ala Leu Ala His Met Ile Lys Phe
225                 230                 235                 240

Arg Gly His Phe Leu Ile Glu Gly Asp Leu Asn Pro Asp Asn Ser Asp
                245                 250                 255

Val Asp Lys Leu Phe Ile Gln Leu Val Gln Thr Tyr Asn Gln Leu Phe
                260                 265                 270

Glu Glu Asn Pro Ile Asn Ala Ser Gly Val Asp Ala Lys Ala Ile Leu
                275                 280                 285

Ser Ala Arg Leu Ser Lys Ser Arg Arg Leu Glu Asn Leu Ile Ala Gln
                290                 295                 300

Leu Pro Gly Glu Lys Lys Asn Gly Leu Phe Gly Asn Leu Ile Ala Leu
305                 310                 315                 320

Ser Leu Gly Leu Thr Pro Asn Phe Lys Ser Asn Phe Asp Leu Ala Glu
                325                 330                 335

Asp Ala Lys Leu Gln Leu Ser Lys Asp Thr Tyr Asp Asp Asp Leu Asp
                340                 345                 350

Asn Leu Leu Ala Gln Ile Gly Asp Gln Tyr Ala Asp Leu Phe Leu Ala
                355                 360                 365

Ala Lys Asn Leu Ser Asp Ala Ile Leu Leu Ser Asp Ile Leu Arg Val
                370                 375                 380

Asn Thr Glu Ile Thr Lys Ala Pro Leu Ser Ala Ser Met Ile Lys Arg
385                 390                 395                 400

Tyr Asp Glu His His Gln Asp Leu Thr Leu Leu Lys Ala Leu Val Arg
                405                 410                 415

Gln Gln Leu Pro Glu Lys Tyr Lys Glu Ile Phe Phe Asp Gln Ser Lys
                420                 425                 430

Asn Gly Tyr Ala Gly Tyr Ile Asp Gly Gly Ala Ser Gln Glu Glu Phe
                435                 440                 445

Tyr Lys Phe Ile Lys Pro Ile Leu Glu Lys Met Asp Gly Thr Glu Glu
                450                 455                 460

Leu Leu Val Lys Leu Asn Arg Glu Asp Leu Leu Arg Lys Gln Arg Thr
465                 470                 475                 480

Phe Asp Asn Gly Ser Ile Pro His Gln Ile His Leu Gly Glu Leu His
                485                 490                 495
```

-continued

```
Ala Ile Leu Arg Arg Gln Glu Asp Phe Tyr Pro Phe Leu Lys Asp Asn
            500                 505                 510

Arg Glu Lys Ile Glu Lys Ile Leu Thr Phe Arg Ile Pro Tyr Tyr Val
        515                 520                 525

Gly Pro Leu Ala Arg Gly Asn Ser Arg Phe Ala Trp Met Thr Arg Lys
    530                 535                 540

Ser Glu Glu Thr Ile Thr Pro Trp Asn Phe Glu Val Val Asp Lys
545                 550                 555                 560

Gly Ala Ser Ala Gln Ser Phe Ile Glu Arg Met Thr Asn Phe Asp Lys
                565                 570                 575

Asn Leu Pro Asn Glu Lys Val Leu Pro Lys His Ser Leu Leu Tyr Glu
            580                 585                 590

Tyr Phe Thr Val Tyr Asn Glu Leu Thr Lys Val Lys Tyr Val Thr Glu
        595                 600                 605

Gly Met Arg Lys Pro Ala Phe Leu Ser Gly Glu Gln Lys Lys Ala Ile
    610                 615                 620

Val Asp Leu Leu Phe Lys Thr Asn Arg Lys Val Thr Val Lys Gln Leu
625                 630                 635                 640

Lys Glu Asp Tyr Phe Lys Lys Ile Glu Cys Phe Asp Ser Val Glu Ile
                645                 650                 655

Ser Gly Val Glu Asp Arg Phe Asn Ala Ser Leu Gly Thr Tyr His Asp
            660                 665                 670

Leu Leu Lys Ile Ile Lys Asp Lys Asp Phe Leu Asp Asn Glu Glu Asn
        675                 680                 685

Glu Asp Ile Leu Glu Asp Ile Val Leu Thr Leu Thr Leu Phe Glu Asp
    690                 695                 700

Arg Glu Met Ile Glu Glu Arg Leu Lys Thr Tyr Ala His Leu Phe Asp
705                 710                 715                 720

Asp Lys Val Met Lys Gln Leu Lys Arg Arg Tyr Thr Gly Trp Gly
                725                 730                 735

Arg Leu Ser Arg Lys Leu Ile Asn Gly Ile Arg Asp Lys Gln Ser Gly
            740                 745                 750

Lys Thr Ile Leu Asp Phe Leu Lys Ser Asp Gly Phe Ala Asn Arg Asn
        755                 760                 765

Phe Met Gln Leu Ile His Asp Asp Ser Leu Thr Phe Lys Glu Asp Ile
    770                 775                 780

Gln Lys Ala Gln Val Ser Gly Gln Gly Asp Ser Leu His Glu His Ile
785                 790                 795                 800

Ala Asn Leu Ala Gly Ser Pro Ala Ile Lys Lys Gly Ile Leu Gln Thr
                805                 810                 815

Val Lys Val Val Asp Glu Leu Val Lys Val Met Gly Arg His Lys Pro
            820                 825                 830

Glu Asn Ile Val Ile Glu Met Ala Arg Glu Asn Gln Thr Thr Gln Lys
        835                 840                 845

Gly Gln Lys Asn Ser Arg Glu Arg Met Lys Arg Ile Glu Glu Gly Ile
    850                 855                 860

Lys Glu Leu Gly Ser Gln Ile Leu Lys Glu His Pro Val Glu Asn Thr
865                 870                 875                 880

Gln Leu Gln Asn Glu Lys Leu Tyr Leu Tyr Tyr Leu Gln Asn Gly Arg
                885                 890                 895

Asp Met Tyr Val Asp Gln Glu Leu Asp Ile Asn Arg Leu Ser Asp Tyr
            900                 905                 910
```

```
Asp Val Asp His Ile Val Pro Gln Ser Phe Leu Lys Asp Ser Ile
            915                 920                 925

Asp Asn Lys Val Leu Thr Arg Ser Asp Lys Asn Arg Gly Lys Ser Asp
    930                 935                 940

Asn Val Pro Ser Glu Glu Val Val Lys Met Lys Asn Tyr Trp Arg
945                 950                 955                 960

Gln Leu Leu Asn Ala Lys Leu Ile Thr Gln Arg Lys Phe Asp Asn Leu
                965                 970                 975

Thr Lys Ala Glu Arg Gly Gly Leu Ser Glu Leu Asp Lys Ala Gly Phe
            980                 985                 990

Ile Lys Arg Gln Leu Val Glu Thr Arg Gln Ile Thr Lys His Val Ala
            995                 1000                1005

Gln Ile Leu Asp Ser Arg Met Asn Thr Lys Tyr Asp Glu Asn Asp
    1010                1015                1020

Lys Leu Ile Arg Glu Val Lys Val Ile Thr Leu Lys Ser Lys Leu
    1025                1030                1035

Val Ser Asp Phe Arg Lys Asp Phe Gln Phe Tyr Lys Val Arg Glu
    1040                1045                1050

Ile Asn Asn Tyr His His Ala His Asp Ala Tyr Leu Asn Ala Val
    1055                1060                1065

Val Gly Thr Ala Leu Ile Lys Lys Tyr Pro Lys Leu Glu Ser Glu
    1070                1075                1080

Phe Val Tyr Gly Asp Tyr Lys Val Tyr Asp Val Arg Lys Met Ile
    1085                1090                1095

Ala Lys Ser Glu Gln Glu Ile Gly Lys Ala Thr Ala Lys Tyr Phe
    1100                1105                1110

Phe Tyr Ser Asn Ile Met Asn Phe Phe Lys Thr Glu Ile Thr Leu
    1115                1120                1125

Ala Asn Gly Glu Ile Arg Lys Arg Pro Leu Ile Glu Thr Asn Gly
    1130                1135                1140

Glu Thr Gly Glu Ile Val Trp Asp Lys Gly Arg Asp Phe Ala Thr
    1145                1150                1155

Val Arg Lys Val Leu Ser Met Pro Gln Val Asn Ile Val Lys Lys
    1160                1165                1170

Thr Glu Val Gln Thr Gly Gly Phe Ser Lys Glu Ser Ile Leu Pro
    1175                1180                1185

Lys Arg Asn Ser Asp Lys Leu Ile Ala Arg Lys Lys Asp Trp Asp
    1190                1195                1200

Pro Lys Lys Tyr Gly Gly Phe Asp Ser Pro Thr Val Ala Tyr Ser
    1205                1210                1215

Val Leu Val Val Ala Lys Val Glu Lys Gly Lys Ser Lys Lys Leu
    1220                1225                1230

Lys Ser Val Lys Glu Leu Leu Gly Ile Thr Ile Met Glu Arg Ser
    1235                1240                1245

Ser Phe Glu Lys Asn Pro Ile Asp Phe Leu Glu Ala Lys Gly Tyr
    1250                1255                1260

Lys Glu Val Lys Lys Asp Leu Ile Ile Lys Leu Pro Lys Tyr Ser
    1265                1270                1275

Leu Phe Glu Leu Glu Asn Gly Arg Lys Arg Met Leu Ala Ser Ala
    1280                1285                1290

Gly Glu Leu Gln Lys Gly Asn Glu Leu Ala Leu Pro Ser Lys Tyr
    1295                1300                1305

Val Asn Phe Leu Tyr Leu Ala Ser His Tyr Glu Lys Leu Lys Gly
```

```
                    1310                1315                1320

Ser Pro Glu Asp Asn Glu Gln Lys Gln Leu Phe Val Glu Gln His
    1325                1330                1335

Lys His Tyr Leu Asp Glu Ile Ile Glu Gln Ile Ser Glu Phe Ser
    1340                1345                1350

Lys Arg Val Ile Leu Ala Asp Ala Asn Leu Asp Lys Val Leu Ser
    1355                1360                1365

Ala Tyr Asn Lys His Arg Asp Lys Pro Ile Arg Glu Gln Ala Glu
    1370                1375                1380

Asn Ile Ile His Leu Phe Thr Leu Thr Asn Leu Gly Ala Pro Ala
    1385                1390                1395

Ala Phe Lys Tyr Phe Asp Thr Thr Ile Asp Arg Lys Arg Tyr Thr
    1400                1405                1410

Ser Thr Lys Glu Val Leu Asp Ala Thr Leu Ile His Gln Ser Ile
    1415                1420                1425

Thr Gly Leu Tyr Glu Thr Arg Ile Asp Leu Ser Gln Leu Gly Gly
    1430                1435                1440

Asp Ser Arg Ala Asp Pro Lys Lys Lys Arg Lys Val
    1445                1450                1455

<210> SEQ ID NO 54
<211> LENGTH: 1455
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly Asp Lys Lys
65                  70                  75                  80

Tyr Ser Ile Gly Leu Asp Ile Gly Thr Asn Ser Val Gly Trp Ala Val
                85                  90                  95

Ile Thr Asp Glu Tyr Lys Val Pro Ser Lys Lys Phe Lys Val Leu Gly
            100                 105                 110

Asn Thr Asp Arg His Ser Ile Lys Lys Asn Leu Ile Gly Ala Leu Leu
        115                 120                 125

Phe Asp Ser Gly Glu Thr Ala Glu Ala Thr Arg Leu Lys Arg Thr Ala
    130                 135                 140

Arg Arg Arg Tyr Thr Arg Arg Lys Asn Arg Ile Cys Tyr Leu Gln Glu
145                 150                 155                 160

Ile Phe Ser Asn Glu Met Ala Lys Val Asp Asp Ser Phe Phe His Arg
                165                 170                 175

Leu Glu Glu Ser Phe Leu Val Glu Glu Asp Lys Lys His Glu Arg His
            180                 185                 190

Pro Ile Phe Gly Asn Ile Val Asp Glu Val Ala Tyr His Glu Lys Tyr
        195                 200                 205
```

```
Pro Thr Ile Tyr His Leu Arg Lys Lys Leu Val Asp Ser Thr Asp Lys
    210                 215                 220

Ala Asp Leu Arg Leu Ile Tyr Leu Ala Leu Ala His Met Ile Lys Phe
225                 230                 235                 240

Arg Gly His Phe Leu Ile Glu Gly Asp Leu Asn Pro Asp Asn Ser Asp
                245                 250                 255

Val Asp Lys Leu Phe Ile Gln Leu Val Gln Thr Tyr Asn Gln Leu Phe
            260                 265                 270

Glu Glu Asn Pro Ile Asn Ala Ser Gly Val Asp Ala Lys Ala Ile Leu
                275                 280                 285

Ser Ala Arg Leu Ser Lys Ser Arg Arg Leu Glu Asn Leu Ile Ala Gln
290                 295                 300

Leu Pro Gly Glu Lys Lys Asn Gly Leu Phe Gly Asn Leu Ile Ala Leu
305                 310                 315                 320

Ser Leu Gly Leu Thr Pro Asn Phe Lys Ser Asn Phe Asp Leu Ala Glu
                325                 330                 335

Asp Ala Lys Leu Gln Leu Ser Lys Asp Thr Tyr Asp Asp Asp Leu Asp
                340                 345                 350

Asn Leu Leu Ala Gln Ile Gly Asp Gln Tyr Ala Asp Leu Phe Leu Ala
                355                 360                 365

Ala Lys Asn Leu Ser Asp Ala Ile Leu Leu Ser Asp Ile Leu Arg Val
370                 375                 380

Asn Thr Glu Ile Thr Lys Ala Pro Leu Ser Ala Ser Met Ile Lys Arg
385                 390                 395                 400

Tyr Asp Glu His His Gln Asp Leu Thr Leu Leu Lys Ala Leu Val Arg
                405                 410                 415

Gln Gln Leu Pro Glu Lys Tyr Lys Glu Ile Phe Phe Asp Gln Ser Lys
                420                 425                 430

Asn Gly Tyr Ala Gly Tyr Ile Asp Gly Gly Ala Ser Gln Glu Glu Phe
                435                 440                 445

Tyr Lys Phe Ile Lys Pro Ile Leu Glu Lys Met Asp Gly Thr Glu Glu
                450                 455                 460

Leu Leu Val Lys Leu Asn Arg Glu Asp Leu Leu Arg Lys Gln Arg Thr
465                 470                 475                 480

Phe Asp Asn Gly Ser Ile Pro His Gln Ile His Leu Gly Glu Leu His
                485                 490                 495

Ala Ile Leu Arg Arg Gln Glu Asp Phe Tyr Pro Phe Leu Lys Asp Asn
                500                 505                 510

Arg Glu Lys Ile Glu Lys Ile Leu Thr Phe Arg Ile Pro Tyr Tyr Val
                515                 520                 525

Gly Pro Leu Ala Arg Gly Asn Ser Arg Phe Ala Trp Met Thr Arg Lys
530                 535                 540

Ser Glu Glu Thr Ile Thr Pro Trp Asn Phe Glu Glu Val Val Asp Lys
545                 550                 555                 560

Gly Ala Ser Ala Gln Ser Phe Ile Glu Arg Met Thr Asn Phe Asp Lys
                565                 570                 575

Asn Leu Pro Asn Glu Lys Val Leu Pro Lys His Ser Leu Leu Tyr Glu
                580                 585                 590

Tyr Phe Thr Val Tyr Asn Glu Leu Thr Lys Val Lys Tyr Val Thr Glu
                595                 600                 605

Gly Met Arg Lys Pro Ala Phe Leu Ser Gly Glu Gln Lys Lys Ala Ile
                610                 615                 620

Val Asp Leu Leu Phe Lys Thr Asn Arg Lys Val Thr Val Lys Gln Leu
```

```
                625                 630                 635                 640
Lys Glu Asp Tyr Phe Lys Lys Ile Glu Cys Phe Asp Ser Val Glu Ile
                645                 650                 655

Ser Gly Val Glu Asp Arg Phe Asn Ala Ser Leu Gly Thr Tyr His Asp
                660                 665                 670

Leu Leu Lys Ile Ile Lys Asp Lys Asp Phe Leu Asp Asn Glu Glu Asn
                675                 680                 685

Glu Asp Ile Leu Glu Asp Ile Val Leu Thr Leu Thr Leu Phe Glu Asp
                690                 695                 700

Arg Glu Met Ile Glu Glu Arg Leu Lys Thr Tyr Ala His Leu Phe Asp
705                 710                 715                 720

Asp Lys Val Met Lys Gln Leu Lys Arg Arg Arg Tyr Thr Gly Trp Gly
                725                 730                 735

Arg Leu Ser Arg Lys Leu Ile Asn Gly Ile Arg Asp Lys Gln Ser Gly
                740                 745                 750

Lys Thr Ile Leu Asp Phe Leu Lys Ser Asp Gly Phe Ala Asn Arg Asn
                755                 760                 765

Phe Met Gln Leu Ile His Asp Asp Ser Leu Thr Phe Lys Glu Asp Ile
                770                 775                 780

Gln Lys Ala Gln Val Ser Gly Gln Gly Asp Ser Leu His Glu His Ile
785                 790                 795                 800

Ala Asn Leu Ala Gly Ser Pro Ala Ile Lys Lys Gly Ile Leu Gln Thr
                805                 810                 815

Val Lys Val Val Asp Glu Leu Val Lys Val Met Gly Arg His Lys Pro
                820                 825                 830

Glu Asn Ile Val Ile Glu Met Ala Arg Glu Asn Gln Thr Thr Gln Lys
                835                 840                 845

Gly Gln Lys Asn Ser Arg Glu Arg Met Lys Arg Ile Glu Glu Gly Ile
                850                 855                 860

Lys Glu Leu Gly Ser Gln Ile Leu Lys Glu His Pro Val Glu Asn Thr
865                 870                 875                 880

Gln Leu Gln Asn Glu Lys Leu Tyr Leu Tyr Tyr Leu Gln Asn Gly Arg
                885                 890                 895

Asp Met Tyr Val Asp Gln Glu Leu Asp Ile Asn Arg Leu Ser Asp Tyr
                900                 905                 910

Asp Val Asp His Ile Val Pro Gln Ser Phe Leu Lys Asp Asp Ser Ile
                915                 920                 925

Asp Asn Lys Val Leu Thr Arg Ser Asp Lys Asn Arg Gly Lys Ser Asp
930                 935                 940

Asn Val Pro Ser Glu Glu Val Val Lys Lys Met Lys Asn Tyr Trp Arg
945                 950                 955                 960

Gln Leu Leu Asn Ala Lys Leu Ile Thr Gln Arg Lys Phe Asp Asn Leu
                965                 970                 975

Thr Lys Ala Glu Arg Gly Gly Leu Ser Glu Leu Asp Lys Ala Gly Phe
                980                 985                 990

Ile Lys Arg Gln Leu Val Glu Thr Arg Gln Ile Thr Lys His Val Ala
                995                 1000                1005

Gln Ile Leu Asp Ser Arg Met Asn Thr Lys Tyr Asp Glu Asn Asp
                1010                1015                1020

Lys Leu Ile Arg Glu Val Lys Val Ile Thr Leu Lys Ser Lys Leu
                1025                1030                1035

Val Ser Asp Phe Arg Lys Asp Phe Gln Phe Tyr Lys Val Arg Glu
                1040                1045                1050
```

```
Ile Asn Asn Tyr His His Ala His Asp Ala Tyr Leu Asn Ala Val
1055             1060                 1065

Val Gly Thr Ala Leu Ile Lys Lys Tyr Pro Lys Leu Glu Ser Glu
1070             1075                 1080

Phe Val Tyr Gly Asp Tyr Lys Val Tyr Asp Val Arg Lys Met Ile
1085             1090                 1095

Ala Lys Ser Glu Gln Glu Ile Gly Lys Ala Thr Ala Lys Tyr Phe
1100             1105                 1110

Phe Tyr Ser Asn Ile Met Asn Phe Phe Lys Thr Glu Ile Thr Leu
1115             1120                 1125

Ala Asn Gly Glu Ile Arg Lys Arg Pro Leu Ile Glu Thr Asn Gly
1130             1135                 1140

Glu Thr Gly Glu Ile Val Trp Asp Lys Gly Arg Asp Phe Ala Thr
1145             1150                 1155

Val Arg Lys Val Leu Ser Met Pro Gln Val Asn Ile Val Lys Lys
1160             1165                 1170

Thr Glu Val Gln Thr Gly Gly Phe Ser Lys Glu Ser Ile Leu Pro
1175             1180                 1185

Lys Arg Asn Ser Asp Lys Leu Ile Ala Arg Lys Lys Asp Trp Asp
1190             1195                 1200

Pro Lys Lys Tyr Gly Gly Phe Asp Ser Pro Thr Val Ala Tyr Ser
1205             1210                 1215

Val Leu Val Val Ala Lys Val Glu Lys Gly Lys Ser Lys Lys Leu
1220             1225                 1230

Lys Ser Val Lys Glu Leu Leu Gly Ile Thr Ile Met Glu Arg Ser
1235             1240                 1245

Ser Phe Glu Lys Asn Pro Ile Asp Phe Leu Glu Ala Lys Gly Tyr
1250             1255                 1260

Lys Glu Val Lys Lys Asp Leu Ile Ile Lys Leu Pro Lys Tyr Ser
1265             1270                 1275

Leu Phe Glu Leu Glu Asn Gly Arg Lys Arg Met Leu Ala Ser Ala
1280             1285                 1290

Gly Glu Leu Gln Lys Gly Asn Glu Leu Ala Leu Pro Ser Lys Tyr
1295             1300                 1305

Val Asn Phe Leu Tyr Leu Ala Ser His Tyr Glu Lys Leu Lys Gly
1310             1315                 1320

Ser Pro Glu Asp Asn Glu Gln Lys Gln Leu Phe Val Glu Gln His
1325             1330                 1335

Lys His Tyr Leu Asp Glu Ile Ile Glu Gln Ile Ser Glu Phe Ser
1340             1345                 1350

Lys Arg Val Ile Leu Ala Asp Ala Asn Leu Asp Lys Val Leu Ser
1355             1360                 1365

Ala Tyr Asn Lys His Arg Asp Lys Pro Ile Arg Glu Gln Ala Glu
1370             1375                 1380

Asn Ile Ile His Leu Phe Thr Leu Thr Asn Leu Gly Ala Pro Ala
1385             1390                 1395

Ala Phe Lys Tyr Phe Asp Thr Thr Ile Asp Arg Lys Arg Tyr Thr
1400             1405                 1410

Ser Thr Lys Glu Val Leu Asp Ala Thr Leu Ile His Gln Ser Ile
1415             1420                 1425

Thr Gly Leu Tyr Glu Thr Arg Ile Asp Leu Ser Gln Leu Gly Gly
1430             1435                 1440
```

```
Asp Ser Arg Ala Asp Pro Lys     Lys Lys Arg Lys Val
    1445                1450                    1455
```

<210> SEQ ID NO 55
<211> LENGTH: 1455
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

```
Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly Phe Asp Lys Lys
65                  70                  75                  80

Tyr Ser Ile Gly Leu Asp Ile Gly Thr Asn Ser Val Gly Trp Ala Val
                85                  90                  95

Ile Thr Asp Glu Tyr Lys Val Pro Ser Lys Lys Phe Lys Val Leu Gly
            100                 105                 110

Asn Thr Asp Arg His Ser Ile Lys Lys Asn Leu Ile Gly Ala Leu Leu
        115                 120                 125

Phe Asp Ser Gly Glu Thr Ala Glu Ala Thr Arg Leu Lys Arg Thr Ala
    130                 135                 140

Arg Arg Arg Tyr Thr Arg Arg Lys Asn Arg Ile Cys Tyr Leu Gln Glu
145                 150                 155                 160

Ile Phe Ser Asn Glu Met Ala Lys Val Asp Asp Ser Phe Phe His Arg
                165                 170                 175

Leu Glu Glu Ser Phe Leu Val Glu Glu Asp Lys Lys His Glu Arg His
            180                 185                 190

Pro Ile Phe Gly Asn Ile Val Asp Glu Val Ala Tyr His Glu Lys Tyr
        195                 200                 205

Pro Thr Ile Tyr His Leu Arg Lys Lys Leu Val Asp Ser Thr Asp Lys
    210                 215                 220

Ala Asp Leu Arg Leu Ile Tyr Leu Ala Leu Ala His Met Ile Lys Phe
225                 230                 235                 240

Arg Gly His Phe Leu Ile Glu Gly Asp Leu Asn Pro Asp Asn Ser Asp
                245                 250                 255

Val Asp Lys Leu Phe Ile Gln Leu Val Gln Thr Tyr Asn Gln Leu Phe
            260                 265                 270

Glu Glu Asn Pro Ile Asn Ala Ser Gly Val Asp Ala Lys Ala Ile Leu
        275                 280                 285

Ser Ala Arg Leu Ser Lys Ser Arg Arg Leu Glu Asn Leu Ile Ala Gln
    290                 295                 300

Leu Pro Gly Glu Lys Lys Asn Gly Leu Phe Gly Asn Leu Ile Ala Leu
305                 310                 315                 320

Ser Leu Gly Leu Thr Pro Asn Phe Lys Ser Asn Phe Asp Leu Ala Glu
                325                 330                 335

Asp Ala Lys Leu Gln Leu Ser Lys Asp Thr Tyr Asp Asp Asp Leu Asp
            340                 345                 350
```

-continued

```
Asn Leu Leu Ala Gln Ile Gly Asp Gln Tyr Ala Asp Leu Phe Leu Ala
            355                 360                 365
Ala Lys Asn Leu Ser Asp Ala Ile Leu Leu Ser Asp Ile Leu Arg Val
    370                 375                 380
Asn Thr Glu Ile Thr Lys Ala Pro Leu Ser Ala Ser Met Ile Lys Arg
385                 390                 395                 400
Tyr Asp Glu His His Gln Asp Leu Thr Leu Leu Lys Ala Leu Val Arg
                405                 410                 415
Gln Gln Leu Pro Glu Lys Tyr Lys Glu Ile Phe Phe Asp Gln Ser Lys
            420                 425                 430
Asn Gly Tyr Ala Gly Tyr Ile Asp Gly Gly Ala Ser Gln Glu Glu Phe
        435                 440                 445
Tyr Lys Phe Ile Lys Pro Ile Leu Glu Lys Met Asp Gly Thr Glu Glu
    450                 455                 460
Leu Leu Val Lys Leu Asn Arg Glu Asp Leu Leu Arg Lys Gln Arg Thr
465                 470                 475                 480
Phe Asp Asn Gly Ser Ile Pro His Gln Ile His Leu Gly Glu Leu His
                485                 490                 495
Ala Ile Leu Arg Arg Gln Glu Asp Phe Tyr Pro Phe Leu Lys Asp Asn
            500                 505                 510
Arg Glu Lys Ile Glu Lys Ile Leu Thr Phe Arg Ile Pro Tyr Tyr Val
        515                 520                 525
Gly Pro Leu Ala Arg Gly Asn Ser Arg Phe Ala Trp Met Thr Arg Lys
    530                 535                 540
Ser Glu Glu Thr Ile Thr Pro Trp Asn Phe Glu Val Val Asp Lys
545                 550                 555                 560
Gly Ala Ser Ala Gln Ser Phe Ile Glu Arg Met Thr Asn Phe Asp Lys
                565                 570                 575
Asn Leu Pro Asn Glu Lys Val Leu Pro Lys His Ser Leu Leu Tyr Glu
            580                 585                 590
Tyr Phe Thr Val Tyr Asn Glu Leu Thr Lys Val Lys Tyr Val Thr Glu
        595                 600                 605
Gly Met Arg Lys Pro Ala Phe Leu Ser Gly Glu Gln Lys Lys Ala Ile
    610                 615                 620
Val Asp Leu Leu Phe Lys Thr Asn Arg Lys Val Thr Val Lys Gln Leu
625                 630                 635                 640
Lys Glu Asp Tyr Phe Lys Lys Ile Glu Cys Phe Asp Ser Val Glu Ile
                645                 650                 655
Ser Gly Val Glu Asp Arg Phe Asn Ala Ser Leu Gly Thr Tyr His Asp
            660                 665                 670
Leu Leu Lys Ile Ile Lys Asp Lys Asp Phe Leu Asp Asn Glu Glu Asn
        675                 680                 685
Glu Asp Ile Leu Glu Asp Ile Val Leu Thr Leu Thr Leu Phe Glu Asp
    690                 695                 700
Arg Glu Met Ile Glu Glu Arg Leu Lys Thr Tyr Ala His Leu Phe Asp
705                 710                 715                 720
Asp Lys Val Met Lys Gln Leu Lys Arg Arg Arg Tyr Thr Gly Trp Gly
                725                 730                 735
Arg Leu Ser Arg Lys Leu Ile Asn Gly Ile Arg Asp Lys Gln Ser Gly
            740                 745                 750
Lys Thr Ile Leu Asp Phe Leu Lys Ser Asp Gly Phe Ala Asn Arg Asn
        755                 760                 765
```

```
Phe Met Gln Leu Ile His Asp Asp Ser Leu Thr Phe Lys Glu Asp Ile
770                 775                 780

Gln Lys Ala Gln Val Ser Gly Gln Gly Asp Ser Leu His Glu His Ile
785                 790                 795                 800

Ala Asn Leu Ala Gly Ser Pro Ala Ile Lys Lys Gly Ile Leu Gln Thr
                805                 810                 815

Val Lys Val Val Asp Glu Leu Val Lys Val Met Gly Arg His Lys Pro
            820                 825                 830

Glu Asn Ile Val Ile Glu Met Ala Arg Glu Asn Gln Thr Thr Gln Lys
        835                 840                 845

Gly Gln Lys Asn Ser Arg Glu Arg Met Lys Arg Ile Glu Glu Gly Ile
850                 855                 860

Lys Glu Leu Gly Ser Gln Ile Leu Lys Glu His Pro Val Glu Asn Thr
865                 870                 875                 880

Gln Leu Gln Asn Glu Lys Leu Tyr Leu Tyr Tyr Leu Gln Asn Gly Arg
                885                 890                 895

Asp Met Tyr Val Asp Gln Glu Leu Asp Ile Asn Arg Leu Ser Asp Tyr
            900                 905                 910

Asp Val Asp His Ile Val Pro Gln Ser Phe Leu Lys Asp Asp Ser Ile
        915                 920                 925

Asp Asn Lys Val Leu Thr Arg Ser Asp Lys Asn Arg Gly Lys Ser Asp
930                 935                 940

Asn Val Pro Ser Glu Glu Val Val Lys Lys Met Lys Asn Tyr Trp Arg
945                 950                 955                 960

Gln Leu Leu Asn Ala Lys Leu Ile Thr Gln Arg Lys Phe Asp Asn Leu
                965                 970                 975

Thr Lys Ala Glu Arg Gly Gly Leu Ser Glu Leu Asp Lys Ala Gly Phe
            980                 985                 990

Ile Lys Arg Gln Leu Val Glu Thr Arg Gln Ile Thr Lys His Val Ala
        995                 1000                1005

Gln Ile Leu Asp Ser Arg Met Asn Thr Lys Tyr Asp Glu Asn Asp
        1010                1015                1020

Lys Leu Ile Arg Glu Val Lys Val Ile Thr Leu Lys Ser Lys Leu
        1025                1030                1035

Val Ser Asp Phe Arg Lys Asp Phe Gln Phe Tyr Lys Val Arg Glu
        1040                1045                1050

Ile Asn Asn Tyr His His Ala His Asp Ala Tyr Leu Asn Ala Val
        1055                1060                1065

Val Gly Thr Ala Leu Ile Lys Lys Tyr Pro Lys Leu Glu Ser Glu
        1070                1075                1080

Phe Val Tyr Gly Asp Tyr Lys Val Tyr Asp Val Arg Lys Met Ile
        1085                1090                1095

Ala Lys Ser Glu Gln Glu Ile Gly Lys Ala Thr Ala Lys Tyr Phe
        1100                1105                1110

Phe Tyr Ser Asn Ile Met Asn Phe Phe Lys Thr Glu Ile Thr Leu
        1115                1120                1125

Ala Asn Gly Glu Ile Arg Lys Arg Pro Leu Ile Glu Thr Asn Gly
        1130                1135                1140

Glu Thr Gly Glu Ile Val Trp Asp Lys Gly Arg Asp Phe Ala Thr
        1145                1150                1155

Val Arg Lys Val Leu Ser Met Pro Gln Val Asn Ile Val Lys Lys
        1160                1165                1170

Thr Glu Val Gln Thr Gly Gly Phe Ser Lys Glu Ser Ile Leu Pro
```

```
                1175                1180                1185

Lys Arg Asn Ser Asp Lys Leu Ile Ala Arg Lys Lys Asp Trp Asp
    1190                1195                1200

Pro Lys Lys Tyr Gly Gly Phe Asp Ser Pro Thr Val Ala Tyr Ser
    1205                1210                1215

Val Leu Val Val Ala Lys Val Glu Lys Gly Lys Ser Lys Lys Leu
    1220                1225                1230

Lys Ser Val Lys Glu Leu Leu Gly Ile Thr Ile Met Glu Arg Ser
    1235                1240                1245

Ser Phe Glu Lys Asn Pro Ile Asp Phe Leu Glu Ala Lys Gly Tyr
    1250                1255                1260

Lys Glu Val Lys Lys Asp Leu Ile Ile Lys Leu Pro Lys Tyr Ser
    1265                1270                1275

Leu Phe Glu Leu Glu Asn Gly Arg Lys Arg Met Leu Ala Ser Ala
    1280                1285                1290

Gly Glu Leu Gln Lys Gly Asn Glu Leu Ala Leu Pro Ser Lys Tyr
    1295                1300                1305

Val Asn Phe Leu Tyr Leu Ala Ser His Tyr Glu Lys Leu Lys Gly
    1310                1315                1320

Ser Pro Glu Asp Asn Glu Gln Lys Gln Leu Phe Val Glu Gln His
    1325                1330                1335

Lys His Tyr Leu Asp Glu Ile Ile Glu Gln Ile Ser Glu Phe Ser
    1340                1345                1350

Lys Arg Val Ile Leu Ala Asp Ala Asn Leu Asp Lys Val Leu Ser
    1355                1360                1365

Ala Tyr Asn Lys His Arg Asp Lys Pro Ile Arg Glu Gln Ala Glu
    1370                1375                1380

Asn Ile Ile His Leu Phe Thr Leu Thr Asn Leu Gly Ala Pro Ala
    1385                1390                1395

Ala Phe Lys Tyr Phe Asp Thr Thr Ile Asp Arg Lys Arg Tyr Thr
    1400                1405                1410

Ser Thr Lys Glu Val Leu Asp Ala Thr Leu Ile His Gln Ser Ile
    1415                1420                1425

Thr Gly Leu Tyr Glu Thr Arg Ile Asp Leu Ser Gln Leu Gly Gly
    1430                1435                1440

Asp Ser Arg Ala Asp Pro Lys Lys Lys Arg Lys Val
    1445                1450                1455

<210> SEQ ID NO 56
<211> LENGTH: 1455
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60
```

-continued

```
Ser Thr Leu His Leu Val Leu Arg Leu Arg Gly Glu Asp Lys Lys
 65                  70                  75                  80

Tyr Ser Ile Gly Leu Asp Ile Gly Thr Asn Ser Val Gly Trp Ala Val
             85                  90                  95

Ile Thr Asp Glu Tyr Lys Val Pro Ser Lys Lys Phe Lys Val Leu Gly
         100                 105                 110

Asn Thr Asp Arg His Ser Ile Lys Lys Asn Leu Ile Gly Ala Leu Leu
     115                 120                 125

Phe Asp Ser Gly Glu Thr Ala Glu Ala Thr Arg Leu Lys Arg Thr Ala
130                 135                 140

Arg Arg Arg Tyr Thr Arg Arg Lys Asn Arg Ile Cys Tyr Leu Gln Glu
145                 150                 155                 160

Ile Phe Ser Asn Glu Met Ala Lys Val Asp Asp Ser Phe Phe His Arg
                165                 170                 175

Leu Glu Glu Ser Phe Leu Val Glu Glu Asp Lys Lys His Glu Arg His
             180                 185                 190

Pro Ile Phe Gly Asn Ile Val Asp Glu Val Ala Tyr His Glu Lys Tyr
         195                 200                 205

Pro Thr Ile Tyr His Leu Arg Lys Lys Leu Val Asp Ser Thr Asp Lys
     210                 215                 220

Ala Asp Leu Arg Leu Ile Tyr Leu Ala Leu Ala His Met Ile Lys Phe
225                 230                 235                 240

Arg Gly His Phe Leu Ile Glu Gly Asp Leu Asn Pro Asp Asn Ser Asp
                245                 250                 255

Val Asp Lys Leu Phe Ile Gln Leu Val Gln Thr Tyr Asn Gln Leu Phe
             260                 265                 270

Glu Glu Asn Pro Ile Asn Ala Ser Gly Val Asp Ala Lys Ala Ile Leu
         275                 280                 285

Ser Ala Arg Leu Ser Lys Ser Arg Arg Leu Glu Asn Leu Ile Ala Gln
     290                 295                 300

Leu Pro Gly Glu Lys Lys Asn Gly Leu Phe Gly Asn Leu Ile Ala Leu
305                 310                 315                 320

Ser Leu Gly Leu Thr Pro Asn Phe Lys Ser Asn Phe Asp Leu Ala Glu
                325                 330                 335

Asp Ala Lys Leu Gln Leu Ser Lys Asp Thr Tyr Asp Asp Asp Leu Asp
             340                 345                 350

Asn Leu Leu Ala Gln Ile Gly Asp Gln Tyr Ala Asp Leu Phe Leu Ala
         355                 360                 365

Ala Lys Asn Leu Ser Asp Ala Ile Leu Leu Ser Asp Ile Leu Arg Val
     370                 375                 380

Asn Thr Glu Ile Thr Lys Ala Pro Leu Ser Ala Ser Met Ile Lys Arg
385                 390                 395                 400

Tyr Asp Glu His His Gln Asp Leu Thr Leu Leu Lys Ala Leu Val Arg
                405                 410                 415

Gln Gln Leu Pro Glu Lys Tyr Lys Glu Ile Phe Phe Asp Gln Ser Lys
             420                 425                 430

Asn Gly Tyr Ala Gly Tyr Ile Asp Gly Gly Ala Ser Gln Glu Glu Phe
         435                 440                 445

Tyr Lys Phe Ile Lys Pro Ile Leu Glu Lys Met Asp Gly Thr Glu Glu
     450                 455                 460

Leu Leu Val Lys Leu Asn Arg Glu Asp Leu Leu Arg Lys Gln Arg Thr
465                 470                 475                 480

Phe Asp Asn Gly Ser Ile Pro His Gln Ile His Leu Gly Glu Leu His
```

-continued

```
                485                 490                 495
Ala Ile Leu Arg Arg Gln Glu Asp Phe Tyr Pro Phe Leu Lys Asp Asn
                500                 505                 510

Arg Glu Lys Ile Glu Lys Ile Leu Thr Phe Arg Ile Pro Tyr Tyr Val
                515                 520                 525

Gly Pro Leu Ala Arg Gly Asn Ser Arg Phe Ala Trp Met Thr Arg Lys
                530                 535                 540

Ser Glu Glu Thr Ile Thr Pro Trp Asn Phe Glu Glu Val Val Asp Lys
545                 550                 555                 560

Gly Ala Ser Ala Gln Ser Phe Ile Glu Arg Met Thr Asn Phe Asp Lys
                565                 570                 575

Asn Leu Pro Asn Glu Lys Val Leu Pro Lys His Ser Leu Leu Tyr Glu
                580                 585                 590

Tyr Phe Thr Val Tyr Asn Glu Leu Thr Lys Val Lys Tyr Val Thr Glu
                595                 600                 605

Gly Met Arg Lys Pro Ala Phe Leu Ser Gly Glu Gln Lys Lys Ala Ile
                610                 615                 620

Val Asp Leu Leu Phe Lys Thr Asn Arg Lys Val Thr Val Lys Gln Leu
625                 630                 635                 640

Lys Glu Asp Tyr Phe Lys Lys Ile Glu Cys Phe Asp Ser Val Glu Ile
                645                 650                 655

Ser Gly Val Glu Asp Arg Phe Asn Ala Ser Leu Gly Thr Tyr His Asp
                660                 665                 670

Leu Leu Lys Ile Ile Lys Asp Lys Asp Phe Leu Asp Asn Glu Glu Asn
                675                 680                 685

Glu Asp Ile Leu Glu Asp Ile Val Leu Thr Leu Thr Leu Phe Glu Asp
                690                 695                 700

Arg Glu Met Ile Glu Glu Arg Leu Lys Thr Tyr Ala His Leu Phe Asp
705                 710                 715                 720

Asp Lys Val Met Lys Gln Leu Lys Arg Arg Arg Tyr Thr Gly Trp Gly
                725                 730                 735

Arg Leu Ser Arg Lys Leu Ile Asn Gly Ile Arg Asp Lys Gln Ser Gly
                740                 745                 750

Lys Thr Ile Leu Asp Phe Leu Lys Ser Asp Gly Phe Ala Asn Arg Asn
                755                 760                 765

Phe Met Gln Leu Ile His Asp Asp Ser Leu Thr Phe Lys Glu Asp Ile
                770                 775                 780

Gln Lys Ala Gln Val Ser Gly Gln Gly Asp Ser Leu His Glu His Ile
785                 790                 795                 800

Ala Asn Leu Ala Gly Ser Pro Ala Ile Lys Lys Gly Ile Leu Gln Thr
                805                 810                 815

Val Lys Val Val Asp Glu Leu Val Lys Val Met Gly Arg His Lys Pro
                820                 825                 830

Glu Asn Ile Val Ile Glu Met Ala Arg Glu Asn Gln Thr Thr Gln Lys
                835                 840                 845

Gly Gln Lys Asn Ser Arg Glu Arg Met Lys Arg Ile Glu Glu Gly Ile
                850                 855                 860

Lys Glu Leu Gly Ser Gln Ile Leu Lys Glu His Pro Val Glu Asn Thr
865                 870                 875                 880

Gln Leu Gln Asn Glu Lys Leu Tyr Leu Tyr Tyr Leu Gln Asn Gly Arg
                885                 890                 895

Asp Met Tyr Val Asp Gln Glu Leu Asp Ile Asn Arg Leu Ser Asp Tyr
                900                 905                 910
```

```
Asp Val Asp His Ile Val Pro Gln Ser Phe Leu Lys Asp Asp Ser Ile
        915                 920                 925

Asp Asn Lys Val Leu Thr Arg Ser Asp Lys Asn Arg Gly Lys Ser Asp
    930                 935                 940

Asn Val Pro Ser Glu Glu Val Val Lys Lys Met Lys Asn Tyr Trp Arg
945                 950                 955                 960

Gln Leu Leu Asn Ala Lys Leu Ile Thr Gln Arg Lys Phe Asp Asn Leu
                965                 970                 975

Thr Lys Ala Glu Arg Gly Gly Leu Ser Glu Leu Asp Lys Ala Gly Phe
            980                 985                 990

Ile Lys Arg Gln Leu Val Glu Thr Arg Gln Ile Thr Lys His Val Ala
        995                 1000                1005

Gln Ile Leu Asp Ser Arg Met Asn Thr Lys Tyr Asp Glu Asn Asp
    1010                1015                1020

Lys Leu Ile Arg Glu Val Lys Val Ile Thr Leu Lys Ser Lys Leu
    1025                1030                1035

Val Ser Asp Phe Arg Lys Asp Phe Gln Phe Tyr Lys Val Arg Glu
    1040                1045                1050

Ile Asn Asn Tyr His His Ala His Asp Ala Tyr Leu Asn Ala Val
    1055                1060                1065

Val Gly Thr Ala Leu Ile Lys Lys Tyr Pro Lys Leu Glu Ser Glu
    1070                1075                1080

Phe Val Tyr Gly Asp Tyr Lys Val Tyr Asp Val Arg Lys Met Ile
    1085                1090                1095

Ala Lys Ser Glu Gln Glu Ile Gly Lys Ala Thr Ala Lys Tyr Phe
    1100                1105                1110

Phe Tyr Ser Asn Ile Met Asn Phe Phe Lys Thr Glu Ile Thr Leu
    1115                1120                1125

Ala Asn Gly Glu Ile Arg Lys Arg Pro Leu Ile Glu Thr Asn Gly
    1130                1135                1140

Glu Thr Gly Glu Ile Val Trp Asp Lys Gly Arg Asp Phe Ala Thr
    1145                1150                1155

Val Arg Lys Val Leu Ser Met Pro Gln Val Asn Ile Val Lys Lys
    1160                1165                1170

Thr Glu Val Gln Thr Gly Gly Phe Ser Lys Glu Ser Ile Leu Pro
    1175                1180                1185

Lys Arg Asn Ser Asp Lys Leu Ile Ala Arg Lys Lys Asp Trp Asp
    1190                1195                1200

Pro Lys Lys Tyr Gly Gly Phe Asp Ser Pro Thr Val Ala Tyr Ser
    1205                1210                1215

Val Leu Val Val Ala Lys Val Glu Lys Gly Lys Ser Lys Lys Leu
    1220                1225                1230

Lys Ser Val Lys Glu Leu Leu Gly Ile Thr Ile Met Glu Arg Ser
    1235                1240                1245

Ser Phe Glu Lys Asn Pro Ile Asp Phe Leu Glu Ala Lys Gly Tyr
    1250                1255                1260

Lys Glu Val Lys Lys Asp Leu Ile Ile Lys Leu Pro Lys Tyr Ser
    1265                1270                1275

Leu Phe Glu Leu Glu Asn Gly Arg Lys Arg Met Leu Ala Ser Ala
    1280                1285                1290

Gly Glu Leu Gln Lys Gly Asn Glu Leu Ala Leu Pro Ser Lys Tyr
    1295                1300                1305
```

Val Asn Phe Leu Tyr Leu Ala Ser His Tyr Glu Lys Leu Lys Gly
    1310                1315                1320

Ser Pro Glu Asp Asn Glu Gln Lys Gln Leu Phe Val Glu Gln His
    1325                1330                1335

Lys His Tyr Leu Asp Glu Ile Ile Glu Gln Ile Ser Glu Phe Ser
    1340                1345                1350

Lys Arg Val Ile Leu Ala Asp Ala Asn Leu Asp Lys Val Leu Ser
    1355                1360                1365

Ala Tyr Asn Lys His Arg Asp Lys Pro Ile Arg Glu Gln Ala Glu
    1370                1375                1380

Asn Ile Ile His Leu Phe Thr Leu Thr Asn Leu Gly Ala Pro Ala
    1385                1390                1395

Ala Phe Lys Tyr Phe Asp Thr Thr Ile Asp Arg Lys Arg Tyr Thr
    1400                1405                1410

Ser Thr Lys Glu Val Leu Asp Ala Thr Leu Ile His Gln Ser Ile
    1415                1420                1425

Thr Gly Leu Tyr Glu Thr Arg Ile Asp Leu Ser Gln Leu Gly Gly
    1430                1435                1440

Asp Ser Arg Ala Asp Pro Lys Lys Lys Arg Lys Val
    1445                1450                1455

<210> SEQ ID NO 57
<211> LENGTH: 1455
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly Arg Asp Lys Lys
65                  70                  75                  80

Tyr Ser Ile Gly Leu Asp Ile Gly Thr Asn Ser Val Gly Trp Ala Val
                85                  90                  95

Ile Thr Asp Glu Tyr Lys Val Pro Ser Lys Lys Phe Lys Val Leu Gly
            100                 105                 110

Asn Thr Asp Arg His Ser Ile Lys Lys Asn Leu Ile Gly Ala Leu Leu
        115                 120                 125

Phe Asp Ser Gly Glu Thr Ala Glu Ala Thr Arg Leu Lys Arg Thr Ala
    130                 135                 140

Arg Arg Arg Tyr Thr Arg Arg Lys Asn Arg Ile Cys Tyr Leu Gln Glu
145                 150                 155                 160

Ile Phe Ser Asn Glu Met Ala Lys Val Asp Asp Ser Phe Phe His Arg
                165                 170                 175

Leu Glu Glu Ser Phe Leu Val Glu Glu Asp Lys Lys His Glu Arg His
            180                 185                 190

Pro Ile Phe Gly Asn Ile Val Asp Glu Val Ala Tyr His Glu Lys Tyr
        195                 200                 205

-continued

```
Pro Thr Ile Tyr His Leu Arg Lys Lys Leu Val Asp Ser Thr Asp Lys
    210                 215                 220

Ala Asp Leu Arg Leu Ile Tyr Leu Ala Leu Ala His Met Ile Lys Phe
225                 230                 235                 240

Arg Gly His Phe Leu Ile Glu Gly Asp Leu Asn Pro Asp Asn Ser Asp
                245                 250                 255

Val Asp Lys Leu Phe Ile Gln Leu Val Gln Thr Tyr Asn Gln Leu Phe
            260                 265                 270

Glu Glu Asn Pro Ile Asn Ala Ser Gly Val Asp Ala Lys Ala Ile Leu
        275                 280                 285

Ser Ala Arg Leu Ser Lys Ser Arg Arg Leu Glu Asn Leu Ile Ala Gln
290                 295                 300

Leu Pro Gly Glu Lys Lys Asn Gly Leu Phe Gly Asn Leu Ile Ala Leu
305                 310                 315                 320

Ser Leu Gly Leu Thr Pro Asn Phe Lys Ser Asn Phe Asp Leu Ala Glu
                325                 330                 335

Asp Ala Lys Leu Gln Leu Ser Lys Asp Thr Tyr Asp Asp Asp Leu Asp
            340                 345                 350

Asn Leu Leu Ala Gln Ile Gly Asp Gln Tyr Ala Asp Leu Phe Leu Ala
        355                 360                 365

Ala Lys Asn Leu Ser Asp Ala Ile Leu Leu Ser Asp Ile Leu Arg Val
370                 375                 380

Asn Thr Glu Ile Thr Lys Ala Pro Leu Ser Ala Ser Met Ile Lys Arg
385                 390                 395                 400

Tyr Asp Glu His His Gln Asp Leu Thr Leu Leu Lys Ala Leu Val Arg
                405                 410                 415

Gln Gln Leu Pro Glu Lys Tyr Lys Glu Ile Phe Phe Asp Gln Ser Lys
            420                 425                 430

Asn Gly Tyr Ala Gly Tyr Ile Asp Gly Gly Ala Ser Gln Glu Glu Phe
        435                 440                 445

Tyr Lys Phe Ile Lys Pro Ile Leu Glu Lys Met Asp Gly Thr Glu Glu
450                 455                 460

Leu Leu Val Lys Leu Asn Arg Glu Asp Leu Leu Arg Lys Gln Arg Thr
465                 470                 475                 480

Phe Asp Asn Gly Ser Ile Pro His Gln Ile His Leu Gly Glu Leu His
                485                 490                 495

Ala Ile Leu Arg Arg Gln Glu Asp Phe Tyr Pro Phe Leu Lys Asp Asn
            500                 505                 510

Arg Glu Lys Ile Glu Lys Ile Leu Thr Phe Arg Ile Pro Tyr Tyr Val
        515                 520                 525

Gly Pro Leu Ala Arg Gly Asn Ser Arg Phe Ala Trp Met Thr Arg Lys
530                 535                 540

Ser Glu Glu Thr Ile Thr Pro Trp Asn Phe Glu Glu Val Val Asp Lys
545                 550                 555                 560

Gly Ala Ser Ala Gln Ser Phe Ile Glu Arg Met Thr Asn Phe Asp Lys
                565                 570                 575

Asn Leu Pro Asn Glu Lys Val Leu Pro Lys His Ser Leu Leu Tyr Glu
            580                 585                 590

Tyr Phe Thr Val Tyr Asn Glu Leu Thr Lys Val Lys Tyr Val Thr Glu
        595                 600                 605

Gly Met Arg Lys Pro Ala Phe Leu Ser Gly Glu Gln Lys Lys Ala Ile
610                 615                 620
```

Val Asp Leu Leu Phe Lys Thr Asn Arg Lys Val Thr Val Lys Gln Leu
625                 630                 635                 640

Lys Glu Asp Tyr Phe Lys Lys Ile Glu Cys Phe Asp Ser Val Glu Ile
            645                 650                 655

Ser Gly Val Glu Asp Arg Phe Asn Ala Ser Leu Gly Thr Tyr His Asp
        660                 665                 670

Leu Leu Lys Ile Ile Lys Asp Lys Asp Phe Leu Asp Asn Glu Glu Asn
            675                 680                 685

Glu Asp Ile Leu Glu Asp Ile Val Leu Thr Leu Thr Leu Phe Glu Asp
    690                 695                 700

Arg Glu Met Ile Glu Glu Arg Leu Lys Thr Tyr Ala His Leu Phe Asp
705                 710                 715                 720

Asp Lys Val Met Lys Gln Leu Lys Arg Arg Arg Tyr Thr Gly Trp Gly
            725                 730                 735

Arg Leu Ser Arg Lys Leu Ile Asn Gly Ile Arg Asp Lys Gln Ser Gly
        740                 745                 750

Lys Thr Ile Leu Asp Phe Leu Lys Ser Asp Gly Phe Ala Asn Arg Asn
            755                 760                 765

Phe Met Gln Leu Ile His Asp Asp Ser Leu Thr Phe Lys Glu Asp Ile
770                 775                 780

Gln Lys Ala Gln Val Ser Gly Gln Gly Asp Ser Leu His Glu His Ile
785                 790                 795                 800

Ala Asn Leu Ala Gly Ser Pro Ala Ile Lys Lys Gly Ile Leu Gln Thr
            805                 810                 815

Val Lys Val Val Asp Glu Leu Val Lys Val Met Gly Arg His Lys Pro
            820                 825                 830

Glu Asn Ile Val Ile Glu Met Ala Arg Glu Asn Gln Thr Thr Gln Lys
            835                 840                 845

Gly Gln Lys Asn Ser Arg Glu Arg Met Lys Arg Ile Glu Glu Gly Ile
850                 855                 860

Lys Glu Leu Gly Ser Gln Ile Leu Lys Glu His Pro Val Glu Asn Thr
865                 870                 875                 880

Gln Leu Gln Asn Glu Lys Leu Tyr Leu Tyr Tyr Leu Gln Asn Gly Arg
            885                 890                 895

Asp Met Tyr Val Asp Gln Glu Leu Asp Ile Asn Arg Leu Ser Asp Tyr
        900                 905                 910

Asp Val Asp His Ile Val Pro Gln Ser Phe Leu Lys Asp Asp Ser Ile
            915                 920                 925

Asp Asn Lys Val Leu Thr Arg Ser Asp Lys Asn Arg Gly Lys Ser Asp
930                 935                 940

Asn Val Pro Ser Glu Glu Val Val Lys Lys Met Lys Asn Tyr Trp Arg
945                 950                 955                 960

Gln Leu Leu Asn Ala Lys Leu Ile Thr Gln Arg Lys Phe Asp Asn Leu
            965                 970                 975

Thr Lys Ala Glu Arg Gly Gly Leu Ser Glu Leu Asp Lys Ala Gly Phe
        980                 985                 990

Ile Lys Arg Gln Leu Val Glu Thr Arg Gln Ile Thr Lys His Val Ala
            995                 1000                1005

Gln Ile Leu Asp Ser Arg Met Asn Thr Lys Tyr Asp Glu Asn Asp
        1010                1015                1020

Lys Leu Ile Arg Glu Val Lys Val Ile Thr Leu Lys Ser Lys Leu
    1025                1030                1035

Val Ser Asp Phe Arg Lys Asp Phe Gln Phe Tyr Lys Val Arg Glu

```
              1040                1045                1050
Ile  Asn  Asn  Tyr  His  His  Ala  His  Asp  Ala  Tyr  Leu  Asn  Ala  Val
              1055                1060                1065
Val  Gly  Thr  Ala  Leu  Ile  Lys  Lys  Tyr  Pro  Lys  Leu  Glu  Ser  Glu
              1070                1075                1080
Phe  Val  Tyr  Gly  Asp  Tyr  Lys  Val  Tyr  Asp  Val  Arg  Lys  Met  Ile
              1085                1090                1095
Ala  Lys  Ser  Glu  Gln  Glu  Ile  Gly  Lys  Ala  Thr  Ala  Lys  Tyr  Phe
              1100                1105                1110
Phe  Tyr  Ser  Asn  Ile  Met  Asn  Phe  Phe  Lys  Thr  Glu  Ile  Thr  Leu
              1115                1120                1125
Ala  Asn  Gly  Glu  Ile  Arg  Lys  Arg  Pro  Leu  Ile  Glu  Thr  Asn  Gly
              1130                1135                1140
Glu  Thr  Gly  Glu  Ile  Val  Trp  Asp  Lys  Gly  Arg  Asp  Phe  Ala  Thr
              1145                1150                1155
Val  Arg  Lys  Val  Leu  Ser  Met  Pro  Gln  Val  Asn  Ile  Val  Lys  Lys
              1160                1165                1170
Thr  Glu  Val  Gln  Thr  Gly  Gly  Phe  Ser  Lys  Glu  Ser  Ile  Leu  Pro
              1175                1180                1185
Lys  Arg  Asn  Ser  Asp  Lys  Leu  Ile  Ala  Arg  Lys  Lys  Asp  Trp  Asp
              1190                1195                1200
Pro  Lys  Lys  Tyr  Gly  Gly  Phe  Asp  Ser  Pro  Thr  Val  Ala  Tyr  Ser
              1205                1210                1215
Val  Leu  Val  Val  Ala  Lys  Val  Glu  Lys  Gly  Lys  Ser  Lys  Lys  Leu
              1220                1225                1230
Lys  Ser  Val  Lys  Glu  Leu  Leu  Gly  Ile  Thr  Ile  Met  Glu  Arg  Ser
              1235                1240                1245
Ser  Phe  Glu  Lys  Asn  Pro  Ile  Asp  Phe  Leu  Glu  Ala  Lys  Gly  Tyr
              1250                1255                1260
Lys  Glu  Val  Lys  Lys  Asp  Leu  Ile  Ile  Lys  Leu  Pro  Lys  Tyr  Ser
              1265                1270                1275
Leu  Phe  Glu  Leu  Glu  Asn  Gly  Arg  Lys  Arg  Met  Leu  Ala  Ser  Ala
              1280                1285                1290
Gly  Glu  Leu  Gln  Lys  Gly  Asn  Glu  Leu  Ala  Leu  Pro  Ser  Lys  Tyr
              1295                1300                1305
Val  Asn  Phe  Leu  Tyr  Leu  Ala  Ser  His  Tyr  Glu  Lys  Leu  Lys  Gly
              1310                1315                1320
Ser  Pro  Glu  Asp  Asn  Glu  Gln  Lys  Gln  Leu  Phe  Val  Glu  Gln  His
              1325                1330                1335
Lys  His  Tyr  Leu  Asp  Glu  Ile  Ile  Glu  Gln  Ile  Ser  Glu  Phe  Ser
              1340                1345                1350
Lys  Arg  Val  Ile  Leu  Ala  Asp  Ala  Asn  Leu  Asp  Lys  Val  Leu  Ser
              1355                1360                1365
Ala  Tyr  Asn  Lys  His  Arg  Asp  Lys  Pro  Ile  Arg  Glu  Gln  Ala  Glu
              1370                1375                1380
Asn  Ile  Ile  His  Leu  Phe  Thr  Leu  Thr  Asn  Leu  Gly  Ala  Pro  Ala
              1385                1390                1395
Ala  Phe  Lys  Tyr  Phe  Asp  Thr  Thr  Ile  Asp  Arg  Lys  Arg  Tyr  Thr
              1400                1405                1410
Ser  Thr  Lys  Glu  Val  Leu  Asp  Ala  Thr  Leu  Ile  His  Gln  Ser  Ile
              1415                1420                1425
Thr  Gly  Leu  Tyr  Glu  Thr  Arg  Ile  Asp  Leu  Ser  Gln  Leu  Gly  Gly
              1430                1435                1440
```

-continued

Asp Ser Arg Ala Asp Pro Lys Lys Lys Arg Lys Val
    1445                1450               1455

<210> SEQ ID NO 58
<211> LENGTH: 1455
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly Gln Asp Lys Lys
65                  70                  75                  80

Tyr Ser Ile Gly Leu Asp Ile Gly Thr Asn Ser Val Gly Trp Ala Val
                85                  90                  95

Ile Thr Asp Glu Tyr Lys Val Pro Ser Lys Lys Phe Lys Val Leu Gly
            100                 105                 110

Asn Thr Asp Arg His Ser Ile Lys Lys Asn Leu Ile Gly Ala Leu Leu
        115                 120                 125

Phe Asp Ser Gly Glu Thr Ala Glu Ala Thr Arg Leu Lys Arg Thr Ala
    130                 135                 140

Arg Arg Arg Tyr Thr Arg Arg Lys Asn Arg Ile Cys Tyr Leu Gln Glu
145                 150                 155                 160

Ile Phe Ser Asn Glu Met Ala Lys Val Asp Asp Ser Phe Phe His Arg
                165                 170                 175

Leu Glu Glu Ser Phe Leu Val Glu Glu Asp Lys Lys His Glu Arg His
            180                 185                 190

Pro Ile Phe Gly Asn Ile Val Asp Glu Val Ala Tyr His Glu Lys Tyr
        195                 200                 205

Pro Thr Ile Tyr His Leu Arg Lys Lys Leu Val Asp Ser Thr Asp Lys
    210                 215                 220

Ala Asp Leu Arg Leu Ile Tyr Leu Ala Leu Ala His Met Ile Lys Phe
225                 230                 235                 240

Arg Gly His Phe Leu Ile Glu Gly Asp Leu Asn Pro Asp Asn Ser Asp
                245                 250                 255

Val Asp Lys Leu Phe Ile Gln Leu Val Gln Thr Tyr Asn Gln Leu Phe
            260                 265                 270

Glu Glu Asn Pro Ile Asn Ala Ser Gly Val Asp Ala Lys Ala Ile Leu
        275                 280                 285

Ser Ala Arg Leu Ser Lys Ser Arg Arg Leu Glu Asn Leu Ile Ala Gln
    290                 295                 300

Leu Pro Gly Glu Lys Lys Asn Gly Leu Phe Gly Asn Leu Ile Ala Leu
305                 310                 315                 320

Ser Leu Gly Leu Thr Pro Asn Phe Lys Ser Asn Phe Asp Leu Ala Glu
                325                 330                 335

Asp Ala Lys Leu Gln Leu Ser Lys Asp Thr Tyr Asp Asp Asp Leu Asp

```
                340                 345                 350
Asn Leu Leu Ala Gln Ile Gly Asp Gln Tyr Ala Asp Leu Phe Leu Ala
            355                 360                 365

Ala Lys Asn Leu Ser Asp Ala Ile Leu Leu Ser Asp Ile Leu Arg Val
370                 375                 380

Asn Thr Glu Ile Thr Lys Ala Pro Leu Ser Ala Ser Met Ile Lys Arg
385                 390                 395                 400

Tyr Asp Glu His His Gln Asp Leu Thr Leu Leu Lys Ala Leu Val Arg
                405                 410                 415

Gln Gln Leu Pro Glu Lys Tyr Lys Glu Ile Phe Phe Asp Gln Ser Lys
            420                 425                 430

Asn Gly Tyr Ala Gly Tyr Ile Asp Gly Gly Ala Ser Gln Glu Glu Phe
            435                 440                 445

Tyr Lys Phe Ile Lys Pro Ile Leu Glu Lys Met Asp Gly Thr Glu Glu
            450                 455                 460

Leu Leu Val Lys Leu Asn Arg Glu Asp Leu Leu Arg Lys Gln Arg Thr
465                 470                 475                 480

Phe Asp Asn Gly Ser Ile Pro His Gln Ile His Leu Gly Glu Leu His
                485                 490                 495

Ala Ile Leu Arg Arg Gln Glu Asp Phe Tyr Pro Phe Leu Lys Asp Asn
            500                 505                 510

Arg Glu Lys Ile Glu Lys Ile Leu Thr Phe Arg Ile Pro Tyr Tyr Val
            515                 520                 525

Gly Pro Leu Ala Arg Gly Asn Ser Arg Phe Ala Trp Met Thr Arg Lys
            530                 535                 540

Ser Glu Glu Thr Ile Thr Pro Trp Asn Phe Glu Glu Val Val Asp Lys
545                 550                 555                 560

Gly Ala Ser Ala Gln Ser Phe Ile Glu Arg Met Thr Asn Phe Asp Lys
                565                 570                 575

Asn Leu Pro Asn Glu Lys Val Leu Pro Lys His Ser Leu Leu Tyr Glu
            580                 585                 590

Tyr Phe Thr Val Tyr Asn Glu Leu Thr Lys Val Lys Tyr Val Thr Glu
            595                 600                 605

Gly Met Arg Lys Pro Ala Phe Leu Ser Gly Glu Gln Lys Lys Ala Ile
            610                 615                 620

Val Asp Leu Leu Phe Lys Thr Asn Arg Lys Val Thr Val Lys Gln Leu
625                 630                 635                 640

Lys Glu Asp Tyr Phe Lys Lys Ile Glu Cys Phe Asp Ser Val Glu Ile
                645                 650                 655

Ser Gly Val Glu Asp Arg Phe Asn Ala Ser Leu Gly Thr Tyr His Asp
            660                 665                 670

Leu Leu Lys Ile Ile Lys Asp Lys Asp Phe Leu Asp Asn Glu Glu Asn
            675                 680                 685

Glu Asp Ile Leu Glu Asp Ile Val Leu Thr Leu Thr Leu Phe Glu Asp
            690                 695                 700

Arg Glu Met Ile Glu Glu Arg Leu Lys Thr Tyr Ala His Leu Phe Asp
705                 710                 715                 720

Asp Lys Val Met Lys Gln Leu Lys Arg Arg Arg Tyr Thr Gly Trp Gly
                725                 730                 735

Arg Leu Ser Arg Lys Leu Ile Asn Gly Ile Arg Asp Lys Gln Ser Gly
            740                 745                 750

Lys Thr Ile Leu Asp Phe Leu Lys Ser Asp Gly Phe Ala Asn Arg Asn
            755                 760                 765
```

```
Phe Met Gln Leu Ile His Asp Asp Ser Leu Thr Phe Lys Glu Asp Ile
    770                 775                 780

Gln Lys Ala Gln Val Ser Gly Gln Gly Asp Ser Leu His Glu His Ile
785                 790                 795                 800

Ala Asn Leu Ala Gly Ser Pro Ala Ile Lys Lys Gly Ile Leu Gln Thr
                805                 810                 815

Val Lys Val Val Asp Glu Leu Val Lys Val Met Gly Arg His Lys Pro
            820                 825                 830

Glu Asn Ile Val Ile Glu Met Ala Arg Glu Asn Gln Thr Thr Gln Lys
        835                 840                 845

Gly Gln Lys Asn Ser Arg Glu Arg Met Lys Arg Ile Glu Glu Gly Ile
    850                 855                 860

Lys Glu Leu Gly Ser Gln Ile Leu Lys Glu His Pro Val Glu Asn Thr
865                 870                 875                 880

Gln Leu Gln Asn Glu Lys Leu Tyr Leu Tyr Tyr Leu Gln Asn Gly Arg
                885                 890                 895

Asp Met Tyr Val Asp Gln Glu Leu Asp Ile Asn Arg Leu Ser Asp Tyr
            900                 905                 910

Asp Val Asp His Ile Val Pro Gln Ser Phe Leu Lys Asp Ser Ile
        915                 920                 925

Asp Asn Lys Val Leu Thr Arg Ser Asp Lys Asn Arg Gly Lys Ser Asp
930                 935                 940

Asn Val Pro Ser Glu Glu Val Val Lys Lys Met Lys Asn Tyr Trp Arg
945                 950                 955                 960

Gln Leu Leu Asn Ala Lys Leu Ile Thr Gln Arg Lys Phe Asp Asn Leu
                965                 970                 975

Thr Lys Ala Glu Arg Gly Gly Leu Ser Glu Leu Asp Lys Ala Gly Phe
            980                 985                 990

Ile Lys Arg Gln Leu Val Glu Thr Arg Gln Ile Thr Lys His Val Ala
        995                 1000                1005

Gln Ile Leu Asp Ser Arg Met Asn Thr Lys Tyr Asp Glu Asn Asp
    1010                1015                1020

Lys Leu Ile Arg Glu Val Lys Val Ile Thr Leu Lys Ser Lys Leu
    1025                1030                1035

Val Ser Asp Phe Arg Lys Asp Phe Gln Phe Tyr Lys Val Arg Glu
    1040                1045                1050

Ile Asn Asn Tyr His His Ala His Asp Ala Tyr Leu Asn Ala Val
    1055                1060                1065

Val Gly Thr Ala Leu Ile Lys Lys Tyr Pro Lys Leu Glu Ser Glu
    1070                1075                1080

Phe Val Tyr Gly Asp Tyr Lys Val Tyr Asp Val Arg Lys Met Ile
    1085                1090                1095

Ala Lys Ser Glu Gln Glu Ile Gly Lys Ala Thr Ala Lys Tyr Phe
    1100                1105                1110

Phe Tyr Ser Asn Ile Met Asn Phe Phe Lys Thr Glu Ile Thr Leu
    1115                1120                1125

Ala Asn Gly Glu Ile Arg Lys Arg Pro Leu Ile Glu Thr Asn Gly
    1130                1135                1140

Glu Thr Gly Glu Ile Val Trp Asp Lys Gly Arg Asp Phe Ala Thr
    1145                1150                1155

Val Arg Lys Val Leu Ser Met Pro Gln Val Asn Ile Val Lys Lys
    1160                1165                1170
```

-continued

```
Thr Glu Val Gln Thr Gly Gly Phe Ser Lys Glu Ser Ile Leu Pro
    1175                1180                1185

Lys Arg Asn Ser Asp Lys Leu Ile Ala Arg Lys Lys Asp Trp Asp
    1190                1195                1200

Pro Lys Lys Tyr Gly Gly Phe Asp Ser Pro Thr Val Ala Tyr Ser
    1205                1210                1215

Val Leu Val Val Ala Lys Val Glu Lys Gly Lys Ser Lys Lys Leu
    1220                1225                1230

Lys Ser Val Lys Glu Leu Leu Gly Ile Thr Ile Met Glu Arg Ser
    1235                1240                1245

Ser Phe Glu Lys Asn Pro Ile Asp Phe Leu Glu Ala Lys Gly Tyr
    1250                1255                1260

Lys Glu Val Lys Lys Asp Leu Ile Ile Lys Leu Pro Lys Tyr Ser
    1265                1270                1275

Leu Phe Glu Leu Glu Asn Gly Arg Lys Arg Met Leu Ala Ser Ala
    1280                1285                1290

Gly Glu Leu Gln Lys Gly Asn Glu Leu Ala Leu Pro Ser Lys Tyr
    1295                1300                1305

Val Asn Phe Leu Tyr Leu Ala Ser His Tyr Glu Lys Leu Lys Gly
    1310                1315                1320

Ser Pro Glu Asp Asn Glu Gln Lys Gln Leu Phe Val Glu Gln His
    1325                1330                1335

Lys His Tyr Leu Asp Glu Ile Ile Glu Gln Ile Ser Glu Phe Ser
    1340                1345                1350

Lys Arg Val Ile Leu Ala Asp Ala Asn Leu Asp Lys Val Leu Ser
    1355                1360                1365

Ala Tyr Asn Lys His Arg Asp Lys Pro Ile Arg Glu Gln Ala Glu
    1370                1375                1380

Asn Ile Ile His Leu Phe Thr Leu Thr Asn Leu Gly Ala Pro Ala
    1385                1390                1395

Ala Phe Lys Tyr Phe Asp Thr Thr Ile Asp Arg Lys Arg Tyr Thr
    1400                1405                1410

Ser Thr Lys Glu Val Leu Asp Ala Thr Leu Ile His Gln Ser Ile
    1415                1420                1425

Thr Gly Leu Tyr Glu Thr Arg Ile Asp Leu Ser Gln Leu Gly Gly
    1430                1435                1440

Asp Ser Arg Ala Asp Pro Lys Lys Lys Arg Lys Val
    1445                1450                1455
```

<210> SEQ ID NO 59
<211> LENGTH: 1454
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 59

```
Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60
```

```
Ser Thr Leu His Leu Val Arg Leu Arg Gly Val Asp Lys Lys Tyr
 65                  70                  75                  80

Ser Ile Gly Leu Asp Ile Gly Thr Asn Ser Val Gly Trp Ala Val Ile
                 85                  90                  95

Thr Asp Glu Tyr Lys Val Pro Ser Lys Lys Phe Lys Val Leu Gly Asn
            100                 105                 110

Thr Asp Arg His Ser Ile Lys Lys Asn Leu Ile Gly Ala Leu Leu Phe
            115                 120                 125

Asp Ser Gly Glu Thr Ala Glu Ala Thr Arg Leu Lys Arg Thr Ala Arg
        130                 135                 140

Arg Arg Tyr Thr Arg Arg Lys Asn Arg Ile Cys Tyr Leu Gln Glu Ile
145                 150                 155                 160

Phe Ser Asn Glu Met Ala Lys Val Asp Asp Ser Phe Phe His Arg Leu
                165                 170                 175

Glu Glu Ser Phe Leu Val Glu Glu Asp Lys Lys His Glu Arg His Pro
            180                 185                 190

Ile Phe Gly Asn Ile Val Asp Glu Val Ala Tyr His Glu Lys Tyr Pro
        195                 200                 205

Thr Ile Tyr His Leu Arg Lys Lys Leu Val Asp Ser Thr Asp Lys Ala
210                 215                 220

Asp Leu Arg Leu Ile Tyr Leu Ala Leu Ala His Met Ile Lys Phe Arg
225                 230                 235                 240

Gly His Phe Leu Ile Glu Gly Asp Leu Asn Pro Asp Asn Ser Asp Val
                245                 250                 255

Asp Lys Leu Phe Ile Gln Leu Val Gln Thr Tyr Asn Gln Leu Phe Glu
            260                 265                 270

Glu Asn Pro Ile Asn Ala Ser Gly Val Asp Ala Lys Ala Ile Leu Ser
        275                 280                 285

Ala Arg Leu Ser Lys Ser Arg Arg Leu Glu Asn Leu Ile Ala Gln Leu
290                 295                 300

Pro Gly Glu Lys Lys Asn Gly Leu Phe Gly Asn Leu Ile Ala Leu Ser
305                 310                 315                 320

Leu Gly Leu Thr Pro Asn Phe Lys Ser Asn Phe Asp Leu Ala Glu Asp
                325                 330                 335

Ala Lys Leu Gln Leu Ser Lys Asp Thr Tyr Asp Asp Asp Leu Asp Asn
            340                 345                 350

Leu Leu Ala Gln Ile Gly Asp Gln Tyr Ala Asp Leu Phe Leu Ala Ala
        355                 360                 365

Lys Asn Leu Ser Asp Ala Ile Leu Leu Ser Asp Ile Leu Arg Val Asn
370                 375                 380

Thr Glu Ile Thr Lys Ala Pro Leu Ser Ala Ser Met Ile Lys Arg Tyr
385                 390                 395                 400

Asp Glu His His Gln Asp Leu Thr Leu Leu Lys Ala Leu Val Arg Gln
                405                 410                 415

Gln Leu Pro Glu Lys Tyr Lys Glu Ile Phe Phe Asp Gln Ser Lys Asn
            420                 425                 430

Gly Tyr Ala Gly Tyr Ile Asp Gly Gly Ala Ser Gln Glu Glu Phe Tyr
        435                 440                 445

Lys Phe Ile Lys Pro Ile Leu Glu Lys Met Asp Gly Thr Glu Glu Leu
        450                 455                 460

Leu Val Lys Leu Asn Arg Glu Asp Leu Leu Arg Lys Gln Arg Thr Phe
465                 470                 475                 480
```

```
Asp Asn Gly Ser Ile Pro His Gln Ile His Leu Gly Glu Leu His Ala
            485                 490                 495

Ile Leu Arg Arg Gln Glu Asp Phe Tyr Pro Phe Leu Lys Asp Asn Arg
        500                 505                 510

Glu Lys Ile Glu Lys Ile Leu Thr Phe Arg Ile Pro Tyr Tyr Val Gly
    515                 520                 525

Pro Leu Ala Arg Gly Asn Ser Arg Phe Ala Trp Met Thr Arg Lys Ser
530                 535                 540

Glu Glu Thr Ile Thr Pro Trp Asn Phe Glu Val Val Asp Lys Gly
545                 550                 555                 560

Ala Ser Ala Gln Ser Phe Ile Glu Arg Met Thr Asn Phe Asp Lys Asn
                565                 570                 575

Leu Pro Asn Glu Lys Val Leu Pro Lys His Ser Leu Leu Tyr Glu Tyr
            580                 585                 590

Phe Thr Val Tyr Asn Glu Leu Thr Lys Val Lys Tyr Val Thr Glu Gly
        595                 600                 605

Met Arg Lys Pro Ala Phe Leu Ser Gly Glu Gln Lys Lys Ala Ile Val
    610                 615                 620

Asp Leu Leu Phe Lys Thr Asn Arg Lys Val Thr Val Lys Gln Leu Lys
625                 630                 635                 640

Glu Asp Tyr Phe Lys Lys Ile Glu Cys Phe Asp Ser Val Glu Ile Ser
                645                 650                 655

Gly Val Glu Asp Arg Phe Asn Ala Ser Leu Gly Thr Tyr His Asp Leu
            660                 665                 670

Leu Lys Ile Ile Lys Asp Lys Asp Phe Leu Asp Asn Glu Glu Asn Glu
        675                 680                 685

Asp Ile Leu Glu Asp Ile Val Leu Thr Leu Thr Leu Phe Glu Asp Arg
    690                 695                 700

Glu Met Ile Glu Glu Arg Leu Lys Thr Tyr Ala His Leu Phe Asp Asp
705                 710                 715                 720

Lys Val Met Lys Gln Leu Lys Arg Arg Arg Tyr Thr Gly Trp Gly Arg
                725                 730                 735

Leu Ser Arg Lys Leu Ile Asn Gly Ile Arg Asp Lys Gln Ser Gly Lys
            740                 745                 750

Thr Ile Leu Asp Phe Leu Lys Ser Asp Gly Phe Ala Asn Arg Asn Phe
        755                 760                 765

Met Gln Leu Ile His Asp Asp Ser Leu Thr Phe Lys Glu Asp Ile Gln
    770                 775                 780

Lys Ala Gln Val Ser Gly Gln Gly Asp Ser Leu His Glu His Ile Ala
785                 790                 795                 800

Asn Leu Ala Gly Ser Pro Ala Ile Lys Lys Gly Ile Leu Gln Thr Val
                805                 810                 815

Lys Val Val Asp Glu Leu Val Lys Val Met Gly Arg His Lys Pro Glu
            820                 825                 830

Asn Ile Val Ile Glu Met Ala Arg Glu Asn Gln Thr Thr Gln Lys Gly
        835                 840                 845

Gln Lys Asn Ser Arg Glu Arg Met Lys Arg Ile Glu Glu Gly Ile Lys
    850                 855                 860

Glu Leu Gly Ser Gln Ile Leu Lys Glu His Pro Val Glu Asn Thr Gln
865                 870                 875                 880

Leu Gln Asn Glu Lys Leu Tyr Leu Tyr Tyr Leu Gln Asn Gly Arg Asp
                885                 890                 895

Met Tyr Val Asp Gln Glu Leu Asp Ile Asn Arg Leu Ser Asp Tyr Asp
```

```
                    900             905             910
Val Asp His Ile Val Pro Gln Ser Phe Leu Lys Asp Asp Ser Ile Asp
            915             920             925
Asn Lys Val Leu Thr Arg Ser Asp Lys Asn Arg Gly Lys Ser Asp Asn
            930             935             940
Val Pro Ser Glu Glu Val Val Lys Lys Met Lys Asn Tyr Trp Arg Gln
945             950             955             960
Leu Leu Asn Ala Lys Leu Ile Thr Gln Arg Lys Phe Asp Asn Leu Thr
                965             970             975
Lys Ala Glu Arg Gly Gly Leu Ser Glu Leu Asp Lys Ala Gly Phe Ile
            980             985             990
Lys Arg Gln Leu Val Glu Thr Arg Gln Ile Thr Lys His Val Ala Gln
            995             1000            1005
Ile Leu Asp Ser Arg Met Asn Thr Lys Tyr Asp Glu Asn Asp Lys
        1010            1015            1020
Leu Ile Arg Glu Val Lys Val Ile Thr Leu Lys Ser Lys Leu Val
        1025            1030            1035
Ser Asp Phe Arg Lys Asp Phe Gln Phe Tyr Lys Val Arg Glu Ile
        1040            1045            1050
Asn Asn Tyr His His Ala His Asp Ala Tyr Leu Asn Ala Val Val
        1055            1060            1065
Gly Thr Ala Leu Ile Lys Lys Tyr Pro Lys Leu Glu Ser Glu Phe
        1070            1075            1080
Val Tyr Gly Asp Tyr Lys Val Tyr Asp Val Arg Lys Met Ile Ala
        1085            1090            1095
Lys Ser Glu Gln Glu Ile Gly Lys Ala Thr Ala Lys Tyr Phe Phe
        1100            1105            1110
Tyr Ser Asn Ile Met Asn Phe Phe Lys Thr Glu Ile Thr Leu Ala
        1115            1120            1125
Asn Gly Glu Ile Arg Lys Arg Pro Leu Ile Glu Thr Asn Gly Glu
        1130            1135            1140
Thr Gly Glu Ile Val Trp Asp Lys Gly Arg Asp Phe Ala Thr Val
        1145            1150            1155
Arg Lys Val Leu Ser Met Pro Gln Val Asn Ile Val Lys Lys Thr
        1160            1165            1170
Glu Val Gln Thr Gly Gly Phe Ser Lys Glu Ser Ile Leu Pro Lys
        1175            1180            1185
Arg Asn Ser Asp Lys Leu Ile Ala Arg Lys Lys Asp Trp Asp Pro
        1190            1195            1200
Lys Lys Tyr Gly Gly Phe Asp Ser Pro Thr Val Ala Tyr Ser Val
        1205            1210            1215
Leu Val Val Ala Lys Val Glu Lys Gly Lys Ser Lys Lys Leu Lys
        1220            1225            1230
Ser Val Lys Glu Leu Leu Gly Ile Thr Ile Met Glu Arg Ser Ser
        1235            1240            1245
Phe Glu Lys Asn Pro Ile Asp Phe Leu Glu Ala Lys Gly Tyr Lys
        1250            1255            1260
Glu Val Lys Lys Asp Leu Ile Ile Lys Leu Pro Lys Tyr Ser Leu
        1265            1270            1275
Phe Glu Leu Glu Asn Gly Arg Lys Arg Met Leu Ala Ser Ala Gly
        1280            1285            1290
Glu Leu Gln Lys Gly Asn Glu Leu Ala Leu Pro Ser Lys Tyr Val
        1295            1300            1305
```

```
Asn Phe Leu Tyr Leu Ala Ser His Tyr Glu Lys Leu Lys Gly Ser
    1310                1315                1320

Pro Glu Asp Asn Glu Gln Lys Gln Leu Phe Val Glu Gln His Lys
    1325                1330                1335

His Tyr Leu Asp Glu Ile Ile Glu Gln Ile Ser Glu Phe Ser Lys
    1340                1345                1350

Arg Val Ile Leu Ala Asp Ala Asn Leu Asp Lys Val Leu Ser Ala
    1355                1360                1365

Tyr Asn Lys His Arg Asp Lys Pro Ile Arg Glu Gln Ala Glu Asn
    1370                1375                1380

Ile Ile His Leu Phe Thr Leu Thr Asn Leu Gly Ala Pro Ala Ala
    1385                1390                1395

Phe Lys Tyr Phe Asp Thr Thr Ile Asp Arg Lys Arg Tyr Thr Ser
    1400                1405                1410

Thr Lys Glu Val Leu Asp Ala Thr Leu Ile His Gln Ser Ile Thr
    1415                1420                1425

Gly Leu Tyr Glu Thr Arg Ile Asp Leu Ser Gln Leu Gly Gly Asp
    1430                1435                1440

Ser Arg Ala Asp Pro Lys Lys Lys Arg Lys Val
    1445                1450
```

<210> SEQ ID NO 60
<211> LENGTH: 228
<212> TYPE: DNA
<213> ORGANISM: Unknown
<220> FEATURE:
<223> OTHER INFORMATION: Description of Unknown:
      ubiquitin sequence

<400> SEQUENCE: 60

```
accacctctc agacgcagga ccaggtgcag ggtcgactcc ttctggatgt tgtagtcaga    60
aagagtgcgg ccatcttcca gctgcttgcc tgcaaagatg agcctctgct ggtcgggagg   120
gatgccttct ttatcctgga tcttggcctt cacattttcg atggtgtcac tgggctccac   180
ttccagggtg atggtcttgc cggtcagggt cttcacgaag atctgcat               228
```

<210> SEQ ID NO 61
<211> LENGTH: 4134
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 61

```
gacaagaagt actccattgg gctcgatatc ggcacaaaca gcgtcggctg ggccgtcatt    60
acggacgagt acaaggtgcc gagcaaaaaa ttcaaagttc tgggcaatac cgatcgccac   120
agcataaaga gaaccctcat tggcgccctc ctgttcgact ccggggagac ggccgaagcc   180
acgcggctca aaagaacagc acggcgcaga tatacccgca gaaagaatcg gatctgctac   240
ctgcaggaga tctttagtaa tgagatggct aaggtggatg actctttctt ccataggctg   300
gaggagtcct ttttggtgga ggaggataaa agcacgagcc gcacccaat ctttggcaat   360
atcgtggacg aggtggcgta ccatgaaaag tacccaacca tatatcatct gaggaagaag   420
cttgtagaca gtactgataa ggctgacttg cggttgatct atctcgcgct ggcgcatatg   480
atcaaatttc ggggacactt cctcatcgag ggggacctga acccagacaa cagcgatgtc   540
```

```
gacaaactct ttatccaact ggttcagact tacaatcagc ttttcgaaga gaacccgatc    600
aacgcatccg gagttgacgc caaagcaatc ctgagcgcta ggctgtccaa atcccggcgg    660
ctcgaaaacc tcatcgcaca gctccctggg gagaagaaga acggcctgtt tggtaatctt    720
atcgccctgt cactcgggct gaccccaac tttaaatcta acttcgacct ggccgaagat     780
gccaagcttc aactgagcaa agacacctac gatgatgatc tcgacaatct gctggcccag    840
atcggcgacc agtacgcaga ccttttttg gcggcaaaga acctgtcaga cgccattctg     900
ctgagtgata ttctgcgagt gaacacggag atcaccaaag ctccgctgag cgctagtatg    960
atcaagcgct atgatgagca ccaccaagac ttgactttgc tgaaggccct tgtcagacag   1020
caactgcctg agaagtacaa ggaaattttc ttcgatcagt ctaaaaatgg ctacgccgga   1080
tacattgacg gcggagcaag ccaggaggaa ttttacaaat ttattaagcc catcttggaa   1140
aaaatggacg gcaccgagga gctgctggta agcttaaca gagaagatct gttgcgcaaa    1200
cagcgcactt tcgacaatgg aagcatcccc caccagattc acctgggcga actgcacgct   1260
atcctcaggc ggcaagagga tttctacccc tttttgaaag ataacaggga aaagattgag    1320
aaaatcctca catttcggat accctactat gtaggccccc tcgcccgggg aaattccaga   1380
ttcgcgtgga tgactcgcaa atcagaagag accatcactc cctggaactt cgaggaagtc   1440
gtggataagg gggcctctgc ccagtccttc atcgaaagga tgactaactt tgataaaaat   1500
ctgcctaacg aaaaggtgct tcctaaacac tctctgctgt acgagtactt cacagtttat   1560
aacgagctca ccaaggtcaa atacgtcaca gaagggatga gaaagccagc attcctgtct   1620
ggagagcaga agaaagctat cgtggacctc ctcttcaaga cgaaccggaa agttaccgtg   1680
aaacagctca agaagactta tttcaaaaag attgaatgtt tcgactctgt tgaaatcagc   1740
ggagtggagg atcgcttcaa cgcatccctg gaacgtatc acgatctcct gaaaatcatt    1800
aaagacaagg acttcctgga caatgaggag aacgaggaca ttcttgagga cattgtcctc   1860
acccttacgt tgtttgaaga tagggagatg attgaagaac gcttgaaaac ttacgctcat   1920
ctcttcgacg acaaagtcat gaaacagctc aagaggcgcc gatatacagg atgggggcgg   1980
ctgtcaagaa aactgatcaa tgggatccga gacaagcaga gtggaaagac aatcctggat   2040
tttcttaagt ccgatggatt tgccaaccgg aacttcatgc agttgatcca tgatgactct   2100 ctcacctttta aggaggacat ccagaaagca caagtttctg gccagggga cagtcttcac    2160 gagcacatcg ctaatcttgc aggtagccca gctatcaaaa agggaatact gcagaccgtt   2220
aaggtcgtgg atgaactcgt caaagtaatg ggaaggcata agcccgagaa tatcgttatc   2280
gagatggccc gagagaacca aactacccag aagggacaga gaacagtag ggaaaggatg     2340 aagaggattg aagagggtat aaagaactg gggtcccaaa tccttaagga cacccagtt      2400 gaaaacaccc agcttcagaa tgagaagctc tacctgtact acctgcagaa cggcagggac   2460
atgtacgtgg atcaggaact ggacatcaat cggctctccg actacgacgt ggatcatatc   2520 gtgcccagt cttttctcaa agatgattct attgataata aagtgttgac aagatccgat     2580
aaaaatagag ggaagagtga taacgtcccc tcagaagaag ttgtcaagaa aatgaaaaat   2640
tattggcggc agctgctgaa cgccaaactg atcacacaac ggaagttcga taatctgact   2700
aaggctgaac gaggtggcct gtctgagttg gataaagccg gcttcatcaa aaggcagctt   2760
gttgagacac gccagatcac caagcacgtg gcccaaattc tcgattcacg catgaacacc   2820
aagtacgatg aaaatgacaa actgattcga gaggtgaaag ttattactct gaagtctaag   2880
ctggtctcag atttcagaaa ggactttcag ttttataagg tgagagagat caacaattac   2940
```

| | | |
|---|---|---|
| caccatgcgc atgatgccta cctgaatgca gtggtaggca ctgcacttat caaaaaatat | 3000 | |
| cccaagcttg aatctgaatt tgtttacgga gactataaag tgtacgatgt taggaaaatg | 3060 | |
| atcgcaaagt ctgagcagga ataggcaag gccaccgcta agtacttctt ttacagcaat | 3120 | |
| attatgaatt ttttcaagac cgagattaca ctggccaatg agagattcg gaagcgacca | 3180 | |
| cttatcgaaa caaacggaga aacaggagaa atcgtgtggg acaagggtag ggatttcgcg | 3240 | |
| acagtccgga aggtcctgtc catgccgcag gtgaacatcg ttaaaaagac cgaagtacag | 3300 | |
| accggaggct ctccaagga aagtatcctc ccgaaaagga acagcgacaa gctgatcgca | 3360 | |
| cgcaaaaaag attgggaccc caagaaatac ggcggattcg attctcctac agtcgcttac | 3420 | |
| agtgtactgg ttgtggccaa agtggagaaa gggaagtcta aaaaactcaa agcgtcaag | 3480 | |
| gaactgctgg gcatcacaat catggagcga tcaagcttcg aaaaaaaccc catcgacttt | 3540 | |
| ctcgaggcga aggatataa agaggtcaaa aaagacctca tcattaagct tcccaagtac | 3600 | |
| tctctctttg agcttgaaaa cggccggaaa cgaatgctcg ctagtgcggg cgagctgcag | 3660 | |
| aaaggtaacg agctggcact gccctctaaa tacgttaatt tcttgtatct ggccagccac | 3720 | |
| tatgaaaagc tcaaagggtc tcccgaagat aatgagcaga agcagctgtt cgtggaacaa | 3780 | |
| cacaaacact accttgatga gatcatcgag caaataagcg aattctccaa aagagtgatc | 3840 | |
| ctcgccgacg ctaacctcga taaggtgctt tctgcttaca ataagcacag ggataagccc | 3900 | |
| atcagggagc aggcagaaaa cattatccac ttgtttactc tgaccaactt gggcgcgcct | 3960 | |
| gcagccttca gtacttcga caccaccata gacagaaagc ggtacacctc tacaaaggag | 4020 | |
| gtcctggacg ccacactgat tcatcagtca attacggggc tctatgaaac aagaatcgac | 4080 | |
| ctctctcagc tcggtggaga cagcagggct gaccccaaga agaagaggaa ggtg | 4134 | |

<210> SEQ ID NO 62
<211> LENGTH: 6929
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 62

| | | |
|---|---|---|
| cctgctgtct ccaccgagct gagagaggtc gattcttgtt tcatagagcc ccgtaattga | 60 | |
| ctgatgaatc agtgtggcgt ccaggacctc ctttgtagag gtgtaccgct ttctgtctat | 120 | |
| ggtggtgtcg aagtacttga aggctgcagg cgcgcccaag ttggtcagag taaacaagtg | 180 | |
| gataatgttt tctgcctgct ccctgatggg cttatccctg tgcttattgt aagcagaaag | 240 | |
| caccttatcg aggttagcgt cggcgaggat cactcttttg gagaattcgc ttatttgctc | 300 | |
| gatgatctca tcaaggtagt gtttgtgttg ttccacgaac agctgcttct gctcattatc | 360 | |
| ttcgggagac cctttgagct tttcatagtg gctggccaga tacaagaaat taacgtattt | 420 | |
| agagggcagt gccagctcgt tacctttctg cagctcgccc gcactagcga gcattcgttt | 480 | |
| ccggccgttt tcaagctcaa agagagagta cttgggaagc ttaatgatga ggtctttttt | 540 | |
| gacctcttta tatcctttcg cctcgagaaa gtcgatgggg tttttttcga agcttgatcg | 600 | |
| ctccatgatt gtgatgccca gcagttcctt gacgcttttg agttttttag acttcccttt | 660 | |
| ctccactttg gccacaacca gtacactgta agcgactgta ggagaatcga atccgccgta | 720 | |
| tttcttgggg tcccaatctt ttttgcgtgc gatcagcttg tcgctgttcc ttttcgggag | 780 | |
| gatactttcc ttggagaagc ctccggtctg tacttcggtc tttttaacga tgttcacctg | 840 | |

```
cggcatggac aggaccttcc ggactgtcgc gaaatcccta cccttgtccc acacgatttc    900
tcctgtttct ccgtttgttt cgataagtgg tcgcttccga atctctccat tggccagtgt    960
aatctcggtc ttgaaaaaat tcataatatt gctgtaaaag aagtacttag cggtggcctt   1020
gcctatttcc tgctcagact ttgcgatcat tttcctaaca tcgtacactt tatagtctcc   1080
gtaaacaaat tcagattcaa gcttgggata ttttttgata agtgcagtgc ctaccactgc   1140
attcaggtag gcatcatgcg catggtggta attgttgatc tctctcacct tataaaactg   1200
aaagtccttt ctgaaatctg agaccagctt agacttcaga gtaataactt tcacctctcg   1260
aatcagtttg tcattttcat cgtacttggt gttcatgcgt gaatcgagaa tttgggccac   1320
gtgcttggtg atctggcgtg tctcaacaag ctgccttttg atgaagccgg ctttatccaa   1380
ctcagacagg ccacctcgtt cagccttagt cagattatcg aacttccgtt gtgtgatcag   1440
tttggcgttc agcagctgcc gccaataatt tttcattttc ttgacaactt cttctgaggg   1500
gacgttatca ctcttccctc tattttatc ggatcttgtc aacactttat tatcaataga   1560
atcatctttg agaaaagact ggggcacgat atgatccacg tcgtagtcgg agagccgatt   1620
gatgtccagt tcctgatcca cgtacatgtc cctgccgttc tgcaggtagt acaggtagag   1680
cttctcattc tgaagctggg tgttttcaac tgggtgttcc ttaaggattt gggaccccag   1740
ttcttttata ccctcttcaa tcctcttcat cctttcccta ctgttcttct gtcccttctg   1800
ggtagtttgg ttctctcggg ccatctcgat aacgatattc tcgggcttat gccttcccat   1860
tactttgacg agttcatcca cgaccttaac ggtctgcagt attcccttt tgatagctgg   1920 gctacctgca agattagcga tgtgctcgtg aagactgtcc cctggccag aaacttgtgc   1980 tttctggatg tcctccttaa aggtgagaga gtcatcatgg atcaactgca tgaagttccg   2040
gttggcaaat ccatcggact taagaaaatc caggattgtc tttccactct gcttgtctcg   2100
gatcccattg atcagttttc ttgacagccg cccccatcct gtatatcggc gcctcttgag   2160
ctgtttcatg actttgtcgt cgaagagatg agcgtaagtt ttcaagcgtt cttcaatcat   2220
ctccctatct tcaaacaacg taagggtgag gacaatgtcc tcaagaatgt cctcgttctc   2280
ctcattgtcc aggaagtcct tgtctttaat gattttcagg agatcgtgat acgttcccag   2340
ggatgcgttg aagcgatcct ccactccgct gatttcaaca gagtcgaaac attcaatctt   2400
tttgaaatag tcttctttga gctgtttcac ggtaactttc cggttcgtct tgaagaggag   2460
gtccacgata gctttcttct gctctccaga caggaatgct ggctttctca tcccttctgt   2520
gacgtatttg accttggtga gctcgttata aactgtgaag tactcgtaca gcagagagtg   2580
tttaggaagc accttttcgt taggcagatt tttatcaaag ttagtcatcc tttcgatgaa   2640
ggactgggca gaggccccct tatccacgac ttcctcgaag ttccagggag tgatggtctc   2700
ttctgatttg cgagtcatcc acgcgaatct ggaatttccc cgggcgaggg ggcctacata   2760
gtagggtatc cgaaatgtga ggattttctc aatcttttcc ctgttatctt tcaaaaaggg   2820
gtagaaatcc tcttgccgcc tgaggatagc gtgcagttcg cccaggtgaa tctggtgggg   2880
gatgcttcca ttgtcgaaag tgcgctgttt gcgcaacaga tcttctctgt taagctttac   2940
cagcagctcc tcggtgccgt ccattttttc caagatgggt taataaatt tgtaaaattc   3000 ctcctggctt gctccgccgt caatgtatcc ggcgtagcca ttttagact gatcgaagaa   3060 aatttccttg tacttctcag gcagttgctg tctgacaagg gccttcagca aagtcaagtc   3120
ttggtggtgc tcatcatagc gcttgatcat actagcgctc agcggagctt tggtgatctc   3180
```

```
cgtgttcact cgcagaatat cactcagcag aatggcgtct gacaggttct ttgccgccaa   3240
aaaaaggtct gcgtactggt cgccgatctg ggccagcaga ttgtcgagat catcatcgta   3300
ggtgtctttg ctcagttgaa gcttggcatc ttcggccagg tcgaagttag atttaaagtt   3360
gggggtcagc ccgagtgaca gggcgataag attaccaaac aggccgttct tcttctcccc   3420
agggagctgt gcgatgaggt tttcgagccg ccgggatttg gacagcctag cgctcaggat   3480
tgctttggcg tcaactccgg atgcgttgat cgggttctct tcgaaaagct gattgtaagt   3540
ctgaaccagt tggataaaga gtttgtcgac atcgctgttg tctgggttca ggtccccctc   3600
gatgaggaag tgtccccgaa atttgatcat atgcgccagc gcgagataga tcaaccgcaa   3660
gtcagcctta tcagtactgt ctacaagctt cttcctcaga tgatatatgg ttgggtactt   3720
ttcatggtac gccacctcgt ccacgatatt gccaaagatt gggtggcgct cgtgcttttt   3780
atcctcctcc accaaaaagg actcctccag cctatggaag aaagagtcat ccaccttagc   3840
catctcatta ctaaagatct cctgcaggta gcagatccga ttctttctgc gggtatatct   3900
gcgccgtgct gttcttttga gccgcgtggc ttcggccgtc tccccggagt cgaacaggag   3960
ggcgccaatg aggttcttct ttatgctgtg gcgatcggta ttgcccagaa ctttgaattt   4020
tttgctcggc accttgtact cgtccgtaat gacggcccag ccgacgctgt ttgtgccgat   4080
atcgagccca atggagtact tcttgtccat ggtggcggct cttgaaggac gacgtcatca   4140
tcccttgccc ggatgcgcgg gcttcttgtc tagcacagga gcctggggta gagcgcatgc   4200
aaattacgcg ctgtgctttg tgggaaatca ccctaaacga aaaatttatt cctctttcga   4260
gccttatagt ggcggccggt ctacatccta ggttttagag ctagaaatag caagttaaaa   4320
taaggctagt ccgttatcaa cttgaaaaag tggcaccgag tcggtgcttt tttgttaacg   4380
cggccgccta gagtcgacct gcaggcatgc aagcttggcg taatcatggt catagctgtt   4440
tcctgtgtga attgttatc cgctcacaat tccacacaac atacgagccg aagcataaa    4500 gtgtaaagcc tggggtgcct aatgagtgag ctaactcaca ttaattgcgt tgcgctcact   4560
gcccgctttc cagtcgggaa acctgtcgtg ccagctgcat taatgaatcg gccaacgcgc   4620
ggggagaggc ggtttgcgta ttgggcgctc ttccgcttcc tcgctcactg actcgctgcg   4680
ctcggtcgtt cggctgcggc gagcggtatc agctcactca aaggcggtaa tacggttatc   4740
cacagaatca ggggataacg caggaaagaa catgtgagca aaaggccagc aaaaggccag   4800
gaaccgtaaa aaggccgcgt tgctggcgtt tttccatagg ctccgccccc ctgacgagca   4860
tcacaaaaat cgacgctcaa gtcagaggtg gcgaaacccg acaggactat aaagatacca   4920
ggcgtttccc cctggaagct ccctcgtgcg ctctcctgtt ccgaccctgc cgcttaccgg   4980
atacctgtcc gcctttctcc cttcgggaag cgtggcgctt tctcatagct cacgctgtag   5040
gtatctcagt tcggtgtagg tcgttcgctc caagctgggc tgtgtgcacg aaccccccgt   5100
tcagcccgac cgctgcgcct tatccggtaa ctatcgtctt gagtccaacc cggtaagaca   5160
cgacttatcg ccactggcag cagccactgg taacaggatt agcagagcga ggtatgtagg   5220
cggtgctaca gagttcttga agtggtggcc taactacggc tacactagaa gaacagtatt   5280
tggtatctgc gctctgctga agccagttac cttcggaaaa agagttggta gctcttgatc   5340
cggcaaacaa accaccgctg gtagcggtgg tttttttgtt tgcaagcagc agattacgcg   5400
cagaaaaaaa ggatctcaag aagatccttt gatcttttct acgggtctg acgctcagtg    5460 gaacgaaaac tcacgttaag ggattttggt catgagatta tcaaaaagga tcttcaccta   5520 gatccttta aattaaaaat gaagttttaa atcaatctaa agtatatatg agtaaacttg    5580
```

```
gtctgacagt taccaatgct taatcagtga ggcacctatc tcagcgatct gtctatttcg    5640
ttcatccata gttgcctgac tccccgtcgt gtagataact acgatacggg agggcttacc    5700
atctggcccc agtgctgcaa tgataccgcg agacccacgc tcaccggctc cagatttatc    5760
agcaataaac cagccagccg aagggccga gcgcagaagt ggtcctgcaa ctttatccgc     5820
ctccatccag tctattaatt gttgccggga agctagagta agtagttcgc cagttaatag    5880
tttgcgcaac gttgttgcca ttgctacagg catcgtggtg tcacgctcgt cgtttggtat    5940
ggcttcattc agctccggtt cccaacgatc aaggcgagtt acatgatccc ccatgttgtg    6000
caaaaaagcg gttagctcct tcggtcctcc gatcgttgtc agaagtaagt tggccgcagt    6060
gttatcactc atggttatgg cagcactgca taattctctt actgtcatgc catccgtaag    6120
atgcttttct gtgactggtg agtactcaac caagtcattc tgagaatagt gtatgcggcg    6180
accgagttgc tcttgcccgg cgtcaatacg ggataatacc gcgccacata gcagaacttt    6240
aaaagtgctc atcattggaa aacgttcttc ggggcgaaaa ctctcaagga tcttaccgct    6300
gttgagatcc agttcgatgt aacccactcg tgcacccaac tgatcttcag catcttttac    6360
tttcaccagc gtttctgggt gagcaaaaac aggaaggcaa aatgccgcaa aaaagggaat    6420
aagggcgaca cggaaatgtt gaatactcat actcttcctt tttcaatatt attgaagcat    6480
ttatcagggt tattgtctca tgagcggata catatttgaa tgtatttaga aaaataaaca    6540
aataggggtt ccgcgcacat ttccccgaaa agtgccacct gacgtctaag aaaccattat    6600
tatcatgaca ttaacctata aaaataggcg tatcacgagg ccctttcgtc tcgcgcgttt    6660
cggtgatgac ggtgaaaacc tctgacacat gcagctcccg gagacggtca cagcttgtct    6720
gtaagcggat gccgggagca gacaagcccg tcagggcgcg tcagcgggtg ttggcgggtg    6780
tcggggctgg cttaactatg cggcatcaga gcagattgta ctgagagtgc accatagcgg    6840
ccgcggtacc cacacaaaaa accaacacac agatgtaatg aaaataaaga tattttattt    6900
cacaccttcc tcttcttctt ggggtcagc                                      6929

<210> SEQ ID NO 63
<211> LENGTH: 7177
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 63
ctgcaggcat gcaagcttgg cgtaatcatg gtcatagctg tttcctgtgt gaaattgtta      60
tccgctcaca attccacaca acatacgagc cggaagcata agtgtaaag cctggggtgc      120 ctaatgagtg agctaactca cattaattgc gttgcgctca ctgcccgctt tccagtcggg     180
aaacctgtcg tgccagctgc attaatgaat cggccaacgc gcggggagag gcggtttgcg     240
tattgggcgc tcttccgctt cctcgctcac tgactcgctg cgctcggtcg ttcggctgcg     300
gcgagcggta tcagctcact caaaggcggt aatacggtta ccacagaat caggggataa      360 cgcaggaaag aacatgtgag caaaaggcca gcaaaggcc aggaaccgta aaaaggccgc      420
gttgctggcg ttttttccata ggctccgccc cctgacgag catcacaaaa atcgacgctc     480
aagtcagagg tggcgaaacc cgacaggact ataaagatac caggcgtttc ccctggaag     540 ctcccctcgtg cgctctcctg ttccgaccct gccgcttacc ggatacctgt ccgcctttct    600
cccttcggga agcgtggcgc tttctcatag ctcacgctgt aggtatctca gttcggtgta    660
```

```
ggtcgttcgc tccaagctgg gctgtgtgca cgaaccccc  gttcagcccg accgctgcgc      720
cttatccggt aactatcgtc ttgagtccaa cccggtaaga cacgacttat cgccactggc      780
agcagccact ggtaacagga ttagcagagc gaggtatgta ggcggtgcta cagagttctt      840
gaagtggtgg cctaactacg gctacactag aagaacagta tttggtatct gcgctctgct      900
gaagccagtt accttcggaa aaagagttgg tagctcttga tccggcaaac aaaccaccgc      960
tggtagcggt ggttttttg  tttgcaagca gcagattacg cgcagaaaaa aaggatctca     1020
agaagatcct ttgatctttt ctacggggtc tgacgctcag tggaacgaaa actcacgtta     1080
agggattttg gtcatgagat tatcaaaaag gatcttcacc tagatccttt taaattaaaa     1140
atgaagtttt aaatcaatct aaagtatata tgagtaaact tggtctgaca gttaccaatg     1200
cttaatcagt gaggcaccta tctcagcgat ctgtctattt cgttcatcca tagttgcctg     1260
actccccgtc gtgtagataa ctacgatacg ggagggctta ccatctggcc ccagtgctgc     1320
aatgataccg cgagacccac gctcaccggc tccagattta tcagcaataa accagccagc     1380
cggaagggcc gagcgcagaa gtggtcctgc aactttatcc gcctccatcc agtctattaa     1440
ttgttgccgg gaagctagag taagtagttc gccagttaat agtttgcgca acgttgttgc     1500
cattgctaca ggcatcgtgg tgtcacgctc gtcgtttggt atggcttcat tcagctccgg     1560
ttcccaacga tcaaggcgag ttacatgatc ccccatgttg tgcaaaaaag cggttagctc     1620
cttcggtcct ccgatcgttg tcagaagtaa gttggccgca gtgttatcac tcatggttat     1680
ggcagcactg cataattctc ttactgtcat gccatccgta agatgctttt ctgtgactgg     1740
tgagtactca accaagtcat tctgagaata gtgtatgcgg cgaccgagtt gctcttgccc     1800
ggcgtcaata cgggataata ccgcgccaca tagcagaact ttaaaagtgc tcatcattgg     1860
aaaacgttct cggggcgaa  aactctcaag gatcttaccg ctgttgagat ccagttcgat     1920
gtaacccact cgtgcaccca actgatcttc agcatctttt actttcacca gcgtttctgg     1980
gtgagcaaaa acaggaaggc aaaatgccgc aaaaaaggga ataagggcga cacggaaatg     2040
ttgaatactc atactcttcc ttttcaata  ttattgaagc atttatcagg gttattgtct     2100
catgagcgga tacatatttg aatgtattta gaaaaataaa caaatagggg ttccgcgcac     2160
atttccccga aaagtgccac ctgacgtcta agaaaccatt attatcatga cattaaccta     2220
taaaaatagg cgtatcacga ggccctttcg tctcgcgcgt ttcggtgatg acggtgaaaa     2280
cctctgacac atgcagctcc cggagacggt cacagcttgt ctgtaagcgg atgccgggag     2340
cagacaagcc cgtcagggcg cgtcagcggg tgttggcggg tgtcggggct ggcttaacta     2400
tgcggcatca gagcagattg tactgagagt gcaccatagc ggccgcggta cccacacaaa     2460
aaaccaacac acagatgtaa tgaaaataaa gatattttat ttcacacctt cctcttcttc     2520
ttggggtcag ccctgctgtc tccaccgagc tgagagaggt cgattcttgt ttcatagagc     2580
cccgtaattg actgatgaat cagtgtggcg tccaggacct cctttgtaga ggtgtaccgc     2640
tttctgtcta tggtggtgtc gaagtacttg aaggctgcag gcgcgcccaa gttggtcaga     2700
gtaaacaagt ggataatgtt ttctgcctgc tccctgatgg gcttatccct gtgcttattg     2760
taagcagaaa gcaccttatc gaggttagcg tcggcgagga tcactctttt ggagaattcg     2820
cttatttgct cgatgatctc atcaaggtag tgtttgtgtt gttccacgaa cagctgcttc     2880
tgctcattat cttcgggaga ccctttgagc ttttcatagt ggctggccag atacaagaaa     2940
ttaacgtatt tagagggcag tgccagctcg ttaccttttct gcagctcgcc cgcactagcg     3000
```

```
agcattcgtt tccggccgtt ttcaagctca aagagagagt acttgggaag cttaatgatg    3060
aggtcttttt tgacctcttt atatcctttc gcctcgagaa agtcgatggg gttttttccg    3120
aagcttgatc gctccatgat tgtgatgccc agcagttcct tgacgctttt gagttttta    3180
gacttccctt tctccacttt ggccacaacc agtacactgt aagcgactgt aggagaatcg    3240
aatccgccgt atttcttggg gtcccaatct ttttgcgtg cgatcagctt gtcgctgttc    3300
cttttcggga ggatactttc cttggagaag cctccggtct gtacttcggt ctttttaacg    3360
atgttcacct gcggcatgga caggaccttc cggactgtcg cgaaatccct acccttgtcc    3420
cacacgattt ctcctgtttc tccgtttgtt tcgataagtg gtcgcttccg aatctctcca    3480
ttggccagtg taatctcggt cttgaaaaaa ttcataatat tgctgtaaaa gaagtactta    3540
gcggtggcct tgcctatttc ctgctcagac tttgcgatca ttttcctaac atcgtacact    3600
ttatagtctc cgtaaacaaa ttcagattca agcttgggat attttttgat aagtgcagtg    3660
cctaccactg cattcaggta ggcatcatgc gcatggtggt aattgttgat ctctctcacc    3720
ttataaaact gaaagtcctt tctgaaatct gagaccagct tagacttcag agtaataact    3780
ttcacctctc gaatcagttt gtcattttca tcgtacttgg tgttcatgcg tgaatcgaga    3840
atttgggcca cgtgcttggt gatctggcgt gtctcaacaa gctgccttt gatgaagccg    3900
gctttatcca actcagacag gccacctcgt tcagccttag tcagattatc gaacttccgt    3960
tgtgtgatca gtttggcgtt cagcagctgc cgccaataat ttttcatttt cttgacaact    4020
tcttctgagg ggacgttatc actcttccct ctattttat cggatcttgt caacacttta    4080
ttatcaatag aatcatcttt gagaaaagac tggggcacga tatgatccac gtcgtagtcg    4140
gagagccgat tgatgtccag ttcctgatcc acgtacatgt ccctgccgtt ctgcaggtag    4200
tacaggtaga gcttctcatt ctgaagctgg gtgttttcaa ctgggtgttc cttaaggatt    4260
tgggacccca gttctttat accctcttca atcctcttca tcctttccct actgttcttc    4320
tgtcccttct gggtagtttg gttctctcgg gccatctcga taacgatatt ctcgggctta    4380
tgccttccca ttactttgac gagttcatcc acgaccttaa cggtctgcag tattccctt    4440
ttgatagctg ggctacctgc aagattagcg atgtgctcgt gaagactgtc cccctggcca    4500
gaaacttgtg ctttctggat gtcctcctta aggtgagag agtcatcatg gatcaactgc    4560
atgaagttcc ggttggcaaa tccatcggac ttaagaaaat ccaggattgt ctttccactc    4620
tgcttgtctc ggatcccatt gatcagtttt cttgacagcc gccccatcc tgtatatcgg    4680
cgcctcttga gctgtttcat gactttgtcg tcgaagagat gagcgtaagt tttcaagcgt    4740
tcttcaatca tctccctatc ttcaaacaac gtaagggtga ggacaatgtc ctcaagaatg    4800
tcctcgttct cctcattgtc caggaagtcc ttgtctttaa tgattttcag gagatcgtga    4860
tacgttccca gggatgcgtt gaagcgatcc tccactccgc tgatttcaac agagtcgaaa    4920
cattcaatct ttttgaaata gtcttctttg agctgtttca cggtaacttt ccggttcgtc    4980
ttgaagagga ggtccacgat agctttcttc tgctctccag acaggaatgc tggctttctc    5040
atcccttctg tgacgtattt gaccttggtg agctcgttat aaactgtgaa gtactcgtac    5100
agcagagagt gtttaggaag cacctttcg ttaggcagat ttttatcaaa gttagtcatc    5160
ctttcgatga aggactgggc agaggccccc ttatccacga cttcctcgaa gttccaggga    5220
gtgatggtct cttctgattt gcgagtcatc cacgcgaatc tggaattcc ccgggcgagg    5280
gggcctacat agtagggtat ccgaaatgtg aggattttct caatcttttc cctgttatct    5340
ttcaaaaagg ggtagaaatc ctcttgccgc ctgaggatag cgtgcagttc gcccaggtga    5400
```

```
atctggtggg ggatgcttcc attgtcgaaa gtgcgctgtt tgcgcaacag atcttctctg    5460
ttaagcttta ccagcagctc ctcggtgccg tccattttt ccaagatggg cttaataaat    5520
ttgtaaaatt cctcctggct tgctccgccg tcaatgtatc cggcgtagcc attttagac    5580
tgatcgaaga aaatttcctt gtacttctca ggcagttgct gtctgacaag ggccttcagc    5640
aaagtcaagt cttggtggtg ctcatcatag cgcttgatca tactagcgct cagcggagct    5700
ttggtgatct ccgtgttcac tcgcagaata tcactcagca gaatgcgtc tgacaggttc    5760
tttgccgcca aaaaaggtc tgcgtactgg tcgccgatct gggccagcag attgtcgaga    5820
tcatcatcgt aggtgtcttt gctcagttga agcttggcat cttcggccag gtcgaagtta    5880
gatttaaagt tgggggtcag cccgagtgac agggcgataa gattaccaaa caggccgttc    5940
ttcttctccc cagggagctg tgcgatgagg ttttcgagcc gccggatttt ggacagccta    6000
gcgctcagga ttgctttggc gtcaactccg gatgcgttga tcgggttctc ttcgaaaagc    6060
tgattgtaag tctgaaccag ttggataaag agtttgtcga catcgctgtt gtctgggttc    6120
aggtccccct cgatgaggaa gtgtccccga aatttgatca tatgcgccag cgcgagatag    6180
atcaaccgca agtcagcctt atcagtactg tctacaagct tcttcctcag atgatatatg    6240
gttgggtact tttcatggta cgccacctcg tccacgatat tgccaaagat tgggtggcgc    6300
tcgtgctttt tatcctcctc caccaaaaag gactcctcca gcctatggaa gaaagagtca    6360
tccaccttag ccatctcatt actaaagatc tcctgcaggt agcagatccg attctttctg    6420
cgggtatatc tgcgccgtgc tgttctttg agccgcgtgg cttcggccgt ctccccggag    6480
tcgaacagga gggcgccaat gaggttcttc tttatgctgt ggcgatcggt attgcccaga    6540
actttgaatt ttttgctcgg caccttgtac tcgtccgtaa tgacggccca gccgacgctg    6600
tttgtgccga tatcgagccc aatggagtac ttcttgtcca tggtggcggc tcttgaagga    6660
cgacgtcatc atcccttgcc cggatgcgcg ggcttcttgt ctagcacagg agcctggggt    6720
agagcgcatg caaattacgc gctgtgcttt gtgggaaatc accctaaacg aaaaatttat    6780
tcctctttcg agccttatag tggcggccgg tctacatcct aggttttaga gctagaaata    6840
gcaagttaaa ataaggctag tccgttatca acttgaaaaa gtggcaccga gtcggtgctt    6900
ttttgttgat atggtgctgt gtaggctcat atgtggatct cagaacccac atgtactctg    6960
ctccccaggt cttggtgcgc tttctattct ctgtcagcaa agcctatcga gaatcacct    7020
accacaactg gcgccacggc ttcaatgtag cccagaccat gtttacccta ctcatggtac    7080
gtatgtaaat tggatgggct agatgaatca gagggctggg gcaaggacca cagctaacta    7140
tcttctggcc caaggaacgc ggccgcctag agtcgac                             7177
```

<210> SEQ ID NO 64  
<211> LENGTH: 7181  
<212> TYPE: DNA  
<213> ORGANISM: Artificial Sequence  
<220> FEATURE:  
<223> OTHER INFORMATION: Description of Artificial Sequence: Synthetic polynucleotide

<400> SEQUENCE: 64

```
atgtaatgaa ataaagata tttatttca caccttcctc ttcttcttgg ggtcagccct      60
gctgtctcca ccgagctgag agaggtcgat tcttgtttca tagagccccg taattgactg    120
atgaatcagt gtggcgtcca ggacctcctt tgtagaggtg taccgctttc tgtctatggt    180
ggtgtcgaag tacttgaagg ctgcaggcgc gcccaagttg gtcagagtaa acaagtggat    240
```

-continued

```
aatgttttct gcctgctccc tgatgggctt atccctgtgc ttattgtaag cagaaagcac    300
cttatcgagg ttagcgtcgg cgaggatcac tcttttggag aattcgctta tttgctcgat    360
gatctcatca aggtagtgtt tgtgttgttc cacgaacagc tgcttctgct cattatcttc    420
gggagaccct ttgagctttt catagtggct ggccagatac aagaaattaa cgtatttaga    480 ggcagtgcc agctcgttac ctttctgcag ctcgcccgca ctagcgagca ttcgtttccg    540
gccgttttca agctcaaaga gagagtactt gggaagctta atgatgaggt cttttttgac    600
ctctttatat cctttcgcct cgagaaagtc gatggggttt ttttcgaagc ttgatcgctc    660
catgattgtg atgcccagca gttccttgac gcttttgagt ttttagact tcccttctc    720 cactttggcc acaaccagta cactgtaagc gactgtagga aatcgaatc cgccgtattt    780 cttggggtcc caatcttttt tgcgtgcgat cagcttgtcg ctgttccttt cgggaggat    840 actttccttg gagaagcctc cggtctgtac ttcggtcttt ttaacgatgt tcacctgcgg    900
catggacagg accttccgga ctgtcgcgaa atccctaccc ttgtcccaca cgatttctcc    960
tgtttctccg tttgtttcga taagtggtcg cttccgaatc tctccattgg ccagtgtaat   1020
ctcggtcttg aaaaaattca taatattgct gtaaaagaag tacttagcgg tggccttgcc   1080
tatttcctgc tcagactttg cgatcatttt cctaacatcg tacactttat agtctccgta   1140
aacaaattca gattcaagct tgggatattt tttgataagt gcagtgccta ccactgcatt   1200
caggtaggca tcatgcgcat ggtggtaatt gttgatctct ctcaccttat aaaactgaaa   1260 gtccttctg aaatctgaga ccagcttaga cttcagagta ataactttca cctctcgaat   1320
cagtttgtca ttttcatcgt acttggtgtt catgcgtgaa tcgagaattt gggccacgtg   1380
cttggtgatc tggcgtgtct caacaagctg ccttttgatg aagccggctt tatccaactc   1440
agacaggcca cctcgttcag ccttagtcag attatcgaac ttccgttgtg tgatcagttt   1500
ggcgttcagc agctgccgcc aataattttt cattttcttg acaacttctt ctgaggggac   1560
gttatcactc ttccctctat ttttatcgga tcttgtcaac actttattat caatagaatc   1620
atctttgaga aaagactggg gcacgatatg atccacgtcg tagtcggaga gccgattgat   1680
gtccagttcc tgatccacgt acatgtccct gccgttctgc aggtagtaca ggtagagctt   1740
ctcattctga agctgggtgt tttcaactgg gtgttcctta aggatttggg accccagttc   1800
ttttataccc tcttcaatcc tcttcatcct ttccctactg ttcttctgtc ccttctgggt   1860
agtttggttc tctcgggcca tctcgataac gatattctcg ggcttatgcc ttcccattac   1920
tttgacgagt tcatccacga ccttaacggt ctgcagtatt ccctttttga tagctgggct   1980
acctgcaaga ttagcgatgt gctcgtgaag actgtccccc tggccagaaa cttgtgcttt   2040
ctggatgtcc tccttaaagg tgagagagtc atcatggatc aactgcatga agttccggtt   2100
ggcaaatcca tcggacttaa gaaaatccag gattgtcttt ccactctgct tgtctcggat   2160
cccattgatc agttttcttg acagccgccc ccatcctgta tatcggcgcc tcttgagctg   2220
tttcatgact ttgtcgtcga agagatgagc gtaagttttc aagcgttctt caatcatctc   2280
cctatcttca aacaacgtaa gggtgaggac aatgtcctca gaatgtcct cgttctcctc   2340 attgtccagg aagtccttgt ctttaatgat tttcaggaga tcgtgatacg ttcccaggga   2400
tgcgttgaag cgatcctcca ctccgctgat ttcaacagag tcgaaacatt caatcttttt   2460
gaaatagtct tctttgagct gtttcacggt aactttccgg ttcgtcttga agaggaggtc   2520
cacgatagct ttcttctgct ctccagacag gaatgctggc tttctcatcc cttctgtgac   2580
```

```
gtatttgacc ttggtgagct cgttataaac tgtgaagtac tcgtacagca gagagtgttt    2640
aggaagcacc ttttcgttag gcagattttt atcaaagtta gtcatccttt cgatgaagga    2700
ctgggcagag gcccccttat ccacgacttc ctcgaagttc agggagtga tggtctcttc     2760
tgatttgcga gtcatccacg cgaatctgga atttccccgg gcgagggggc ctacatagta    2820
gggtatccga aatgtgagga ttttctcaat cttttccctg ttatctttca aaaggggta     2880
gaaatcctct tgccgcctga ggatagcgtg cagttcgccc aggtgaatct ggtgggggat    2940
gcttccattg tcgaaagtgc gctgtttgcg caacagatct tctctgttaa gctttaccag    3000
cagctcctcg gtgccgtcca ttttttccaa gatgggctta ataaatttgt aaaattcctc    3060
ctggcttgct ccgccgtcaa tgtatccggc gtagccattt ttagactgat cgaagaaaat    3120
ttccttgtac ttctcaggca gttgctgtct gacaagggcc ttcagcaaag tcaagtcttg    3180
gtggtgctca tcatagcgct tgatcatact agcgctcagc ggagctttgg tgatctccgt    3240
gttcactcgc agaatatcac tcagcagaat ggcgtctgac aggttctttg ccgccaaaaa    3300
aaggtctgcg tactggtcgc cgatctgggc cagcagattg tcgagatcat catcgtaggt    3360
gtctttgctc agttgaagct tggcatcttc ggccaggtcg aagttagatt taaagttggg    3420
ggtcagcccg agtgacaggg cgataagatt accaaacagg ccgttcttct tctccccagg    3480
gagctgtgcg atgaggtttt cgagccgccg ggatttggac agcctagcgc tcaggattgc    3540
tttggcgtca actccggatg cgttgatcgg gttctcttcg aaaagctgat tgtaagtctg    3600
aaccagttgg ataaagagtt tgtcgacatc gctgttgtct gggttcaggt cccctcgat    3660
gaggaagtgt ccccgaaatt tgatcatatg cgccagcgcg agatagatca accgcaagtc    3720
agccttatca gtactgtcta caagcttctt cctcagatga tatatggttg ggtacttttc    3780
atggtacgcc acctcgtcca cgatattgcc aaagattggg tggcgctcgt gcttttttatc   3840
ctcctccacc aaaaggact cctccagcct atggaagaaa gagtcatcca ccttagccat     3900
ctcattacta aagatctcct gcaggtagca gatccgattc tttctgcggg tatatctgcg    3960
ccgtgctgtt cttttgagcc gcgtggcttc ggccgtctcc ccggagtcga acaggagggc    4020
gccaatgagg ttcttcttta tgctgtggcg atcggtattg cccagaactt tgaattttt     4080
gctcggcacc ttgtactcgt ccgtaatgac ggcccagccg acgctgtttg tgccgatatc    4140
gagcccaatg gagtacttct tgtccatggt ggcggctctt gaaggacgac gtcatcatcc    4200
cttgcccgga tgcgcgggct tcttgtctag cacaggagcc tggggtagag cgcatgcaaa    4260
ttacgcgctg tgctttgtgg gaaatcaccc taaacgaaaa atttattcct ctttcgagcc    4320
ttatagtggc ggccggtcta catcctaggt tttagagcta gaaatagcaa gttaaaataa    4380
ggctagtccg ttatcaactt gaaaaagtgg caccgagtcg gtgctttttt gttaacgcgg    4440
ccgcctagag tcgacctgca ggcatgcaag cttggcgtaa tcatggtcat agctgtttcc    4500
tgtgtgaaat tgttatccgc tcacaattcc acacaacata cgagccggaa gcataaagtg    4560
taaagcctgg ggtgcctaat gagtgagcta actcacatta attgcgttgc gctcactgcc    4620
cgctttccag tcgggaaacc tgtcgtgcca gctgcattaa tgaatcggcc aacgcgcggg    4680
gagaggcggt ttgcgtattg ggcgctcttc cgcttcctcg ctcactgact cgctgcgctc    4740
ggtcgttcgg ctgcggcgag cggtatcagc tcactcaaag gcggtaatac ggttatccac    4800
agaatcaggg gataacgcag gaaagaacat gtgagcaaaa ggccagcaaa aggccaggaa    4860
ccgtaaaaag gccgcgttgc tggcgttttt ccataggctc cgcccccctg acgagcatca    4920
caaaaatcga cgctcaagtc agaggtggcg aaacccgaca ggactataaa gataccaggc    4980
```

```
gtttccccct ggaagctccc tcgtgcgctc tcctgttccg accctgccgc ttaccggata    5040
cctgtccgcc tttctccctt cgggaagcgt ggcgctttct catagctcac gctgtaggta    5100
tctcagttcg gtgtaggtcg ttcgctccaa gctgggctgt gtgcacgaac cccccgttca    5160
gcccgaccgc tgcgccttat ccggtaacta tcgtcttgag tccaacccgg taagacgacga   5220 cttatcgcca ctggcagcag ccactggtaa caggattagc agagcgaggt atgtaggcgg    5280
tgctacagag ttcttgaagt ggtggcctaa ctacggctac actagaagaa cagtatttgg    5340
tatctgcgct ctgctgaagc cagttacctt cggaaaaaga gttggtagct cttgatccgg    5400
caaacaaacc accgctggta gcggtggttt ttttgtttgc aagcagcaga ttacgcgcag    5460
aaaaaaagga tctcaagaag atcctttgat cttttctacg gggtctgacg ctcagtggaa    5520
cgaaaactca cgttaaggga ttttggtcat gagattatca aaaaggatct tcacctagat    5580
ccttttaaat taaaaatgaa gttttaaatc aatctaaagt atatatgagt aaacttggtc    5640
tgacagttac caatgcttaa tcagtgaggc acctatctca gcgatctgtc tatttcgttc    5700
atccatagtt gcctgactcc ccgtcgtgta gataactacg atacgggagg gcttaccatc    5760
tggccccagt gctgcaatga taccgcgaga cccacgctca ccggctccag atttatcagc    5820
aataaaccag ccagccggaa gggccgagcg cagaagtggt cctgcaactt tatccgcctc    5880
catccagtct attaattgtt gccgggaagc tagagtaagt agttcgccag ttaatagttt    5940
gcgcaacgtt gttgccattg ctacaggcat cgtggtgtca cgctcgtcgt ttggtatggc    6000
ttcattcagc tccggttccc aacgatcaag gcgagttaca tgatccccca tgttgtgcaa    6060
aaaagcggtt agctccttcg gtcctccgat cgttgtcaga agtaagttgg ccgcagtgtt    6120
atcactcatg gttatggcag cactgcataa ttctcttact gtcatgccat ccgtaagatg    6180
cttttctgtg actggtgagt actcaaccaa gtcattctga atagtgta tgcggcgacc     6240 gagttgctct tgcccggcgt caatacggga taataccgcg ccacatagca gaactttaaa    6300
agtgctcatc attggaaaac gttcttcggg gcgaaaactc tcaaggatct taccgctgtt    6360
gagatccagt tcgatgtaac ccactcgtgc acccaactga tcttcagcat cttttacttt    6420
caccagcgtt tctgggtgag caaaaacagg aaggcaaaat gccgcaaaaa agggaataag    6480
ggcgacacgg aaatgttgaa tactcatact cttccttttt caatattatt gaagcattta    6540
tcagggttat tgtctcatga gcggatacat atttgaatgt atttagaaaa ataaacaaat    6600
aggggttccg cgcacatttc cccgaaaagt gccacctgac gtctaagaaa ccattattat    6660
catgacatta acctataaaa ataggcgtat cacgaggccc tttcgtctcg cgcgtttcgg    6720
tgatgacggt gaaaacctct gacacatgca gctcccggag acggtcacag cttgtctgta    6780
agcggatgcc gggagcagac aagcccgtca gggcgcgtca gcgggtgttg gcgggtgtcg    6840
gggctggctt aactatgcgg catcagagca gattgtactg agagtgcacc atagcggccg    6900
cggtacgata tggtgctgtg taggctcata tgtggatctc agaacccaca tgtactctgc    6960
tccccaggtc ttggtgcgct ttctattctc tgtcagcaaa gcctatcgaa gaatcaccta    7020
ccacaactgg cgccacggct tcaatgtagc ccagaccatg tttaccctac tcatggtacg    7080
tatgtaaatt ggatgggcta gatgaatcag agggctgggg caaggaccac agctaactat    7140
cttctggccc aagggtaccc acacaaaaaa ccaacacaca g                       7181

<210> SEQ ID NO 65
<211> LENGTH: 7179
<212> TYPE: DNA
```

<213> ORGANISM: Artificial Sequence
<220> FEATURE:
<223> OTHER INFORMATION: Description of Artificial Sequence: Synthetic polynucleotide

<400> SEQUENCE: 65

| | | | | | |
|---|---|---|---|---|---|
| ctgcaggcat | gcaagcttgg | cgtaatcatg | gtcatagctg | tttcctgtgt | gaaattgtta | 60 |
| tccgctcaca | attccacaca | acatacgagc | cggaagcata | aagtgtaaag | cctggggtgc | 120 |
| ctaatgagtg | agctaactca | cattaattgc | gttgcgctca | ctgcccgctt | tccagtcggg | 180 |
| aaacctgtcg | tgccagctgc | attaatgaat | cggccaacgc | gcggggagag | gcggtttgcg | 240 |
| tattgggcgc | tcttccgctt | cctcgctcac | tgactcgctg | cgctcggtcg | ttcggctgcg | 300 |
| gcgagcggta | tcagctcact | caaaggcggt | aatacggtta | tccacagaat | caggggataa | 360 |
| cgcaggaaag | aacatgtgag | caaaaggcca | gcaaaaggcc | aggaaccgta | aaaaggccgc | 420 |
| gttgctggcg | ttttccata | ggctccgccc | ccctgacgag | catcacaaaa | atcgacgctc | 480 |
| aagtcagagg | tggcgaaacc | cgacaggact | ataaagatac | caggcgtttc | cccctggaag | 540 |
| ctccctcgtg | cgctctcctg | ttccgaccct | gccgcttacc | ggatacctgt | ccgcctttct | 600 |
| cccttcggga | agcgtggcgc | tttctcatag | ctcacgctgt | aggtatctca | gttcggtgta | 660 |
| ggtcgttcgc | tccaagctgg | gctgtgtgca | cgaaccccc | gttcagcccg | accgctgcgc | 720 |
| cttatccggt | aactatcgtc | ttgagtccaa | cccggtaaga | cacgacttat | cgccactggc | 780 |
| agcagccact | ggtaacagga | ttagcagagc | gaggtatgta | ggcggtgcta | cagagttctt | 840 |
| gaagtggtgg | cctaactacg | gctacactag | aagaacagta | tttggtatct | gcgctctgct | 900 |
| gaagccagtt | accttcggaa | aaagagttgg | tagctcttga | tccggcaaac | aaaccaccgc | 960 |
| tggtagcggt | ggtttttttg | tttgcaagca | gcagattacg | cgcagaaaaa | aaggatctca | 1020 |
| agaagatcct | ttgatctttt | ctacggggtc | tgacgctcag | tggaacgaaa | actcacgtta | 1080 |
| agggattttg | gtcatgagat | tatcaaaaag | gatcttcacc | tagatccttt | taaattaaaa | 1140 |
| atgaagtttt | aaatcaatct | aaagtatata | tgagtaaact | tggtctgaca | gttaccaatg | 1200 |
| cttaatcagt | gaggcaccta | tctcagcgat | ctgtctattt | cgttcatcca | tagttgcctg | 1260 |
| actccccgtc | gtgtagataa | ctacgatacg | ggagggctta | ccatctggcc | ccagtgctgc | 1320 |
| aatgataccg | cgagacccac | gctcaccggc | tccagattta | tcagcaataa | accagccagc | 1380 |
| cggaagggcc | gagcgcagaa | gtggtcctgc | aactttatcc | gcctccatcc | agtctattaa | 1440 |
| ttgttgccgg | gaagctagag | taagtagttc | gccagttaat | agtttgcgca | acgttgttgc | 1500 |
| cattgctaca | ggcatcgtgg | tgtcacgctc | gtcgtttggt | atggcttcat | tcagctccgg | 1560 |
| ttcccaacga | tcaaggcgag | ttacatgatc | ccccatgttg | tgcaaaaaag | cggttagctc | 1620 |
| cttcggtcct | ccgatcgttg | tcagaagtaa | gttggccgca | gtgttatcac | tcatggttat | 1680 |
| ggcagcactg | cataattctc | ttactgtcat | gccatccgta | agatgctttt | ctgtgactgg | 1740 |
| tgagtactca | accaagtcat | tctgagaata | gtgtatgcgg | cgaccgagtt | gctcttgccc | 1800 |
| ggcgtcaata | cgggataata | ccgcgccaca | tagcagaact | ttaaaagtgc | tcatcattgg | 1860 |
| aaaacgttct | cggggcgaaa | actctcaag | gatcttaccg | ctgttgagat | ccagttcgat | 1920 |
| gtaacccact | cgtgcaccca | actgatcttc | agcatctttt | actttcacca | gcgtttctgg | 1980 |
| gtgagcaaaa | acaggaaggc | aaaatgccgc | aaaaaaggga | ataagggcga | cacggaaatg | 2040 |
| ttgaatactc | atactcttcc | tttttcaata | ttattgaagc | atttatcagg | gttattgtct | 2100 |
| catgagcgga | tacatatttg | aatgtattta | gaaaaataaa | caaataggg | ttccgcgcac | 2160 |

```
atttccccga aaagtgccac ctgacgtcta agaaaccatt attatcatga cattaaccta    2220
taaaaatagg cgtatcacga ggccctttcg tctcgcgcgt ttcggtgatg acggtgaaaa    2280
cctctgacac atgcagctcc cggagacggt cacagcttgt ctgtaagcgg atgccgggag    2340
cagacaagcc cgtcagggcg cgtcagcggg tgttggcggg tgtcggggct ggcttaacta    2400
tgcggcatca gagcagattg tactgagagt gcaccatagc ggccgcggta cccacacaaa    2460
aaaccaacac acagatgtaa tgaaaataaa gatattttat ttcacacctt cctcttcttc    2520
ttggggtcag ccctgctgtc tccaccgagc tgagagaggt cgattcttgt ttcatagagc    2580
cccgtaattg actgatgaat cagtgtggcg tccaggacct cctttgtaga ggtgtaccgc    2640
tttctgtcta tggtggtgtc gaagtacttg aaggctgcag gcgcgcccaa gttggtcaga    2700
gtaaacaagt ggataatgtt ttctgcctgc tccctgatgg gcttatccct gtgcttattg    2760
taagcagaaa gcaccttatc gaggttagcg tcggcgagga tcactctttt ggagaattcg    2820
cttatttgct cgatgatctc atcaaggtag tgtttgtgtt gttccacgaa cagctgcttc    2880
tgctcattat cttcgggaga ccctttgagc ttttcatagt ggctgccag atacaagaaa     2940 ttaacgtatt tagagggcag tgccagctcg ttacctttct gcagctcgcc cgcactagcg    3000
agcattcgtt tccggccgtt ttcaagctca aagagagagt acttgggaag cttaatgatg    3060 aggtctttt tgacctcttt atatcctttc gcctcgagaa agtcgatggg gttttttcg       3120 aagcttgatc gctccatgat tgtgatgccc agcagttcct tgacgctttt gagttttta    3180 gacttccctt tctccacttt ggccacaacc agtacactgt aagcgactgt aggagaatcg    3240
aatccgccgt atttcttggg gtcccaatct tttttgcgtg cgatcagctt gtcgctgttc    3300
cttttcggga ggatactttc cttggagaag cctccggtct gtacttcggt ctttttaacg    3360
atgttcacct gcggcatgga caggaccttc cggactgtcg cgaaatccct acccttgtcc    3420
cacacgattt ctcctgtttc tccgtttgtt tcgataagtg gtcgcttccg aatctctcca    3480
ttggccagtg taatctcggt cttgaaaaaa ttcataatat tgctgtaaaa gaagtactta    3540
gcggtggcct tgcctatttc ctgctcagac tttgcgatca ttttcctaac atcgtacact    3600
ttatagtctc cgtaaacaaa ttcagattca agcttgggat attttttgat aagtgcagtg    3660
cctaccactg cattcaggta ggcatcatgc gcatggtggt aattgttgat ctctctcacc    3720
ttataaaact gaaagtcctt tctgaaatct gagaccagct tagacttcag agtaataact    3780
ttcacctctc gaatcagttt gtcattttca tcgtacttgg tgttcatgcg tgaatcgaga    3840
atttgggcca cgtgcttggt gatctggcgt gtctcaacaa gctgcctttt gatgaagccg    3900
gctttatcca actcagacag gccacctcgt tcagccttag tcagattatc gaacttccgt    3960
tgtgtgatca gtttggcgtt cagcagctgc cgccaataat ttttcatttt cttgacaact    4020
tcttctgagg ggacgttatc actcttccct ctattttat cggatcttgt caacacttta    4080
ttatcaatag aatcatcttt gagaaaagac tggggcacga tatgatccac gtcgtagtcg    4140
gagagccgat tgatgtccag ttcctgatcc acgtacatgt ccctgccgtt ctgcaggtag    4200
tacaggtaga gcttctcatt ctgaagctgg gtgttttcaa ctgggtgttc cttaaggatt    4260
tgggacccca gttcttttat accctcttca atcctcttca tcctttccct actgttcttc    4320
tgtcccttct gggtagtttg gttctctcgg gccatctcga taacgatatt ctcgggctta    4380
tgccttccca ttactttgac gagttcatcc acgaccttaa cggtctgcag tattcccttt    4440
ttgatagctg ggctacctgc aagattagcg atgtgctcgt gaagactgtc ccctggcca    4500 gaaacttgtg ctttctggat gtcctcctta aggtgagag agtcatcatg gatcaactgc    4560
```

```
atgaagttcc ggttggcaaa tccatcggac ttaagaaaat ccaggattgt ctttccactc    4620
tgcttgtctc ggatcccatt gatcagtttt cttgacagcc gcccccatcc tgtatatcgg    4680
cgcctcttga gctgtttcat gactttgtcg tcgaagagat gagcgtaagt tttcaagcgt    4740
tcttcaatca tctccctatc ttcaaacaac gtaagggtga ggacaatgtc ctcaagaatg    4800
tcctcgttct cctcattgtc caggaagtcc ttgtctttaa tgattttcag gagatcgtga    4860
tacgttccca gggatgcgtt gaagcgatcc tccactccgc tgatttcaac agagtcgaaa    4920
cattcaatct ttttgaaata gtcttctttg agctgtttca cggtaacttt ccggttcgtc    4980
ttgaagagga ggtccacgat agctttcttc tgctctccag acaggaatgc tggctttctc    5040
atcccttctg tgacgtattt gaccttggtg agctcgttat aaactgtgaa gtactcgtac    5100
agcagagagt gtttaggaag caccttttcg ttaggcagat ttttatcaaa gttagtcatc    5160
ctttcgatga aggactgggc agaggccccc ttatccacga cttcctcgaa gttccaggga    5220
gtgatggtct cttctgattt gcgagtcatc cacgcgaatc tggaatttcc ccgggcgagg    5280
gggcctacat agtagggtat ccgaaatgtg aggattttct caatcttttc cctgttatct    5340
ttcaaaaagg ggtagaaatc ctcttgccgc ctgaggatag cgtgcagttc gcccaggtga    5400
atctggtggg ggatgcttcc attgtcgaaa gtgcgctgtt tgcgcaacag atcttctctg    5460
ttaagcttta ccagcagctc ctcggtgccg tccatttttt ccaagatggg cttaataaat    5520
ttgtaaaatt cctcctggct tgctccgccg tcaatgtatc cggcgtagcc attttagac     5580 tgatcgaaga aaatttcctt gtacttctca ggcagttgct gtctgacaag gccttcagc     5640 aaagtcaagt cttggtggtg ctcatcatag cgcttgatca tactagcgct cagcggagct    5700
ttggtgatct ccgtgttcac tcgcagaata tcactcagca gaatggcgtc tgacaggttc    5760
tttgccgcca aaaaaggtc tgcgtactgg tcgccgatct gggccagcag attgtcgaga    5820
tcatcatcgt aggtgtcttt gctcagttga agcttggcat cttcggccag gtcgaagtta    5880
gatttaaagt tgggggtcag cccgagtgac agggcgataa gattaccaaa caggccgttc    5940
ttcttctccc cagggagctg tgcgatgagg ttttcgagcc gccgggattt ggacagccta    6000
gcgctcagga ttgctttggc gtcaactccg gatgcgttga tcgggttctc ttcgaaaagc    6060
tgattgtaag tctgaaccag ttggataaag agtttgtcga catcgctgtt gtctgggttc    6120
aggtccccct cgatgaggaa gtgtccccga aatttgatca tatgcgccag cgcgagatag    6180
atcaaccgca agtcagcctt atcagtactg tctacaagct tcttcctcag atgatatatg    6240
gttgggtact tttcatggta cgccacctcg tccacgtat tgccaaagat tgggtggcgc    6300
tcgtgctttt tatcctcctc caccaaaaag gactcctcca gcctatggaa gaaagagtca    6360
tccaccttag ccatctcatt actaaagatc tcctgcaggt agcagatccg attctttctg    6420
cgggtatatc tgcgccgtgc tgttcttttg agccgcgtgg cttcggccgt ctccccggag    6480
tcgaacagga gggcgccaat gaggttcttc tttatgctgt ggcgatcggt attgcccaga    6540
actttgaatt ttttgctcgg caccttgtac tcgtccgtaa tgacggccca gccgacgctg    6600
tttgtgccga tatcgagccc aatggagtac ttccttgtcca tggtggcggc tcttgaagga    6660
cgacgtcatc atcccttgcc cggatgcgcg ggcttcttgt ctagcacagg agcctggggt    6720
agagcgcatg caaattacgc gctgtgcttt gtgggaaatc accctaaacg aaaaatttat    6780 tcctcttcg agccttatag tggcggccgg tctacatcct aggttttaga gctagaaata    6840
gcaagttaaa ataaggctag tccgttatca acttgaaaaa gtggcaccga gtcggtgctt    6900
```

```
ttttgttgtt ctgtctatag gtaagctgac aaataacaaa taggcacata gaaaatctag    6960
taagtagtac cacctgatat ctcactttgc tgcaggcagg attccctct ggctcactgg     7020 cagtctcctc cggtgtgggc cagggctctt tgaagttgga tctgagcctt tctatcacct    7080
gtttgatgga caagccctt tgcacaagtt tgacttcaag gagggccatg tcacatacca     7140
cagaaggtaa gtccatgaac gcggccgcct agagtcgac                          7179
```

<210> SEQ ID NO 66
<211> LENGTH: 7179
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 66

```
atgtaatgaa aataaagata ttttatttca caccttcctc ttcttcttgg ggtcagccct     60
gctgtctcca ccgagctgag agaggtcgat tcttgtttca tagagcccg taattgactg     120 atgaatcagt gtggcgtcca ggacctcctt tgtagaggtg taccgctttc tgtctatggt    180
ggtgtcgaag tacttgaagg ctgcaggcgc gcccaagttg gtcagagtaa acaagtggat    240
aatgttttct gcctgctccc tgatgggctt atccctgtgc ttattgtaag cagaaagcac    300
cttatcgagg ttagcgtcgg cgaggatcac tcttttggag aattcgctta tttgctcgat    360
gatctcatca aggtagtgtt tgtgttgttc cacgaacagc tgcttctgct cattatcttc    420
gggagaccct ttgagctttt catagtggct ggccagatac aagaaattaa cgtatttaga    480
gggcagtgcc agctcgttac ctttctgcag ctcgcccgca ctagcgagca ttcgtttccg    540
gccgttttca agctcaaaga gagtactt gggaagctta atgatgaggt cttttttgac     600
ctctttatat cctttcgcct cgagaaagtc gatgggggttt tttcgaagc ttgatcgctc    660 catgattgtg atgcccagca gttccttgac gcttttgagt tttttagact tccctttctc    720
cactttggcc acaaccagta cactgtaagc gactgtagga gaatcgaatc cgccgtattt    780
cttggggtcc caatcttttt tgcgtgcgat cagcttgtcg ctgttccttt tcgggaggat    840
actttccttg gagaagcctc cggtctgtac ttcggtctttt taacgatgt tcacctgcgg    900 catggacagg accttccgga ctgtcgcgaa atccctaccc ttgtcccaca cgatttctcc    960
tgtttctccg tttgtttcga taagtggtcg cttccgaatc tctccattgg ccagtgtaat   1020
ctcggtcttg aaaaaattca taatattgct gtaaagaag tacttagcgg tggccttgcc    1080
tatttcctgc tcagactttg cgatcatttt cctaacatcg tacactttat agtctccgta    1140
aacaaattca gattcaagct tgggatattt tttgataagt gcagtgccta ccactgcatt    1200
caggtaggca tcatgcgcat ggtggtaatt gttgatctct ctcaccttat aaaactgaaa    1260 gtccttctg aaatctgaga ccagcttaga cttcagagta ataactttca cctctcgaat    1320
cagtttgtca ttttcatcgt acttggtgtt catgcgtgaa tcgagaattt gggccacgtg    1380
cttggtgatc tggcgtgtct caacaagctg ccttttgatg aagccggctt tatccaactc    1440
agacaggcca cctcgttcag ccttagtcag attatcgaac ttccgttgtg tgatcagttt    1500
ggcgttcagc agctgccgcc aataattttt cattttcttg acaacttctt ctgagggac    1560 gttatcactc ttccctctat ttttatcgga tcttgtcaac actttattat caatagaatc    1620
atctttgaga aaagactggg gcacgatatg atccacgtcg tagtcggaga gccgattgat   1680
gtccagttcc tgatccacgt acatgtccct gccgttctgc aggtagtaca ggtagagctt   1740
```

```
ctcattctga agctgggtgt tttcaactgg gtgttcctta aggatttggg accccagttc    1800
ttttataccc tcttcaatcc tcttcatcct ttccctactg ttcttctgtc ccttctgggt    1860
agtttggttc tctcgggcca tctcgataac gatattctcg ggcttatgcc ttcccattac    1920
tttgacgagt tcatccacga ccttaacggt ctgcagtatt ccctttttga tagctgggct    1980
acctgcaaga ttagcgatgt gctcgtgaag actgtccccc tggccagaaa cttgtgcttt    2040
ctggatgtcc tccttaaagg tgagagagtc atcatggatc aactgcatga agttccggtt    2100
ggcaaatcca tcggacttaa gaaaatccag gattgtcttt ccactctgct tgtctcggat    2160
cccattgatc agttttcttg acagccgccc ccatcctgta tatcggcgcc tcttgagctg    2220
tttcatgact ttgtcgtcga agagatgagc gtaagttttc aagcgttctt caatcatctc    2280
cctatcttca acaacgtaa gggtgaggac aatgtcctca agaatgtcct cgttctcctc    2340
attgtccagg aagtccttgt ctttaatgat tttcaggaga tcgtgatacg ttcccaggga    2400
tgcgttgaag cgatcctcca ctccgctgat ttcaacagag tcgaaacatt caatcttttt    2460
gaaatagtct tctttgagct gtttcacggt aactttccgg ttcgtcttga agaggaggtc    2520
cacgatagct tcttctgct ctccagacag gaatgctggc tttctcatcc cttctgtgac    2580
gtatttgacc ttggtgagct cgttataaac tgtgaagtac tcgtacagca gagagtgttt    2640
aggaagcacc ttttcgttag gcagatttt atcaaagtta gtcatccttt cgatgaagga    2700
ctgggcagag gcccccttat ccacgacttc ctcgaagttc cagggagtga tggtctcttc    2760
tgatttgcga gtcatccacg cgaatctgga atttccccgg gcgagggggc ctacatagta    2820
gggtatccga aatgtgagga ttttctcaat cttttccctg ttatctttca aaaggggta    2880
gaaatcctct tgccgcctga ggatagcgtg cagttcgccc aggtgaatct ggtgggggat    2940
gcttccattg tcgaaagtgc gctgtttgcg caacagatct tctctgttaa gctttaccag    3000
cagctcctcg gtgccgtcca ttttttccaa gatgggctta ataaatttgt aaaattcctc    3060
ctggcttgct ccgccgtcaa tgtatccggc gtagccattt ttagactgat cgaagaaaat    3120
ttccttgtac ttctcaggca gttgctgtct gacaagggcc ttcagcaaag tcaagtcttg    3180
gtggtgctca tcatagcgct tgatcatact agcgctcagc ggagctttgg tgatctccgt    3240
gttcactcgc agaatatcac tcagcagaat ggcgtctgac aggttctttg ccgccaaaaa    3300
aaggtctgcg tactggtcgc cgatctgggc cagcagattg tcgagatcat catcgtaggt    3360
gtctttgctc agttgaagct tggcatcttc ggccaggtcg aagttagatt taaagttggg    3420
ggtcagcccg agtgacaggg cgataagatt accaaacagg ccgttcttct tctccccagg    3480
gagctgtgcg atgaggtttt cgagccgccg ggatttggac agcctagcgc tcaggattgc    3540
tttggcgtca actccggatg cgttgatcgg gttctcttcg aaaagctgat tgtaagtctg    3600
aaccagttgg ataaagagtt tgtcgacatc gctgttgtct gggttcaggt cccctcgat    3660
gaggaagtgt ccccgaaatt tgatcatatg cgccagcgcg agatagatca accgcaagtc    3720
agccttatca gtactgtcta caagcttctt cctcagatga tatatggttg ggtactttc     3780
atggtacgcc acctcgtcca cgatattgcc aaagattggg tggcgctcgt gctttttatc    3840
ctcctccacc aaaaaggact cctccagcct atggaagaaa gagtcatcca ccttagccat    3900
ctcattacta agatctcct gcaggtagca gatccgattc tttctgcggg tatatctgcg    3960
ccgtgctgtt cttttgagcc gcgtggcttc ggccgtctcc ccggagtcga acaggagggc    4020
gccaatgagg ttcttcttta tgctgtggcg atcggtattg cccagaactt tgaatttttt    4080
gctcggcacc ttgtactcgt ccgtaatgac ggcccagccg acgctgtttg tgccgatatc    4140
```

```
gagcccaatg gagtacttct tgtccatggt ggcggctctt gaaggacgac gtcatcatcc   4200
cttgcccgga tgcgcgggct tcttgtctag cacaggagcc tggggtagag cgcatgcaaa   4260
ttacgcgctg tgctttgtgg gaaatcaccc taaacgaaaa atttattcct ctttcgagcc   4320
ttatagtggc ggccggtcta catcctaggt tttagagcta gaaatagcaa gttaaaataa   4380
ggctagtccg ttatcaactt gaaaagtgg  caccgagtcg gtgctttttt gttaacgcgg   4440
ccgcctagag tcgacctgca ggcatgcaag cttggcgtaa tcatggtcat agctgtttcc   4500
tgtgtgaaat tgttatccgc tcacaattcc acacaacata cgagccggaa gcataaagtg   4560
taaagcctgg ggtgcctaat gagtgagcta actcacatta attgcgttgc gctcactgcc   4620
cgctttccag tcgggaaacc tgtcgtgcca gctgcattaa tgaatcggcc aacgcgcggg   4680
gagaggcggt ttgcgtattg ggcgctcttc cgcttcctcg ctcactgact cgctgcgctc   4740
ggtcgttcgg ctgcggcgag cggtatcagc tcactcaaag gcggtaatac ggttatccac   4800
agaatcaggg gataacgcag gaaagaacat gtgagcaaaa ggccagcaaa aggccaggaa   4860
ccgtaaaaag gccgcgttgc tggcgttttt ccataggctc cgcccccctg acgagcatca   4920
caaaaatcga cgctcaagtc agaggtggcg aaacccgaca ggactataaa gataccaggc   4980
gtttccccct ggaagctccc tcgtgcgctc tcctgttccg accctgccgc ttaccggata   5040
cctgtccgcc tttctccctt cgggaagcgt ggcgctttct catagctcac gctgtaggta   5100
tctcagttcg gtgtaggtcg ttcgctccaa gctgggctgt gtgcacgaac cccccgttca   5160
gcccgaccgc tgcgccttat ccggtaacta tcgtcttgag tccaacccgg taagacacga   5220
cttatcgcca ctggcagcag ccactggtaa caggattagc agagcgaggt atgtaggcgg   5280
tgctacagag ttcttgaagt ggtggcctaa ctacggctac actagaagaa cagtatttgg   5340
tatctgcgct ctgctgaagc cagttacctt cggaaaaaga gttggtagct cttgatccgg   5400
caaacaaacc accgctggta gcggtggttt tttgtttgc aagcagcaga ttacgcgcag   5460
aaaaaaagga tctcaagaag atcctttgat cttttctacg gggtctgacg ctcagtggaa   5520
cgaaaactca cgttaaggga ttttggtcat gagattatca aaaaggatct tcacctagat   5580
ccttttaaat taaaaatgaa gttttaaatc aatctaaagt atatatgagt aaacttggtc   5640
tgacagttac caatgcttaa tcagtgaggc acctatctca gcgatctgtc tatttcgttc   5700
atccatagtt gcctgactcc ccgtcgtgta gataactacg atacgggagg gcttaccatc   5760
tggccccagt gctgcaatga taccgcgaga cccacgctca ccggctccag atttatcagc   5820
aataaaccag ccagccggaa gggccgagcg cagaagtggt cctgcaactt tatccgcctc   5880
catccagtct attaattgtt gccgggaagc tagagtaagt agttcgccag ttaatagttt   5940
gcgcaacgtt gttgccattg ctacaggcat cgtggtgtca cgctcgtcgt ttggtatggc   6000
ttcattcagc tccggttccc aacgatcaag gcgagttaca tgatccccca tgttgtgcaa   6060
aaaagcggtt agctccttcg gtcctccgat cgttgtcaga agtaagttgg ccgcagtgtt   6120
atcactcatg gttatggcag cactgcataa ttctcttact gtcatgccat ccgtaagatg   6180
cttttctgtg actggtgagt actcaaccaa gtcattctga gaatagtgta tgcggcgacc   6240
gagttgctct tgcccggcgt caatacggga taataccgcg ccacatagca gaactttaaa   6300
agtgctcatc attggaaaac gttcttcggg gcgaaaactc tcaaggatct taccgctgtt   6360
gagatccagt tcgatgtaac ccactcgtgc acccaactga tcttcagcat cttttacttt   6420
caccagcgtt tctgggtgag caaaaacagg aaggcaaaat gccgcaaaaa agggaataag   6480
```

-continued

| | |
|---|---|
| ggcgacacgg aaatgttgaa tactcatact cttcctttt caatattatt gaagcattta | 6540 |
| tcagggttat tgtctcatga gcggatacat atttgaatgt atttagaaaa ataaacaaat | 6600 |
| aggggttccg cgcacatttc cccgaaaagt gccacctgac gtctaagaaa ccattattat | 6660 |
| catgacatta acctataaaa ataggcgtat cacgaggccc tttcgtctcg cgcgtttcgg | 6720 |
| tgatgacggt gaaaacctct gacacatgca gctcccggag acggtcacag cttgtctgta | 6780 |
| agcggatgcc gggagcagac aagcccgtca gggcgcgtca gcgggtgttg gcgggtgtcg | 6840 |
| gggctggctt aactatgcgg catcagagca gattgtactg agagtgcacc atagcggccg | 6900 |
| cggttctgtc tataggtaag ctgacaaata acaaataggc acatagaaaa tctagtaagt | 6960 |
| agtaccacct gatatctcac tttgctgcag gcaggattcc cctctggctc actggcagtc | 7020 |
| tcctccggtg tgggccaggg ctctttgaag ttggatctga gcctttctat cacctgtttg | 7080 |
| atggacaagc ccttttgcac aagtttgact tcaaggaggg ccatgtcaca taccacagaa | 7140 |
| ggtaagtcca tggtacccac acaaaaaacc aacacacag | 7179 |

<210> SEQ ID NO 67
<211> LENGTH: 6079
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 67

| | |
|---|---|
| gcttggcgta atcatggtca tagctgtttc ctgtgtgaaa ttgttatccg ctcacaattc | 60 |
| cacacaacat acgagccgga agcataaagt gtaaagcctg gggtgcctaa tgagtgagct | 120 |
| aactcacatt aattgcgttg cgctcactgc ccgctttcca gtcgggaaac ctgtcgtgcc | 180 |
| agctgcatta atgaatcggc caacgcgcgg ggagaggcgg tttgcgtatt gggcgctctt | 240 |
| ccgcttcctc gctcactgac tcgctgcgct cggtcgttcg gctgcggcga gcggtatcag | 300 |
| ctcactcaaa ggcggtaata cggttatcca cagaatcagg ggataacgca ggaaagaaca | 360 |
| tgtgagcaaa aggccagcaa aaggccagga accgtaaaaa ggccgcgttg ctggcgtttt | 420 |
| tccataggct ccgcccccct gacgagcatc acaaaaatcg acgctcaagt cagaggtggc | 480 |
| gaaacccgac aggactataa agataccagg cgtttccccc tggaagctcc ctcgtgcgct | 540 |
| ctcctgttcc gaccctgccg cttaccggat acctgtccgc ctttctccct tcgggaagcg | 600 |
| tggcgctttc tcatagctca cgctgtaggt atctcagttc ggtgtaggtc gttcgctcca | 660 |
| agctgggctg tgtgcacgaa ccccccgttc agcccgaccg ctgcgcctta tccggtaact | 720 |
| atcgtcttga gtccaacccg gtaagacacg acttatcgcc actggcagca gccactggta | 780 |
| acaggattag cagagcgagg tatgtaggcg gtgctacaga gttcttgaag tggtggccta | 840 |
| actacggcta cactagaaga acagtatttg gtatctgcgc tctgctgaag ccagttacct | 900 |
| tcggaaaaag agttggtagc tcttgatccg gcaaacaaac caccgctggt agcggtggtt | 960 |
| tttttgtttg caagcagcag attacgcgca gaaaaaaagg atctcaagaa gatcctttga | 1020 |
| tcttttctac ggggtctgac gctcagtgga acgaaaactc acgttaaggg attttggtca | 1080 |
| tgagattatc aaaaaggatc ttcacctaga tccttttaaa ttaaaaatga agttttaaat | 1140 |
| caatctaaag tatatatgag taaacttggt ctgacagtta ccaatgctta atcagtgagg | 1200 |
| cacctatctc agcgatctgt ctatttcgtt catccatagt tgcctgactc cccgtcgtgt | 1260 |
| agataactac gatacgggag ggcttaccat ctggccccag tgctgcaatg ataccgcgag | 1320 |

-continued

```
acccacgctc accggctcca gatttatcag caataaacca gccagccgga agggccgagc    1380
gcagaagtgg tcctgcaact ttatccgcct ccatccagtc tattaattgt tgccgggaag    1440
ctagagtaag tagttcgcca gttaatagtt tgcgcaacgt tgttgccatt gctacaggca    1500
tcgtggtgtc acgctcgtcg tttggtatgg cttcattcag ctccggttcc caacgatcaa    1560
ggcgagttac atgatccccc atgttgtgca aaaaagcggt tagctccttc ggtcctccga    1620
tcgttgtcag aagtaagttg gccgcagtgt tatcactcat ggttatggca gcactgcata    1680
attctcttac tgtcatgcca tccgtaagat gcttttctgt gactggtgag tactcaacca    1740
agtcattctg agaatagtgt atgcggcgac cgagttgctc ttgcccggcg tcaatacggg    1800
ataataccgc gccacatagc agaactttaa aagtgctcat cattggaaaa cgttcttcgg    1860
ggcgaaaact ctcaaggatc ttaccgctgt tgagatccag ttcgatgtaa cccactcgtg    1920
cacccaactg atcttcagca tcttttactt tcaccagcgt ttctgggtga gcaaaaacag    1980
gaaggcaaaa tgccgcaaaa aagggaataa gggcgacacg gaaatgttga atactcatac    2040
tcttcctttt tcaatattat tgaagcattt atcagggtta ttgtctcatg agcggataca    2100
tatttgaatg tatttagaaa aataaacaaa taggggttcc gcgcacattt ccccgaaaag    2160
tgccacctga cgtctaagaa accattatta tcatgacatt aacctataaa aataggcgta    2220
tcacgaggcc ctttcgtctc gcgcgtttcg gtgatgacgg tgaaaacctc tgacacatgc    2280
agctcccgga cggtcaca gcttgtctgt aagcggatgc cgggagcaga caagcccgtc    2340
agggcgcgtc agcgggtgtt ggcgggtgtc ggggctggct taactatgcg gcatcagagc    2400
agattgtact gagagtgcac catagcggcc gcggtaccca cacaaaaaac caacacacag    2460
atgtaatgaa aataaagata ttttattagg ctgatcagcg agctctagga attcttagga    2520
tccctttttc ttttttgcct ggccggcctt tttcgtggcc gccggccttt tgccctttt    2580
gatgatctga gggtgcttct tagatttcac ttcatacagg ttgcccagaa tgtctgtgct    2640
gtacttctta atgctctggg tcttggaggc gattgtctta atgatcctgg ggggcctctt    2700
gtcgttcatg ttttccaggt actcgcggta ggtgatgtcg atcatgttca cttcgatccg    2760
gttcagcagg tcgttgttca cgccgatcac tctatacagc tcgccgttga tcttgatcag    2820
atcgttgttg tagaaggagg cgataaactc ggcctggttg ctgatcttct tcagcttctt    2880
agcttcctca tagcacttgc tattcacttc gtagtagttt tctttttga tcacatccag    2940
attcttcacg gtcacgaact tgtacacgcc attgtccagg tacacgtcga atctgtaggg    3000
cttcagggac agcttcacga ccttgtttct gctgttgggg tagtcgtcgg tgatgtccag    3060
atgggcgttc agtttgttgc cgtaatactt aatcttcttg atcacggggc cgttgtcctt    3120
tttggagtac ttggtcaggt agttcccggt ttcctcgtag tacttgtaca ggggattctt    3180
ctcgtcgccg tactgttcca taatcagctt cagtttctgg taggtctggg ggtcgtggtg    3240
gtacatcagc agcttttcgg ggctcttgtt gatcagcttt tcagcttgt cattgtcctt    3300
gtcgtacagg ccgttcagat tgttcacgat cagggtgttg cccttgtcgt ccttccgggt    3360
ggagtacagg gtgtcgttaa tcagctctct attaggcttc ttgtccaccc ggtggctgta    3420
cttgtagtcc ttgaagtcct taatgtgctt gatctggtgg ggggtgatga agatctcttt    3480
gtactcctgc tcggtttcga tctcgggcat gctctcggcc tgcttttcct cgaacatctg    3540
gttttccatc actttttgg ccttgtccag tttcttccac tctttgaaga tgaaatcggc    3600
gttggcaatg atcagggcgt cctcggcgtg gtgcttgtac cccttgttcc gctctttctt    3660
aaacttccac ttccgccgca gaaagctggt gaagccgcca ttgatggact tcactttcac    3720
```

```
gtccaggttg ttcactctga agtagctccg cagcaggttc atcaggcctc tggtggcgta  3780
tctggtatcc accaggttcc ggttgatgaa gtctttctgc acggagaacc tgttgatgtc  3840
ccgttcttcc agcagatact ctttcttggt cttgctgatt ctgcccttgc ccttggccag  3900
attcaggatg tgcttcttga aggtttcgta gctgatcttg ctgtcgctgc tgctcaggta  3960
ctggaatggg gtccggttgc ccttcttgct gttttcttcc tgcttcacga gcaccttgtt  4020
gttgaagctg ttgtcgaagg acacgcttct ggggatgatg tggtccacct catagttgaa  4080
ggggttgttc agcagatctt ccagagggat ggcttccagg ctgtacaggc acttgccttc  4140
ctgcatgtcg tgcagcttga tcttctcgat caggtacttg gcgttctctt tgccggtggt  4200
ccggatgatt tcctcgatcc gctcgttggt ctgccggttc cgcttctgca tctcgttgat  4260
cattttctgg gcgtccttgg agttcttctc gcgggccagc tcgataatga tgtcgttggg  4320
caggccgtac ttcttgatga tggcgttgat cactttgatg ctctggatga agcttctctt  4380
cacgacgggg ctcaggatga agtcgtccac caggtggtg gggatctctt tctgctggga  4440
caggtccacc ttcttgggca ccagcttcag ccggttgaag atagcgatct ggttgtcgtt  4500
ggtgtgccac agctcgtcca ggatcaggtt gatggcttc aggctcaggt tgtgggtgcc  4560
ggtatagccc ttcagattag agatctgctc gatctcttcc tgggtcagct cggagttcag  4620
attggtcagt tcttcctgga tgtcctcgct gctctggtag atggtcagga tcttggcaat  4680
ctgatccagc agctcggcgt tctcaataat ctctttccgg gcggtaatgt ccttgatgtc  4740
gtggtacacc ttcaggttgg tgaactcggg cttgccggtg ctggtcactc tgtagcccct  4800
aatatcctct tcgttcacga ggatttcttt ggcgatctgc ttcagggtgg gcttcttctt  4860
ctgcttgaac acgttctcga tgatctggaa cttctcgtaa tattccagct tctcgttctc  4920
gtccctggtg atcacgagat tgttcaggtc gttcagggcg ttgtacaggt cggcgttgta  4980
ggcgtacttc acgctccgca gttcctcggg gaagtaggtg cagtggccca tcagcatctc  5040
gtaccattct ttgatgtcct tccagccgaa ggggctgccc tcgccaggtc cctcatagta  5100
ggtccgccgg gtttccagca ggtcgatgta ggtgtcgatg aagctctggt ccagctggtg  5160
gtaggccttc tgcaccttca gcagctgttt ggcttctttc acgtagtcgc tggtcttgaa  5220
tctgttgatg ctgccccgca cttcgccgtc tttcttcagc cgttccagct gcagttcggc  5280
cacgtatttc tcttccaggg ccttgctgtt ccggctgatc tgctcttttgg tggacagctc  5340
gttgccggtg tcctcttcca cctcgttcac gttgtgcacg cctcttctct tggccaggtg  5400
cagcagggcg gcagagaact cttcctcgct cagcttctgg ctcaggccct tcactctggc  5460
ctcgtagggg ttgatgccgc tcagctcgct gtggtcggtc agcaggttgt agtcgaacag  5520
cagcttcttc actctctgga ttctatgccg cctccgccgc ttcagccttc tggcgcctct  5580
cttgctccgc ctgccctcgt tgttttccac gttggcctct ttgaacagcc gcacgccggc  5640
atcgatcacg tcccgtgtct cgtagtcgat gatgccgtag cccacgctgg tgatgccgat  5700
gtccaggccc aggatgtagt tccgcttggc tgctgggact ccgtggatac cgaccttccg  5760
cttcttcttt ggggccatgt ggcggctctt gaaggacgac gtcatcatcc cttgcccgga  5820
tgcgcgggct tcttgtctag cacaggagcc tggggtagag cgcatgcaaa ttacgcgctg  5880
tgctttgtgg gaaatcaccc taaacgaaaa atttattcct ctttcgagcc ttatagtggc  5940
ggccggtcta catcctaggt tttagtactc tggaaacaga atctactaaa acaaggcaaa  6000
atgccgtgtt tatctcgtca acttgttggc gagatttttt gttaacgcgg ccgcctagag  6060
```

-continued tcgacctgca ggcatgcaa                                                6079

<210> SEQ ID NO 68
<211> LENGTH: 23
<212> TYPE: DNA
<213> ORGANISM: Homo sapiens

<400> SEQUENCE: 68
agtactgtgg gtactcgaag ggg                                           23

<210> SEQ ID NO 69
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (24)..(26)
<223> OTHER INFORMATION: a, c, t, g, unknown or other

<400> SEQUENCE: 69
gagagtgcac catagcggcc gcgnnngtac ccacacaaaa aaccaacaca cag           53

<210> SEQ ID NO 70
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (26)..(31)
<223> OTHER INFORMATION: a, c, t, g, unknown or other

<400> SEQUENCE: 70
ggcaccgagt cggtgctttt ttgttnnnnn naacgcggcc gcctagagtc gac           53

<210> SEQ ID NO 71
<211> LENGTH: 230
<212> TYPE: DNA
<213> ORGANISM: Homo sapiens

<400> SEQUENCE: 71
ggaattcgaa cgctgacgtc atcaacccgc tccaaggaat cgcgggccca gtgtcactag   60
gcgggaacac ccagcgcgcg tgcgccctgg caggaagatg gctgtgaggg acaggggagt  120
ggcgccctgc aatatttgca tgtcgctatg tgttctggga aatcaccata aacgtgaaat  180
gtctttggat ttgggaatct tataagttct gtatgagacc acttttttccc            230

<210> SEQ ID NO 72
<211> LENGTH: 233
<212> TYPE: DNA
<213> ORGANISM: Homo sapiens

<400> SEQUENCE: 72
cttgctctca gcagtgcaac gaggtaaaag gaagaagctg gcccacgcat gcgctcttca   60 aattttgag acagtttacc cagaatgcag tgctcaaagg aaacgcgtgc gcagtgtggt  120
caggttgttt cgctgggtga gtaaaatgaa atcttagagg cgttgtgggc tggcccagtt  180
gatgacgtca ccataccaca gcttctagtg ctattctgcg ccggtatccg acc         233

<210> SEQ ID NO 73
<211> LENGTH: 239
<212> TYPE: DNA
<213> ORGANISM: Homo sapiens

<400> SEQUENCE: 73

```
agtatttagc atgccccacc catctgcaag gcattctgga tagtgtcaaa acagccggaa      60
atcaagtccg tttatctcaa actttagcat tttgggaata aatgatattt gctatgctgg     120
ttaaattaga ttttagttaa atttcctgct gaagctctag tacgataagc aacttgacct     180
aagtgtaaag ttgagacttc cttcaggttt atatagcttg tgcgccgctt gggtacctc      239
```

<210> SEQ ID NO 74
<211> LENGTH: 308
<212> TYPE: DNA
<213> ORGANISM: Homo sapiens

<400> SEQUENCE: 74

```
gtctctctct tagcgggata tcttccgcaa gcactgggaa tgtggacatg gaaagtaaat      60
tgagtctccg tgggggagtg agacagggag tgagggtgt tggacgcggc acgggaacct     120
ggccagagtc agcggaccca attggctgct ctctctcaga tgcagttccc cttcctccct     180
ccagggggcg ccacggaacg cagggccctc actggccctg ggactgggt gacgtcaggg     240
atgagcctct tgtgattggc tccatcaccc tgcgtaagat caaagggaag aaaggatggg     300
cccgacaa                                                              308
```

<210> SEQ ID NO 75
<211> LENGTH: 308
<212> TYPE: DNA
<213> ORGANISM: Homo sapiens

<400> SEQUENCE: 75

```
gtctctctct tagcgggata tcttccgcaa gcactgggga tgtggacatg gaaagtaaat      60
tgagtctccg tgggggagtg agacagggag tgagggtgt tggacgcggc acgggaaccc     120
ggccggagtc agcggaccca attggctgct ctctctcaga tacagttccc cttcctccct     180
ccagggggcg ccacggaacg cagggccctc actggccctg ggactgggt gacgtcaggg     240
gtgagcctct cctgattggc tccatcaccc tgcgtaaggt caaaaggaag aaaggagatc     300
cccgacac                                                              308
```

<210> SEQ ID NO 76
<211> LENGTH: 361
<212> TYPE: DNA
<213> ORGANISM: Homo sapiens

<400> SEQUENCE: 76

```
tgccggccca cgggtggagg gatcgggcgg gcggtgccga agcggtccgg cattggccgg      60
ccgcccaac gcgcacgcgc acgcgagcag gccggccggc tccggggagg ccacgccac      120
tccccgtagg gcggggccag accatatttg cataagatag tgtcattcta gctttcctgt     180
atttgttcat ttcgtgtcta ttagctattc tgctagccac aatgcctctg aaagcctata     240
gtcttagaaa gttatgcccg aaaacggttt ttttaatctc acgccaccaa ctttctcacc     300
ctaatcataa aacacaattt ctttagggct ataaaatact actctgtgaa gctgaggacg     360
t                                                                     361
```

<210> SEQ ID NO 77

```
<211> LENGTH: 376
<212> TYPE: DNA
<213> ORGANISM: Homo sapiens

<400> SEQUENCE: 77
tctttccgct ccaggaccgc cctgggcctg caggatcctg ggcgggagcc caggtgtccg       60
ggatctgggc cactagggac tggggaggaa cctctcagag aagcccatag cccgcagcgg      120
ccccgcgcgg ccggttccgg cgccgcactg ttccagcctc tactatggta cagtccctgc      180
gtcgcagcct cggcggggc tctaagaacg ggaggcagaa aaagctcaat cagcagcagg       240
cgagcttcac ccgctgcttc caaatctgtg ccaaaatatt ctatgctgca cagataaaat      300
cctctgtcgg ttctacaagc ctggcttttc ctatagagaa ccctcttata agcaaaaagt      360
aaagctctcg tgaaga                                                     376

<210> SEQ ID NO 78
<211> LENGTH: 412
<212> TYPE: DNA
<213> ORGANISM: Homo sapiens

<400> SEQUENCE: 78
gagggcagtc accagctcct ggcccgtgcg ccaagctcag cgggcgtccg cggtgcgatc       60
ttccctagcg cctcgggtct ggcgccgcca tcttcctcgg taacaaccag tcgcctgagg      120 cgtgggccg cctcccaaag acttctggga gggcggtgcg gctcaggctc tgccccgcct       180
ccggggctat ttgcatacga ccatttccag taattcccag cagccaccgt agctatattt      240
ggtagaacaa cgagcacttt ctcaactcca gtcaataact acgttagttg cattacacat      300
tgggctaata taaatagagg ttaaatctct aggtcattta agagaagtcg gcctatgtgt      360
acagacattt gttccagggg ctttaaatag ctggtggtgg aactcaatat tc             412

<210> SEQ ID NO 79
<211> LENGTH: 484
<212> TYPE: DNA
<213> ORGANISM: Homo sapiens

<400> SEQUENCE: 79
taaccgctca gctgacctca ggagggcagg ggtgccttct aaagggtcca gagagcctcc       60
attccagctg caggcgtggg acacagaccg ggacgtgggg cggcggccgg actgggcagg      120
tcgtcccggg tccagcggcg cctcacggtc gcggctccat gcccgggact gcgaccccgg      180
aagtggcggg agcgggggac gacagccgcg cggacacag gggacccgcc ggctcaggca       240
cctttgaccc ggaagttgag cgacccaggc ggcggcctgg gattggacac caccaggcac      300
gtaccaaggc gtccgcggcg cttgggggg agcccgcggc gcggcggcct aaggtgcgta      360
acgccccatg aacgacatct tccggtgggt tagggagaga ccccccctg tgacttggta       420 tcactcagtc aaacccatga tccccccacta ttaaggatat ccggagagga tgctacctat      480
cagg                                                                  484

<210> SEQ ID NO 80
<211> LENGTH: 861
<212> TYPE: DNA
<213> ORGANISM: Homo sapiens

<400> SEQUENCE: 80
tcctgactgc agcaccagaa ggctggtctc tcccacagaa cgaggatgga ggcggggagg       60
gatccgttga agagggaagg agcgatcacc caaagagaac taaaatcaaa taaaataaaa      120
```

```
cagagagatg tcttggagga gggggcgagt ctgaccggga taagaataaa gagaaagggt    180
gaacccggga ggcggagttt gcagtgagcc gagatcgcgc cactgcactc cagcctgggc    240
gacagagtga gactccgtct cagtaaaaaa aaaaaaaaaa aaaagaataa agaggaaagg    300
acgcaagaaa gggaagggg actctcaggg agtaaaagag tcttacactt ttaacagtga    360
cgttaaaaga ctactgttgc ctttctgaag actaaaaaga aaaaaactt aaaaatttaa    420 agaaataaac ttctgagcca tgtcaccaac ttaaccaccc ccaggtacct gcaacggctc    480
gcgcccgccg tgtctaaca ggatccggac ctagctcata ttgctgccgc aaaacgcaag    540
gctagcttcc gccagtactg ccgcaacacc ttcttatttc acgacgtatg gtcgtaaagc    600
aataaagatc caggctcggg aaaatgacgg agaggtggaa ctatagagaa taaatttgca    660
tatataataa tccgctcgct aattgtgttt ctgttttcct ttgctaaggt agaaacaaaa    720
gaataatcac agaatctcag tgggactttg aaaatatcca ggattttata cgtgaagaat    780
ggatgtatcg cattacggta gtcaccctat gtgtaaatta gtggcacata cttggcactc    840
cttaatgtca actataagat g                                              861

<210> SEQ ID NO 81
<211> LENGTH: 172
<212> TYPE: DNA
<213> ORGANISM: Mus musculus

<400> SEQUENCE: 81
cgctcttgaa ggacgacgtc atcatcctt gcccggatgc gcgggcttct tgtctagcac    60
aggagcctgg ggtagagcgc atgcaaatta cgcgctgtgc tttgtgggaa atcaccctaa   120
acgaaaaatt tattcctctt tcgagcctta tagtggcggc cggtctacat cc            172

<210> SEQ ID NO 82
<211> LENGTH: 201
<212> TYPE: DNA
<213> ORGANISM: Rattus norvegicus

<400> SEQUENCE: 82
ggctgatgag cttccccgc ccactaggag tgtgaagacc tgccgccata ataagactcc     60
aaaagacagt gaatttaaca cttacggtga cttcccacaa agcacagcgt gtaatttgca   120
tgcgctctag cccaggctcc agctccggac cagaagcccg cgcatcccgg caaagggtga   180
tgacgtcgtc cttcaagcgc t                                              201

<210> SEQ ID NO 83
<211> LENGTH: 525
<212> TYPE: DNA
<213> ORGANISM: Homo sapiens

<400> SEQUENCE: 83
gcctcccagc gtcgcgccct aacgacccgc aagtgtccga gggcgcctcc cggccgccat    60
cggccgccct cgcagccgcc gctctcctca cggcctcccg gccgccgccg ccatcttccg   120
ctttctcgtc cggctgcggc gctgctgacg ctagcgagtc gccacgccgg gcaagagcgg   180 ccccctgcg cccgcagaga acgctgggat gccagcggcg cccgcggagg cctcacccc    240 tacctcggcc gctccagggg gcgggcctgc atctgggcca cctcttttgc atattggcac   300
ccacaatcca ccgcggctat gaggccagta taaggcggta aaattacgat aagatatggg   360
attttacgtg atcgaagaca tcaaagtaag cgtaagcacg aaagttgttc tgcaacatac   420
```

```
cactgtagga aattatgcta aatatgaaac cgaccataag ttatcctaac caaaagatga    480
tttgattgaa gggcttaaaa taggtgtgac agtaaccctt gagtc                   525

<210> SEQ ID NO 84
<211> LENGTH: 176
<212> TYPE: DNA
<213> ORGANISM: Mus musculus

<400> SEQUENCE: 84
ttcaggatgt agaccggccg ccactataag gctcgaaaga ggaataaatt tttcgtttag    60
ggtgatttcc cacaaagcac agcgcgtaat ttgcatgcgc tctacccag gctcctgtgc    120 tagacaagaa gcccgcgcat ccgggcaagg gatgatgacg tcgtccttca agagcg       176

<210> SEQ ID NO 85
<211> LENGTH: 176
<212> TYPE: DNA
<213> ORGANISM: Rattus norvegicus

<400> SEQUENCE: 85
aggagtgtga agacctgccg ccataataag actccaaaag acagtgaatt taacacttac    60
ggtgacttcc cacaaagcac agcgtgtaat ttgcatgcgc tctagcccag gctccagctc    120
cggaccagaa gcccgcgcat cccggcaaag ggtgatgacg tcgtccttca agcgct        176

<210> SEQ ID NO 86
<211> LENGTH: 225
<212> TYPE: DNA
<213> ORGANISM: Dipodomys ordii

<400> SEQUENCE: 86
aggaaagact tcgctgaggc agactttata aggctcccgc gcagaaagaa actttatagt    60
tatggtgatt tcccacaagc cactgcgtca tgcaaataaa gcagggtacg gcttccatgt    120
accttaaggt tttttctag gccgcgtacg ctctgcgtat tcagccacgt gaccctgagc    180
cagtggttgt tgggagcacg ttgtggacct ctgcgtttgg attcc                   225

<210> SEQ ID NO 87
<211> LENGTH: 222
<212> TYPE: DNA
<213> ORGANISM: Ictidomys tridecemlineatus

<400> SEQUENCE: 87
gaaagggact ccgcacaagc agagtttata aggctcccat ctgtacagcc atttctcggt    60
catggtaact acccacaaca cacagcgata tgcaaatata gcagagcgtg tcttcccgcg    120
cgcgcctggt cgtctcggcg ccggcgcgct gcgtggggcg gaactgtgac agagaccctg    180
cgattcctgg gagctggctg atgacatcag tgtctaacct cc                      222

<210> SEQ ID NO 88
<211> LENGTH: 225
<212> TYPE: DNA
<213> ORGANISM: Cavia porcellus

<400> SEQUENCE: 88
gagaaagaaa ggctcaaacc tagccttata aggctcccaa atgtcggtat attttttggt    60
tatggtgact tcccacaatg catagcgata tgtagatatt gccaggagta cctcccactt    120
ctggtcctgt cagctctttt ctaggacgcg cgcgctgcag gttccagcc tgtgattggg    180 ccagcaattc cgggaatgaa ttgatgacgt cagcgtttga attcc                   225
```

```
<210> SEQ ID NO 89
<211> LENGTH: 211
<212> TYPE: DNA
<213> ORGANISM: Ochotona princeps

<400> SEQUENCE: 89
gggggaagct gggctcgatc agcctttata aagctccaaa aactcaagac attttctgt      60 tacggtggct ccccacagta cacagcgaca tgcaaatagc ttgccaatga attcgcggac    120
cgcttcccgc cccggcgcag gcgcgcggac gctgtctccc ctggacgcgc gctcgcggtt    180
cccgggagct ggctgatgac gttcggtctc c                                   211

<210> SEQ ID NO 90
<211> LENGTH: 211
<212> TYPE: DNA
<213> ORGANISM: Oryctolagus cuniculus

<400> SEQUENCE: 90
ggggagaggt ggatccgaac agactttata aagctccgaa agcccaaggc atctttccct     60
tacggtagct cccacaaga catagcgaca tgcaaatttc ttgaagtatg cttcagacgc    120
gcttctcgcc acagcgcaag cgcgctgtgt gctgacgcgg gaacgggcca gggcgcggtt    180
cccgggagcg ggttgatgac gttagatctc c                                   211

<210> SEQ ID NO 91
<211> LENGTH: 229
<212> TYPE: DNA
<213> ORGANISM: Callithrix jacchus

<400> SEQUENCE: 91
gaggaaaagt agtcccacag acaacttata agattcccat accctaagac atttcacgat     60
tatggtgact cccagaaga cacagcgaca tgcaaatatt gcaggtcgtg tttcgcctgt    120
ccctcacagt cgtcttcctg ccagggcgca cgcgcgctgg gtttcccgcc aactgacgct    180
gggctcgcga ttccttggag cggggttgatg acgtcagcgt ttgaattcc                229

<210> SEQ ID NO 92
<211> LENGTH: 230
<212> TYPE: DNA
<213> ORGANISM: Chlorocebus sabaeus

<400> SEQUENCE: 92
ggggaagggt ggtcccttac agaacttata agattcccaa actcaaagac atttcacgtt     60
tatggtgact cccagaaga catagcgaca tgcaaatatt gcagggcgtc acacccctct    120
ccctcacagt catcttcctg ccagggcgca cgcgcgctgg gtgttctcgc gtagtgacac    180
tgggcccgcg attccttgga gcgggttgat gacgtcagcg ttcgaattcc                230

<210> SEQ ID NO 93
<211> LENGTH: 230
<212> TYPE: DNA
<213> ORGANISM: Macaca mulatta

<400> SEQUENCE: 93
ggggaagggt ggtcccacac agaacttata agattcccat actcaaagac atttctcgtt     60
tatggtgact cccagaaga cacagcgaca tgcaaatatt gtagggcgtc acacccctgt    120
ccctcacagt catcttcctg ccagggcgca cgcgcgctgg gtgttcccgc gtagtgacac    180
tgggcccgcg attccttgga gcgggttgat gacgtcagcg ttcgaattcc                230
```

<210> SEQ ID NO 94
<211> LENGTH: 231
<212> TYPE: DNA
<213> ORGANISM: Papio anubis

<400> SEQUENCE: 94

| | | |
|---|---|---|
| ggggaaaggt ggtaccatac agaacttata agattcccat actcaaagac atttcacgat | 60 |
| tatggtgact tcccagaaga cacagcgaca tgcaaatatt gtagggcgtc acacccctg | 120 |
| tccctcacag tcatcttcct gccagggcgc acgcgcgctg ggtgttcccg cgtagtgaca | 180 |
| ctgggcccgc gattccttgg agcgggttga tgacgtcagc gttcgaattc c | 231 |

<210> SEQ ID NO 95
<211> LENGTH: 230
<212> TYPE: DNA
<213> ORGANISM: Gorilla gorilla

<400> SEQUENCE: 95

| | | |
|---|---|---|
| gggaaagggt ggtcccacac agaacttata agactcccat atccaaagac atttcacggt | 60 |
| tatggtgatt tcccagaaca catagcgaca tgtaaatatt gcagggcgcc actccccagt | 120 |
| ccctcacagc catcttcctg ccagggcgca cgcgcgctgg gtgttcccgc ctagtgacac | 180 |
| tgggcccgcg attccttgga gcgggttgat gacgtcagcg ttcgaattcc | 230 |

<210> SEQ ID NO 96
<211> LENGTH: 230
<212> TYPE: DNA
<213> ORGANISM: Homo sapiens

<400> SEQUENCE: 96

| | | |
|---|---|---|
| gggaaaaagt ggtctcatac agaacttata agattcccaa atccaaagac atttcacgtt | 60 |
| tatggtgatt tcccagaaca catagcgaca tgcaaatatt gcagggcgcc actcccctgt | 120 |
| ccctcacagc catcttcctg ccagggcgca cgcgcgctgg gtgttcccgc ctagtgacac | 180 |
| tgggcccgcg attccttgga gcgggttgat gacgtcagcg ttcgaattcc | 230 |

<210> SEQ ID NO 97
<211> LENGTH: 230
<212> TYPE: DNA
<213> ORGANISM: Pan troglodytes

<400> SEQUENCE: 97

| | | |
|---|---|---|
| gggaaagggt ggtgccacac agaacttata agattcccat atgcaaagac atttcacgtt | 60 |
| tatggtgatt tcccagaaca catagcgaca tgcaaatatt gcagggcgcc actcccctgt | 120 |
| ccctcactgc catcttcctg ccagggcgca cgcgcgctgg gtgttcccgc ctagtgacac | 180 |
| tgggcccgcg attccttgga gcgggttgat gacgtcagcg ttcgaattcc | 230 |

<210> SEQ ID NO 98
<211> LENGTH: 229
<212> TYPE: DNA
<213> ORGANISM: Pongo abelii

<400> SEQUENCE: 98

| | | |
|---|---|---|
| gagaaagggt ggtcccgtcc agaacttata agattcccat acccaaagac atttcacgtt | 60 |
| tatggtgact tcccagaatg catagcgaca tgcaaatatt gcaggggcgtc actcccctgt | 120 |
| ccctcacagc catcttcctg ccagggcgcc cgcgcgctgg tgttcccgcc tagtgacact | 180 |
| gggcccacga ttccttggag cgggttgatg acgtcagcgc tcgtattcc | 229 |

```
<210> SEQ ID NO 99
<211> LENGTH: 223
<212> TYPE: DNA
<213> ORGANISM: Nomascus leucogenys

<400> SEQUENCE: 99
ggggaaaagt agtagacctt ataagattcc caaacccaaa gacatttctc gtttatggtg      60
acttcccaga agacatagcg acatgcaaat attgcagggc gccactcccc tgtccctcac     120
agccatcttc ctgccagggc gcacgcgcgc tgggtgttcc cgcctagtga cactcggccc     180
gcgattcctt ggagcgggtt gatgacgtca gcgttcgaat tcc                       223

<210> SEQ ID NO 100
<211> LENGTH: 227
<212> TYPE: DNA
<213> ORGANISM: Tarsius syrichta

<400> SEQUENCE: 100
gcgagagggt gggtccacac agagcttata aggttcacaa gtaaagatat ttcacggtga      60
cggtgacttc ccacaataca ctgcgacatg caaatatagc cgggcgtgcc tccccgatcc     120
cggaagagcg actcctagcc agtgcgcacg cgcgctgcgt gttcgcgtcc taggtcgctg     180
ggcccgcggt tcctgggagc gggtggtgac gtcagcggcc cagcttc                   227

<210> SEQ ID NO 101
<211> LENGTH: 230
<212> TYPE: DNA
<213> ORGANISM: Otolemur garnettii

<400> SEQUENCE: 101
gcctaaaagg gcgcttgcac agaatttata aggttcccaa acagagacac atttcattat      60
tatggtgact tcccacaatg cacagcgcca tgcaaatatg ctaggacgcc tccccccgct     120
accttaaggt cgtcaactaa ccagtgcgcg cgcgcactgc gcgtttcccg ccggtgactc     180
aatgcccgcg tttggtggga gctagttggt gacctcagtt ctggaggctc                230

<210> SEQ ID NO 102
<211> LENGTH: 201
<212> TYPE: DNA
<213> ORGANISM: Tupaia belangeri

<400> SEQUENCE: 102
gggggaagct gggtccactg agttcttata aggtttccag tcctagagcg atttaccat       60 tgcggtgatt tccagcatcc cgtagctaca tgcaaatagc gcggggcgcg tctctcaggt     120
ccctccccgc cctctcactg tacgtacccg cgtcctaggg acgccgcgcc cggggttccc     180
ggacgtcagc gttccgacgc a                                               201

<210> SEQ ID NO 103
<211> LENGTH: 226
<212> TYPE: DNA
<213> ORGANISM: Ailuropoda melanoleuca

<400> SEQUENCE: 103
agggaaagcc gcgcctgggg cggatttata aggcttccat atctaaaggc atttcacagt      60
catggtgact tcccacaata catagcaaca tgcaaatatc gcgggagaa cctcccctgt      120 cccttgtacg cggcttctaa agacgcacg gcgctctgtg ttcccgccct gtgactctag      180
gcgggcaatt cctgggacag tgttctgacg ggaacgttca ggctcc                    226
```

<210> SEQ ID NO 104
<211> LENGTH: 227
<212> TYPE: DNA
<213> ORGANISM: Mustela putorius

<400> SEQUENCE: 104
gggaaagggt ggacccaccg agcatttata aggctcccgc atctaaagac attttacagt    60
tatggtgact tcccacaacg cgtagcaaca tgcaaatatc gtggagagta ccgcccctgt   120
cccatgcacg cgtcttctca gcagcacgca cgcgcgctgt gttcccgccc tgtgactcca   180
ggcgggtatt tccaggggcg ggttgctgac aggaacgttc aggcttc                 227

<210> SEQ ID NO 105
<211> LENGTH: 229
<212> TYPE: DNA
<213> ORGANISM: Canis familiaris

<400> SEQUENCE: 105
gcagcgcagc cctctcgccg cttataaagt gccgcccgca cggcccttct cgctcacggc    60
gacttcccat aacacacagc agcatgcaaa taccgcgggg agccccgccc cgccccggcc   120
cccgcaccgc ctcgggacgc atgcgccggc tctccgttcc cgccttgggc cggcggcggg   180
cgggcgggcg agcgggcggg agcggctccg gcggggacga gcgggcgcc               229

<210> SEQ ID NO 106
<211> LENGTH: 228
<212> TYPE: DNA
<213> ORGANISM: Felis catus

<400> SEQUENCE: 106
gggaaagggt ggccccgccg agcatttata agactcccat acctaaagac atttctcagt    60
tatggtgatt tcccacaaca cacagcaaca tgcaaatatc gagggtgta ccgcccctgt    120 cctttgtaga cgtcttctct ccaggacgca cgcgcgctgt attcccgcct tgtgactcta   180
ggcgggcgat tcctgggaga gggttgatga cgtccaagtt ctggcttc                228

<210> SEQ ID NO 107
<211> LENGTH: 227
<212> TYPE: DNA
<213> ORGANISM: Equus caballus

<400> SEQUENCE: 107
gggggaaaac agcccatggc tgcatttata agactcacag atctaaagcc atttcacgaa    60
tagggtgact tcccacaata cacagcgaca tgcaaacata gcggggcgtg cctttcctgt   120
accctgtggg catctctcct ggacgcacgc gcgccgggtg ttcccgcgct gtgactctag   180
gcaagcgctt cctgggagag agttgatgac ggcagcattc gggctcc                 227

<210> SEQ ID NO 108
<211> LENGTH: 225
<212> TYPE: DNA
<213> ORGANISM: Myotis lucifugus

<400> SEQUENCE: 108
gggagaagga ggcgtagagg atatataagg cccccttatg tgtagtcctt ttacggttag    60
ggtgacttcc cacaacgcat agcgacatgc aaatttgacg ggcgtgcctc ctctgtcct   120 gcgggcaact tctctcctgg acgcgcgcgc gctgcgtgtt cccgccttt gactccagcc    180 gagcgaatcc tgggagaggg caggtgacgt caacagtcag gctcg                   225

```
<210> SEQ ID NO 109
<211> LENGTH: 227
<212> TYPE: DNA
<213> ORGANISM: Pteropus vampyrus

<400> SEQUENCE: 109
gcgagaaaaa ttcttcacgc agaatatata aggatcccat atctgaagac attttacgat      60
tacggcgatt cccacaaca catagcgaca tgtaaatgta gtggggcatg cctcccctgt      120
cccttgtggg cagcttctcg ccagaacgca cgcgcggtgc gtgttcccgc cttgtgacta    180
agttggcgag tcagggagga gattgatgac gtcagctcac ccgctcc                  227

<210> SEQ ID NO 110
<211> LENGTH: 218
<212> TYPE: DNA
<213> ORGANISM: Bos taurus

<400> SEQUENCE: 110
ggcaaacacc gcacgcaaat agcacttata atgtgctcat acctagagcc acttttcggt     60
tacggtgact tctcaaaaag acagtggaac atgcaaatat tacagtgcgt cccgcccctg    120
gtaggtctac gctaggacgc acgcgcacta cggttcccgc ctatagactg cgctggcgat    180
tcctgggagc ggactgatga cgtcagcgtt cgggatcc                           218

<210> SEQ ID NO 111
<211> LENGTH: 216
<212> TYPE: DNA
<213> ORGANISM: Ovis aries

<400> SEQUENCE: 111
ggcgaacaat gcgcgcaaac agcatttata atgagctcat acctaaagcc actttacggt     60
tacggtgact tcccacaaga cattgcggca tgcaaatatt ttagtgcgtc ccgcccctgg    120
tagttccacg ctaggacgca cacgcactac ggttcccgcc tttagactgc gctggcgatt   180
ccaggagcgg actgatgacg tcagcgttgg ggctcc                              216

<210> SEQ ID NO 112
<211> LENGTH: 218
<212> TYPE: DNA
<213> ORGANISM: Tursiops truncatus

<400> SEQUENCE: 112
gccgaaaacc aggctcaagc cacatttata aggctcccaa atctaagtac atttgtcggt     60
tatggtgact tcccgcacca cattgcgaca tgcaaatact gcggagcgtc cctcccctgg   120
caactcctcg ctgggacgca cgcgcgctac gtgctcccgc cttttgactg cgccggcgat   180
acttgggaga gggttgatga cgtcagcgtt ctggctcc                            218

<210> SEQ ID NO 113
<211> LENGTH: 226
<212> TYPE: DNA
<213> ORGANISM: Vicugna pacos

<400> SEQUENCE: 113
gggaaagggt gggctcacgc agcctttata agactcccaa acttaaagac atttctcggt     60
tatggcgact tcccacaaga catagcgaca tgcaaatact gcagggcgcc gacccggtcc   120
tgtgcagcca tctttcggct gggacgcacg cgcgctgcgt gttcccgccc tgtgactgcg    180
ccggcgatta ctgggagagg attgatgacg tcaacgttcg ggttcc                   226
```

<210> SEQ ID NO 114
<211> LENGTH: 228
<212> TYPE: DNA
<213> ORGANISM: Sus scrofa

<400> SEQUENCE: 114

| | | |
|---|---|---|
| gtaggaaaac tgcttctgtg agcacttata aaactcccat aagtagagag atttcatagt | 60 |
| tatggtgatt tcccataaga cattgcgaca tgcaaatatt gtggcgcgtt cgtccccgtc | 120 |
| cggtgcaggc agcttcgctc caggacgcac gcgcaataca tgttcccgcc ttgagactgc | 180 |
| gccggcagat tcctaggaag tggttgatga cgtcgatgtt agggatcc | 228 |

<210> SEQ ID NO 115
<211> LENGTH: 210
<212> TYPE: DNA
<213> ORGANISM: Erinaceus europaeus

<400> SEQUENCE: 115

| | | |
|---|---|---|
| gcctaaaccg gctctttcga cagacttata aggacctctt atcttaggac attttttttgt | 60 |
| tagggtaact tcccacgatg catagcgata tgtaaatatg gcgccgcgag tctctcctag | 120 |
| gcgtctcccc aggacgcagg cgcactgctt gttcccgcgt taacattgct gattctggga | 180 |
| gactgctgat gacgtcagcg tccagtctac | 210 |

<210> SEQ ID NO 116
<211> LENGTH: 211
<212> TYPE: DNA
<213> ORGANISM: Choloepus hoffmanni

<400> SEQUENCE: 116

| | | |
|---|---|---|
| agaaaaaaat agtttatgct ggatttataa gattcccaaa tctaaagcca tttcacagtt | 60 |
| acggtgattc cccactacac acggcgatat gcaaatatag cggaagtgtt cctgaggcgt | 120 |
| ggtaaagcgc gcgcgcgctg agagttcccg ccctgtggtg ctgggctgga gatgcctgag | 180 |
| aactggctga tgacggcaac gttcgggctc c | 211 |

<210> SEQ ID NO 117
<211> LENGTH: 208
<212> TYPE: DNA
<213> ORGANISM: Dasypus novemcinctus

<400> SEQUENCE: 117

| | | |
|---|---|---|
| aaagcgatag ttttttaaac tggacttata aggcacccat atctacgtat atttcatggt | 60 |
| tagggtgatt tcccacaaca catagcgaaa tgcaaatatt ggagggcgct gaggcgtggt | 120 |
| cgggcgcaag cgcgctgcga cttcccgcct ttcggcccta ggcccagat tcctgggagc | 180 |
| tggatgatga cgttgacgtt cggatacc | 208 |

<210> SEQ ID NO 118
<211> LENGTH: 227
<212> TYPE: DNA
<213> ORGANISM: Loxodonta africana

<400> SEQUENCE: 118

| | | |
|---|---|---|
| gggaaggaac aaattcgtca ggatttataa gactctcaga gctgtagaca tttcacagtt | 60 |
| agggcgatgt cccacaatac atagcaacat gcaaatattc taggaggcca gcctccccgt | 120 |
| ccgcgtggtc atcttctcgc tagggcgcac gcccgctgcg tgttcccgct ctgtgaccag | 180 |
| gcaggcgatt cctgagaacc gcttggtgac gtcagtgttc tggctcc | 227 |

-continued

```
<210> SEQ ID NO 119
<211> LENGTH: 225
<212> TYPE: DNA
<213> ORGANISM: Procavia capensis

<400> SEQUENCE: 119
agggtaaatc ggcgctgctc agcatttaaa agaatcccaa atgtgtcgcc attttacgct      60
tagggtgata tcccacaaga cacagcgaca tgcaaatatc gtgagtctct gtttccctgt     120
ccacgagggc gtcctctcgc tggggcgcac gcgcggtgtg tgtgccccg ttgtgtgttc     180 ccgcgattcc aaagaactgg ttgataacgt tagacttccg gctgc                    225

<210> SEQ ID NO 120
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
aataaaatat ctttattttc attacatctg tgtgttggtt ttttgtgtg                  49

<210> SEQ ID NO 121
<211> LENGTH: 154
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 121
aataaaatat ctttattttc attacatctg tgtgttggtt ttttgtgtga atcgatagta      60
ctaacatacg ctctccatca aaacaaaacg aaacaaaaca aactagcaaa ataggctgtc    120
cccagtgcaa gtgcaggtgc cagaacattt ctct                                154

<210> SEQ ID NO 122
<211> LENGTH: 240
<212> TYPE: DNA
<213> ORGANISM: Simian virus 40

<400> SEQUENCE: 122
atctagataa ctgatcataa tcagccatac cacatttgta gaggttttac ttgctttaaa     60
aaacctccca cacctccccc tgaacctgaa acataaaatg aatgcaattg ttgttgttaa    120
cttgtttatt gcagcttata atggttacaa ataaagcaat agcatcacaa atttcacaaa    180
taaagcattt ttttcactgc attctagttg tggtttgtcc aaactcatca atgtatctta    240

<210> SEQ ID NO 123
<211> LENGTH: 120
<212> TYPE: DNA
<213> ORGANISM: Simian virus 40

<400> SEQUENCE: 123
ttgtttattg cagcttataa tggttacaaa taaagcaata gcatcacaaa tttcacaaat     60
aaagcatttt tttcactgca ttctagttgt ggtttgtcca aactcatcaa tgtatcttat    120

<210> SEQ ID NO 124
<211> LENGTH: 228
<212> TYPE: DNA
<213> ORGANISM: Unknown
```

```
<220> FEATURE:
<223> OTHER INFORMATION: Description of Unknown:
      terminator sequence

<400> SEQUENCE: 124
cgactgtgcc ttctagttgc cagccatctg ttgtttgccc ctcccccgtg ccttccttga      60
ccctggaagg tgccactccc actgtccttt cctaataaaa tgaggaaatt gcatcgcatt    120
gtctgagtag gtgtcattct attctggggg gtggggtggg gcaggacagc aaggggagg     180 attgggaaga caatagcagg catgctgggg atgcggtggg ctctatgg                 228

<210> SEQ ID NO 125
<211> LENGTH: 271
<212> TYPE: DNA
<213> ORGANISM: Unknown
<220> FEATURE:
<223> OTHER INFORMATION: Description of Unknown:
      terminator sequence

<400> SEQUENCE: 125
gggggaggct aactgaaaca cggaaggaga caataccgga aggaacccgc gctatgacgg     60
caataaaaag acagaataaa acgcacgggt gttgggtcgt ttgttcataa acgcggggtt   120
cggtcccagg gctggcactc tgtcgatacc ccaccgagac cccattgggg ccaatacgcc   180
cgcgtttctt cctttccccc accccacccc ccaagttcgg gtgaaggccc agggctcgca   240
gccaacgtcg gggcggcagg ccctgccata g                                   271

<210> SEQ ID NO 126
<211> LENGTH: 32
<212> TYPE: DNA
<213> ORGANISM: Unknown
<220> FEATURE:
<223> OTHER INFORMATION: Description of Unknown:
      terminator sequence

<400> SEQUENCE: 126
ggtatcaaat aaaatacgaa atgtgacaga tt                                   32

<210> SEQ ID NO 127
<211> LENGTH: 26
<212> TYPE: DNA
<213> ORGANISM: Unknown
<220> FEATURE:
<223> OTHER INFORMATION: Description of Unknown:
      terminator sequence

<400> SEQUENCE: 127
aaataaaata cgaaatgtga cagatt                                          26

<210> SEQ ID NO 128
<211> LENGTH: 100
<212> TYPE: DNA
<213> ORGANISM: Unknown
<220> FEATURE:
<223> OTHER INFORMATION: Description of Unknown:
      terminator sequence

<400> SEQUENCE: 128
ggttgctgat ttctccacag cttgcatttc tgaaccaaag gccctttca gggccgccca     60 actaaacaaa agaagagctg tatccattaa gtcaagaagc                         100
```

```
<210> SEQ ID NO 129
<211> LENGTH: 174
<212> TYPE: DNA
<213> ORGANISM: Unknown
<220> FEATURE:
<223> OTHER INFORMATION: Description of Unknown:
      terminator sequence

<400> SEQUENCE: 129
gattcgtcag tagggttgta aaggttttc ttttcctgag aaacaacct tttgttttct      60 caggttttgc tttttggcct ttccctagct ttaaaaaaaa aaaagcaaaa gacgctggtg    120
gctggcactc ctggtttcca ggacggggtt caagtccctg cggtgtcttt gctt          174

<210> SEQ ID NO 130
<211> LENGTH: 123
<212> TYPE: DNA
<213> ORGANISM: Unknown
<220> FEATURE:
<223> OTHER INFORMATION: Description of Unknown:
      terminator sequence

<400> SEQUENCE: 130
aaaggttttt cttttcctga gaaatttctc aggttttgct tttaaaaaa aaagcaaaag      60 acgctggtgg ctggcactcc tggtttccag gacggggttc aagtccctgc ggtgtctttg    120
ctt                                                                  123

<210> SEQ ID NO 131
<211> LENGTH: 204
<212> TYPE: DNA
<213> ORGANISM: Homo sapiens

<400> SEQUENCE: 131
gagggcagtc accagctcct ggcccgtgcg ccaagctcag cgggcgtccg cggtgcgatc     60
ttccctagcg cctcgggtct ggcgccgcca tcttcctcgg taacaaccag tcgcctgagg    120
cgtggggccg cctcccaaag acttctggga gggcggtgcg gctcaggctc tgccccgcct    180
ccggggctat ttgcatacga ccat                                           204

<210> SEQ ID NO 132
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
acgggtgtgg tacgcagccc ctgaattcac ccacagtact acctggctga               50

<210> SEQ ID NO 133
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
acgggtgtgg tacgcagccc cttcgagtac ccacagtact acctggctga               50
```

-continued

```
<210> SEQ ID NO 134
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(102)
<220> FEATURE:
<221> NAME/KEY: CDS
<222> LOCATION: (106)..(177)
<220> FEATURE:
<221> NAME/KEY: CDS
<222> LOCATION: (181)..(327)
<220> FEATURE:
<221> NAME/KEY: CDS
<222> LOCATION: (331)..(351)

<400> SEQUENCE: 134 tgg agc cct gag tgg ctg agc tca ggc ctt cgc agc att ctt ggg tgg       48
Trp Ser Pro Glu Trp Leu Ser Ser Gly Leu Arg Ser Ile Leu Gly Trp
1               5                   10                  15 gag cag cca cgg gtc agc cac aag ggc cac agc cat gaa tgg cac aga       96
Glu Gln Pro Arg Val Ser His Lys Gly His Ser His Glu Trp His Arg
            20                  25                  30 agg ccc taa ctt cta cgt gcc ctt ctc caa tgc gac ggg tgt ggt acg      144
Arg Pro     Leu Leu Arg Ala Leu Leu Gln Cys Asp Gly Cys Gly Thr
        35                  40                  45 cag ccc ctg aat tca ccc aca gta cta cct ggc tga gcc atg gca gtt      192
Gln Pro Leu Asn Ser Pro Thr Val Leu Pro Gly     Ala Met Ala Val
            50                  55                      60 ctc cat gct ggc cgc cta cat gtt tct gct gat cgt gct ggg ctt ccc      240
Leu His Ala Gly Arg Leu His Val Ser Ala Asp Arg Ala Gly Leu Pro
65                  70                  75 cat caa ctt cct cac gct cta cgt cac cgt cca gca caa gaa gct gcg      288
His Gln Leu Pro His Ala Leu Arg His Arg Pro Ala Gln Glu Ala Ala
            80                  85                  90 cac gcc tct caa cta cat cct gct caa cct agc cgt ggc tga cct ctt      336
His Ala Ser Gln Leu His Pro Ala Gln Pro Ser Arg Gly     Pro Leu
        95                  100                 105 cat ggt cct agg tgg                                                   351
His Gly Pro Arg Trp
110

<210> SEQ ID NO 135
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

Trp Ser Pro Glu Trp Leu Ser Ser Gly Leu Arg Ser Ile Leu Gly Trp
1               5                   10                  15

Glu Gln Pro Arg Val Ser His Lys Gly His Ser His Glu Trp His Arg
            20                  25                  30

Arg Pro

<210> SEQ ID NO 136
<211> LENGTH: 24
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 136

Leu Leu Arg Ala Leu Leu Gln Cys Asp Gly Cys Gly Thr Gln Pro Leu
1               5                   10                  15

Asn Ser Pro Thr Val Leu Pro Gly
            20

<210> SEQ ID NO 137
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

Ala Met Ala Val Leu His Ala Gly Arg Leu His Val Ser Ala Asp Arg
1               5                   10                  15

Ala Gly Leu Pro His Gln Leu Pro His Ala Leu Arg His Arg Pro Ala
            20                  25                  30

Gln Glu Ala Ala His Ala Ser Gln Leu His Pro Ala Gln Pro Ser Arg
        35                  40                  45

Gly

<210> SEQ ID NO 138
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Pro Leu His Gly Pro Arg Trp
1               5

<210> SEQ ID NO 139
<211> LENGTH: 151
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (3)..(149)

<400> SEQUENCE: 139 gc agg att ccc ctc tgg ctc act ggc agt ctc ctc cga tgt ggg cca         47
   Arg Ile Pro Leu Trp Leu Thr Gly Ser Leu Leu Arg Cys Gly Pro
   1               5                   10                  15 ggg ctc ttt gaa gtt gga tct gag cct ttc tat cac ctg ttt gat gga        95
Gly Leu Phe Glu Val Gly Ser Glu Pro Phe Tyr His Leu Phe Asp Gly
                20                  25                  30 caa gcc ctt ttg cac aag ttt gac ttc aag gag ggc cat gtc aca tac       143
Gln Ala Leu Leu His Lys Phe Asp Phe Lys Glu Gly His Val Thr Tyr
            35                  40                  45 cac aga ag                                                            151
His Arg
```

```
<210> SEQ ID NO 140
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Arg Ile Pro Leu Trp Leu Thr Gly Ser Leu Leu Arg Cys Gly Pro Gly
1               5                   10                  15

Leu Phe Glu Val Gly Ser Glu Pro Phe Tyr His Leu Phe Asp Gly Gln
            20                  25                  30

Ala Leu Leu His Lys Phe Asp Phe Lys Glu Gly His Val Thr Tyr His
        35                  40                  45

Arg

<210> SEQ ID NO 141
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(12)
<220> FEATURE:
<221> NAME/KEY: CDS
<222> LOCATION: (16)..(39)
<220> FEATURE:
<221> NAME/KEY: CDS
<222> LOCATION: (43)..(225)
<220> FEATURE:
<221> NAME/KEY: CDS
<222> LOCATION: (229)..(243)
<220> FEATURE:
<221> NAME/KEY: CDS
<222> LOCATION: (247)..(324)

<400> SEQUENCE: 141 tat aac aga ctc taa tgc aag cag tat gag agg ctt gga tag gct ctg         48
Tyr Asn Arg Leu     Cys Lys Gln Tyr Glu Arg Leu Gly     Ala Leu
1               5                   10 ata tgg tgc tgt gta ggc tca tat gtg gat ctc aga acc cac atg tac         96
Ile Trp Cys Cys Val Gly Ser Tyr Val Asp Leu Arg Thr His Met Tyr
15                  20                  25                  30 tct gct ccc cag gtc ttg gtg cgc ttt cta ttc tct gtc agc aaa gcc        144
Ser Ala Pro Gln Val Leu Val Arg Phe Leu Phe Ser Val Ser Lys Ala
                35                  40                  45 tat cga aga atc acc tac cac aac tgg tgc cac ggc ttc aat gta gcc        192
Tyr Arg Arg Ile Thr Tyr His Asn Trp Cys His Gly Phe Asn Val Ala
            50                  55                  60 cag acc atg ttt acc cta ctc atg gta cgt atg taa att gga tgg gct        240
Gln Thr Met Phe Thr Leu Leu Met Val Arg Met     Ile Gly Trp Ala
65                  70                          75 aga tga atc aga ggg ctg ggg caa gga cca cag cta act atc ttc tgg        288
Arg     Ile Arg Gly Leu Gly Gln Gly Pro Gln Leu Thr Ile Phe Trp
            80                  85                  90 ccc aag gat gcc aat tgt gtg tat cca gtc cta gca                        324
Pro Lys Asp Ala Asn Cys Val Tyr Pro Val Leu Ala
        95                  100
```

```
<210> SEQ ID NO 142
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Tyr Asn Arg Leu
1

<210> SEQ ID NO 143
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Cys Lys Gln Tyr Glu Arg Leu Gly
1               5

<210> SEQ ID NO 144
<211> LENGTH: 61
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Ala Leu Ile Trp Cys Cys Val Gly Ser Tyr Val Asp Leu Arg Thr His
1               5                   10                  15

Met Tyr Ser Ala Pro Gln Val Leu Val Arg Phe Leu Phe Ser Val Ser
            20                  25                  30

Lys Ala Tyr Arg Arg Ile Thr Tyr His Asn Trp Cys His Gly Phe Asn
        35                  40                  45

Val Ala Gln Thr Met Phe Thr Leu Leu Met Val Arg Met
    50                  55                  60

<210> SEQ ID NO 145
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Ile Gly Trp Ala Arg
1               5

<210> SEQ ID NO 146
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 146

Ile Arg Gly Leu Gly Gln Gly Pro Gln Leu Thr Ile Phe Trp Pro Lys
1               5                   10                  15

Asp Ala Asn Cys Val Tyr Pro Val Leu Ala
            20                  25

<210> SEQ ID NO 147
<211> LENGTH: 85
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 147
ggacgcgacc gaaauggmga aggacggggu ccagugcgaa acacgcacug uugaguagag      60
ugugagcucc guaacugguc gcguc                                           85
```

COMPOSITIONS AND METHODS COMPRISING IMPROVEMENTS OF CRISPR GUIDE RNAS USING THE H1 PROMOTER

CROSS-REFERENCE

This application claims the benefit of U.S. Provisional Application No. 62/358,335, filed Jul. 5, 2016, the entirety of which is hereby incorporated by reference.

GOVERNMENT SUPPORT

This invention was made with government support under grants T32 EY007143, RO1 EY009769, and P30 EY001765 awarded by the National Institutes of Health. The government has certain rights in the invention.

SEQUENCE LISTING

The application contains a Sequence Listing which has been submitted electronically in ASCII format and is hereby incorporated by reference in its entirety. Said ASCII copy, created on Mar. 18, 2019, is named JHV-15525 SL.txt and is 454,327 bytes in size.

BACKGROUND

Clustered Regularly Interspaced Short Palindromic Repeats (CRISPR) together with cas (CRISPR-associated) genes comprise an adaptive immune system that provides acquired resistance against invading foreign nucleic acids in bacteria and archaea (Barrangou et al. (2007) *Science* 315: 1709-12). CRISPR consists of arrays of short conserved repeat sequences interspaced by unique variable DNA sequences of similar size called spacers, which often originate from phage or plasmid DNA (Barrangou et al. (2007) *Science* 315:1709-12; Bolotin et al. (2005) *Microbiology* 151:2551-61; Mojica et al. (2005) *J. Mol. Evol.* 60:174-82). The CRISPR-Cas system functions by acquiring short pieces of foreign DNA (spacers) which are inserted into the CRISPR region and provide immunity against subsequent exposures to phages and plasmids that carry matching sequences (Barrangou et al. (2007) *Science* 315:1709-12; Brouns et al. (2008) *Science* 321:960-64). It is this CRISPR-Cas interference/immunity that enables crRNA-mediated silencing of foreign nucleic acids (Horvath & Barrangou (2010) *Science* 327:167-70; Deveau et al. (2010) *Annu. Rev. Microbiol.* 64:475-93; Marraffini & Sontheimer (2010) *Nat. Rev. Genet.* 11:181-90; Bhaya et al. (2011) *Annu. Rev. Genet.* 45:273-97; Wiedenheft et al. (2012) *Nature* 482:331-338).

Use of CRISPR constructs that rely upon the nuclease activity of the Cas9 protein (Makarova et al. (2011) *Nat. Rev. Microbiol.* 9:467-77) coupled with a synthetic guide RNA (gRNA) has recently revolutionized genomic-engineering, allowing for unprecedented manipulation of DNA sequences. CRISPR/Cas9 constructs are simple and fast to synthesize and can be multiplexed. However, despite the relative ease of their synthesis, CRISPRs have technological restrictions related to their access to targetable genome space, which is a function of both the properties of Cas9 itself and the synthesis of its gRNA.

Cleavage by the CRISPR system requires complementary base pairing of the gRNA to a 20-nucleotide DNA sequence and the requisite protospacer-adjacent motif (PAM), a short nucleotide motif found 3' to the target site (Jinek et al. (2012) *Science* 337: 816-821). One can, theoretically, target any unique $N_{20}$-PAM sequence in the genome using CRISPR technology. The DNA binding specificity of the PAM sequence, which varies depending upon the species of origin of the specific Cas9 employed, provides one constraint. Currently, the least restrictive and most commonly used Cas9 protein is from *S. pyogenes*, which recognizes the sequence NGG, and thus, any unique 21-nucleotide sequence in the genome followed by two guanosine nucleotides ($N_{20}$NGG) can be targeted. Expansion of the available targeting space imposed by the protein component is limited to the discovery and use of novel Cas9 proteins with altered PAM requirements (Cong et al. (2013) *Science* 339: 819-823; Hou et al. (2013) *Proc. Natl. Acad. Sci. U.S.A.* 110 (39):15644-9), or pending the generation of novel Cas9 variants via mutagenesis or directed evolution.

The second technological constraint of the CRISPR system arises from gRNA expression initiating at a 5' guanosine nucleotide. Use of the type III class of RNA polymerase III promoters has been particularly amenable for gRNA expression because these short non-coding transcripts have well-defined ends, and all the necessary elements for transcription, with the exclusion of the 1+ nucleotide, are contained in the upstream promoter region. However, since the commonly used U6 promoter requires a guanosine nucleotide to initiate transcription, use of the U6 promoter has further constrained genomic targeting sites to $GN_{19}NGG$ (Mali et al. (2013) *Science* 339:823-826; Ding et al. (2013) *Cell Stem Cell* 12:393-394 Ranganathan, V et al. *Nature communications* 5, 4516 (2014)). Alternative approaches, such as in vitro transcription by T7, T3, or SP6 promoters, would also require initiating guanosine nucleotide(s) (Adhya et al. (1981) *Proc. Natl. Acad. Sci. U.S.A.* 78:147-151; Melton et al. (1984) *Nucleic Acids Res.* 12:7035-7056; Pleiss et al. (1998) *RNA* 4:1313-1317).

SUMMARY

The practice of the present invention will typically employ, unless otherwise indicated, conventional techniques of cell biology, cell culture, molecular biology, transgenic biology, microbiology, recombinant nucleic acid (e.g., DNA) technology, immunology, and RNA interference (RNAi) which are within the skill of the art. Non-limiting descriptions of certain of these techniques are found in the following publications: Ausubel, F., et al., (eds.), *Current Protocols in Molecular Biology, Current Protocols in Immunology, Current Protocols in Protein Science*, and *Current Protocols in Cell Biology*, all John Wiley & Sons, N.Y., edition as of December 2008; Sambrook, Russell, and Sambrook, *Molecular Cloning. A Laboratory Manual*, 3$^{rd}$ ed., Cold Spring Harbor Laboratory Press, Cold Spring Harbor, 2001; Harlow, E. and Lane, D., *Antibodies—A Laboratory Manual*, Cold Spring Harbor Laboratory Press, Cold Spring Harbor, 1988; Freshney, R. I., "Culture of Animal Cells, A Manual of Basic Technique", 5th ed., John Wiley & Sons, Hoboken, N.J., 2005. Non-limiting information regarding therapeutic agents and human diseases is found in Goodman and Gilman's The Pharmacological Basis of Therapeutics, 11th Ed., McGraw Hill, 2005, Katzung, B. (ed.) Basic and Clinical Pharmacology, McGraw-Hill/Appleton & Lange 10$^{th}$ ed. (2006) or 11th edition (July 2009). Non-limiting information regarding genes and genetic disorders is found in McKusick, V. A.: Mendelian Inheritance in Man. A Catalog of Human Genes and Genetic Disorders. Baltimore: Johns Hopkins University Press, 1998 (12th edition) or the more recent online database: Online Mendelian Inheritance in Man, OMIM™. McKusick-Nathans Institute of Genetic Medicine, Johns Hopkins University (Baltimore, Md.) and National Center for Biotechnology Information, National Library of Medicine (Bethesda, Md.), as of May 1, 2010, available on the World Wide Web: http://www.ncbi.nlm.nih.gov/omim/ and in Online Mendelian Inheritance in Animals (OMIA), a database of genes, inherited disorders and traits in animal species (other than human and mouse), available on the World Wide Web: http://omia.angis.org.au/contact.shtml. All patents, patent applications, and other publications (e.g., scientific articles, books, websites, and databases) mentioned herein are incorporated by reference in their entirety. In case of a conflict between the specification and any of the incorporated references, the specification (including any amendments thereof, which may be based on an incorporated reference), shall control. Standard art-accepted meanings of terms are used herein unless indicated otherwise. Standard abbreviations for various terms are used herein.

Provided herein are compositions and methods comprising improvements of a CRISPR/Cas9 system (i.e., CRISPR guide RNAs using the H1 promoter). In some embodiments, the improvements comprise modifications to the H1 promoter region. In some embodiments, the compositions comprise enhancing H1 bidirectional pol II expression using 5'UTR modifications. In some embodiments, the compositions comprise modulating bidirectional expression through use of different orthologous sequences of the H1 promoter. In some embodiments, the compositions comprise novel compact bidirectional promoter sequences with both pol II and pol III activity (e.g., 7sk, 5'UTRs, Kozak consensus sequences, or combinations thereof). In some embodiments, the method comprises an expression screen for bidirectional promoters with both RNA pol II and RNA pol III activities. In some embodiments, the compositions comprise conditional pol II/pol III bidirectional promoter expression (e.g., TetR and TetO sites) which can regulate ribonucleoprotein enzymatic activity or RNA-directed nucleases. In some embodiments, the improvements comprise addition of a donor template sequence for correcting mutations (e.g., homology directed repair (HDR)).

In other embodiments of the present invention, the improvements comprise modifications to a component of the CRISPR/Cas9 system. In some embodiments, the modifications are made to nucleases (e.g., RNA-guided nucleases). In some embodiments, the nuclease (e.g., Cas9) is modified through post-transcriptional cell-cycle regulation (e.g., fusion proteins comprising Geminin (Gem) or Cdt1). In some embodiments, the nuclease (e.g., Cas9) is modified by engineering partial target sites such that the nuclease can bind without DNA cleavage. In some embodiments, the nuclease (e.g., Cas9) is modified by modulating its half-life using N-terminal amino acid identity.

One aspect of the invention relates to a non-naturally occurring nuclease system comprising one or more vectors comprising: a) a promoter operably linked to at least one nucleotide sequence encoding a nuclease system guide RNA (gRNA), wherein the gRNA hybridizes with a target sequence of a DNA molecule or RNA molecule in a cell, and wherein the DNA molecule or RNA encodes one or more gene products expressed in the cell; and b) a regulatory element operable in a cell operably linked to a nucleotide sequence encoding a genome-targeted nuclease, wherein components (a) and (b) are located on the same or different vectors of the system, wherein the gRNA targets and hybridizes with the target sequence and the nuclease cleaves the DNA molecule or RNA to alter expression of the one or more gene products.

In some embodiments, the system is CRISPR (e.g. CRISPR associated (Cas) 9 (CRISPR-Cas9, non-Cas9 CRISPR systems, CRISPR-Cpf-1 system, and the like).

In some embodiments, the system is packaged into a single adeno-associated virus (AAV) particle.

In some embodiments, the adeno-associated packaging virus is selected from adenovirus serotype 2, adenovirus serotype 5, or adenovirus serotype 35.

In some embodiments, the adeno-associated packaging virus is adenovirus serotype 5.

In some embodiments, the system inactivates one or more gene products.

In some embodiments, the nuclease system excises at least one gene mutation.

In some embodiments, the promoter is selected from the group consisting of H1 promoter, 7sk, human RPPH1-PARP2, SRP-RPS29, 7sk1-GSTA4, SNAR-G-1-CGB1, SNAR-CGB2, RMRP-CCDC107, tRNA(Lys)-ALOXE3, RNU6-9-MED16: tRNA (Gly)-DPP9, RNU6-2-THEM259, SNORD13-C8orf41, mouse RPPH1-PARP2, and rat RPPH1-PARP2.

In some embodiments, the promoter is a H1 promoter.

In some embodiments, the H1 promoter comprises a nucleotide sequence having at least 80% identity to the nucleotide sequence set forth in SEQ ID NO: 12 or 32.

In some embodiments, the H1 promoter comprises a nucleotide sequence having the nucleotide sequence set forth in SEQ ID NO: 12.

In some embodiments, the H1 promoter comprises a nucleotide sequence having the nucleotide sequence set forth in SEQ ID NO: 32.

In some embodiments, the promoter is orthologous to the H1 promoter.

In some embodiments, the orthologous H1 promoter is derived from eutherian mammals.

In some embodiments, the orthologous H1 promoter is derived from *Ailuropoda melanoleuca, Bos taurus, Callithrix jacchus, Canis familiaris, Cavia porcellus, Chlorocebus sabaeus, Choloepus hoffmanni, Dasypus novemcinctus, Dipodomys ordii, equus caballus, Erinaceus europaeus, Felis catus, Gorilla gorilla, Homo sapiens, Ictidomys tridecemlineatus, Loxodonta africana, Macaca mulatta, Mus musculus, Mustela putorius faro, Myotis lucifugus, Nomascus leucogenys, Ochotona princeps, Oryctolagus cuniculus, Otolemur garnettii, Ovis aries, Pan troglodytes, Papio anubis, Pongo abelii, Procavia capensis, Pteropus vampyrus, Rattus norvegicus, Sus scrofa, Tarsius syrichta, Tupaia belangeri, Tursiops truncatus, Vicugna pacos.*

In some embodiments, the orthologous H1 promoter is derived from mouse or rat.

In some embodiments, the orthologous H1 promoter comprises a nucleotide sequence having at least 80%, 85%, 90%, 95%, 98%, 99%, or 100% identity to the nucleotide sequence set forth in SEQ ID NOs: 84-119.

In some embodiments, the orthologous H1 promoter comprises a nucleotide sequences set forth in the group consisting of SEQ ID NOs: 84-119.

In some embodiments, the H1 promoter is bidirectional. The H1 promoter is both a pol II and pol III promoter In some embodiments, the H1 promoter comprises: a) control elements that provide for transcription in one direction of at least one nucleotide sequence encoding a gRNA; and b) control elements that provide for transcription in the opposite direction of a nucleotide sequence encoding a genome-targeted nuclease.

In some embodiments, the promoter is a 7sk promoter.

In some embodiments, the 7sk promoter is derived from human, rat, or mouse.

In some embodiments, the 7sk promoter is selected from the group consisting of 7sk1, 7sk2, and 7sk3.

In some embodiments, the 7sk promoter is 7sk1.

In some embodiments, the 7sk1 is derived from human.

In some embodiments, the human 7sk1 comprises a nucleotide sequence having at least 80% identity to the nucleotide sequence set forth in SEQ ID NO: 3.

In some embodiments, the human 7sk1 comprises a nucleotide sequence having the nucleotide sequence set forth in SEQ ID NO: 3.

In some embodiments, the 7sk1 is derived from mouse.

In some embodiments, the mouse 7sk1 comprises a nucleotide sequence having at least 80% identity to SEQ ID NO: 6.

In some embodiments, the mouse 7sk1 comprises a nucleotide sequence having the nucleotide sequence set forth in SEQ ID NO: 6.

In some embodiments, the 7sk promoter is 7sk2.

In some embodiments, the 7sk2 is derived from human.

In some embodiments, the human 7sk2 comprises a nucleotide sequence having at least 80% identity to SEQ ID NO: 4.

In some embodiments, the human 7sk2 comprises a nucleotide sequence having the nucleotide sequence set forth in SEQ ID NO: 4.

In some embodiments, the 7sk2 is derived from mouse.

In some embodiments, the mouse 7sk2 comprises a nucleotide sequence having at least 80% identity to SEQ ID NO: 7.

In some embodiments, the mouse 7sk2 comprises a nucleotide sequence having the nucleotide sequence set forth in SEQ ID NO: 7.

In some embodiments, the 7sk promoter is 7sk3.

In some embodiments, the 7sk3 is derived from human.

In some embodiments, the human 7sk3 comprises a nucleotide sequence having at least 80% identity to SEQ ID NO: 5.

In some embodiments, the human 7sk3 comprises a nucleotide sequence having the nucleotide sequence set forth in SEQ ID NO: 5.

In some embodiments, the 7sk3 is derived from mouse.

In some embodiments, the mouse 7sk3 comprises a nucleotide sequence having at least 80% identity to SEQ ID NO: 8.

In some embodiments, the mouse 7sk3 comprises a nucleotide sequence having the nucleotide sequence set forth in SEQ ID NO: 8.

In some embodiments, the promoter has at least one modification.

In some embodiments, the at least one modification of the promoter comprises an element that allows conditional regulation.

In some embodiments, the element is a tet-responsive promoter.

In some embodiments, the tet-response promoter comprises a Tet repressor (TetR) and Tet operator (TetO) engineered into the H1 promoter.

In some embodiments, the TetR comprises an amino acid sequence having at least 80% identity to SEQ ID NO: 14.

In some embodiments, the TetR comprises an amino acid sequence having the amino acid sequence set forth in SEQ ID NO: 14.

In some embodiments, the TetO comprises a nucleotide sequence having at least 80% identity to the nucleotide sequence set forth in SEQ ID NO: 11.

In some embodiments, the TetO comprises a nucleotide sequence having the nucleotide sequence set forth in SEQ ID NO: 11.

In some embodiments, the H1-TetO comprises a nucleotide sequence having at least 80% identity to the nucleotide sequence set forth in SEQ ID NO: 13.

In some embodiments, the H1-TetO comprises a nucleotide sequence having the nucleotide sequence set forth in SEQ ID NO: 13.

In some embodiments, the at least one modification of the promoter comprises a site that allows auto-regulation.

In some embodiments, the auto-regulation site comprises a nucleotide sequence having at least 80% identity to the nucleotide sequence set forth in SEQ ID NO: 33 or 34.

In some embodiments, the auto-regulation site comprises the nucleotide sequence set forth in SEQ ID NO: 33.

In some embodiments, the auto-regulation site comprises the nucleotide sequence set forth in SEQ ID NO: 34.

In some embodiments, the method further comprises at least one terminator sequence.

In some embodiments, the at least one terminator sequence is selected from the group consisting of SV40 or synthetic poly A (SPA) sequences.

In some embodiments, the terminator sequences is a SV40 120 (SEQ ID NO: 123) or 240 (SEQ ID NO: 122) base pair sequence.

In some embodiments, the terminator sequences is a SPA 49 base pair sequence.

In some embodiments, the method further comprises 5' untranslated region (5'UTR) sequences.

In some embodiments, the method further comprises a Kozak sequence.

In some embodiments, the Kozak sequence comprises a nucleotide sequence having at least 80% identity to SEQ ID NO: 1 or 2.

In some embodiments, the Kozak sequence comprises the nucleotide sequence set forth in SEQ ID NO: 1.

In some embodiments, the Kozak sequence comprises the nucleotide sequence set forth in SEQ ID NO: 2.

In some embodiments, the method further comprises a RNA sequence that mediates cap-independent initiation of translation.

In some embodiments, the RNA sequence is selected from the group consisting of 6.947 or 6.967.

In some embodiments, the genome-targeted nuclease is Cas9 protein.

In some embodiments, the Cas9 comprises a nucleotide sequence having at least 80% identity to the nucleotide sequence set forth in SEQ ID NO: 61.

In some embodiments, the Cas9 comprises the nucleotide sequence set forth in SEQ ID NO: 61.

In some embodiments, the Cas9 comprises at least one modification.

In some embodiments, the at least one modification in the Cas9 comprises an alteration in the cleaving sequence.

In some embodiments, the alteration in the cleaving sequence selected from the group consisting of T2A, P2A, E2A, and F2A.

In some embodiments, the T2A comprises an amino acid sequence. having at least 80% identity to the nucleotide sequence set forth in SEQ ID NO: 36.

In some embodiments, the T2A comprises an amino acid sequence having the nucleotide sequence set forth in SEQ ID NO: 36.

In some embodiments, the P2A comprises an amino acid sequence having at least 80% identity to the nucleotide sequence set forth in SEQ ID NO: 35.

In some embodiments, the P2A comprises an amino acid sequence having the nucleotide sequence set forth in SEQ ID NO: 35.

In some embodiments, the E2A comprises an amino acid sequence having at least 80% identity to the nucleotide sequence set forth in SEQ ID NO: 37.

In some embodiments, the E2A comprises an amino acid sequence having the nucleotide sequence set forth in SEQ ID NO: 37.

In some embodiments, the F2A comprises an amino acid sequence having at least 80% identity to the nucleotide sequence set forth in SEQ ID NO: 38.

In some embodiments, the F2A comprises an amino acid sequence having the nucleotide sequence set forth in SEQ ID NO: 38.

In some embodiments, the at least one modification in the Cas9 comprises a codon optimized for expression in the cell.

In some embodiments, the Cas9 further comprises a linker sequence operably fused in frame to a cell-cycle dependent protein (Cas9 fusion).

In some embodiments, the cell cycle-dependent protein is selected from the group consisting of APE2, ATR, BRCA1, Chk1, Cdc5, Cdc6, Cdc7, Cdc45, Cdt1, CSA, CSB, Ctf18, DDB1, DDB2, DNA2, DUT, Elg1, EndoV, Esp1, Exonuclease1, FBH1, FEN1, Geminin, Hus1, KNTC2 (NDC80), Ku80, Ligase1, Mad2, MBD4, Mcm3, Mcm4, Mcm5, Mcm6, Mcm7, Mcm8, Mcm10, MGMT, MLH3, Mms4, MPG, MSH2, Mus81, NBS1, NEIL2, NEIL3, NTH1, Orc1, Orc3, PARP1, PCNA, Pif1, PMS1, PMS2, PNK, Pola p180, Pola p'70, Pola Spp1 (Prim2a), Polb, Pold p125, Pole Dpb3, Pole Dpb4, Pole Pol2, Poli, Poll, Polm, Psf1, Psf2, Psf3, Rad1, Rad18, Rad23A, Rad23B, Rad51, Rad51D, Rad54, Rad6A, RPA34, RPA70, Scc1, Scc3, Sir2, SIRT1 (Sirtuin), TDG, TDP1, TIMELESS, Tin2, Topoisomerase I, Topoisomerase IIIa, Topoisomerase IIIb, Ubc13, UNG, XAB2, XPC, XPF, XPG, Xrcc2, and XRCC4.

In some embodiments, the cell cycle-dependent protein is Geminin.

In some embodiments, the cell cycle-dependent protein is human Geminin.

In some embodiments, the human Geminin comprises the amino acids from positions 1-110 (hGem(1-110)).

In some embodiments, the hGem(1-110) comprises an amino acid sequence having at least 80% identity to the amino acid sequence set forth in SEQ ID NO: 19.

In some embodiments, the hGem(1-110) comprises the amino acid sequence set forth in SEQ ID NO: 19.

In some embodiments, the cell cycle-dependent protein is Cdt1.

In some embodiments, the cell cycle-dependent protein is human Cdt1.

In some embodiments, the human Cdt1 comprises amino acids from positions 30-120 (hCdt1(30-120)).

In some embodiments, the hCdt1(30-120) comprises an amino acid sequence having at least 80% identity to the amino acid sequence set forth in SEQ ID NO: 18.

In some embodiments, the hCdt1(30-120) comprises the amino acid sequence set forth in SEQ ID NO: 18.

In some embodiments, the Cas9 fusion comprises an amino acid sequence having at least 80% identity to the amino acid sequence selected from the group consisting of SEQ ID NO: 20-27.

In some embodiments, the Cas9 fusion comprises the amino acid sequence selected from the group consisting of SEQ ID NO: 20-27.

In some embodiments, the Cas9 is operably fused in frame to a ubiquitin protein (Ub-Cas9).

In some embodiments, the Ub-Cas9 at least one N-terminal modification.

In some embodiments, the N-terminal modified Ub-Cas9 comprises an amino acid sequence having at least 80% identity to the amino acid sequence selected from the group consisting of SEQ ID NO: 39-58

In some embodiments, the N-terminal modified Ub-Cas9 comprises the amino acid sequence selected from the group consisting of SEQ ID NO: 39-58.

In some embodiments, the ubiquitin protein comprises a nucleotide sequence having at least 80% identity to the nucleotide sequence set forth in SEQ ID NO: 60.

In some embodiments, the ubiquitin protein comprises the nucleotide sequence set forth in SEQ ID NO: 60.

In some embodiments, the method further comprises a SaCas9 nickase.

In some embodiments, the method further comprises a donor template sequence.

In some embodiments, the at least one vector comprises a nucleotide sequence having at least 80% identity to the nucleotide sequence set forth in SEQ ID NO: 62 or 67.

In some embodiments, the at least one vector comprises the nucleotide sequence set forth in SEQ ID NO: 62.

In some embodiments, the at least one vector comprises the nucleotide sequence set forth in SEQ ID NO: 67.

In some embodiments, the donor template sequence corrects at least one gene mutation.

In some embodiments, the at least one gene mutation is rd10 or rd12.

In some embodiments, the at least one vector comprises a nucleotide sequence having at least 80% identity to the nucleotide sequence set forth in SEQ ID NO: 63 or 64.

In some embodiments, the at least one vector comprises the nucleotide sequence set forth in SEQ ID NO: 63.

In some embodiments, the at least one vector comprises the nucleotide sequence set forth in SEQ ID NO: 64.

In some embodiments, the at least one vector comprises a nucleotide sequence having at least 80% identity to the nucleotide sequence set forth in SEQ ID NO: 65 or 66.

In some embodiments, the at least one vector comprises the nucleotide sequence set forth in SEQ ID NO: 65.

In some embodiments, the at least one vector comprises the nucleotide sequence set forth in SEQ ID NO: 66.

In some embodiments, the promoter is operably linked to at least one, two, three, four, five, six, seven, eight, nine, or ten gRNA.

In some embodiments, the target sequence comprises the nucleotide sequence $AN_{19}NGG$, $GN_{19}NGG$, $CN_{19}NGG$, or $TN_{19}NGG$.

In some embodiments, the cell is a eukaryotic or or non-eukaryotic cell.

In some embodiments, the eukaryotic cell is a mammalian or human cell.

In some embodiments, the eukaryotic cell is a retinal photoreceptor cell.

In some embodiments, the one or more gene products are rhodopsin.

In some embodiments, the expression of the one or more gene products is decreased.

Another aspect of the invention relates to a method of altering expression of one or more gene products in a cell, wherein the cell comprises a DNA molecule encoding the one or more gene products, the method comprising introducing into the cell a non-naturally occurring nuclease system as set forth above.

In some embodiments, the system inactivates one or more gene products.

In some embodiments, the nuclease system excises at least one gene mutation.

In some embodiments, the expression of the one or more gene products is decreased.

In some embodiments, the cell is a eukaryotic or non-eukaryotic cell.

In some embodiments, the eukaryotic cell is a mammalian or human cell.

In some embodiments, the cell is a retinal photoreceptor cell.

In some embodiments, the cell is a retinal ganglion cell. 130. In some embodiments, the eukaryotic cell is a cancerous cell.

In some embodiments, cell proliferation is inhibited or reduced in the cancerous cell.

In some embodiments, apoptosis is enhanced or increased in the cancerous cell.

Another aspect of the invention relates to a method for treating a disease selected from the group consisting of retinal dystrophy, corneal dystrophy, microsatellite expansion diseases, and cancer in a subject in need thereof, the method comprising: (a) providing a non-naturally occurring nuclease system as set forth above; and (b) administering to the subject an effective amount of the system.

In some embodiments, the disease is corneal dystrophy.

In some embodiments, the disease is a retinal dystrophy.

In some embodiments, the retinal dystrophy is selected from the group consisting of Leber's congenital amaurosis (LCA), retinitis pigmentosa (RP), and glaucoma.

In some embodiments, the corneal dystrophy is selected from the group consisting of Epithelial Basement Membrane Dystrophy, Epithelial Recurrent Erosion Dystrophies, Subepithelial Mucinous Corneal Dystrophy, Meesmann Corneal Dystrophy, Lisch Epithelial Corneal Dystrophy, Gelatinous Drop-like Corneal Dystrophy, Reis-Bucklers Corneal Dystrophy, Thiel-Behnke Corneal Dystrophy, Lattice Corneal Dystrophy, Type 1 (Classic), Lattice Corneal Dystrophy, Type 2, Lattice Corneal Dystrophy, Type III, Lattice Corneal Dystrophy, Type IIIA, Lattice Corneal Dystrophy, Type I/IIIA, Lattice Corneal Dystrophy, Type IV, Polymorphic (Corneal) Amyloidosis, Granular Corneal Dystrophy, Type 1, Granular Corneal Dystrophy, Type 2, Macular Corneal Dystrophy, Schnyder Corneal Dystrophy, Congenital Stromal Corneal Dystrophy, Fleck Corneal Dystrophy, Posterior Amorphous Corneal Dystrophy, Central Cloudy Dystrophy of Francois, Pre-Descemet Corneal Dystrophy, Fuchs Endothelial Corneal Dystrophy, Posterior Polymorphous Corneal Dystrophy, Congenital Hereditary Endothelial Dystrophy, and X-linked Endothelial Corneal Dystrophy.

In some embodiments, the microsatellite expansion diseases is selected from the group consisting of Blepharophimosis, ptosis and epicanthus inversus syndactyly, Cleidocranial dysplasia, Congenital central hypoventilation syndrome, Haddad syndrome DM (Myotonic dystrophy), FRAXA (Fragile X syndrome), FRAXE (Fragile XE mental retardation), FRDA (Friedreich's ataxia), Fuchs' Endothelial Corneal Dystrophy, FXTAS (Fragile X-associated tremor/ataxia syndrome), Hand-foot-genital syndrome, HD (Huntington's disease), Holoprosencephaly, Mental retardation with growth hormone deficiency, Mental retardation, epilepsy, West syndrome, Partington syndrome, Oculopharyngeal muscular dystrophy, SBMA (Spinal and bulbar muscular atrophy), SCA1 (Spinocerebellar ataxia Type 1), SCA12 (Spinocerebellar ataxia Type 12), SCA17 (Spinocerebellar ataxia Type 17), SCA2 (Spinocerebellar ataxia Type 2), SCA3 (Spinocerebellar ataxia Type 3 or Machado-Joseph disease), SCA6 (Spinocerebellar ataxia Type 6), SCAT (Spinocerebellar ataxia Type 7), SCA8 (Spinocerebellar ataxia Type 8), and Synpolydactyly.

In some embodiments, administering to the subject occurs by implantation, injection, or virally.

In some embodiments, administering to the subject occurs by subretinal injection.

In some embodiments, administering to the subject occurs topically, intravascularly, intradermally, transdermally, parenterally, intravenously, intramuscularly, intranasally, subcutaneously, regionally, percutaneously, intratracheally, intraperitoneally, intraarterially, intravesically, intratumorally, peritumorally, inhalationly, systematically, perfusionly, lavagely, directly via injection, or orally via administration and formulation.

In some embodiments, administering to the subject occurs topically to the surface of the eye.

In some embodiments, administering to the subject occurs on or outside the cornea, sclera, to the intraocular, subconjunctival, sub-tenon, or retrobulbar space, or in or around the eyelids.

In some embodiments, the subject is treated with at least one additional anti-cancer agent.

In some embodiments, the anti-cancer agent is selected from the group consisting of paclitaxel, cisplatin, topotecan, gemcitabine, bleomycin, etoposide, carboplatin, docetaxel, doxorubicin, topotecan, cyclophosphamide, trabectedin, olaparib, tamoxifen, letrozole, and bevacizumab.

In some embodiments, the subject is treated with at least one additional anti-cancer therapy.

In some embodiments, the anti-cancer therapy is radiation therapy, chemotherapy, or surgery.

In some embodiments, the cancer is a solid tumor.

In some embodiments, the cancer is selected from the group consisting of brain cancer, gastrointestinal cancer, oral cancer, breast cancer, ovarian cancer, prostate cancer, pancreatic cancer, lung cancer, liver cancer, throat cancer, stomach cancer, and kidney cancer.

In some embodiments, the cancer is brain cancer.

In some embodiments, the systematic administration is selected from the group consisting of oral, intravenous, intradermal, intraperitoneal, subcutaneous, and intramuscular administration.

In some embodiments, the subject is a mammal.

In some embodiments, the mammal is human.

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE FIGURES

Having thus described the presently disclosed subject matter in general terms, reference will now be made to the accompanying Figures, which are not necessarily drawn to scale, and wherein:

FIG. 1 comprises six panels, A-F showing the effects of 5'UTR sequences on H1 Pol II expression. FIG. 1A-1C show the effects of 5'UTR and translation enhancerson H1 Pol II expression. FIGS. 1D and 1E show the effects of 5'UTR Kozak sequences on H1 Pol II expression. FIG. 1F depicts terminator sequences. The functional terminators were roughly equivalent. The shortest effective terminator is the 49 bp SPA terminator.

Figure 2C:
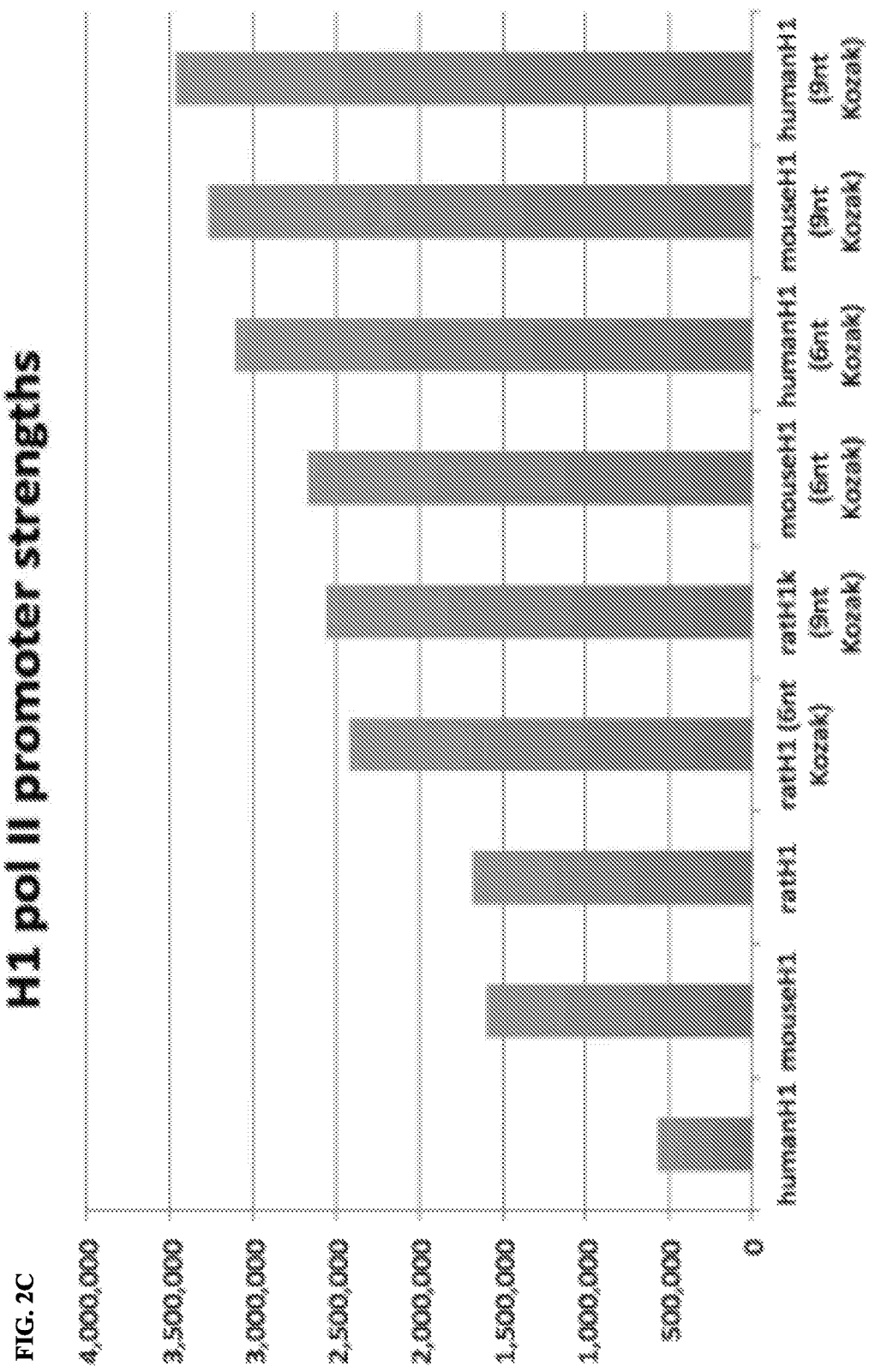

FIG. 2 comprises three panels, A, B, and C showing modulating bidirectional expression through the use of different orthologous sequences.

Figure 3A:
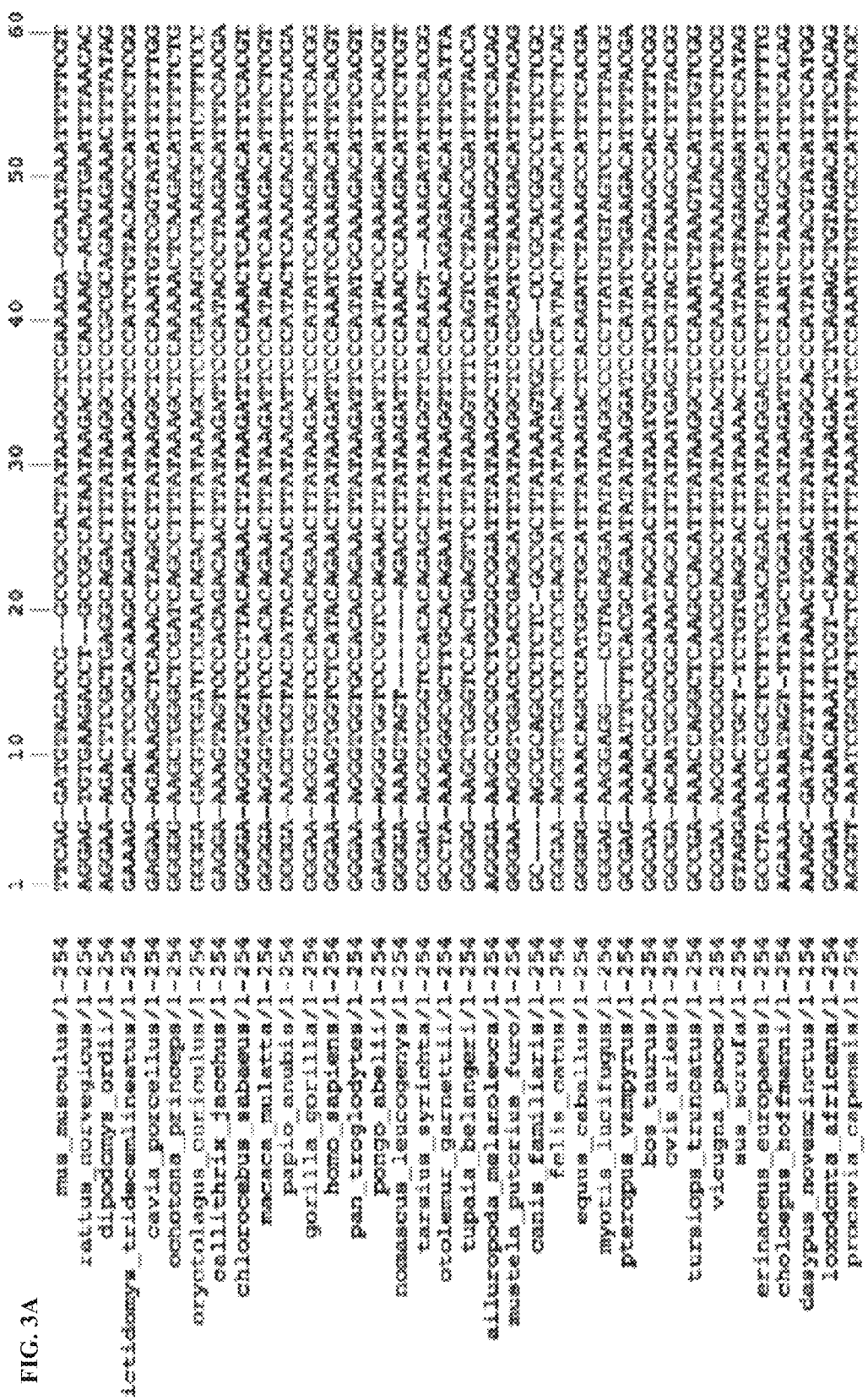
Figure 3B:
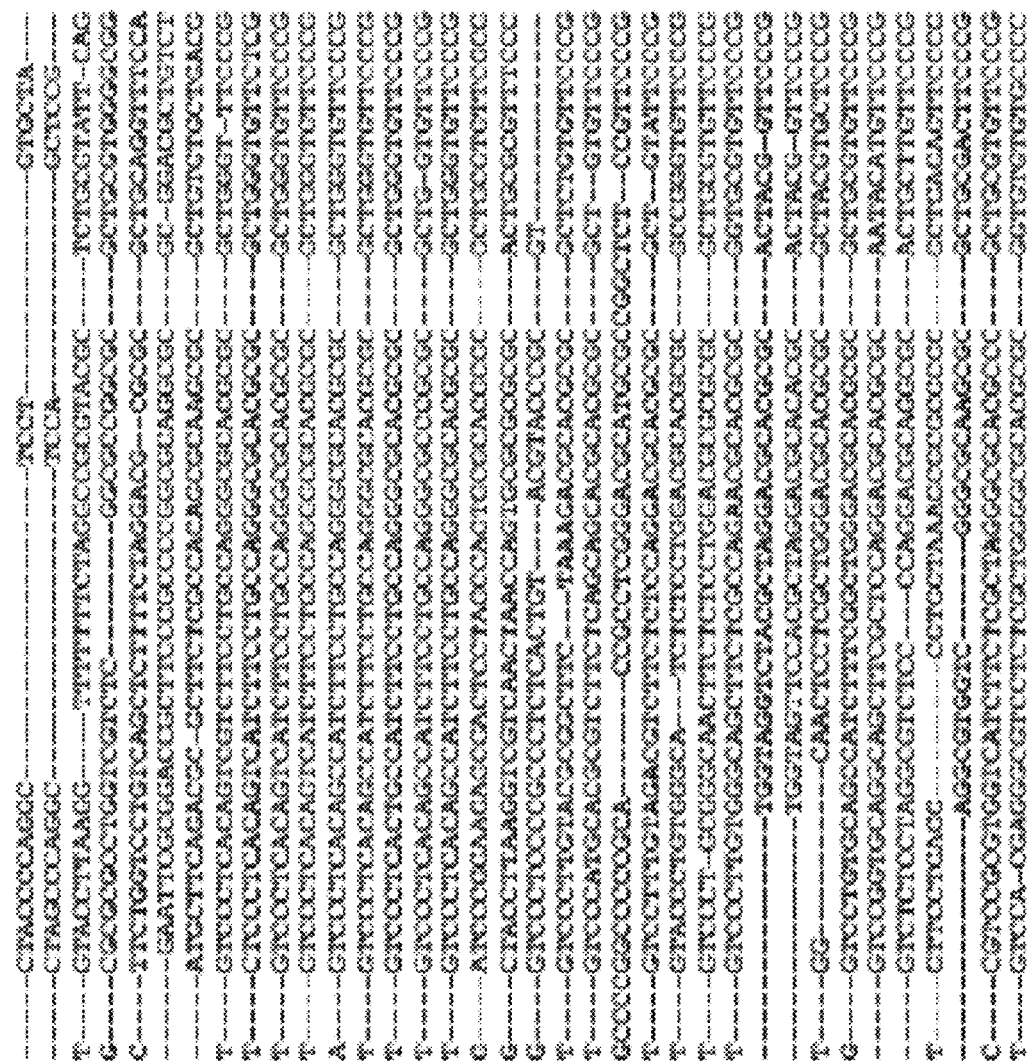

FIG. 3 comprises two panels, A and B showing H1 alignments of different orghologous sequences (SEQ ID NOS: 84-119; *Mus musculus* to *Procavia capensis*, respectively, in each of panels A and B).

Figure 4A:
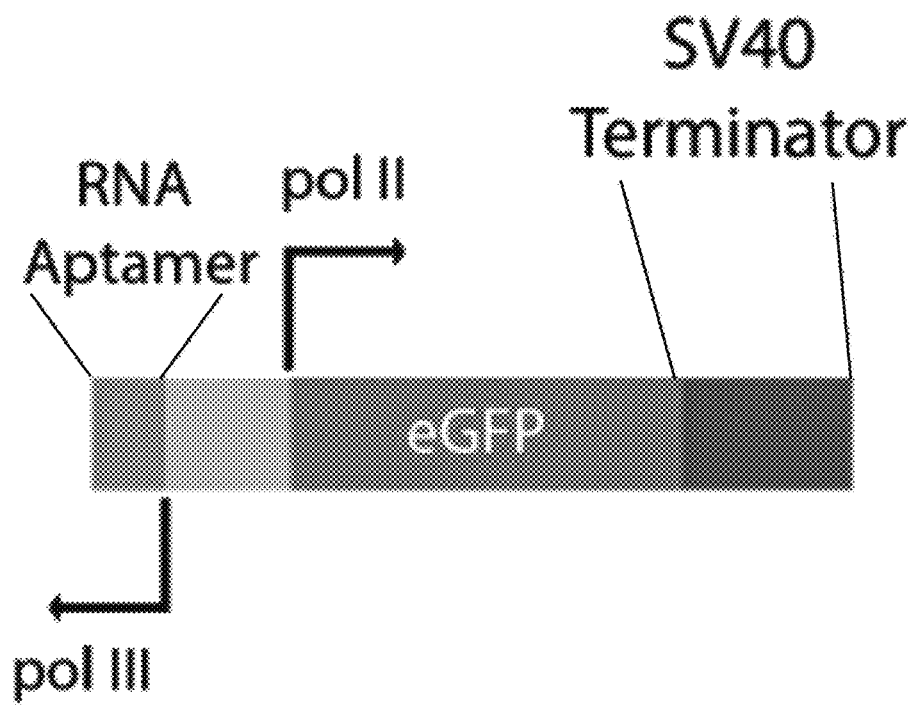
Figure 4B:
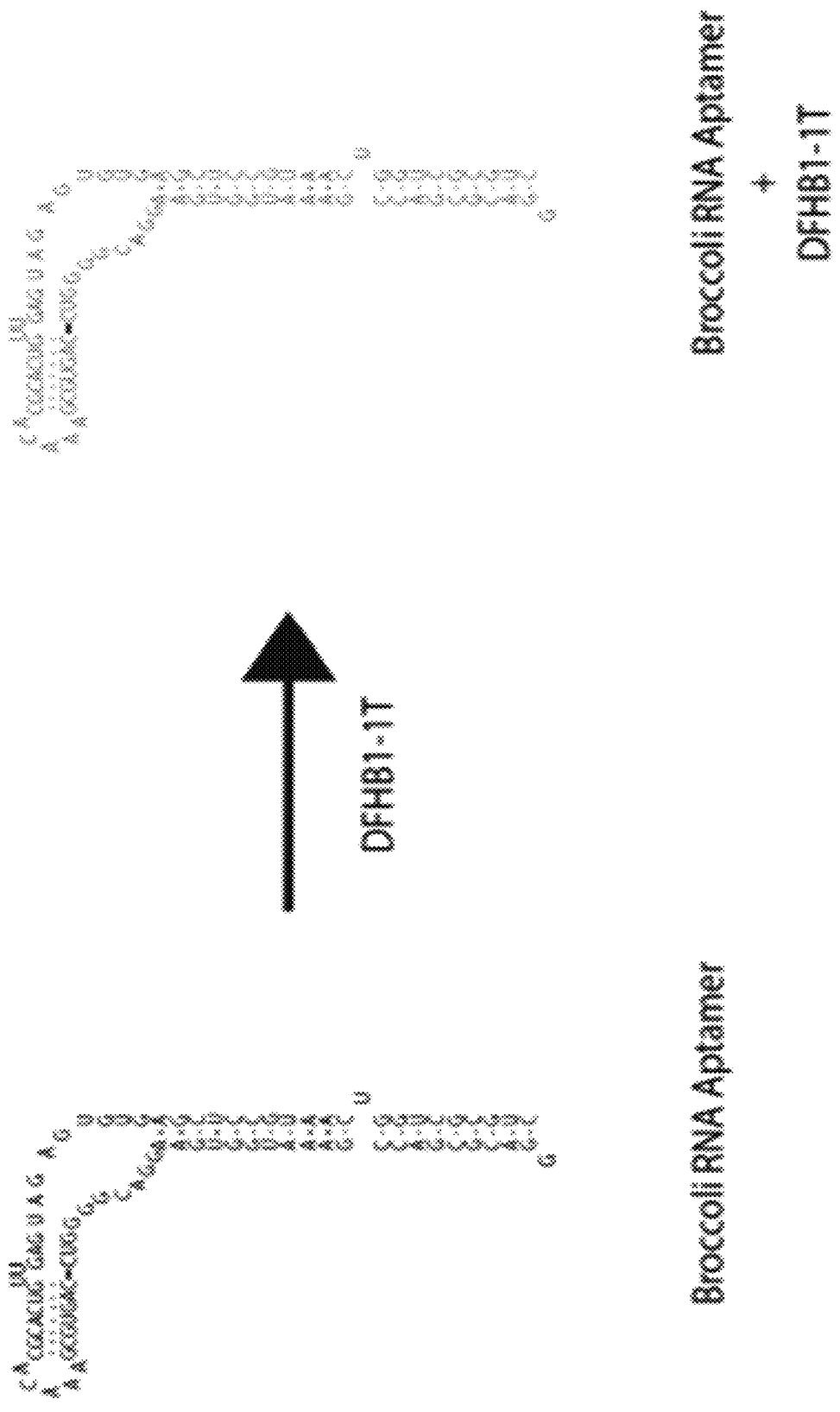

FIG. 4 comprises two panels, A and B showing a screen for Pol II and Pol III mutants from bidirectional promoters, including a fluorescence screen using a Broccoli RNA Aptamer (SEQ ID NO: 147) that becomes fluorescent in the presence of DFHB1-1T.

FIG. 5 shows further H1 alignments of different orghologous sequences (SEQ ID NOS: 84-119; *Mus musculus* to *Procavia capensis*, respectively.

FIG. 6 comprises two panels, A and B, showing conditional expression of H1 Pol III expression using TetO on regulating ribonucleoprotein enzymatic activity.

Figure 6A:
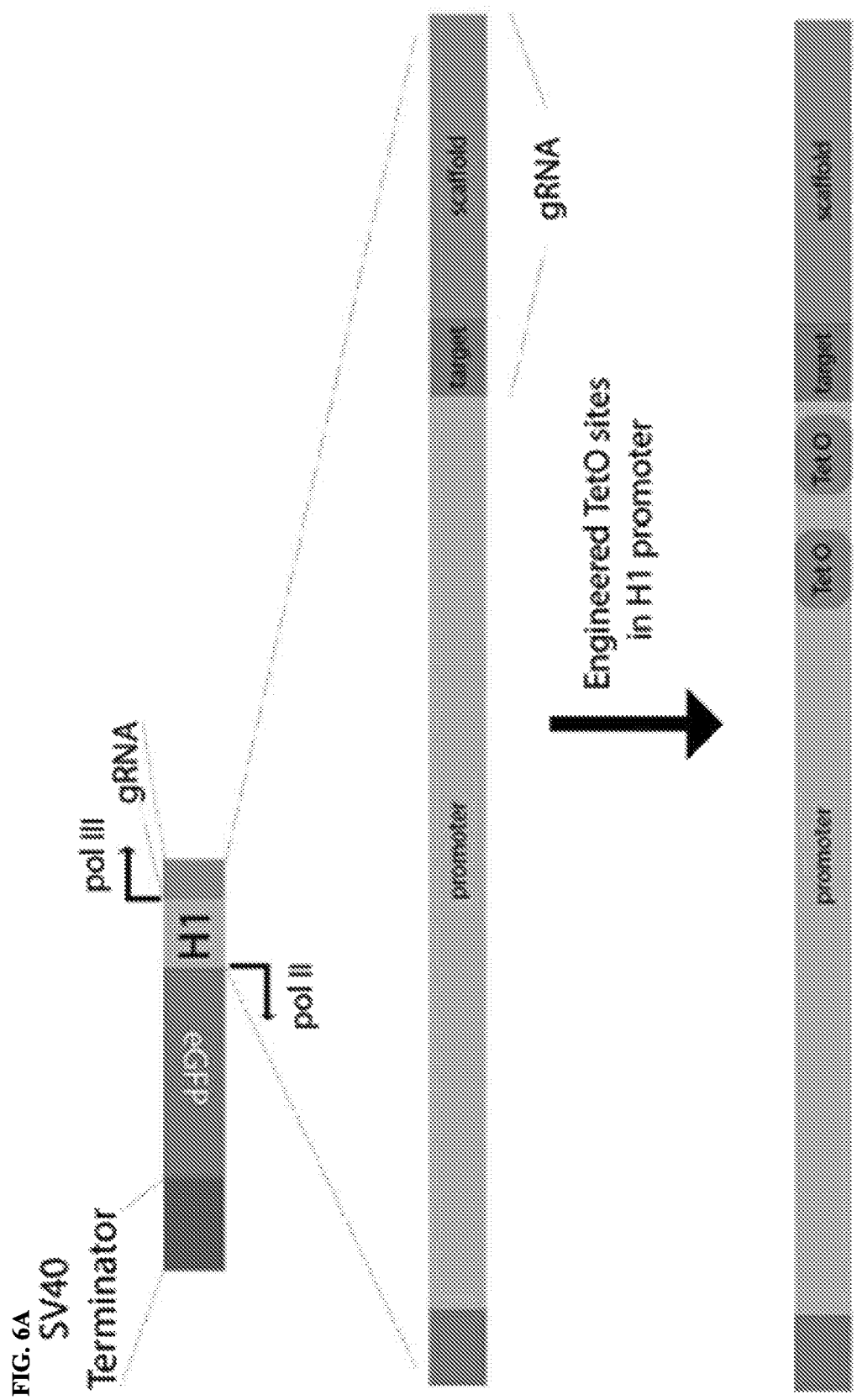
Figure 6B:
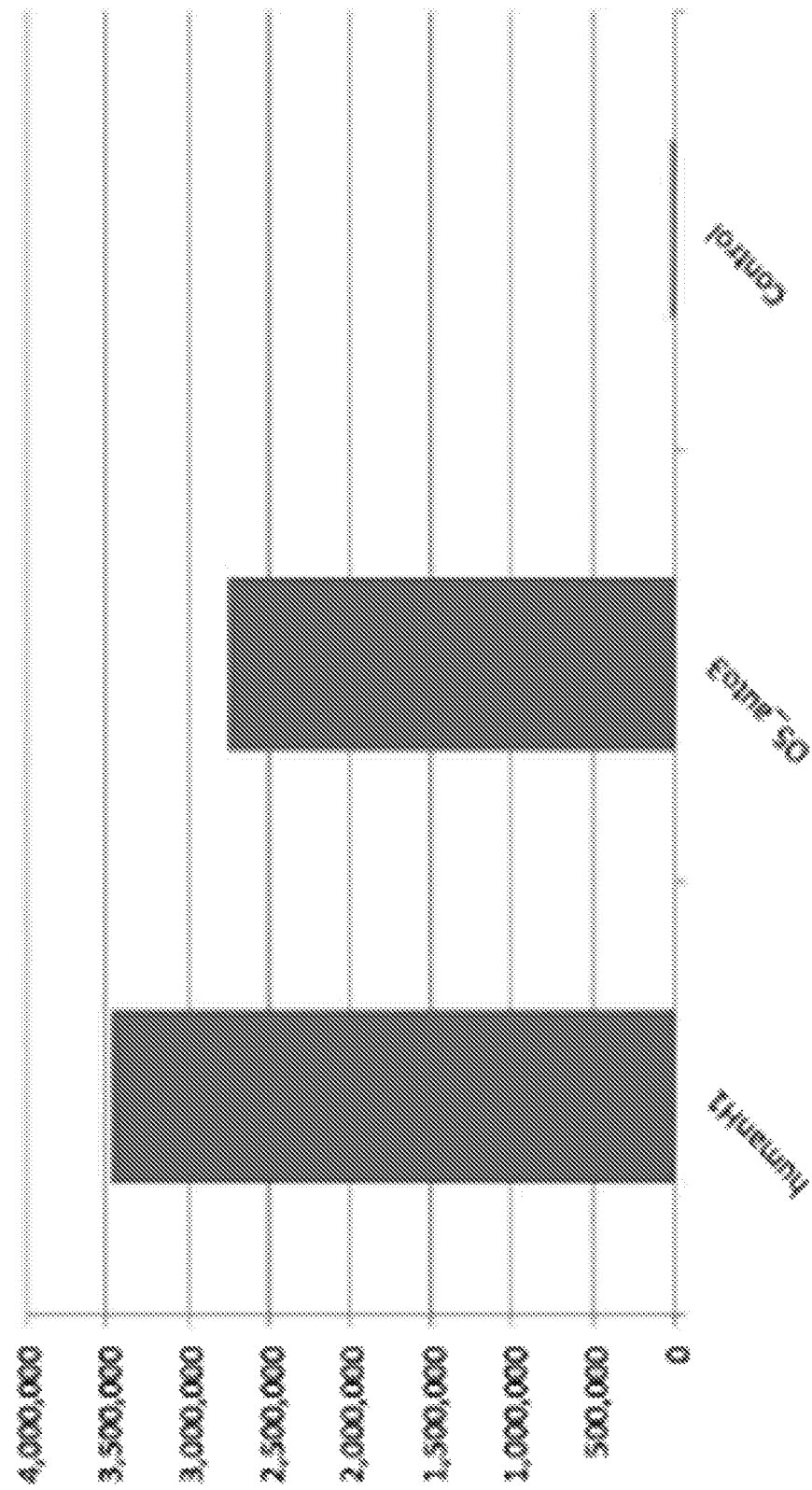

FIG. 6A shows a schematic of the engineered TetO sites in the H1 promoter. FIG. 6B shows that Pol II expression from engineered H1 is not greatly affected by the presence of Tet operator sequences. Upside-down text indicates directionality of transcription from bidirectional promoter.

Figure 7B:
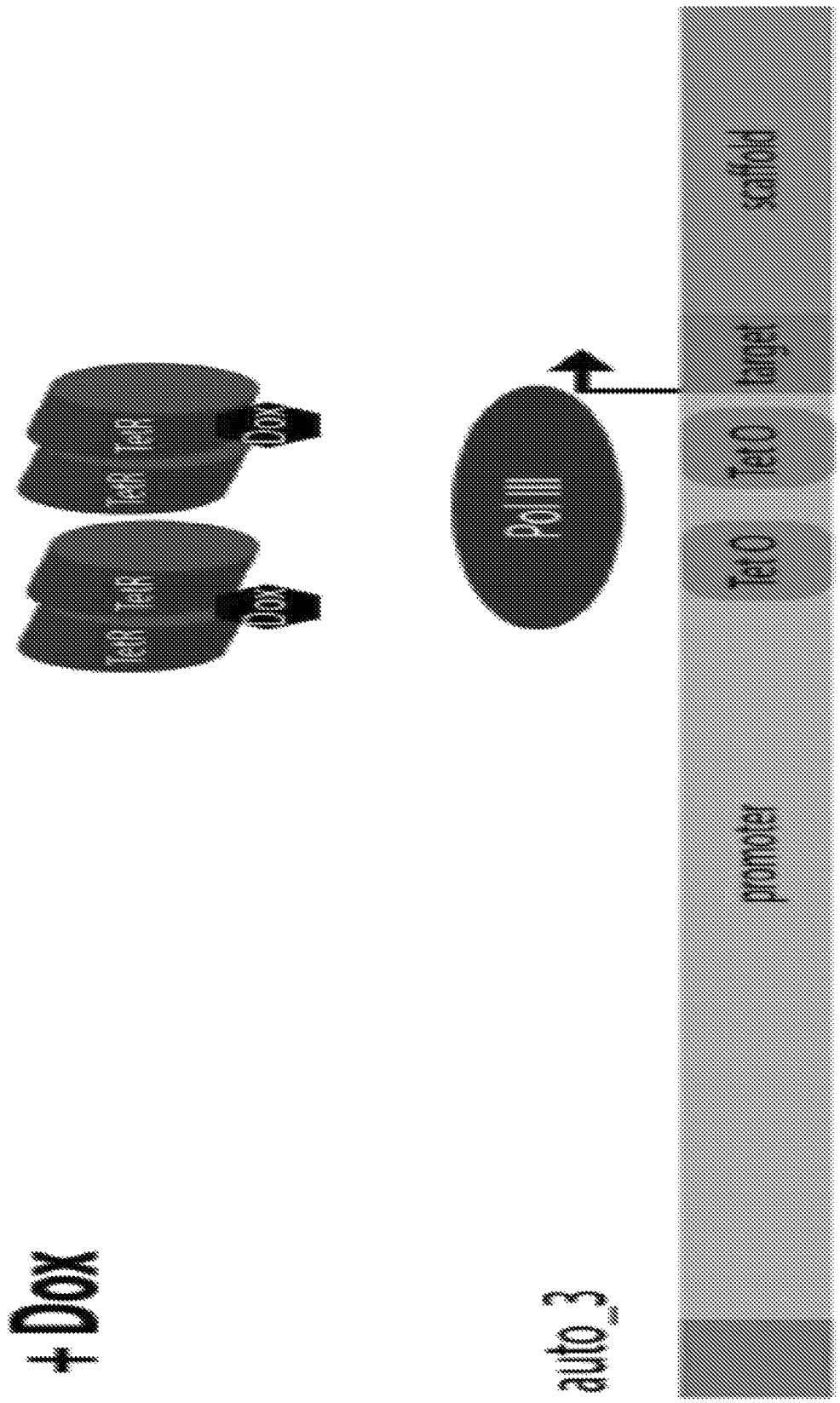

FIG. 7 comprises two panels, A and B, showing conditional expression of H1 Pol III expression regulating ribonucleoprotein enzymatic activity. FIG. 7A shows that Pol III expression is repressed in the presence of TetR and absence of doxycycline. FIG. 7B shows that Pol III expression is derepressed in the presence of TetR and presence of doxycycline.

Figure 8A:
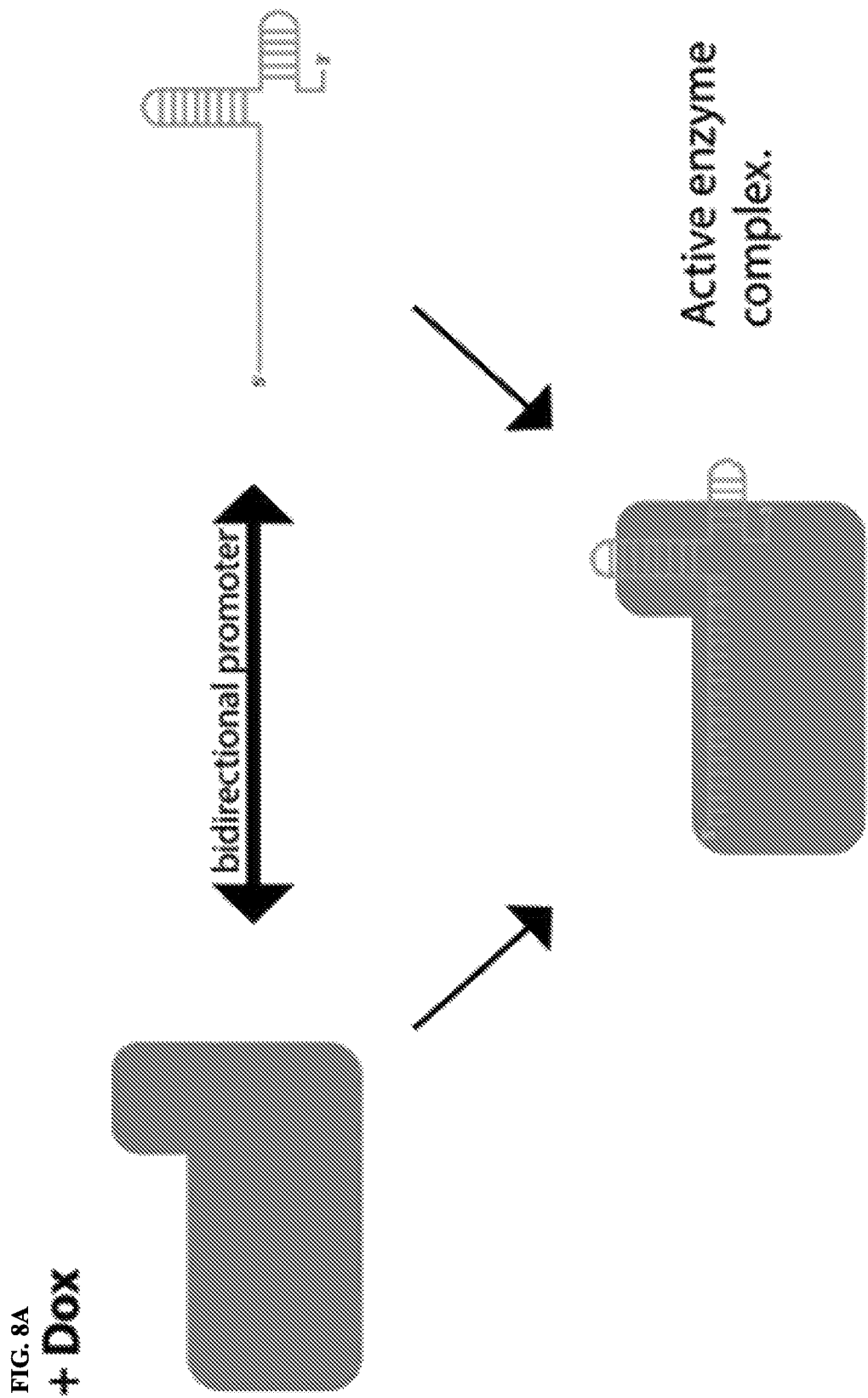

FIG. 8 comprises two panels, A and B, showing show conditional expression of H1 Pol III expression regulating ribonucleoprotein enzymatic activity. FIG. 8A shows the active enzyme complex in the presence of doxycycline. FIG. 8B shows the inactive enzyme complex in the absence of doxycycline.

Figure 9A:
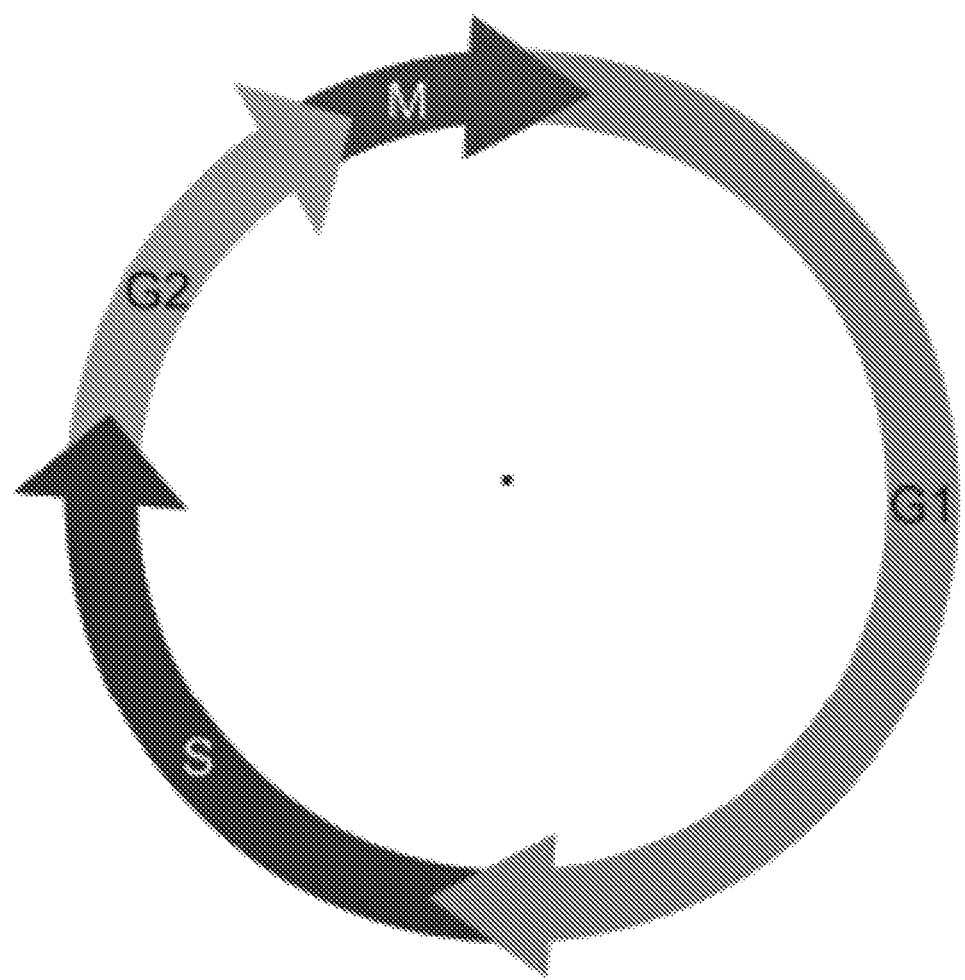
Figure 9B:
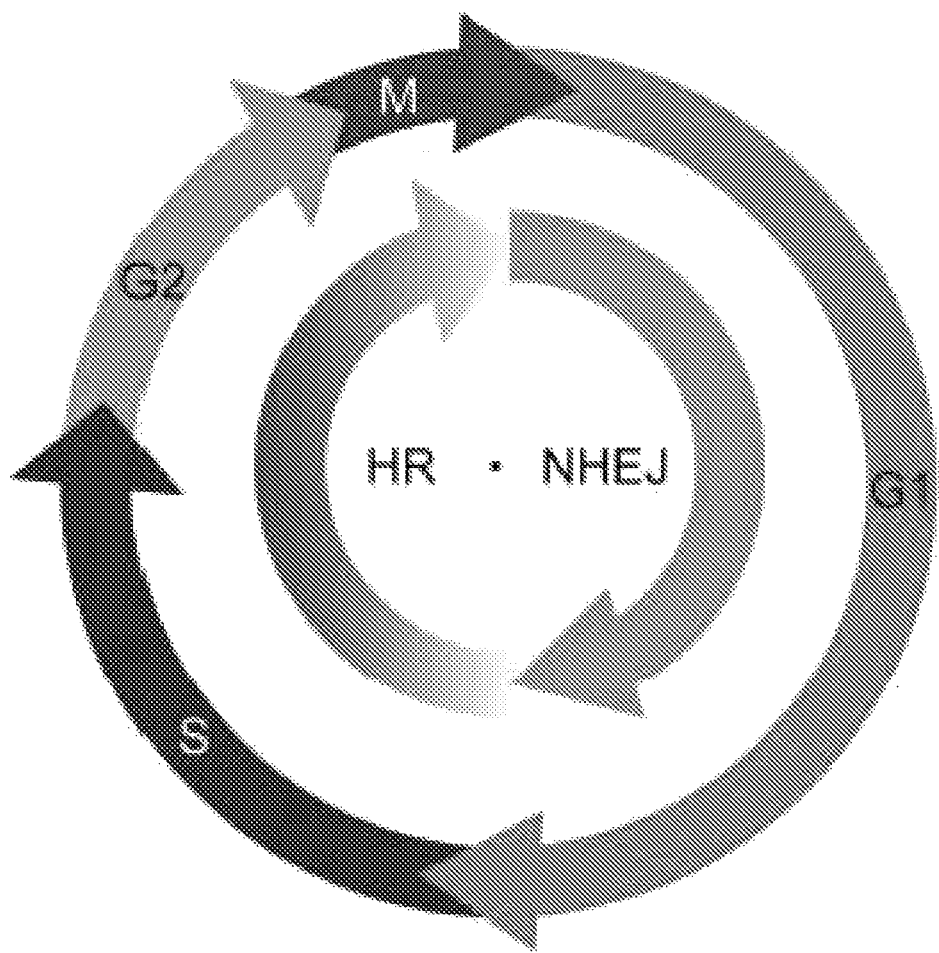
Figure 9C:
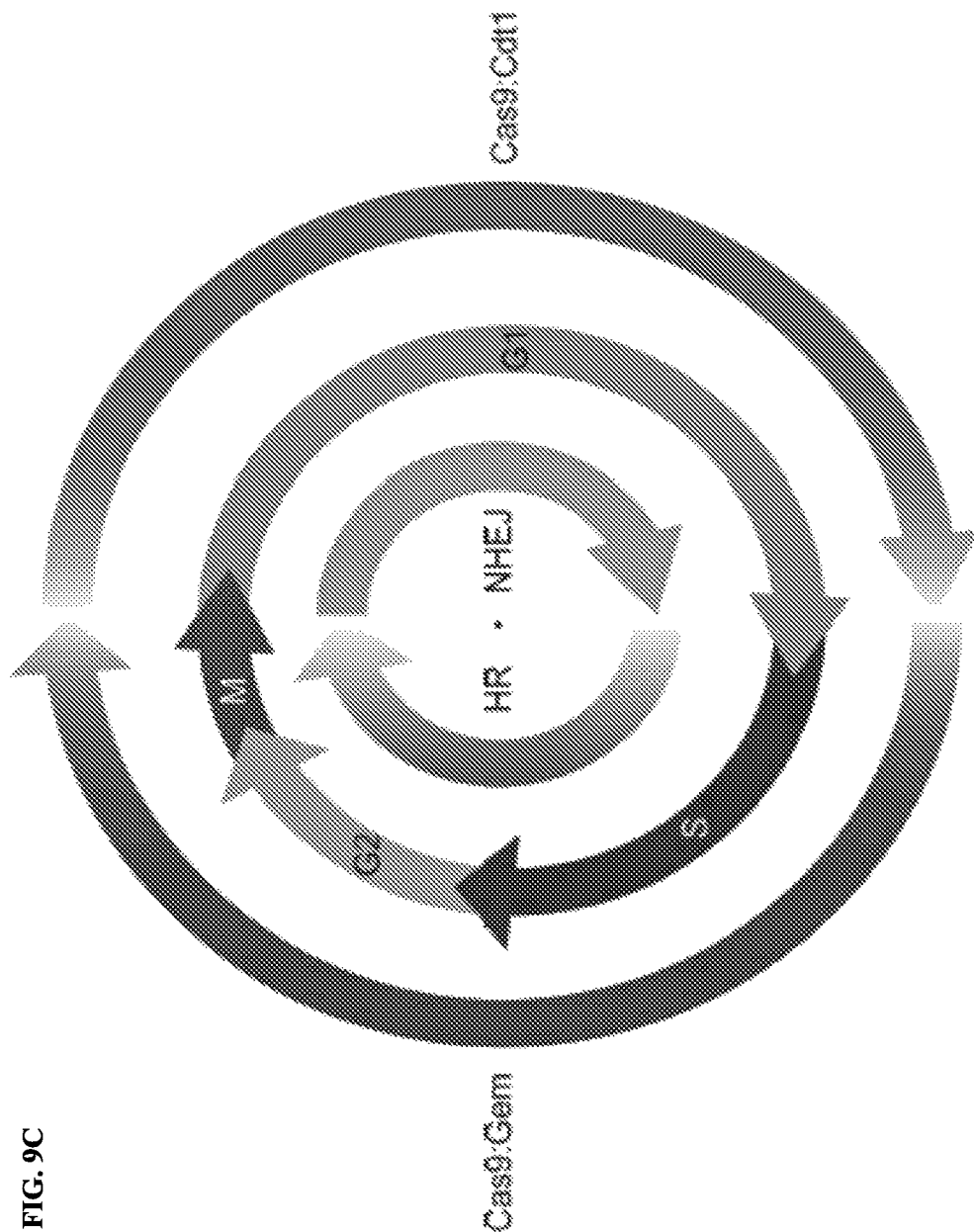
Figure 10A:
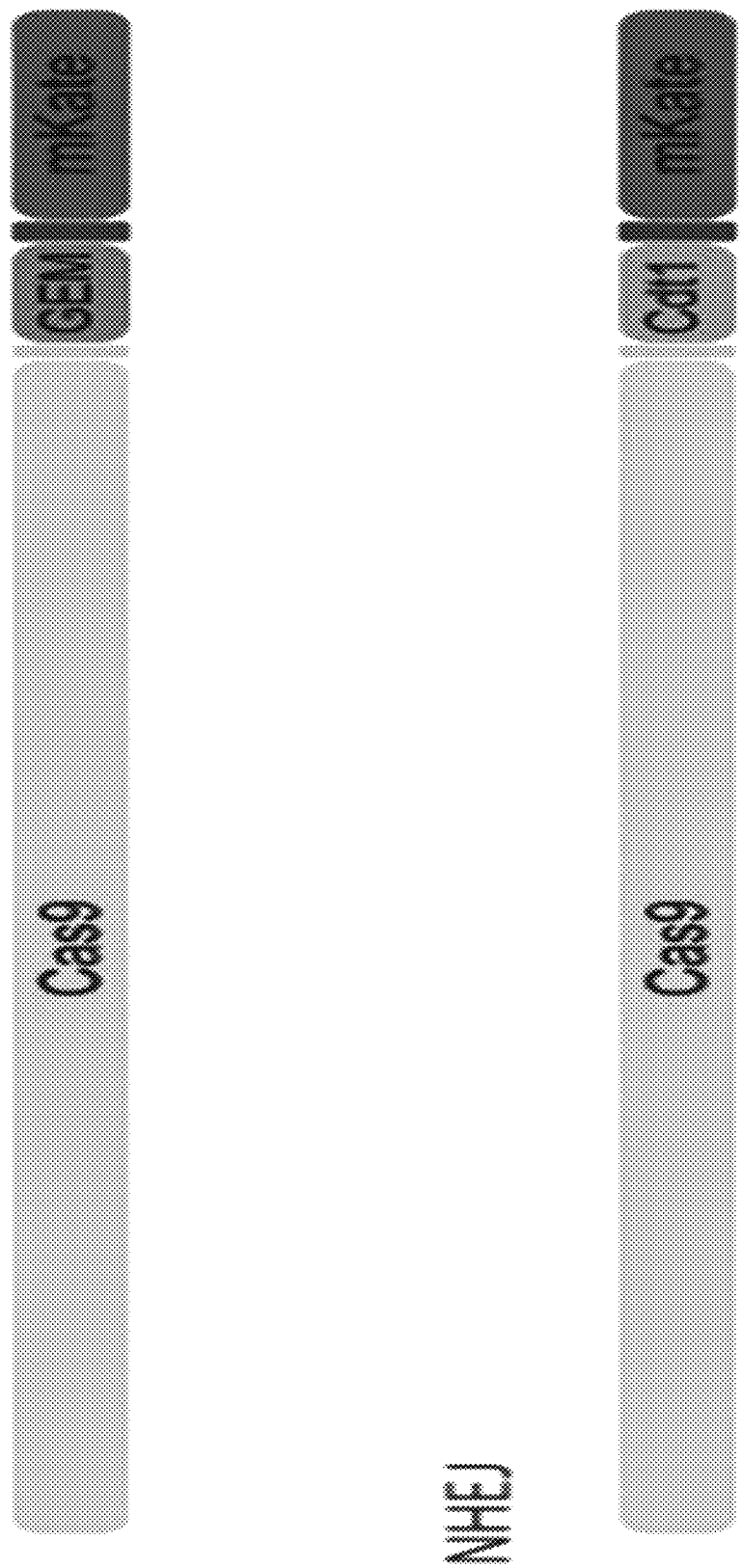
Figure 10C:
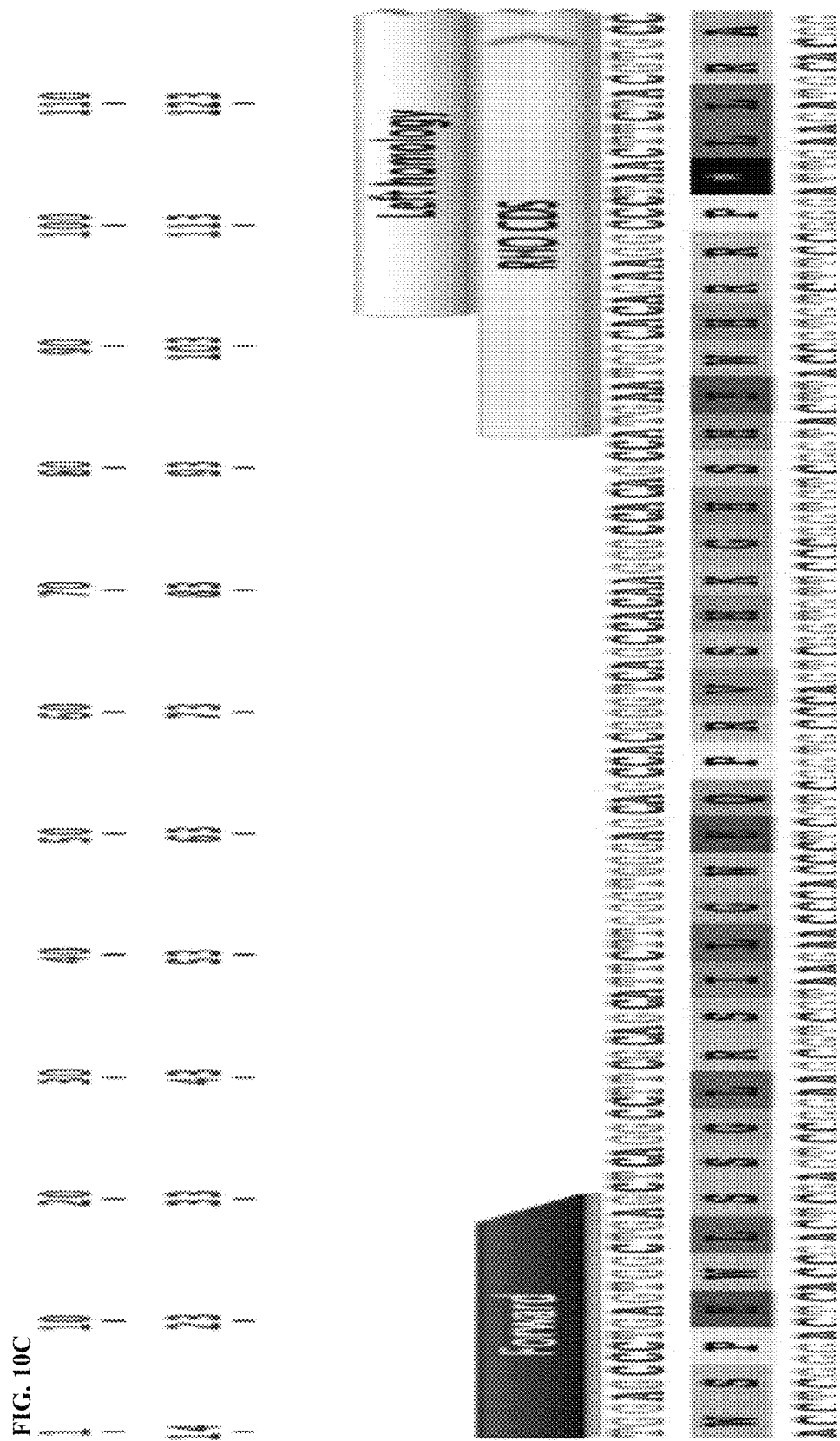
Figure 10C:
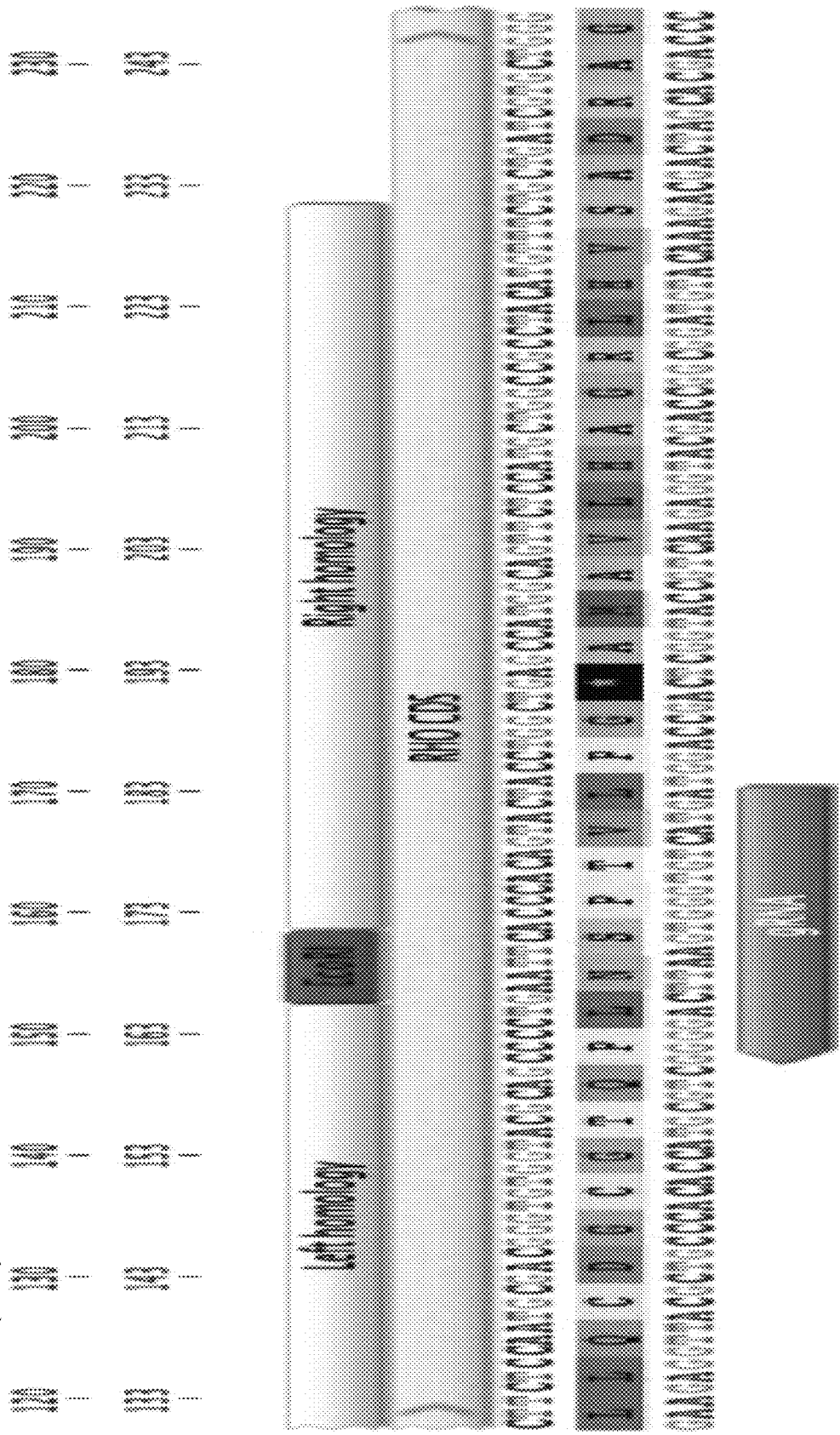
Figure 10C:
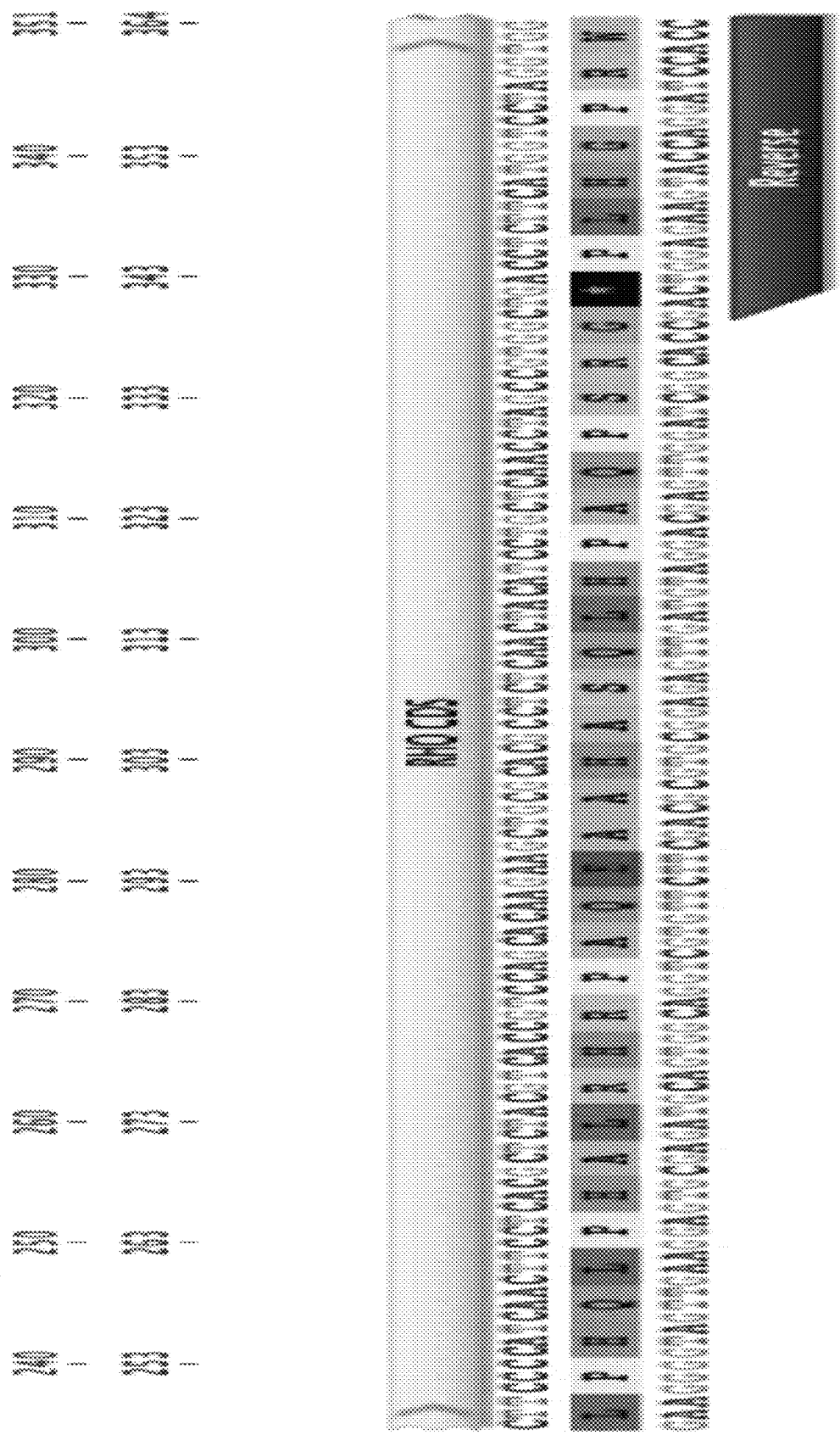

FIG. 9 comprises three panels, A, B, and C, showing a schematic of the cellular response to DNA breaks. FIG. 9A shows that the cellular response to DNA breaks is modulated by the cell-cycle. FIG. 9B shows that the phase of the cell-cycle largely dictates the choice of DNA pathway. FIG. 9C shows that RNA-directed nucleases can be fused to either hGEM1 or hCDT1 domains, resulting in cell-cycle dependent regulation of these proteins.

FIG. 10 comprises three panels, A, B, and C. FIG. 10A shows the cell-cycle regulated construct that is active during S, G2 and M phase (top), and the cell-cycle regulated construct that is active during G1 phase (bottom). FIG. 10B shows the oligo sequence used to knock-in an EcoRI site into the Rhodopsin gene, and the location of the CRISPR target and cut site (SEQ ID NOS: 132 and 133). FIG. 10C shows the sequence after successful HDR into the Rhodopsin gene and the incorporation of an EcoRI site into the gene (SEQ ID NOS: 134-138).

Figure 11A:
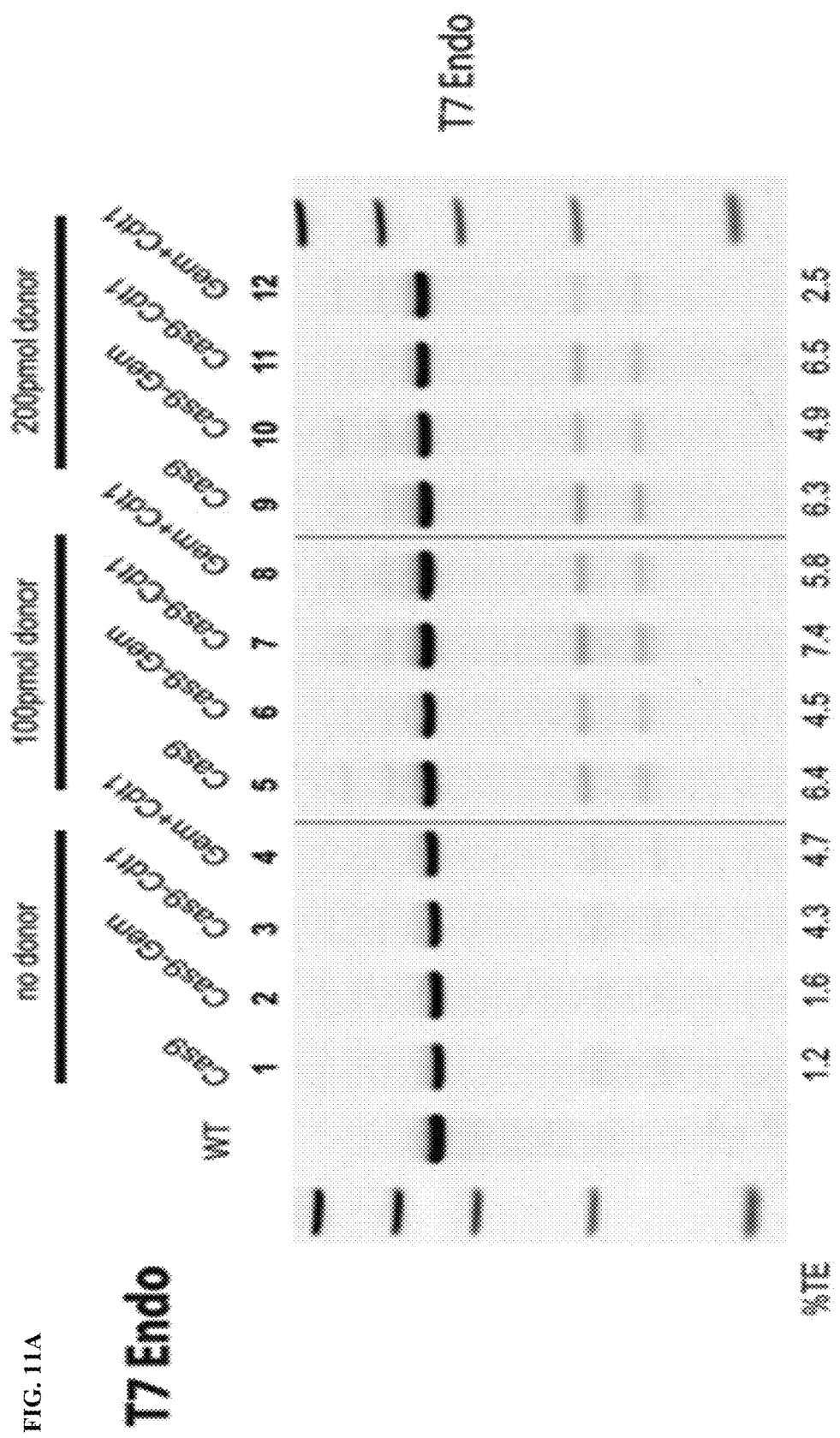
Figure 11B:
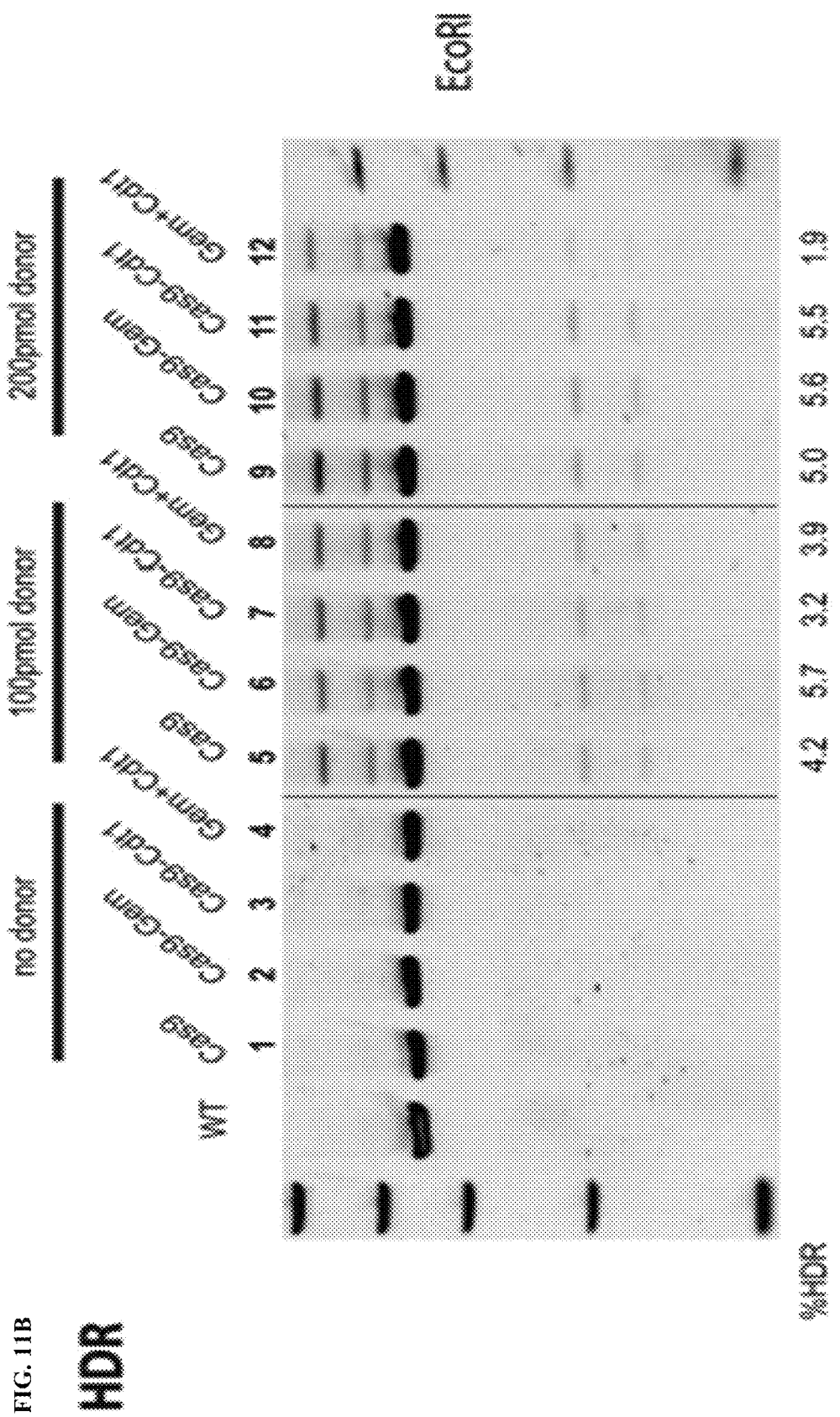
Figure 11C:
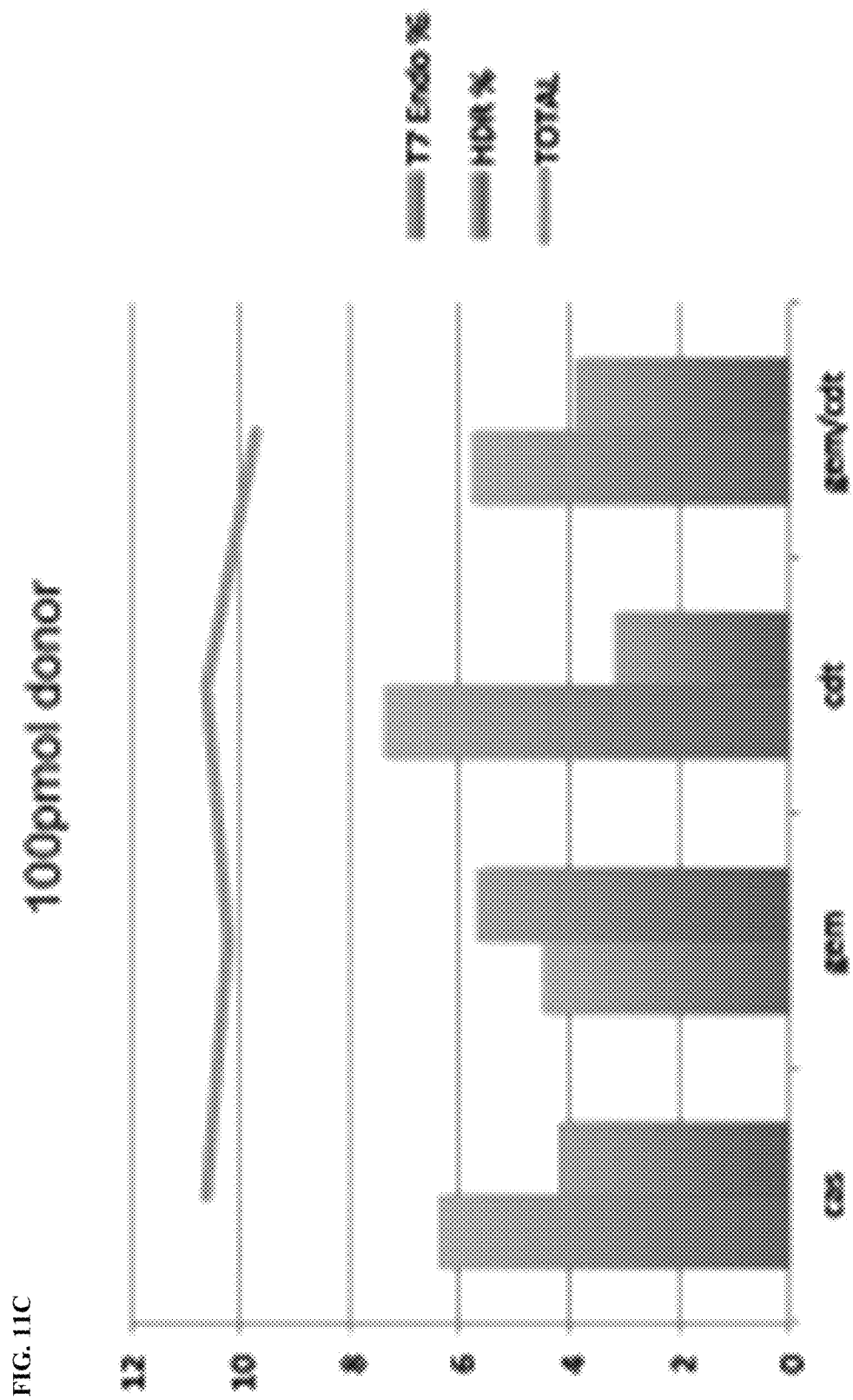

FIG. 11 comprises three panels, A, B, and C. FIG. 11A shows the quantification of NHEJ using T7 EndoI assay for the different cell-cycle regulated constructs and with different amounts of the donor oligo sequence. FIG. 11B shows the quantification of HDR using EcoRI assay for the different cell-cycle regulated constructs and with different amounts of the donor oligo sequence. FIG. 11C shows the quantification of the NHEJ and HDR data. The Gem constructs preferentially induce HDR while Cdt constructs preferentially induce NHEJ. Mixture of both (gem/cdt) is similar Cas9 with no fusion, and the overall rate of NHEJ and HDR is approximately equal across all conditions, as is expected.

Figure 12A:
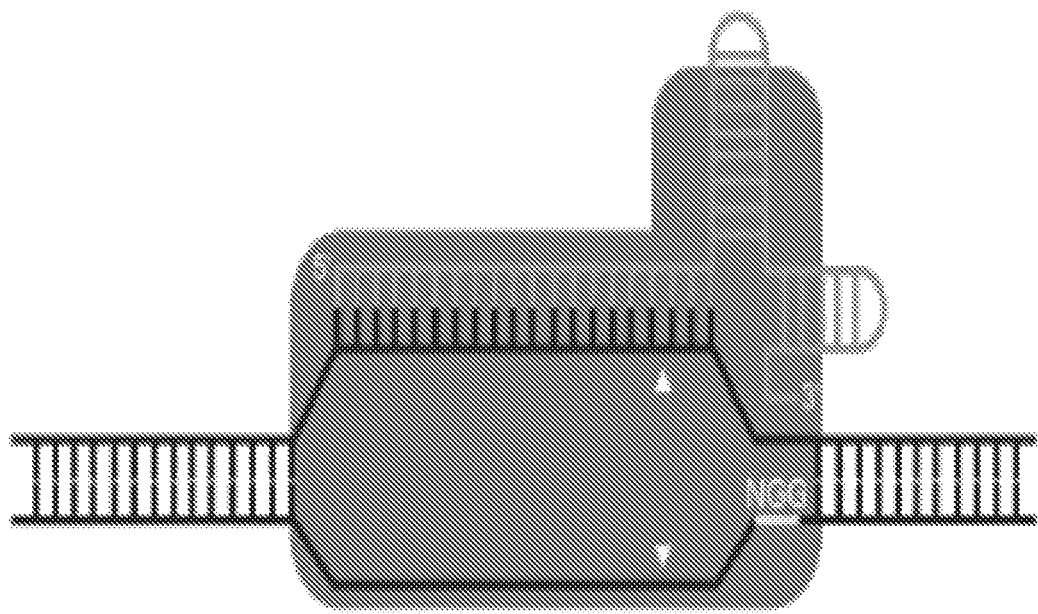
Figure 12B:
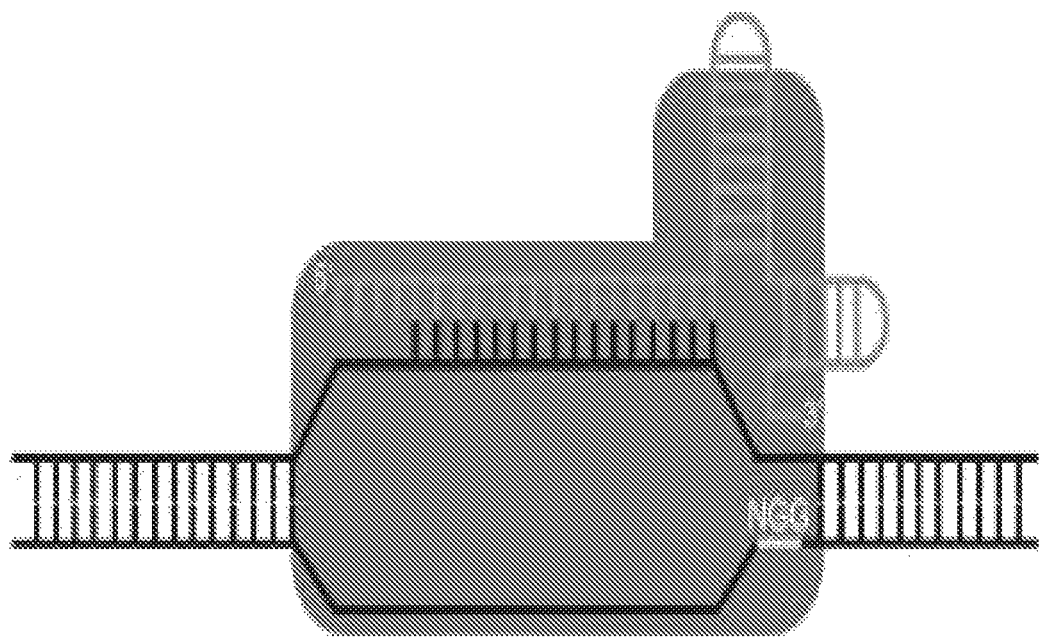

FIG. 12 comprises two panels, A and B, showing auto-regulation of RNA-guided nucleases using partial target sites. FIG. 12A shows Cas9 with perfect complementarity at a target site results in DNA cleavage (white arrows). FIG. 12B shows Cas9 with extensive base pairing but without complementarity still binds, however there is no DNA cleavage activity.

Figure 13A:
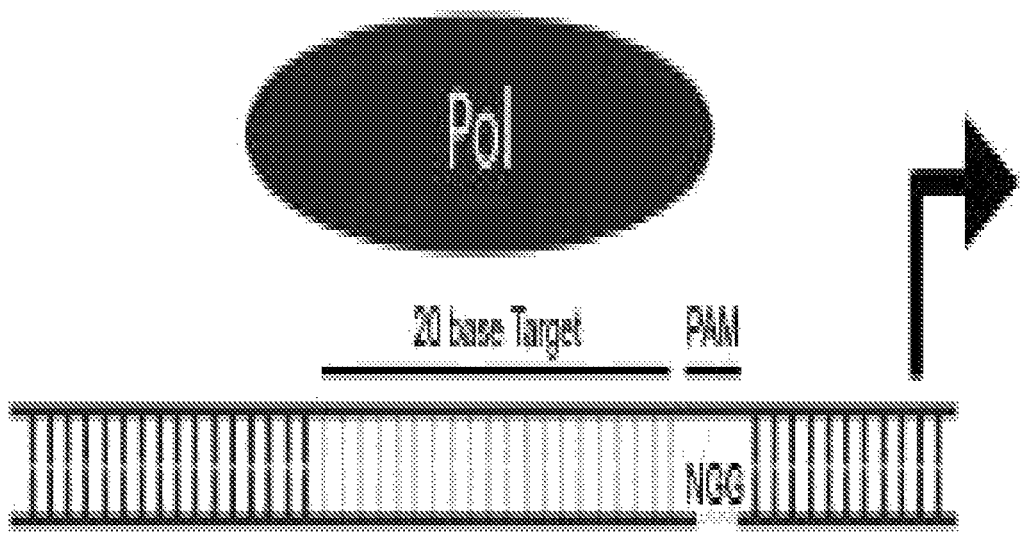
Figure 13B:
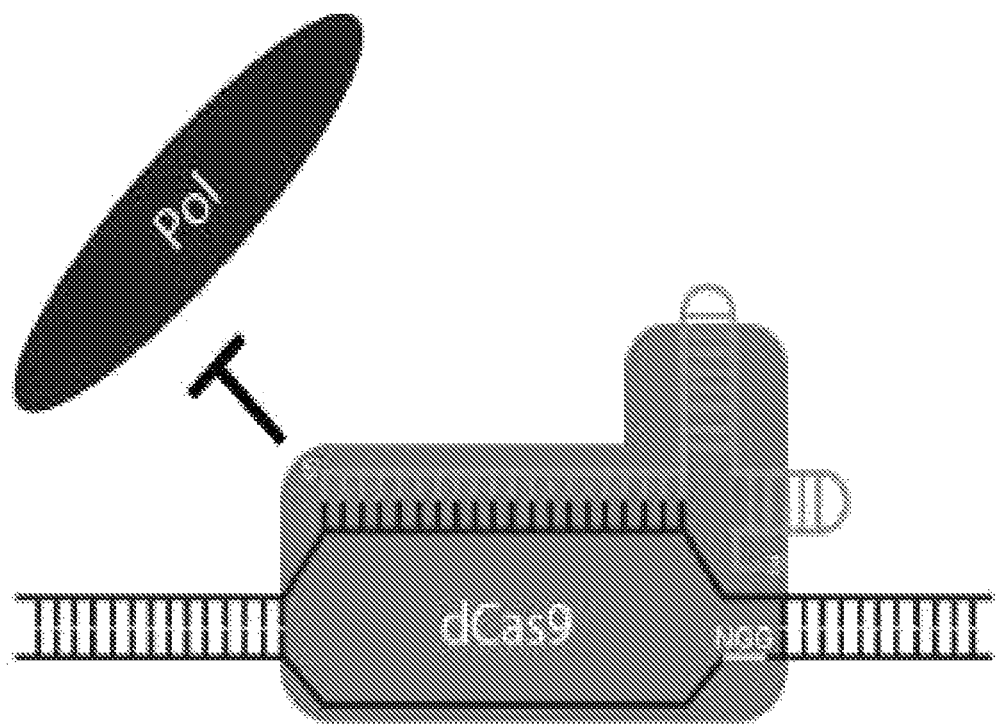
Figure 13C:
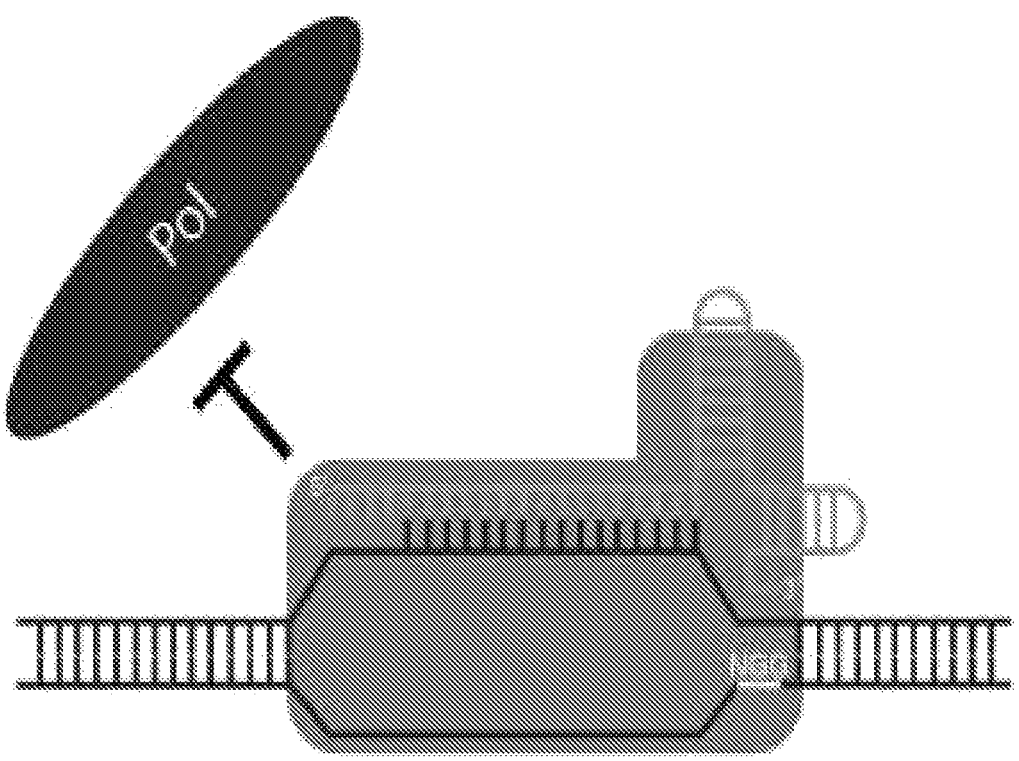

FIG. 13 comprises three panels, A, B, and C, showing auto-regulation of RNA-guided nucleases using partial target sites. FIG. 13A shows polymerase binding to a 20 base target sequence. FIG. 13B shows dCas9 (nuclease-dead version of Cas9), binds to DNA but does not cut. When bound to a promoter region and areas of active transcription, this can inhibit transcription, likely due to steric effects. FIG. 13C shows Cas9 with extensive base pairing but without complementarity still binds, however there is no DNA cleavage activity.

Figure 14:
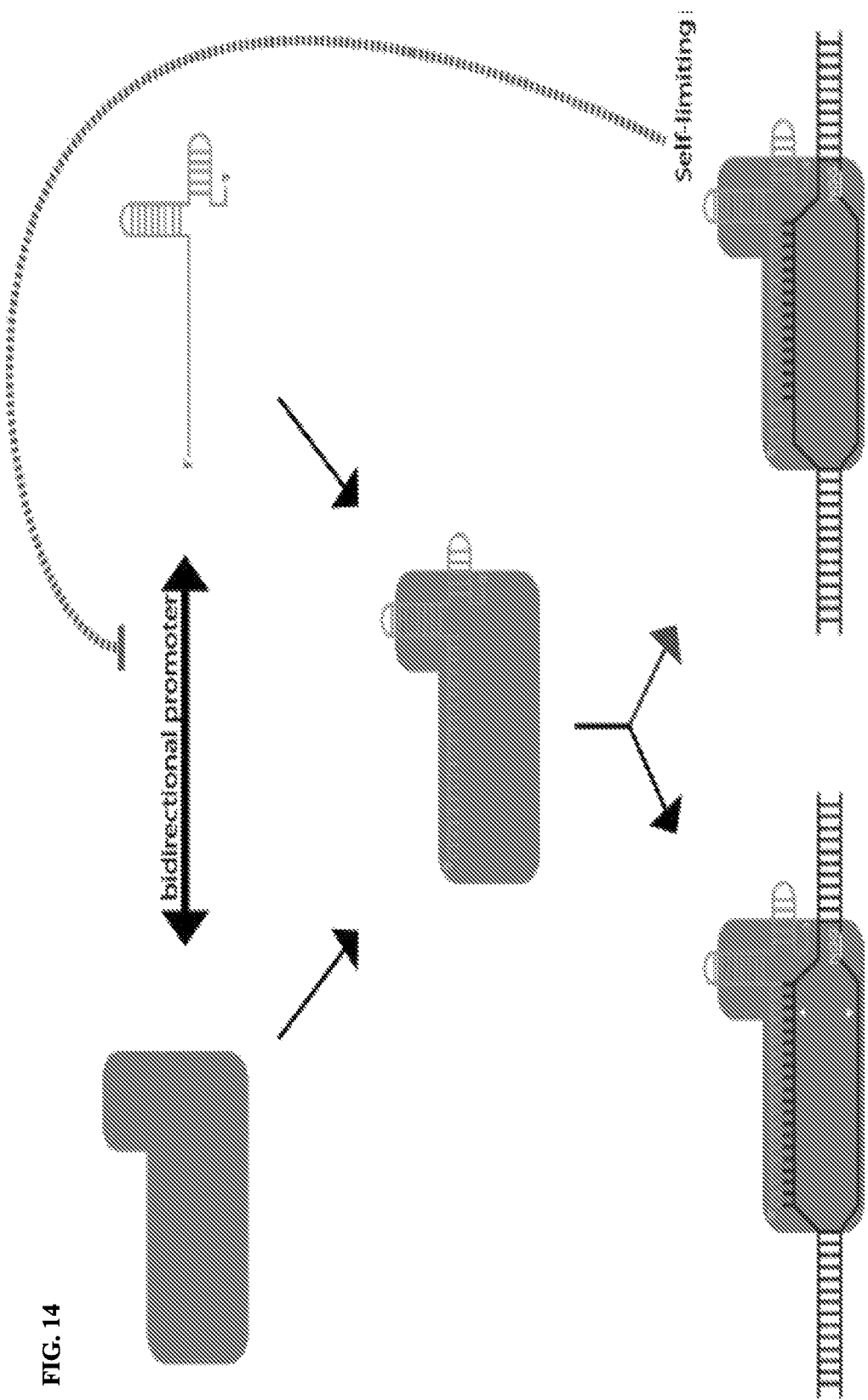

FIG. 14 shows auto-regulation of RNA-guided nucleases using partial target sites. Perfect complementarity at desired site results in DNA cleavage (white arrows) (left bottom depiction). Imperfect complementarity at engineered promoter site results in no DNA cleavage and suppression of its own expression (right bottom depiction).

Figure 15:
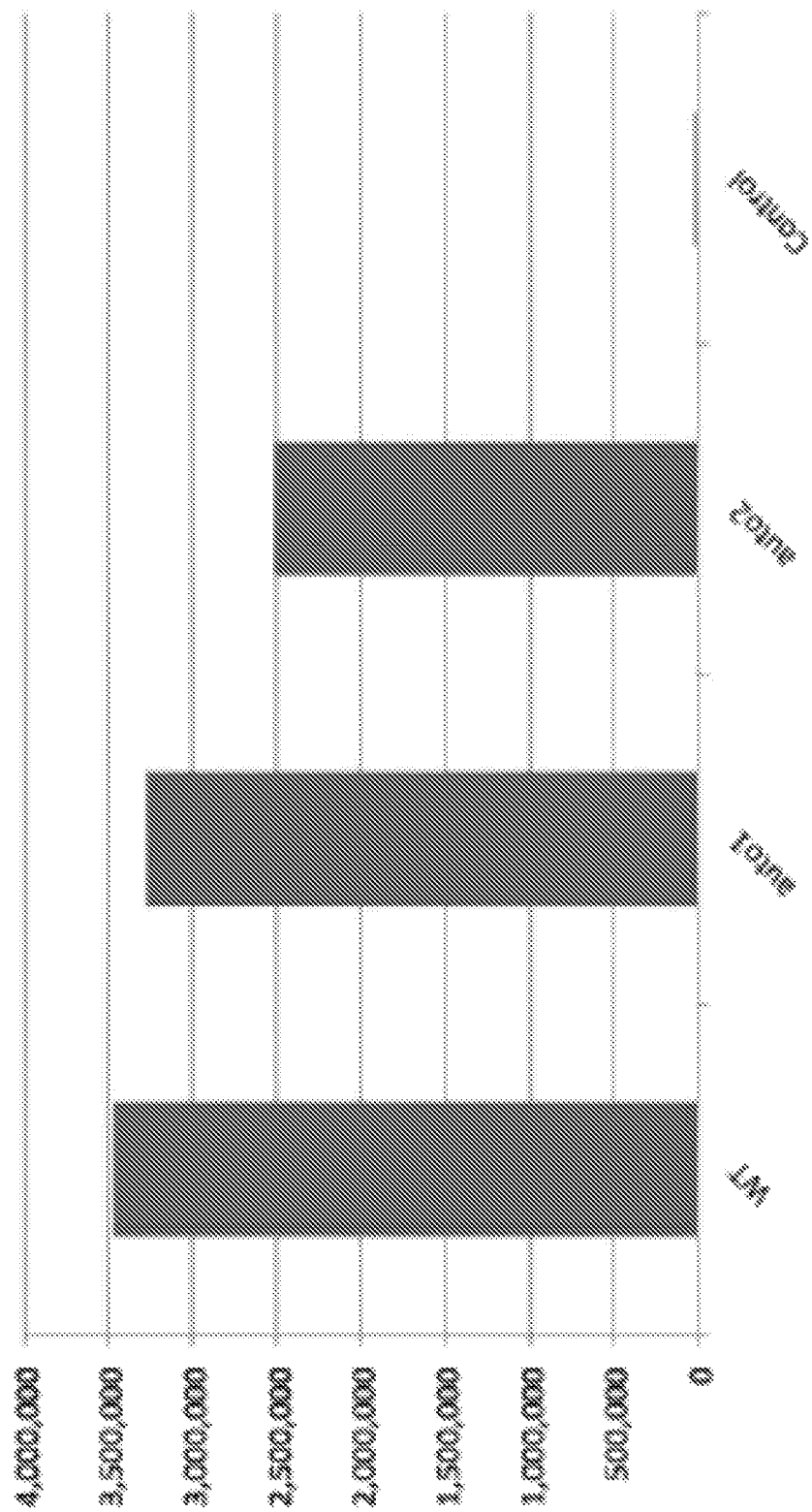

FIG. 15 shows auto-regulation of RNA-guided nucleases using partial target sites:GFP reporter. The bar graphs show that Pol II expression from engineered H1 is not greatly affected by presence of partial target sequences.

Figure 16:
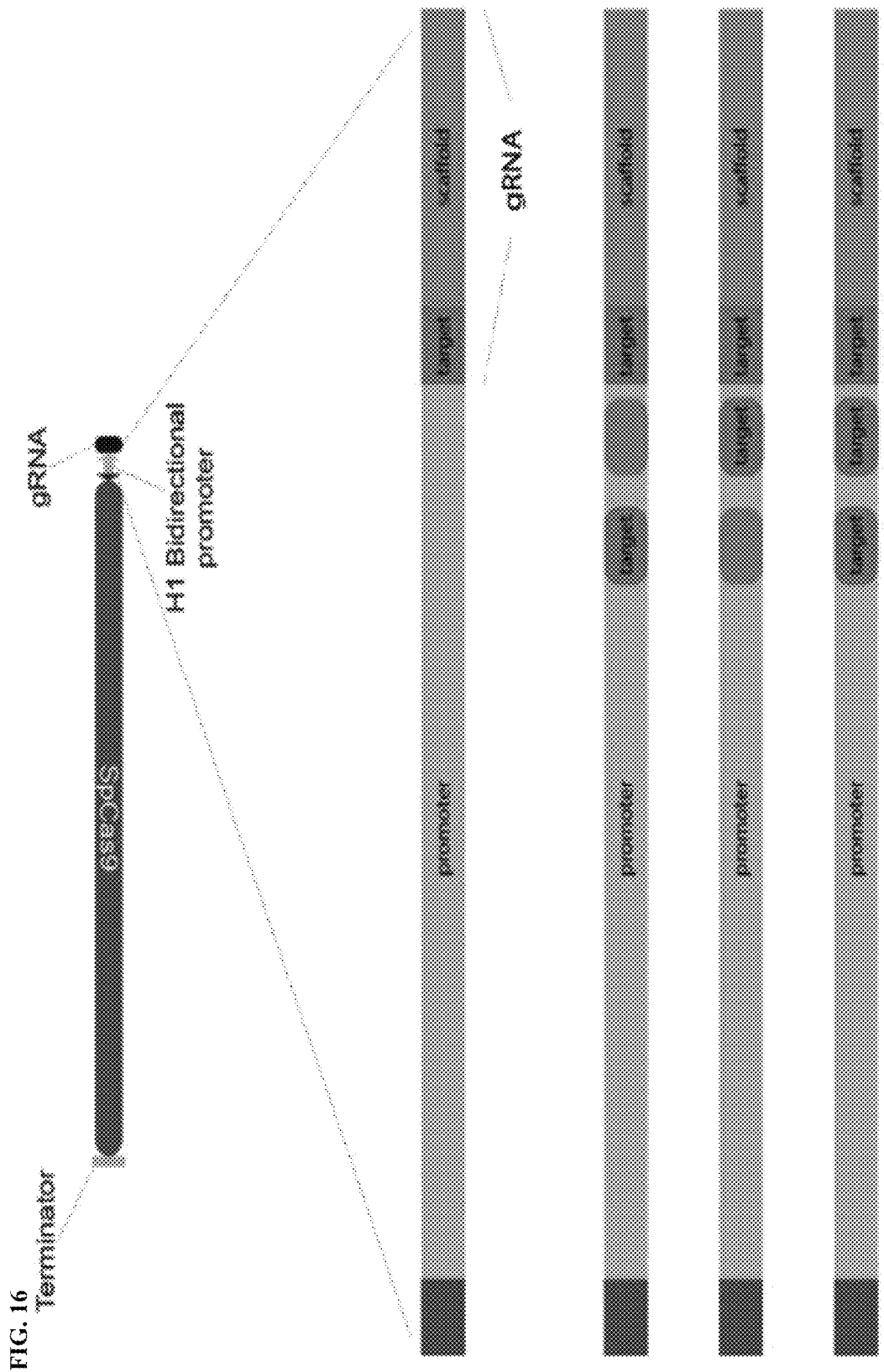

FIG. 16 shows auto-regulation of RNA-guided nucleases using partial target sites:Cas9 and gRNA.

Figure 17B:
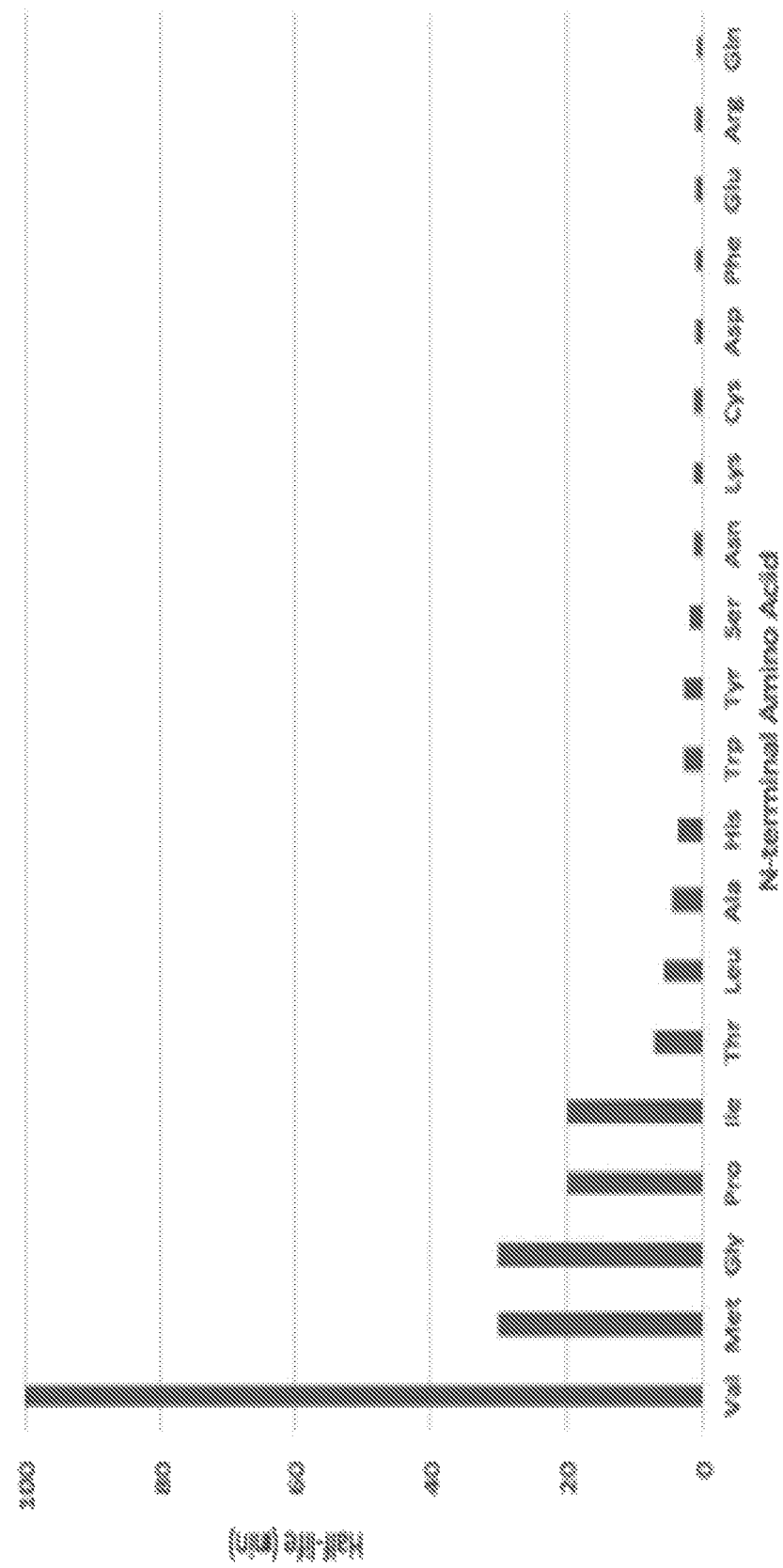
Figure 18:
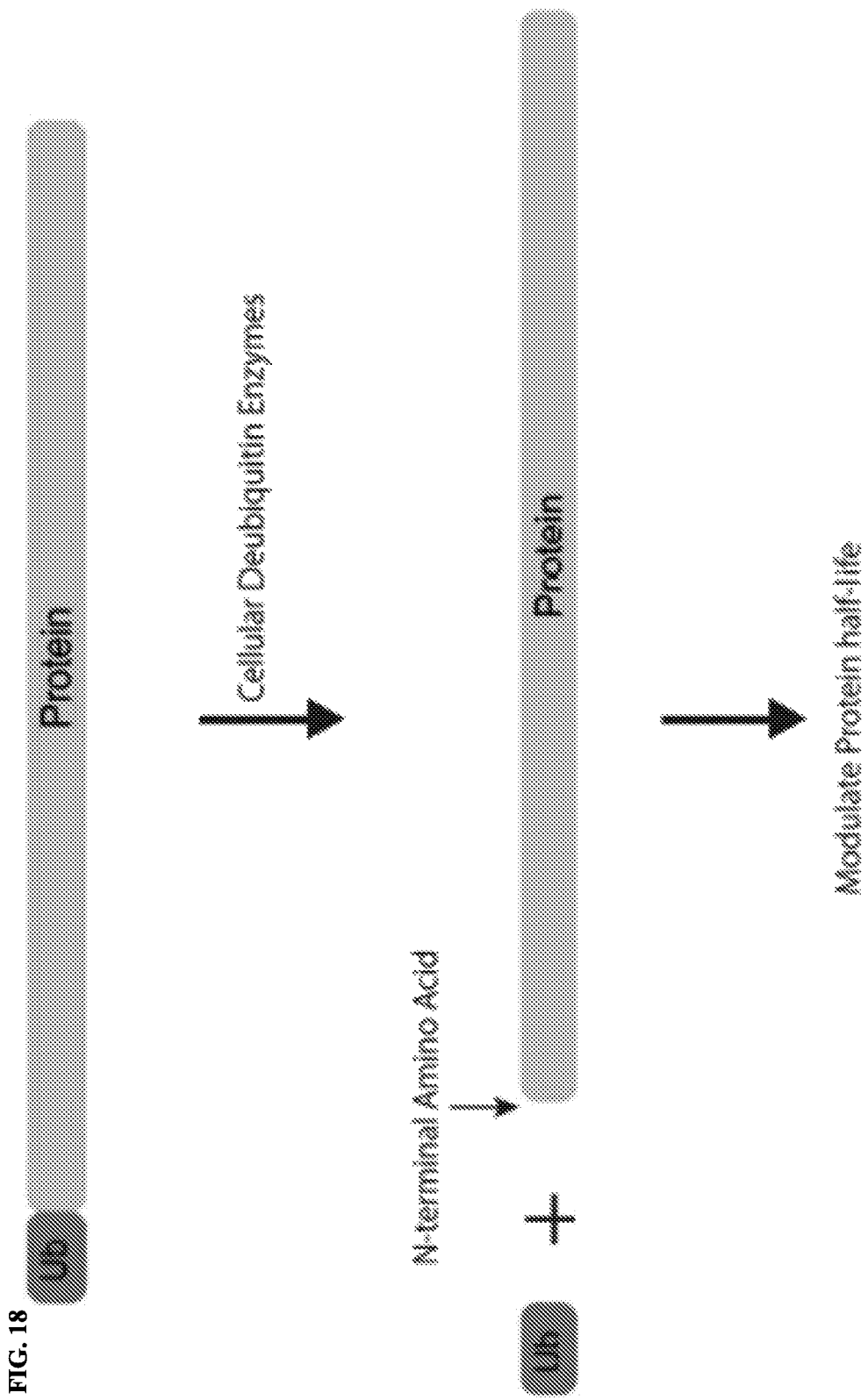

FIG. 17 comprises two panels, A and B. FIG. 17A shows Methionine (Met) followed by a glycine (Gly), proline (Pro), serine (Ser), threonine (Thr), alanine (Ala), valine (Val), or cysteine (Cys) are processed by Methionineaminopeptidases, which cleave off the N-terminal methionine. FIG. 17B shows that the N-end rule serves as an estimation of a proteins half-life within a cell FIG. 18 shows that linear poly-ubiquitin is recognized in the cell by deubiquitin enzymes which cleave the individual Ub peptides. This process can be co-opted to generate specific N-terminal residues by fusing Ub to the N-terminus of any protein.

FIG. 19 comprises two panels, A and B, showing that simple changes in the N-terminal amino acids, either through Met-aminopeptidases, deubiquintation, or alternative methods, can accomplish the regulation of RNA-guided nuclease half-life.

Figure 19A:
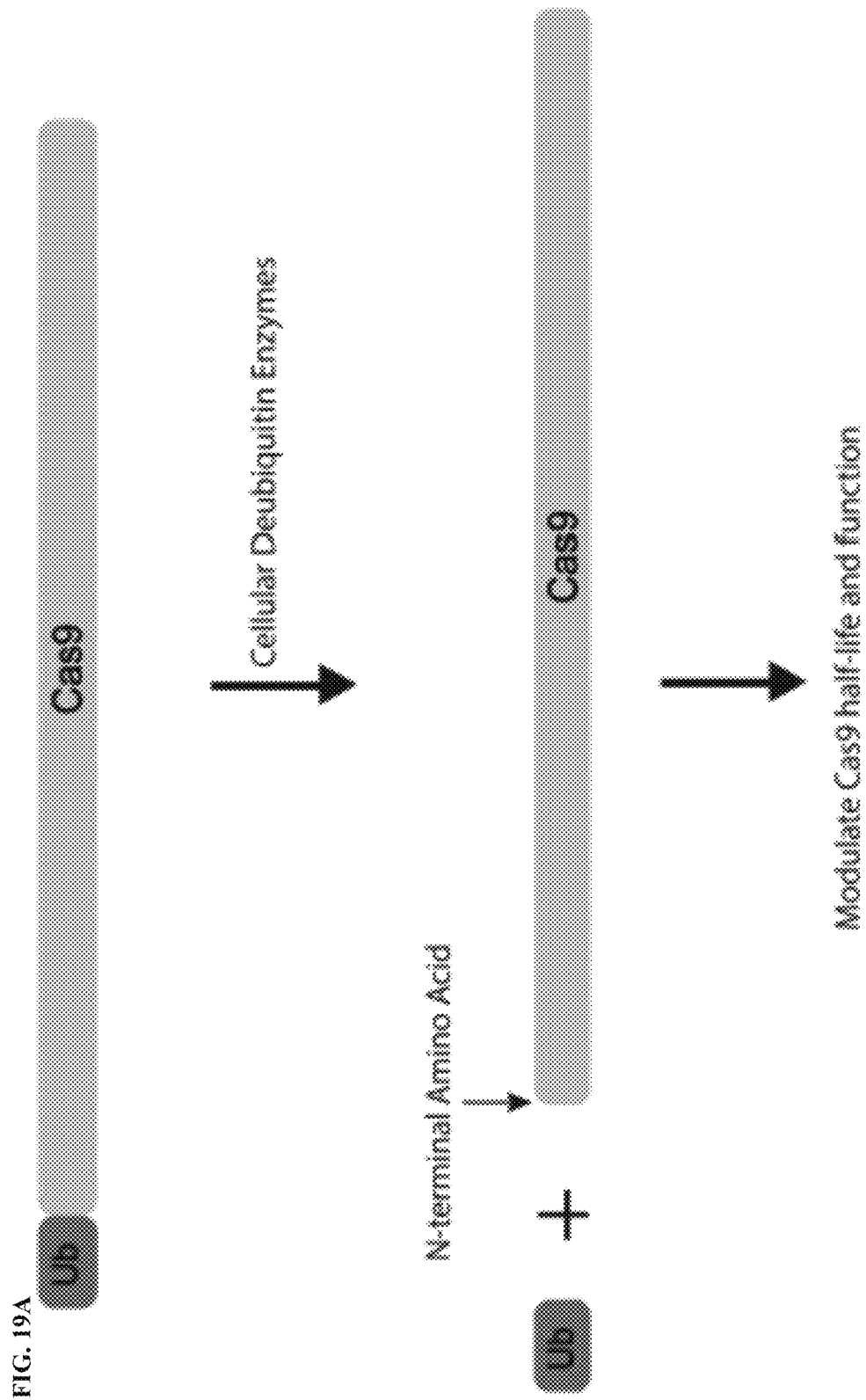

FIGS. 19A and 19B show that the levels of Cas9, an RNA-guided nuclease, can be modulated by the identity of the N-terminal amino acid, by as much as 8-10-fold, a significant range of expression for a nuclease.

Figure 20:
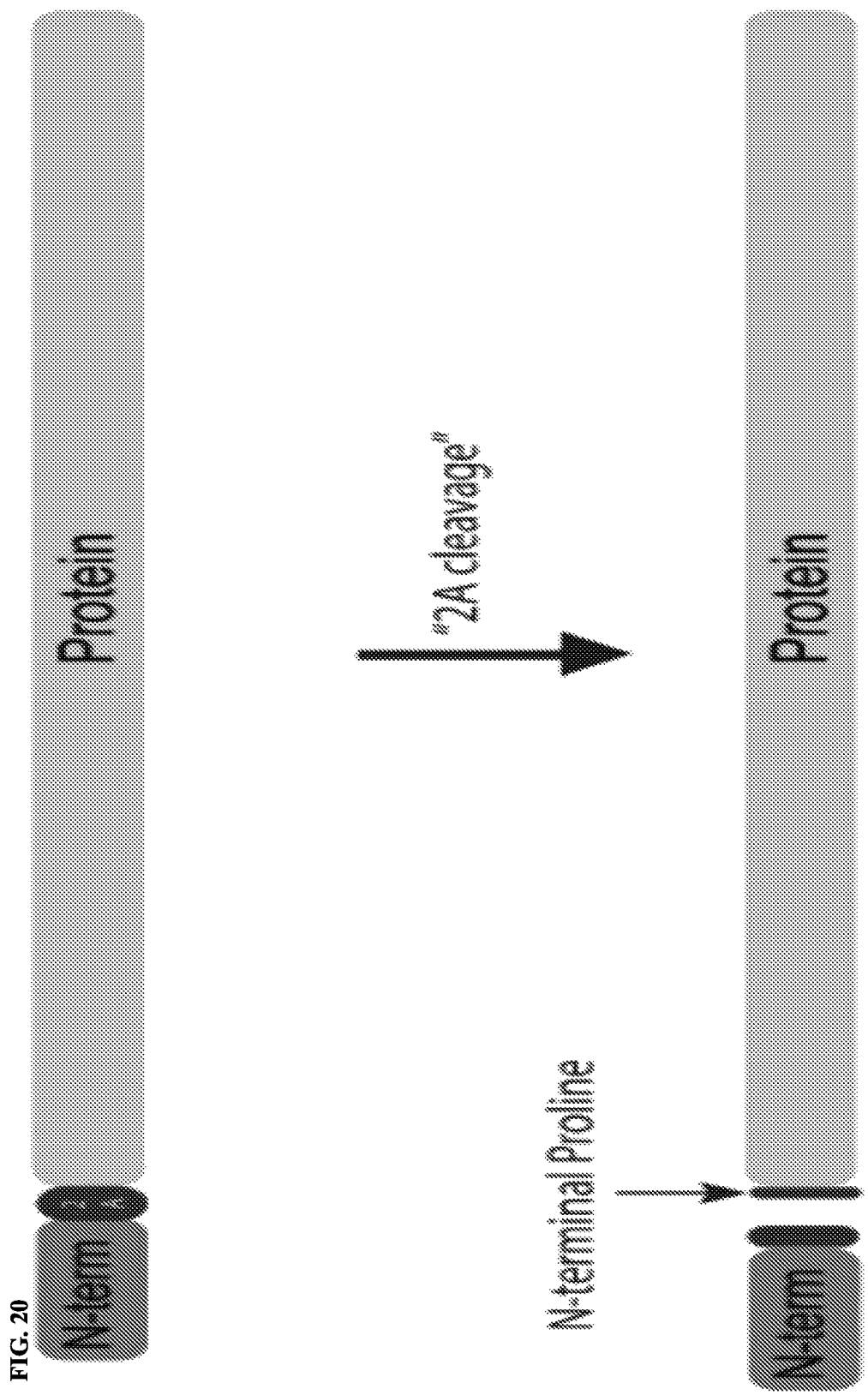

FIG. 20 shows how commonly used 2A peptides can also be leveraged to modulate protein levels in the cell.

Figure 21A:
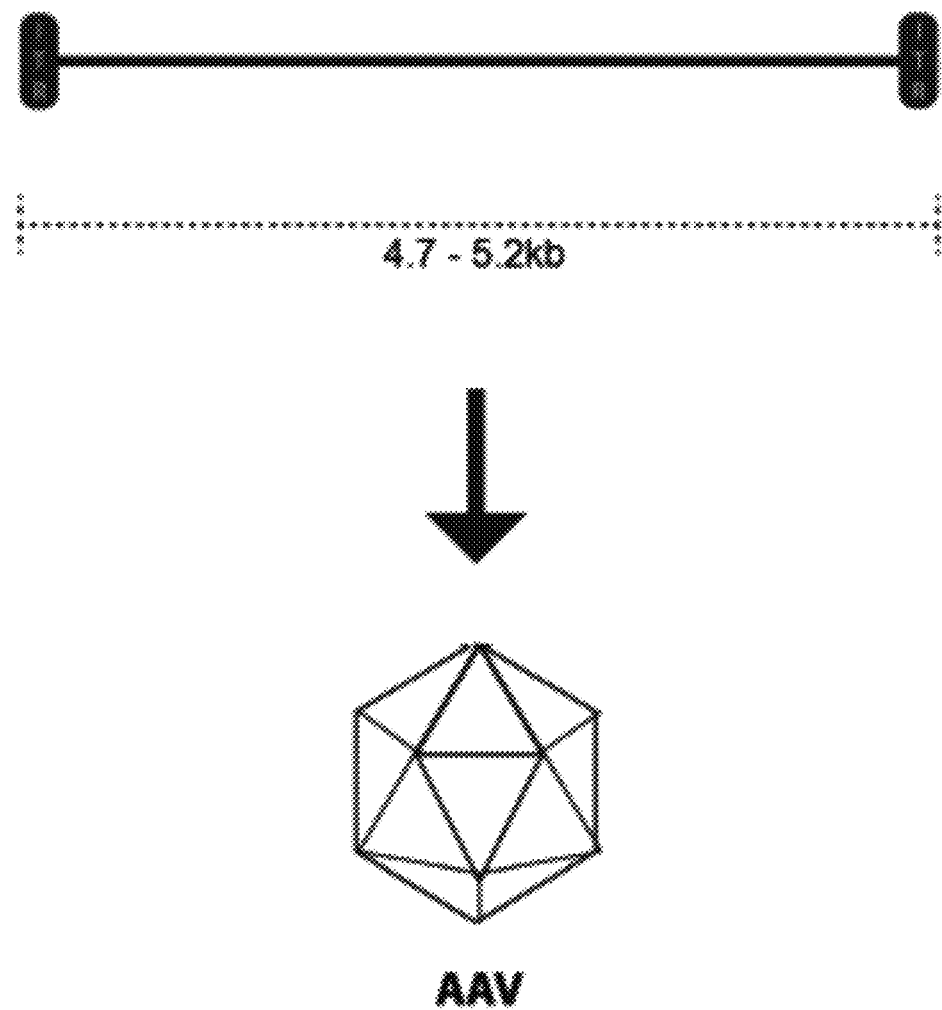
Figure 21B:
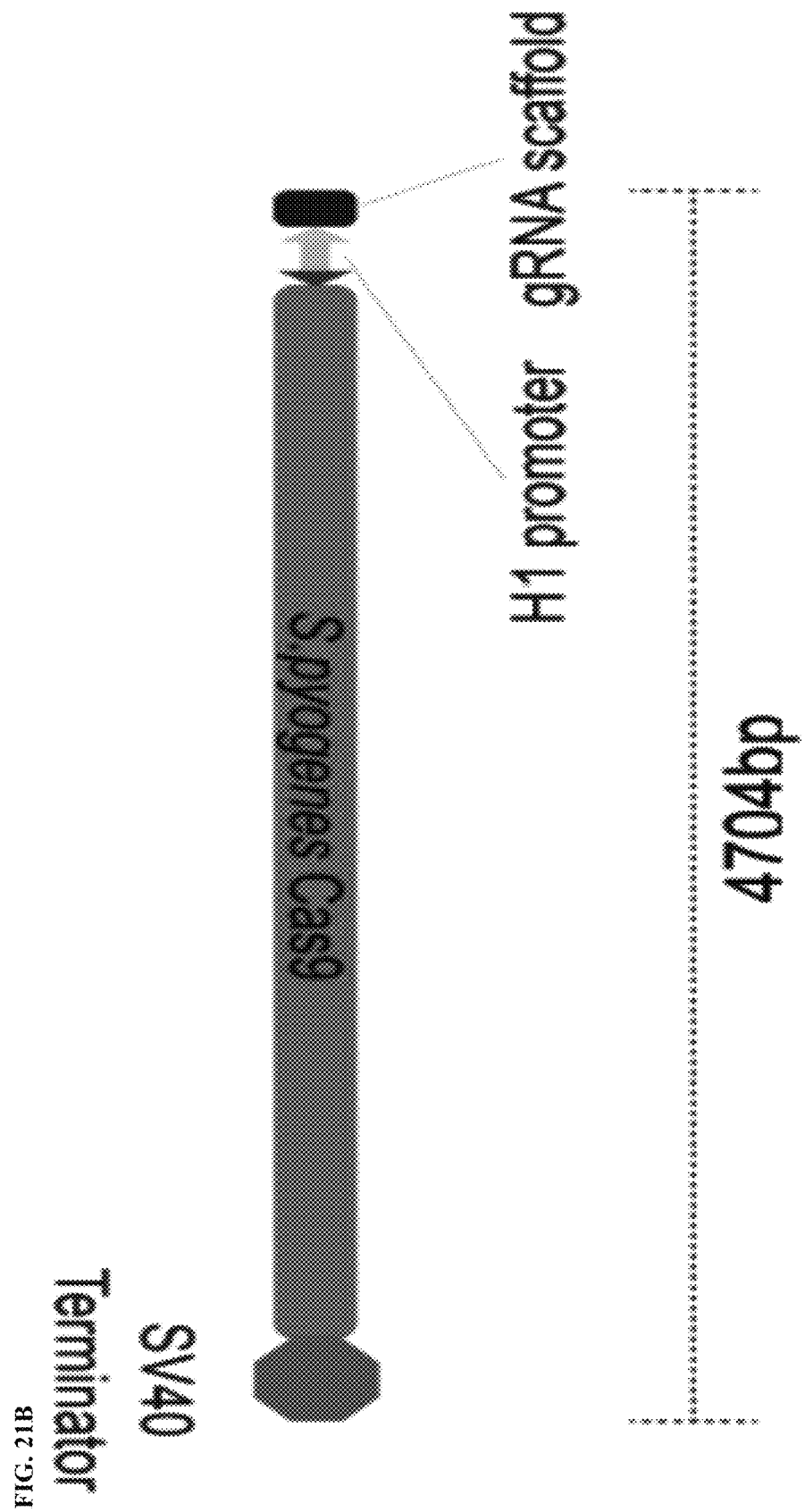
Figure 21C:
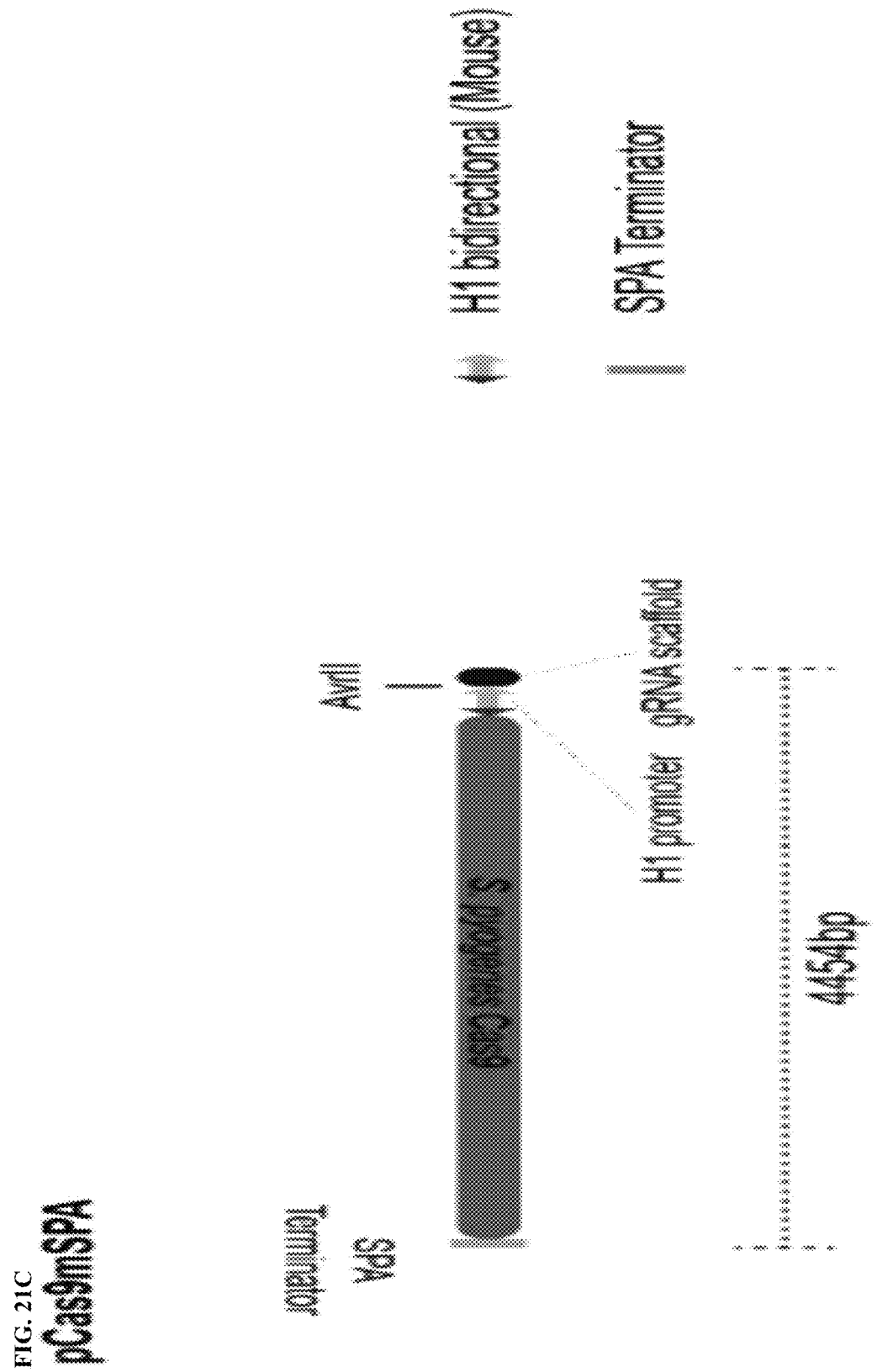
Figure 22A:
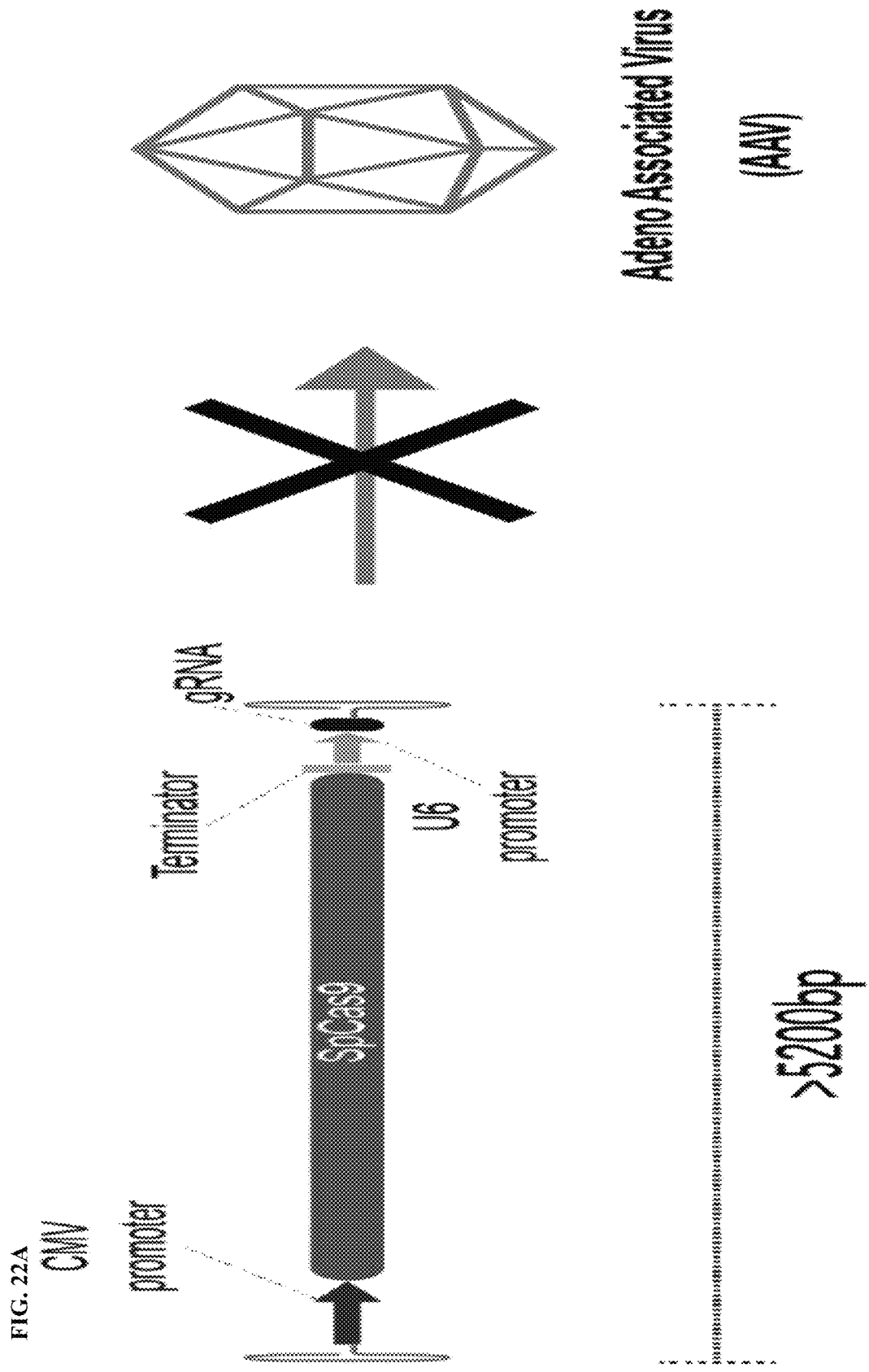
Figure 22A:
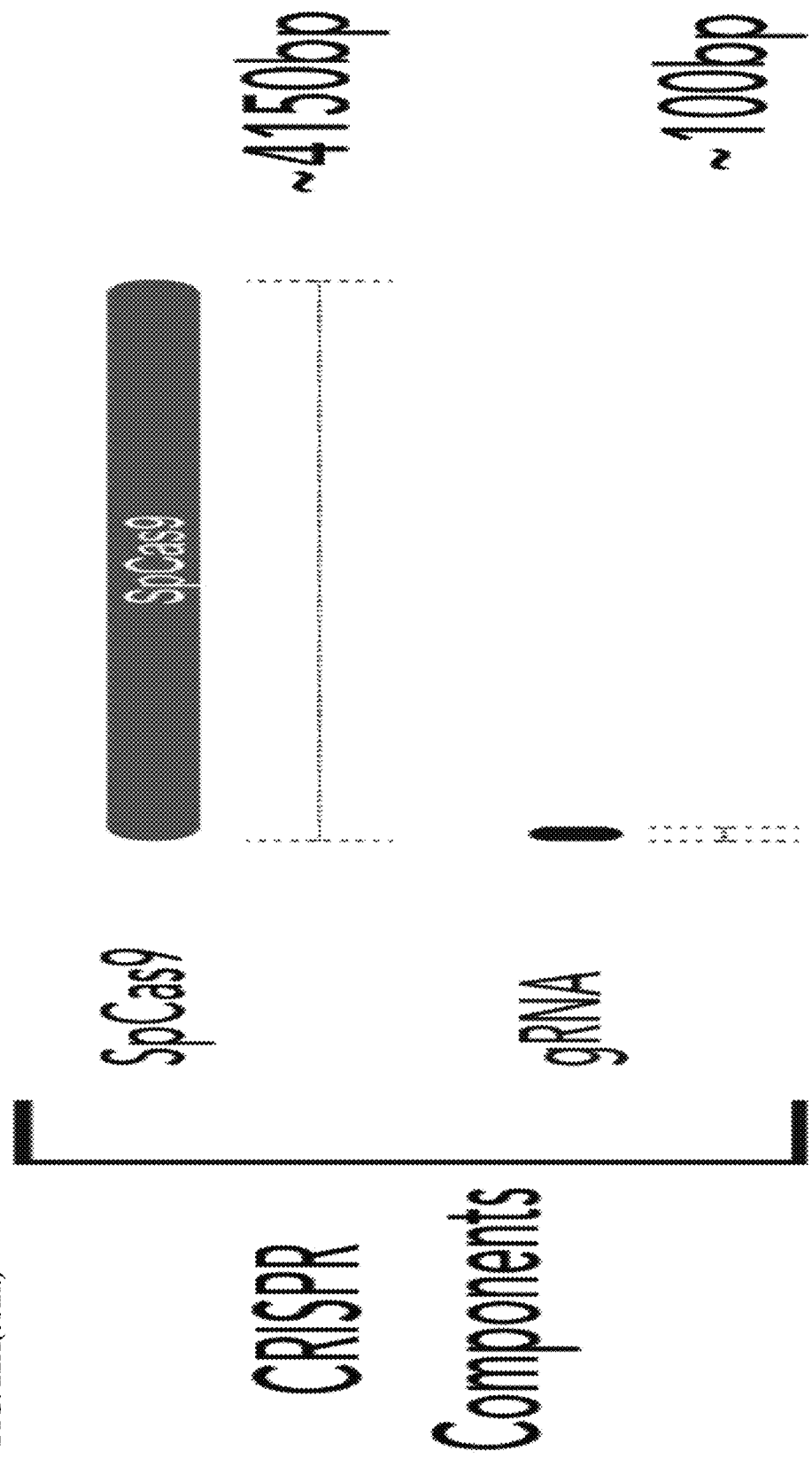
Figure 22A:
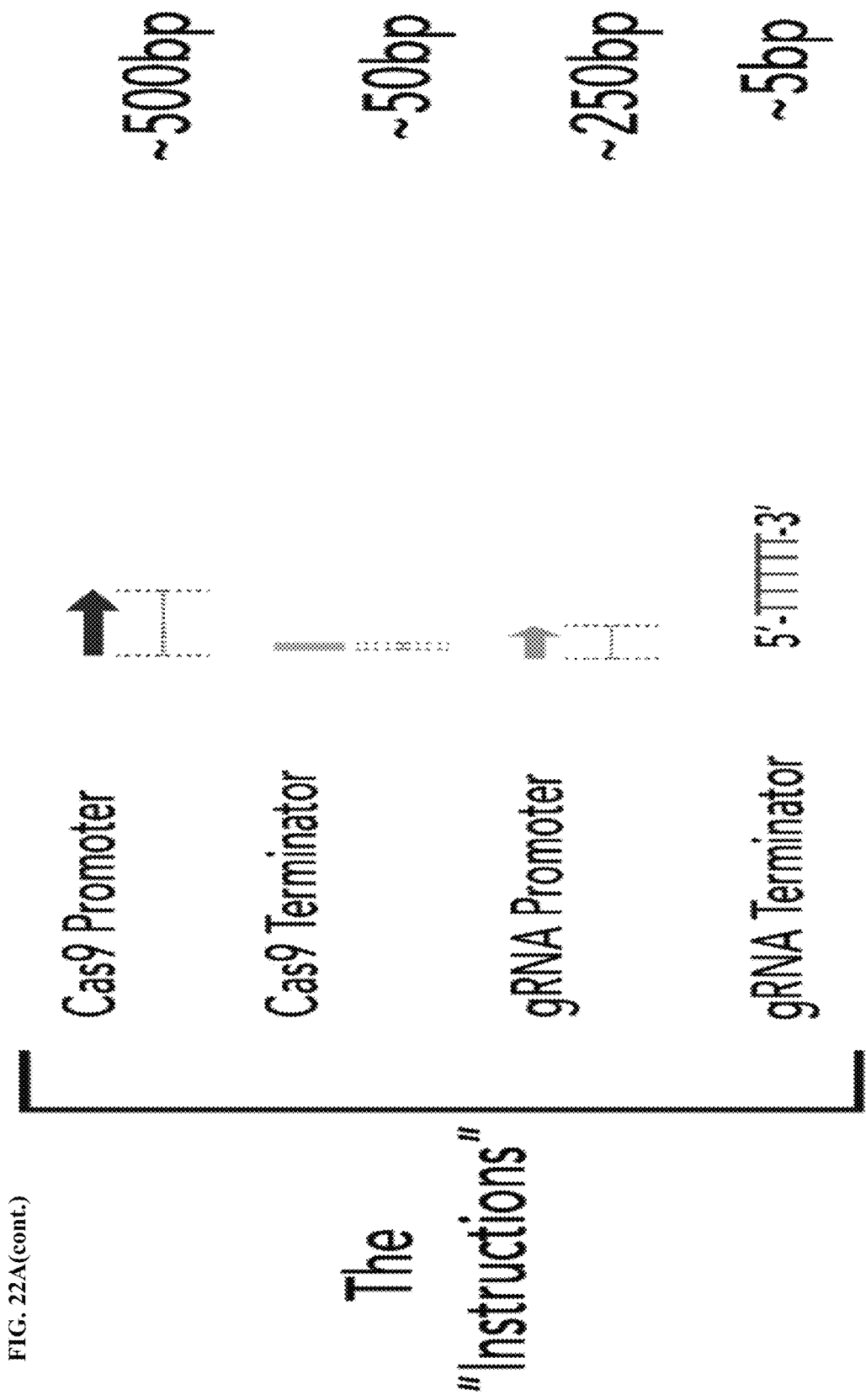
Figure 22A:
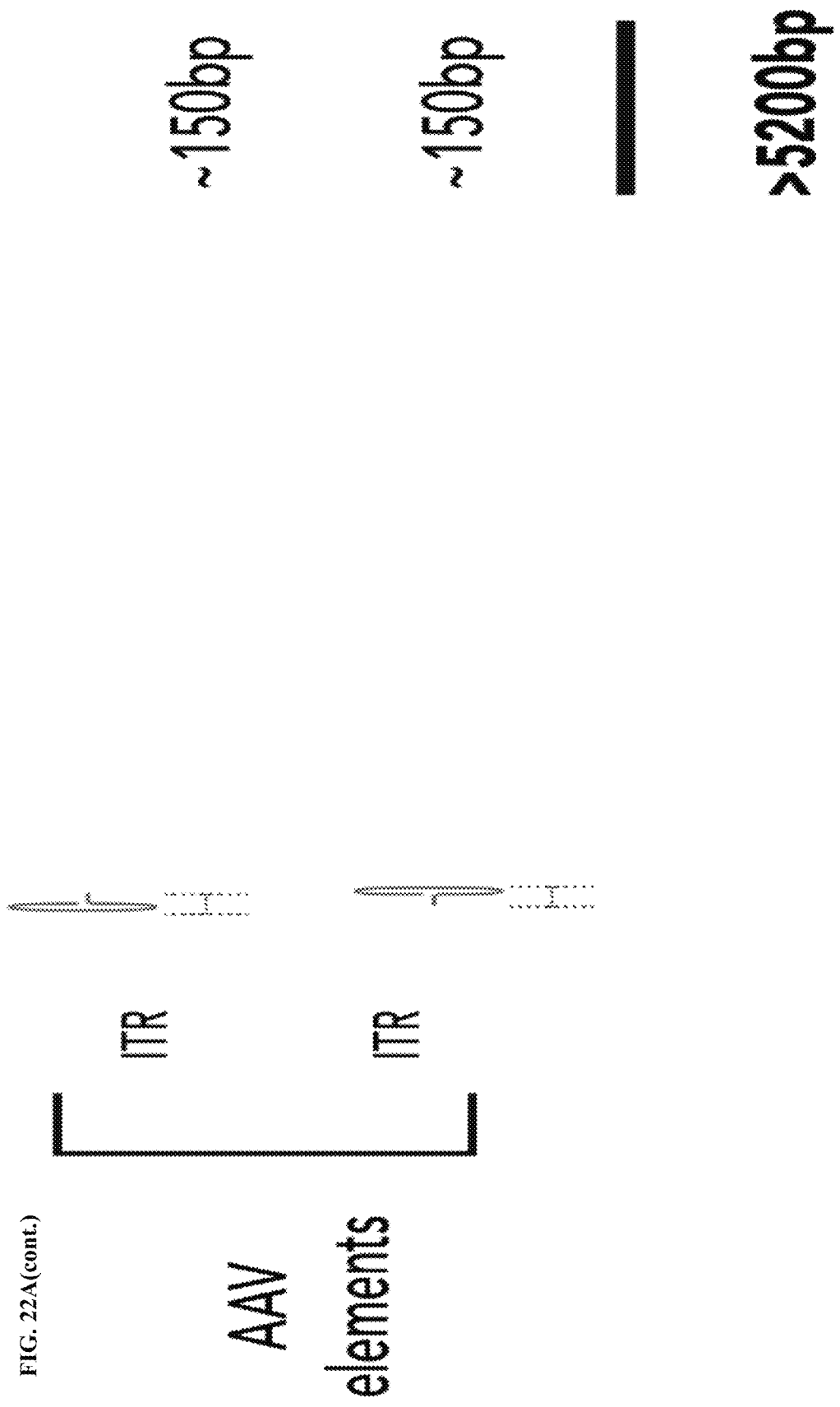
Figure 22C:
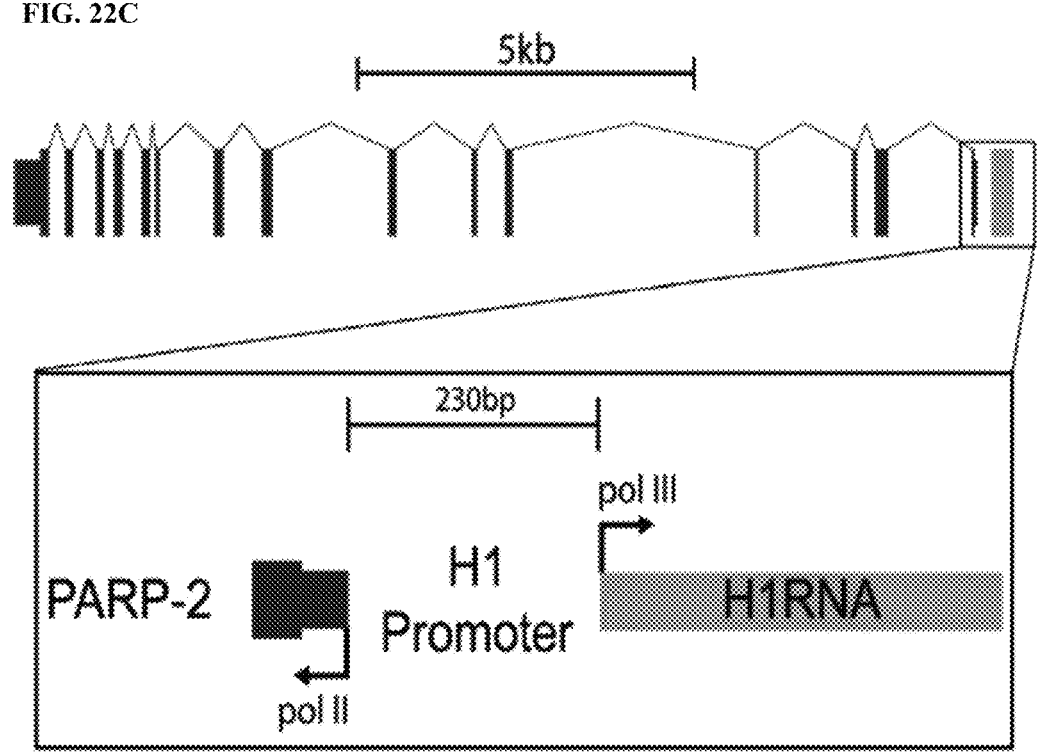
Figure 22D:
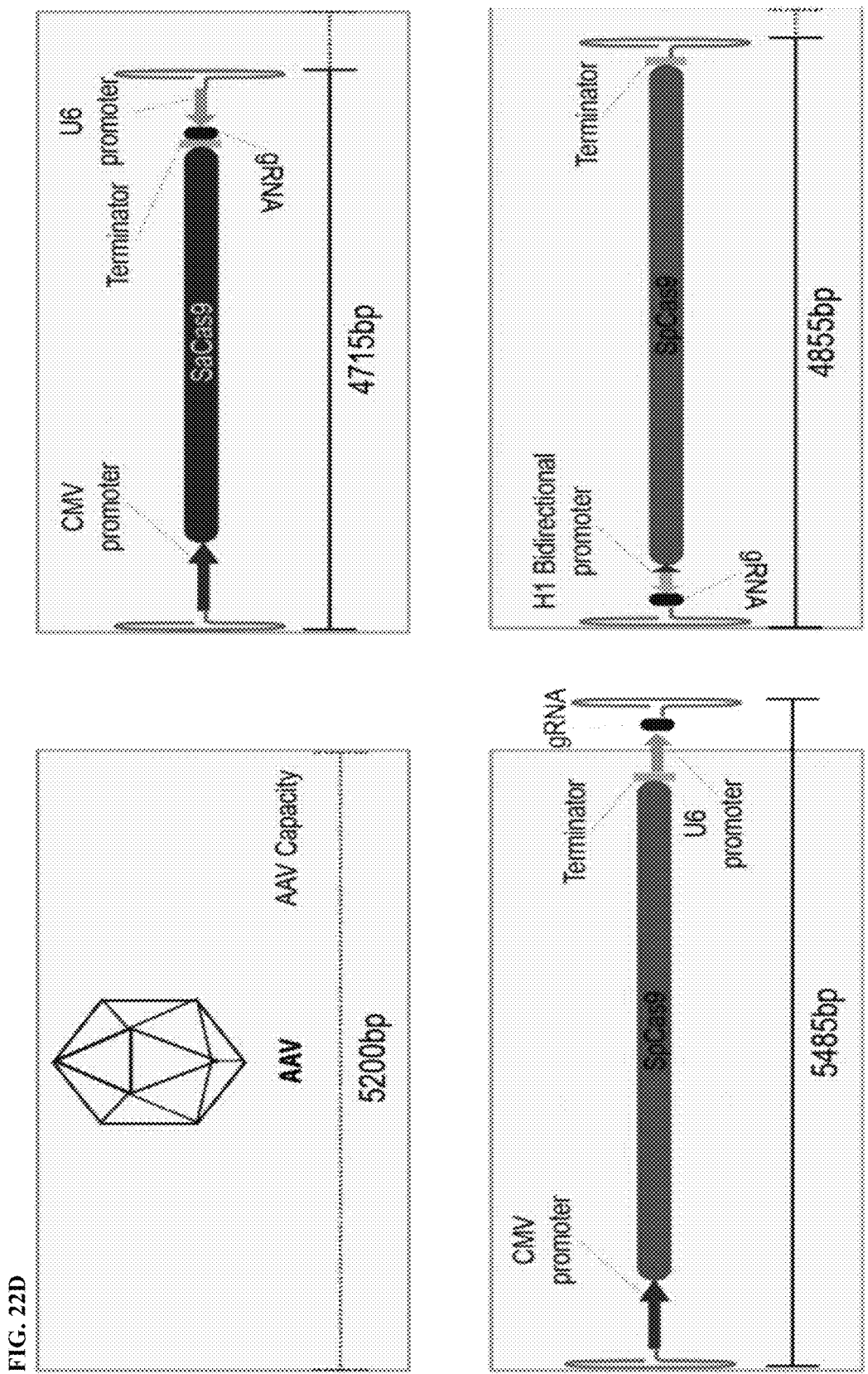
Figure 22D:
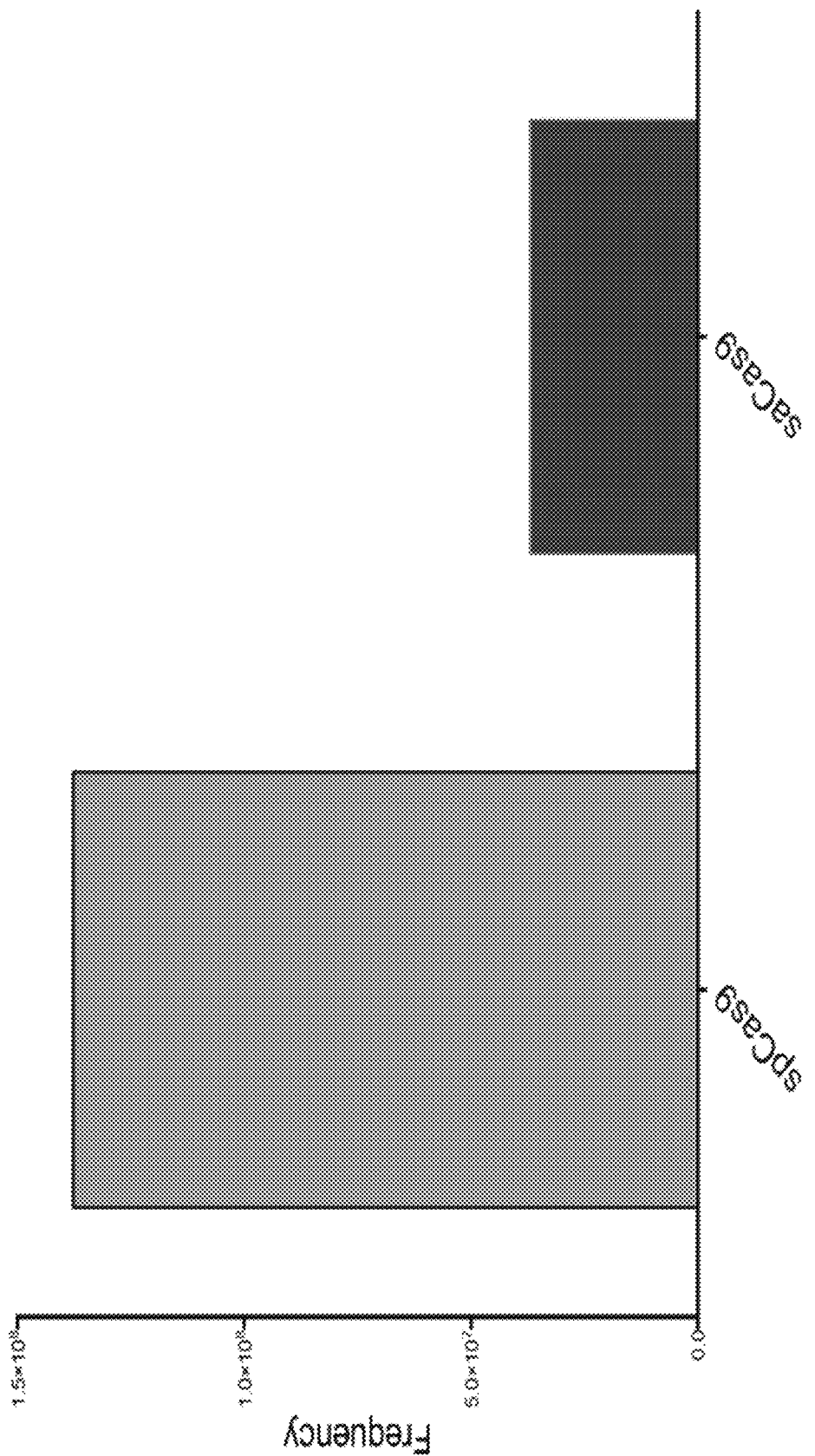
Figure 22E:
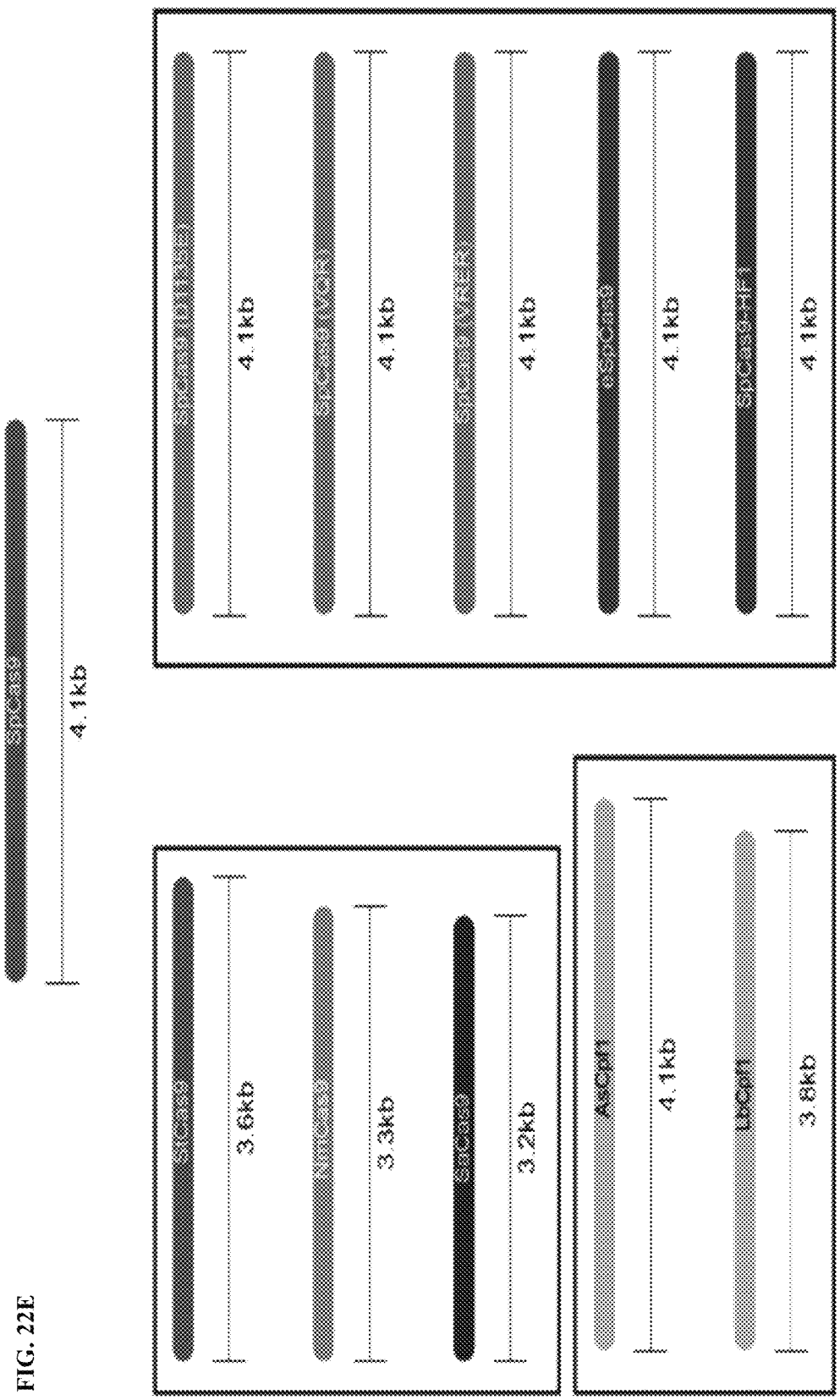
Figure 22F:
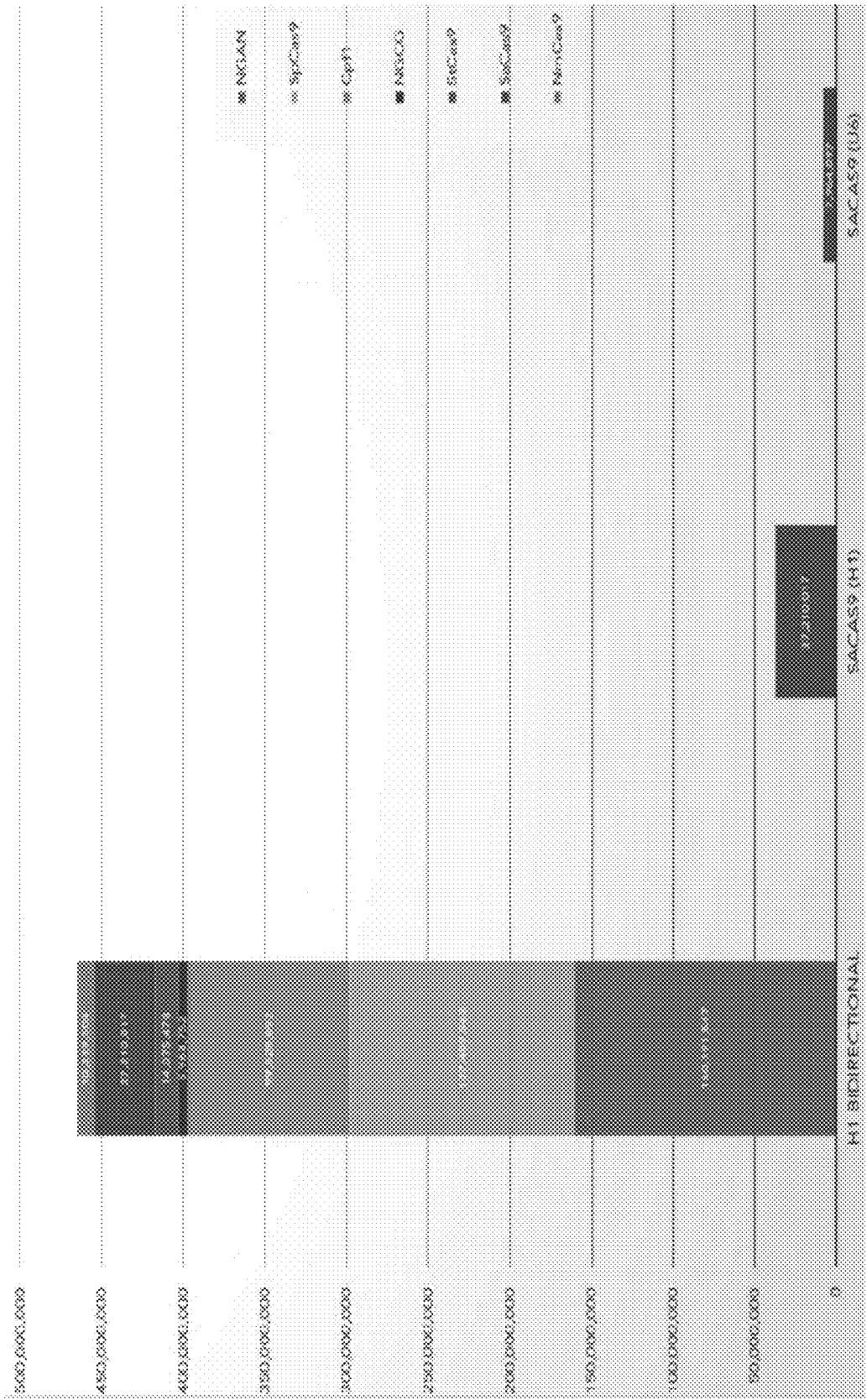
Figure 22G:
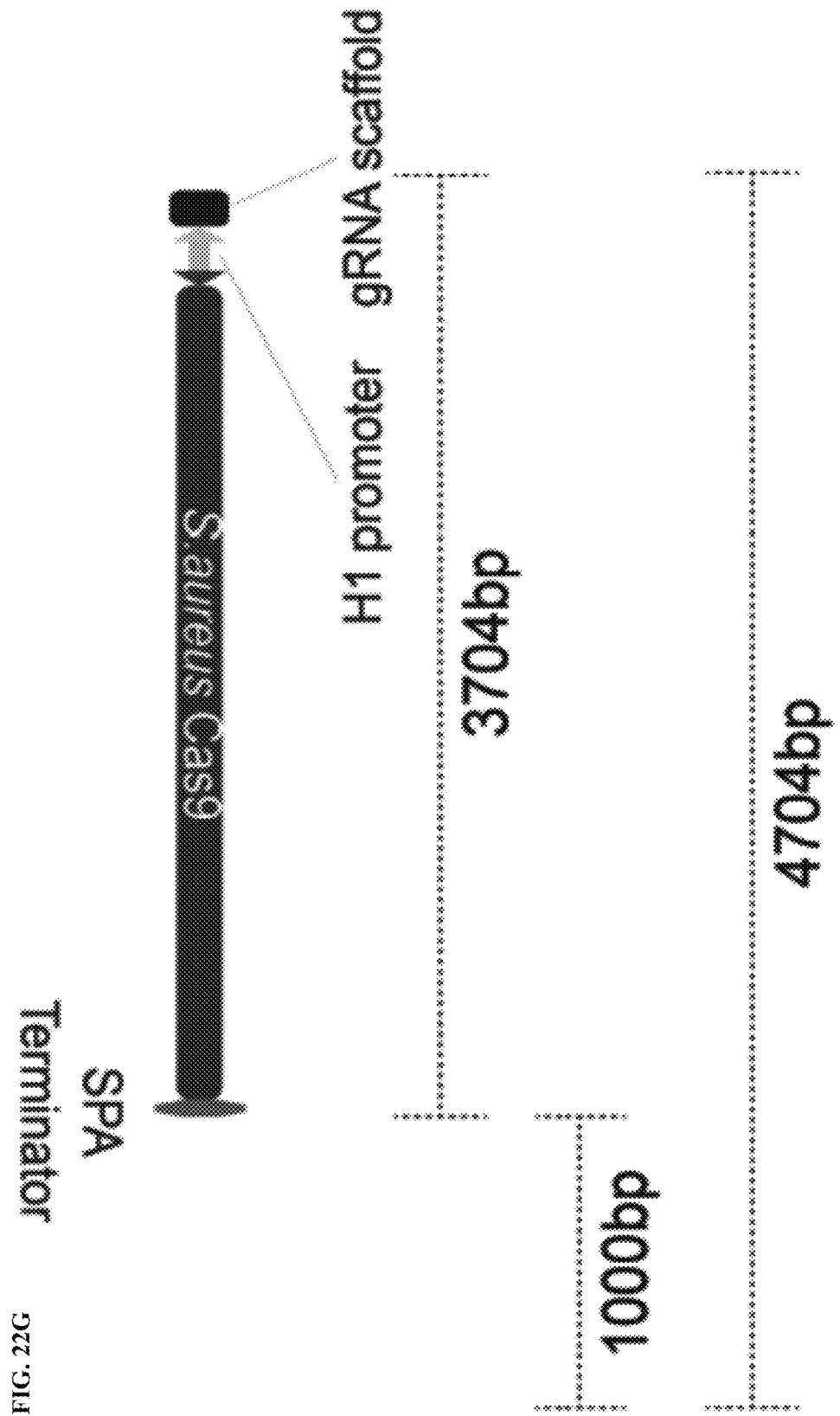
Figure 22H:
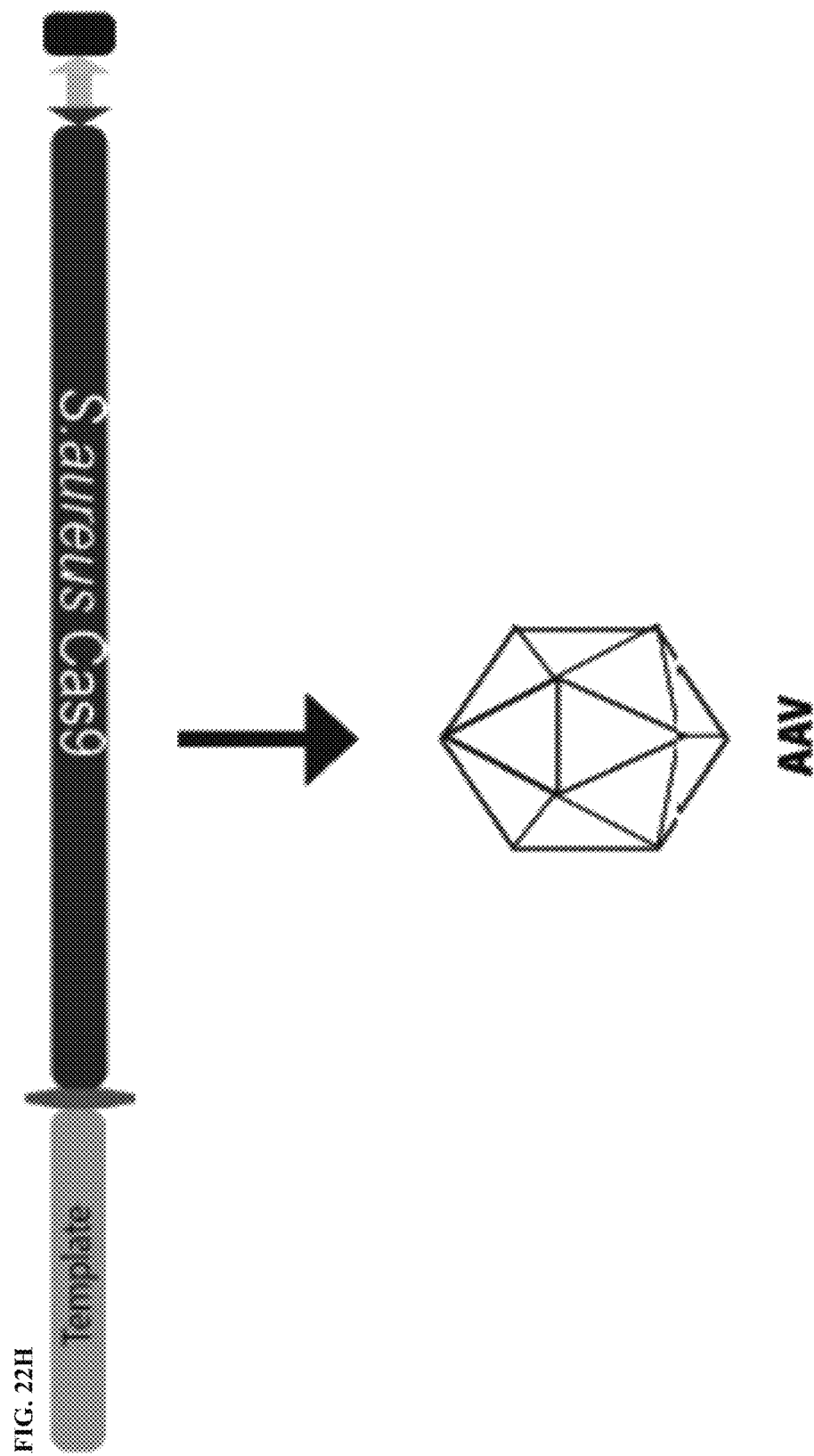
Figure 22I:
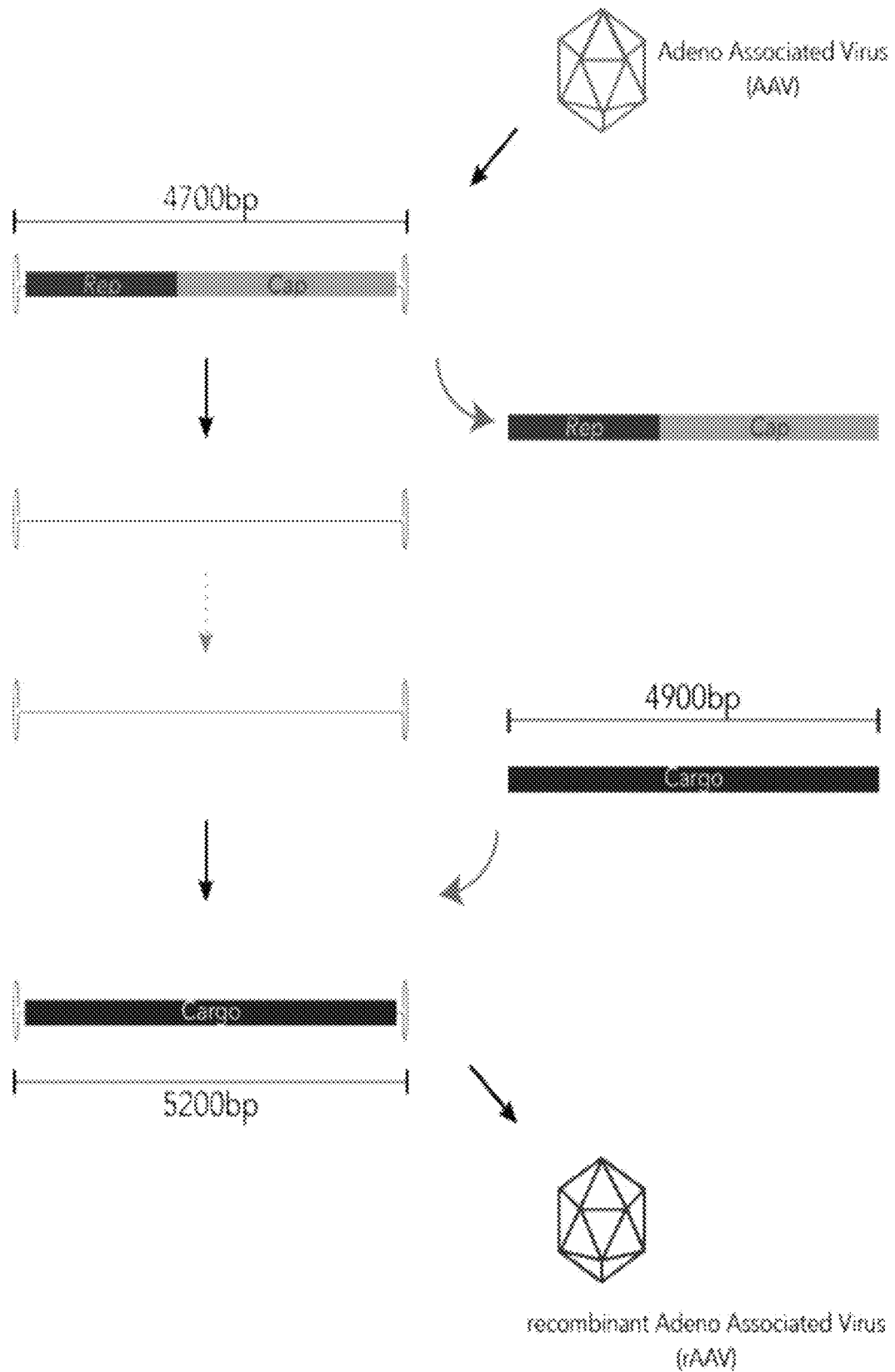

FIG. 21 comprises three panels, A-C, depicting an illustration of the AAV packaging capacity. Wildtype AAV is ~4.7 kb and recombinant AAV can be stuffed up to 5.2 kb. FIG. 21B depicts an illustration of AAV virus size using the H1 bidirectional promoter to express SpCas9 and a single gRNA. FIG. 21C depicts a construct using the stronger mouse promoter. The first set of experiments were carried out using the human promoter. FIG. 21B constructs used the SV40 terminator which was replaced with the smaller SPA terminator. Upside-down text indicates directionality of transcription from bidirectional promoter.

FIG. 22 comprises nine panels, A-I. FIG. 22A depicts the AAV delivery problem. The DNA required to express Cas9 and the gRNA, by conventional methods, exceeds 5.2 kb: Pol II promoter (~0.5 kb), SpCas9 (~4.1 kb), Pol II terminator (~0.2 kb), U6 promoter (~0.3 kb), and the gRNA (~0.1 kb). FIG. 22B shows the *S. aureus* Cas9 is ~1 kb smaller than the *S. pyogenes* Cas9 which allows it to be packaged into AAV. FIG. 22C depicts the H1 genomic locus indicating the H1RNA (a pol III transcript) expressed in the forward orientation, and the PARP-2 gene (a pot II transcript) transcribed in the opposite orientation. This ~200 bp sequence is an extremely compact bidirectional promoter. FIG. 22D depicts shrinking the "instructions" to deliver SpCas9, the most-commonly used and most-widely studied Cas9 protein. Importantly, the SpCas9 protein can target a far greater numbers of genomic sites than the SaCas9 protein. This means that more mutations/diseases can be targeted. FIG. 22E shows shrinking the "instructions" to deliver a number of other Cas9 proteins that have been shown to be effective at genome-editing in eukaryotic cells. We can also delivery SaCas9 in a much more compact vector than by using standard promoters. FIG. 22F shows that the present invention is able to potential for far-far greater number of genomic targets, and hence a far greater number of potential mutations and diseases. FIG. 22G depicts an illustration of AAV virus size using the H1 bidirectional promoter to express SaCas9 and a single gRNA. Approximately 1 kb of space is available as an HDR template. FIG. 22H depicts an illustration of AAV virus size using the H1 bidirectional promoter to express SaCas9 and a single gRNA and a template. FIG. 22I shows the following: 1. Adeno Associated Virus (AAV) is the safest and most-commonly used vector in gene therapy. The virus has one drawback: It is very small. 2. Naturally, it consists of a single-stranded DNA genome of 4700 nucleotides. The ends of the genome are inverted repeat sequences known as ITRs (orange). 3. These sequences (~1.50 bp each) are the only required elements for packaging DNA into AAV, so the viral sequences (Rep and Cap) can be gutted. 4. Any cargo (blue) can be inserted in between the ITRs and the virus can be stuffed up to 5200 nucleotides total, meaning that the virus can accommodate cargo up to 4900 nucleotides. 5. Recombinant Adeno Associated Virus (rAAV) is used as a high-efficiency vehicle for delivering cargo into a cell. Once inside the cell the single-stranded genome will become double-stranded and will remain inside for the lifetime of the cell. Upside-down text indicates directionality of transcription from bidirectional promoter.

Figure 23:
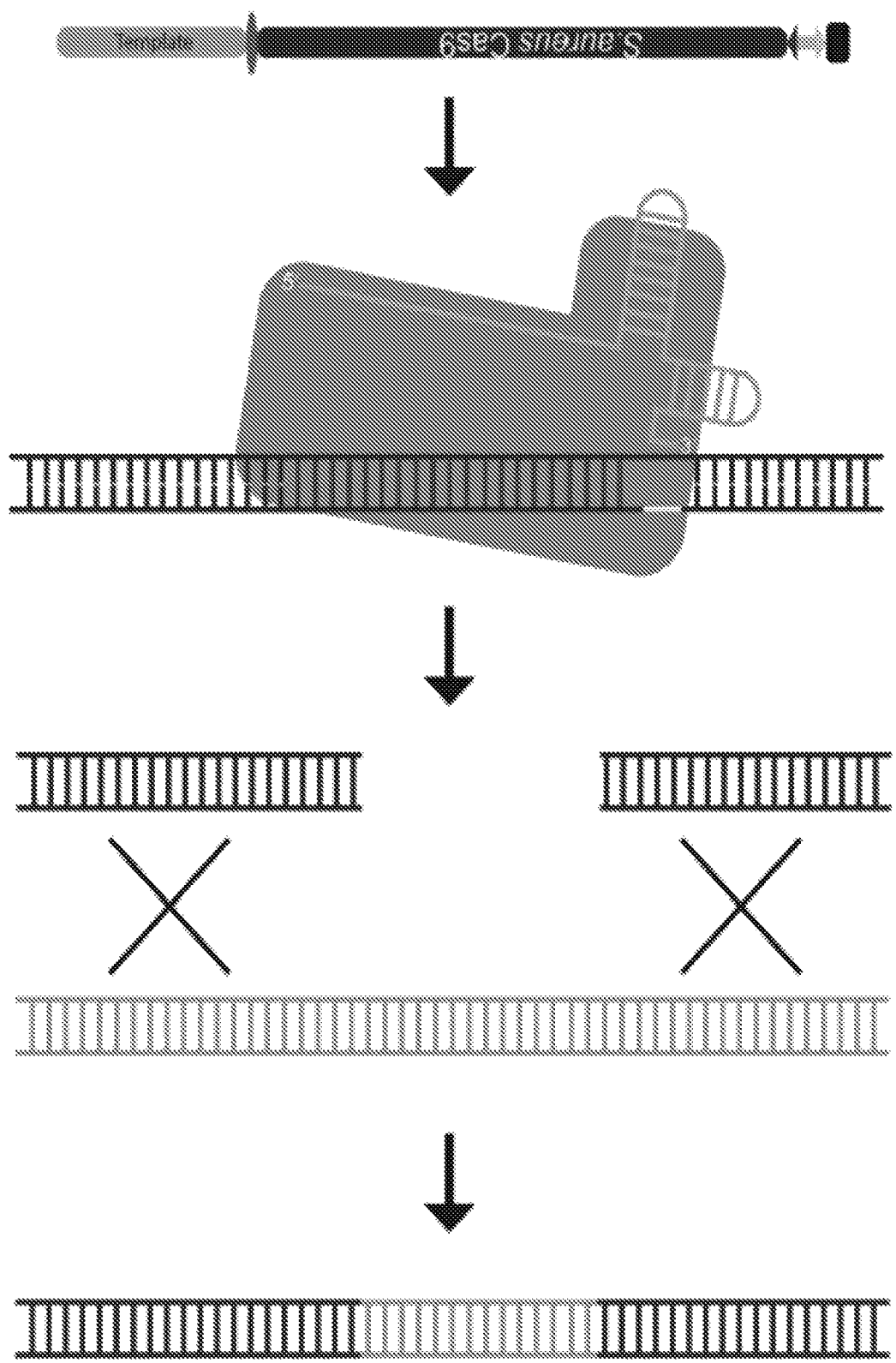

FIG. 23 shows the mechanism for site-specific recombination from a single AAV virus containing Cas9 a single gRNA and a template.

Figure 24B:
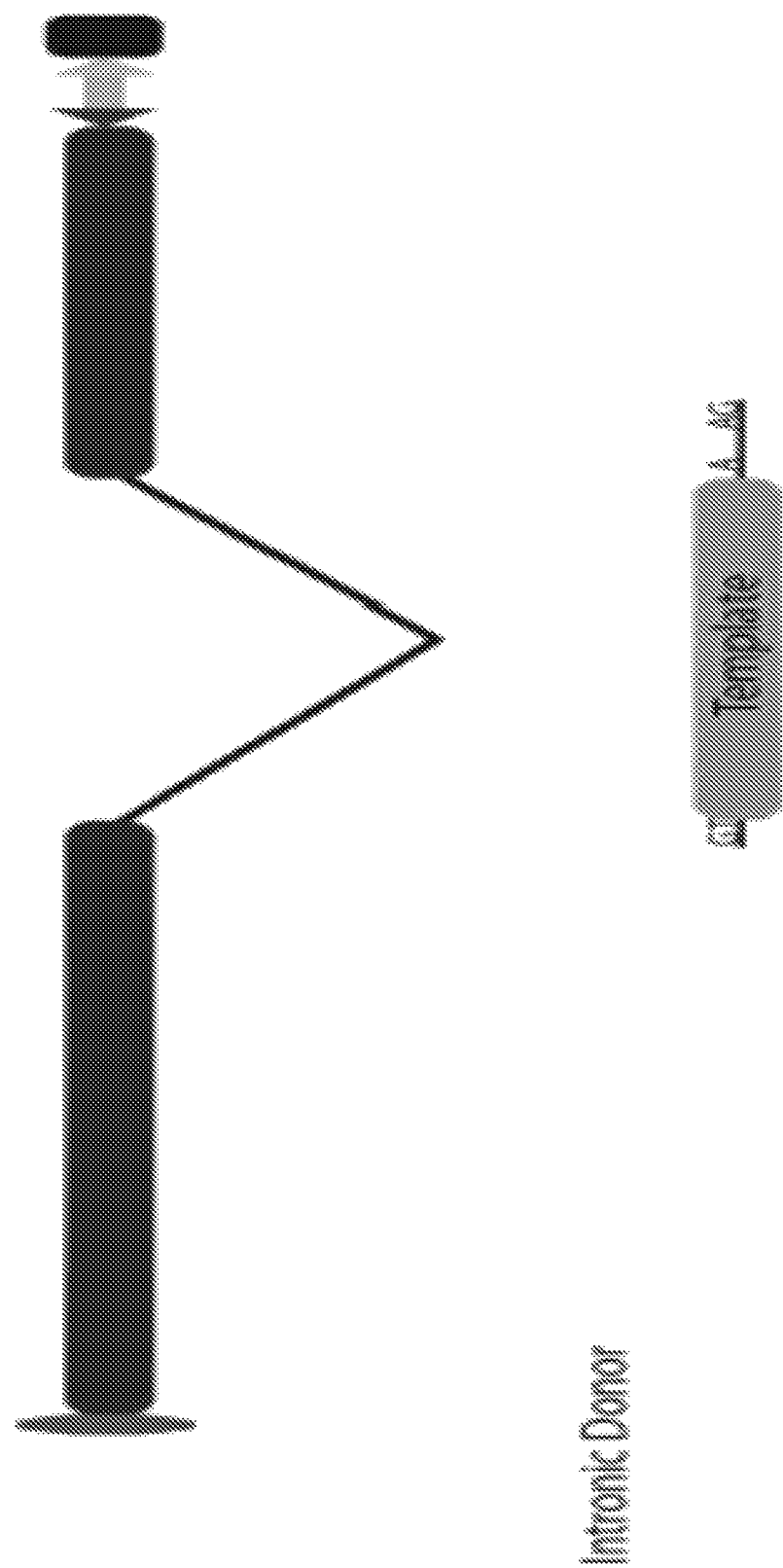

FIG. 24 comprises two panels, A and B. FIG. 24A shows potential configurations for HDR delivery within AAV vector. FIG. 24B shows potential configurations for HDR delivery within an intronic region of an RNA-directed polymerase within an AAV vector. Upside-down text indicates directionality of transcription from bidirectional promoter.

Figure 25A:
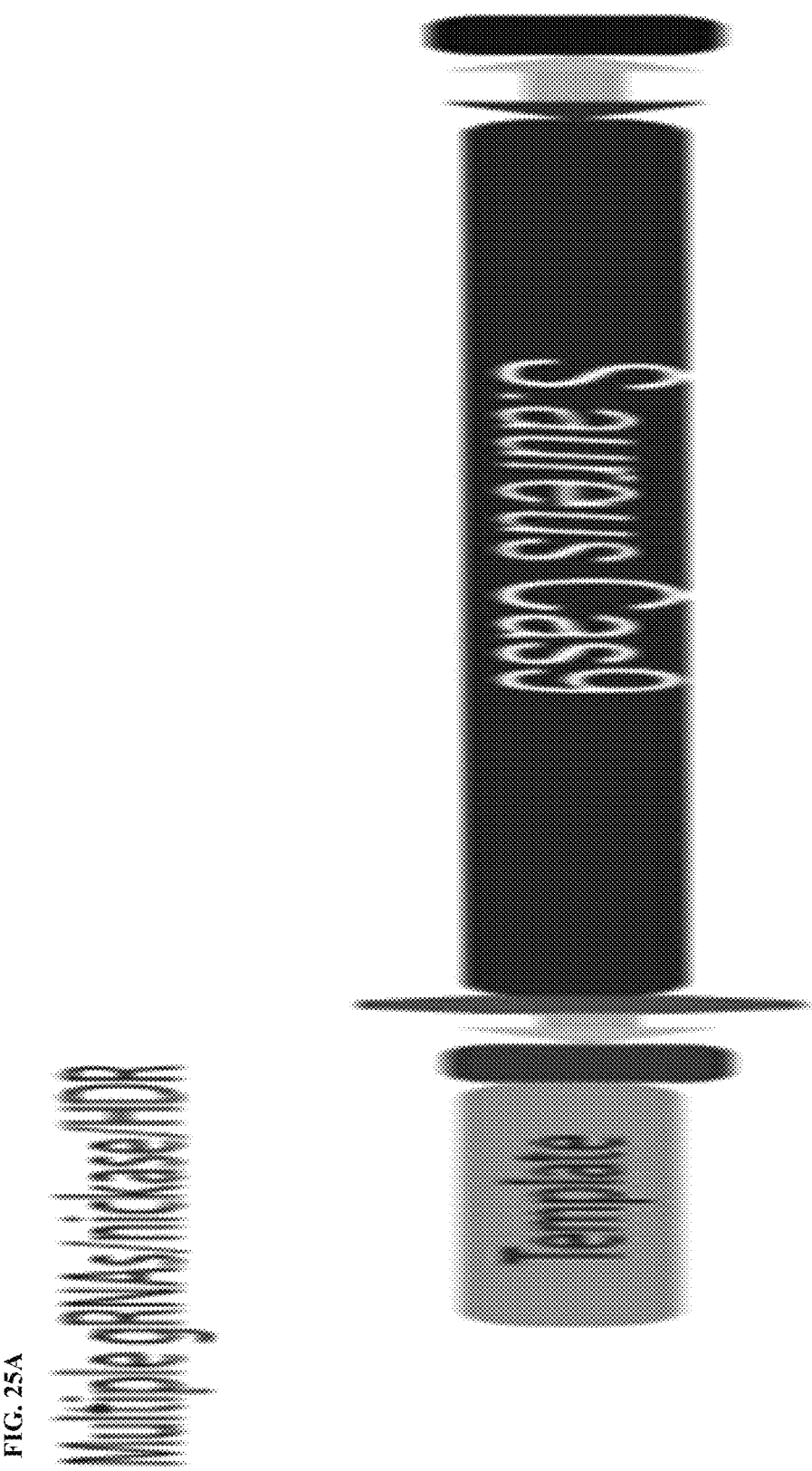

FIG. 25 comprises two panels, A and B. FIG. 25A shows an illustration of the Cas9 Nickase approach using the SaCas9 and a single gRNA and a template.

Figure 25B:
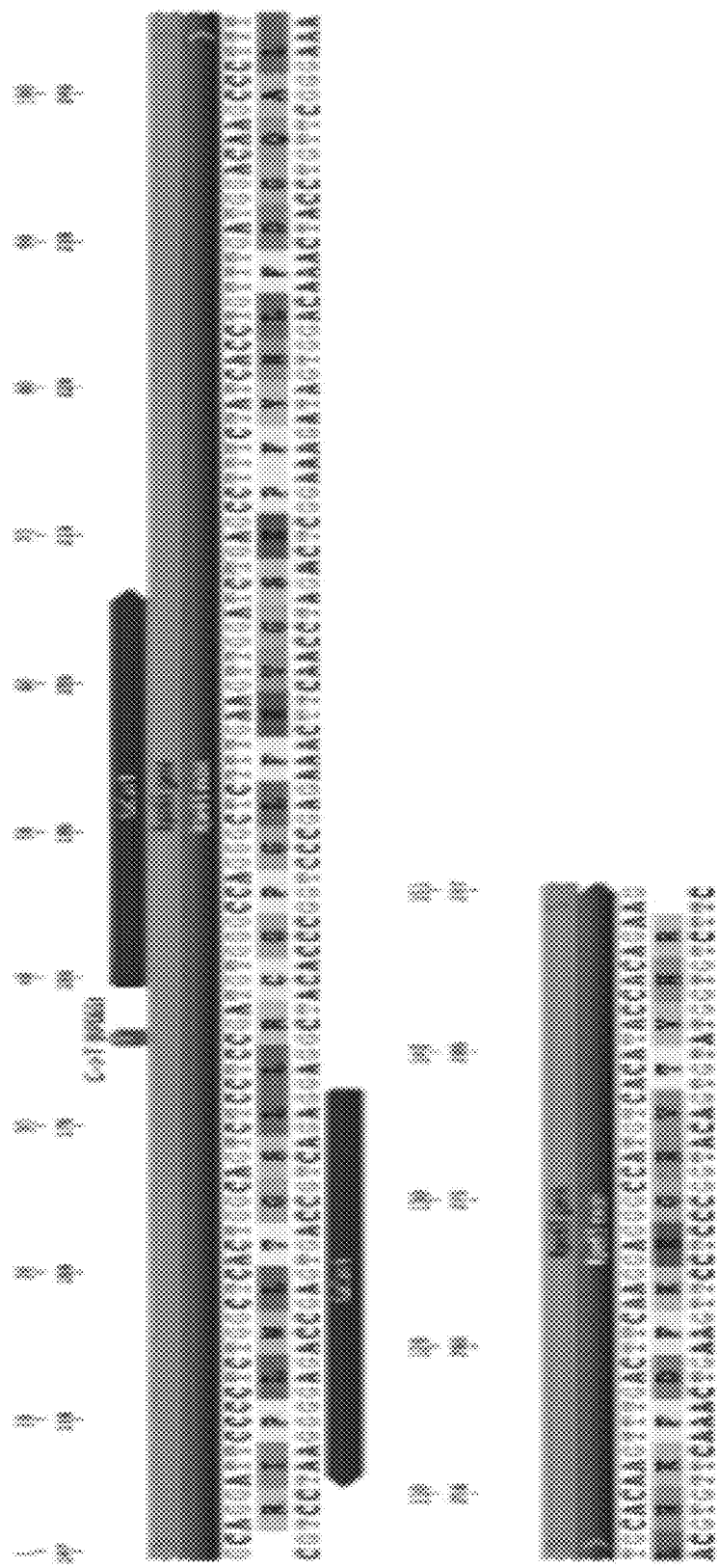

FIG. 25B shows a depiction of the rd12 targeting sequence to correct a recessive RPE65 mutation (SEQ ID NOS: 139 and 140).

Figure 26A:
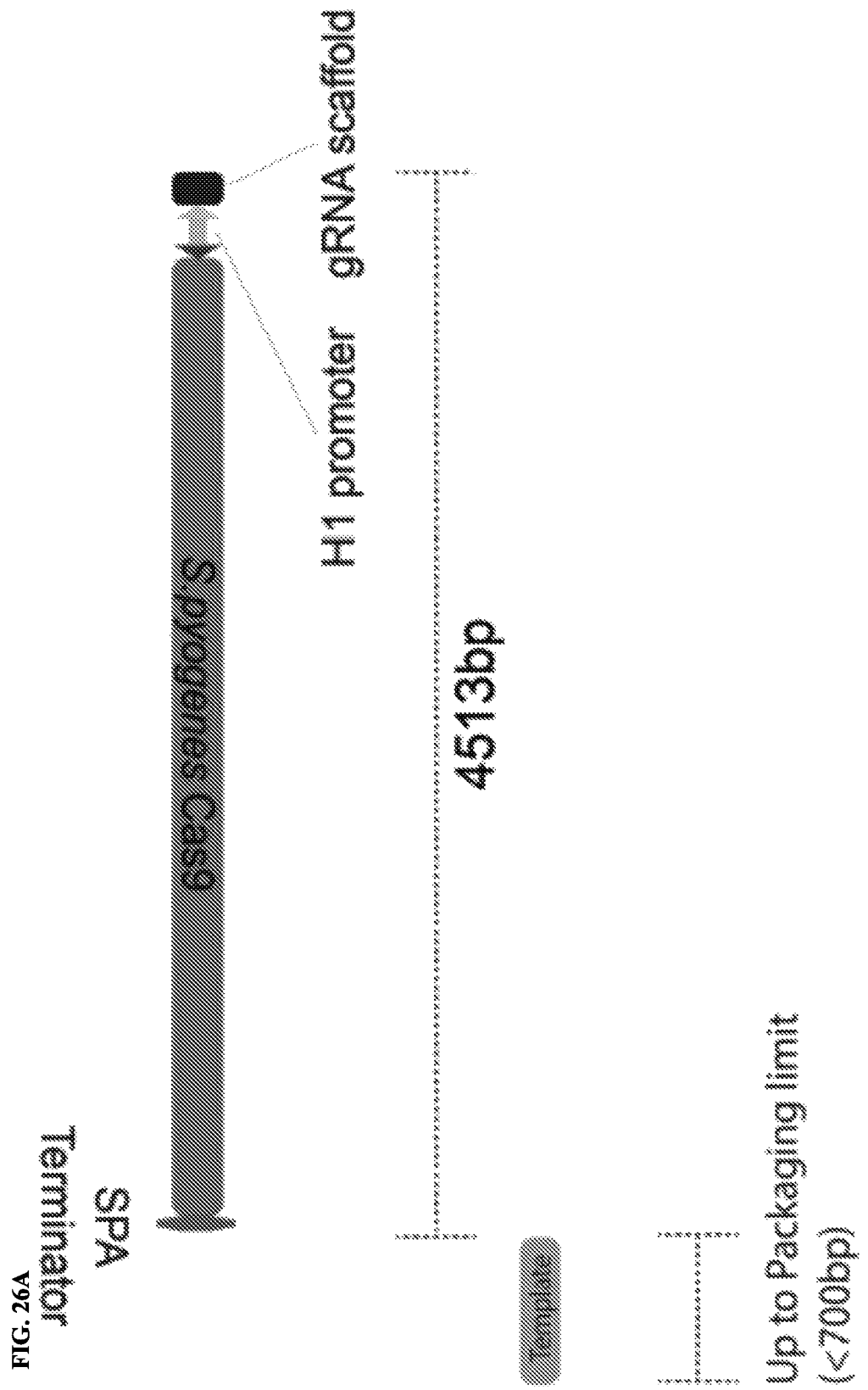
Figure 26B:
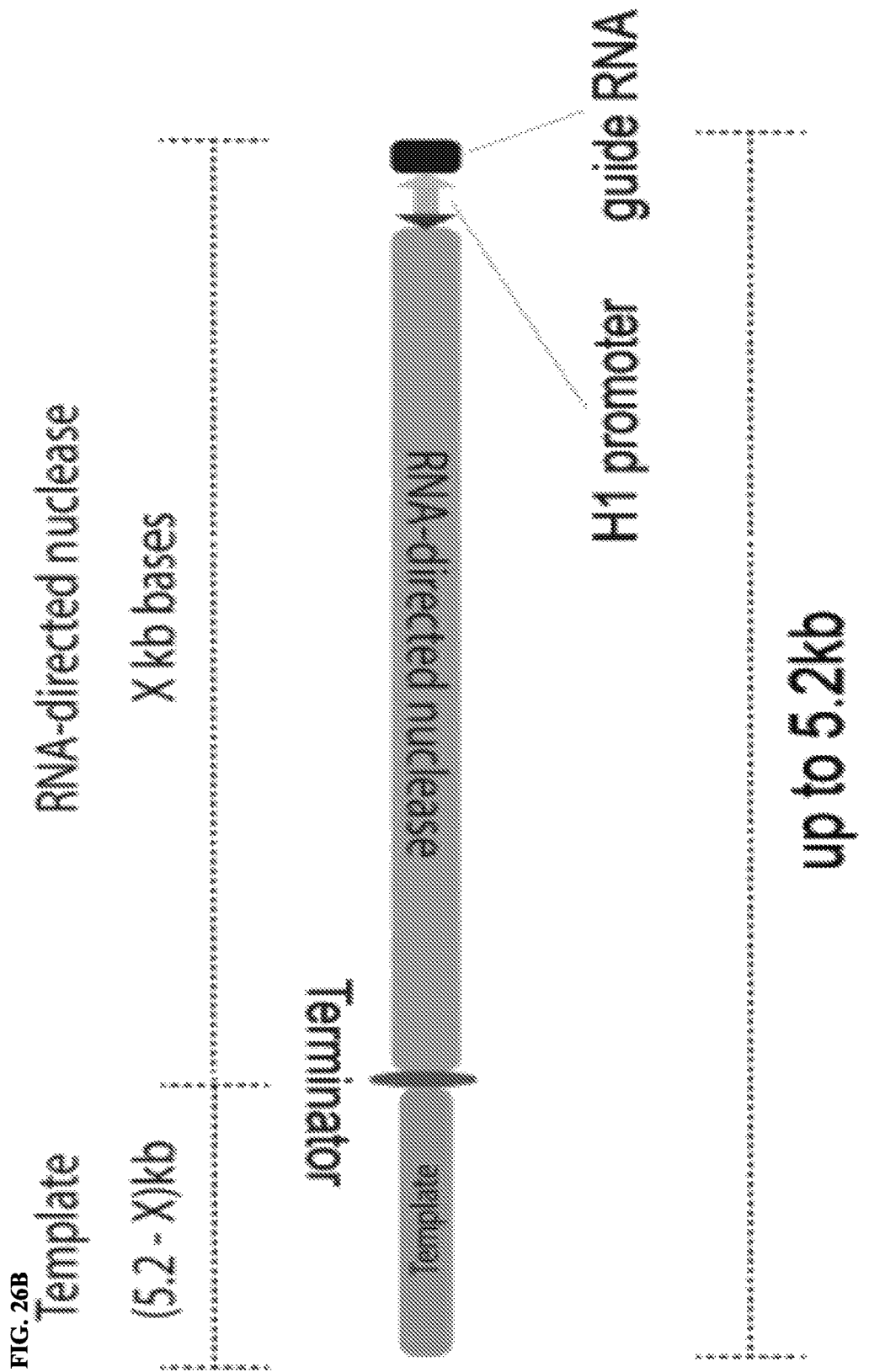

FIG. 26 comprises two panels, A and B. FIG. 26A shows an illustration of AAV virus size using the H1 bidirectional promoter to express SpCas9 and a single gRNA. Approximately 0.7 kb of space is available as an HDR template. FIG. 26B shows a generic approach for delivery of an RNA-directed nucleases, guide RNA, and template in a single AAV. Upside-down text indicates directionality of transcription from bidirectional promoter.

Figure 27:
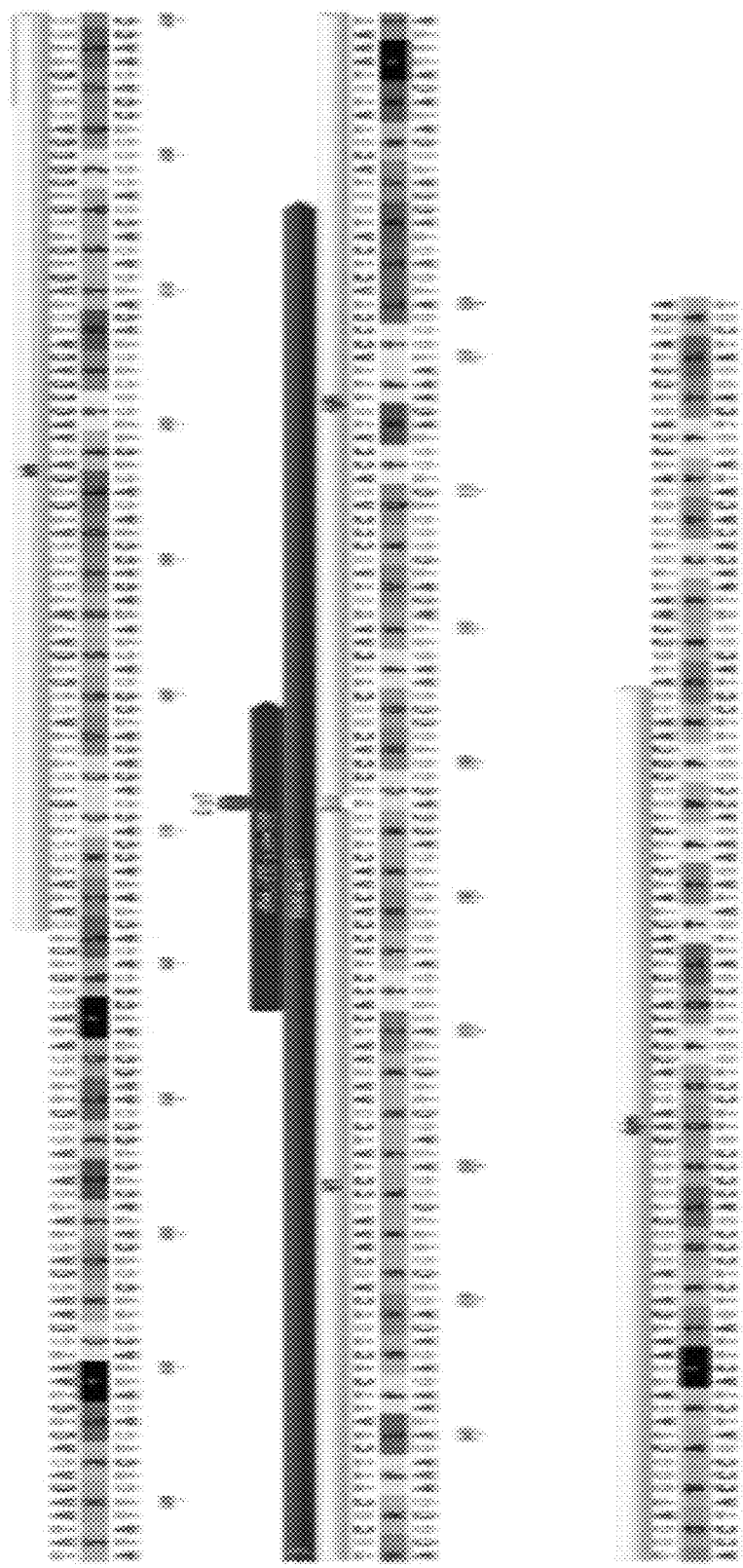

FIG. 27 depicts the rd10 targeting sequence to correct a recessive PDE6b mutation (SEQ ID NOS: 141-146).

Figure 28:
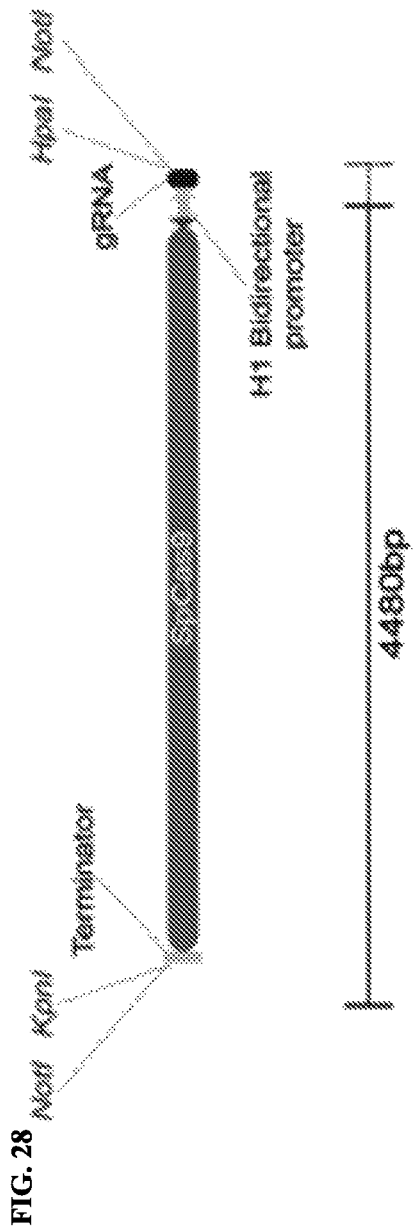

FIG. 28 depicts a cloning vector that is easily customizable by insertion of HDR templates (SEQ ID NOS: 69 AND 70).

Figure 29A:
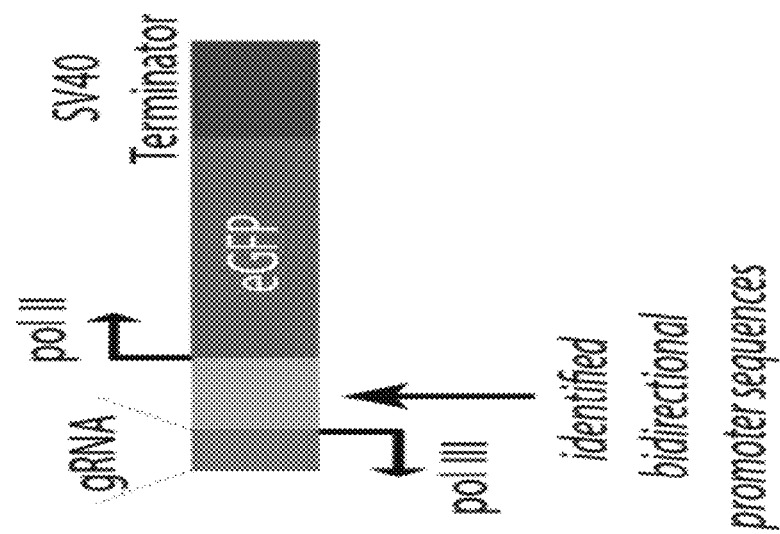
Figure 29B:
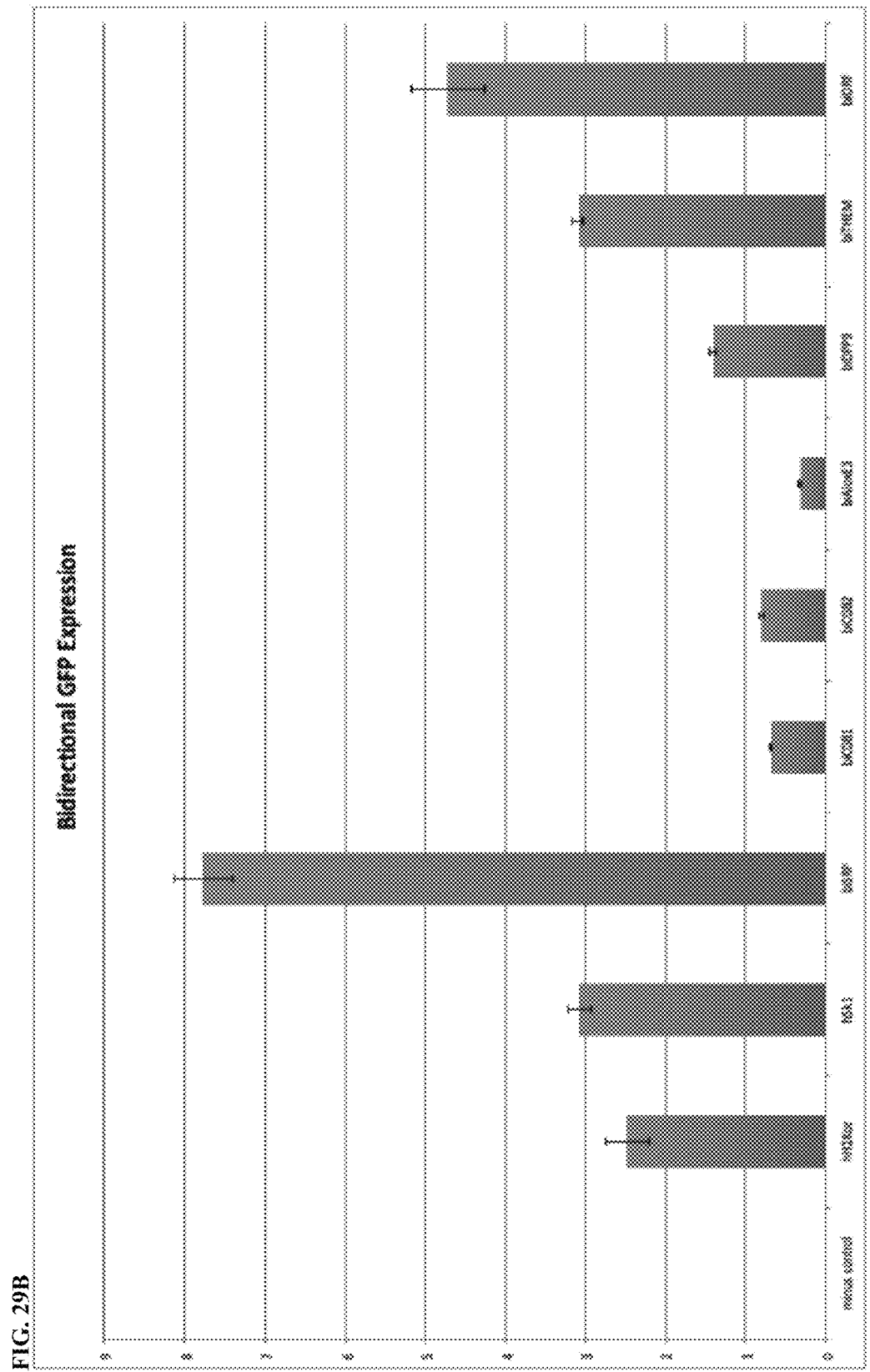

FIG. 29 contains two panels, A and B. FIG. 29A depicts a cartoon schematic and table of compact bidirectional promoter sequences with both pol II and III activity. FIG. 29B depicts a bar graph showing GFP expression of constructs comprising the compact bidirectional promoter sequences shown in FIG. 29A. FIG. 29B shows starting from the y-axis on the right and moving left along the x-axis, the following labels for the bars, 1) minus control, 2) hH1Koz (SEQ ID NO: 71 (or SEQ ID NO: 12 or 32)), 3) hSk1 (SEQ ID NO: 73), 4) biSRP (SEQ ID NO: 72), 5) biCGB1 (SEQ ID NO: 74), 6) biAloxE3 (SEQ ID NO: 77), 7) biDPP9 (SEQ ID NO: 79), 8) biTHEM (SEQ ID NO: 83), and 9) biORF (SEQ ID NO: 80).

Figure 30A:
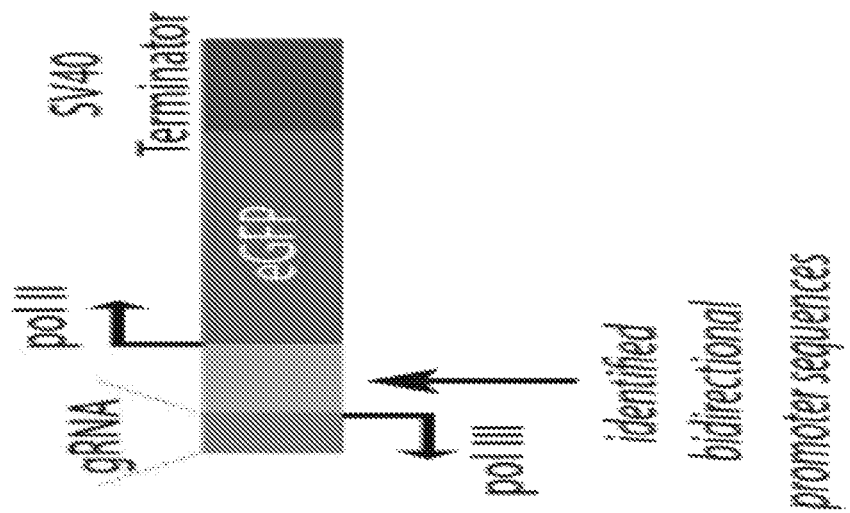
Figure 30B:
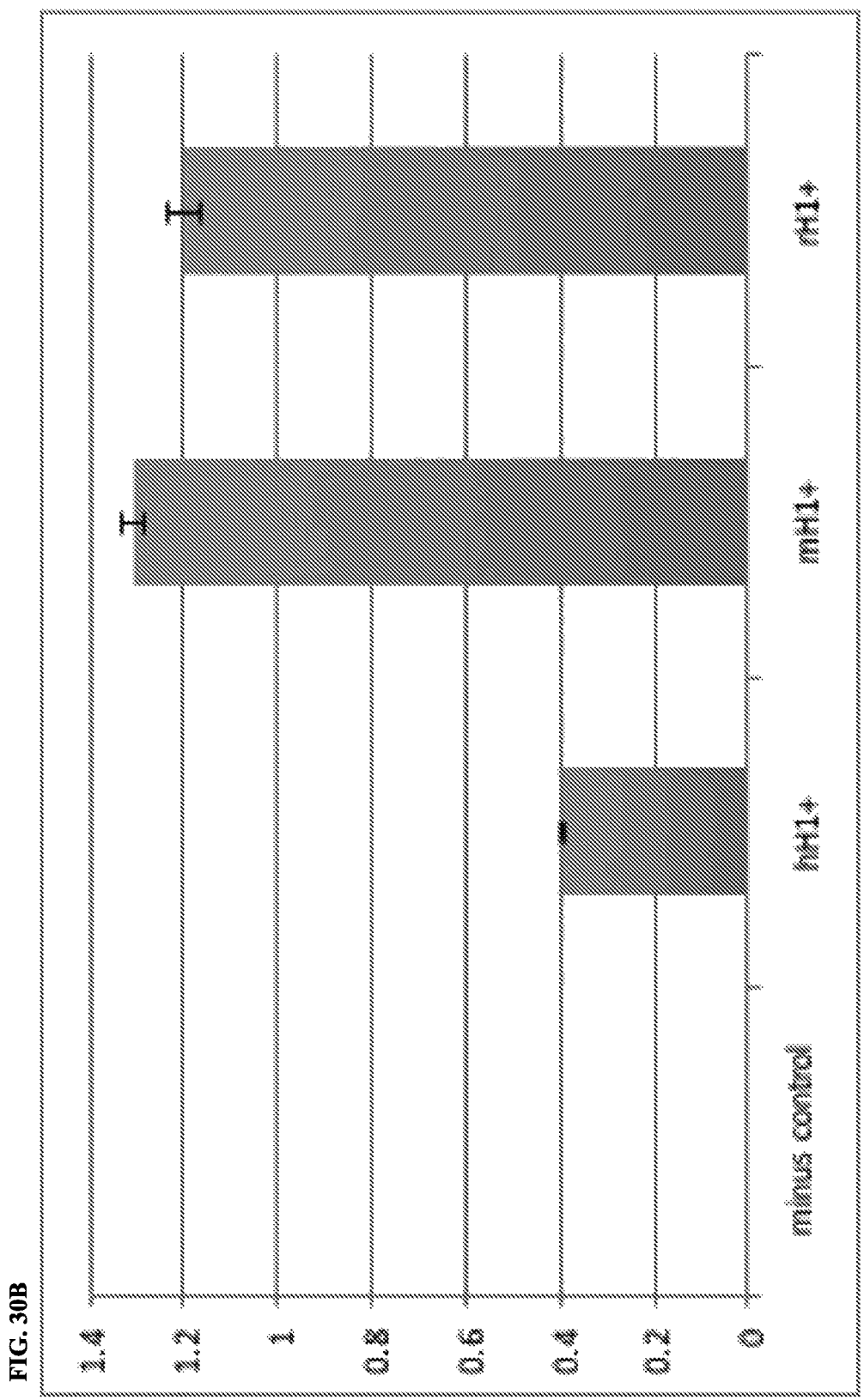

FIG. 30 contains two panels, A and B. FIG. 30A depicts a cartoon schematic and table of orthologous bidirectional promoter sequences with both pol II and III activity. FIG. 30B depicts a bar graph showing GFP expression of constructs comprising the orthologous bidirectional promoter sequences shown in FIG. 30A.

FIG. 30B shows starting from the y-axis on the right and moving left along the x-axis, the following labels for the bars, 1) minus control, 2) hH1+(corresponding to human RPPH1-PARP2), 3) mH1+(corresponding to mouse RPPH1-PARP2), and 4) rH1+(corresponding to rat RPPH1-PARP2).

DETAILED DESCRIPTION

The presently disclosed subject matter now will be described more fully hereinafter with reference to the accompanying Figures, in which some, but not all embodiments of the presently disclosed subject matter are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

Genome-editing technologies such as zinc fingers nucleases (ZFN) (Porteus, and Baltimore (2003) *Science* 300: 763; Miller et al. (2007) *Nat. Biotechnol.* 25:778-785; Sander et al. (2011) *Nature Methods* 8:67-69; Wood et al. (2011) *Science* 333:307) and transcription activator-like effectors nucleases (TALEN) (Wood et al. (2011) *Science* 333:307; Boch et al. (2009) *Science* 326:1509-1512; Moscou and Bogdanove (2009) *Science* 326:1501; Christian et al. (2010) *Genetics* 186:757-761; Miller et al. (2011) *Nat. Biotechnol.* 29:143-148; Zhang et al. (2011) *Nat. Biotechnol.* 29:149-153; Reyon et al. (2012) *Nat. Biotechnol.* 30:460-465) have empowered the ability to generate targeted genome modifications and offer the potential to correct disease mutations with precision. While effective, these technologies are encumbered by practical limitations as both ZFN and TALEN pairs require synthesizing large and unique recognition proteins for a given DNA target site. Several groups have recently reported high-efficiency genome editing through the use of an engineered type II CRISPR/Cas9 system that circumvents these key limitations (Cong et al. (2013) *Science* 339:819-823; Jinek et al. (2013)

eLife 2:e00471; Mali et al. (2013) *Science* 339:823-826; Cho et al. (2013) *Nat. Biotechnol.* 31:230-232; Hwang et al. (2013) *Nat. Biotechnol.* 31:227-229). Unlike ZFNs and TALENs, which are relatively time consuming and arduous to make, the CRISPR constructs, which rely upon the nuclease activity of the Cas9 protein coupled with a synthetic guide RNA (gRNA), are simple and fast to synthesize and can be multiplexed. However, despite the relative ease of their synthesis, CRISPRs have technological restrictions related to their access to targetable genome space, which is a function of both the properties of Cas9 itself and the synthesis of its gRNA.

Cleavage by the CRISPR system requires complementary base pairing of the gRNA to a 20-nucleotide DNA sequence and the requisite protospacer-adjacent motif (PAM), a short nucleotide motif found 3' to the target site (Jinek et al. (2012) *Science* 337: 816-821). One can, theoretically, target any unique $N_{20}$-PAM sequence in the genome using CRISPR technology. The DNA binding specificity of the PAM sequence, which varies depending upon the species of origin of the specific Cas9 employed, provides one constraint. Currently, the least restrictive and most commonly used Cas9 protein is from *S. pyogenes*, which recognizes the sequence NGG, and thus, any unique 21-nucleotide sequence in the genome followed by two guanosine nucleotides ($N_{20}$NGG) can be targeted. Expansion of the available targeting space imposed by the protein component is limited to the discovery and use of novel Cas9 proteins with altered PAM requirements (Cong et al. (2013) *Science* 339: 819-823; Hou et al. (2013) *Proc. Natl. Acad. Sci. U.S.A.*, 110 (39):15644-9), or pending the generation of novel Cas9 variants via mutagenesis or directed evolution. The second technological constraint of the CRISPR system arises from gRNA expression initiating at a 5' guanosine nucleotide. Use of the type III class of RNA polymerase III promoters has been particularly amenable for gRNA expression because these short non-coding transcripts have well-defined ends, and all the necessary elements for transcription, with the exclusion of the 1+ nucleotide, are contained in the upstream promoter region. However, since the commonly used U6 promoter requires a guanosine nucleotide to initiate transcription, use of the U6 promoter has further constrained genomic targeting sites to $GN_{19}NGG$ (Mali et al. (2013) *Science* 339:823-826; Ding et al. (2013) *Cell Stem Cell* 12:393-394). Alternative approaches, such as in vitro transcription by T7, T3, or SP6 promoters, would also require initiating guanosine nucleotide(s) (Adhya et al. (1981) *Proc. Natl. Acad. Sci. U.S.A.* 78:147-151; Melton et al. (1984) *Nucleic Acids Res.* 12:7035-7056; Pleiss et al. (1998) *RNA* 4:1313-1317).

The presently disclosed subject matter relates to compositions and methods comprising improvements of a CRISPR/Cas9 system (i.e., CRISPR guide RNAs using the H1 promoter; WO2015/19561, herein incorporated by reference in its entirety). Such a modified CRISPR/Cas9 system may comprise modifications to the H1 promoter region. In some embodiments, the modified CRISPR/Cas9 system comprises enhancing H1 bidirectional pol II expression using 5'UTR modifications. In some embodiments, the modified CRISPR/Cas9 system comprises modulating bidirectional expression through use of different orthologous sequences of the H1 promoter. In some embodiments, the modified CRISPR/Cas9 system comprises novel compact bidirectional promoter (including compact and orthologous promoter) sequences with both pol II and pol III activity (e.g., 7sk, 5'UTRs, Kozak consensus sequences, or combinations thereof).

In some embodiments, the modified CRISPR/Cas9 system comprises conditional pol II/pol III bidirectional promoter (including compact and orthologous promoter) expression (e.g., TetR and TetO sites) which can regulate ribonucleoprotein enzymatic activity or RNA-directed nucleases. In some embodiments, the improvements comprise addition of a donor template sequence for correcting mutations (e.g., homology directed repair (HDR)).

In some embodiments, compact bidirectional promoters include, but not limited to, RPPH1-PARP2 (Human), SRP-RPS29, 7sk1-GSTA4, SNAR-G-1-CGB1, SNAR-CGB2, RMRP-CCDC107, tRNA(Lys)-ALOXE3, RNU6-9-MED16, tRNA (Gly)-DPP9, RNU6-2-THEM259, or SNORD13-C8orf41.

In some embodiments, orthologous bidirectional promoters include, but not limited to, RPPH1-PARP2 (Mouse) or RPPH1-PARP2 (Rat), or those derived from *Ailuropoda melanoleuca, Bos taurus, Callithrix jacchus, Canis familiaris, Cavia porcellus, Chlorocebus sabaeus, Choloepus hoffmanni, Dasypus novemcinctus, Dipodomys ordii, Equus caballus, Erinaceus europaeus, Felis catus, Gorilla gorilla, Homo sapiens, Ictidomys tridecemlineatus, Loxodonta africana, Macaca mulatta, Mus musculus, Mustela putorius faro, Myotis lucifugus, Nomascus leucogenys, Ochotona princeps, Oryctolagus cuniculus, Otolemur garnettii, Ovis aries, Pan troglodytes, Papio anubis, Pongo abelii, Procavia capensis, Pteropus vampyrus, Rattus norvegicus, Sus scrofa, Tarsius syrichta, Tupaia belangeri, Tursiops truncatus, Vicugna pacos.*

TABLE 3

Examples of compact bidirectional promoters

| ncRNA gene | Protein gene | Distance |
|---|---|---|
| RPPH1 | PARP2 | 230 bp |
| SRP | RPS29 | 233 bp |
| 7sk1 | GSTA4 | 239 bp |
| SNAR-G1 | CGB1 | 308 bp |
| SNAR | CGB2 | 308 bp |
| RMRP | CCDC107 | 361 bp |
| tRNA(Lys) | ALOXE3 | 376 bp |
| RNU6-9 | MED16 | 412 bp |
| tRNA (Gly) | DPP9 | 484 bp |
| SNORD13 | C8orf41 | 847 bp |
| RNU6-2 | THEM259 | 525 bp |

RPPH1-PARP2 (Human):
(SEQ ID NO: 71)
GGAATTCGAACGCTGACGTCATCAACCCGCTCCAAGGAATCGCGGGCCCA

GTGTCACTAGGCGGGAACACCCAGCGCGCGTGCGCCCTGGCAGGAAGATG

GCTGTGAGGGACAGGGGAGTGGCGCCCTGCAATATTTGCATGTCGCTATG

TGTTCTGGGAAATCACCATAAACGTGAAATGTCTTTGGATTTGGGAATCT

TATAAGTTCTGTATGAGACCACTTTTTCCC

SRP-RPS29:
(SEQ ID NO: 72)
CTTGCTCTCAGCAGTGCAACGAGGTAAAAGGAAGAAGCTGGCCCACGCAT

GCGCTCTTCAAATTTTTGAGACAGTTTACCCAGAATGCAGTGCTCAAAGG

AAACGCGTGCGCAGTGTGGTCAGGTTGTTTCGCTGGGTGAGTAAAATGAA

ATCTTAGAGGCGTTGTGGGCTGGCCCAGTTGATGACGTCACCATACCACA

GCTTCTAGTGCTATTCTGCGCCGGTATCCGACC

7sk1-GSTA4:
(SEQ ID NO: 73)
AGTATTTAGCATGCCCCACCCATCTGCAAGGCATTCTGGATAGTGTCAAA

ACAGCCGGAAATCAAGTCCGTTTATCTCAAACTTTAGCATTTTGGGAATA

AATGATATTTGCTATGCTGGTTAAATTAGATTTTAGTTAAATTTCCTGCT

GAAGCTCTAGTACGATAAGCAACTTGACCTAAGTGTAAAGTTGAGACTTC

CTTCAGGTTTATATAGCTTGTGCGCCGCTTGGGTACCTC

SNAR-G-1-CGB1:
(SEQ ID NO: 74)
GTCTCTCTCTTAGCGGGATATCTTCCGCAAGCACTGGGAATGTGGACATG

GAAAGTAAATTGAGTCTCCGTGGGGGAGTGAGACAGGGAGTGAGGGGTGT

TGGACGCGGCACGGGAACCTGGCCAGAGTCAGCGGACCCAATTGGCTGCT

CTCTCTCAGATGCAGTTCCCCTTCCTCCCTCCAGGGGCGCCACGGAACG

CAGGGCCCTCACTGGCCCTGGGGACTGGGTGACGTCAGGGATGAGCCTCT

TGTGATTGGCTCCATCACCCTGCGTAAGATCAAAGGGAAGAAAGGATGGG

CCCGACAA

SNAR-CGB2:
(SEQ ID NO: 75)
GTCTCTCTCTTAGCGGGATATCTTCCGCAAGCACTGGGGATGTGGACATG

GAAAGTAAATTGAGTCTCCGTGGGGGAGTGAGACAGGGAGTGAGGGGTGT

TGGACGCGGCACGGGAACCCGGCCGGAGTCAGCGGACCCAATTGGCTGCT

CTCTCTCAGATACAGTTCCCCTTCCTCCCTCCAGGGGCGCCACGGAACG

CAGGGCCCTCACTGGCCCTGGGGACTGGGTGACGTCAGGGGTGAGCCTCT

CCTGATTGGCTCCATCACCCTGCGTAAGGTCAAAAGGAAGAAAGGAGATC

CCCGACAC

RMRP-CCDC107:
(SEQ ID NO: 76)
TGCCGGCCCACGGGTGGAGGGATCGGCGGGCGGTGCCGAAGCGGTCCGG

CATTGGCCGGCCGCCCCAACGCGCACGCGCACGCGAGCAGGCCGGCCGGC

TCCGGGGAGGCCACGCCCACTCCCCGTAGGGCGGGGCCAGACCATATTTG

CATAAGATAGTGTCATTCTAGCTTTCCTGTATTTGTTCATTTCGTGTCTA

TTAGCTATTCTGCTAGCCACAATGCCTCTGAAAGCCTATAGTCTTAGAAA

GTTATGCCCGAAAACGGTTTTTTTAATCTCACGCCACCAACTTTCTCACC

CTAATCATAAAACACAATTTCTTTAGGGCTATAAAATACTACTCTGTGAA

GCTGAGGACGT tRNA(Lys)-ALOXE3:
(SEQ ID NO: 77)
TCTTTCCGCTCCAGGACCGCCCTGGGCCTGCAGGATCCTGGGCGGGAGCC

CAGGTGTCCGGGATCTGGGCCACTAGGGACTGGGGAGGAACCTCTCAGAG

AAGCCCATAGCCCGCAGCGGCCCCGCGCGGCCGGTTCCGGCGCCGCACTG

TTCCAGCCTCTACTATGGTACAGTCCCTGCGTCGCAGCCTCGGCGGGGC

TCTAAGAACGGGAGGCAGAAAAAGCTCAATCAGCAGCAGGCGAGCTTCAC

CCGCTGCTTCCAAATCTGTGCCAAAATATTCTATGCTGCACAGATAAAAT

CCTCTGTCGGTTCTACAAGCCTGGCTTTTCCTATAGAGAACCCTCTTATA

AGCAAAAAGTAAAGCTCTCGTGAAGA

RNU6-9-MED16:
(SEQ ID NO: 78)
GAGGGCAGTCACCAGCTCCTGGCCCGTGCGCCAAGCTCAGCGGGCGTCCG

CGGTGCGATCTTCCCTAGCGCCTCGGGTCTGGCGCCGCCATCTTCCTCGG

TAACAACCAGTCGCCTGAGGCGTGGGGCCGCCTCCCAAAGACTTCTGGGA

GGGCGGTGCGGCTCAGGCTCTGCCCCGCCTCCGGGGCTATTTGCATACGA

CCATTTCCAGTAATTCCCAGCAGCCACCGTAGCTATATTTGGTAGAACAA

CGAGCACTTTCTCAACTCCAGTCAATAACTACGTTAGTTGCATTACACAT

TGGGCTAATATAAATAGAGGTTAAATCTCTAGGTCATTTAAGAGAAGTCG

GCCTATGTGTACAGACATTTGTTCCAGGGGCTTTAAATAGCTGGTGGTGG

AACTCAATATTC tRNA(Gly)-DPP9:
(SEQ ID NO: 79)
TAACCGCTCAGCTGACCTCAGGAGGGCAGGGGTGCCTTCTAAAGGGTCCA

GAGAGCCTCCATTCCAGCTGCAGGCGTGGGACACAGACCGGGACGTGGGG

CGGCGGCCGGACTGGGCAGGTCGTCCCGGGTCCAGCGGCGCCTCACGGTC

GCGGCTCCATGCCCGGACTGCGACCCCGGAAGTGGCGGGAGCGGGGGAC

GACAGCCGCGGCGGACACAGGGGACCCGCCGGCTCAGGCACCTTTGACCC

GGAAGTTGAGCGACCCAGGCGGCGGCCTGGGATTGGACACCACCAGGCAC

GTACCAAGGCGTCCGCGGCGCTTGGGGGGAGCCCGCGGCGCGGCGGCCT

AAGGTGCGTAACGCCCCATGAACGACATCTTCCGGTGGGTTAGGGAGAGA

CACCCCCCTGTGACTTGGTATCACTCAGTCAAACCCATGATCCCCCACTA

TTAAGGATATCCGGAGAGGATGCTACCTATCAGG

SNORD13-C8orf41:
(SEQ ID NO: 80)
TCCTGACTGCAGCACCAGAAGGCTGGTCTCTCCCACAGAACGAGGATGGA

GGCGGGAGGGATCCGTTGAAGAGGGAAGGAGCGATCACCCAAAGAGAAC

TAAAATCAAATAAAATAAAACAGAGAGATGTCTTGGAGGAGGGGGCGAGT

CTGACCGGGATAAGAATAAAGAGAAAGGGTGAACCCGGGAGGCGGAGTTT

GCAGTGAGCCGAGATCGCGCCACTGCACTCCAGCCTGGGCGACAGAGTGA

GACTCCGTCTCAGTAAAAAAAAAAAAAAAAAAAAAGAATAAAGAGGAAAGG

ACGCAAGAAAGGGAAAGGGGACTCTCAGGGAGTAAAAGAGTCTTACACTT

TTAACAGTGACGTTAAAAGACTACTGTTGCCTTTCTGAAGACTAAAAAGA

AAAAAAACTTAAAAATTTAAAGAAATAAACTTCTGAGCCATGTCACCAAC

TTAACCACCCCAGGTACCTGCAACGGCTCGCGCCCGCCGGTGTCTAACA

GGATCCGGACCTAGCTCATATTGCTGCCGCAAAACGCAAGGCTAGCTTCC

GCCAGTACTGCCGCAACACCTTCTTATTTCACGACGTATGGTCGTAAAGC

AATAAAGATCCAGGCTCGGGAAAATGACGGAGAGGTGGAACTATAGAGAA

TAAATTTGCATATATAATAATCCGCTCGCTAATTGTGTTTCTGTTTTCCT

TTGCTAAGGTAGAAACAAAAGAATAATCACAGAATCTCAGTGGGACTTTG

AAAATATCCAGGATTTTATACGTGAAGAATGGATGTATCGCATTACGGTA

GTCACCCTATGTGTAAATTAGTGGCACATACTTGGCACTCCTTAATGTCA

ACTATAAGATG

-continued

RNU6-2-THEM259;
(SEQ ID NO: 83)
GCCTCCCAGCGTCGCGCCCTAACGACCCGCAAGTGTCCGAGGGCGCCTCC

CGGCCGCCATCGGCCGCCCTCGCAGCCGCCGCTCTCCTCACGGCCTCCCG

GCCGCCGCCGCCATCTTCCGCTTTCTCGTCCGGCTGCGGCGCTGCTGACG

CTAGCGAGTCGCCACGCCGGGCAAGAGCGGCCCCCCTGCGCCCGCAGAGA

ACGCTGGGATGCCAGCGGCGCCCGCGGAGGCCTCACCCCCTACCTCGGCC

GCTCCAGGGGCGGGCCTGCATCTGGGCCACCTCTTTTGCATATTGGCAC

CCACAATCCACCGCGGCTATGAGGCCAGTATAAGGCGGTAAAATTACGAT

AAGATATGGGATTTTACGTGATCGAAGACATCAAAGTAAGCGTAAGCACG

AAAGTTGTTCTGCAACATACCACTGTAGGAAATTATGCTAAATATGAAAC

CGACCATAAGTTATCCTAACCAAAAGATGATTTGATTGAAGGGCTTAAAA

TAGGTGTGACAGTAACCCTTGAGTC

TABLE 4

Examples of orthologous bidirectional promoters

| ncRNA gene | Protein gene | Distance | Organism |
|---|---|---|---|
| RPPH1 | PARP2 | 230 bp | Human |
| RPPH1 | PARP2 | 172 bp | Mouse |
| RPPH1 | PARP2 | 201 bp | Rat |

RPPH1-PARP2 (Mouse):
(SEQ ID NO: 81)
CGCTCTTGAAGGACGACGTCATCATCCCTTGCCCGGATGCGCGGGCTTCT

TGTCTAGCACAGGAGCCTGGGGTAGAGCGCATGCAAATTACGCGCTGTGC

TTTGTGGGAAATCACCCTAAACGAAAAATTTATTCCTCTTTCGAGCCTTA

TAGTGGCGGCCGGTCTACATCC

RPPH1-PARP2 (Rat):
(SEQ ID NO: 82)
GGCTGATGAGCTTCCCCCGCCCACTAGGAGTGTGAAGACCTGCCGCCATA

ATAAGACTCCAAAAGACAGTGAATTTAACACTTACGGTGACTTCCCACAA

AGCACAGCGTGTAATTTGCATGCGCTCTAGCCCAGGCTCCAGCTCCGGAC

CAGAAGCCCGCGCATCCCGGCAAAGGGTGATGACGTCGTCCTTCAAGCGC

T

In some embodiments, the modifications are made to nucleases (e.g., RNA-guided nucleases). In some embodiments, the nuclease (e.g., Cas9) is modified through post-transcriptional Cell-cycle regulation (e.g., fusion proteins comprising Geminin (Gem) or Cdt1). In some embodiments, the nuclease (e.g., Cas9) is modified by engineering partial target sites such that the nuclease can bind without DNA cleavage. In some embodiments, the nuclease (e.g., Cas9) is modified by modulating its half-life using N-terminal amino acid identity.

Such a modified CRISPR/Cas9 system can precisely target genomic sites, or facilitate the repair of a defective genomic sites, with greater efficacy, safety, and precision. Moreover, this modification provides a compact CRISPR/Cas9 system that allows for higher-resolution targeting of oncogenes over existing CRISPR, TALEN, or Zinc-finger technologies.

Other aspects of the invention relate to methods comprising expression screens for additional bidirectional promoters with both RNA pol II and RNA pol III activities.

I. Improvements/Modifications Crispr/Cas9 System.

A. Compositions

In some embodiments, the presently disclosed subject matter relates to compositions comprising improvements of a CRISPR/Cas9 system previously described in WO2015/195621 (herein incorporated by reference in its entirety). Such improvements comprise a non-naturally occurring nuclease system (e.g., CRISPR-Cas9) comprising one or more vectors comprising: a) a promoter (e.g., orthologous H1 promoter or 7sk) operably linked to at least one nucleotide sequence encoding a nuclease system guide RNA (gRNA), wherein the gRNA hybridizes with a target sequence of a DNA molecule in a cell, and wherein the DNA molecule encodes one or more gene products expressed in the cell; and b) a regulatory element operable in a cell operably linked to a nucleotide sequence encoding a genome-targeted nuclease (e.g., modified Cas9 protein), wherein components (a) and (b) are located on the same or different vectors of the system, wherein the gRNA targets and hybridizes with the target sequence and the nuclease cleaves the DNA molecule to alter expression of the one or more gene products. In some embodiments, the system is packaged into a single adeno-associated virus (AAV) particle. In some embodiments, the system inactivates one or more gene products. In some embodiments, the system excises at least one gene mutation. In some embodiments, the H1 promoter comprises a nucleotide sequence having at least 80%, 85%, 90%, 95%, 98%, 99%, or 100% identity to the nucleotide sequence set forth in SEQ ID NO: 12 or 32. In some embodiments, the orthologous H1 promoter is derived from mouse or rat. In some embodiments, the orthologous H1 promoter comprises a nucleotide sequence having at least 80%, 85%, 90%, 95%, 98%, 99%, or 100% identity to the nucleotide sequence set forth in SEQ ID NOs: 84-119. In some embodiments, the orthologous H1 promoter comprises a nucleotide sequences set forth in the group consisting of SEQ ID NOs: 84-119. In some embodiments, the H1 promoter comprises: a) control elements that provide for transcription in one direction of at least one nucleotide sequence encoding a gRNA; and b) control elements that provide for transcription in the opposite direction of a nucleotide sequence encoding a genome-targeted nuclease. In some embodiments, the promoter is the human, mouse, or rat 7sk promoter. In some embodiments, the 7sk is selected from the group consisting of 7sk1 (variant 1 of 7sk which uses the endogenous GSTA4 5'UTR), 7sk2 (variant 2 of 7sk which uses just a kozak sequence in the 5'UTR), and 7sk3 (variant of 7sk which uses the beta globin 5'UTR). In some embodiments, the human 7sk1 comprises a nucleotide sequence having at least 80%, 85%, 90%, 95%, 98%, 99%, or 100% identity to the nucleotide sequence set forth in SEQ ID NO: 3. In some embodiments, the mouse 7sk1 comprises a nucleotide sequence having at least 80%, 85%, 90%, 95%, 98%, 99%, or 100% identity to SEQ ID NO: 6. In some embodiments, the human 7sk2 comprises a nucleotide sequence having at least 80%, 85%, 90%, 95%, 98%, 99%, or 100% identity to SEQ ID NO: 4. In some embodiments, the mouse 7sk2 comprises a nucleotide sequence having at least 80%, 85%, 90%, 95%, 98%, 99%, or 100% identity to SEQ ID NO: 7. In some embodiments, the human 7sk3 comprises a nucleotide sequence having at least 80%, 85%, 90%, 95%, 98%, 99%, or 100% identity to SEQ ID NO: 5. In some embodiments, the mouse 7sk3 comprises a nucleotide sequence having at least 80%, 85%, 90%, 95%, 98%, 99%, or 100% identity to SEQ ID NO: 8. In some embodiments, the orthologous H1 promoter or 7sk promoter has at least one modification. In some embodiments, the at least one modification of the promoter comprises an element that allows conditional regulation. In some embodiments, the element is a tet-responsive promoter. In some embodiments, the tet-response promoter comprises a Tet repressor (TetR) and Tet operator (TetO) engineered into the H1 promoter. In some embodiments, the TetR comprises an amino acid sequence having at least 80%, 85%, 90%, 95%, 98%, 99%, or 100% identity to SEQ ID NO: 14. In some embodiments, the TetO comprises a nucleotide sequence having at least 80%, 85%, 90%, 95%, 98%, 99%, or 100% identity to the nucleotide sequence set forth in SEQ ID NO: 11. In some embodiments, the H1-TetO comprises a nucleotide sequence having at least 80%, 85%, 90%, 95%, 98%, 99%, or 100% identity to the nucleotide sequence set forth in SEQ ID NO: 13. In some embodiments, the at least one modification of the promoter comprises a site that allows auto-regulation. In some embodiments, the auto-regulation site comprises a nucleotide sequence having at least 80%, 85%, 90%, 95%, 98%, 99%, or 100% identity to the nucleotide sequence set forth in SEQ ID NO: 33 or 34. In some embodiments, the nuclease system further comprising at least one terminator sequence. In some embodiments, the terminator sequence is any nucleic acid selected from the group consisting of SEQ ID NOs: 120-130. In some embodiments, the at least one terminator sequence is selected from the group consisting of SV40 or synthetic poly A (SPA) sequences. In some embodiments, the terminator sequences is a SV40 120 (SEQ ID NO: 123) or 240 (SEQ ID NO: 122) base pair sequence. In some embodiments, the terminator sequences is a SPA 49 base pair equence. In some embodiments, the nuclease system further comprises 5' untranslated region (5'UTR) sequences. In some embodiments, the nuclease system further comprises a Kozak sequence. In some embodiments, the Kozak sequence comprises a nucleotide sequence having at least 80%, 85%, 90%, 95%, 98%, 99%, or 100% identity to SEQ ID NO: 1 or 2. In some embodiments, the nuclease system further comprises a RNA sequence that mediates cap-independent initiation of translation. In some embodiments, the RNA sequence is selected from the group consisting of 6.947 or 6.967 (Wellensiek I. (2013) *Nature Methods*, 10:747-750). In some embodiments, the Cas9 comprises a nucleotide sequence having at least 80%, 85%, 90%, 95%, 98%, 99%, or 100% identity to the nucleotide sequence set forth in SEQ ID NO: 61. In some embodiments, the Cas9 comprises at least one modification. In some embodiments, the at least one modification in the Cas9 comprises an alteration in the cleaving sequence. In some embodiments, the nuclease is selected from the group consisting of Cas1, Cas1B, Cas2, Cas3, Cas4, Cas5, Cas6, Cas7, Cas8, Cas9 (also known as Csn1 and Csx12), Cas10, Cas13a, Csy1, Csy2, Csy3, Cse1, Cse2, Cse1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15. Csf1, Csf2, Csf3, Csf4, Cpf1, C2c1, C2c2, and C2c3. In some embodiments, the alteration in the cleaving sequence selected from the group consisting of T2A, P2A, E2A, and F2A. In some embodiments, the T2A comprises an amino acid sequence. having at least 80%, 85%, 90%, 95%, 98%, 99%, or 100% identity to the nucleotide sequence set forth in SEQ ID NO: 36. In some embodiments, the P2A comprises an amino acid sequence having at least 80%, 85%, 90%, 95%, 98%, 99%, or 100% identity to the nucleotide sequence set forth in SEQ ID NO: 35. In some embodiments, the P2A comprises an amino acid sequence having the nucleotide sequence set forth in SEQ ID NO: 35. In some embodiments, the E2A comprises an amino acid sequence having at least 80%, 85%, 90%, 95%, 98%, 99%, or 100% identity to the nucleotide sequence set forth in SEQ ID NO: 37. In some embodiments, the F2A comprises an amino acid sequence having at least 80%, 85%, 90%, 95%, 98%, 99%, or 100% identity to the nucleotide sequence set forth in SEQ ID NO: 38. In some embodiments, the at least one modification in the Cas9 comprises a codon optimized for expression in the cell. In some embodiments, the Cas9 further comprises a linker sequence operably fused in frame to a cell-cycle dependent protein (Cas9 fusion). In some embodiments, the cell cycle-dependent protein is selected from the group consisting of APE2, ATR, 53BP1, BRCA1, Chk1, Cdc5, Cdc6, Cdc7, Cdc45, Cdt1, CSA, CSB, Ctf18, CtIP, DDB1, DDB2, DNA2, DUT, Elg1, EndoV, Esp1, Exonuclease1, FBH1, FEN1, Geminin, Hus1, KNTC2 (NDC80), Ku80, Ligase1, Mad2, MBD4, Mcm3, Mcm4, Mcm5, Mcm6, Mcm7, Mcm8, Mcm10, MGMT, MLH3, Mms4, MPG, MSH2, Mus81, NBS1, NEIL2, NEIL3, NTH1, Orc1, Orc3, PARP1, PCNA, Pif1, Pin1, PMS1, PMS2, PNK, Pola p180, Pola p'70, Pola Spp1 (Prim2a), Polb, Pold p125, Pole Dpb3, Pole Dpb4, Pole Pol2, Poli, Poll, Polm, Psf1, Psf2, Psf3, Rad1, Rad18, Rad23A, Rad23B, Rad51, Rad51D, Rad54, Rad6A, Rag1, Rag2, RPA34, RPA70, Scc1, Scc3, Sir2, SIRT1 (Sirtuin), TDG, TDP1, TIMELESS, Tin2, Topoisomerase I, Topoisomerase IIIa, Topoisomerase IIIb, Ubc13, UNG, XAB2, XPC, XPF, XPG, Xrcc2, and XRCC4. In some embodiments, the cell cycle-dependent protein is Geminin. In some embodiments, the cell cycle-dependent protein is human Geminin. In some embodiments, the human Geminin comprises the amino acids from positions 1-110 (hGem(1-110)). In some embodiments, the hGem(1-110) comprises an amino acid sequence having at least 80%, 85%, 90%, 95%, 98%, 99%, or 100% identity to the amino acid sequence set forth in SEQ ID NO: 19. In some embodiments, the cell cycle-dependent protein is Cdt1. In some embodiments, the cell cycle-dependent protein is human Cdt1. In some embodiments, the human Cdt1 comprises amino acids from positions 30-120 (hCdt1(30-120)). In some embodiments, the hCdt1(30-120) comprises an amino acid sequence having at least 80%, 85%, 90%, 95%, 98%, 99%, or 100% identity to the amino acid sequence set forth in SEQ ID NO: 18. In some embodiments, the Cas9 fusion comprises an amino acid sequence having at least 80%, 85%, 90%, 95%, 98%, 99%, or 100% identity to the amino acid sequence selected from the group consisting of SEQ ID NO: 20-27. In some embodiments, the Cas9 is operably fused in frame to ubiquitin (Ub-Cas9). In some embodiments, the Ub-Cas9 at least one N-terminal modification. In some embodiments, the N-terminal modified Ub-Cas9 comprises an amino acid sequence having at least 80%, 85%, 90%, 95%, 98%, 99%, or 100% identity to the amino acid sequence selected from the group consisting of SEQ ID NO: 39-58. In some embodiments, the ubiquitin protein comprises a nucleotide sequence having at least 80%, 85%, 90%, 95%, 98%, 99%, or 100% identity to the nucleotide sequence set forth in SEQ ID NO: 60. In some embodiments, the nuclease system further comprises a SaCas9 nickase. In some embodiments, the nuclease system further comprises a donor template sequence. In some embodiments, the at least one vector comprises a nucleotide sequence having at least 80%, 85%, 90%, 95%, 98%, 99%, or 100% identity to the nucleotide sequence set forth in SEQ ID NO: 62 or 67. In some embodiments, the donor template sequence corrects at least one gene mutation. In some embodiments, the at least one gene mutation is rd10 or rd12.

In some embodiments, the at least one vector comprises a nucleotide sequence having at least 80%, 85%, 90%, 95%, 98%, 99%, or 100% identity to the nucleotide sequence set forth in SEQ ID NO: 63 or 64. In some embodiments, the at least one vector comprises a nucleotide sequence having at least 80%, 85%, 90%, 95%, 98%, 99%, or 100% identity to the nucleotide sequence set forth in SEQ ID NO: 65 or 66. In some embodiments, the promoter is operably linked to at least one, two, three, four, five, six, seven, eight, nine, or ten gRNA. In some embodiments, the target sequence comprises the nucleotide sequence $AN_{19}NGG$, $GN_{19}NGG$, $CN_{19}NGG$, or $TN_{19}NGG$. In some embodiments, the cell is a eukaryotic or or non-eukaryotic cell. In some embodiments, the eukaryotic cell is a mammalian or human cell. In some embodiments, the eukaryotic cell is a retinal photoreceptor cell. In some embodiments, the one or more gene products are rhodopsin. In some embodiments, the expression of the one or more gene products is decreased.

TABLE 5

Examples of Orthologous H1 sequences mus_musculus
TTCAGGATGTAGACCGGCCGCCACTATAAGGCTCGAAAGAGGAATAAATTTTT
CGTTTAGGGTGATTTCCCACAAAGCACAGCGCGTAATTTGCATGCGCTCTACCC
CAGGCTCCTGTGCTAGACAAGAAGCCCGCGCATCCGGGCAAGGGATGATGACG
TCGTCCTTCAAGAGCG (SEQ ID NO: 84)

rattus_norvegicus
AGGAGTGTGAAGACCTGCCGCCATAATAAGACTCCAAAAGACAGTGAATTTAA
CACTTACGGTGACTTCCCACAAAGCACAGCGTGTAATTTGCATGCGCTCTAGCC
CAGGCTCCAGCTCCGGACCAGAAGCCCGCGCATCCCGGCAAAGGGTGATGACG
TCGTCCTTCAAGCGCT (SEQ ID NO: 85)

dipodomys_ordii
AGGAAAGACTTCGCTGAGGCAGACTTTATAAGGCTCCCGCGCAGAAAGAAACT
TTATAGTTATGGTGATTTCCCACAAGCCACTGCGTCATGCAAATAAAGCAGGGT
ACGGCTTCCATGTACCTTAAGGTTTTTTTCTAGGCCGCGTACGCTCTGCGTATTC
AGCCACGTGACCCTGAGCCAGTGGTTGTTGGGAGCACGTTGTGGACCTCTGCGT
TTGGATTCC (SEQ ID NO: 86)

ictidomys_tridecemlineatus
GAAAGGGACTCCGCACAAGCAGAGTTTATAAGGCTCCCATCTGTACAGCCATTT
CTCGGTCATGGTAACTACCCACAACACACAGCGATATGCAAATATAGCAGAGC
GTGTCTTCCCGCGCGCGCCTGGTCGTCTCGGCGCCGGCGCGCTGCGTGGGCGG
AACTGTGACAGAGACCCTGCGATTCCTGGGAGCTGGCTGATGACATCAGTGTCT
AACCTCC (SEQ ID NO: 87)

cavia_porcellus
GAGAAAGAAAGGCTCAAACCTAGCCTTATAAGGCTCCCAAATGTCGGTATATT
TTTTGGTTATGGTGACTTCCCACAATGCATAGCGATATGTAGATATTGCCAGGA
GTACCTCCCACTTCTGGTCCTGTCAGCTCTTTTCTAGGACGCGCGCGCTGCAGGT
TTCCAGCCTGTGATTGGGCCAGCAATTCCGGGAATGAATTGATGACGTCAGCGT
TTGAATTCC (SEQ ID NO: 88)

ochotona_princeps
GGGGGAAGCTGGGCTCGATCAGCCTTTATAAAGCTCCAAAAACTCAAGACATT
TTTCTGTTACGGTGGCTTCCCACAGTACACAGCGACATGCAAATAGCTTGCCAA
TGAATTCGCGGACCGCTTCCCGCCCCGGCGCAGGCGCGCGGACGCTGTCTCCCC
TGGACGCGCGCTCGCGGTTCCCGGGAGCTGGCTGATGACGTTCGGTCTCC (SEQ ID NO: 89)

oryctolagus_cuniculus
GGGGAGAGGTGGATCCGAACAGACTTTATAAAGCTCCGAAAGCCCAAGGCATC
TTTCCCTTACGGTAGCTTCCCACAAGACATAGCGACATGCAAATTTCTTGAAGT
ATGCTTCAGACGCGCTTCTCGCCACAGCGCAAGCGCGCTGTGTGCTGACGCGGG
AACGGGCCAGGGCGCGGTTCCCGGGAGCGGGTTGATGACGTTAGATCTCC (SEQ ID NO: 90)

callithrix_jacchus
GAGGAAAAGTAGTCCCACAGACAACTTATAAGATTCCCATACCCTAAGACATT
TCACGATTATGGTGACTTCCCAGAAGACACAGCGACATGCAAATATTGCAGGT
CGTGTTTCGCCTGTCCCTCACAGTCGTCTTCCTGCCAGGGCGCACGCGCGCTGG
GTTTCCCGCCAACTGACGCTGGGCTCGCGATTCCTTGGAGCGGGTTGATGACGT
CAGCGTTTGAATTCC (SEQ ID NO: 91)

chlorocebus_sabaeus
GGGGAAGGGTGGTCCCTTACAGAACTTATAAGATTCCCAAACTCAAAGACATT
TCACGTTTATGGTGACTTCCCAGAAGACATAGCGACATGCAAATATTGCAGGGC
GTCACACCCCTCTCCCTCACAGTCATCTTCCTGCCAGGGCGCACGCGCGCTGGG
TGTTCTCGCGTAGTGACACTGGGCCCGCGATTCCTTGGAGCGGGTTGATGACGT
CAGCGTTCGAATTCC (SEQ ID NO: 92)

TABLE 5-continued

Examples of Orthologous H1 sequences macaca_mulatta
GGGGAAGGGTGGTCCCACACAGAACTTATAAGATTCCCATACTCAAAGACATT
TCTCGTTTATGGTGACTTCCCAGAAGACACAGCGACATGCAAATATTGTAGGGC
GTCACACCCCTGTCCCTCACAGTCATCTTCCTGCCAGGGCGCACGCGCGCTGGG
TGTTCCCGCGTAGTGACACTGGGCCCGCGATTCCTTGGAGCGGGTTGATGACGT
CAGCGTTCGAATTCC (SEQ ID NO: 93)

papio_anubis
GGGGAAAGGTGGTACCATACAGAACTTATAAGATTCCCATACTCAAAGACATT
TCACGATTATGGTGACTTCCCAGAAGACACAGCGACATGCAAATATTGTAGGG
CGTCACACCCCCTGTCCCTCACAGTCATCTTCCTGCCAGGGCGCACGCGCGCTG
GGTGTTCCCGCGTAGTGACACTGGGCCCGCGATTCCTTGGAGCGGGTTGATGAC
GTCAGCGTTCGAATTCC (SEQ ID NO: 94)

gorilla_gorilla
GGGAAAGGGTGGTCCCACACAGAACTTATAAGACTCCCATATCCAAAGACATT
TCACGGTTATGGTGATTTCCCAGAACACATAGCGACATGTAAATATTGCAGGGC
GCCACTCCCCAGTCCCTCACAGCCATCTTCCTGCCAGGGCGCACGCGCGCTGGG
TGTTCCCGCCTAGTGACACTGGGCCCGCGATTCCTTGGAGCGGGTTGATGACGT
CAGCGTTCGAATTCC (SEQ ID NO: 95)

homo_sapiens
GGGAAAAAGTGGTCTCATACAGAACTTATAAGATTCCCAAATCCAAAGACATT
TCACGTTTATGGTGATTTCCCAGAACACATAGCGACATGCAAATATTGCAGGGC
GCCACTCCCCTGTCCCTCACAGCCATCTTCCTGCCAGGGCGCACGCGCGCTGGG
TGTTCCCGCCTAGTGACACTGGGCCCGCGATTCCTTGGAGCGGGTTGATGACGT
CAGCGTTCGAATTCC (SEQ ID NO: 96)

pan_troglodytes
GGGAAAGGGTGGTGCCACACAGAACTTATAAGATTCCCATATGCAAAGACATT
TCACGTTTATGGTGATTTCCCAGAACACATAGCGACATGCAAATATTGCAGGGC
GCCACTCCCCTGTCCCTCACTGCCATCTTCCTGCCAGGGCGCACGCGCGCTGGG
TGTTCCCGCCTAGTGACACTGGGCCCGCGATTCCTTGGAGCGGGTTGATGACGT
CAGCGTTCGAATTCC (SEQ ID NO: 97)

pongo_abelii
GAGAAAGGGTGGTCCCGTCCAGAACTTATAAGATTCCCATACCCAAAGACATT
TCACGTTTATGGTGACTTCCCAGAATGCATAGCGACATGCAAATATTGCAGGGC
GTCACTCCCCTGTCCCTCACAGCCATCTTCCTGCCAGGGCGCCCGCGCGCTGGT
GTTCCCGCCTAGTGACACTGGGCCCACGATTCCTTGGAGCGGGTTGATGACGTC
AGCGCTCGTATTCC (SEQ ID NO: 98)

nomascus_leucogenys
GGGGAAAAGTAGTAGACCTTATAAGATTCCCAAACCCAAAGACATTTCTCGTTT
ATGGTGACTTCCCAGAAGACATAGCGACATGCAAATATTGCAGGGCGCCACTC
CCCTGTCCCTCACAGCCATCTTCCTGCCAGGGCGCACGCGCGCTGGGTGTTCCC
GCCTAGTGACACTCGGCCCGCGATTCCTTGGAGCGGGTTGATGACGTCAGCGTT
CGAATTCC (SEQ ID NO: 99)

tarsius_syrichta
GCGAGAGGGTGGGTCCACACAGAGCTTATAAGGTTCACAAGTAAAGATATTTC
ACGGTGACGGTGACTTCCCACAATACACTGCGACATGCAAATATAGCCGGGCG
TGCCTCCCCGATCCCGGAAGAGCGACTCCTAGCCAGTGCGCACGCGCGCTGCG
TGTTCGCGTCCTAGGTCGCTGGGCCCGCGGTTCCTGGGAGCGGGTGGTGACGTC
AGCGGCCCAGCTTC (SEQ ID NO: 100)

otolemur_garnettii
GCCTAAAAGGGCGCTTGCACAGAATTTATAAGGTTCCCAAACAGAGACACATT
TCATTATTATGGTGACTTCCCACAATGCACAGCGCCATGCAAATATGCTAGGAC
GCCTCCCCCCGCTACCTTAAGGTCGTCAACTAACCAGTGCGCGCGCACTGCG
CGTTTCCCGCCGGTGACTCAATGCCCGCGTTTGGTGGGAGCTAGTTGGTGACCT
CAGTTCTGGAGGCTC (SEQ ID NO: 101)

tupaia_belangeri
GGGGGAAGCTGGGTCCACTGAGTTCTTATAAGGTTTCCAGTCCTAGAGCGATTT
TACCATTGCGGTGATTTCCCAGCATCCGTAGCTACATGCAAATAGCGCGGGGCG
CGTCTCTCAGGTCCCTCCCCGCCCTCTCACTGTACGTACCCGCGTCCTAGGGAC
GCCGCGCCCGGGGTTCCCGGACGTCAGCGTTCCGACGCA (SEQ ID NO: 102)

ailuropoda_melanoleuca
AGGGAAAGCCGCGCCTGGGGCGGATTTATAAGGCTTCCATATCTAAAGGCATT
TCACAGTCATGGTGACTTCCCACAATACATAGCAACATGCAAATATCGCGGGG
AGAACCTCCCCTGTCCCTTGTACGCGGCTTCTAAAGACGCACGCGCGCTCTGTG
TTCCCGCCCTGTGACTCTAGGCGGGCAATTCCTGGGACAGTGTTCTGACGGGAA
CGTTCAGGCTCC (SEQ ID NO: 103)

TABLE 5-continued

Examples of Orthologous H1 sequences mustela_putorius_furo
GGGAAAGGGTGGACCCACCGAGCATTTATAAGGCTCCCGCATCTAAAGACATT
TTACAGTTATGGTGACTTCCCACAACGCGTAGCAACATGCAAATATCGTGGAGA
GTACCGCCCCTGTCCCATGCACGCGTCTTCTCAGCAGCACGCACGCGCGCTGTG
TTCCCGCCCTGTGACTCCAGGCGGGTATTTCCAGGGGCGGGTTGCTGACAGGAA
CGTTCAGGCTTC (SEQ ID NO: 104)

canis_familiaris
GCAGCGCAGCCCTCTCGCCGCTTATAAAGTGCCGCCCGCACGGCCCTTCTCGCT
CACGGCGACTTCCCATAACACACAGCAGCATGCAAATACCGCGGGGAGCCCCG
CCCCGCCCCGGCCCCGCACCGCCTCGGGACGCATGCGCCGGCTCTCCGTTCCC
GCCTTGGGCCGGCGGCGGGCGGGCGGGCGAGCGGGCGGGAGCGGCTCCGGCG
GGGACGAGCGGGCGCC (SEQ ID NO: 105)

felis_catus
GGGAAAGGGTGGCCCCGCCGAGCATTTATAAGACTCCCATACCTAAAGACATT
TCTCAGTTATGGTGATTTCCCACAACACACAGCAACATGCAAATATCGAGGGGT
GTACCGCCCCTGTCCTTTGTAGACGTCTTCTCTCAGGACGCACGCGCGCTGTA
TTCCCGCCTTGTGACTCTAGGCGGGCGATTCCTGGGAGAGGGTTGATGACGTCC
AAGTTCTGGCTTC (SEQ ID NO: 106)

equus_caballus
GGGGGAAAACAGCCCATGGCTGCATTTATAAGACTCACAGATCTAAAGCCATT
TCACGAATAGGGTGACTTCCCACAATACACAGCGACATGCAAACATAGCGGGG
CGTGCCTTTCCTGTACCCTGTGGGCATCTCTCCTGGACGCACGCGCGCCGGGTG
TTCCCGCGCTGTGACTCTAGGCAAGCGCTTCCTGGGAGAGAGTTGATGACGGCA
GCATTCGGGCTCC (SEQ ID NO: 107)

myotis_lucifugus
GGGAGAAGGAGGCGTAGAGGATATATAAGGCCCCCTTATGTGTAGTCCTTTTA
CGGTTAGGGTGACTTCCCACAACGCATAGCGACATGCAAATTTGACGGGCGTG
CCTCCTCTGTCCCTGCGGGCAACTTCTCTCCTGGACGCGCGCGCGCTGCGTGTTC
CCGCCTTTTGACTCCAGCCGAGCGAATCCTGGGAGAGGGCAGGTGACGTCAAC
AGTCAGGCTCG (SEQ ID NO: 108)

pteropus_vampyrus
GCGAGAAAAATTCTTCACGCAGAATATATAAGGATCCCATATCTGAAGACATTT
TACGATTACGGCGATTTCCCACAACACATAGCGACATGTAAATGTAGTGGGGC
ATGCCTCCCCTGTCCCTTGTGGGCAGCTTCTCGCCAGAACGCACGCGCGGTGCG
TGTTCCCGCCTTGTGACTAAGTTGGCGAGTCAGGGAGGAGATTGATGACGTCAG
CTCACCCGCTCC (SEQ ID NO: 109)

bos_taurus
GGCAAACACCGCACGCAAATAGCACTTATAATGTGCTCATACCTAGAGCCACTT
TTCGGTTACGGTGACTTCTCAAAAAGACAGTGGAACATGCAAATATTACAGTGC
GTCCCGCCCCTGGTAGGTCTACGCTAGGACGCACGCGCACTACGGTTCCCGCCT
ATAGACTGCGCTGGCGATTCCTGGGAGCGGACTGATGACGTCAGCGTTCGGGA
TCC (SEQ ID NO: 110)

ovis_aries
GGCGAACAATGCGCGCAAACAGCATTTATAATGAGCTCATACCTAAAGCCACT
TTACGGTTACGGTGACTTCCCACAAGACATTGCGGCATGCAAATATTTTAGTGC
GTCCCGCCCCTGGTAGTTCCACGCTAGGACGCACACGCACTACGGTTCCCGCCT
TTAGACTGCGCTGGCGATTCCAGGAGCGGACTGATGACGTCAGCGTTGGGGCT
CC (SEQ ID NO: 111)

tursiops_truncatus
GCCGAAAACCAGGCTCAAGCCACATTTATAAGGCTCCCAAATCTAAGTACATTT
GTCGGTTATGGTGACTTCCCGCACCACATTGCGACATGCAAATACTGCGGAGCG
TCCCTCCCCTGGCAACTCCTCGCTGGGACGCACGCGCGCTACGTGCTCCCGCCT
TTTGACTGCGCCGGCGATACTTGGGAGAGGGTTGATGACGTCAGCGTTCTGGCT
CC (SEQ ID NO: 112)

vicugna_pacos
GGGAAAGGGTGGGCTCACGCAGCCTTTATAAGACTCCCAAACTTAAAGACATT
TCTCGGTTATGGCGACTTCCCACAAGACATAGCGACATGCAAATACTGCAGGG
CGCCGACCCGGTCCTGTGCAGCCATCTTTCGGCTGGGACGCACGCGCGCTGCGT
GTTCCCGCCCTGTGACTGCGCCGGCGATTACTGGGAGAGGATTGATGACGTCAA
CGTTCGGGTTCC (SEQ ID NO: 113)

sus_scrofa
GTAGGAAAACTGCTTCTGTGAGCACTTATAAAACTCCCATAAGTAGAGAGATTT
CATAGTTATGGTGATTTCCCATAAGACATTGCGACATGCAAATATTGTGGCGCG
TTCGTCCCCGTCCGGTGCAGGCAGCTTCGCTCCAGGACGCACGCGCAATACATG
TTCCCGCCTTGAGACTGCGCCGGCAGATTCCTAGGAAGTGGTTGATGACGTCGA
TGTTAGGGATCC (SEQ ID NO: 114)

TABLE 5-continued

Examples of Orthologous H1 sequences erinaceus_europaeus
GCCTAAACCGGCTCTTTCGACAGACTTATAAGGACCTCTTATCTTAGGACATTT
TTTTGTTAGGGTAACTTCCCACGATGCATAGCGATATGTAAATATGGCGCCGCG
AGTCTCTCCTAGGCGTCTCCCCAGGACGCAGGCGCACTGCTTGTTCCCGCGTTA
ACATTGCTGATTCTGGGAGACTGCTGATGACGTCAGCGTCCAGTCTAC (SEQ ID
NO: 115)

choloepus_hoffmanni
AGAAAAAAATAGTTTATGCTGGATTTATAAGATTCCCAAATCTAAAGCCATTTC
ACAGTTACGGTGATTCCCCACTACACACGGCGATATGCAAATATAGCGGAAGT
GTTCCTGAGGCGTGGTAAAGCGCGCGCGCGCTGAGAGTTCCCGCCCTGTGGTGC
TGGGCTGGAGATGCCTGAGAACTGGCTGATGACGGCAACGTTCGGGCTCC (SEQ
ID NO: 116)

dasypus_novemcinctus
AAAGCGATAGTTTTTTAAACTGGACTTATAAGGCACCCATATCTACGTATATTT
CATGGTTAGGGTGATTTCCCACAACACATAGCGAAATGCAAATATTGGAGGGC
GCTGAGGCGTGGTCGGGCGCAAGCGCGCTGCGACTTCCCGCCTTTCGGCCCTAG
GCCCCAGATTCCTGGGAGCTGGATGATGACGTTGACGTTCGGATACC (SEQ ID
NO: 117)

loxodonta_africana
GGGAAGGAACAAATTCGTCAGGATTTATAAGACTCTCAGAGCTGTAGACATTT
CACAGTTAGGGCGATGTCCCACAATACATAGCAACATGCAAATATTCTAGGAG
GCCAGCCTCCCCGTCCGCGTGGTCATCTTCTCGCTAGGGCGCACGCCCGCTGCG
TGTTCCCGCTCTGTGACCAGGCAGGCGATTCCTGAGAACGCTTGGTGACGTCA
GTGTTCTGGCTCC (SEQ ID NO: 118)

procavia_capensis
AGGGTAAATCGGCGCTGCTCAGCATTTAAAAGAATCCCAAATGTGTCGC
CATTTTACGCTTAGGGTGATATCCCACAAGACACAGCGACATGCAAATATCGTG
AGTCTCTGTTTCCCTGTCCACGAGGGCGTCCTCTCGCTGGGGCGCACGCGCGGT
GTGTGTGCCCCCGTTGTGTGTTCCCGCGATTCCAAAGAACTGGTTGATAACGTT
AGACTTCCGGCTGC (SEQ ID NO: 119)

TABLE 6

Examples of terminators

SPA
AATAAAATATCTTTATTTTCATTACATCTGTGTGTTGGTTTTTTGTGTG
(SEQ ID NO: 120)

SPA and Pause
AATAAAATATCTTTATTTTCATTACATCTGTGTGTTGGTTTTTTGTGTGA
ATCGATAGTACTAACATACGCTCTCCATCAAAACAAAACGAAACAAAACA
AACTAGCAAAATAGGCTGTCCCCAGTGCAAGTGCAGGTGCCAGAACATTT
CTCT (SEQ ID NO: 121)

SV40 (240bp)
ATCTAGATAACTGATCATAATCAGCCATACCACATTTGTAGAGGTTTTAC
TTGCTTTAAAAAACCTCCCACACCTCCCCCTGAACCTGAAACATAAAATG
AATGCAATTGTTGTTGTTAACTTGTTTATTGCAGCTTATAATGGTTACAA
ATAAAGCAATAGCATCACAAATTTCACAAATAAAGCATTTTTTTCACTGC
ATTCTAGTTGTGGTTTGTCCAAACTCATCAATGTATCTTA
(SEQ ID NO: 122)

SV40-mini (120bp)
TTGTTTATTGCAGCTTATAATGGTTACAAATAAAGCAATAGCATCACAAA
TTTCACAAATAAAGCATTTTTTTCACTGCATTCTAGTTGTGGTTTGTCCA
AACTCATCAATGTATCTTAT (SEQ ID NO: 123)

bGH polyA
CGACTGTGCCTTCTAGTTGCCAGCCATCTGTTGTTTGCCCCTCCCCCGTG
CCTTCCTTGACCCTGGAAGGTGCCACTCCCACTGTCCTTTCCTAATAAAA
TGAGGAAATTGCATCGCATTGTCTGAGTAGGTGTCATTCTATTCTGGGGG
GTGGGGTGGGGCAGGACAGCAAGGGGGAGGATTGGGAAGACAATAGCAGG
CATGCTGGGGATGCGGTGGGCTCTATGG (SEQ ID NO: 124)

TK polyA
GGGGGAGGCTAACTGAAACACGGAAGGAGACAATACCGGAAGGAACCCGC
GCTATGACGGCAATAAAAAGACAGAATAAAACGCACGGGTGTTGGGTCGT
TTGTTCATAAACGCGGGGTTCGGTCCCAGGGCTGGCACTCTGTCGATACC
CCACCGAGACCCCATTGGGCCAATACGCCCGCGTTTCTTCCTTTTCCCC
ACCCCACCCCCCAAGTTCGGGTGAAGGCCCAGGGCTCGCAGCCAACGTCG
GGGCGGCAGGCCCTGCCATAG (SEQ ID NO: 125)

sNRP1
GGTATCAAATAAAATACGAAATGTGACAGATT (SEQ ID NO: 126)

sNRP1a
AAATAAAATACGAAATGTGACAGATT (SEQ ID NO: 127)

Histone H4B
GGTTGCTGATTTCTCCACAGCTTGCATTTCTGAACCAAAGGCCCTTTTCA
GGGCCGCCCAACTAAACAAAAGAAGAGCTGTATCCATTAAGTCAAGAAGC
(SEQ ID NO: 128)

MALAT-1
GATTCGTCAGTAGGGTTGTAAAGGTTTTTCTTTTCCTGAGAAAACAACCT
TTTGTTTTCTCAGGTTTTGCTTTTTGGCCTTTCCCTAGCTTTAAAAAAAA
AAAAGCAAAAGACGCTGGTGGCTGGCACTCCTGGTTTCCAGGACGGGGTT
CAAGTCCCTGCGGTGTCTTTGCTT (SEQ ID NO: 129)

MALAT-comp14
AAAGGTTTTTCTTTTCCTGAGAAATTTCTCAGGTTTTGCTTTTTAAAAAA
AAAGCAAAAGACGCTGGTGGCTGGCACTCCTGGTTTCCAGGACGGGGTTC
AAGTCCCTGCGGTGTCTTTGCTT (SEQ ID NO: 130)

The term "homologous" refers to the "% homology" and is used interchangeably herein with the term "% identity" herein, and relates to the level of nucleic acid sequence identity when aligned using a sequence alignment program.

For example, as used herein, 80% homology means the same thing as 80% sequence identity determined by a defined algorithm, and accordingly a homologue of a given sequence has greater than 80% sequence identity over a length of the given sequence. Preferred levels of sequence identity include, but are not limited to about, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8% or more sequence identity to the nucleotide sequences set forth in SEQ ID NOs: 1-82. Exemplary levels of sequence identity include, but are not limited to, about, 80%, 81%, 82%, 83%, 84%, 85%, 86%, 87%, 88%, 89%, 90%, 91%, 92%, 93%, 94%, 95%, 96%, 97%, 98%, 99.1%, 99.2%, 99.3%, 99.4%, 99.5%, 99.6%, 99.7%, 99.8% or more sequence identity to the nucleotide sequences set forth in SEQ ID NO: 1-82.

In some embodiments, the presently disclosed subject matter provides a non-naturally occurring CRISPR-Cas system comprising one or more vectors comprising: a) an H1 promoter operably linked to at least one nucleotide sequence encoding a CRISPR-Cas system guide RNA (gRNA), wherein the gRNA hybridizes with a target sequence of a DNA molecule in a cell, and wherein the DNA molecule encodes one or more gene products expressed in the cell; and b) a regulatory element operable in a cell operably linked to a nucleotide sequence encoding a Cas9 protein, wherein components (a) and (b) are located on the same or different vectors of the system, wherein the gRNA targets and hybridizes with the target sequence and the Cas9 protein cleaves the DNA molecule to alter expression of the one or more gene products.

In some embodiments, the presently disclosed subject matter provides a non-naturally occurring CRISPR-Cas system comprising one or more vectors comprising: a) an H1 promoter operably linked to at least one nucleotide sequence encoding a CRISPR-Cas system guide RNA (gRNA), wherein the gRNA hybridizes with a target sequence of a DNA molecule in a eukaryotic cell, and wherein the DNA molecule encodes one or more gene products expressed in the eukaryotic cell; and b) a regulatory element operable in a eukaryotic cell operably linked to a nucleotide sequence encoding a Type-II Cas9 protein, wherein components (a) and (b) are located on the same or different vectors of the system, whereby the gRNA targets and hybridizes with the target sequence and the Cas9 protein cleaves the DNA molecule, and whereby expression of the one or more gene products is altered. In one aspect, the target sequence can be a target sequence that starts with any nucleotide, for example, $N_{20}NGG$. In some embodiments, the target sequence comprises the nucleotide sequence $AN_{19}NGG$. In some embodiments, the target sequence comprises the nucleotide sequence $GN_{19}NGG$. In some embodiments, the target sequence comprises the nucleotide sequence $CN_{19}NGG$. In some embodiments, the target sequence comprises the nucleotide sequence $TN_{19}NGG$. In some embodiments, the target sequence comprises the nucleotide sequence $AN_{19}NGG$ or $GN_{19}NGG$. In another aspect, the Cas9 protein is codon optimized for expression in the cell. In another aspect, the Cas9 protein is codon optimized for expression in the eukaryotic cell. In a further aspect, the eukaryotic cell is a mammalian or human cell. In yet another aspect, the expression of the one or more gene products is decreased.

The presently disclosed subject matter also provides a non-naturally occurring CRISPR-Cas system comprising a vector comprising a bidirectional H1 promoter, wherein the bidirectional H1 promoter comprises: a) control elements that provide for transcription in one direction of at least one nucleotide sequence encoding a CRISPR-Cas system guide RNA (gRNA), wherein the gRNA hybridizes with a target sequence of a DNA molecule in a eukaryotic cell, and wherein the DNA molecule encodes one or more gene products expressed in the eukaryotic cell; and b) control elements that provide for transcription in the opposite direction of a nucleotide sequence encoding a Type-II Cas9 protein, whereby the gRNA targets and hybridizes with the target sequence and the Cas9 protein cleaves the DNA molecule, and whereby expression of the one or more gene products is altered. In one aspect, the target sequence can be a target sequence that starts with any nucleotide, for example, $N_{20}NGG$. In some embodiments, the target sequence comprises the nucleotide sequence $AN_{19}NGG$. In some embodiments, the target sequence comprises the nucleotide sequence $GN_{19}NGG$. In some embodiments, the target sequence comprises the nucleotide sequence $CN_{19}NGG$. In some embodiments, the target sequence comprises the nucleotide sequence $TN_{19}NGG$. In some embodiments, the target sequence comprises the nucleotide sequence $AN_{19}NGG$ or $GN_{19}NGG$. In another aspect, the Cas9 protein is codon optimized for expression in the cell. In another aspect, the Cas9 protein is codon optimized for expression in the eukaryotic cell. In a further aspect, the eukaryotic cell is a mammalian or human cell. In yet another aspect, the expression of the one or more gene products is decreased.

In some embodiments, the CRISPR complex comprises one or more nuclear localization sequences of sufficient strength to drive accumulation of the CRISPR complex in a detectable amount in the nucleus of a cell (e.g., eukaryotic cell). Without wishing to be bound by theory, it is believed that a nuclear localization sequence is not necessary for CRISPR complex activity in eukaryotes, but that including such sequences enhances activity of the system, especially as to targeting nucleic acid molecules in the nucleus. In some embodiments, the CRISPR enzyme is a type II CRISPR system enzyme. In some embodiments, the CRISPR enzyme is a Cas9 enzyme. In some embodiments, the Cas9 enzyme is *C. jejuni*, *G. stearothermophilus*, *N. meningitidis*, *S. aureus*, *S. pneumoniae*, *S. pyogenes*, or *S. thermophilus* Cas9, and may include mutated Cas9 derived from these organisms. The enzyme May be a Cas9 homolog or ortholog such as Cpf1 or Cas13a/C2c2.

In general, and throughout this specification, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g. retroviruses, replication defective retroviruses, adenoviruses, replication defective adenoviruses, and adeno-associated viruses). Viral vectors also include polynucleotides carried by a virus for transfection into a host cell.

Certain vectors are capable of autonomous replication in a host cell into which they are introduced (e.g. bacterial vectors having a bacterial origin of replication and episomal mammalian vectors). Other vectors e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids.

Recombinant expression vectors can comprise a nucleic acid of the presently disclosed subject matter in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed.

Within a recombinant expression vector, "operably linked" is intended to mean a the nucleotide sequence of interest is linked to the regulatory element(s) in a manner that allows for expression of the nucleotide sequence (e.g. in an in vitro transcription/translation system or in a host cell when the vector is introduced into the host cell).

The term "regulatory element" is intended to include promoters, enhancers, internal ribosomal entry sites (IRES), and other expression control elements (e.g. transcription termination signals, such as polyadenylation signals and poly-U sequences). Such regulatory elements are described, for example, in Goeddel (1990) Gene Expression Technology: Methods in Enzymology 185, Academic Press, San Diego, Calif. Regulatory elements include those that direct constitutive expression of a nucleotide sequence in many types of host cell and those that direct expression of the nucleotide sequence only in certain host cells (e.g., tissue-specific regulatory sequences). A tissue-specific promoter may direct expression primarily in a desired tissue of interest, such as muscle, neuron, bone, skin, blood, specific organs (e.g. pancreas), or particular cell types (e.g. lymphocytes). Regulatory elements may also direct expression in a temporal-dependent manner, such as in a cell-cycle dependent or developmental stage-dependent manner, which may or may not also be tissue or cell-type specific.

In some embodiments, a vector comprises one or more pol III promoters, one or more pol II promoters, one or more pol I promoters, or combinations thereof. Examples of pol III promoters include, but are not limited to, U6 and H1 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer) (e.g., Boshart et al. (1985) *Cell* 41:521-530), the SV40 promoter, the dihydrofolate reductase promoter, the β-actin promoter, the phosphoglycerol kinase (PGK) promoter, and EF1α, promoter.

Also encompassed by the term "regulatory element" are enhancer elements, such as WPRE; CMV enhancers; the R-US' segment in LTR of HTLV-I (Takebe et al. (1988) *Mol. Cell. Biol.* 8:466-472); SV40 enhancer; and the intron sequence between exons 2 and 3 of rabbit β-globin (O'Hare et al. (1981) *Proc. Natl. Read. Sci. USA*. 78(3):1527-31). It will be appreciated by those skilled in the art that the design of the expression vector can depend on such factors as the choice of the host cell to be transformed, the level of expression desired, etc. A vector can be introduced into host cells to thereby produce transcripts, proteins, or peptides, including fusion proteins or peptides, encoded by nucleic acids as described herein (e.g., clustered regularly interspersed short palindromic repeats (CRISPR) transcripts, proteins, enzymes, mutant forms thereof, fusion proteins thereof, etc.). Advantageous vectors include lentiviruses and adeno-associated viruses, and types of such vectors can also be selected for targeting particular types of cells.

The terms "polynucleotide", "nucleotide", "nucleotide sequence", "nucleic acid" and "oligonucleotide" are used interchangeably. They refer to a polymeric form of nucleotides of any length, either deoxyribonucleotides or ribonucleotides, or analogs thereof. Polynucleotides may have any three dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant polynucleotides, branched polynucleotides, plasmids, vectors, isolated. DNA of any sequence, isolated RNA of any sequence, nucleic acid probes, and primers. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

In aspects of the presently disclosed subject matter the terms "chimeric RNA". "chimeric guide RNA", "guide RNA", "single guide RNA", "synthetic guide RNA" and "crRNA" are used interchangeably and refer to the polynucleotide sequence comprising the guide sequence. The term "guide sequence" refers to the about 20 bp sequence within the guide RNA that specifies the target site and may be used interchangeably with the terms "guide" or "spacer".

As used herein the term "wild type" is a term of the art understood by skilled persons and means the typical form of an organism, strain, gene or characteristic as it occurs in nature as distinguished from mutant or variant forms.

As used herein the term "variant" should be taken to mean the exhibition of qualities that have a pattern that deviates from what occurs in nature.

The terms "non-naturally occurring" or "engineered" are used interchangeably and indicate the involvement of the hand of man. The terms, when referring to nucleic acid molecules or polypeptides mean that the nucleic acid molecule or the polypeptide is at least substantially free from at least one other component with which they are naturally associated in nature and as found in nature.

"Complementarily" refers to the ability of a nucleic acid to form hydrogen bond(s) with another nucleic acid sequence by either traditional Watson-Crick or other non-traditional types. A percent complementarily indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" as used herein refers to a degree of complementarily that is at least 60%, 65%, 70%, 75%, 80%, 85%, 90%, 95%. 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

As used herein, "stringent conditions" for hybridization refer to conditions under which a nucleic acid having complementarily to a target sequence predominantly hybridizes with the target sequence, and substantially does not hybridize to non-target sequences. Stringent conditions are generally sequence-dependent, and vary depending on a number of factors. In general, the longer the sequence, the higher the temperature at which the sequence specifically hybridizes to its target sequence. Non-limiting examples of stringent conditions are described in detail in Tijssen (1993), Laboratory Techniques In Biochemistry And Molecular Biology-Hybridization With Nucleic Acid Probes Part 1, Second Chapter "Overview of principles of hybridization and the strategy of nucleic acid probe assay", Elsevier, N.Y.

"Hybridization" refers to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi stranded complex, a single self hybridizing strand, or any combination of these. A hybridization reaction may constitute a step in a more extensive process, such as the initiation of PCR, or the cleavage of a polynucleotide by an enzyme. A sequence capable of hybridizing with a given sequence is referred to as the "complement" of the given sequence.

As used herein, "expression" refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

The terms "polypeptide", "peptide" and "protein" are used interchangeably herein to refer to polymers of amino acids of any length. The polymer may be linear or branched, it may comprise modified amino acids, and it may be interrupted by non amino acids. The terms also encompass an amino acid polymer that has been modified; for example, disulfide bond formation, glycosylation, lipidation, acetylation, phosphorylation, or any other manipulation, such as conjugation with a labeling component.

As used herein the term "amino acid" includes natural and/or unnatural or synthetic amino acids, including glycine and both the D or L optical isomers, and amino acid analogs and peptidomimetics.

The practice of the present presently disclosed subject matter employs, unless otherwise indicated, conventional techniques of immunology, biochemistry, chemistry, molecular biology, microbiology, cell biology, genomics and recombinant DNA, which are within the skill of the art (Sambrook, Fritsch and Maniatis (1989) Molecular Cloning: A Laboratory Manual, 2nd edition; Ausubel et al., eds. (1987) Current Protocols in Molecular Biology); MacPherson et al., eds. (1995) Methods in Enzymology (Academic Press, Inc.): PCR 2: A Practical Approach); Harlow and Lane, eds. (1988) Antibodies, A Laboratory Manual; Freshney, ed. (1987) Animal Cell Culture).

Several aspects of the presently disclosed subject matter relate to vector systems comprising one or more vectors, or vectors as such. Vectors can be designed for expression of CRISPR transcripts (e.g. nucleic acid transcripts, proteins, or enzymes) in prokaryotic or eukaryotic cells. For example, CRISPR transcripts can be expressed in bacterial cells such as *Escherichia coli*, insect cells (using baculovirus expression vectors), yeast cells, or mammalian cells. Suitable host cells are discussed further in Goeddel (1990) Gene Expression Technology: Methods in Enzymology 185, Academic Press, San Diego, Calif. Alternatively, the recombinant expression vector can be transcribed and translated in vitro, for example using T7 promoter regulatory sequences and T7 polymerase.

Vectors may be introduced and propagated in a prokaryote. In some embodiments, a prokaryote is used to amplify copies of a vector to be introduced into a eukaryotic cell or as an intermediate vector in the production of a vector to be introduced into a eukaryotic cell (e.g. amplifying a plasmid as part of a viral vector packaging system). In some embodiments, a prokaryote is used to amplify copies of a vector and express one or more nucleic acids, such as to provide a source of one or more proteins for delivery to a host cell or host organism. Expression of proteins in prokaryotes is most often carried out in *Escherichia coli* with vectors containing constitutive or inducible promoters directing the expression of either fusion or non-fusion proteins.

Fusion vectors add a number of amino acids to a protein encoded therein, such as to the amino terminus of the recombinant protein. Such fusion vectors may serve one or more purposes, such as: (i) to increase expression of recombinant protein; (ii) to increase the solubility of the recombinant protein; and (iii) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Example fusion expression vectors include pGEX (Pharmacia Biotech Inc; Smith and Johnson (1988) *Gene* 67: 31-40), pMAL (New England Biolabs, Beverly, Mass.) and pRIT5 (Pharmacia, Piscataway, N.J.) that fuse glutathione S-transferase (GST), maltose E binding protein, or protein A. respectively, to the target recombinant protein.

Examples of suitable inducible non-fusion *E. coli* expression vectors include pTrc (Amrann et al. (1988) *Gene* 69:301-315) and pET 11d (Studier et al. (1990) Gene Expression Technology: Methods in Enzymology 185, Academic Press, San Diego, Calif.).

In some embodiments, a vector is a yeast expression vector. Examples of vectors for expression in yeast *Saccharomyces cerivisae* include pYepSec1 (Baldari, et al. (1987) *EMBO J.* 6: 229-234), pMFa (Kuijan and Herskowitz (1982) *Cell* 30: 933-943), pJRY88 (Schultz et al. (1987) *Gene* 54: 113-123), pYES2 (Invitrogen Corporation, San Diego, Calif.), and picZ (InVitrogen Corp, San Diego, Calif.).

In some embodiments, a vector is capable of driving expression of one or more sequences in mammalian cells using a mammalian expression vector. Examples of mammalian expression vectors include pCDM8 (Seed (1987) *Nature* 329: 840) and pMT2PC (Kaufman et al. (1987) *EMBO J.* 6: 187-195). When used in mammalian cells, the expression vector's control functions are typically provided by one or more regulatory elements. For example, commonly used promoters are derived from polyoma, adenovirus 2, cytomegalovirus, simian virus 40, and others disclosed herein and known in the art. For other suitable expression systems for both prokaryotic and eukaryotic cells see, e.g., Chapters 16 and 17 of Sambrook et al. (1989) Molecular Cloning: A Laboratory Manual, 2nd ed., Cold Spring Harbor Laboratory, Cold Spring Harbor Laboratory Press, Cold Spring Harbor, N.Y.

In some embodiments, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1: 268-277), lymphoid-specific promoters (Calame and Eaton (1988) *Adv. Immunol.* 43: 235-275), in particular promoters of T cell receptors (Winoto and Baltimore (1989) *EMBO J.* 8: 729-733) and immunoglobulins (Baneiji et al. (1983) *Cell* 33: 729-740; Queen and Baltimore (1983) *Cell* 33: 741-748), neuron-specific promoters (e.g., the neurofilament promoter; Byrne and Ruddle (1989) *Proc. Natl. Acad. Sci. USA* 86: 5473-5477), pancreas-specific promoters (Edlund et al. (1985) *Science* 230: 912-916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss (1990) *Science* 249: 374-379) and the α-fetoprotein promoter (Campes and Tilghman (1989) *Genes Dev.* 3: 537-546).

In some embodiments, a regulatory element is operably linked to one or more elements of a CRISPR system so as to drive expression of the one or more elements of the CRISPR system. In general, CRISPRs (Clustered Regularly Interspaced Short Palindromic Repeats), also known as SPIDRs (SPacer Interspersed Direct Repeats), constitute a family of DNA loci that are usually specific to a particular bacterial species. The CRISPR locus comprises a distinct class of interspersed short sequence repeats (SSRs) that were recognized in *E. coli* (Ishino et al, (1987) *J. Bacterial.,* 169:5429-5433; and Nakata et al. (1989) *J. Bacterial.,* 171:3553-3556), and associated genes. Similar interspersed SSRs have been identified in *Haloferax mediterranei*, *Streptococcus pyogenes*, *Anabaena*, and *Mycobacterium tuberculosis* (Groenen et al. (1993) *Mol. Microbial.,* 10:1057-1065; Hoe et al. (1999) *Emerg. Infect. Dis.,* 5:254-263; Masepohl et al. (1996) *Biochim. Biophys. Acta* 1307:26-30; and. Mojica et al. (1995) *Mol. Microbial.,* 17:85-93). The CRISPR loci typically differ from other SSRs by the structure of the repeats, which have been teen led short regularly spaced repeats (SRSRs) (Janssen et al. (2002) *OMICS J. Integ. Biol.,* 6:23-33; and Mojica et al, (2000) *Mol. Microbial.,* 36:244-246). In general, the repeats are short elements that occur in clusters that are regularly spaced by unique intervening sequences with a substantially constant length (Mojica et al. (2000) *Mol. Microbial.,* 36:244-246). Although the repeat sequences are highly conserved between strains, the number of interspersed repeats and the sequences of the spacer regions typically differ from strain to strain (van Embden et al (2000) *J. Bacterial.,* 182:2393-2401). CRISPR loci have been identified in more than 40 prokaryotes (e.g., Jansen et al, (2002) *Mol. Microbial.,* 43:1565-1575; and Mojica et al, (2005) *J. Mal, Evol.* 60:174-82) including, but not limited to *Aeropyrum, Pyrobaculum, Sulfolobus, Archaeoglobus, Halocarcula, Methanobacterium, Methanococcus, Methanosarcina, Methanopyrus, Pyrococcus, Picrophilus, Thernioplasnia, Corynebacterium, Mycobacterium, Streptomyces, Aquifrx, Porphvromonas, Chlorobium, Thermus,* Bacillus, *Listeria, Staphylococcus, Clostridium, Thernioanaerobacter, Mycoplasma, Fusobacterium, Azarcus, Chromobacterium, Neisseria, Nitrosomonas, Desulfovibrio, Geobacter, Myrococcus, Campylobacter, Wolinella, Acinetobacter, Erwinia, Escherichia, Legionella, Methylococcus, Pasteurella, Photobacterium, Salmonella, Xanthomonas, Yersinia, Treponema,* and *Thermotoga.*

In general, "CRISPR system" refers collectively to transcripts and other elements involved in the expression of or directing the activity of CRISPR-associated ("Cas") genes, including sequences encoding a Cas gene, a guide sequence (also referred to as a "spacer" in the context of an endogenous CRISPR system), or other sequences and transcripts from a CRISPR locus. In some embodiments, one or more elements of a CRISPR system is derived from a type I, type II, or type III CRISPR system. In some embodiments, one or more elements of a CRISPR system is derived from a particular organism comprising an endogenous CRISPR system, such as *Streptococcus pyogenes*. In general, a CRISPR system is characterized by elements that promote the formation of a CRISPR complex at the site of a target sequence (also referred to as a protospacer in the context of an endogenous CRISPR system).

In the context of formation of a CRISPR complex, "target sequence" refers to a sequence to which a guide sequence is designed to have complementarity, where hybridization between a target sequence and a guide sequence promotes the formation of a CRISPR complex. Full complementarity is not necessarily required, provided there is sufficient complementarity to cause hybridization and promote formation of a CRISPR complex. A target sequence may comprise any polynucleotide, such as DNA or RNA polynucleotides. In some embodiments, a target sequence is located in the nucleus or cytoplasm of a cell. In some embodiments, the target sequence may be within an organelle of a eukaryotic cell, for example, mitochondrion or chloroplast. A sequence or template that may be used for recombination into the targeted locus comprising the target sequences is referred to as an "editing template" or "editing polynucleotide" or "editing sequence". In aspects of the presently disclosed subject matter, an exogenous template polynucleotide may be referred to as an editing template. In an aspect of the presently disclosed subject matter the recombination is homologous recombination.

In some embodiments, a vector comprises one or more insertion sites, such as a restriction endonuclease recognition sequence (also referred to as a "cloning site"). In some embodiments, one or more insertion sites (e.g. about or more than about 1, 2, 3, 4, 5, 6, 7, 8, 9, 10, or more insertion sites) are located upstream and/or downstream of one or more sequence elements of one or more vectors. When multiple different guide sequences are used, a single expression construct may be used to target CRISPR activity to multiple different, corresponding target sequences within a cell. For example, a single vector may comprise about or more than about 1, 2, 3, 4, 5, 6, 7, 8, 9, 10, 15, 20, or more guide sequences. In some embodiments, about or more than about 1, 2, 3, 4, 5, 6, 7, 8, 9, 10, or more such guide-sequence-containing vectors may be provided, and optionally delivered to a cell.

In some embodiments, a vector comprises a regulatory element operably linked to an enzyme-coding sequence encoding a CRISPR enzyme, such as a Cas protein. Non-limiting examples of Cas proteins include Cas1, Cas1B, Cas2, Cas3, Cas4, Cas5, Cas6, Cas7, Cas8, Cas9 (also known as Csn1 and Csx12), Cas10, Cas13a, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologs thereof, or modified versions thereof. These enzymes are known for example, the amino acid sequence of *S. pyogenes* Cas9 protein may be found in the SwissProt database under accession number Q99ZW2. In some embodiments, the unmodified CRISPR enzyme has DNA cleavage activity, such as Cas9. In some embodiments the CRISPR enzyme is Cas9, and may be Cas9 from *S. pyogenes* or *S. pneumoniae*.

In some embodiments, the CRISPR enzyme directs cleavage of one or both strands at the location of a target sequence, such as within the target sequence and/or within the complement of the target sequence. In some embodiments, the CRISPR enzyme directs cleavage of one or both strands within about 1, 2, 3, 4, 5, 6, 7, 8, 9, 10, 15, 20, 25, 50, 100, 200, 500, or more base pairs from the first or last nucleotide of a target sequence. In some embodiments, a vector encodes a CRISPR enzyme that is mutated to with respect to a corresponding wild-type enzyme such that the mutated CRISPR enzyme lacks the ability to cleave one or both strands of a target polynucleotide containing a target sequence.

In some embodiments, an enzyme coding sequence encoding a CRISPR enzyme is codon optimized for expression in particular cells, such as eukaryotic cells. The eukaryotic cells may be those of or derived from a particular organism, such as a mammal, including but not limited to human, mouse, rat, rabbit, dog, or non-human primate. In general, codon optimization refers to a process of modifying a nucleic acid sequence for enhanced expression in the host cells of interest by replacing at least one codon (e.g. about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database", and these tables can be adapted in a number of ways. See Nakamura et al. (2000) *Nucl. Acids Res.* 28:292. Computer algorithms for codon optimizing a particular sequence for expression in a particular host cell are also available, such as Gene Forge (Aptagen; Jacobus, Pa.), are also available. In some embodiments, one or more codons (e.g. 1, 2, 3, 4, 5, 10, 15, 20, 25, 50, or more, or all codons) in a sequence encoding a CRISPR enzyme correspond to the most frequently used codon for a particular amino acid.

In general, a guide sequence is any polynucleotide sequence having sufficient complementarity with a target polynucleotide sequence to hybridize with the target sequence and direct sequence-specific binding of a CRISPR complex to the target sequence. In some embodiments, the degree of complementarily between a guide sequence and its corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), ClustalW, Clustal X, BLAT, Novoalign (Novocraft Technologies, ELAND (Illumina, San Diego, Calif.), SOAP (available at soap.genomics.org.cn), and Maq (available at maq.sourceforge.net). In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length.

The ability of a guide sequence to direct sequence-specific binding of a CRISPR complex to a target sequence may be assessed by any suitable assay. For example, the components of a CRISPR system sufficient to form a CRISPR complex, including the guide sequence to be tested, may be provided to a host cell having the corresponding target sequence, such as by transfection with vectors encoding the components of the CRISPR sequence, followed by an assessment of preferential cleavage within the target sequence, such as by Surveyor assay as described herein. Similarly, cleavage of a target polynucleotide sequence may be evaluated in a test tube by providing the target sequence, components of a CRISPR complex, including the guide sequence to be tested and a control guide sequence different from the test guide sequence, and comparing binding or rate of cleavage at the target sequence between the test and control guide sequence reactions. Other assays are possible, and will occur to those skilled in the art.

A guide sequence may be selected to target any target sequence. In some embodiments, the target sequence is a sequence within a genome of a cell. Exemplary target sequences include those that are unique in the target genome.

In some embodiments, the CRISPR enzyme is part of a fusion protein comprising one or more heterologous protein domains (e.g. about or more than about 1, 2, 3, 4, 5, 6, 7, 8, 9, 10, or more domains in addition to the CRISPR enzyme). A CRISPR enzyme fusion protein may comprise any additional protein sequence, and optionally a linker sequence between any two domains. Examples of protein domains that may be fused to a CRISPR enzyme include, without limitation, epitope tags, reporter gene sequences, and protein domains having one or more of the following activities: methylase activity, demethylase activity, transcription activation activity, transcription repression activity, transcription release factor activity, histone modification activity, RNA cleavage activity and nucleic acid binding activity. Non-limiting examples of epitope tags include histidine (His) tags, V5 tags, FLAG tags, influenza hemagglutinin (HA) tags, Myc tags, VSV-G tags, and thioredoxin (Trx) tags. Examples of reporter genes include, but are not limited to, glutathione-5-transferase (GST), horseradish peroxidase (HRP), chloramphenicol acetyltransferase (CAT) beta-galactosidase, beta-glucuronidase, luciferase, green fluorescent protein (GIF), HeRed, DsRed, cyan fluorescent protein (CFP), yellow fluorescent protein (YIP), and autofluorescent proteins including blue fluorescent protein (BIP). A CRISPR enzyme may be fused to a gene sequence encoding a protein or a fragment of a protein that bind DNA molecules or bind other cellular molecules, including but not limited to maltose binding protein (MBP), S-tag, Lex A DNA binding domain (DBD) fusions, GAL4A DNA binding domain fusions, and herpes simplex virus (RSV) BP16 protein fusions. Additional domains that may form part of a fusion protein comprising a CR NPR enzyme are described in US20110059502, incorporated herein by reference. In some embodiments, a tagged CRISPR enzyme is used to identify the location of a target sequence.

In an aspect of the presently disclosed subject matter, a reporter gene which includes but is not limited to glutathione-5-transferase (GST), horseradish peroxidase (HRP), chloramphenicol acetyltransferase (CAT) beta-galactosidase, beta-glucuronidase, luciferase, green fluorescent protein (GFP), HcRed, DsRed, cyan fluorescent protein (CFP), yellow fluorescent protein (YIP), and autofluorescent proteins including blue fluorescent protein (BFP), may be introduced into a cell to encode a gene product which serves as a marker by which to measure the alteration or modification of expression of the gene product. In a further embodiment of the presently disclosed subject matter, the DNA molecule encoding the gene product may be introduced into the cell via a vector. In a preferred embodiment of the presently disclosed subject matter the gene product is luciferase. In a further embodiment of the presently disclosed subject matter the expression of the gene product is decreased.

Generally, promoter embodiments of the present presently disclosed subject matter comprise: 1) a complete Pol III promoter, which includes a TATA box, a Proximal Sequence Element (PSE), and a Distal Sequence Element (DSE); and 2) a second basic Pol. III promoter that includes a PSE and TATA box fused to the 5' terminus of the DSE in reverse orientation. The TATA box, which is named for its nucleotide sequence, is a major determinant of Pol III specificity. It, is usually located at a position between nt. −23 and −30 relative to the transcribed sequence, and is a primary determinant of the beginning of the transcribed sequence. The PSE is usually located between nt. −45 and −66. The DSE enhances the activity of the basic Pol III promoter. In the H1 promoter, there is no gap between the PSE and the DSE.

Bidirectional promoters refer to any promoter (typically pol II) that are orientated in head-tail-tail-head fasion—basically any control region that direct divergent transcription. In some embodiments, the bidirectional H1 promoter could be pol II and pol II or pol III and pol III, or combinations thereof. The H1 bidirectional, as well as 7Sk and others described herein, are unique in that they are bidirectional which is itself uncommon in eukaryotic genomes, but most importantly here, directs a protein coding gene on one side (pol II), and an RNA gene on the other side (pol III).

In some embodiments, bidirectional promoters consists of: 1) a complete, conventional, unidirectional Pol III promoter that contains 3 external control elements: a DSE, a PSE, and a TATA box; and 2) a second basic Pol III promoter that includes a PSE and a TATA box fused to the 5' terminus of the DSE in reverse orientation. The TATA box, which is recognized by the TATA binding protein, is essential for recruiting Pol III to the promoter region. Binding of the TATA binding protein to the TATA box is stabilized by the interaction of SNAPc with the PSE. Together, these elements position Pol III correctly so that it can transcribe the expressed sequence. The DSE is also essential for full activity of the Pol III promoter (Murphy et al. (1992) *Mol. Cell Biol.* 12:3247-3261; Mittal et al. (1996) *Mol. Cell Biol.* 16:1955-1965; Ford and Hernandez (1997) *J. Biol. Chem.*, 272:16048-16055; Ford et al. (1998) *Genes, Dev.*, 12:3528-3540; Hovde et al. (2002) *Genes Dev.* 16:2772-2777). Transcription is enhanced up to 100-fold by interaction of the transcription factors Oct-1 and/or SBF/Staf with their motifs within the DSE (Kunkel and Hixon (1998) *Nucl. Acid Res.*, 26:1536-1543). Since the forward and reverse oriented basic promoters direct transcription of sequences on opposing strands of the double-stranded DNA templates, the positive strand of the reverse oriented basic promoter is appended to the 5' end of the negative strand of the DSE. Transcripts expressed under the control of the H1 promoter are terminated by an unbroken sequence of 4 or 5 T's.

In the H1 promoter, the DSE is adjacent to the PSE and the TATA box (Myslinski et al. (2001) *Nucl. Acid Res.* 29:2502-2509). To minimize sequence repetition, this promoter was rendered bidirectional by creating a hybrid promoter, in which transcription in the reverse direction is controlled by appending a PSE and TATA box derived from the U6 promoter. To facilitate construction of the bidirectional H1 promoter, a small spacer sequence may also inserted between the reverse oriented basic promoter and the DSE.

Examples of cell cycle dependent proteins may comprise any of the following: (a) Chromosomal DNA Replication Reaction Including Initiation of Chromosomal DNA Replication and Progression of Replication Fork Mcm10, Orc1, Orc3, Cdc6, Cdt1, Geminin, Mcm3, Mcm4, Mcm5, Mcm6, Mcm7, Mcm8, Cdc7, Cdc5, Psf1, Psf2, Psf3, Cdc45, Pola p180, Pola p70, Pola Spp1(Prim2a), RPA70, RPA34, PCNA, Elg1, Ligase1, Pole Pol2, Pole Dpb3, Topoisomerase I, TDP1, Orc2, Orc4, Orc5, Orc6, Mcm2, Dbf4, TopBP1, Sld5, Pola Spp2, RFC1, RFC2, RFC3, RFC4, RFC5, Pif1, Pold p50, Pole Dpb2, Topoisomerase IIa, Topoisomerase IIb, RPAI4, FEN1, DNA2, Pold p125, Pold p68, Pold p12, Pole Dpb4

(b) DNA Damage Checkpoints

ATR, Chk1, NBS1, Hus1, Rad1, Mad2, BubR1, ATM, Rad50, Mre11, Mdc1, 53BP1, Rad17, BubR1, ATRIP, Chk2, H2AX, RFC1, RFC2, RFC3, RFC4, RFC5, ATM, BRCA1, Chk1, Chk2, 14-3-3eta, 14-3-3sigma, cdc25A, cdc25c, wee1, ATR, ATRIP, Rad17, RFC2, RFC3, RFC4, RFC5, HUS1, Rad1, Rad9, P53, Rad50, Mre11, NBS1, TopBP1, 53BP1, H2AX (c) Sister Chromatid Agglutination and Separation Ctf18, Scc1, Scc3, Dcc1, Trf4-1, Trf4-2, Smc1, Smc3, Pds1 (Securin), Mad-2, BubR1, Esp1

(d) Base Excision Repair

UNG, MBD4, TDG, NTH1, NEIL2, NEIL3, APE2, PARP1, PNK, Polb, OGG1, APE1, XRCC1, Ligase3, SMUG1, TDG, MYH, MPG, NEIL1, ADPRT, ADPRTL2, MGMT, ABH1, ABH2, ABH3

(e) Mismatch Excision Repair

MSH2, PMS1, PMS2, MLH3, Exonuclease1, MSH3, MSH6, MSH5, MLH1, MSH4, PMS2L3, Trex1, Trex2, PMS2L4

(f) Nucleotide Excision Repair

XPC, Rad23A, Rad23B, CSA, CSB, XPG, XPF, DDB1, DDB2, XAB2, XPB, ERCC1, XPD, XPA, DDB2, Mms19, CETN2, RPA70, RPA34, RPAI4, GTF2H1, GTF2H2, GTF2H3, GTF2H4, CDK7, CCNH, MNAT1, Ligase1, CSA, CSB (g) Homologous Recombination Repair Rad51, Rad51L1, Rad51C, Rad51L3, DMC1, XRCC2, XRCC3, Rad52, Rad54L, Rad54B, BRCA1, BRCA2, Rad50, Mre11, NBS1, Topoisomerase IIIa, Topoisomerase IIIb, WHIP, WRN, BLM, RecQ1, RecQ5

(h) Non-Homologous End-Joining Repair (Non-Homologous Recombination Repair)

Ku70, Ku80, DNA-pk, Ligase4, XRCC4, Artemis, WRN i) Double-Strand DNA Break Repair Rad51, Rad51D, Xrcc2, Rad54, BRCA1, Ku80, XRCC4, Rad52, Rad51C, Dmc1, Rad54B, DNA-pk, Ku70, Ligase4, Rad51B, XRCC3, BRCA2, Artemis (j) DNA Post-Replication Repair (DNA Damage Tolerance)

Rad6A, Rad6B, Rad18, Ubc13, FBH1

(k) DNA Crosslink Damage Repair

FANCA, FANCC, FANCD2, FANCE, FANCF, FANCG (l) DNA-Protein Crosslink Damage Repair

TDP1

(m) DNA Polymerase

Poli, Polh, Polq, Polk, Polz (REV3), Poll, Polm, Rev1, Polb, Polg, Pold p50, Pole Pol2, REV7, Poln, Pola P180, Pola p'70, Pola Spp1, Pola Spp2, Pold p68, Pold p12, Pole Dpb2, Pole Dpb3, Pole Dpb4

(n) Nucleotide Cleansing

MTH1, DUT, p53R2

(o) Chromatin Structure Maintenance

H2AX, Sir2, SIRT1 (Sirtuin)

(p) Telomere Structure Maintenance

Tin2, Sir2, hTert, TRF1, TRF2, Tankyrase, Pot1, Rap1, Pif1 Preferred examples of genes associated with each of the aforementioned functions (a) to (p) include the genes described in Examples below. More specifically, examples of such genes are as follows: APE2, ATR, BRCA1, Chk1, Cdc5, Cdc6, Cdc7, Cdc45, Cdt1, CSA, CSB, Ctf18, DDB1, DDB2, DNA2, DUT, Elg1, EndoV, Esp1, Exonuclease1, FBH1, FEN1, Geminin, Hus1, KNTC2 (NDC80), Ku80, Ligase1, Mad2, MBD4, Mcm3, Mcm4, Mcm5, Mcm6, Mcm7, Mcm8, Mcm10, MGMT, MLH3, Mms4, MPG, MSH2, Mus81, NBS1, NEIL2, NEIL3, NTH1, Orc1, Orc3, PARP1, PCNA, Pif1, PMS1, PMS2, PNK, Pola p180, Pola p'70, Pola Spp1(Prim2a), Polb, Pold p125, Pole Dpb3, Pole Dpb4, Pole Pol2, Poli, Poll, Polm, Psf1, Psf2, Psf3, Rad1, Rad18, Rad23A, Rad23B, Rad51, Rad51D, Rad54, Rad6A, RPA34, RPA70, Scc1, Scc3, Sir2, SIRT1 (Sirtuin), TDG, TDP1, TIMELESS, Tin2, Topoisomerase I, Topoisomerase IIIa, Topoisomerase IIIb, Ubc13, UNG, XAB2, XPC, XPF, XPG, Xrcc2, and XRCC4.

Since the gene names described in the present specification are names which are widely and generally known, those skilled in the art are able to suitably acquire data on the nucleotide sequences of said genes from a public reference database or gene database (e.g., GenBank) based on the gene name.

B. Methods

In some embodiments, the presently disclosed subject matter also provides a method of altering expression of one or more gene products in a eukaryotic or non-eukaryotic cell, wherein the cell comprises a DNA molecule encoding the one or more gene products, the method comprising introducing into the cell an improved and modified non-naturally occurring CRISPR-Cas system previously described in WO2015/195621 (herein incorporated by reference in its entirety). Such improvements comprise a non-naturally occurring nuclease system (e.g., CRISPR-Cas9) comprising one or more vectors comprising: a) a promoter (e.g., orthologous H1 promoter or 7sk) operably linked to at least one nucleotide sequence encoding a nuclease system guide RNA (gRNA), wherein the gRNA hybridizes with a target sequence of a DNA molecule in a cell, and wherein the DNA molecule encodes one or more gene products expressed in the cell; and b) a regulatory element operable in a cell operably linked to a nucleotide sequence encoding a genome-targeted nuclease (e.g., modified Cas9 protein), wherein components (a) and (b) are located on the same or different vectors of the system, wherein the gRNA targets and hybridizes with the target sequence and the nuclease cleaves the DNA molecule to alter expression of the one or more gene products. In some embodiments, the system is packaged into a single adeno-associated virus (AAV) particle. In some embodiments, the system inactivates one or more gene products. In some embodiments, the system excises at least one gene mutation. In some embodiments, the H1 promoter comprises a nucleotide sequence having at least 80%, 85%, 90%, 95%, 98%, 99%, or 100% identity to the nucleotide sequence set forth in SEQ ID NO: 12 or 32. In some embodiments, the orthologous H1 promoter is derived from mouse or rat. In some embodiments, the orthologous H1 promoter comprises a nucleotide sequence having at least 80%, 85%, 90%, 95%, 98%, 99%, or 100% identity to the nucleotide sequence set forth in SEQ ID NOs: 84-119. In some embodiments, the orthologous H1 promoter comprises a nucleotide sequences set forth in the group consisting of SEQ ID NOs: 84-119. In some embodiments, the H1 promoter comprises: a) control elements that provide for transcription in one direction of at least one nucleotide sequence encoding a gRNA; and b) control elements that provide for transcription in the opposite direction of a nucleotide sequence encoding a genome-targeted nuclease. In some embodiments, the promoter is the human, mouse, or rat 7sk promoter. In some embodiments, the 7sk is selected from the group consisting of 7sk1 (variant 1 of 7sk which uses the endogenous GSTA4 5'UTR), 7sk2 (variant 2 of 7sk which uses just a kozak sequence in the 5'UTR), and 7sk3 (variant of 7sk which uses the beta globin 5'UTR). In some embodiments, the human 7sk1 comprises a nucleotide sequence having at least 80%, 85%, 90%, 95%, 98%, 99%, or 100% identity to the nucleotide sequence set forth in SEQ ID NO: 3. In some embodiments, the mouse 7sk1 comprises a nucleotide sequence having at least 80%, 85%, 90%, 95%, 98%, 99%, or 100% identity to SEQ ID NO: 6. In some embodiments, the human 7sk2 comprises a nucleotide sequence having at least 80%, 85%, 90%, 95%, 98%, 99%, or 100% identity to SEQ ID NO: 4. In some embodiments, the mouse 7sk2 comprises a nucleotide sequence having at least 80%, 85%, 90%, 95%, 98%, 99%, or 100% identity to SEQ ID NO: 7. In some embodiments, the human 7sk3 comprises a nucleotide sequence having at least 80%, 85%, 90%, 95%, 98%, 99%, or 100% identity to SEQ ID NO: 5. In some embodiments, the mouse 7sk3 comprises a nucleotide sequence having at least 80%, 85%, 90%, 95%, 98%, 99%, or 100% identity to SEQ ID NO: 8. In some embodiments, the orthologous H1 promoter or 7sk promoter has at least one modification. In some embodiments, the at least one modification of the promoter comprises an element that allows conditional regulation. In some embodiments, the element is a tet-responsive promoter. In some embodiments, the tet-response promoter comprises a Tet repressor (TetR) and Tet operator (TetO) engineered into the H1 promoter. In some embodiments, the TetR comprises an amino acid sequence having at least 80%, 85%, 90%, 95%, 98%, 99%, or 100% identity to SEQ ID NO: 14. In some embodiments, the TetO comprises a nucleotide sequence having at least 80%, 85%, 90%, 95%, 98%, 99%, or 100% identity to the nucleotide sequence set forth in SEQ ID NO: 11. In some embodiments, the H1-TetO comprises a nucleotide sequence having at least 80%, 85%, 90%, 95%, 98%, 99%, or 100% identity to the nucleotide sequence set forth in SEQ ID NO: 13. In some embodiments, the at least one modification of the promoter comprises a site that allows auto-regulation. In some embodiments, the auto-regulation site comprises a nucleotide sequence having at least 80%, 85%, 90%, 95%, 98%, 99%, or 100% identity to the nucleotide sequence set forth in SEQ ID NO: 33 or 34. In some embodiments, the nuclease system further comprising at least one terminator sequence. In some embodiments, the at least one terminator sequence is selected from the group consisting of SV40 or synthetic poly A (SPA) sequences. In some embodiments, the terminator sequences is a SV40 120 (SEQ ID NO: 123) or 240 (SEQ ID NO: 122) base pair sequence. In some embodiments, the terminator sequences is a SPA 49 base pair equence. In some embodiments, the nuclease system further comprises 5' untranslated region (5'UTR) sequences. In some embodiments, the nuclease system further comprises a Kozak sequence. In some embodiments, the Kozak sequence comprises a nucleotide sequence having at least 80%, 85%, 90%, 95%, 98%, 99%, or 100% identity to SEQ ID NO: 1 or 2. In some embodiments, the nuclease system further comprises a RNA sequence that mediates cap-independent initiation of translation. In some embodiments, the RNA sequence is selected from the group consisting of 6.947 or 6.967. In some embodiments, the Cas9 comprises a nucleotide sequence having at least 80%, 85%, 90%, 95%, 98%, 99%, or 100% identity to the nucleotide sequence set forth in SEQ ID NO: 61. In some embodiments, the Cas9 comprises at least one modification. In some embodiments, the at least one modification in the Cas9 comprises an alteration in the cleaving sequence. In some embodiments, the nuclease is selected from the group consisting of Cas1, Cas1B, Cas2, Cas3, Cas4, Cas5, Cas6, Cas7, Cas8, Cas9 (also known as Csn1 and Csx12), Cas10, Cas13a, Csy1, Csy2, Csy3, Cse1, Cse2, Cse1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1, C2c1, C2c2, and C2c3. In some embodiments, the alteration in the cleaving sequence selected from the group consisting of T2A, P2A, E2A, and F2A. In some embodiments, the T2A comprises an amino acid sequence. having at least 80%, 85%, 90%, 95%, 98%, 99%, or 100% identity to the nucleotide sequence set forth in SEQ ID NO: 36. In some embodiments, the P2A comprises an amino acid sequence having at least 80%, 85%, 90%, 95%, 98%, 99%, or 100% identity to the nucleotide sequence set forth in SEQ ID NO: 35. In some embodiments, the P2A comprises an amino acid sequence having the nucleotide sequence set forth in SEQ ID NO: 35. In some embodiments, the E2A comprises an amino acid sequence having at least 80%, 85%, 90%, 95%, 98%, 99%, or 100% identity to the nucleotide sequence set forth in SEQ ID NO: 37. In some embodiments, the F2A comprises an amino acid sequence having at least 80%, 85%, 90%, 95%, 98%, 99%, or 100% identity to the nucleotide sequence set forth in SEQ ID NO: 38. In some embodiments, the at least one modification in the Cas9 comprises a codon optimized for expression in the cell. In some embodiments, the Cas9 further comprises a linker sequence operably fused in frame to a cell-cycle dependent protein (Cas9 fusion). In some embodiments, the cell cycle-dependent protein is selected from the group consisting of APE2, ATR, BRCA1, Chk1, Cdc5, Cdc6, Cdc7, Cdc45, Cdt1, CSA, CSB, Ctf18, DDB1, DDB2, DNA2, DUT, Elg1, EndoV, Esp1, Exonuclease1, FBH1, FEN1, Geminin, Hus1, KNTC2 (NDC80), Ku80, Ligase1, Mad2, MBD4, Mcm3, Mcm4, Mcm5, Mcm6, Mcm7, Mcm8, Mcm10, MGMT, MLH3, Mms4, MPG, MSH2, Mus81, NBS1, NEIL2, NEIL3, NTH1, Orc1, Orc3, PARP1, PCNA, Pif1, PMS1, PMS2, PNK, Pola p180, Pola p70, Pola Spp1 (Prim2a), Polb, Pold p125, Pole Dpb3, Pole Dpb4, Pole Pol2, Poli, Poll, Polm, Psf1, Psf2, Psf3, Rad1, Rad18, Rad23A, Rad23B, Rad51, Rad51D, Rad54, Rad6A, RPA34, RPA70, Scc1, Scc3, Sir2, SIRT1 (Sirtuin), TDG, TDP1, TIMELESS, Tin2, Topoisomerase I, Topoisomerase IIIa, Topoisomerase IIIb, Ubc13, UNG, XAB2, XPC, XPF, XPG, Xrcc2, and XRCC4. In some embodiments, the cell cycle-dependent protein is Geminin. In some embodiments, the cell cycle-dependent protein is human Geminin. In some embodiments, the human Geminin comprises the amino acids from positions 1-110 (hGem(1-110)). In some embodiments, the hGem(1-110) comprises an amino acid sequence having at least 80%, 85%, 90%, 95%, 98%, 99%, or 100% identity to the amino acid sequence set forth in SEQ ID NO: 19. In some embodiments, the cell cycle-dependent protein is Cdt1. In some embodiments, the cell cycle-dependent protein is human Cdt1. In some embodiments, the human Cdt1 comprises amino acids from positions 30-120 (hCdt1(30-120)). In some embodiments, the hCdt1(30-120) comprises an amino acid sequence having at least 80%, 85%, 90%, 95%, 98%, 99%, or 100% identity to the amino acid sequence set forth in SEQ ID NO: 18. In some embodiments, the Cas9 fusion comprises an amino acid sequence having at least 80%, 85%, 90%, 95%, 98%, 99%, or 100% identity to the amino acid sequence selected from the group consisting of SEQ ID NO: 20-27. In some embodiments, the Cas9 is operably fused in frame to a ubiquitin protein (Ub-Cas9). In some embodiments, the Ub-Cas9 at least one N-terminal modification. In some embodiments, the N-terminal modified Ub-Cas9 comprises an amino acid sequence having at least 80%, 85%, 90%, 95%, 98%, 99%, or 100% identity to the amino acid sequence selected from the group consisting of SEQ ID NO: 39-58. In some embodiments, the ubiquitin protein comprises a nucleotide sequence having at least 80%, 85%, 90%, 95%, 98%, 99%, or 100% identity to the nucleotide sequence set forth in SEQ ID NO: 60. In some embodiments, the nuclease system further comprises a SaCas9 nickase. In some embodiments, the nuclease system further comprises a donor template sequence. In some embodiments, the at least one vector comprises a nucleotide sequence having at least 80%, 85%, 90%, 95%, 98%, 99%, or 100% identity to the nucleotide sequence set forth in SEQ ID NO: 62 or 67. In some embodiments, the donor template sequence corrects at least one gene mutation. In some embodiments, the at least one gene mutation is rd10 or rd12. In some embodiments, the at least one vector comprises a nucleotide sequence having at least 80%, 85%, 90%, 95%, 98%, 99%, or 100% identity to the nucleotide sequence set forth in SEQ ID NO: 63 or 64. In some embodiments, the at least one vector comprises a nucleotide sequence having at least 80%, 85%, 90%, 95%, 98%, 99%, or 100% identity to the nucleotide sequence set forth in SEQ ID NO: 65 or 66. In some embodiments, the promoter is operably linked to at least one, two, three, four, five, six, seven, eight, nine, or ten gRNA. In some embodiments, the target sequence comprises the nucleotide sequence $AN_{19}NGG$, $GN_{19}NGG$, $CN_{19}NGG$, or $TN_{19}NGG$. In some embodiments, the cell is a eukaryotic or or non-eukaryotic cell. In some embodiments, the eukaryotic cell is a mammalian or human cell. In some embodiments, the eukaryotic cell is a retinal photoreceptor cell. In some embodiments, the one or more gene products are rhodopsin. In some embodiments, the expression of the one or more gene products is decreased. In some embodiments, the system inactivates one or more gene products. In some embodiments, the nuclease system excises at least one gene mutation. In some embodiments, the expression of the one or more gene products is decreased. In some embodiments, the cell is a retinal ganglion cell. In some embodiments, the eukaryotic cell is a cancerous cell. In some embodiments, cell proliferation is inhibited or reduced in the cancerous cell. In some embodiments, the apoptosis is enhanced or increased in the cancerous cell.

In some embodiments, the presently disclosed subject matter also provides a method of altering expression of one or more gene products in a cell, wherein the cell comprises a DNA molecule encoding the one or more gene products, the method comprising introducing into the cell a non-naturally occurring CRISPR-Cas system comprising one or more vectors comprising: a) an H1 promoter operably linked to at least one nucleotide sequence encoding a CRISPR-Cas system guide RNA (gRNA), wherein the gRNA hybridizes with a target sequence of the DNA molecule; and b) a regulatory element operable in the cell operably linked to a nucleotide sequence encoding a Cas9 protein, wherein components (a) and (b) are located on the same or different vectors of the system, wherein the gRNA targets and hybridizes with the target sequence and the Cas9 protein cleaves the DNA molecule to alter expression of the one or more gene products.

In some embodiments, the presently disclosed subject matter also provides a method of altering expression of one or more gene products in a eukaryotic cell, wherein the cell comprises a DNA molecule encoding the one or more gene products, the method comprising introducing into the cell a non-naturally occurring CRISPR-Cas system comprising one or more vectors comprising: a) an H1 promoter operably linked to at least one nucleotide sequence encoding a CRISPR-Cas system guide RNA (gRNA), wherein the gRNA hybridizes with a target sequence of the DNA molecule; and b) a regulatory element operable in the eukaryotic cell operably linked to a nucleotide sequence encoding a Type-II Cas9 protein, wherein components (a) and (b) are located on the same or different vectors of the system, whereby the gRNA targets and hybridizes with the target sequence and the Cas9 protein cleaves the DNA molecule, and whereby expression of the one or more gene products is altered. In one aspect, the target sequence can be a target sequence that starts with any nucleotide, for example, $N_{20}NGG$. In some embodiments, the target sequence comprises the nucleotide sequence $AN_{19}NGG$. In some embodiments, the target sequence comprises the nucleotide sequence $GN_{19}NGG$. In some embodiments, the target sequence comprises the nucleotide sequence $CN_{19}NGG$. In some embodiments, the target sequence comprises the nucleotide sequence $TN_{19}NGG$. In some embodiments, the target sequence comprises the nucleotide sequence $AN_{19}NGG$ or $GN_{19}NGG$. In another aspect, the Cas9 protein is codon optimized for expression in the cell. In yet another aspect, the Cas9 protein is codon optimized for expression in the eukaryotic cell. In a further aspect, the eukaryotic cell is a mammalian or human cell. In another aspect, the expression of the one or more gene products is decreased.

The presently disclosed subject matter also provides a method of altering expression of one or more gene products in a eukaryotic cell, wherein the cell comprises a DNA molecule encoding the one or more gene products, the method comprising introducing into the cell a non-naturally occurring CRISPR-Cas system comprising a vector comprising a bidirectional H1 promoter, wherein the bidirectional H1 promoter comprises: a) control elements that provide for transcription in one direction of at least one nucleotide sequence encoding a CRISPR-Cas system guide RNA (gRNA), wherein the gRNA hybridizes with a target sequence of the DNA molecule; and b) control elements that provide for transcription in the opposite direction of a nucleotide sequence encoding a Type-II Cas9 protein, whereby the gRNA targets and hybridizes with the target sequence and the Cas9 protein cleaves the DNA molecule, and whereby expression of the one or more gene products is altered. In one aspect, the target sequence can be a target sequence that starts with any nucleotide, for example, $N_{20}NGG$. In some embodiments, the target sequence comprises the nucleotide sequence $AN_{N}NGG$. In some embodiments, the target sequence comprises the nucleotide sequence $GN_{19}NGG$. In some embodiments, the target sequence comprises the nucleotide sequence $CN_{19}NGG$. In some embodiments, the target sequence comprises the nucleotide sequence $TN_{19}NGG$. In another aspect, the target sequence comprises the nucleotide sequence $AN_{19}NGG$ or $GN_{19}NGG$. In another aspect, the Cas9 protein is codon optimized for expression in the cell. In yet another aspect, the Cas9 protein is codon optimized for expression in the eukaryotic cell. In a further aspect, the eukaryotic cell is a mammalian or human cell. In another aspect, the expression of the one or more gene products is decreased.

In some aspects, the presently disclosed subject matter provides methods comprising delivering one or more polynucleotides, such as or one or more vectors as described herein, one or more transcripts thereof, and/or one or proteins transcribed therefrom, to a host cell. In some aspects, the presently disclosed subject matter further provides cells produced by such methods, and organisms (such as animals, plants, or fungi) comprising or produced from such cells. In some embodiments, a CRISPR enzyme in combination with (and optionally complexed with) a guide sequence is delivered to a cell. Conventional viral and non-viral based gene transfer methods can be used to introduce nucleic acids in mammalian cells or target tissues. Such methods can be used to administer nucleic acids encoding components of a CRISPR system to cells in culture, or in a host organism. Non-viral vector delivery systems include DNA plasmids, RNA (e.g. a transcript of a vector described herein), naked nucleic acid, and nucleic acid complexed with a delivery vehicle, such as a liposome. Viral vector delivery systems include DNA and RNA viruses, which have either episomal or integrated genomes after delivery to the cell. For a review of gene therapy procedures, see Anderson (1992) *Science* 256:808-813; Nahel and Feigner (1993) TIBTECH 11:211-217; Mitani and Caskey (1993) TIBTECH 11:162-166; Dillon (1993) TWITCH 11:167-175; Miller (1992) *Nature* 357:455-460; Van Brunt (1998) *Biotechnology* 6(10): 1149-1154; Vigne (1995) *Restorative Neurology and Neuroscience* 8:35-36; Kremer and Perricaudet (1995) *British Medical Bulletin* 51(1):31-44; Haddada et al. (1995) Current Topics in Microbiology and Immunology. Doerfler and. Bohm (eds); and Yu et al. (1994) *Gene Therapy* 1:13-26.

Methods of non-viral delivery of nucleic acids include lipofection, nucleofection, microinjection, biolistics, virosomes, liposomes, immunoliposomes, polycation or lipid:nucleic acid conjugates, naked DNA, artificial virions, and agent-enhanced uptake of DNA. Lipofection is described in e.g., U.S. Pat. Nos. 5,049,386, 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Feigner, WO 91/17424; WO 91/16024. Delivery can be to cells (e.g. in vitro or ex vivo administration) or target tissues (e.g. in vivo administration).

The preparation of lipid:nucleic acid complexes, including targeted liposomes such as immunolipid complexes, is well known to one of skill in the art Crystal (1995) *Science* 270:404-410; Blaese et al. (1.995) *Cancer Gene Ther.* 2:291-297: Behr et al. (1994) *Bioconjugate Chem.* 5:382-389; Remy et al. (1994) *Bioconjugate Chem.* 5:647-654; Cao et al. (1995) *Gene Therapy* 2:710-722; Ahmad et al. (1992) *Cancer Res.* 52:4817-4820; U.S. Pat. Nos. 4,186,183, 4,217, 344, 4,235,871, 4,261,975, 4,485,054, 4,501,728, 4,774,085, 4,837,028, and 4,946,787).

The use of RNA or DNA viral based systems for the delivery of nucleic acids take advantage of highly evolved processes for targeting a virus to specific cells in the body and trafficking the viral payload to the nucleus. Viral vectors can be administered directly to patients (in vivo) or they can be used to treat cells in vitro, and the modified cells may optionally be administered to patients (ex vivo). Conventional viral based systems could include retroviral, lentivirus, adenoviral, adeno-associated and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system would therefore depend on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immuno deficiency virus (SIV), human immuno deficiency virus (HIV), and combinations thereof (e.g., Buchscher et al. (1992) J. Virol. 66:2731-2739; Johann et al. (1992) J. Virol. 66:1635-1640; Sommnerfelt et al. (1990) J. Virol. 176:58-59; Wilson et al. (1989) J. Virol. 63:2374-2378; Miller et al. (1991) J. Virol. 65:2220-2224; PCT/US94/05700). In applications where transient expression is preferred, adenoviral based systems may be used. Adenoviral based vectors are capable of very high transduction efficiency in many cell types and do not require cell division. With such vectors, high titer and levels of expression have been obtained. This vector can be produced in large quantities in a relatively simple system. Adeno-associated virus ("AAV") vectors may also be used to transduce cells with target nucleic acids, e.g., in the in vitro production of nucleic acids and peptides, and for in vivo and ex vivo gene therapy procedures (e.g., West et al. (1987) Virology 160:38-47; U.S. Pat. No. 4,797, 368; WO 93/24641; Kotin (1994) Human Gene Therapy 5:793-801; Muzyczka (1994) Clin. Invest. 94:1351. Construction of recombinant AAV vectors are described in a number of publications, including U.S. Pat. No. 5,173,414; Tratschin et al. (1985) Mol. Cell. Biol. 5:3251-3260; Tratschin et al. (1984) Mol. Cell. Biol. 4:2072-2081; Hermonat and Muzyczka (1984) Proc. Natl. Acad. Sci. U.S.A. 81:6466-6470; and Samulski et al. (1989) J. Virol. 63:03822-3828.

Packaging cells are typically used to form virus particles that are capable of infecting a host cell. Such cells include 293 cells, which package adenovirus, and ψ2 cells or PA317 cells, which package retrovirus. Viral vectors used in gene therapy are usually generated by producing a cell line that packages a nucleic acid vector into a viral particle. The vectors typically contain the minimal viral sequences required for packaging and subsequent integration into a host, other viral sequences being replaced by an expression cassette for the polynucleotide(s) to be expressed. The missing viral functions are typically supplied in trans by the packaging cell line. For example, AAV vectors used in gene therapy typically only possess ITR sequences from the AAV genome which are required for packaging and integration into the host genome. Viral DNA is packaged in a cell line, which contains a helper plasmid encoding the other AAV genes, namely rep and cap, but lacking ITR sequences. The cell line may also be infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV. Additional methods for the delivery of nucleic acids to cells are known to those skilled in the art. See, for example, US20030087817, incorporated herein by reference.

In some embodiments, a host cell is transiently or non-transiently transfected with one or more vectors described herein. In some embodiments, a cell is transfected as it, naturally occurs in a subject. In some embodiments, a cell that is transfected is taken from a subject. In some embodiments, the cell is derived from cells taken from a subject, such as a cell line. A wide variety of cell lines for tissue culture are known in the art. Examples of cell lines include, but are not limited to, C8161, CCRF-CEM, MOLT, mIMCD-3, NHDF, HeLa-S3, Huh1, Huh4, Huh7, HUVEC, HASMC, HEKn, HEKa, MiaPaCell, Panel, PC-3, TF1, CTLL-2, C1R, Rat6, CV1, RPTE, A10, T24, J82, A375, ARH-77, Calu1, SW480, SW620, SKOV3, SK-UT, CaCo2, P388D1, SEM-K2, WEHI-231, HB56, TIB55, Jurkat, J45.01, LRMB, Bcl-1, BC-3, IC21, DLD2, Raw264.7, NRK, NRK-52E, MRCS, MEF, Hep G2, HeLa B, HeLa T4, COS, COS-1, COS-6, COS-M6A, BS-C-1 monkey kidney epithelial, BALB/3T3 mouse embryo fibroblast, 3T3 Swiss, 3T3-L1, 132-d5 human fetal fibroblasts; 10.1 mouse fibroblasts, 293-T, 3T3, 721, 9L, A2780, A2780ADR, A2780cis, A172, A20, A253, A431, A-549, ALC, B16, 1335, BCP-1 cells, BEAS-2B, bEnd.3, BHK-21, BR 293, BxPC3, C3H-10T1/2, C6/36, Cal-27, CHO, CHO-7, CHO-K1, CHO-K2, CHO-T, CHO Dhfr-/-, COR-L23, COR-L23/CPR, COR-L23/5010, COR-L23/R23, COS-7, COV-434, CML T1, CMT, CT26, D17, DH82, DU145, DuCaP, EL4, EM2, EM3, EMT6/AR1, EMT6/AR10.0, FM3, H1299, H69, HB54, HB55, HCA2, HEK-293, HeLa, Hepa1c1c7, HL-60, HMEC, HT-29, Jurkat, JY cells, K562 cells, Ku812, KCL22, KG1, KYO1, LNCap, Ma-Mel 1-48, MC-38, MCF-7, MCF-10A, MDA-MB-231, MDA-MB-468, MDA-MB-435, MDCK 11, MDCK II, MOR/0.2R, MONO-MAC 6, MTD-1A, MyEnd, NCI-H69/CPR, NCI-H69/LX10, NCI-H69/LX20, H69/LX4, NIH-3T3, NALM-1, NW-145, OPCN/OPCT cell lines, Peer, PNT-1A/PNT 2, RenCa, RIN-5F, RMA/RMAS, Saos-2 cells, Sf-9, SkBr3, T2, T-47D, T84, THP1 cell line, U373, U87, U937, VCaP, Vero cells, WM39, WT-49, X63, YAC-1, YAR, and transgenic varieties thereof. Cell lines are available from a variety of sources known to those with skill in the art (see, e.g., the American Type Culture Collection (ATCC) (Manassas, Va.)). In some embodiments, a cell transfected with one or more vectors described herein is used to establish a new cell line comprising one or more vector-derived sequences. In some embodiments, a cell transiently transfected with the components of a CRISPR system as described herein (such as by transient transfection of one or more vectors, or transfection with RNA), and modified through the activity of a CRISPR complex, is used to establish a new cell line comprising cells containing the modification but lacking any other exogenous sequence, in some embodiments, cells transiently or non-transiently transfected with one or more vectors described herein, or cell lines derived from such cells are used in assessing one or more test compounds.

In some embodiments, one or more vectors described herein are used to produce a non-human transgenic animal. In some embodiments, the transgenic animal is a mammal, such as a mouse, rat, or rabbit. In certain embodiments, the organism or subject is a plant. Methods for producing transgenic animals are known in the art, and generally begin with a method of cell transfection, such as described herein.

In one aspect, the presently disclosed subject matter provides for methods of modifying a target polynucleotide in a eukaryotic cell, which may be in vivo, ex vivo or in vitro. In some embodiments, the method comprises sampling a cell or population of cells from a human or non-human animal, and modifying the cell or cells. Culturing may occur at any stage ex vivo. The cell or cells may even be re-introduced into the non-human animal.

In one aspect, the presently disclosed subject matter provides for methods of modifying a target polynucleotide in a eukaryotic cell. In some embodiments, the method comprises allowing a CRISPR complex to bind to the target polynucleotide to effect cleavage of the target polynucleotide thereby modifying the target polynucleotide, wherein the CRISPR complex comprises a CRISPR enzyme complexed with a guide sequence hybridized to a target sequence within the target polynucleotide.

In one aspect, the presently disclosed subject matter provides a method of modifying expression of a polynucleotide in a eukaryotic cell. In some embodiments, the method comprises allowing a CRISPR complex to bind to the polynucleotide such that the binding results in increased or decreased expression of the polynucleotide; wherein the CRISPR complex comprises a CRISPR enzyme complexed with a guide sequence hybridized to a target sequence within the polynucleotide.

In one aspect, the presently disclosed subject matter provides methods for using one or more elements of a CRISPR system. The CRISPR complex of the presently disclosed subject matter provides an effective means for modifying a target polynucleotide. The CRISPR complex of the presently disclosed subject matter has a wide variety of utility including modifying (e.g., deleting, inserting, translocating, inactivating, activating) a target polynucleotide in a multiplicity of cell types. As such the CRISPR complex of the presently disclosed subject matter has a broad spectrum of applications in, e.g., gene therapy, drug screening, disease diagnosis, and prognosis. An exemplary CRISPR complex comprises a CRISPR enzyme complexed with a guide sequence hybridized to a target sequence within the target The target polynucleotide of a CRISPR complex can be any polynucleotide endogenous or exogenous to the eukaryotic cell. For example, the target polynucleotide can be a polynucleotide residing in the nucleus of the eukaryotic cell. The target polynucleotide can be a sequence coding a gene product (e.g., a protein) or a non-coding sequence (e.g., a regulatory polynucleotide or a junk DNA). Without wishing to be bound by theory, it is believed that the target sequence should be associated with a PAM (protospacer adjacent motif); that is, a short sequence recognized by the CRISPR complex. The precise sequence and length requirements for the PAM differ depending on the CRISPR enzyme used, but PAMs are typically 2-5 base pair sequences adjacent the protospacer (that is, the target sequence). Examples of PAM sequences are given in the examples section below, and the skilled person will be able to identify further PAM sequences for use with a given CRISPR enzyme.

Examples of target polynucleotides include a sequence associated with a signaling biochemical pathway, e.g., a signaling biochemical pathway-associated gene or polynucleotide. Examples of target polynucleotides include a disease associated gene or polynucleotide. A "disease-associated" gene or polynucleotide refers to any gene or polynucleotide which is yielding transcription or translation products at an abnormal level or in an abnormal form in cells derived from a disease-affected tissues compared with tissues or cells of a non disease control. It may be a gene that becomes expressed at an abnormally high level; it may be a gene that becomes expressed at an abnormally low level, where the altered expression correlates with the occurrence and/or progression of the disease. A disease-associated gene also refers to a gene possessing mutation(s) or genetic variation that is directly responsible or is in linkage disequilibrium with a gene(s) that is responsible for the etiology of a disease. The transcribed or translated products may be known or unknown, and may be at a normal or abnormal level.

Embodiments of the presently disclosed subject matter also relate to methods and compositions related to knocking out genes, amplifying genes and repairing particular mutations associated with DNA repeat instability and neurological disorders (Robert D. Wells, Tetsuo Ashizawa, Genetic Instabilities and Neurological Diseases, Second Edition, Academic Press, Oct. 13, 2011-Medical). Specific aspects of tandem repeat sequences have been found to be responsible for more than twenty human diseases (McIvor et al (2010) *RNA Biol.* 7(5):551-8). The CRISPR-Cas system may be harnessed to correct these defects of genomic In yet another aspect of the presently disclosed subject matter, the CRISPR-Cas system may be used to correct ocular defects that arise from several genetic mutations further described in Traboulsi, ed. (2012) Genetic Diseases of the Eye, Second Edition, Oxford University Press.

Several further aspects of the presently disclosed subject matter relate to correcting defects associated with a wide range of genetic diseases. For example, genetic brain diseases may include but are not limited to Adrenoleukodystrophy, Agenesis of the Corpus Callosum, Aicardi Syndrome, Alpers' Disease. Alzheimer's Disease, Barth Syndrome, Batten Disease, CADASIL, Cerebellar Degeneration, Fabry's Disease, Gerstmann-Straussler-Scheinker Disease, Huntington's Disease and other Triplet Repeat Disorders, Leigh's Disease, Lesch-Nyhan Syndrome, Menkes Disease, Mitochondrial Myopathies and NINDS Colpocephaly.

In some embodiments, the condition may be neoplasia. In some embodiments, the condition may be Age-related Macular Degeneration. In some embodiments, the condition may be a Schizophrenic Disorder. In some embodiments, the condition may be a Trinucleotide Repeat Disorder. In some embodiments, the condition may be Fragile X Syndrome. In some embodiments, the condition may be a Secretase Related Disorder. In some embodiments, the condition may be a Prion related disorder. In some embodiments, the condition may be ALS. In some embodiments, the condition may be a drug addiction. In some embodiments, the condition may be Autism. In some embodiments, the condition may be Alzheimer's Disease. In some embodiments, the condition may be inflammation. In some embodiments, the condition may be Parkinson's Disease.

Examples of proteins associated with Parkinson's disease include but are not limited to α-synuclein, DJ-1, LRRK2, PINK1, Parkin, UCHL1, Synphilin-1, and NURR1.

Examples of addiction-related proteins may include ABAT for example.

Examples of inflammation-related proteins may include the monocyte chemoattractant protein-1 (MCP1) encoded by the Ccr2 gene, the C—C chemokine receptor type 5 (CCR5) encoded by the Ccr5 gene, the IgG receptor IIB (FCGR2b, also termed CD32) encoded by the Fcgr2b gene, or the Fc epsilon Rig (FCER1g) protein encoded by the Fcer1g gene, for example.

Examples of cardiovascular disease associated proteins may include IL1B (interleukin 1, beta), XDH (xanthine dehydrogenase), TP53 (tumor protein p53), PTGIS (prostaglandin 12 (prostacyclin) synthase), MB (myoglobin), IL4 (interleukin 4), ANGPT1 (angiopoietin 1), ABCG8 (ATP-binding cassette, sub-family G (WHITE), member 8), or CTSK (cathepsin K), for example.

Examples of Alzheimer's disease associated proteins may include the very low density lipoprotein receptor protein (VLDLR) encoded by the VLDLR gene, the ubiquitin-like modifier activating enzyme 1 (UBA1) encoded by the UBA1 gene, or the NEDD8-activating enzyme E1 catalytic subunit protein (UBE1C) encoded by the UBA3 gene, for example.

Examples of proteins associated Autism Spectrum Disorder may include the benzodiazapine receptor (peripheral) associated protein 1 (BZRAP1) encoded by the BZRAP1 gene, the AF4/FMR2 family member 2 protein (AFF2) encoded by the AFF2 gene (also termed MFR2), the fragile X mental retardation autosomal homolog 1 protein (FXR1) encoded by the FXR1 gene, or the fragile X mental retardation autosomal homolog 2 protein (FXR2) encoded by the FXR2 gene, fir example.

Examples of proteins associated Macular Degeneration may include the ATP-binding cassette, sub-family A (ABC1) member 4 protein (ABCA4) encoded by the ABCR gene, the apolipoprotein E protein (APOE) encoded by the APOE gene, or the chemokine (C—C motif) Ligand 2 protein (CCL2) encoded by the CCL2 gene, for example.

Examples of proteins associated Schizophrenia may include NRG1, ErbB4, CPLX1, TPH1, TPH2, NRXN1, GSK3A, BDNF, DISC1, GSK3B, and combinations thereof.

Examples of proteins involved in tumor suppression may include ATM (ataxia telangiectasia mutated), ATR (ataxia telangiectasia and Rad3 related), EGFR (epidermal growth factor receptor), ERBB2 (v-erb-b2 erythroblastic leukemia viral oncogene homolog 2), ERBB3 (v-erb-b2 erythroblastic leukemia viral oncogene homolog 3), ERBB4 (v-erb-b2 erythroblastic leukemia viral oncogene homolog 4), Notch 1, Notch2, Notch 3, or Notch 4, for example.

Examples of proteins associated with a secretase disorder may include PSENEN (presenilin enhancer 2 homolog (*C. elegans*)), CTSB (cathepsin B), PSEN1 (presenilin 1), APP (amyloid beta (A4) precursor protein), Anil B (anterior pharynx defective 1 homolog B (*C. elegans*)), PSEN2 (presenilin 2 (Alzheimer disease 4)), or BACE1 (beta-site APP-cleaving enzyme 1), for example.

Examples of proteins associated with Amyotrophic Lateral Sclerosis may include SOD1 (superoxide dismutase 1), ALS2 (amyotrophic lateral sclerosis 2), FUS (fused in sarcoma), TARDBP (TAR DNA binding protein), VAGFA (vascular endothelial growth factor A), VAGFB (vascular endothelial growth factor B), and VAGFC (vascular endothelial growth factor C), and any combination thereof.

Examples of proteins associated with prion diseases may include SODI (superoxide dismutase 1), ALS2 (amyotrophic lateral sclerosis 2), FUS (fused in sarcoma), TARDBP (TAR DNA binding protein), VAGFA (vascular endothelial growth factor A), VAGFB (vascular endothelial growth factor B), and VAGFC (vascular endothelial growth factor C), and any combination thereof.

Examples of proteins related to neurodegenerative conditions in prion disorders may include A2M (Alpha-2-Macroglobulin), AATF (Apoptosis antagonizing transcription factor), ACPP (Acid phosphatase prostate), ACTA2 (Actin alpha 2 smooth muscle aorta), ADAM22 (ADAM metallopeptidase domain), ADORA3 (Adenosine A3 receptor), or ADRA1D (Alpha-1D adrenergic receptor for Alpha-ID adrenoreceptor), for example.

Examples of proteins associated with immunodeficiency may include A2M [alpha-2-macroglobulin]; AANAT [arylalkylamine N-acetyltransferase]; ABCA1 [ATP-binding cassette, sub-family A (ABC1), member 1]; ABCA2 [ATP-binding cassette, sub-family A (ABC1), member 2]; or ABCA3 [ATP-binding cassette, sub-family A (ABC1), member 3]; for example.

Examples of proteins associated with Trinucleotide Repeat Disorders include AR (androgen receptor), FMR1 (fragile X mental retardation 1), HTT (huntingtin), or DMPK (dystrophia myotonica-protein kinase), FXN (frataxin), ATXN2 (ataxin 2), for example.

Examples of proteins associated with Neurotransmission Disorders include SST (somatostatin), NOS1 (nitric oxide synthase 1 (neuronal)), ADRA2A (adrenergic, alpha-2A-, receptor), ADRA2C (adrenergic, alpha-2C-, receptor), TACR1 (tachykinin receptor 1), or HTR2c (5-hydroxytryptamine (serotonin) receptor 2C), for example.

Examples of neurodevelopmental-associated sequences include A2BP1 (ataxin 2-binding protein 1), AADAT (aminoadipate aminotransferase), AANAT (arylalkylamine N-acetyltransferase), ABAT (4-aminobutyrate aminotransferase), ABCA1 (ATP-binding cassette, sub-family A (ABC1), member 1), or ABCA13 (ATP-binding cassette, sub-family A (ABC1), member 13), for example.

Further examples of preferred conditions treatable with the present system include may be selected from: Aicardi-Goutières Syndrome; Alexander Disease; Allan-Herndon-Dudley Syndrome; POLO-Related Disorders; Alpha-Mannosidosis (Type II and III); Alström Syndrome; Angelman; Syndrome; Ataxia-Telangiectasia; Neuronal Ceroid-Lipofuscinoses; Beta-Thalassemia; Bilateral Optic Atrophy and (Infantile) Optic Atrophy Type 1; Retinoblastoma (bilateral); Canavan Disease; Cerebrooculofacioskeletal Syndrome 1 (COFS1); Cerebrotendinous Xanthomatosis; Cornelia de Lange Syndrome; MAPT-Related Disorders; Genetic Prion Diseases; Dravet Syndrome; Early-Onset Familial Alzheimer Disease; Friedreich Ataxia [FRDA]; Fryns Syndrome; Fucosidosis; Fukuyama Congenital Muscular Dystrophy, Galactosialidosis; Gaucher Disease; Organic Acidemias; Hemophagocytic Lymphohistiocytosis; Hutchinson-Gilford Progeria Syndrome; Mucolipidosis II; Infantile Free Sialic Acid Storage Disease; PLA2G6-Associated Neurodegeneration; Jervell and Lange-Nielsen Syndrome; Junctional Epidermolysis Bullosa; Huntington Disease; Krabbe Disease (infantile) Mitochondrial DNA-Associated Leigh Syndrome and NARP; Lesch-Nyhan Syndrome; LIS1-Associated Lissencephaly; Lowe Syndrome; Maple Syrup Urine Disease; MECP2 Duplication Syndrome; ATP7A-Related Copper Transport Disorders; LAMA2-Related Muscular Dystrophy; Arylsulfatase A Deficiency; Mucopolysaccharidosis Types I, II or Peroxisome Biogenesis Disorders, Zellweger Syndrome Spectrum; Neurodegeneration with Brain Iron Accumulation Disorders; Acid Sphingomyelinase Deficiency; Niemann-Pick Disease Type C; Glycine Encephalopathy; ARX-Related Disorders; Urea Cycle Disorders; COL1A 1/2-Related Osteogenesis Imperfecta; Mitochondrial DNA Deletion Syndromes; PLP1-Related Disorders; Perry Syndrome; Phelan-McDermid Syndrome; Glycogen Storage Disease Type II (Pompe Disease) (Infantile); MAPT-Related Disorders; MECP2-Related Disorders; Rhizomelic Chondrodysplasia Punctata Type 1; Roberts Syndrome; Sandhoff Disease; Schindler Disease—Type 1; Adenosine Deaminase Deficiency; Smith-Lemli-Opitz Syndrome; Spinal Muscular Atrophy, Infantile-Onset Spinocerebellar Ataxia; Hexosaminidase A Deficiency; Thanatophoric Dysplasia Type 1; Collagen Type VI-Related Disorders; Usher Syndrome Type Congenital Muscular Dystrophy; Wolf-Hirschhorn Syndrome; Lysosomal Acid. Lipase Deficiency; and Xeroderma Pigmentosum.

II. Methods for Treating Neurodegenerative Diseases

The presently disclosed subject matter also provides methods for treating a disease selected from the group consisting of retinal dystrophy, corneal dystrophy, microsatellite expansion diseases, cancer, and neurodegenerative diseases in a subject in need thereof, the method comprising: (a) providing a non-naturally occurring nuclease system (e.g., CRISPR associated (Cas) 9 (CRISPR-Cas9, non-Cas9 CRISPR systems, CRISPR-Cpf-1 system, and the like) comprising one or more vectors comprising: a) a promoter (e.g., orthologous H1 promoter or 7sk) operably linked to at least one nucleotide sequence encoding a nuclease system guide RNA (gRNA), wherein the gRNA hybridizes with a target sequence of a DNA molecule in a cell, and wherein the DNA molecule encodes one or more gene products expressed in the cell; and b) a regulatory element operable in a cell operably linked to a nucleotide sequence encoding a genome-targeted nuclease (e.g., modified Cas9 protein), wherein components (a) and (b) are located on the same or different vectors of the system, wherein the gRNA targets and hybridizes with the target sequence and the nuclease cleaves the DNA molecule to alter expression of the one or more gene products; and (b) administering to the subject an effective amount of the system. In some embodiments, the system is packaged into a single adeno-associated virus (AAV) particle. In some embodiments, the system inactivates one or more gene products. In some embodiments, the system excises at least one gene mutation. In some embodiments, the H1 promoter comprises a nucleotide sequence having at least 80%, 85%, 90%, 95%, 98%, 99%, or 100% identity to the nucleotide sequence set forth in SEQ ID NO: 12 or 32. In some embodiments, the orthologous H1 promoter is derived from mouse or rat. In some embodiments, the orthologous H1 promoter comprises a nucleotide sequence having at least 80%, 85%, 90%, 95%, 98%, 99%, or 100% identity to the nucleotide sequence set forth in SEQ ID NOs: 84-119. In some embodiments, the orthologous H1 promoter comprises a nucleotide sequences set forth in the group consisting of SEQ ID NOs: 84-119. In some embodiments, the H1 promoter comprises: a) control elements that provide for transcription in one direction of at least one nucleotide sequence encoding a gRNA; and b) control elements that provide for transcription in the opposite direction of a nucleotide sequence encoding a genome-targeted nuclease. In some embodiments, the promoter is the human, mouse, or rat 7sk promoter. In some embodiments, the 7sk is selected from the group consisting of 7sk1 (variant 1 of 7sk which uses the endogenous GSTA4 5'UTR), 7sk2 (variant 2 of 7sk which uses just a kozak sequence in the 5'UTR), and 7sk3 (variant of 7sk which uses the beta globin 5'UTR). In some embodiments, the human 7sk1 comprises a nucleotide sequence having at least 80%, 85%, 90%, 95%, 98%, 99%, or 100% identity to the nucleotide sequence set forth in SEQ ID NO: 3. In some embodiments, the mouse 7sk1 comprises a nucleotide sequence having at least 80%, 85%, 90%, 95%, 98%, 99%, or 100% identity to SEQ ID NO: 6. In some embodiments, the human 7sk2 comprises a nucleotide sequence having at least 80%, 85%, 90%, 95%, 98%, 99%, or 100% identity to SEQ ID NO: 4. In some embodiments, the mouse 7sk2 comprises a nucleotide sequence having at least 80%, 85%, 90%, 95%, 98%, 99%, or 100% identity to SEQ ID NO: 7. In some embodiments, the human 7sk3 comprises a nucleotide sequence having at least 80%, 85%, 90%, 95%, 98%, 99%, or 100% identity to SEQ ID NO: 5. In some embodiments, the mouse 7sk3 comprises a nucleotide sequence having at least 80%, 85%, 90%, 95%, 98%, 99%, or 100% identity to SEQ ID NO: 8. In some embodiments, the orthologous H1 promoter or 7sk promoter has at least one modification. In some embodiments, the at least one modification of the promoter comprises an element that allows conditional regulation. In some embodiments, the element is a tet-responsive promoter. In some embodiments, the tet-response promoter comprises a Tet repressor (TetR) and Tet operator (TetO) engineered into the H1 promoter. In some embodiments, the TetR comprises an amino acid sequence having at least 80%, 85%, 90%, 95%, 98%, 99%, or 100% identity to SEQ ID NO: 14. In some embodiments, the TetO comprises a nucleotide sequence having at least 80%, 85%, 90%, 95%, 98%, 99%, or 100% identity to the nucleotide sequence set forth in SEQ ID NO: 11. In some embodiments, the H1-TetO comprises a nucleotide sequence having at least 80%, 85%, 90%, 95%, 98%, 99%, or 100% identity to the nucleotide sequence set forth in SEQ ID NO: 13. In some embodiments, the at least one modification of the promoter comprises a site that allows auto-regulation. In some embodiments, the auto-regulation site comprises a nucleotide sequence having at least 80%, 85%, 90%, 95%, 98%, 99%, or 100% identity to the nucleotide sequence set forth in SEQ ID NO: 33 or 34. In some embodiments, the nuclease system further comprising at least one terminator sequence. In some embodiments, the at least one terminator sequence is selected from the group consisting of SV40 or synthetic poly A (SPA) sequences. In some embodiments, the terminator sequences is a SV40 120 (SEQ ID NO: 123) or 240 (SEQ ID NO: 122) base pair sequence. In some embodiments, the terminator sequences is a SPA 49 base pair equence. In some embodiments, the nuclease system further comprises 5' untranslated region (5'UTR) sequences. In some embodiments, the nuclease system further comprises a Kozak sequence. In some embodiments, the Kozak sequence comprises a nucleotide sequence having at least 80%, 85%, 90%, 95%, 98%, 99%, or 100% identity to SEQ ID NO: 1 or 2. In some embodiments, the nuclease system further comprises a RNA sequence that mediates cap-independent initiation of translation. In some embodiments, the RNA sequence is selected from the group consisting of 6.947 or 6.967. In some embodiments, the Cas9 comprises a nucleotide sequence having at least 80%, 85%, 90%, 95%, 98%, 99%, or 100% identity to the nucleotide sequence set forth in SEQ ID NO: 61. In some embodiments, the Cas9 comprises at least one modification. In some embodiments, the at least one modification in the Cas9 comprises an alteration in the cleaving sequence. In some embodiments, the nuclease is selected from the group consisting of Cas1, Cas1B, Cas2, Cas3, Cas4, Cas5, Cas6, Cas7, Cas8, Cas9 (also known as Csn1 and Csx12), Cas10, Cas13a, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1, C2c1, C2c2, and C2c3. In some embodiments, the alteration in the cleaving sequence selected from the group consisting of T2A, P2A, E2A, and F2A. In some embodiments, the T2A comprises an amino acid sequence. having at least 80%, 85%, 90%, 95%, 98%, 99%, or 100% identity to the nucleotide sequence set forth in SEQ ID NO: 36. In some embodiments, the P2A comprises an amino acid sequence having at least 80%, 85%, 90%, 95%, 98%, 99%, or 100% identity to the nucleotide sequence set forth in SEQ ID NO: 35. In some embodiments, the P2A comprises an amino acid sequence having the nucleotide sequence set forth in SEQ ID NO: 35. In some embodiments, the E2A comprises an amino acid sequence having at least 80%, 85%, 90%, 95%, 98%, 99%, or 100% identity to the nucleotide sequence set forth in SEQ ID NO: 37. In some embodiments, the F2A comprises an amino acid sequence having at least 80%, 85%, 90%, 95%, 98%, 99%, or 100% identity to the nucleotide sequence set forth in SEQ ID NO: 38. In some embodiments, the at least one modification in the Cas9 comprises a codon optimized for expression in the cell. In some embodiments, the Cas9 further comprises a linker sequence operably fused in frame to a cell-cycle dependent protein (Cas9 fusion). In some embodiments, the cell cycle-dependent protein is selected from the group consisting of APE2, ATR, BRCA1, Chk1, Cdc5, Cdc6, Cdc7, Cdc45, Cdt1, CSA, CSB, Ctf18, DDB1, DDB2, DNA2, DUT, Elg1, EndoV, Esp1, Exonuclease1, FBH1, FEN1, Geminin, Hus1, KNTC2 (NDC80), Ku80, Ligase1, Mad2, MBD4, Mcm3, Mcm4, Mcm5, Mcm6, Mcm7, Mcm8, Mcm10, MGMT, MLH3, Mms4, MPG, MSH2, Mus81, NBS1, NEIL2, NEIL3, NTH1, Orc1, Orc3, PARP1, PCNA, Pif1, PMS1, PMS2, PNK, Pola p180, Pola p'70, Pola Spp1 (Prim2a), Polb, Pold p125, Pole Dpb3, Pole Dpb4, Pole Pol2, Poli, Poll, Polm, Psf1, Psf2, Psf3, Rad1, Rad18, Rad23A, Rad23B, Rad51, Rad51D, Rad54, Rad6A, RPA34, RPA70, Scc1, Scc3, Sir2, SIRT1 (Sirtuin), TDG, TDP1, TIMELESS, Tin2, Topoisomerase I, Topoisomerase IIIa, Topoisomerase IIIb, Ubc13, UNG, XAB2, XPC, XPF, XPG, Xrcc2, and XRCC4. In some embodiments, the cell cycle-dependent protein is Geminin. In some embodiments, the cell cycle-dependent protein is human Geminin. In some embodiments, the human Geminin comprises the amino acids from positions 1-110 (hGem(1-110)). In some embodiments, the hGem(1-110) comprises an amino acid sequence having at least 80%, 85%, 90%, 95%, 98%, 99%, or 100% identity to the amino acid sequence set forth in SEQ ID NO: 19. In some embodiments, the cell cycle-dependent protein is Cdt1. In some embodiments, the cell cycle-dependent protein is human Cdt1. In some embodiments, the human Cdt1 comprises amino acids from positions 30-120 (hCdt1 (30-120)). In some embodiments, the hCdt1(30-120) comprises an amino acid sequence having at least 80%, 85%, 90%, 95%, 98%, 99%, or 100% identity to the amino acid sequence set forth in SEQ ID NO: 18. In some embodiments, the Cas9 fusion comprises an amino acid sequence having at least 80%, 85%, 90%, 95%, 98%, 99%, or 100% identity to the amino acid sequence selected from the group consisting of SEQ ID NO: 20-27. In some embodiments, the Cas9 is operably fused in frame to a ubiquitin protein (Ub-Cas9). In some embodiments, the Ub-Cas9 at least one N-terminal modification. In some embodiments, the N-terminal modified Ub-Cas9 comprises an amino acid sequence having at least 80%, 85%, 90%, 95%, 98%, 99%, or 100% identity to the amino acid sequence selected from the group consisting of SEQ ID NO: 39-58. In some embodiments, the ubiquitin protein comprises a nucleotide sequence having at least 80%, 85%, 90%, 95%, 98%, 99%, or 100% identity to the nucleotide sequence set forth in SEQ ID NO: 60. In some embodiments, the nuclease system further comprises a SaCas9 nickase. In some embodiments, the nuclease system further comprises a donor template sequence. In some embodiments, the at least one vector comprises a nucleotide sequence having at least 80%, 85%, 90%, 95%, 98%, 99%, or 100% identity to the nucleotide sequence set forth in SEQ ID NO: 62 or 67. In some embodiments, the donor template sequence corrects at least one gene mutation. In some embodiments, the at least one gene mutation is rd10 or rd12. In some embodiments, the at least one vector comprises a nucleotide sequence having at least 80%, 85%, 90%, 95%, 98%, 99%, or 100% identity to the nucleotide sequence set forth in SEQ ID NO: 63 or 64. In some embodiments, the at least one vector comprises a nucleotide sequence having at least 80%, 85%, 90%, 95%, 98%, 99%, or 100% identity to the nucleotide sequence set forth in SEQ ID NO: 65 or 66. In some embodiments, the promoter is operably linked to at least one, two, three, four, five, six, seven, eight, nine, or ten gRNA. In some embodiments, the target sequence comprises the nucleotide sequence $AN_{19}NGG$, $GN_{19}NGG$, $CN_{19}NGG$, or $TN_{19}NGG$. In some embodiments, the cell is a eukaryotic or or non-eukaryotic cell. In some embodiments, the eukaryotic cell is a mammalian or human cell. In some embodiments, the eukaryotic cell is a retinal photoreceptor cell. In some embodiments, the one or more gene products are rhodopsin. In some embodiments, the expression of the one or more gene products is decreased. In some embodiments, the system inactivates one or more gene products. In some embodiments, the nuclease system excises at least one gene mutation. In some embodiments, the expression of the one or more gene products is decreased. In some embodiments, the cell is a retinal ganglion cell. In some embodiments, the eukaryotic cell is a cancerous cell. In some embodiments, cell proliferation is inhibited or reduced in the cancerous cell. In some embodiments, the apoptosis is enhanced or increased in the cancerous cell. In some embodiments, the disease is corneal dystrophy. In some embodiments, the disease is a retinal dystrophy. In some embodiments, the retinal dystrophy is selected from the group consisting of Leber's congenital amaurosis (LCA), retinitis pigmentosa (RP), and glaucoma. In some embodiments, the corneal dystrophy is selected from the group consisting of Epithelial Basement Membrane Dystrophy, Epithelial Recurrent Erosion Dystrophies, Subepithelial Mucinous Corneal Dystrophy, Meesmann Corneal Dystrophy, Lisch Epithelial Corneal Dystrophy, Gelatinous Droplike Corneal Dystrophy, Reis-Bucklers Corneal Dystrophy, Thiel-Behnke Corneal Dystrophy, Lattice Corneal Dystrophy, Type 1 (Classic), Lattice Corneal Dystrophy, Type 2, Lattice Corneal Dystrophy, Type III, Lattice Corneal Dystrophy, Type IIIA, Lattice Corneal Dystrophy, Type VIIIA, Lattice Corneal Dystrophy, Type IV, Polymorphic (Corneal) Amyloidosis, Granular Corneal Dystrophy, Type 1, Granular Corneal Dystrophy, Type 2, Macular Corneal Dystrophy, Schnyder Corneal Dystrophy, Congenital Stromal Corneal Dystrophy, Fleck Corneal Dystrophy, Posterior Amorphous Corneal Dystrophy, Central Cloudy Dystrophy of Francois, Pre-Descemet Corneal Dystrophy, Fuchs Endothelial Corneal Dystrophy, Posterior Polymorphous Corneal Dystrophy, Congenital Hereditary Endothelial Dystrophy, and X-linked Endothelial Corneal Dystrophy. In some embodiments, the microsatellite expansion diseases is selected from the group consisting of Blepharophimosis, ptosis and epicanthus inversus syndactyly, Cleidocranial dysplasia, Congenital central hypoventilation syndrome, Haddad syndrome DM (Myotonic dystrophy), FRAXA (Fragile X syndrome), FRAXE (Fragile XE mental retardation), FRDA (Friedreich's ataxia), Fuchs' Endothelial Corneal Dystrophy, FXTAS (Fragile X-associated tremor/ataxia syndrome), Hand-foot-genital syndrome, HD (Huntington's disease), Holoprosencephaly, Mental retardation with growth hormone deficiency, Mental retardation, epilepsy, West syndrome, Partington syndrome, Oculopharyngeal muscular dystrophy, SBMA (Spinal and bulbar muscular atrophy), SCA1 (Spinocerebellar ataxia Type 1), SCA12 (Spinocerebellar ataxia Type 12), SCA17 (Spinocerebellar ataxia Type 17), SCA2 (Spinocerebellar ataxia Type 2), SCA3 (Spinocerebellar ataxia Type 3 or Machado-Joseph disease), SCA6 (Spinocerebellar ataxia Type 6), SCAT (Spinocerebellar ataxia Type 7), SCA8 (Spinocerebellar ataxia Type 8), and Synpolydactyly. In some embodiments, administering to the subject occurs by implantation, injection, or virally. In some embodiments, administering to the subject occurs by subretinal injection. In some embodiments, administering to the subject occurs topically, intravascularly, intradermally, transdermally, parenterally, intravenously, intramuscularly, intranasally, subcutaneously, regionally, percutaneously, intratracheally, intraperitoneally, intraarterially, intravesically, intratumorally, peritumorally, inhalationly, systematically, perfusionly, lavagely, directly via injection, or orally via administration and formulation. In some embodiments, administering to the subject occurs topically to the surface of the eye. In some embodiments, administering to the subject occurs on or outside the cornea, sclera, to the intraocular, subconjunctival, sub-tenon, or retrobulbar space, or in or around the eyelids. In some embodiments, the subject is treated with at least one additional anti-cancer agent. In some embodiments, the anti-cancer agent is selected from the group consisting of paclitaxel, cisplatin, topotecan, gemcitabine, bleomycin, etoposide, carboplatin, docetaxel, doxorubicin, topotecan, cyclophosphamide, trabectedin, olaparib, tamoxifen, letrozole, and bevacizumab. In some embodiments, the subject is treated with at least one additional anti-cancer therapy. In some embodiments, the anti-cancer therapy is radiation therapy, chemotherapy, or surgery. In some embodiments, the cancer is a solid tumor. In some embodiments, the cancer is selected from the group consisting of brain cancer, gastrointestinal cancer, oral cancer, breast cancer, ovarian cancer, prostate cancer, pancreatic cancer, lung cancer, liver cancer, throat cancer, stomach cancer, and kidney cancer. In some embodiments, the cancer is brain cancer. In some embodiments, the systematic administration is selected from the group consisting of oral, intravenous, intradermal, intraperitoneal, subcutaneous, and intramuscular administration. In some embodiments, the subject is a mammal. In some embodiments, the mammal is human.

In some embodiments, the presently disclosed subject matter provides a method for treating an ocular neurodegenerative disease in a subject in need thereof, the method comprising: (a) providing a non-naturally occurring CRISPR-Cas system comprising one or more vectors comprising: i) an H1 promoter operably linked to at least one nucleotide sequence encoding a CRISPR-Cas system guide RNA (gRNA), wherein the gRNA hybridizes with a target sequence of a DNA molecule in a cell of the subject, and wherein the DNA molecule encodes one or more gene products expressed in the cell; and ii) a regulatory element operable in a cell operably linked to a nucleotide sequence encoding a Cas9 protein, wherein components (i) and (ii) are located on the same or different vectors of the system, wherein the gRNA targets and hybridizes with the target sequence and the Cas9 protein cleaves the DNA molecule to alter expression of the one or more gene products; and (b) administering to the subject an effective amount of the system.

By "neurodegenerative disease, disorder, or condition" is meant a disease, disorder, or condition (including a neuropathy) associated with degeneration or dysfunction of neurons or other neural cells, such as retinal photoreceptor cells. A neurodegenerative disease, disorder, or condition can be any disease, disorder, or condition in which decreased function or dysfunction of neurons, or loss or neurons or other neural cells, can occur.

Such diseases, disorders, or conditions include, but are not limited to, glaucoma, and neurodegenerative diseases, disorders, or conditions of the nervous systems, such as or associated with amyotrophic lateral sclerosis (ALS), trigeminal neuralgia, glossopharyngeal neuralgia, Bell's Palsy, myasthenia gravis, muscular dystrophy, progressive muscular atrophy, primary lateral sclerosis (PLS), pseudobulbar palsy, progressive bulbar palsy, spinal muscular atrophy, inherited muscular atrophy, invertebrate disk syndromes, cervical spondylosis, plexus disorders, thoracic outlet destruction syndromes, peripheral neuropathies, prophyria, Alzheimer's disease, Huntington's disease, Parkinson's disease, Parkinson's-plus diseases, multiple system atrophy, progressive supranuclear palsy, corticobasal degeneration, dementia with Lewy bodies, frontotemporal dementia, demyelinating diseases, Guillain-Barre syndrome, multiple sclerosis, Charcot-Marie-Tooth disease, prion diseases, Creutzfeldt-Jakob disease, Gerstmann-Straussler-Scheinker syndrome (GSS), fatal familial insomnia (FFI), bovine spongiform encephalopathy (BSE), Pick's disease, epilepsy, and AIDS demential complex.

Other neurodegenerative diseases, disorders, or conditions of the nervous systems, such as or associated with alcoholism, Alexander's disease, Alper's disease, ataxia telangiectasia, Batten disease (also known as Spielmeyer-Vogt-Sjogren-Batten disease), Canavan disease, Cockayne syndrome, diabetic neuropathy, frontotemporal lobar degeneration, HIV-associated dementia, Kennedy's disease, Krabbe's disease, neuroborreliosis, Machado-Joseph disease (Spinocerebellar ataxia type 3), wet or dry macular degeneration, Niemann Pick disease, Pelizaeus-Merzbacher Disease, photoreceptor degenerative diseases, such as retinitis pigmentosa and associated diseases, Refsum's disease, Sandhoffs disease, Schilder's disease, subacute combined degeneration of spinal cord secondary to pernicious anemia, Spielmeyer-Vogt-Sjogren-Batten disease (also known as Batten disease), spinocerebellar ataxia (multiple types with varying characteristics), Steele-Richardson-Olszewski disease, and tabes dorsalis.

Examples of ocular-related neurodegeneration include, but are not limited to, glaucoma, lattice dystrophy, retinitis pigmentosa, age-related macular degeneration (AMD), photoreceptor degeneration associated with wet or dry AMD, other retinal degeneration such as retinitis pigmentosa (RP), optic nerve drusen, optic neuropathy, and optic neuritis, such as optic neuritis resulting from multiple sclerosis. In some embodiments, the ocular neurodegenerative disease is selected from the group consisting of glaucoma, retinal degeneration, and age-related macular degeneration. In some embodiments, the ocular neurodegenerative disease is retinitis pigmentosa (RP).

Non-limiting examples of different types of glaucoma that can be prevented or treated according to the presently disclosed subject matter include primary glaucoma (also known as primary open-angle glaucoma, chronic open-angle glaucoma, chronic simple glaucoma, and glaucoma simplex), low-tension glaucoma, primary angle-closure glaucoma (also known as primary closed-angle glaucoma, narrow-angle glaucoma, pupil-block glaucoma, and acute congestive glaucoma), acute angle-closure glaucoma, chronic angle-closure glaucoma, intermittent angle-closure glaucoma, chronic open-angle closure glaucoma, pigmentary glaucoma, exfoliation glaucoma (also known as pseudoexfoliative glaucoma or glaucoma capsulare), developmental glaucoma (e.g., primary congenital glaucoma and infantile glaucoma), secondary glaucoma (e.g., inflammatory glaucoma (e.g., uveitis and Fuchs heterochromic iridocyclitis)), phacogenic glaucoma (e.g., angle-closure glaucoma with mature cataract, phacoanaphylactic glaucoma secondary to rupture of lens capsule, phacolytic glaucoma due to phacotoxic meshwork blockage, and subluxation of lens), glaucoma secondary to intraocular hemorrhage (e.g., hyphema and hemolytic glaucoma, also known as erythroclastic glaucoma), traumatic glaucoma (e.g., angle recession glaucoma, traumatic recession on anterior chamber angle, postsurgical glaucoma, aphakic pupillary block, and ciliary block glaucoma), neovascular glaucoma, drug-induced glaucoma (e.g., corticosteroid induced glaucoma and alpha-chymotrypsin glaucoma), toxic glaucoma, and glaucoma associated with intraocular tumors, retinal detachments, severe chemical burns of the eye, and iris atrophy. In certain embodiments, the neurodegenerative disease, disorder, or condition is a disease, disorder, or condition that is not associated with excessive angiogenesis, for example, a glaucoma that is not neovascular glaucoma.

As used herein, the term "disorder" in general refers to any condition that would benefit from treatment with a compound against one of the identified targets, or pathways, including any disease, disorder, or condition that can be treated by an effective amount of a compound against one of the identified targets, or pathways, or a pharmaceutically acceptable salt thereof.

As used herein, the term "treating" can include reversing, alleviating, inhibiting the progression of, preventing or reducing the likelihood of the disease, disorder, or condition to which such term applies, or one or more symptoms or manifestations of such disease, disorder or condition (e.g., a disease or disorder that causes dysfunction and/or death of retinal photoreceptor cells). In some embodiments, the treatment reduces the dysfunction and/or death of retinal photoreceptor cells. For example, the treatment can reduce the dysfunction and/or death of retinal photoreceptor cells by at least 5%, 10%, 15%, 20%, 25%, 30%, 33%, 35%, 40%, 45%, 50%, 55%, 60%, 66%, 70%, 75%, 80%, 85%, 90%, 91%, 92%, 93%, 94%, 95%, 96%, 97%, 98%, 99% or more as compared to the dysfunction and/or death of retinal photoreceptor cells in a subject before undergoing treatment or in a subject who does not undergo treatment. In some embodiments, the treatment completely inhibits dysfunction and/or death of retinal photoreceptor cells in the subject. As used herein, a "retinal photoreceptor cell" is a specialized type of neuron found in the retina that is capable of phototransduction. In some embodiments, at least one gene product is rhodopsin.

In some embodiments, the system is packaged into a single adeno-associated virus (AAV) particle before administering to the subject. In some embodiments, administering to the subject occurs by subretinal injection. The treatment, administration, or therapy can be consecutive or intermittent. Consecutive treatment, administration, or therapy refers to treatment on at least a daily basis without interruption in treatment by one or more days. Intermittent treatment or administration, or treatment or administration in an intermittent fashion, refers to treatment that is not consecutive, but rather cyclic in nature. Treatment according to the presently disclosed methods can result in complete relief or cure from a disease, disorder, or condition, or partial amelioration of one or more symptoms of the disease, disease, or condition, and can be temporary or permanent. The term "treatment" also is intended to encompass prophylaxis, therapy and cure.

The term "effective amount" or "therapeutically effective amount" refers to the amount of an agent that is sufficient to effect beneficial or desired results. The therapeutically effective amount may vary depending upon one or more of: the subject and disease condition being treated, the weight and age of the subject, the severity of the disease condition, the manner of administration and the like, which can readily be determined by one of ordinary skill in the art. The term also applies to a dose that will provide an image for detection by any one of the imaging methods described herein. The specific dose may vary depending on one or more of: the particular agent chosen, the dosing regimen to be followed, whether it is administered in combination with other compounds, timing of administration, the tissue to be imaged, and the physical delivery system in which it is carried.

The terms "subject" and "patient" are used interchangeably herein. The subject treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing condition or disease or the prophylactic treatment for preventing the onset of a condition or disease, or an animal subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a condition or disease.

IV. General Definitions

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXEMPLIFICATIONS

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

Background

The development of CRISPR-Cas9 technology has revolutionized the field of gene-editing and offers a profoundly new approach to treating genetic diseases. The CRISPR-Cas9 system is composed of a guide RNA (gRNA) that targets the Cas9 nuclease in a sequence-specific fashion. Cleavage by the CRISPR system requires complementary base pairing of the gRNA to a DNA sequence and the requisite protospaceradjacent motif (PAM), a short nucleotide motif found 3' to the target site (Dalkara, D. et al. *Science translational medicine* 5, 189ra176 (2013); Berns, K I et al. Fundamental Virology (ed B. N. Fields, and Knipe, D. M.) 545-562 (Raven Press, 1986).). Currently, the least restrictive and most commonly used Cas9 protein is from *S. pyogenes*, which recognizes the sequence NGG, and thus, the CRISPR targeting sequence is N20NGG. While numerous studies have shown that disease mutations can be efficiently targeted in vitro, the development of CRISPR-Cas9-based therapeutics for in vivo use is been hampered by safety concerns and delivery constraints.

While CRISPR targeting of disease mutations has been shown to be effective in numerous in vitro settings, and as well in vivo through mouse and other animal studies, all current approaches are still far from clinical use due in large part to delivery constraints. AAV vectors are the most frequently and successfully used viral vectors in ocular gene therapy injection (Swiech, L. et al. *Nature biotechnology* 33, 102-106 (2015); Jinek, M. et al. *Science* 337, 816-821 (2012); Cong, L. et al. *Science* 339, 819-823 (2013); Mali, P. et al. *Science* 339, 823-826 (2013)). Several features make AAV the most attractive choice: the virus is nonpathogenic, it infects both dividing and non-dividing cells, expression can persist for long periods of time, and it is particularly noteworthy for its history of safety, efficacy and a general lack of toxicity in clinical trials. Additionally, specific AAV serotypes are effective in targeting photoreceptor cells after subretinal injection. While AAV vectors provide a safe means of delivering therapeutic CRISPR components, there is one major technical obstacle that limits their utility—their size. Wild type AAV genomes are ~4.7 kb in length and recombinant viruses can package up to ~5.2 kb (Mancuso, K. et al. *Nature* 461, 784-787 (2009); Beltran, W A et al. *Proceedings of the National Academy of Sciences of the United States of America* 109, 2132-2137 (2012)). This packaging capacity defines the upper limit of the DNA that can be used for a single viral vector.

The DNA required to express Cas9 and the gRNA, by conventional methods, exceeds 5.2 kb: Pol II promoter (~0.5 kb), SpCas9 (~4.1 kb), Pol II terminator (~0.2 kb), U6 promoter (~0.3 kb), and the gRNA (~0.1 kb). One approach to AAV delivery challenge is a two-vector approach: one AAV vector to deliver the Cas9, and another AAV vector for the gRNA (Petrs-Silva, H. et al. *Molecular therapy: the journal of the American Society of Gene Therapy* 19, 293-301 (2011)). However, the double AAV approach utilizes the small mouse Mecp2 promoter, a gene that has been found to be expressed in retinal cells—with the critical exception of rods (Song, C. et al. *Epigenetics & chromatin* 7, 17 (2014); Jain, D. et al. *Pediatric neurology* 43, 35-40 (2010))—suggesting that, aside from the potential toxicity due to increased viral delivery load, the co-delivery approach would likely fail to target the vast majority of LCA mutations a priori. While this is a potentially viable approach for other gene therapy-mediated genomic editing, provided herein is a single vector approach for retinal gene editing that should increase efficiency, target photoreceptors specifically, and reduce potential toxicity from viral load delivery.

It was recently reported that use of the H1 promoter, rather than the more traditionally used U6 promoter, to direct gRNA transcription allows an approximate doubling of the available CRISPR gene targeting space (Ranganathan, V et al. *Nature communications* 5, 4516 (2014)). Notably, it was also detected a lower propensity for off-target cutting suggesting that the H1 promoter would be more favorable for therapeutic approaches. During these studies, it was noticed the presence of a protein coding gene (PARP-2) in close genomic proximity to the endogenous H1RNA gene (Baer, M. et al. *Nucleic acids research* 18, 97-103 (1990); Myslinski, E. et al. *Nucleic acids research* 29, 2502-2509 (2001); Ame J C et al. *J Biol Chem.* 276(14):11092-9 (2001)). The sequence between the start of the H1RNA (a pol III RNA transcript) and the PARP-2 gene (a pol II transcript) is 230 bp (FIG. 2), indicating that this relatively small sequence can function as a compact bidirectional promoter. It was hypothesized that these fortuitous properties of the H1 promoter might overcome the size hurdles of packaging both CRISPR components into a single AAV.

A. Enhancing H1 Bidirectional Pol II Expression Using 5'UTR Modifications.

Figures 1A, 1B:
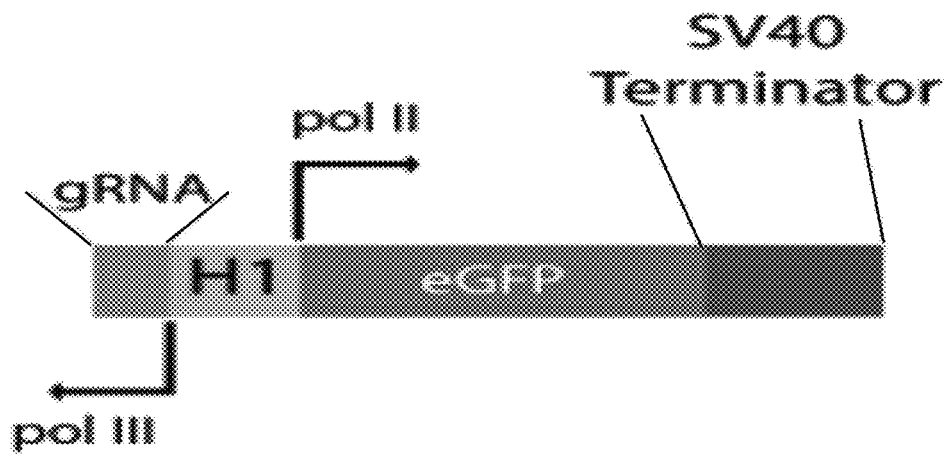
Figures 1C, 1D:
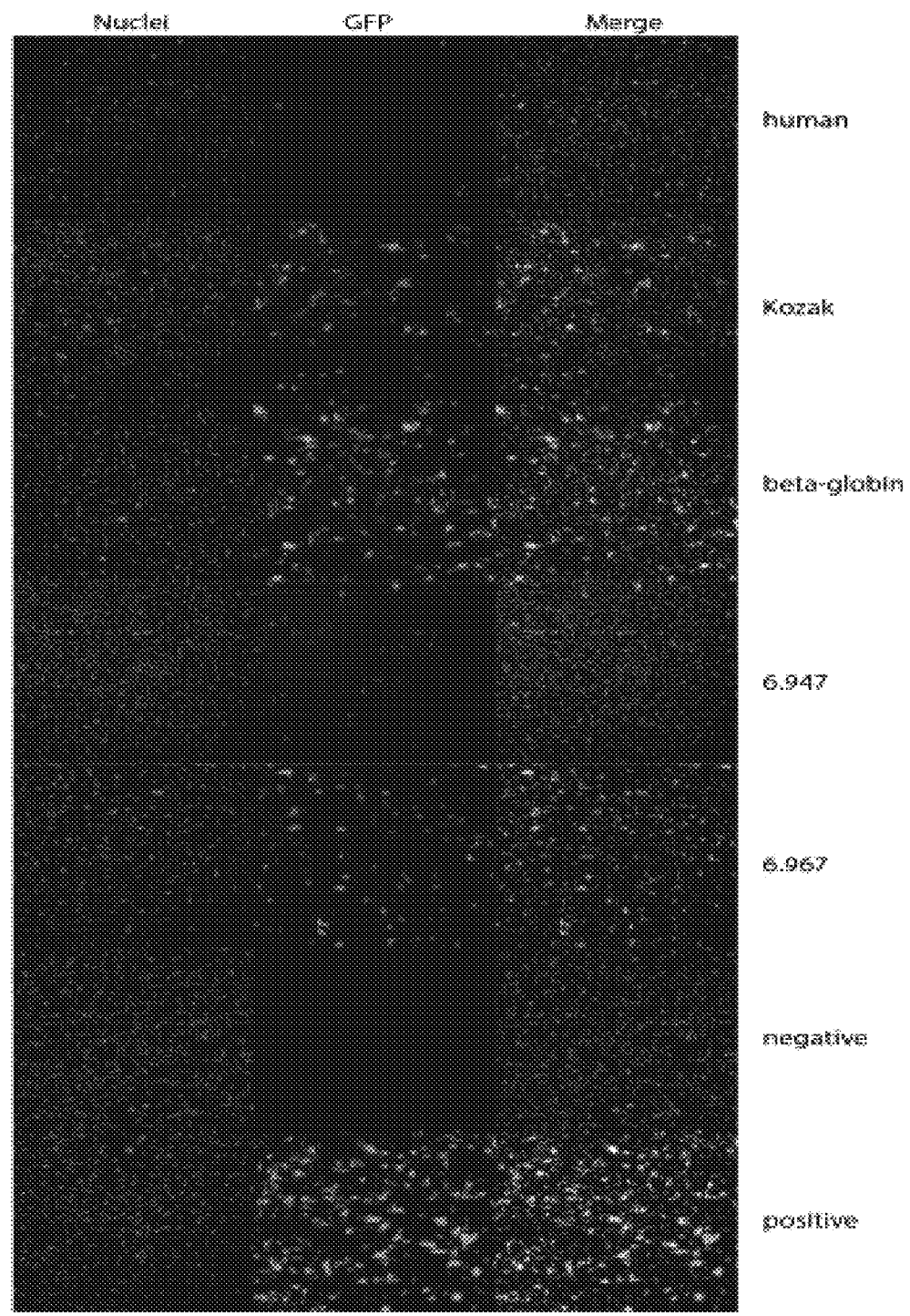
Figure 1E:
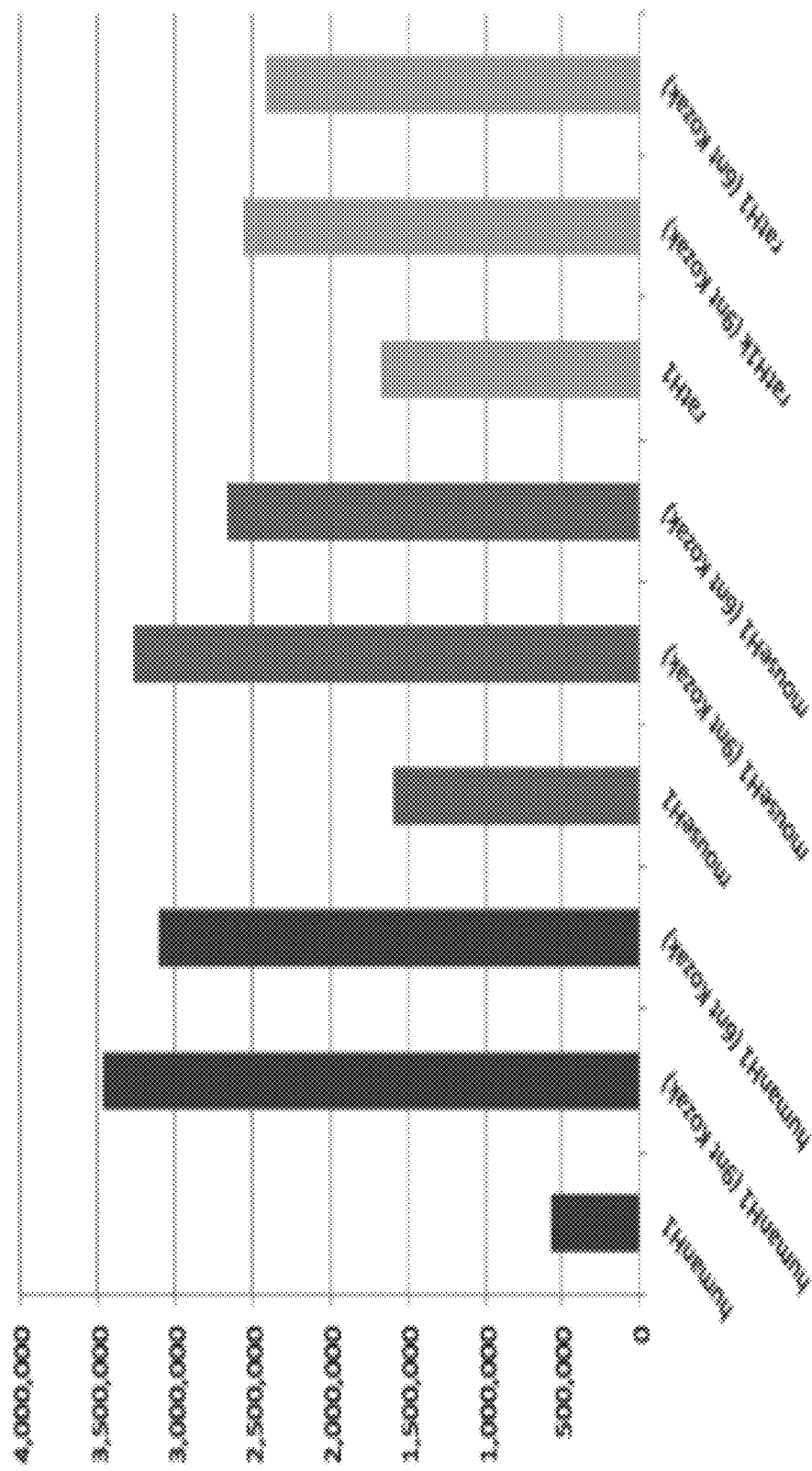
Figure 1F:
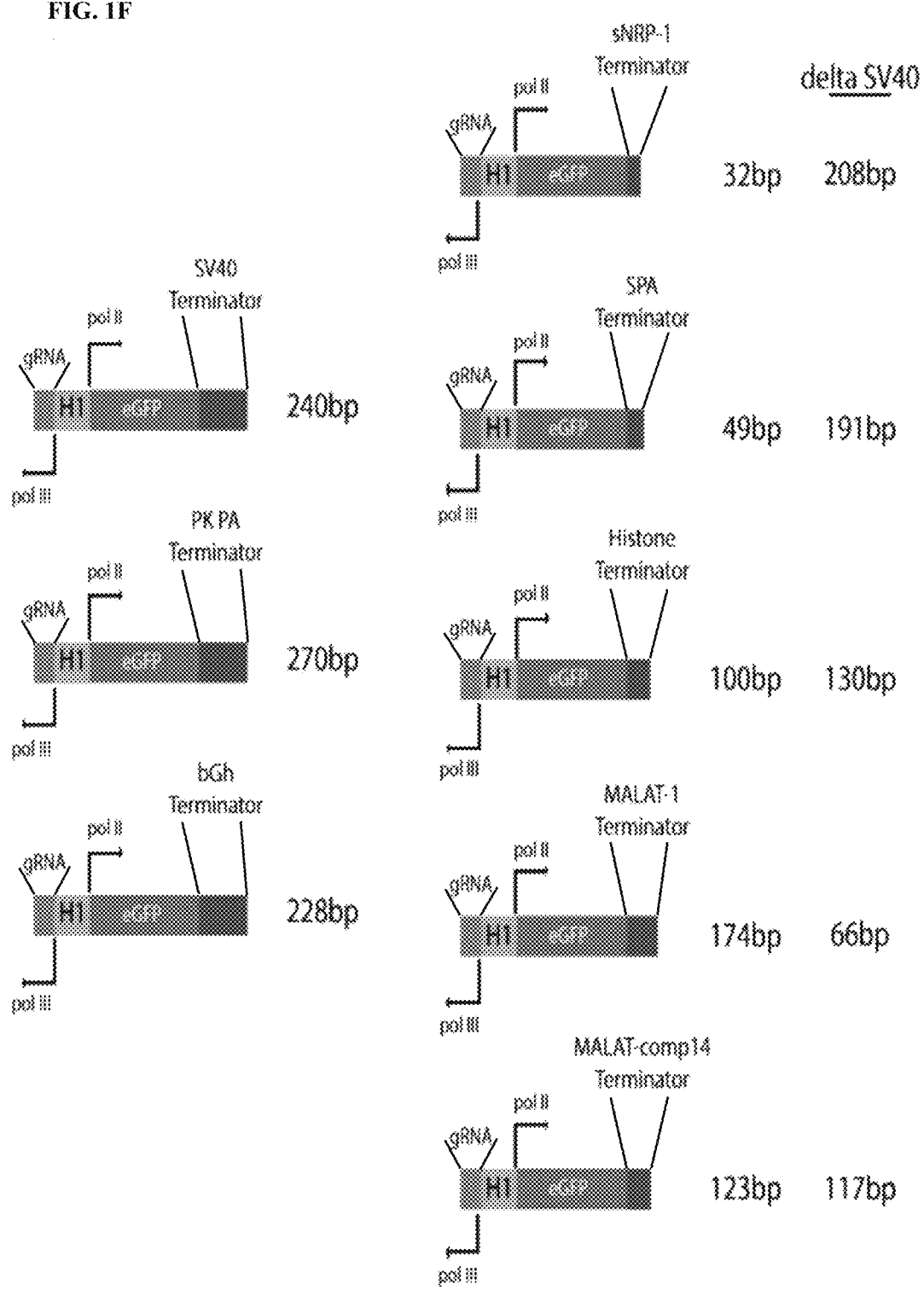

To develop H1 as a bidirectional pol II/III promoter, and because the polI III activity is already well characterized, an eGFP reporter construct was created to better optimize its pol II activity (FIG. 1A). Human (HEK293) and mouse cells (NIH3T3) demonstrated a weak, but clearly detectable GFP fluorescence, indicating that the H1 promoter could direct pol II expression. Using this GFP reporter system, experiments were performed to increase pol II expression while maintaining compactness by evaluating the three variable components in the system: (a) the promoter sequence, (b) the 5'UTR, and (c) the terminator sequence.

To evaluate different terminator sequences, seven different sequences were tested. It was found that the SV40 (240 bp and 120 bp) terminators and a 49 bp synthetic poly(A) sequence (SPA) were both functional for GFP expression, expression, although the SPA sequence did not work as well.

It was explored whether optimizing translation efficiency through modification of the 5'UTR would improve reporter expression. It was found that insertion of a 50 bp sequence taken from the beta-globin 5'UTR sequence was able to significantly improve reporter expression, and consistent with this notion, the simple insertion of 9 bases encoding a strong Kozak sequence (5'-GCCGCCACC-3' SEQ ID NO: 1) was sufficient to approximate these levels.

Also, using sequences identified as RNA sequences that mediate cap-independent initiation of translation (Wellensiek et al. *Nature Methods* 10, 747-750 (2013)) were also effective (6.947, and 6.967).

Focusing on the Kozak sequence, it was found that both a strong 9-base consensus (5'-GCCGCCACC-3' SEQ ID NO: 1) or a smaller 6-base consensus (5'-GCCACC-3' SEQ ID NO: 2) could enhanced GFP expression (FIG. 1). The 9-base sequence was slightly better consistently across different H1 bidirectional sequences.

B. Modulating Bidirectional Expression Through Use of Different Orthologous Sequences.

Testing H1 promoter sequences from different organisms indicated that both mouse (176 bp) and rat (207 bp) sequences were able to drive stronger GFP expression than the human H1 promoter (~7 and ~6-fold higher, respectively). This result is contrary to that reported in other studies, for example Hung et al. (2006) *Biochemical and Biophysical Research Communication* 339:1035-1042, which reported that the human sequence was expressed at higher levels.

Genomic alignments were performed from the orthologous region of 36 eutherian mammals using the H1 promoter sequence. These provide additional sequences (SEQ ID NOs: 84-119) that can be used to fine-tune bidirectional expression.

C. Novel Compact Bidirectional Promoter Sequences with Both Pol II and Pol III Activity After identifying that the H1 bidirectional promoter sequence could effectively direct the expression of both pol II and pol III genes, the genome for other potentially compact bidirectional sequences were searched.

A custom perl script was developed to compare the 5' transcriptional start sites of pol III genes with that of pol II genes. The results were filtered for those that are orientated in opposite directions (divergent transcription). The input files could be annotated genome files or transcriptional data (pol II or pol III ChIP sites). Some ChIP sites that were identified from the human genome include, but not limited to:

ALOXE3-tRNA(lys):
TCTTTCCGCTCCAGGACCGCCCTGGGCCTGCAGGATCCTGGGCGGGAGCC

CAGGTGTCCGGGATCTGGGCCACTAGGGACTGGGGAGGAACCTCTCAGAG

AAGCCCATAGCCCGCAGCGGCCCCGCGCGGCCGGTTCCGGCGCCGCACTG

TTCCAGCCTCTACTATGGTACAGTCCCTGCGTCGCAGCCTCGGCGGGGGC

TCTAAGAACGGGAGGCAGAAAAAGCTCAATCAGCAGCAGGCGAGCTTCAC

CCGCTGCTTCCAAATCTGTGCCAAAATATTCTATGCTGCACAGATAAAAT

CCTCTGTCGGTTCTACAAGCCTGGCTTTTCCTATAGAGAACCCTCTTATA

AGCAAAAAGTAAAGCTCTCGTGAAGA;

C8orf41-SNORD13:
TCCTGACTGCAGCACCAGAAGGCTGGTCTCTCCCACAGAACGAGGATGGA

GGCGGGGAGGGATCCGTTGAAGAGGGAAGGAGCGATCACCCAAAGAGAAC

TAAAATCAAATAAAATAAAACAGAGAGATGTCTTGGAGGAGGGGCGAGT

CTGACCGGGATAAGAATAAAGAGAAAGGGTGAACCCGGGAGGCGGAGTTT

GCAGTGAGCCGAGATCGCGCCACTGCACTCCAGCCTGGGCGACAGAGTGA

GACTCCGTCTCAGTAAAAAAAAAAAAAAAAAAAAGAATAAAGAGGAAAGG

ACGCAAGAAAGGGAAAGGGGACTCTCAGGGAGTAAAAGAGTCTTACACTT

TTAACAGTGACGTTAAAAGACTACTGTTGCCTTTCTGAAGACTAAAAAGA

AAAAAAACTTAAAAATTTAAAGAAATAAACTTCTGAGCCATGTCACCAAC

TTAACCACCCCCAGGTACCTGCAACGGCTCGCGCCCGCCGGTGTCTAACA

GGATCCGGACCTAGCTCATATTGCTGCCGCAAAACGCAAGGCTAGCTTCC

GCCAGTACTGCCGCAACACCTTCTTATTTCACGACGTATGGTCGTAAAGC

AATAAAGATCCAGGCTCGGGAAAATGACGGAGAGGTGGAACTATAGAGAA

TAAATTTGCATATATAATAATCCGCTCGCTAATTGTGTTTCTGTTTTCCT

TTGCTAAGGTAGAAACAAAAGAATAATCACAGAATCTCAGTGGGACTTTG

AAAATATCCAGGATTTTATACGTGAAGAATGGATGTATCGCATTACGGTA

GTCACCCTATGTGTAAATTAGTGGCACATACTTGGCACTCCTTAATGTCA

ACTATAAGATG;

CGB1:
GTCTCTCTCTTAGCGGGATATCTTCCGCAAGCACTGGGAATGTGGACATG

GAAAGTAAATTGAGTCTCCGTGGGGGAGTGAGACAGGGAGTGAGGGGTGT

TGGACGCGGCACGGGAACCTGGCCAGAGTCAGCGGACCCAATTGGCTGCT

CTCTCTCAGATGCAGTTCCCCTTCCTCCCTCCAGGGGGCGCCACGGAACG

CAGGGCCCTCACTGGCCCTGGGGACTGGGTGACGTCAGGGATGAGCCTCT

TGTGATTGGCTCCATCACCCTGCGTAAGATCAAAGGGAAGAAAGGATGGG

CCCGACAA;

CGB2:
GTCTCTCTCTTAGCGGGATATCTTCCGCAAGCACTGGGGATGTGGACATG

GAAAGTAAATTGAGTCTCCGTGGGGGAGTGAGACAGGGAGTGAGGGGTGT

TGGACGCGGCACGGGAACCCGGCCGGAGTCAGCGGACCCAATTGGCTGCT

```
-continued
CTCTCTCAGATACAGTTCCCCTTCCTCCCTCCAGGGGGCGCCACGGAACG

CAGGGCCCTCACTGGCCCTGGGGACTGGGTGACGTCAGGGGTGAGCCTCT

CCTGATTGGCTCCATCACCCTGCGTAAGGTCAAAAGGAAGAAAGGAGATC

CCCGACAC;

DPP9-tRNA(gly):
TAACCGCTCAGCTGACCTCAGGAGGGCAGGGGTGCCTTCTAAAGGGTCCA

GAGAGCCTCCATTCCAGCTGCAGGCGTGGGACACAGACCGGGACGTGGGG

CGGCGGCCGGACTGGGCAGGTCGTCCCGGGTCCAGCGGCGCCTCACGGTC

GCGGCTCCATGCCCGGGACTGCGACCCCGGAAGTGGCGGGAGCGGGGGAC

GACAGCCGCGGCGGACACAGGGGACCCGCCGGCTCAGGCACCTTTGACCC

GGAAGTTGAGCGACCCAGGCGGCGGCCTGGGATTGGACACCACCAGGCAC

GTACCAAGGCGTCCGCGGCGCTTGGGGGGAGCCCGCGGCGCGGCGGCCT

AAGGTGCGTAACGCCCCATGAACGACATCTTCCGGTGGGTTAGGGAGAGA

CACCCCCCTGTGACTTGGTATCACTCAGTCAAACCCATGATCCCCCACTA

TTAAGGATATCCGGAGAGGATGCTACCTATCAGG;

MED16-RNU6-9:
GAGGGCAGTCACCAGCTCCTGGCCCGTGCGCCAAGCTCAGCGGGCGTCCG

CGGTGCGATCTTCCCTAGCGCCTCGGGTCTGGCGCCGCCATCTTCCTCGG

TAACAACCAGTCGCCTGAGGCGTGGGGCCGCCTCCCAAAGACTTCTGGGA

GGGCGGTGCGGCTCAGGCTCTGCCCCGCCTCCGGGGCTATTTGCATACGA

CCAT
```

To validate this, the 7sk bidirectional promoter, or the region between the GSTA4 gene (pol II gene) and the RN7SK gene (pol III gene) were tested using our GFP reporter assay. The pol III activity of this promoter is well-documented.

Several variants of the 5' UTR were simultaneously tested; endogenously, the annotated 5'UTR for the human GSTA4 gene is split by an intron, which were fused when cloning into our reporter system (7sk1). A shortened form of the 5'UTR or the betaglobin 5'UTR was also tested (7sk3). All of the constructs used incorporated the strong 9-base Kozak consensus sequence (5'-GCCGCCACC-3' SEQ ID NO: 1) (7sk2).

The reporter assay indicated this region was able to direct pol II expression, confirming the ability to act as a bidirectional promoter region. Although this region is slightly larger than the H1 bidirectional promoter region, it was found to be more active.

The ability of orthologous sequences to direct expression was tested. The mouse sequence was also active, and slightly stronger than the human sequence.

These results confirmed the presence of bidirectional promoters with both pol II and pol III activity, and the ability to search genomic sequences for these regions.

D. An Expression Screen for Bidirectional Promoters with Both RNA Pol II and RNA Pol III Activity.
Bioinformatics:

Bidirectional promoter sequences could be used as starting points for the identification of different variants of pol II/pol III activity. A custom perl script was developed to compare the 5' transcriptional start sites of pol III genes with that of pol II genes. The results were filtered for those that are orientated in opposite directions (divergent transcription). The input files could be annotated genome files or transcriptional data (pol II or pol III ChIP sites). Using this information, bidirectional promoters were identified with both RNA pol II and RNA pol III activity. These sequences could be used to generated derivative sequences Targeted Transcription Factor Binding Sites:

Promoter sequences could be used to identify transcription binding sites, or multiple promoter sequences could be aligned to identify transcription factor binding sites which could in turn be used to design a bidirectional promoter. Identification of transcription binding factor sites could be determined by consensus, or by using a differential distance matrix or multidimensional scaling (De Bleser P et al. *Genome Biol.* 2007; 8(5):R83.).

Random Sequence Library:

Alternatively, a synthetic library of random sequences could be used as a starting point to screen for sequences with bidirectional activity. By randomizing, shuffling, or mutating the bidirectional sequence, one can search for DNA sequences that have different pol II or pol III promoter activity.

Screens could be set up using qPCR or fluorescence to read-out pol II and pol III activity. A simple fluorescence screen would use a reporter (GFP, mCherry, etc.) as described, and an RNA aptamer, such as Broccoli that becomes fluorescent in the presence of a small molecule like DFHB1-1T. The screen could use protein readouts such as drug resistance (e.g. antibiotics), antigenic peptides, or cell-surface markers, etc.

Alternative reporters could be function complexes that are comprised of both protein and RNA. For example, the MS2 coat protein binding stem loop could be incorporated into the RNA and the pol II transcription could encode the MS2 coat protein which would in turn bind the RNA sequence. If two binding sites are incorporated into the RNA, then fluorescence complementarity (split protein complementarity) could be used as a readout.

Screens can also be performed by separating and assessing the pol II activity and then the pol III activity. Finally, these sequences could then be combined in a fashion that allows for divergent transcription by both RNA pol II or RNA pol III.

Methods

Plasmid construction: The GFP reporter plasmids were constructed by Gibson Assembly (New England Biolabs, Ipswich, Mass.) (Gibson et al. (2009) *Nature* Methods 6:343-345) with slight modifications.

Human embryonic kidney (HEK) cell line 293T (Life Technologies, Grand Island, N.Y.) was maintained at 37° C. with 5% $CO_2$/20% $O_2$ in Dulbecco's modified Eagle's Medium (DMEM) (Invitrogen) supplemented with 10% fetal bovine serum (heat-inactivated) (Gibco, Life Technologies, Grand Island, N.Y.) and 2 mM GlutaMAX (Invitrogen).

N2A cell line (Life Technologies, Grand Island, N.Y.) was maintained at 37° C. with 5% $CO_2$/20% $O_2$ in Dulbecco's modified Eagle's Medium (DMEM) (Invitrogen) supplemented with 10% fetal bovine serum (Gibco, Life Technologies, Grand Island, N.Y.) and 2 mM GlutaMAX (Invitrogen).

Cells were transfected (Lipofectamine 3000) with each construct. GFP expression was analyzed using flow cytometry.

```
Human 7sk1 (GSTA4 5'UTR with Kozak):
                                             (SEQ ID NO: 3)
GGTGGCGGCGATAGCTTTTCAGGCTTTCTGGAGTCCACTCGGAGGCCTGG

AGCCGCACAAAGCGCCAGGTCAGCGGTCCCGGCTGGGTGAGACCAGCAGG

CGGCTCTAGCGCGCGGGAGCTGGGCGAGGCTCCGGGACGACCTCACCAAT
```

```
GGAGACTGCAGTATTTAGCATGCCCCACCCATCTGCAAGGCATTCTGGAT

AGTGTCAAAACAGCCGGAAATCAAGTCCGTTTATCTCAAACTTTAGCATT

TTGGGAATAAATGATATTTGCTATGCTGGTTAAATTAGATTTTAGTTAAA

TTTCCTGCTGAAGCTCTAGTACGATAAGCAACTTGACCTAAGTGTAAAGT

TGAGACTTCCTTCAGGTTTATATAGCTTGTGCGCCGCTT GGGTACCTC

Human 7sk2 (short 5' UTR):
                                          (SEQ ID NO: 4)
GGTGGCGGCAGTATTTAGCATGCCCCACCCATCTGCAAGGCATTCTGGAT

AGTGTCAAAACAGCCGGAAATCAAGTCCGTTTATCTCAAACTTTAGCATT

TTGGGAATAAATGATATTTGCTATGCTGGTTAAATTAGATTTTAGTTAAA

TTTCCTGCTGAAGCTCTAGTACGATAAGCAACTTGACCTAAGTGTAAAGT

TGAGACTTCCTTCAGGTTTATATAGCT TGTGCGCCGCTTGGGTACCTC

Human 7sk3 (beta-globin 5' UTR):
                                          (SEQ ID NO: 5)
GGTGTCTGTTTGAGGTTGCTAGTGAACACAGTTGTGTCAGAAGCAAATGT

AGTATTTAGCATGCCCCACCCATCTGCAAGGCATTCTGGATAGTGTCAAA

ACAGCCGGAAATCAAGTCCGTTTATCTCAAACTTTAGCATTTTGGGAATA

AATGATATTTGCTATGCTGGTTAAATTAGATTTTAGTTAAATTTCCTGCT

GAAGCTCTAGTACGATAAGCAACTTGACCTAAGTGTAAAGTTGAGACTTC

CTTCAGGTTTATATAGCTTGTGCGCCGCTGG GTACCTC

Mouse 7sk1 (GSTA4 5'UTR with Kozak):
                                          (SEQ ID NO: 6)
GGTGGCGGCCTCGTATGGGACCGCACCGGACACGGGCGCCTGGGCCAGGA

GCAGAGCCGGCCGTAGAATAGACATGGCCGTCGGGGCGGGGCTTCGGA

AGGTTTAACCAATCCAAACTGTTGTATTTTGCATAGCCCCAAAGCATTTT

GGTTAACAGTAAAAACATCCTAAATTTAAGTATTTTAATTTAAACTTAGA

ACGAAGCGAGTATAAAAGGATTATTTAACCCTAAAACGGATTCAGGATT

TGTTATAATATCAAGTACAGTCGGCTACATAAGGTCACCACATGTGTAAA

GTTACAAAATTCTATGGCCTTATATACCTACCAAGA GCCTGCTTACTCT

C

Mouse 7sk2 (short 5' UTR):
                                          (SEQ ID NO: 7)
GGTGGCGGCAGACATGGCCGTCGGGGCGGGGCTTCGGAAGGTTTAACCA

ATCCAAACTGTTGTATTTTGCATAGCCCCAAAGCATTTTGGTTAACAGTA

AAAACATCCTAAATTTAAGTATTTTAATTTAAACTTAGAACGAAGCGAGT

ATAAAAGGATTATTTAACCCTAAAACGGATTCAGGATTTGTTATAATAT

CAAGTACAGTCGGCTACATAAGGTCACCACATGTGTAAAGTTACAAAATT

CTATGGCCTTATATACCTACCAAGAGCCTGCTT ACTCTC

Mouse 7sk3 (beta-globin 5' UTR):
                                          (SEQ ID NO: 8)
GGTGTCTGTTTGAGGTTGCTAGTGAACACAGTTGTGTCAGAAGCAAATGT

AGACATGGCCGTCGGGGCGGGGCTTCGGAAGGTTTAACCAATCCAAACT

GTTGTATTTTGCATAGCCCCAAAGCATTTTGGTTAACAGTAAAAACATCC

TAAATTTAAGTATTTTAATTTAAACTTAGAACGAAGCGAGTATAAAAGG

ATTATTTAACCCTAAAACGGATTCAGGATTTGTTATAATATCAAGTACAG

TCGGCTACATAAGGTCACCACATGTGTAAAGTTACAAAATTCTATGGCCT

TATATACCTACCAAGAGCCTGCTTACTCTC
```

1. Dryja, T P et al. *The New England Journal of Medicine* 323, 1302-1307 (1990).
2. Dryja, T P et al. *Nature* 343, 364-366 (1990).
3. Doudna, J A et al. *Science* 346, 1258096 (2014).
4. Hsu, P D et al. *Cell* 157, 1262-1278 (2014).
5. Liang, Y. et al. *The Journal of Biological Chemistry* 279, 48189-48196 (2004).
6. Dalkara, D. & Sahel, J. A. *Comptes Rendus Biologies* 337, 185-192 (2014).
7. Day, T P. et al. *Advances in Experimental Medicine and Biology* 801, 687-693 (2014).
8. Willett, K. & Bennett, *Frontiers in immunology* 4, 261, (2013).
9. Dinculescu, A. et al. *Human Gene Therapy* 16, 649-663 (2005).
10. Kotterman, M A et al. *Gene Therapy* 22, 116-126 (2015).
11. Mowat, F M et al. *Gene Therapy* 21, 96-105 (2014).
12. Dalkara, D. et al. *Science Translational Medicine* 5, 189ra176 (2013).
13. Berns, K I et al. *Fundamental Virology* (ed B. N. Fields, and Knipe, D. M.) 545-562 (Raven Press, 1986).
14. Swiech, L. et al. *Nature Biotechnology* 33, 102-106 (2015).
15. Jinek, M. et al. *Science* 337, 816-821 (2012).
16. Cong, L. et al. *Science* 339, 819-823 (2013).
17. Mali, P. et al. *Science* 339, 823-826 (2013).
18. Mancuso, K. et al. *Nature* 461, 784-787 (2009).
19. Beltran, W A et al. *Proceedings of the National Academy of Sciences of the United States of America* 109, 2132-2137 (2012).
20. Petrs-Silva, H. et al. *Molecular therapy: The Journal of the American Society of Gene Therapy* 19, 293-301 (2011).
21. Song, C. et al. *Epigenetics & Chromatin* 7, 17 (2014).
22. Jain, D. et al. *Pediatric Neurology* 43, 35-40 (2010).
23. Ranganathan, V et al. *Nature Communications* 5, 4516 (2014).
24. Baer, M. et al. *Nucleic Acids Research* 18, 97-103 (1990).
25. Myslinski, E. et al. *Nucleic Acids Research* 29, 2502-2509 (2001).
26. Ame J C et al. *J Biol Chem.* 276(14):11092-9 (2001).

Example 2

Conditional pol II/pol III bidirectional promoter expression for regulating ribonucleoprotein enzymatic activity or RNA-directed nucleases Previous work has demonstrated that the pol III activity of the H1 promoter can engineered into a tet-responsive promoter and can be regulated by tetracycline. In the presence of the Tet repressor (TetR), the Tet operator (TetO) sequences engineered into the H1 promoter are bound by TetR and repress pol III expression.

This system has not been previously combined with the bidirectional component of the H1 promoter, a system that could allow for regulation of pol II and pol III transcripts. Ribonucleoprotein enzymes or RNA-directed nucleases, could be regulated by tetracycline using an engineered bidirectional promoter system.

Here, it was shown that the pol II activity of H1 was not drastically altered by the presence of TetO operator sites. This provides a mechanism for the inducible activity of ribonucleoprotein enzymes or RNA-directed nucleases, such as Cas9/gRNA. Additionally, placement of the TetO sites could be placed as to specifically repress either the pol II or pol III transcripts, or both.

Such a system would have tremendous clinical advantages for regulating CRISPR activity delivered by AAV viruses and could be used to other compact bidirectional promoters.

1. Matthess et al. *Oncogene*. 2005 Apr. 21; 24(18):2973-80.

Methods

Plasmid construction: The GFP reporter plasmids were constructed by Gibson Assembly (New England Biolabs, Ipswich, Mass.) (Gibson et al. (2009) *Nature* Methods 6:343-345) with slight modifications.

Human embryonic kidney (HEK) cell line 293T (Life Technologies, Grand Island, N.Y.) was maintained at 37° C. with 5% CO$_2$/20% O$_2$ in Dulbecco's modified Eagle's Medium (DMEM) (Invitrogen) supplemented with 10% fetal bovine serum (heat-inactivated) (Gibco, Life Technologies, Grand Island, N.Y.) and 2 mM GlutaMAX (Invitrogen).

N2A cell line (Life Technologies, Grand Island, N.Y.) was maintained at 37° C. with 5% CO$_2$/20% O$_2$ in Dulbecco's modified Eagle's Medium (DMEM) (Invitrogen) supplemented with 10% fetal bovine serum (Gibco, Life Technologies, Grand Island, N.Y.) and 2 mM GlutaMAX (Invitrogen).

Cells were transfected (Lipofectamine 3000) with each construct. GFP expression was analyzed using flow cytometry.

```
mm079 target sequence:
                                  (SEQ ID NO: 9)
GAAGAAGGTTCGAGATCTCA mm079 genomic target site:
                                  (SEQ ID NO: 10)
GAAGAAGGTTCGAGATCTCAAGG TetO site:
                                  (SEQ ID NO: 11)
TCCCTATCAGTGATAGAGA H1_wt:
                                  (SEQ ID NO: 12)
GGAATTCGAACGCTGACGTCATCAACCCGCTCCAAGGAATCGCGGGCCCA

GTGTCACTAGGCGGGAACACCCAGCGCGCGTGCGCCCTGGCAGGAAGATG

GCTGTGAGGGACAGGGGAGTGGCGCCCTGCAATATTTGCATGTCGCTATG

TGTTCTGGGAAATCACCATAAACGTGAAATGTCTTTGGATTTGGGAATCT

TATAAGTTCTGTATGAGACCACTTTTTCCC

H1_TetO:
                                  (SEQ ID NO: 13)
GGAATTCGAACGCTGACGTCATCAACCCGCTCCAAGGAATCGCGGGCCCA

GTGTCACTAGGCGGGAACACCCAGCGCGCGTGCGCCCTGGCAGGAAGATG

GCTGTGAGGGACAGGGGAGTGGCGCCCTGCAATATTTGCATGTCGCTATG

TGTTCTGGGAAATCACCATAAACGTGAAATCCCTATCAGTGATAGAGACT

TATAAGTTCCCTATCAGTGATAGAGATCCC

TetR sequence:
                                  (SEQ ID NO: 14)
MSRLDKSKVINSALELLNEVGIEGLTTRKLAQKLGVEQPTLYWHVKNKRA

LLDALAIEMLDRHHTHFCPLEGESWQDFLRNNAKSFRCALLSHRDGAKVH
```

-continued
```
LGTRPTEKQYETLENQLAFLCQQGFSLENALYALSAVGHFTLGCVLEDQE

HQVAKEERETPTTDSMPPLLRQAIELFDHQGAEPAFLFGLELIICGLEKQ

LKCESGSAYSGSREF
```

Example 3

A. Regulation of Genome-Engineering Nucleases Through Post-Transcriptional Cell-Cycle Regulation The advent of new RNA-directed nucleases has revolutionized genome-editing technology and transformed biological research. These technologies, while providing an unprecedented means to modify genomes with precision, are constrained by cellular processes that modulate how DNA breaks are repaired. For genome-engineering applications, in particular, the ability to modulate a cells response to DNA breaks has enormous consequences. (see Gutschner et. al. (2016) Cell Reports).

Cellular response to DNA breaks occurs primarily through one of two competing pathways: nonhomologous end-joining (NHEJ), or Homology Directed Repair (HDR). NHEJ is generally considered to be an error-prone pathway which results sequence changes around the break point. In general, NHEJ is the more efficient or dominant pathway for DNA repair. On the other hand, HDR pathways are far less error-prone, but require stretches of homology to template and repair. Both pathways have properties that are favorable for different outcomes. For example, if one wishes to "knock-out" a gene, NHEJ is the preferable pathway, as DNA breaks in that gene will largely result in sequence changes. In the laboratory, many genetic screens are dependent on eliminating gene function, and for therapeutic approaches, complete disruption of a gene with a dominant or gain-of-function mutation would be highly desirable. However, if one wishes to introduce a specific sequence change ("knock-in"), one would try to favor repair though a HDR pathway thus allowing for precise cut and paste outcomes. For many scientific applications and most clinical applications this pathway is favorable, as it can allow for precise mutation repair.

It is also known that cellular response to DNA breaks is modulated by the cell-cycle (FIG. 9A); the phase of the cell-cycle largely dictates the choice of DNA pathway (FIG. 9B). NHEJ predominates through G1 of the cell-cycle, while HDR predominates during S and G2 phases. Thus, the ability to modulate the timing of DNA breaks with respect to the cell-cycle, can be a powerful method to bias the cell towards a specific repair pathway.

Many proteins are regulated in cell-cycle-dependent fashion, largely through transcriptional regulation and post-transcriptional mechanisms, notably ubiquitin-mediated proteolysis. Generally, regulation through transcriptional mechanisms are slower, while proteolytic mechanisms are rapid. For genome-editing applications, proteolytic mechanisms likely offer a more favorable method of regulation.

Two well-characterized proteins with opposing, and thus oscillating, expression in the cell are Geminin (Gem) and Cdt1. Cdt1 accumulates in the G1 phase of the cell-cycle, while Gem accumulates during S/G2/M phases. The specific regions of these proteins that are required for cell-cycle regulation have been mapped: amino acids 30-120 for hCdt1, and amino acids 1-110 for hGem (Sakaue-Sawano A et al. Cell 132, 487-498 (2008)). Furthermore, proteins fused to these domains can be made to exhibit cell-cycle-dependent regulation, even if the respective mRNA is constantly being transcribed throughout the cell-cycle. In essence, cellular proteins only recognize the domain during specific phases of the cell-cycle, which results in ubiquitination and then rapid degradation of the fusion protein.

Here, it was shown that genome-editing technologies, such as RNA-directed nucleases, can be fused to either hGem of hCdt1 domains, resulting in cell-cycle dependent regulation of these proteins (FIG. 9C). Consequently, this regulation results in drastically different DNA repair outcomes. Using the CRISPR-Cas9 system, it was shown that either NHEJ and HDR pathways were enhanced or suppressed using Cas9 fused to either hGem or hCdt1. The system is so robust that it can increase the level of HDR to levels greater than NHEJ, which is highly significant considering that HDR is far less efficient in the cell.

Furthermore, the method described is tremendously powerful in its elegance and simplicity. Other attempts to regulate the outcome of genome-editing technologies, have utilized cumbersome methods of arresting cells in certain phases of the cell-cycle followed by technically challenging and inefficient methods of direct protein/RNA delivery. Instead, the method described here relies on simple delivery of a plasmid, mRNA, or protein encoding a fusion to the respective regulatory sequences.

Methods

Plasmid construction: To generate the cell-cycle regulated nucleases proteins, the human codon optimized Cas9 gene from a Cas9:T2A:GFP vector (Addgene 44719) was modified to replace the T2A with a better cleaving P2A sequence. Next the GFP fluorescent reporter was replace with the sequence encoding the mKate2 fluorescent protein. Next, the vector was linearized and gBlocks encoding a flexible 15 amino acid sequence linker fused to either the hGem(1-110) or hCdt1(30-120) domains were inserted in frame to generate Cas9:linker:hGem and Cas9:linker:hCdt1 (referred to as Cas9-Gem or Cas9-Cdt, respectively). All cloning steps were preformed using Gibson Assembly (New England Biolabs, Ipswich, Mass.) (Gibson et al. (2009) *Nature Methods* 6:343-345) with slight modifications.

Human embryonic kidney (HEK) cell line 293T (Life Technologies, Grand Island, N.Y.) was maintained at 37° C. with 5% $CO_2$/20% $O_2$ in Dulbecco's modified Eagle's Medium (DMEM) (Invitrogen) supplemented with 10% fetal bovine serum (Gibco, Life Technologies, Grand Island, N.Y.) and 2 mM GlutaMAX (Invitrogen).

A gRNA targeting Rhodopsin (hs086172175: AGTACTGTGGGTACTCGAAGGGG (SEQ ID NO: 68)) (see Jaskula-Ranga, V., & Zack, D. J. (2016). grID: A CRISPR-Cas9 guide RNA Database and Resource for Genome-Editing. *bioRxiv*, 097352) was generated by overlapping oligos that were annealed and amplified by PCR using two-step amplification Phusion Flash DNA polymerase (Thermo Fisher Scientific, Rockford, Ill.), and subsequently purified using Zymo DNA clean and concentrator columns. The purified PCR products were then resuspended in H2O and quantitated using a NanoDrop 1000 (Thermo Fisher Scientific). The gRNA-expressing constructs were generated using the Gibson Assembly (New England Biolabs, Ipswich, Mass.) (Gibson et al. *Nature Methods* 6:343-345 (2009)) with slight modifications. The total reaction volume was reduced from 20 µl to 2 µl.

HEK293 cells were co-transfected with Cas9 (unmodified, or cell-cycle regulated versions) and the gRNA construct targeting rhodopsin. 48 hrs post transfection, genomic DNA was harvested and the sequence surrounding the target cut sites were amplified according to the primers listed below. The PCR products were then purified and quantitated before performing the T7 Endo I assay. Briefly, 200 ng of PCR product was denatured and then slowly re-annealed to allow for the formation of heteroduplexes, T7 Endonuclease I was added to the PCR products and incubated at 37 C for 25 minutes to cleave heteroduplexes, the reaction was quenched in loading dye, and finally, the reaction was run on a 6% TBE PAGE gel to resolve the products. The gel was stained with SYBR-Gold, visualized, and quantitated using ImageJ. NHEJ frequencies were calculated using the binomial-derived equation:

$$1 - \sqrt{1 - \frac{(a+b)}{(a+b+c)}} \times 100;$$

where the values of "a" and "b" are equal to the integrated area of the cleaved fragments after background subtraction and "c" is equal to the integrated area of the uncleaved PCR product after background subtraction. To calculate HDR frequencies, the same PCR product as above, prior to heteroduplex formation, was mixed with EcoRI for 1 hr, then quenched in loading dye, and finally, the reaction was run on a 6% TBE PAGE gel to resolve the products.

HDR frequencies were calculated using the equation:

$$\% \ HDR = \frac{(a+b)}{(a+b+c)} * 100;$$

where the values of "a" and "b" are equal to the integrated area of the cleaved fragments after background subtraction and "c" is equal to the integrated area of the un-cleaved PCR product after background subtraction.

```
HDR oligo (EcoRI):
                                        (SEQ ID NO: 15)
CAGAAGGCCCTAACTTCTACGTGCCCTTCTCCAATGCGACGGGTGTGGTA

CGCAGCCCCTGAATTCACCCACAGTACTACCTGGCTGAGCCATGGCAGTT

CTCCATGCTGGCCGCCTACATGTTTC

T7EI primers:
Rho_HDR_F;
                                        (SEQ ID NO: 16)
TGGAGCCCTGAGTGGCTGAG Rho_HDR_R;
                                        (SEQ ID NO: 17)
CCACCTAGGACCATGAAGAGGTCAG Protein Sequences:
hCdt1(30-120)
                                        (SEQ ID NO: 18)
PSPARPALRAPASATSGSRKRARPPAAPGRDQARPPARRRLRLSVDEVSS

PSTPEAPDIPACPSPGQKIKKSTPAAGQPPHLTSAQDQDTI hGem (1-110)
                                        (SEQ ID NO: 19)
MNPSMKQKQEEIKENIKNSSVPRRTLKMIQPSASGSLVGRENELSAGLSK

RKHRNDHLTSTTSSPGVIVPESSENKNLGGVTQESFDLMIKENPSSQYWK

EVAEKRRKAL

Cas9:linker:hCdt1
                                        (SEQ ID NO: 20)
MDKKYSIGLDIGTNSVGWAVITDEYKVPSKKFKVLGNTDRHSIKKNLIGA

LLFDSGETAEATRLKRTARRRYTRRKNRICYLQEIFSNEMAKVDDSFFHR
```

-continued

LEESFLVEEDKKHERHPIFGNIVDEVAYHEKYPTIYHLRKKLVDSTDKAD
LRLIYLALAHMIKFRGHFLIEGDLNPDNSDVDKLFIQLVQTYNQLFEENP
INASGVDAKAILSARLSKSRRLENLIAQLPGEKKNGLFGNLIALSLGLTP
NFKSNFDLAEDAKLQLSKDTYDDDLDNLLAQIGDQYADLFLAAKNLSDAI
LLSDILRVNTEITKAPLSASMIKRYDEHHQDLTLLKALVRQQLPEKYKEI
FFDQSKNGYAGYIDGGASQEEFYKFIKPILEKMDGTEELLVKLNREDLLR
KQRTFDNGSIPHQIHLGELHAILRRQEDFYPFLKDNREKIEKILTFRIPY
YVGPLARGNSRFAWMTRKSEETITPWNFEEVVDKGASAQSFIERMTNFDK
NLPNEKVLPKHSLLYEYFTVYNELTKVKYVTEGMRKPAFLSGEQKKAIVD
LLFKTNRKVTVKQLKEDYFKKIECFDSVEISGVEDRFNASLGTYHDLLKI
IKDKDFLDNEENEDILEDIVLTLTLFEDREMIEERLKTYAHLFDDKVMKQ
LKRRRYTGWGRLSRKLINGIRDKQSGKTILDFLKSDGFANRNFMQLIHDD
SLTFKEDIQKAQVSGQGDSLHEHIANLAGSPAIKKGILQTVKVVDELVKV
MGRHKPENIVIEMARENQTTQKGQKNSRERMKRIEEGIKELGSQILKEHP
VENTQLQNEKLYLYYLQNGRDMYVDQELDINRLSDYDVDHIVPQSFLKDD
SIDNKVLTRSDKNRGKSDNVPSEEVVKKMKNYWRQLLNAKLITQRKFDNL
TKAERGGLSELDKAGFIKRQLVETRQITKHVAQILDSRMNTKYDENDKLI
REVKVITLKSKLVSDFRKDFQFYKVREINNYHHAHDAYLNAVVGTALIKK
YPKLESEFVYGDYKVYDVRKMIAKSEQEIGKATAKYFFYSNIMNFFKTEI
TLANGEIRKRPLIETNGETGEIVWDKGRDFATVRKVLSMPQVNIVKKTEV
QTGGFSKESILPKRNSDKLIARKKDWDPKKYGGFDSPTVAYSVLVVAKVE
KGKSKKLKSVKELLGITIMERSSFEKNPIDFLEAKGYKEVKKDLIIKLPK
YSLFELENGRKRMLASAGELQKGNELALPSKYVNFLYLASHYEKLKGSPE
DNEQKQLFVEQHKHYLDEIIEQISEFSKRVILADANLDKVLSAYNKHRDK
PIREQAENIIHLFTLTNLGAPAAFKYFDTTIDRKRYTSTKEVLDATLIHQ
SITGLYETRIDLSQLGGDSRADPKKKRKVRGGGGSGGGGSGGGGSPSPAR
PALRAPASATSGSRKRARPPAAPGRDQARPPARRRLRLSVDEVSSPSTPE
APDIPACPSPGQKIKKSTPAAGQPPHLTSAQDQDTI

Cas9:linker:hGem
(SEQ ID NO: 21)
MDKKYSIGLDIGTNSVGWAVITDEYKVPSKKFKVLGNTDRHSIKKNLIGA
LLFDSGETAEATRLKRTARRRYTRRKNRICYLQEIFSNEMAKVDDSFFHR
LEESFLVEEDKKHERHPIFGNIVDEVAYHEKYPTIYHLRKKLVDSTDKAD
LRLIYLALAHMIKFRGHFLIEGDLNPDNSDVDKLFIQLVQTYNQLFEENP
INASGVDAKAILSARLSKSRRLENLIAQLPGEKKNGLFGNLIALSLGLTP
NFKSNFDLAEDAKLQLSKDTYDDDLDNLLAQIGDQYADLFLAAKNLSDAI
LLSDILRVNTEITKAPLSASMIKRYDEHHQDLTLLKALVRQQLPEKYKEI
FFDQSKNGYAGYIDGGASQEEFYKFIKPILEKMDGTEELLVKLNREDLLR
KQRTFDNGSIPHQIHLGELHAILRRQEDFYPFLKDNREKIEKILTFRIPY
YVGPLARGNSRFAWMTRKSEETITPWNFEEVVDKGASAQSFIERMTNFDK
NLPNEKVLPKHSLLYEYFTVYNELTKVKYVTEGMRKPAFLSGEQKKAIVD
LLFKTNRKVTVKQLKEDYFKKIECFDSVEISGVEDRFNASLGTYHDLLKI
IKDKDFLDNEENEDILEDIVLTLTLFEDREMIEERLKTYAHLFDDKVMKQ
LKRRRYTGWGRLSRKLINGIRDKQSGKTILDFLKSDGFANRNFMQLIHDD
SLTFKEDIQKAQVSGQGDSLHEHIANLAGSPAIKKGILQTVKVVDELVKV
MGRHKPENIVIEMARENQTTQKGQKNSRERMKRIEEGIKELGSQILKEHP
VENTQLQNEKLYLYYLQNGRDMYVDQELDINRLSDYDVDHIVPQSFLKDD
SIDNKVLTRSDKNRGKSDNVPSEEVVKKMKNYWRQLLNAKLITQRKFDNL
TKAERGGLSELDKAGFIKRQLVETRQITKHVAQILDSRMNTKYDENDKLI
REVKVITLKSKLVSDFRKDFQFYKVREINNYHHAHDAYLNAVVGTALIKK
YPKLESEFVYGDYKVYDVRKMIAKSEQEIGKATAKYFFYSNIMNFFKTEI
TLANGEIRKRPLIETNGETGEIVWDKGRDFATVRKVLSMPQVNIVKKTEV
QTGGFSKESILPKRNSDKLIARKKDWDPKKYGGFDSPTVAYSVLVVAKVE
KGKSKKLKSVKELLGITIMERSSFEKNPIDFLEAKGYKEVKKDLIIKLPK
YSLFELENGRKRMLASAGELQKGNELALPSKYVNFLYLASHYEKLKGSPE
DNEQKQLFVEQHKHYLDEIIEQISEFSKRVILADANLDKVLSAYNKHRDK
PIREQAENIIHLFTLTNLGAPAAFKYFDTTIDRKRYTSTKEVLDATLIHQ
SITGLYETRIDLSQLGGDSRADPKKKRKVRGGGGSGGGGSGGGGSMNPSM
KQKQEEIKENIKNSSVPRRTLKMIQPSASGSLVGRENELSAGLSKRKHRN
DHLTSTTSSPGVIVPESSENKNLGGVTQESFDLMIKENPSSQYWKEVAEK
RRKAL Cdt1:linker:Cas9
(SEQ ID NO: 22)
MPSPARPALRAPASATSGSRKRARPPAAPGRDQARPPARRRLRLSVDEVS
SPSTPEAPDIPACPSPGQKIKKSTPAAGQPPHLTSAQDQDTIGGGGSGGG
GSGGGGSDKKYSIGLDIGTNSVGWAVITDEYKVPSKKFKVLGNTDRHSIK
KNLIGALLFDSGETAEATRLKRTARRRYTRRKNRICYLQEIFSNEMAKVD
DSFFHRLEESFLVEEDKKHERHPIFGNIVDEVAYHEKYPTIYHLRKKLVD
STDKADLRLIYLALAHMIKFRGHFLIEGDLNPDNSDVDKLFIQLVQTYNQ
LFEENPINASGVDAKAILSARLSKSRRLENLIAQLPGEKKNGLFGNLIAL
SLGLTPNFKSNFDLAEDAKLQLSKDTYDDDLDNLLAQIGDQYADLFLAAK
NLSDAILLSDILRVNTEITKAPLSASMIKRYDEHHQDLTLLKALVRQQLP
EKYKEIFFDQSKNGYAGYIDGGASQEEFYKFIKPILEKMDGTEELLVKLN
REDLLRKQRTFDNGSIPHQIHLGELHAILRRQEDFYPFLKDNREKIEKIL
TFRIPYYVGPLARGNSRFAWMTRKSEETITPWNFEEVVDKGASAQSFIER
MTNFDKNLPNEKVLPKHSLLYEYFTVYNELTKVKYVTEGMRKPAFLSGEQ
KKAIVDLLFKTNRKVTVKQLKEDYFKKIECFDSVEISGVEDRFNASLGTY
HDLLKIIKDKDFLDNEENEDILEDIVLTLTLFEDREMIEERLKTYAHLFD
DKVMKQLKRRRYTGWGRLSRKLINGIRDKQSGKTILDFLKSDGFANRNFM
QLIHDDSLTFKEDIQKAQVSGQGDSLHEHIANLAGSPAIKKGILQTVKVV
DELVKVMGRHKPENIVIEMARENQTTQKGQKNSRERMKRIEEGIKELGSQ
ILKEHPVENTQLQNEKLYLYYLQNGRDMYVDQELDINRLSDYDVDHIVPQ
SFLKDDSIDNKVLTRSDKNRGKSDNVPSEEVVKKMKNYWRQLLNAKLITQ
RKFDNLTKAERGGLSELDKAGFIKRQLVETRQITKHVAQILDSRMNTKYD ENDKLIREVKVITLKSKLVSDFRKDFQFYKVREINNYHHAHDAYLNAVVG
TALIKKYPKLESEFVYGDYKVYDVRKMIAKSEQEIGKATAKYFFYSNIMN
FFKTEITLANGEIRKRPLIETNGETGEIVWDKGRDFATVRKVLSMPQVNI
VKKTEVQTGGFSKESILPKRNSDKLIARKKDWDPKKYGGFDSPTVAYSVL
VVAKVEKGKSKKLKSVKELLGITIMERSSFEKNPIDFLEAKGYKEVKKDL
IIKLPKYSLFELENGRKRMLASAGELQKGNELALPSKYVNFLYLASHYEK
LKGSPEDNEQKQLFVEQHKHYLDEIIEQISEFSKRVILADANLDKVLSAY
NKHRDKPIREQAENIIHLFTLTNLGAPAAFKYFDTTIDRKRYTSTKEVLD
ATLIHQSITGLYETRIDLSQLGGDSRADPKKKRKVR Gem:linker:Cas9

(SEQ ID NO: 23)

MNPSMKQKQEEIKENIKNSSVPRRTLKMIQPSASGSLVGRENELSAGLSK
RKHRNDHLTSTTSSPGVIVPESSENKNLGGVTQESFDLMIKENPSSQYWK
EVAEKRRKALGGGGSGGGGSGGGGSDKKYSIGLDIGTNSVGWAVITDEYK
VPSKKFKVLGNTDRHSIKKNLIGALLFDSGETAEATRLKRTARRRYTRRK
NRICYLQEIFSNEMAKVDDSFFHRLEESFLVEEDKKHERHPIFGNIVDEV
AYHEKYPTIYHLRKKLVDSTDKADLRLIYLALAHMIKFRGHFLIEGDLNP
DNSDVDKLFIQLVQTYNQLFEENPINASGVDAKAILSARLSKSRRLENLI
AQLPGEKKNGLFGNLIALSLGLTPNFKSNFDLAEDAKLQLSKDTYDDDLD
NLLAQIGDQYADLFLAAKNLSDAILLSDILRVNTEITKAPLSASMIKRYD
EHHQDLTLLKALVRQQLPEKYKEIFFDQSKNGYAGYIDGGASQEEFYKFI
KPILEKMDGTEELLVKLNREDLLRKQRTFDNGSIPHQIHLGELHAILRRQ
EDFYPFLKDNREKIEKILTFRIPYYVGPLARGNSRFAWMTRKSEETITPW
NFEEVVDKGASAQSFIERMTNFDKNLPNEKVLPKHSLLYEYFTVYNELTK
VKYVTEGMRKPAFLSGEQKKAIVDLLFKTNRKVTVKQLKEDYFKKIECFD
SVEISGVEDRFNASLGTYHDLLKIIKDKDFLDNEENEDILEDIVLTLTLF
EDREMIEERLKTYAHLFDDKVMKQLKRRRYTGWGRLSRKLINGIRDKQSG
KTILDFLKSDGFANRNFMQLIHDDSLTFKEDIQKAQVSGQGDSLHEHIAN
LAGSPAIKKGILQTVKVVDELVKVMGRHKPENIVIEMARENQTTQKGQKN
SRERMKRIEEGIKELGSQILKEHPVENTQLQNEKLYLYYLQNGRDMYVDQ
ELDINRLSDYDVDHIVPQSFLKDDSIDNKVLTRSDKNRGKSDNVPSEEVV
KKMKNYWRQLLNAKLITQRKFDNLTKAERGGLSELDKAGFIKRQLVETRQ
ITKHVAQILDSRMNTKYDENDKLIREVKVITLKSKLVSDFRKDFQFYKVR
EINNYHHAHDAYLNAVVGTALIKKYPKLESEFVYGDYKVYDVRKMIAKSE
QEIGKATAKYFFYSNIMNFFKTEITLANGEIRKRPLIETNGETGEIVWDK
GRDFATVRKVLSMPQVNIVKKTEVQTGGFSKESILPKRNSDKLIARKKDW
DPKKYGGFDSPTVAYSVLVVAKVEKGKSKKLKSVKELLGITIMERSSFEK
NPIDFLEAKGYKEVKKDLIIKLPKYSLFELENGRKRMLASAGELQKGNEL
ALPSKYVNFLYLASHYEKLKGSPEDNEQKQLFVEQHKHYLDEIIEQISEF
SKRVILADANLDKVLSAYNKHRDKPIREQAENIIHLFTLTNLGAPAAFKY
FDTTIDRKRYTSTKEVLDATLIHQSITGLYETRIDLSQLGGDSRADPKKK
RKVR

Cas9:Cdt1:

(SEQ ID NO: 24)

ATGGACAAGAAGTACTCCATTGGGCTCGATATCGGCACAAACAGCGTCGG
CTGGGCCGTCATTACGGACGAGTACAAGGTGCCGAGCAAAAAATTCAAAG
TTCTGGGCAATACCGATCGCCACAGCATAAAGAAGAACCTCATTGGCGCC
CTCCTGTTCGACTCCGGGGAGACGGCCGAAGCCACGCGGCTCAAAAGAAC
AGCACGGCGCAGATATACCCGCAGAAAGAATCGGATCTGCTACCTGCAGG
AGATCTTTAGTAATGAGATGGCTAAGGTGGATGACTCTTTCTTCCATAGG
CTGGAGGAGTCCTTTTTGGTGGAGGAGGATAAAAAGCACGAGCGCCACCC
AATCTTTGGCAATATCGTGGACGAGGTGGCGTACCATGAAAAGTACCCAA
CCATATATCATCTGAGGAAGAAGCTTGTAGACAGTACTGATAAGGCTGAC
TTGCGGTTGATCTATCTCGCGCTGGCGCATATGATCAAATTTCGGGGACA
CTTCCTCATCGAGGGGGACCTGAACCCAGACAACAGCGATGTCGACAAAC
TCTTTATCCAACTGGTTCAGACTTACAATCAGCTTTTCGAAGAGAACCCG
ATCAACGCATCCGGAGTTGACGCCAAAGCAATCCTGAGCGCTAGGCTGTC
CAAATCCCGGCGGCTCGAAAACCTCATCGCACAGCTCCCTGGGGAGAAGA
AGAACGGCCTGTTTGGTAATCTTATCGCCCTGTCACTCGGGCTGACCCCC
AACTTTAAATCTAACTTCGACCTGGCCGAAGATGCCAAGCTTCAACTGAG
CAAAGACACCTACGATGATGATCTCGACAATCTGCTGGCCCAGATCGGCG
ACCAGTACGCAGACCTTTTTTTGGCGGCAAAGAACCTGTCAGACGCCATT
CTGCTGAGTGATATTCTGCGAGTGAACACGGAGATCACCAAAGCTCCGCT
GAGCGCTAGTATGATCAAGCGCTATGATGAGCACCACCAAGACTTGACTT
TGCTGAAGGCCCTTGTCAGACAGCAACTGCCTGAGAAGTACAAGGAAATT
TTCTTCGATCAGTCTAAAAATGGCTACGCCGGATACATTGACGGCGGAGC
AAGCCAGGAGGAATTTTACAAATTTATTAAGCCCATCTTGGAAAAAATGG
ACGGCACCGAGGAGCTGCTGGTAAAGCTTAACAGAGAAGATCTGTTGCGC
AAACAGCGCACTTTCGACAATGGAAGCATCCCCCACCAGATTCACCTGGG
CGAACTGCACGCTATCCTCAGGCGGCAAGAGGATTTCTACCCCTTTTTGA
AAGATAACAGGGAAAAGATTGAGAAAATCCTCACATTTCGGATACCCTAC
TATGTAGGCCCCCTCGCCCGGGGAAATTCCAGATTCGCGTGGATGACTCG
CAAATCAGAAGAGACCATCACTCCCTGGAACTTCGAGGAAGTCGTGGATA
AGGGGGCCTCTGCCCAGTCCTTCATCGAAAGGATGACTAACTTTGATAAA
AATCTGCCTAACGAAAAGGTGCTTCCTAAACACTCTCTGCTGTACGAGTA
CTTCACAGTTTATAACGAGCTCACCAAGGTCAAATACGTCACAGAAGGGA
TGAGAAAGCCAGCATTCCTGTCTGGAGAGCAGAAGAAAGCTATCGTGGAC
CTCCTCTTCAAGACGAACCGGAAAGTTACCGTGAAACAGCTCAAAGAAGA
CTATTTCAAAAAGATTGAATGTTTCGACTCTGTTGAAATCAGCGGAGTGG
AGGATCGCTTCAACGCATCCCTGGGAACGTATCACGATCTCCTGAAAATC
ATTAAAGACAAGGACTTCCTGGACAATGAGGAGAACGAGGACATTCTTGA
GGACATTGTCCTCACCCTTACGTTGTTTGAAGATAGGGAGATGATTGAAG
AACGCTTGAAAACTTACGCTCATCTCTTCGACGACAAAGTCATGAAACAG
CTCAAGAGGCGCCGATATACAGGATGGGGGCGGCTGTCAAGAAAACTGAT

-continued

```
CAATGGGATCCGAGACAAGCAGAGTGGAAAGACAATCCTGGATTTTCTTA
AGTCCGATGGATTTGCCAACCGGAACTTCATGCAGTTGATCCATGATGAC
TCTCTCACCTTTAAGGAGGACATCCAGAAAGCACAAGTTTCTGGCCAGGG
GGACAGTCTTCACGAGCACATCGCTAATCTTGCAGGTAGCCCAGCTATCA
AAAAGGGAATACTGCAGACCGTTAAGGTCGTGGATGAACTCGTCAAAGTA
ATGGGAAGGCATAAGCCCGAGAATATCGTTATCGAGATGGCCCGAGAGAA
CCAAACTACCCAGAAGGGACAGAAGAACAGTAGGGAAAGGATGAAGAGGA
TTGAAGAGGGTATAAAAGAACTGGGGTCCCAAATCCTTAAGGAACACCCA
GTTGAAAACACCCAGCTTCAGAATGAGAAGCTCTACCTGTACTACCTGCA
GAACGGCAGGGACATGTACGTGGATCAGGAACTGGACATCAATCGGCTCT
CCGACTACGACGTGGATCATATCGTGCCCCAGTCTTTTCTCAAAGATGAT
TCTATTGATAATAAAGTGTTGACAAGATCCGATAAAAATAGAGGGAAGAG
TGATAACGTCCCCTCAGAAGAAGTTGTCAAGAAAATGAAAAATTATTGGC
GGCAGCTGCTGAACGCCAAACTGATCACACAACGGAAGTTCGATAATCTG
ACTAAGGCTGAACGAGGTGGCCTGTCTGAGTTGGATAAAGCCGGCTTCAT
CAAAAGGCAGCTTGTTGAGACACGCCAGATCACCAAGCACGTGGCCCAAA
TTCTCGATTCACGCATGAACACCAAGTACGATGAAAATGACAAACTGATT
CGAGAGGTGAAAGTTATTACTCTGAAGTCTAAGCTGGTCTCAGATTTCAG
AAAGGACTTTCAGTTTTATAAGGTGAGAGAGATCAACAATTACCACCATG
CGCATGATGCCTACCTGAATGCAGTGGTAGGCACTGCACTTATCAAAAAA
TATCCCAAGCTTGAATCTGAATTTGTTTACGGAGACTATAAAGTGTACGA
TGTTAGGAAAATGATCGCAAAGTCTGAGCAGGAAATAGGCAAGGCCACCG
CTAAGTACTTCTTTTACAGCAATATTATGAATTTTTTCAAGACCGAGATT
ACACTGGCCAATGGAGAGATTCGGAAGCGACCACTTATCGAAACAAACGG
AGAAACAGGAGAAATCGTGTGGGACAAGGGTAGGGATTTCGCGCACAGTCC
GGAAGGTCCTGTCCATGCCGCAGGTGAACATCGTTAAAAAGACCGAAGTA
CAGACCGGAGGCTTCTCCAAGGAAAGTATCCTCCCGAAAAGGAACAGCGA
CAAGCTGATCGCACGCAAAAAGATTGGGACCCCAAGAAATACGGCGGAT
TCGATTCTCCTACAGTCGCTTACAGTGTACTGGTTGTGGCCAAAGTGGAG
AAAGGGAAGTCTAAAAAACTCAAAAGCGTCAAGGAACTGCTGGGCATCAC
AATCATGGAGCGATCAAGCTTCGAAAAAAACCCCATCGACTTTCTCGAGG
CGAAAGGATATAAAGAGGTCAAAAAAGACCTCATCATTAAGCTTCCCAAG
TACTCTCTCTTTGAGCTTGAAAACGGCCGGAAACGAATGCTCGCTAGTGC
GGGCGAGCTGCAGAAAGGTAACGAGCTGGCACTGCCCTCTAAATACGTTA
ATTTCTTGTATCTGGCCAGCCACTATGAAAAGCTCAAAGGGTCTCCCGAA
GATAATGAGCAGAAGCAGCTGTTCGTGGAACAACACAAACACTACCTTGA
TGAGATCATCGAGCAAATAAGCGAATTCTCCAAAAGAGTGATCCTCGCCG
ACGCTAACCTCGATAAGGTGCTTTCTGCTTACAATAAGCACAGGGATAAG
CCCATCAGGGAGCAGGCAGAAAACATTATCCACTTGTTTACTCTGACCAA
CTTGGGCGCGCCTGCAGCCTTCAAGTACTTCGACACCACCATAGACAGAA
AGCGGTACACCTCTACAAAGGAGGTCCTGGACGCCACACTGATTCATCAG
```

-continued

```
TCAATTACGGGGCTCTATGAAACAAGAATCGACCTCTCTCAGCTCGGTGG
AGACAGCAGGGCTGACCCCAAGAAGAAGAGGAAGGTGAGGGGAGGCGGAG
GATCTGGCGGAGGCGGAAGTGGCGGAGGGGGCAGCCCATCTCCTGCCAGA
CCTGCTCTGAGAGCCCCTGCCTCTGCCACAAGCGGCAGCAGAAAGAGAGC
CAGACCTCCTGCCGCCCCTGGCAGAGATCAGGCTAGACCTCCAGCTCGGC
GGGAGACTGAGACTGAGCGTGGACGAGGTGTCCAGCCCTAGCACACCTGAG
GCCCCTGATATCCCCGCCTGTCCTAGCCCTGGCCAGAAGATCAAGAAGTC
CACCCCTGCCGCCGGACAGCCTCCTCATCTGACATCTGCCCAGGACCAGG
ACACCATC
```

Cas9:Gem:

(SEQ ID NO: 25)
```
ATGGACAAGAAGTACTCCATTGGGCTCGATATCGGCACAAACAGCGTCGG
CTGGGCCGTCATTACGGACGAGTACAAGGTGCCGAGCAAAAAATTCAAAG
TTCTGGGCAATACCGATCGCCACAGCATAAAGAAGAACCTCATTGGCGCC
CTCCTGTTCGACTCCGGGGAGACGGCCGAAGCCACGCGGCTCAAAAGAAC
AGCACGGCGCAGATATACCCGCAGAAAGAATCGGATCTGCTACCTGCAGG
AGATCTTTAGTAATGAGATGGCTAAGGTGGATGACTCTTTCTTCCATAGG
CTGGAGGAGTCCTTTTTGGTGGAGGAGGATAAAAAGCACGAGCGCCACCC
AATCTTTGGCAATATCGTGGACGAGGTGGCGTACCATGAAAAGTACCCAA
CCATATATCATCTGAGGAAGAAGCTTGTAGACAGTACTGATAAGGCTGAC
TTGCGGTTGATCTATCTCGCGCTGGCGCATATGATCAAATTTCGGGGACA
CTTCCTCATCGAGGGGGACCTGAACCCAGACAACAGCGATGTCGACAAAC
TCTTTATCCAACTGGTTCAGACTTACAATCAGCTTTTCGAAGAGAACCCG
ATCAACGCATCCGGAGTTGACGCCAAAGCAATCCTGAGCGCTAGGCTGTC
CAAATCCCGGCGGCTCGAAAACCTCATCGCACAGCTCCCTGGGGAGAAGA
AGAACGGCCTGTTTGGTAATCTTATCGCCCTGTCACTCGGGCTGACCCCC
AACTTTAAATCTAACTTCGACCTGGCCGAAGATGCCAAGCTTCAACTGAG
CAAAGACACCTACGATGATGATCTCGACAATCTGCTGGCCCAGATCGGCG
ACCAGTACGCAGACCTTTTTTTGGCGGCAAAGAACCTGTCAGACGCCATT
CTGCTGAGTGATATTCTGCGAGTGAACACGGAGATCACCAAAGCTCCGCT
GAGCGCTAGTATGATCAAGCGCTATGATGAGCACCACCAAGACTTGACTT
TGCTGAAGGCCCTTGTCAGACAGCAACTGCCTGAGAAGTACAAGGAAATT
TTCTTCGATCAGTCTAAAAATGGCTACGCCGGATACATTGACGGCGGAGC
AAGCCAGGAGGAATTTTACAAATTTATTAAGCCCATCTTGGAAAAAATGG
ACGGCACCGAGGAGCTGCTGGTAAAGCTTAACAGAGAAGATCTGTTGCGC
AAACAGCGCACTTTCGACAATGGAAGCATCCCCCACCAGATTCACCTGGG
CGAACTGCACGCTATCCTCAGGCGGCAAGAGGATTTCTACCCCTTTTTGA
AAGATAACAGGGAAAAGATTGAGAAAATCCTCACATTTCGGATACCCTAC
TATGTAGGCCCCCTCGCCCGGGGAAATTCCAGATTCGCGTGGATGACTCG
CAAATCAGAAGAGACCATCACTCCCTGGAACTTCGAGGAAGTCGTGGATA
AGGGGGCCTCTGCCCAGTCCTTCATCGAAAGGATGACTAACTTTGATAAA
AATCTGCCTAACGAAAAGGTGCTTCCTAAACACTCTCTGCTGTACGAGTA
```

```
CTTCACAGTTTATAACGAGCTCACCAAGGTCAAATACGTCACAGAAGGGA
TGAGAAAGCCAGCATTCCTGTCTGGAGAGCAGAAGAAAGCTATCGTGGAC
CTCCTCTTCAAGACGAACCGGAAAGTTACCGTGAAACAGCTCAAAGAAGA
CTATTTCAAAAAGATTGAATGTTTCGACTCTGTTGAAATCAGCGGAGTGG
AGGATCGCTTCAACGCATCCCTGGGAACGTATCACGATCTCCTGAAAATC
ATTAAAGACAAGGACTTCCTGGACAATGAGGAGAACGAGGACATTCTTGA
GGACATTGTCCTCACCCTTACGTTGTTTGAAGATAGGGAGATGATTGAAG
AACGCTTGAAAACTTACGCTCATCTCTTCGACGACAAAGTCATGAAACAG
CTCAAGAGGCGCCGATATACAGGATGGGGCGGCTGTCAAGAAAACTGAT
CAATGGGATCCGAGACAAGCAGAGTGGAAAGACAATCCTGGATTTTCTTA
AGTCCGATGGATTTGCCAACCGGAACTTCATGCAGTTGATCCATGATGAC
TCTCTCACCTTTAAGGAGGACATTCCAGAAAGCACAAGTTTCTGGCCAGGG
GGACAGTCTTCACGAGCACATCGCTAATCTTGCAGGTAGCCCAGCTATCA
AAAAGGGAATACTGCAGACCGTTAAGGTCGTGGATGAACTCGTCAAAGTA
ATGGGAAGGCATAAGCCCGAGAATATCGTTATCGAGATGGCCCGAGAGAA
CCAAACTACCCAGAAGGGACAGAAGAACAGTAGGGAAAGGATGAAGAGGA
TTGAAGAGGGTATAAAAGAACTGGGGTCCCAAATCCTTAAGGAACACCCA
GTTGAAAACACCCAGCTTCAGAATGAGAAGCTCTACCTGTACTACCTGCA
GAACGGCAGGGACATGTACGTGGATCAGGAACTGGACATCAATCGGCTCT
CCGACTACGACGTGGATCATATCGTGCCCCAGTCTTTTCTCAAAGATGAT
TCTATTGATAATAAAGTGTTGACAAGATCCGATAAAAATAGAGGGAAGAG
TGATAACGTCCCCTCAGAAGAAGTTGTCAAGAAAATGAAAAATTATTGGC
GGCAGCTGCTGAACGCCAAACTGATCACACAACGGAAGTTCGATAATCTG
ACTAAGGCTGAACGAGGTGGCCTGTCTGAGTTGGATAAAGCCGGCTTCAT
CAAAAAGGCAGCTTGTTGAGACACGCCAGATCACCAAGCACGTGGCCCAAA
TTCTCGATTCACGCATGAACACCAAGTACGATGAAAATGACAAACTGATT
CGAGAGGTGAAAGTTATTACTCTGAAGTCTAAGCTGGTCTCAGATTTCAG
AAAGGACTTTCAGTTTTATAAGGTGAGAGAGATCAACAATTACCACCATG
CGCATGATGCCTACCTGAATGCAGTGGTAGGCACTGCACTTATCAAAAAA
TATCCCAAGCTTGAATCTGAATTTGTTTACGGAGACTATAAAGTGTACGA
TGTTAGGAAAATGATCGCAAAGTCTGAGCAGGAAATAGGCAAGGCCACCG
CTAAGTACTTCTTTTACAGCAATATTATGAATTTTTTCAAGACCGAGATT
ACACTGGCCAATGGAGAGATTCGGAAGCGACCACTTATCGAAACAAACGG
AGAAACAGGAGAAATCGTGTGGGACAAGGGTAGGGATTTCGCGACAGTCC
GGAAGGTCCTGTCCATGCCGCAGGTGAACATCGTTAAAAAGACCGAAGTA
CAGACCGGAGGCTTCTCCAAGGAAAGTATCCTCCCGAAAAGGAACAGCGA
CAAGCTGATCGCACGCAAAAAGATTGGGACCCCAAGAAATACGGCGGAT
TCGATTCTCCTACAGTCGCTTACAGTGTACTGGTTGTGGCCAAAGTGGAG
AAAGGGAAGTCTAAAAAACTCAAAAGCGTCAAGGAACTGCTGGGCATCAC
AATCATGGAGCGATCAAGCTTCGAAAAAAACCCCATCGACTTTCTCGAGG
CGAAAGGATATAAAGAGGTCAAAAAAGACCTCATCATTAAGCTTCCCAAG
```

```
TACTCTCTCTTTGAGCTTGAAAACGGCCGGAAACGAATGCTCGCTAGTGC
GGGCGAGCTGCAGAAAGGTAACGAGCTGGCACTGCCCTCTAAATACGTTA
ATTTCTTGTATCTGGCCAGCCACTATGAAAAGCTCAAAGGGTCTCCCGAA
GATAATGAGCAGAAGCAGCTGTTCGTGGAACAACACAAACACTACCTTGA
TGAGATCATCGAGCAAATAAGCGAATTCTCCAAAAGAGTGATCCTCGCCG
ACGCTAACCTCGATAAGGTGCTTTCTGCTTACAATAAGCACAGGGATAAG
CCCATCAGGGAGCAGGCAGAAAACATTATCCACTTGTTTACTCTGACCAA
CTTGGGCGCGCCTGCAGCCTTCAAGTACTTCGACACCACCATAGACAGAA
AGCGGTACACCTCTACAAAGGAGGTCCTGGACGCCACACTGATTCATCAG
TCAATTACGGGGCTCTATGAAACAAGAATCGACCTCTCTCAGCTCGGTGG
AGACAGCAGGGCTGACCCCAAGAAGAAGAGGAAGGTGAGGGGAGGCGGAG
GATCTGGCGGAGGCGGAAGTGGCGGAGGGGGCAGCATGAACCCTAGCATG
AAGCAGAAGCAGGAAGAGATCAAAGAGAACATCAAGAACAGCAGCGTGCC
CAGACGGACCCTGAAGATGATCCAGCCTAGCGCCAGCGGCAGCCTCGTGG
GCAGAGAGAATGAACTGTCTGCCGGCCTGAGCAAGCGGAAGCACAGAAAC
GACCACCTGACCAGCACCACCAGCAGCCCTGGCGTGATCGTGCCTGAGAG
CAGCGAGAACAAGAACCTGGGCGGCGTGACCCAGGAATCCTTCGACCTGA
TGATCAAAGAAAACCCCAGCAGCCAGTATTGGAAAGAGGTGGCCGAGAAG
CGGCGGAAGGCCCTG
```

Cdt1:linker:Cas9

(SEQ ID NO: 26)

```
ATGCCATCTCCTGCCAGACCTGCTCTGAGAGCCCCTGCCTCTGCCACAAG
CGGCAGCAGAAAGAGAGCCAGACCTCCTGCCGCCCTGGCAGAGATCAGG
CTAGACCTCCAGCTCGGCGGAGACTGAGACTGAGCGTGGACGAGGTGTCC
AGCCCTAGCACACCTGAGGCCCCTGATATCCCCGCCTGTCCTAGCCCTGG
CCAGAAGATCAAGAAGTCCACCCCTGCCGCCGGACAGCCTCCTCATCTGA
CATCTGCCCAGGACCAGGACACCATCGGAGGCGGAGGATCTGGCGGAGGC
GGAAGTGGCGGAGGGGGCAGCGACAAGAAGTACTCCATTGGGCTCGATAT
CGGCACAAACAGCGTCGGCTGGGCCGTCATTACGGACGAGTACAAGGTGC
CGAGCAAAAATTCAAAGTTCTGGGCAATACCGATCGCCACAGCATAAAG
AAGAACCTCATTGCGCCCCTCCTGTTCGACTCCGGGGAGACGGCCGAAGC
CACGCGGCTCAAAAGAACAGCACGGCGCAGATATACCCGCAGAAAGAATC
GGATCTGCTACCTGCAGGAGATCTTTAGTAATGAGATGGCTAAGGTGGAT
GACTCTTTCTTCCATAGGCTGGAGGAGTCCTTTTTGGTGGAGGAGGATAA
AAAGCACGAGCGCCACCCAATCTTTGGCAATATCGTGGACGAGGTGGCGT
ACCATGAAAGTACCCAACCATATATCATCTGAGGAAGAAGCTTGTAGAC
AGTACTGATAAGCTGACTTGCGGTTGATCTATCTCGCGCTGGCGCATAT
GATCAAATTTCGGGGACACTTCCTCATCGAGGGGGACCTGAACCCAGACA
ACAGCGATGTCGACAAACTCTTTATCCAACTGGTTCAGACTTACAATCAG
CTTTTCGAAGAGAACCCGATCAACGCATCCGGAGTTGACGCCAAAGCAAT
CCTGAGCGCTAGGCTGTCCAAATCCCGGCGGCTCGAAACCTCATCGCAC
AGCTCCCTGGGGAGAAGAAGAACGGCCTGTTTGGTAATCTTATCGCCCTG
```

-continued

```
TCACTCGGGCTGACCCCCAACTTTAAATCTAACTTCGACCTGGCCGAAGA
TGCCAAGCTTCAACTGAGCAAAGACACCTACGATGATGATCTCGACAATC
TGCTGGCCCAGATCGGCGACCAGTACGCAGACCTTTTTTTGGCGGCAAAG
AACCTGTCAGACGCCATTCTGCTGAGTGATATTCTGCGAGTGAACACGGA
GATCACCAAAGCTCCGCTGAGCGCTAGTATGATCAAGCGCTATGATGAGC
ACCACCAAGACTTGACTTTGCTGAAGGCCCTTGTCAGACAGCAACTGCCT
GAGAAGTACAAGGAAATTTTCTTCGATCAGTCTAAAAATGGCTACGCCGG
ATACATTGACGGCGGAGCAAGCCAGGAGGAATTTTACAAATTTATTAAGC
CCATCTTGGAAAAAATGGACGGCACCGAGGAGCTGCTGGTAAAGCTTAAC
AGAGAAGATCTGTTGCGCAAACAGCGCACTTTCGACAATGGAAGCATCCC
CCACCAGATTCACCTGGGCGAACTGCACGCTATCCTCAGGCGGCAAGAGG
ATTTCTACCCCTTTTTGAAAGATAACAGGGAAAAGATTGAGAAAATCCTC
ACATTTCGGATACCCTACTATGTAGGCCCCCTCGCCCGGGGAAATTCCAG
ATTCGCGTGGATGACTCGCAAATCAGAAGAGACCATCACTCCCTGGAACT
TCGAGGAAGTCGTGGATAAGGGGGCCTCTGCCCAGTCCTTCATCGAAAGG
ATGACTAACTTTGATAAAAATCTGCCTAACGAAAAGGTGCTTCCTAAACA
CTCTCTGCTGTACGAGTACTTCACAGTTTATAACGAGCTCACCAAGGTCA
AATACGTCACAGAAGGGATGAGAAAGCCAGCATTCCTGTCTGGAGAGCAG
AAGAAAGCTATCGTGGACCTCCTCTTCAAGACGAACCGGAAAGTTACCGT
GAAACAGCTCAAAGAAGACTATTTCAAAAAGATTGAATGTTTCGACTCTG
TTGAAATCAGCGGAGTGGAGGATCGCTTCAACGCATCCCTGGGAACGTAT
CACGATCTCCTGAAAATCATTAAAGACAAGGACTTCCTGGACAATGAGGA
GAACGAGGACATTCTTGAGGACATTGTCCTCACCCTTACGTTGTTTGAAG
ATAGGGAGATGATTGAAGAACGCTTGAAAACTTACGCTCATCTCTTCGAC
GACAAAGTCATGAAACAGCTCAAGAGGCGCCGATATACAGGATGGGGGCG
GCTGTCAAGAAAACTGATCAATGGGATCCGAGACAAGCAGAGTGGAAAGA
CAATCCTGGATTTTCTTAAGTCCGATGGATTTGCCAACCGGAACTTCATG
CAGTTGATCCATGATGACTCTCTCACCTTTAAGGAGGACATCCAGAAAGC
ACAAGTTTCTGGCCAGGGGACAGTCTTCACGAGCACATCGCTAATCTTG
CAGGTAGCCCAGCTATCAAAAAGGGAATACTGCAGACCGTTAAGGTCGTG
GATGAACTCGTCAAAGTAATGGGAAGGCATAAGCCCGAGAATATCGTTAT
CGAGATGGCCCGAGAGAACCAAACTACCCAGAAGGGACAGAAGAACAGTA
GGGAAAGGATGAAGAGGATTGAAGAGGGTATAAAAGAACTGGGGTCCCAA
ATCCTTAAGGAACACCCAGTTGAAAACACCCAGCTTCAGAATGAGAAGCT
CTACCTGTACTACCTGCAGAACGGCAGGGACATGTACGTGGATCAGGAAC
TGGACATCAATCGGCTCTCCGACTACGACGTGGATCATATCGTGCCCAG
TCTTTTCTCAAAGATGATTCTATTGATAATAAAGTGTTGACAAGATCCGA
TAAAAATAGAGGGAAGAGTGATAACGTCCCCTCAGAAGAAGTTGTCAAGA
AAATGAAAAATTATTGGCGGCAGCTGCTGAACGCCAAACTGATCACACAA
CGGAAGTTCGATAATCTGACTAAGGCTGAACGAGGTGGCCTGTCTGAGTT
GGATAAAGCCGGCTTCATCAAAAGGCAGCTTGTTGAGACACGCCAGATCA
```

-continued

```
CCAAGCACGTGGCCCAAATTCTCGATTCACGCATGAACACCAAGTACGAT
GAAAATGACAAACTGATTCGAGAGGTGAAAGTTATTACTCTGAAGTCTAA
GCTGGTCTCAGATTTCAGAAAGGACTTTCAGTTTTATAAGGTGAGAGAGA
TCAACAATTACCACCATGCGCATGATGCCTACCTGAATGCAGTGGTAGGC
ACTGCACTTATCAAAAAATATCCCAAGCTTGAATCTGAATTTGTTTACGG
AGACTATAAAGTGTACGATGTTAGGAAAATGATCGCAAAGTCTGAGCAGG
AAATAGGCAAGGCCACCGCTAAGTACTTCTTTTACAGCAATATTATGAAT
TTTTTCAAGACCGAGATTACACTGGCCAATGGAGAGATTCGGAAGCGACC
ACTTATCGAAACAAACGGAGAAACAGGAGAAATCGTGTGGGACAAGGGTA
GGGATTTCGCGACAGTCCGGAAGGTCCTGTCCATGCCGCAGGTGAACATC
GTTAAAAAGACCGAAGTACAGACCGGAGGCTTCTCCAAGGAAAGTATCCT
CCCGAAAAGGAACAGCGACAAGCTGATCGCACGCAAAAAAGATTGGGACC
CCAAGAAATACGGCGGATTCGATTCTCCTACAGTCGCTTACAGTGTACTG
GTTGTGGCCAAAGTGGAGAAAGGGAAGTCTAAAAAACTCAAAAGCGTCAA
GGAACTGCTGGGCATCACAATCATGGAGCGATCAAGCTTCGAAAAAAACC
CCATCGACTTTCTCGAGGCGAAAGGATATAAAGAGGTCAAAAAAGACCTC
ATCATTAAGCTTCCCAAGTACTCTCTCTTTGAGCTTGAAAACGGCCGGAA
ACGAATGCTCGCTAGTGCGGGCGAGCTGCAGAAAGGTAACGAGCTGGCAC
TGCCCTCTAAATACGTTAATTTCTTGTATCTGGCCAGCCACTATGAAAAG
CTCAAAGGGTCTCCCGAAGATAATGAGCAGAAGCAGCTGTTCGTGGAACA
ACACAAACACTACCTTGATGAGTCATCGAGCAAATAAGCGAATTCTCCA
AAAGAGTGATCCTCGCCGACGCTAACCTCGATAAGGTGCTTTCTGCTTAC
AATAAGCACAGGGATAAGCCCATCAGGGAGCAGGCAGAAAACATTATCCA
CTTGTTTACTCTGACCAACTTGGGCGCGCCTGCAGCCTTCAAGTACTTCG
ACACCACCATAGACAGAAAGCGGTACACCTCTACAAAGGAGGTCCTGGAC
GCCACACTGATTCATCAGTCAATTACGGGGCTCTATGAAACAAGAATCGA
CCTCTCTCAGCTCGGTGGAGACAGCAGGGCTGACCCCAAGAAGAAGAGGA
AGGTGAGG
```

Gem:linker:Cas9

(SEQ ID NO: 27)

```
ATGAACCCTAGCATGAAGCAGAAGCAGGAAGAGATCAAAGAGAACATCAA
GAACAGCAGCGTGCCCAGACGGACCCTGAAGATGATCCAGCCTAGCGCCA
GCGGCAGCCTCGTGGGCAGAGAGAATGAACTGTCTGCCGGCCTGAGCAAG
CGGAAGCACAGAAACGACCACCTGACCAGCACCACCAGCAGCCCTGGCGT
GATCGTGCCTGAGAGCAGCGAGAACAAGAACCTGGGCGGCGTGACCCAGG
AATCCTTCGACCTGATGATCAAAGAAAACCCCAGCAGCCAGTATTGGAAA
GAGGTGGCCGAGAAGCGGCGGAAGGCCCTGGGAGGCGGAGGATCTGGCGG
AGGCGGAAGTGGCGGAGGGGGCAGCGACAAGAAGTACTCCATTGGGCTCG
ATATCGGCACAAACAGCGTCGGCTGGGCCGTCATTACGGACGAGTACAAG
GTGCCGAGCAAAAAATTCAAAGTTCTGGGCAATACCGATCGCCACAGCAT
AAAGAAGAACCTCATTGGCGCCCTCCTGTTCGACTCCGGGGAGACGGCCG
AAGCCACGCGGCTCAAAAGAACAGCACGGCGCAGATATACCCGCAGAAAG
```

-continued

AATCGGATCTGCTACCTGCAGGAGATCTTTAGTAATGAGATGGCTAAGGT
GGATGACTCTTTCTTCCATAGGCTGGAGGAGTCCTTTTTGGTGGAGGAGG
ATAAAAAGCACGAGCGCCACCCAATCTTTGGCAATATCGTGGACGAGGTG
GCGTACCATGAAAAGTACCCAACCATATATCATCTGAGGAAGAAGCTTGT
AGACAGTACTGATAAGGCTGACTTGCGGTTGATCTATCTCGCGCTGGCGC
ATATGATCAAATTTCGGGGACACTTCCTCATCGAGGGGGACCTGAACCCA
GACAACAGCGATGTCGACAAACTCTTTATCCAACTGGTTCAGACTTACAA
TCAGCTTTTCGAAGAGAACCCGATCAACGCATCCGGAGTTGACGCCAAAG
CAATCCTGAGCGCTAGGCTGTCCAAATCCCGGCGGCTCGAAAACCTCATC
GCACAGCTCCCTGGGGAGAAGAAGAACGGCCTGTTTGGTAATCTTATCGC
CCTGTCACTCGGGCTGACCCCCAACTTTAAATCTAACTTCGACCTGGCCG
AAGATGCCAAGCTTCAACTGAGCAAAGACACCTACGATGATGATCTCGAC
AATCTGCTGGCCCAGATCGGCGACCAGTACGCAGACCTTTTTTTGGCGGC
AAAGAACCTGTCAGACGCCATTCTGCTGAGTGATATTCTGCGAGTGAACA
CGGAGATCACCAAAGCTCCGCTGAGCGCTAGTATGATCAAGCGCTATGAT
GAGCACCACCAAGACTTGACTTTGCTGAAGGCCCTTGTCAGACAGCAACT
GCCTGAGAAGTACAAGGAAATTTTCTTCGATCAGTCTAAAAATGGCTACG
CCGGATACATTGACGGCGGAGCAAGCCAGGAGGAATTTTACAAATTTATT
AAGCCCATCTTGGAAAAAATGGACGGCACCGAGGAGCTGCTGGTAAAGCT
TAACAGAGAAGATCTGTTGCGCAAACAGCGCACTTTCGACAATGGAAGCA
TCCCCCACCAGATTCACCTGGGCGAACTGCACGCTATCCTCAGGCGGCAA
GAGGATTTCTACCCCTTTTTGAAAGATAACAGGGAAAAGATTGAGAAAAT
CCTCACATTTCGGATACCCTACTATGTAGGCCCCCTCGCCCGGGGAAATT
CCAGATTCGCGTGGATGACTCGCAAATCAGAAGAGACCATCACTCCCTGG
AACTTCGAGGAAGTCGTGGATAAGGGGCCTCTGCCCAGTCCTTCATCGA
AAGGATGACTAACTTTGATAAAAATCTGCCTAACGAAAAGGTGCTTCCTA
AACACTCTCTGCTGTACGAGTACTTCACAGTTTATAACGAGCTCACCAAG
GTCAAATACGTCACAGAAGGGATGAGAAAGCCAGCATTCCTGTCTGGAGA
GCAGAAGAAAGCTATCGTGGACCTCCTCTTCAAGACGAACCGGAAAGTTA
CCGTGAAACAGCTCAAAGAAGACTATTTCAAAAAGATTGAATGTTTCGAC
TCTGTTGAAATCAGCGGAGTGGAGGATCGCTTCAACGCATCCCTGGGAAC
GTATCACGATCTCCTGAAAATCATTAAAGACAAGGACTTCCTGGACAATG
AGGAGAACGAGGACATTCTTGAGGACATTGTCCTCACCCTTACGTTGTTT
GAAGATAGGGAGATGATTGAAGAACGCTTGAAAACTTACGCTCATCTCTT
CGACGACAAAGTCATGAAACAGCTCAAGAGGCGCCGATATACAGGATGGG
GGCGGCTGTCAAGAAAACTGATCAATGGGATCCGAGACAAGCAGAGTGGA
AAGACAATCCTGGATTTTCTTAAGTCCGATGGATTTGCCAACCGGAACTT
CATGCAGTTGATCCATGATGACTCTCTCACCTTTAAGGAGGACATCCAGA
AAGCACAAGTTTCTGGCCAGGGGACAGTCTTCACGAGCACATCGCTAAT
CTTGCAGGTAGCCCAGCTATCAAAAAGGGAATACTGCAGACCGTTAAGGT
CGTGGATGAACTCGTCAAAGTAATGGGAAGGCATAAGCCCGAGAATATCG

-continued

TTATCGAGATGGCCCGAGAGAACCAAACTACCCAGAAGGGACAGAAGAAC
AGTAGGGAAAGGATGAAGAGGATTGAAGAGGGTATAAAAGAACTGGGGTC
CCAAATCCTTAAGGAACACCCAGTTGAAAACACCCAGCTTCAGAATGAGA
AGCTCTACCTGTACTACCTGCAGAACGGCAGGGACATGTACGTGGATCAG
GAACTGGACATCAATCGGCTCTCCGACTACGACGTGGATCATATCGTGCC
CCAGTCTTTTCTCAAAGATGATTCTATTGATAATAAAGTGTTGACAAGAT
CCGATAAAAATAGAGGGAAGAGTGATAACGTCCCCTCAGAAGAAGTTGTC
AAGAAAATGAAAAATTATTGGCGGCAGCTGCTGAACGCCAAACTGATCAC
ACAACGGAAGTTCGATAATCTGACTAAGGCTGAACGAGGTGGCCTGTCTG
AGTTGGATAAAGCCGGCTTCATCAAAAGGCAGCTTGTTGAGACACGCCAG
ATCACCAAGCACGTGGCCCAAATTCTCGATTCACGCATGAACACCAAGTA
CGATGAAAATGACAAACTGATTCGAGAGGTGAAAGTTATTACTCTGAAGT
CTAAGCTGGTCTCAGATTTCAGAAAGGACTTTCAGTTTTATAAGGTGAGA
GAGATCAACAATTACCACCATGCGCATGATGCCTACCTGAATGCAGTGGT
AGGCACTGCACTTATCAAAAAATATCCCAAGCTTGAATCTGAATTTGTTT
ACGGAGACTATAAAGTGTACGATGTTAGGAAAATGATCGCAAAGTCTGAG
CAGGAAATAGGCAAGGCCACCGCTAAGTACTTCTTTTACAGCAATATTAT
GAATTTTTTCAAGACCGAGATTACACTGGCCAATGGAGAGATTCGGAAGC
GACCACTTATCGAAACAAACGGAGAAACAGGAGAAATCGTGTGGGACAAG
GGTAGGGATTTCGCGACAGTCCGGAAGGTCCTGTCCATGCCGCAGGTGAA
CATCGTTAAAAAGACCGAAGTACAGACCGGAGGCTTCTCCAAGGAAAGTA
TCCTCCCGAAAAGGAACAGCGACAAGCTGATCGCACGCAAAAAAGATTGG
GACCCCAAGAAATACGGCGGATTCGATTCTCCTACAGTCGCTTACAGTGT
ACTGGTTGTGGCCAAAGTGGAGAAAGGGAAGTCTAAAAAACTCAAAAGCG
TCAAGGAACTGCTGGGCATCACAATCATGGAGCGATCAAGCTTCGAAAAA
AACCCCATCGACTTTCTCGAGGCGAAAGGATATAAAGAGGTCAAAAAAGA
CCTCATCATTAAGCTTCCCAAGTACTCTCTCTTTGAGCTTGAAAACGGCC
GGAAACGAATGCTCGCTAGTGCGGGCGAGCTGCAGAAAGGTAACGAGCTG
GCACTGCCCTCTAAATACGTTAATTTCTTGTATCTGGCCAGCCACTATGA
AAAGCTCAAAGGGTCTCCCGAAGATAATGAGCAGAAGCAGCTGTTCGTGG
AACAACACAAACACTACCTTGATGAGATCATCGAGCAAATAAGCGAATTC
TCCAAAAGAGTGATCCTCGCCGACGCTAACCTCGATAAGGTGCTTTCTGC
TTACAATAAGCACAGGGATAAGCCCATCAGGGAGCAGGCAGAAAACATTA
TCCACTTGTTTACTCTGACCAACTTGGGCGCGCCTGCAGCCTTCAAGTAC
TTCGACACCACCATAGACAGAAAGCGGTACACCTCTACAAAGGAGGTCCT
GGACGCCACACTGATTCATCAGTCAATTACGGGGCTCTATGAAACAAGAA
TCGACCTCTCTCAGCTCGGTGGAGACAGCAGGGCTGACCCCAAGAAGAAG
AGGAAGGTGAGG

Example 4

Auto-Regulation of RNA-Guided Nucleases by Engineering Partial Target Sites

Reducing RNA-directed nuclease activity can be beneficial towards reducing the potential for off-target effects. In a clinical setting, this would be highly significant with viral delivery methods, such as AAV, which are characterized by prolonged or life-time expression.

Here, a self-regulating system is described for the expression of Cas9, an RNA-guided nuclease, that relies upon the use of imperfect target sites encoded within the Cas9/gRNA expression system itself. Cas9 binding (without cleavage) has been shown by numerous studies to be effective at regulating gene expression. Most studies use the nuclease-dead version of Cas9 to prevent cleavage activity, however a system which allows for both cleavage and self-regulation would be highly desirable.

By using engineered sequences that correspond to partial target sites, the cutting and binding activities of Cas9 can be separated; partial sequence complementarity allows Cas9 to bind without DNA cleavage. Using this binding propensity, Cas9 can be directed back to regulating its own expression. For SpCas9, sites that are generally below 17nt of complementarity do not result in cleavage, and even single mismatches can result in no cleavage with high-fidelity or high-specificity Cas9 mutants.

Importantly, all of this regulation occurs with minimal sequence changes, and without additional binding factors, fusions, or other proteins, keeping the expression cassette size small enough to be delivered by AAV.

Methods

Plasmid construction: The GFP reporter plasmids were constructed by Gibson Assembly (New England Biolabs, Ipswich, Mass.) (Gibson et al. (2009) *Nature Methods* 6:343-345) with slight modifications.

Human embryonic kidney (HEK) cell line 293T (Life Technologies, Grand Island, N.Y.) was maintained at 37° C. with 5% $CO_2$/20% $O_2$ in Dulbecco's modified Eagle's Medium (DMEM) (Invitrogen) supplemented with 10% fetal bovine serum (heat-inactivated) (Gibco, Life Technologies, Grand Island, N.Y.) and 2 mM GlutaMAX (Invitrogen).

N2A cell line (Life Technologies, Grand Island, N.Y.) was maintained at 37° C. with 5% $CO_2$/20% $O_2$ in Dulbecco's modified Eagle's Medium (DMEM) (Invitrogen) supplemented with 10% fetal bovine serum (Gibco, Life Technologies, Grand Island, N.Y.) and 2 mM GlutaMAX (Invitrogen).

Cells were transfected (Lipofectamine 3000) with each construct. GFP expression was analyzed using flow cytometry.

```
mm079 target sequence:
                                           (SEQ ID NO: 28)
GAAGAAGGTTCGAGATCTCA mm079 genomic target site:
                                           (SEQ ID NO: 29)
GAAGAAGGTTCGAGATCTCAAGG Auto1 site:
                                           (SEQ ID NO: 30)
GTTCGAGATCTCAGGGAAT Auto2 site:
                                           (SEQ ID NO: 31)
GTTCGAGATCTCAGGGTTT H1_wt:
                                           (SEQ ID NO: 32)
GGAATTCGAACGCTGACGTCATCAACCCGCTCCAAGGAATCGCGGGCCCA

GTGTCACTAGGCGGGAACACCCAGCGCGCGTGCGCCCTGGCAGGAAGATG

GCTGTGAGGGACAGGGGAGTGGCGCCCTGCAATATTTGCATGTCGCTATG

TGTTCTGGGAAATCACCATAAACGTGAAATGTCTTTGGATTTGGGAATCT

TATAAGTTCTGTATGAGACCA CTTTTTCCC

H1_Auto1:
                                           (SEQ ID NO: 33)
GGAATTCGAACGCTGACGTCATCAACCCGCTCCAAGGAATCGCGGGCCCA

GTGTCACTAGGCGGGAACACCCAGCGCGCGTGCGCCCTGGCAGGAAGATG

GCTGTGAGGGACAGGGGAGTGGCGCCCTGCAATATTTGCATGTCGCTATG

TGTTCTGGGAAATCACCATAAACGTGAAAGTTCGAGATCTCAGGGAATCT

TATAAGTTCTGTATGAGACC ACTTTTTCCC

H1_Auto2:
                                           (SEQ ID NO: 34)
GGAATTCGAACGCTGACGTCATCAACCCGCTCCAAGGAATCGCGGGCCCA

GTGTCACTAGGCGGGAACACCCAGCGCGCGTGCGCCCTGGCAGGAAGATG

GCTGTGAGGGACAGGGGAGTGGCGCCCTGCAATATTTGCATGTCGCTATG

TGTTCTGGGAAATCACCATAAACGTGAAATGTCTTTGGATTTGGGAATCT
```

Example 5

Methionine (Met) followed by a glycine (Gly), proline (Pro), serine (Ser), threonine (Thr), alanine (Ala), valine (Val), or cysteine (Cys) are processed by Methionineaminopeptidases, which cleave off the N-terminal met (FIG. 1A). The identity of the position 2 amino-acid then either stabilizes or destabilizes the entire protein. Thus, by changing the identity of the second amino acid, one can alter some proteins half-life through Met-aminopeptidases.

While differing from organism to organism, and variable between proteins, the N-end rule serves as an estimation of a proteins half-life within a cell (FIG. 17B). Protein levels are modulated through the ubiquitin (Ub) proteolytic system. Ubiquitin is a highly conserved protein of 76 amino acids that is typically associated with protein degradation; Ub molecules are conjugated to target proteins marking those proteins for destruction by the proteasome.

Linear poly-ubiquitin is recognized in the cell by deubiquitin enzymes which cleave the individual Ub peptides. This process can be co-opted to generate specific N-terminal residues by fusing Ub to the N-terminus of any protein (FIG. 18). Once inside the cell, deubiquitin enzymes recognize and cleave the Ub moiety, releasing the fused protein. This process can be used to generate precise N-terminal amino-acid residues on a given protein, the identity of which determines the proteins half-life.

Generically, controlling the expression of either the RNA-guided nuclease or the guide RNA can modulate the entire holoenzyme complex; for the CRISPR-Cas9 system, this can be done either by regulating the levels of Cas9 or the gRNA. Furthermore, simple changes in the N-terminal amino acids, either through Met-aminopeptidases, deubiquintation, or alternative methods, can accomplish this regulation (FIG. 19A).

Reducing Cas9 half-life can be beneficial towards reducing the potential for off-target effects. In a clinical setting, this would be highly significant with viral delivery methods, such as AAV, which are characterized by prolonged or life-time expression. Conversely, with inefficient methods of delivery, increased protein half-life could be desirable or necessary to elicit an effect. In various diverse settings, the ability to tune the levels of the nuclease would be highly desirable. Additionally, this approach to regulation is simple and can be used in conjunction with other forms of regulation, such as degrons, inducible degrons, or split variants of RNA-guided nucleases.

Here, it was shown that levels of Cas9, an RNA-guided nuclease, can be modulated by the identity of the N-terminal amino acid, by as much as 8-10-fold, a significant range of expression for a nuclease (FIG. 19A). Also shown is how commonly used 2A peptides can be leveraged to modulate protein levels in the cell (FIG. 20).

Methods

Plasmid construction: To generate the ubiquitin fused Cas9 proteins, ubiquitin was fused to the N-terminus of Cas9 using Gibson Assembly (New England Biolabs, Ipswich, Mass.) (Gibson et al. (2009) *Nature Methods* 6:343-345) with slight modifications. Briefly, primers encoding all 20 amino acids were used to amplify a gBlock encoding ubiquitin, which was then cloned in-frame with Cas9. All constructs were sequenced verified.

Human embryonic kidney (HEK) cell line 293T (Life Technologies, Grand Island, N.Y.) was maintained at 37° C. with 5% $CO_2$/20% $O_2$ in Dulbecco's modified Eagle's Medium (DMEM) (Invitrogen) supplemented with 10% fetal bovine serum (Gibco, Life Technologies, Grand Island, N.Y.) and 2 mM GlutaMAX (Invitrogen).

Cells were transfected with each construct at either 2000 ng, 500 ng, or 125 ng. 48 hrs later cells were harvested for protein and then analyzed on a Simple Simon machine for Cas9 expression or GAPDH for control. The ratios were used to normalize values and to determine protein stability.

1. Tasaki T et al. (2012) *Annu Rev Biochem.* 81:261-89.
2. Varshaysky A et al. (2011) *Protein Sci.* 20(8):1298-345.
3. Bachmair A et al. (1986) *Science.* 234(4773):179-86.

TABLE 1

Approximate half-life of proteins in mammalian cells based on the N-terminal residue

| | |
|---|---|
| Val | 100 hr |
| Met | 30 hr |
| Gly | 30 hr |
| Pro | 20 hr |
| Ile | 20 hr |
| Thr | 7.2 hr |
| Leu | 5.5 hr |
| Ala | 4.4 hr |
| His | 3.5 hr |
| Trp | 2.8 hr |
| Tyr | 2.8 hr |
| Ser | 1.9 hr |
| Asn | 1.4 hr |
| Lys | 1.3 hr |
| Cys | 1.2 hr |
| Asp | 1.1 hr |
| Phe | 1.1 hr |
| Glu | 1.0 hr |
| Arg | 1.0 hr |
| Gln | 0.8 hr |

TABLE 2

List of commonly used 2A sequences

P2A: GSGATNFSLLKQAGDVEENPGP (SEQ ID NO: 35)

T2A: GSGEGRGSLLTCGDVEENPGP (SEQ ID NO: 36)

E2A: GSGQCTNYALLKLAGDVESNPGP (SEQ ID NO: 37)

F2A: GSGVKQTLNFDLLKLAGDVESNPGP (SEQ ID NO: 38)

Protein Sequences

Ub:Val::Cas9

(SEQ ID NO: 39)

MQIFVKTLTGKTITLEVEPSDTIENVKAKIQDKEGIPPDQQRLIFAGKQLEDGRTLSD

YNIQKESTLHLVLRLRGG<u>V</u>DKKYSIGLDIGTNSVGWAVITDEYKVPSKKFKVLGNT

DRHSIKKNLIGALLFDSGETAEATRLKRTARRRYTRRKNRICYLQEIFSNEMAKVD

DSFFHRLEESFLVEEDKKHERHPIFGNIVDEVAYHEKYPTIYHLRKKLVDSTDKADL

RLIYLALAHMIKFRGHFLIEGDLNPDNSDVDKLFIQLVQTYNQLFEENPINASGVDA

KAILSARLSKSRRLENLIAQLPGEKKNGLFGNLIALSLGLTPNFKSNFDLAEDAKLQ

LSKDTYDDDLDNLLAQIGDQYADLFLAAKNLSDAILLSDILRVNTEITKAPLSASMI

KRYDEHHQDLTLLKALVRQQLPEKYKEIFFDQSKNGYAGYIDGGASQEEFYKFIKP

ILEKMDGTEELLVKLNREDLLRKQRTFDNGSIPHQIHLGELHAILRRQEDFYPFLKD

NREKIEKILTFRIPYYVGPLARGNSRFAWMTRKSEETITPWNFEEVVDKGASAQSFI

ERMTNFDKNLPNEKVLPKHSLLYEYFTVYNELTKVKYVTEGMRKPAFLSGEQKKA

IVDLLFKTNRKVTVKQLKEDYFKKIECFDSVEISGVEDRFNASLGTYHDLLKIIKDK

DFLDNEENEDILEDIVLTLTLFEDREMIEERLKTYAHLFDDKVMKQLKRRRYTGWG

RLSRKLINGIRDKQSGKTILDFLKSDGFANRNFMQLIHDDSLTFKEDIQKAQVSGQG

DSLHEHIANLAGSPAIKKGILQTVKVVDELVKVMGRHKPENIVIEMARENQTTQKG

QKNSRERMKRIEEGIKELGSQILKEHPVENTQLQNEKLYLYYLQNGRDMYVDQEL

```
DINRLSDYDVDHIVPQSFLKDDSIDNKVLTRSDKNRGKSDNVPSEEVVKK

MKNYWRQLLNAKLITQRKFDNLTKAERGGLSELDKAGFIKRQLVETRQITKHVAQ

ILDSRMNTKYDENDKLIREVKVITLKSKLVSDFRKDFQFYKVREINNYHHAHDAYL

NAVVGTALIKKYPKLESEFVYGDYKVYDVRKMIAKSEQEIGKATAKYFFYSNIMN

FFKTEITLANGEIRKRPLIETNGETGEIVWDKGRDFATVRKVLSMPQVNIVKKTEVQ

TGGFSKESILPKRNSDKLIARKKDWDPKKYGGFDSPTVAYSVLVVAKVEKGKSKK

LKSVKELLGITIMERSSFEKNPIDFLEAKGYKEVKKDLIIKLPKYSLFELENGRKRML

ASAGELQKGNELALPSKYVNFLYLASHYEKLKGSPEDNEQKQLFVEQHKHYLDEII

EQISEFSKRVILADANLDKVLSAYNKHRDKPIREQAENIIHLFTLTNLGAPAAFKYF

DTTIDRKRYTSTKEVLDATLIHQSITGLYETRIDLSQLGGDSRADPKKKRKV

Ub:Met::Cas9
                                                  (SEQ ID NO: 40)
MQIFVKTLTGKTITLEVEPSDTIENVKAKIQDKEGIPPDQQRLIFAGKQLEDGRTLSD

YNIQKESTLHLVLRLRGGMDKKYSIGLDIGTNSVGWAVITDEYKVPSKKFKVLGNT

DRHSIKKNLIGALLFDSGETAEATRLKRTARRRYTRRKNRICYLQEIFSNEMAKVD

DSFFHRLEESFLVEEDKKHERHPIFGNIVDEVAYHEKYPTIYHLRKKLVDSTDKADL

RLIYLALAHMIKFRGHFLIEGDLNPDNSDVDKLFIQLVQTYNQLFEENPINASGVDA

KAILSARLSKSRRLENLIAQLPGEKKNGLFGNLIALSLGLTPNFKSNFDLAEDAKLQ

LSKDTYDDDLDNLLAQIGDQYADLFLAAKNLSDAILLSDILRVNTEITKAPLSASMI

KRYDEHHQDLTLLKALVRQQLPEKYKEIFFDQSKNGYAGYIDGGASQEEFYKFIKP

ILEKMDGTEELLVKLNREDLLRKQRTFDNGSIPHQIHLGELHAILRRQEDFYPFLKD

NREKIEKILTFRIPYYVGPLARGNSRFAWMTRKSEETITPWNFEEVVDKGASAQSFI

ERMTNFDKNLPNEKVLPKHSLLYEYFTVYNELTKVKYVTEGMRKPAFLSGEQKKA

IVDLLFKTNRKVTVKQLKEDYFKKIECFDSVEISGVEDRFNASLGTYHDLLKIIKDK

DFLDNEENEDILEDIVLTLTLFEDREMIEERLKTYAHLFDDKVMKQLKRRRYTGWG

RLSRKLINGIRDKQSGKTILDFLKSDGFANRNFMQLIHDDSLTFKEDIQKAQVSGQG

DSLHEHIANLAGSPAIKKGILQTVKVVDELVKVMGRHKPENIVIEMARENQTTQKG

QKNSRERMKRIEEGIKELGSQILKEHPVENTQLQNEKLYLYYLQNGRDMYVDQEL

DINRLSDYDVDHIVPQSFLKDDSIDNKVLTRSDKNRGKSDNVPSEEVVKKMKNYW

RQLLNAKLITQRKFDNLTKAERGGLSELDKAGFIKRQLVETRQITKHVAQILDSRM

NTKYDENDKLIREVKVITLKSKLVSDFRKDFQFYKVREINNYHHAHDAYLNAVVG

TALIKKYPKLESEFVYGDYKVYDVRKMIAKSEQEIGKATAKYFFYSNIMNFFKTEIT

LANGEIRKRPLIETNGETGEIVWDKGRDFATVRKVLSMPQVNIVKKTEVQTGGFSK

ESILPKRNSDKLIARKKDWDPKKYGGFDSPTVAYSVLVVAKVEKGKSKKLKSVKE

LLGITIMERSSFEKNPIDFLEAKGYKEVKKDLIIKLPKYSLFELENGRKRMLASAGEL

QKGNELALPSKYVNFLYLASHYEKLKGSPEDNEQKQLFVEQHKHYLDEIIEQISEFS

KRVILADANLDKVLSAYNKHRDKPIREQAENIIHLFTLTNLGAPAAFKYFDTTIDRK

RYTSTKEVLDATLIHQSITGLYETRIDLSQLGGDSRADPKKKRKV

Ub:Gly::Cas9
                                                  (SEQ ID NO: 41)
MQIFVKTLTGKTITLEVEPSDTIENVKAKIQDKEGIPPDQQRLIFAGKQLEDGRTLSD

YNIQKESTLHLVLRLRGGGDKKYSIGLDIGTNSVGWAVITDEYKVPSKKFKVLGNT

DRHSIKKNLIGALLFDSGETAEATRLKRTARRRYTRRKNRICYLQEIFSNEMAKVD
```

-continued

DSFFHRLEESFLVEEDKKHERHPIFGNIVDEVAYHEKYPTIYHLRKKLVDSTDKADL

RLIYLALAHMIKFRGHFLIEGDLNPDNSDVDKLFIQLVQTYNQLFEENPINASGVDA

KAILSARLSKSRRLENLIAQLPGEKKNGLFGNLIALSLGLTPNFKSNFDLAEDAKLQ

LSKDTYDDDLDNLLAQIGDQYADLFLAAKNLSDAILLSDILRVNTEITKAPLSASMI

KRYDEHHQDLTLLKALVRQQLPEKYKEIFFDQSKNGYAGYIDGGASQEEFYKFIKP

ILEKMDGTEELLVKLNREDLLRKQRTFDNGSIPHQIHLGELHAILRRQEDFYPFLKD

NREKIEKILTFRIPYYVGPLARGNSRFAWMTRKSEETITPWNFEEVVDKGASAQSFI

ERMTNFDKNLPNEKVLPKHSLLYEYFTVYNELTKVKYVTEGMRKPAFLSGEQKKA

IVDLLFKTNRKVTVKQLKEDYFKKIECFDSVEISGVEDRFNASLGTYHDLLKIIKDK

DFLDNEENEDILEDIVLTLTLFEDREMIEERLKTYAHLFDDKVMKQLKRRRYTGWG

RLSRKLINGIRDKQSGKTILDFLKSDGFANRNFMQLIHDDSLTFKEDIQKAQVSGQG

DSLHEHIANLAGSPAIKKGILQTVKVVDELVKVMGRHKPENIVIEMARENQTTQKG

QKNSRERMKRIEEGIKELGSQILKEHPVENTQLQNEKLYLYYLQNGRDMYVDQEL

DINRLSDYDVDHIVPQSFLKDDSIDNKVLTRSDKNRGKSDNVPSEEVVKK

MKNYWRQLLNAKLITQRKFDNLTKAERGGLSELDKAGFIKRQLVETRQITKHVAQ

ILDSRMNTKYDENDKLIREVKVITLKSKLVSDFRKDFQFYKVREINNYHHAHDAYL

NAVVGTALIKKYPKLESEFVYGDYKVYDVRKMIAKSEQEIGKATAKYFFYSNIMN

FFKTEITLANGEIRKRPLIETNGETGEIVWDKGRDFATVRKVLSMPQVNIVKKTEVQ

TGGFSKESILPKRNSDKLIARKKDWDPKKYGGFDSPTVAYSVLVVAKVEKGKSKK

LKSVKELLGITIMERSSFEKNPIDFLEAKGYKEVKKDLIIKLPKYSLFELENGRKRML

ASAGELQKGNELALPSKYVNFLYLASHYEKLKGSPEDNEQKQLFVEQHKHYLDEII

EQISEFSKRVILADANLDKVLSAYNKHRDKPIREQAENIIHLFTLTNLGAPAAFKYF

DTTIDRKRYTSTKEVLDATLIHQSITGLYETRIDLSQLGGDSRADPKKKRKV

Ub:Pro::Cas9

(SEQ ID NO: 42)

MQIFVKTLTGKTITLEVEPSDTIENVKAKIQDKEGIPPDQQRLIFAGKQLEDGRTLSD

YNIQKESTLHLVLRLRGGPDKKYSIGLDIGTNSVGWAVITDEYKVPSKKFKVLGNT

DRHSIKKNLIGALLFDSGETAEATRLKRTARRRYTRRKNRICYLQEIFSNEMAKVD

DSFFHRLEESFLVEEDKKHERHPIFGNIVDEVAYHEKYPTIYHLRKKLVDSTDKADL

RLIYLALAHMIKFRGHFLIEGDLNPDNSDVDKLFIQLVQTYNQLFEENPINASGVDA

KAILSARLSKSRRLENLIAQLPGEKKNGLFGNLIALSLGLTPNFKSNFDLAEDAKLQ

LSKDTYDDDLDNLLAQIGDQYADLFLAAKNLSDAILLSDILRVNTEITKAPLSASMI

KRYDEHHQDLTLLKALVRQQLPEKYKEIFFDQSKNGYAGYIDGGASQEEFYKFIKP

ILEKMDGTEELLVKLNREDLLRKQRTFDNGSIPHQIHLGELHAILRRQEDFYPFLKD

NREKIEKILTFRIPYYVGPLARGNSRFAWMTRKSEETITPWNFEEVVDKGASAQSFI

ERMTNFDKNLPNEKVLPKHSLLYEYFTVYNELTKVKYVTEGMRKPAFLSGEQKKA

IVDLLFKTNRKVTVKQLKEDYFKKIECFDSVEISGVEDRFNASLGTYHDLLKIIKDK

DFLDNEENEDILEDIVLTLTLFEDREMIEERLKTYAHLFDDKVMKQLKRRRYTGWG

RLSRKLINGIRDKQSGKTILDFLKSDGFANRNFMQLIHDDSLTFKEDIQKAQVSGQG

DSLHEHIANLAGSPAIKKGILQTVKVVDELVKVMGRHKPENIVIEMARENQTTQKG

QKNSRERMKRIEEGIKELGSQILKEHPVENTQLQNEKLYLYYLQNGRDMYVDQEL

DINRLSDYDVDHIVPQSFLKDDSIDNKVLTRSDKNRGKSDNVPSEEVVKK

-continued

MKNYWRQLLNAKLITQRKFDNLTKAERGGLSELDKAGFIKRQLVETRQITKHVAQ

ILDSRMNTKYDENDKLIREVKVITLKSKLVSDFRKDFQFYKVREINNYHHAHDAYL

NAVVGTALIKKYPKLESEFVYGDYKVYDVRKMIAKSEQEIGKATAKYFFYSNIMN

FFKTEITLANGEIRKRPLIETNGETGEIVWDKGRDFATVRKVLSMPQVNIVKKTEVQ

TGGFSKESILPKRNSDKLIARKKDWDPKKYGGFDSPTVAYSVLVVAKVEKGKSKK

LKSVKELLGITIMERSSFEKNPIDFLEAKGYKEVKKDLIIKLPKYSLFELENGRKRML

ASAGELQKGNELALPSKYVNFLYLASHYEKLKGSPEDNEQKQLFVEQHKHYLDEII

EQISEFSKRVILADANLDKVLSAYNKHRDKPIREQAENIIHLFTLTNLGAPAAFKYF

DTTIDRKRYTSTKEVLDATLIHQSITGLYETRIDLSQLGGDSRADPKKKRKV

Ub:Ile::Cas9

(SEQ ID NO: 43)

MQIFVKTLTGKTITLEVEPSDTIENVKAKIQDKEGIPPDQQRLIFAGKQLEDGRTLSD

YNIQKESTLHLVLRLRGGIDKKYSIGLDIGTNSVGWAVITDEYKVPSKKFKVLGNT

DRHSIKKNLIGALLFDSGETAEATRLKRTARRRYTRRKNRICYLQEIFSNEMAKVD

DSFFHRLEESFLVEEDKKHERHPIFGNIVDEVAYHEKYPTIYHLRKKLVDSTDKADL

RLIYLALAHMIKFRGHFLIEGDLNPDNSDVDKLFIQLVQTYNQLFEENPINASGVDA

KAILSARLSKSRRLENLIAQLPGEKKNGLFGNLIALSLGLTPNFKSNFDLAEDAKLQ

LSKDTYDDDLDNLLAQIGDQYADLFLAAKNLSDAILLSDILRVNTEITKAPLSASMI

KRYDEHHQDLTLLKALVRQQLPEKYKEIFFDQSKNGYAGYIDGGASQEEFYKFIKP

ILEKMDGTEELLVKLNREDLLRKQRTFDNGSIPHQIHLGELHAILRRQEDFYPFLKD

NREKIEKILTFRIPYYVGPLARGNSRFAWMTRKSEETITPWNFEEVVDKGASAQSFI

ERMTNFDKNLPNEKVLPKHSLLYEYFTVYNELTKVKYVTEGMRKPAFLSGEQKKA

IVDLLFKTNRKVTVKQLKEDYFKKIECFDSVEISGVEDRFNASLGTYHDLLKIIKDK

DFLDNEENEDILEDIVLTLTLFEDREMIEERLKTYAHLFDDKVMKQLKRRRYTGWG

RLSRKLINGIRDKQSGKTILDFLKSDGFANRNFMQLIHDDSLTFKEDIQKAQVSGQG

DSLHEHIANLAGSPAIKKGILQTVKVVDELVKVMGRHKPENIVIEMARENQTTQKG

QKNSRERMKRIEEGIKELGSQILKEHPVENTQLQNEKLYLYYLQNGRDMYVDQEL

DINRLSDYDVDHIVPQSFLKDDSIDNKVLTRSDKNRGKSDNVPSEEVVKK

MKNYWRQLLNAKLITQRKFDNLTKAERGGLSELDKAGFIKRQLVETRQITKHVAQ

ILDSRMNTKYDENDKLIREVKVITLKSKLVSDFRKDFQFYKVREINNYHHAHDAYL

NAVVGTALIKKYPKLESEFVYGDYKVYDVRKMIAKSEQEIGKATAKYFFYSNIMN

FFKTEITLANGEIRKRPLIETNGETGEIVWDKGRDFATVRKVLSMPQVNIVKKTEVQ

TGGFSKESILPKRNSDKLIARKKDWDPKKYGGFDSPTVAYSVLVVAKVEKGKSKK

LKSVKELLGITIMERSSFEKNPIDFLEAKGYKEVKKDLIIKLPKYSLFELENGRKRML

ASAGELQKGNELALPSKYVNFLYLASHYEKLKGSPEDNEQKQLFVEQHKHYLDEII

EQISEFSKRVILADANLDKVLSAYNKHRDKPIREQAENIIHLFTLTNLGAPAAFKYF

DTTIDRKRYTSTKEVLDATLIHQSITGLYETRIDLSQLGGDSRADPKKKRKV

Ub:Thr::Cas9

(SEQ ID NO: 44)

MQIFVKTLTGKTITLEVEPSDTIENVKAKIQDKEGIPPDQQRLIFAGKQLEDGRTLSD

YNIQKESTLHLVLRLRGGTDKKYSIGLDIGTNSVGWAVITDEYKVPSKKFKVLGNT

DRHSIKKNLIGALLFDSGETAEATRLKRTARRRYTRRKNRICYLQEIFSNEMAKVD

DSFEHRLEESFLVEEDKKHERHPIFGNIVDEVAYHEKYPTIYHLRKKLVDSTDKADL

-continued

RLIYLALAHMIKFRGHFLIEGDLNPDNSDVDKLFIQLVQTYNQLFEENPINASGVDA

KAILSARLSKSRRLENLIAQLPGEKKNGLFGNLIALSLGLTPNFKSNFDLAEDAKLQ

LSKDTYDDDLDNLLAQIGDQYADLFLAAKNLSDAILLSDILRVNTEITKAPLSASMI

KRYDEHHQDLTLLKALVRQQLPEKYKEIFFDQSKNGYAGYIDGGASQEEFYKFIKP

ILEKMDGTEELLVKLNREDLLRKQRTFDNGSIPHQIHLGELHAILRRQEDFYPFLKD

NREKIEKILTFRIPYYVGPLARGNSRFAWMTRKSEETITPWNFEEVVDKGASAQSFI

ERMTNFDKNLPNEKVLPKHSLLYEYFTVYNELTKVKYVTEGMRKPAFLSGEQKKA

IVDLLFKTNRKVTVKQLKEDYFKKIECFDSVEISGVEDRFNASLGTYHDLLKIIKDK

DFLDNEENEDILEDIVLTLTLFEDREMIEERLKTYAHLFDDKVMKQLKRRRYTGWG

RLSRKLINGIRDKQSGKTILDFLKSDGFANRNFMQLIHDDSLTFKEDIQKAQVSGQG

DSLHEHIANLAGSPAIKKGILQTVKVVDELVKVMGRHKPENIVIEMARENQTTQKG

QKNSRERMKRIEEGIKELGSQILKEHPVENTQLQNEKLYLYYLQNGRDMYVDQEL

DINRLSDYDVDHIVPQSFLKDDSIDNKVLTRSDKNRGKSDNVPSEEVVKK

MKNYWRQLLNAKLITQRKFDNLTKAERGGLSELDKAGFIKRQLVETRQITKHVAQ

ILDSRMNTKYDENDKLIREVKVITLKSKLVSDFRKDFQFYKVREINNYHHAHDAYL

NAVVGTALIKKYPKLESEFVYGDYKVYDVRKMIAKSEQEIGKATAKYFFYSNIMN

FFKTEITLANGEIRKRPLIETNGETGEIVWDKGRDFATVRKVLSMPQVNIVKKTEVQ

TGGFSKESILPKRNSDKLIARKKDWDPKKYGGFDSPTVAYSVLVVAKVEKGKSKK

LKSVKELLGITIMERSSFEKNPIDFLEAKGYKEVKKDLIIKLPKYSLFELENGRKRML

ASAGELQKGNELALPSKYVNFLYLASHYEKLKGSPEDNEQKQLFVEQHKHYLDEII

EQISEFSKRVILADANLDKVLSAYNKHRDKPIREQAENIIHLFTLTNLGAPAAFKYF

DTTIDRKRYTSTKEVLDATLIHQSITGLYETRIDLSQLGGDSRADPKKKRKV

Ub:Leu::Cas9
(SEQ ID NO: 45)
MQIFVKTLTGKTITLEVEPSDTIENVKAKIQDKEGIPPDQQRLIFAGKQLEDGRTLSD

YNIQKESTLHLVLRLRGGLDKKYSIGLDIGTNSVGWAVITDEYKVPSKKFKVLGNT

DRHSIKKNLIGALLFDSGETAEATRLKRTARRRYTRRKNRICYLQEIFSNEMAKVD

DSFFHRLEESFLVEEDKKHERHPIFGNIVDEVAYHEKYPTIYHLRKKLVDSTDKADL

RLIYLALAHMIKFRGHFLIEGDLNPDNSDVDKLFIQLVQTYNQLFEENPINASGVDA

KAILSARLSKSRRLENLIAQLPGEKKNGLFGNLIALSLGLTPNFKSNFDLAEDAKLQ

LSKDTYDDDLDNLLAQIGDQYADLFLAAKNLSDAILLSDILRVNTEITKAPLSASMI

KRYDEHHQDLTLLKALVRQQLPEKYKEIFFDQSKNGYAGYIDGGASQEEFYKFIKP

ILEKMDGTEELLVKLNREDLLRKQRTFDNGSIPHQIHLGELHAILRRQEDFYPFLKD

NREKIEKILTFRIPYYVGPLARGNSRFAWMTRKSEETITPWNFEEVVDKGASAQSFI

ERMTNFDKNLPNEKVLPKHSLLYEYFTVYNELTKVKYVTEGMRKPAFLSGEQKKA

IVDLLFKTNRKVTVKQLKEDYFKKIECFDSVEISGVEDRFNASLGTYHDLLKIIKDK

DFLDNEENEDILEDIVLTLTLFEDREMIEERLKTYAHLFDDKVMKQLKRRRYTGWG

RLSRKLINGIRDKQSGKTILDFLKSDGFANRNFMQLIHDDSLTFKEDIQKAQVSGQG

DSLHEHIANLAGSPAIKKGILQTVKVVDELVKVMGRHKPENIVIEMARENQTTQKG

QKNSRERMKRIEEGIKELGSQILKEHPVENTQLQNEKLYLYYLQNGRDMYVDQEL

DINRLSDYDVDHIVPQSFLKDDSIDNKVLTRSDKNRGKSDNVPSEEVVKK

MKNYWRQLLNAKLITQRKFDNLTKAERGGLSELDKAGFIKRQLVETRQITKHVAQ

ILDSRMNTKYDENDKLIREVKVITLKSKLVSDFRKDFQFYKVREINNYHHAHDAYL

NAVVGTALIKKYPKLESEFVYGDYKVYDVRKMIAKSEQEIGKATAKYFFYSNIMN

FFKTEITLANGEIRKRPLIETNGETGEIVWDKGRDFATVRKVLSMPQVNIVKKTEVQ

TGGFSKESILPKRNSDKLIARKKDWDPKKYGGFDSPTVAYSVLVVAKVEKGKSKK

LKSVKELLGITIMERSSFEKNPIDFLEAKGYKEVKKDLIIKLPKYSLFELENGRKRML

ASAGELQKGNELALPSKYVNFLYLASHYEKLKGSPEDNEQKQLFVEQHKHYLDEII

EQISEFSKRVILADANLDKVLSAYNKHRDKPIREQAENIIHLFTLTNLGAPAAFKYF

DTTIDRKRYTSTKEVLDATLIHQSITGLYETRIDLSQLGGDSRADPKKKRKV

Ub:Ala::Cas9
(SEQ ID NO: 46)
MQIFVKTLTGKTITLEVEPSDTIENVKAKIQDKEGIPPDQQRLIFAGKQLEDGRTLSD

YNIQKESTLHLVLRLRGGADKKYSIGLDIGTNSVGWAVITDEYKVPSKKFKVLGNT

DRHSIKKNLIGALLFDSGETAEATRLKRTARRRYTRRKNRICYLQEIFSNEMAKVD

DSFFHRLEESFLVEEDKKHERHPIFGNIVDEVAYHEKYPTIYHLRKKLVDSTDKADL

RLIYLALAHMIKFRGHFLIEGDLNPDNSDVDKLFIQLVQTYNQLFEENPINASGVDA

KAILSARLSKSRRLENLIAQLPGEKKNGLFGNLIALSLGLTPNFKSNFDLAEDAKLQ

LSKDTYDDDLDNLLAQIGDQYADLFLAAKNLSDAILLSDILRVNTEITKAPLSASMI

KRYDEHHQDLTLLKALVRQQLPEKYKEIFFDQSKNGYAGYIDGGASQEEFYKFIKP

ILEKMDGTEELLVKLNREDLLRKQRTFDNGSIPHQIHLGELHAILRRQEDFYPFLKD

NREKIEKILTFRIPYYVGPLARGNSRFAWMTRKSEETITPWNFEEVVDKGASAQSFI

ERMTNFDKNLPNEKVLPKHSLLYEYFTVYNELTKVKYVTEGMRKPAFLSGEQKKA

IVDLLFKTNRKVTVKQLKEDYFKKIECFDSVEISGVEDRFNASLGTYHDLLKIIKDK

DFLDNEENEDILEDIVLTLTLFEDREMIEERLKTYAHLFDDKVMKQLKRRRYTGWG

RLSRKLINGIRDKQSGKTILDFLKSDGFANRNFMQLIHDDSLTFKEDIQKAQVSGQG

DSLHEHIANLAGSPAIKKGILQTVKVVDELVKVMGRHKPENIVIEMARENQTTQKG

QKNSRERMKRIEEGIKELGSQILKEHPVENTQLQNEKLYLYYLQNGRDMYVDQEL

DINRLSDYDVDHIVPQSFLKDDSIDNKVLTRSDKNRGKSDNVPSEEVVKK

MKNYWRQLLNAKLITQRKFDNLTKAERGGLSELDKAGFIKRQLVETRQITKHVAQ

ILDSRMNTKYDENDKLIREVKVITLKSKLVSDFRKDFQFYKVREINNYHHAHDAYL

NAVVGTALIKKYPKLESEFVYGDYKVYDVRKMIAKSEQEIGKATAKYFFYSNIMN

FFKTEITLANGEIRKRPLIETNGETGEIVWDKGRDFATVRKVLSMPQVNIVKKTEVQ

TGGFSKESILPKRNSDKLIARKKDWDPKKYGGFDSPTVAYSVLVVAKVEKGKSKK

LKSVKELLGITIMERSSFEKNPIDFLEAKGYKEVKKDLIIKLPKYSLFELENGRKRML

ASAGELQKGNELALPSKYVNFLYLASHYEKLKGSPEDNEQKQLFVEQHKHYLDEII

EQISEFSKRVILADANLDKVLSAYNKHRDKPIREQAENIIHLFTLTNLGAPAAFKYF

DTTIDRKRYTSTKEVLDATLIHQSITGLYETRIDLSQLGGDSRADPKKKRKV

Ub:His::Cas9
(SEQ ID NO: 47)
MQIFVKTLTGKTITLEVEPSDTIENVKAKIQDKEGIPPDQQRLIFAGKQLEDGRTLSD

YNIQKESTLHLVLRLRGGHDKKYSIGLDIGTNSVGWAVITDEYKVPSKKFKVLGNT

DRHSIKKNLIGALLFDSGETAEATRLKRTARRRYTRRKNRICYLQEIFSNEMAKVD

DSFFHRLEESFLVEEDKKHERHPIFGNIVDEVAYHEKYPTIYHLRKKLVDSTDKADL

RLIYLALAHMIKFRGHFLIEGDLNPDNSDVDKLFIQLVQTYNQLFEENPINASGVDA

-continued

KAILSARLSKSRRLENLIAQLPGEKKNGLFGNLIALSLGLTPNFKSNFDLAEDAKLQ

LSKDTYDDDLDNLLAQIGDQYADLFLAAKNLSDAILLSDILRVNTEITKAPLSASMI

KRYDEHHQDLTLLKALVRQQLPEKYKEIFFDQSKNGYAGYIDGGASQEEFYKFIKP

ILEKMDGTEELLVKLNREDLLRKQRTFDNGSIPHQIHLGELHAILRRQEDFYPFLKD

NREKIEKILTFRIPYYVGPLARGNSRFAWMTRKSEETITPWNFEEVVDKGASAQSFI

ERMTNFDKNLPNEKVLPKHSLLYEYFTVYNELTKVKYVTEGMRKPAFLSGEQKKA

IVDLLFKTNRKVTVKQLKEDYFKKIECFDSVEISGVEDRFNASLGTYHDLLKIIKDK

DFLDNEENEDILEDIVLTLTLFEDREMIEERLKTYAHLFDDKVMKQLKRRRYTGWG

RLSRKLINGIRDKQSGKTILDFLKSDGFANRNFMQLIHDDSLTFKEDIQKAQVSGQG

DSLHEHIANLAGSPAIKKGILQTVKVVDELVKVMGRHKPENIVIEMARENQTTQKG

QKNSRERMKRIEEGIKELGSQILKEHPVENTQLQNEKLYLYYLQNGRDMYVDQEL

DINRLSDYDVDHIVPQSFLKDDSIDNKVLTRSDKNRGKSDNVPSEEVVKK

MKNYWRQLLNAKLITQRKFDNLTKAERGGLSELDKAGFIKRQLVETRQITKHVAQ

ILDSRMNTKYDENDKLIREVKVITLKSKLVSDFRKDFQFYKVREINNYHHAHDAYL

NAVVGTALIKKYPKLESEFVYGDYKVYDVRKMIAKSEQEIGKATAKYFFYSNIMN

FFKTEITLANGEIRKRPLIETNGETGEIVWDKGRDFATVRKVLSMPQVNIVKKTEVQ

TGGFSKESILPKRNSDKLIARKKDWDPKKYGGFDSPTVAYSVLVVAKVEKGKSKK

LKSVKELLGITIMERSSFEKNPIDFLEAKGYKEVKKDLIIKLPKYSLFELENGRKRML

ASAGELQKGNELALPSKYVNFLYLASHYEKLKGSPEDNEQKQLFVEQHKHYLDEII

EQISEFSKRVILADANLDKVLSAYNKHRDKPIREQAENIIHLFTLTNLGAPAAFKYF

DTTIDRKRYTSTKEVLDATLIHQSITGLYETRIDLSQLGGDSRADPKKKRKV

Ub:Trp::Cas9
(SEQ ID NO: 48)
MQIFVKTLTGKTITLEVEPSDTIENVKAKIQDKEGIPPDQQRLIFAGKQLEDGRTLSD

YNIQKESTLHLVLRLRGGWDKKYSIGLDIGTNSVGWAVITDEYKVPSKKFKVLGN

TDRHSIKKNLIGALLFDSGETAEATRLKRTARRRYTRRKNRICYLQEIFSNEMAKVD

DSFFHRLEESFLVEEDKKHERHPIFGNIVDEVAYHEKYPTIYHLRKKLVDSTDKADL

RLIYLALAHMIKFRGHFLIEGDLNPDNSDVDKLFIQLVQTYNQLFEENPINASGVDA

KAILSARLSKSRRLENLIAQLPGEKKNGLFGNLIALSLGLTPNFKSNFDLAEDAKLQ

LSKDTYDDDLDNLLAQIGDQYADLFLAAKNLSDAILLSDILRVNTEITKAPLSASMI

KRYDEHHQDLTLLKALVRQQLPEKYKEIFFDQSKNGYAGYIDGGASQEEFYKFIKP

ILEKMDGTEELLVKLNREDLLRKQRTFDNGSIPHQIHLGELHAILRRQEDFYPFLKD

NREKIEKILTFRIPYYVGPLARGNSRFAWMTRKSEETITPWNFEEVVDKGASAQSFI

ERMTNFDKNLPNEKVLPKHSLLYEYFTVYNELTKVKYVTEGMRKPAFLSGEQKKA

IVDLLFKTNRKVTVKQLKEDYFKKIECFDSVEISGVEDRFNASLGTYHDLLKIIKDK

DFLDNEENEDILEDIVLTLTLFEDREMIEERLKTYAHLFDDKVMKQLKRRRYTGWG

RLSRKLINGIRDKQSGKTILDFLKSDGFANRNFMQLIHDDSLTFKEDIQKAQVSGQG

DSLHEHIANLAGSPAIKKGILQTVKVVDELVKVMGRHKPENIVIEMARENQTTQKG

QKNSRERMKRIEEGIKELGSQILKEHPVENTQLQNEKLYLYYLQNGRDMYVDQEL

DINRLSDYDVDHIVPQSFLKDDSIDNKVLTRSDKNRGKSDNVPSEEVVKK

MKNYWRQLLNAKLITQRKFDNLTKAERGGLSELDKAGFIKRQLVETRQITKHVAQ

ILDSRMNTKYDENDKLIREVKVITLKSKLVSDFRKDFQFYKVREINNYHHAHDAYL

NAVVGTALIKKYPKLESEFVYGDYKVYDVRKMIAKSEQEIGKATAKYFFYSNIMN

FFKTEITLANGEIRKRPLIETNGETEIVWDKGRDFATVRKVLSMPQVNIVKKTEVQ

TGGFSKESILPKRNSDKLIARKKDWDPKKYGGFDSPTVAYSVLVVAKVEKGKSKK

LKSVKELLGITIMERSSFEKNPIDFLEAKGYKEVKKDLIIKLPKYSLFELENGRKRML

ASAGELQKGNELALPSKYVNFLYLASHYEKLKGSPEDNEQKQLFVEQHKHYLDEII

EQISEFSKRVILADANLDKVLSAYNKHRDKPIREQAENIIHLFTLTNLGAPAAFKYF

DTTIDRKRYTSTKEVLDATLIHQSITGLYETRIDLSQLGGDSRADPKKKRKV

Ub:Try::Cas9

(SEQ ID NO: 49)

MQIFVKTLTGKTITLEVEPSDTIENVKAKIQDKEGIPPDQQRLIFAGKQLEDGRTLSD

YNIQKESTLHLVLRLRGGYDKKYSIGLDIGTNSVGWAVITDEYKVPSKKFKVLGNT

DRHSIKKNLIGALLFDSGETAEATRLKRTARRRYTRRKNRICYLQEIFSNEMAKVD

DSFFHRLEESFLVEEDKKHERHPIFGNIVDEVAYHEKYPTIYHLRKKLVDSTDKADL

RLIYLALAHMIKFRGHFLIEGDLNPDNSDVDKLFIQLVQTYNQLFEENPINASGVDA

KAILSARLSKSRRLENLIAQLPGEKKNGLFGNLIALSLGLTPNFKSNFDLAEDAKLQ

LSKDTYDDDLDNLLAQIGDQYADLFLAAKNLSDAILLSDILRVNTEITKAPLSASMI

KRYDEHHQDLTLLKALVRQQLPEKYKEIFFDQSKNGYAGYIDGGASQEEFYKFIKP

ILEKMDGTEELLVKLNREDLLRKQRTFDNGSIPHQIHLGELHAILRRQEDFYPFLKD

NREKIEKILTFRIPYYVGPLARGNSRFAWMTRKSEETITPWNFEEVVDKGASAQSFI

ERMTNFDKNLPNEKVLPKHSLLYEYFTVYNELTKVKYVTEGMRKPAFLSGEQKKA

IVDLLFKTNRKVTVKQLKEDYFKKIECFDSVEISGVEDRFNASLGTYHDLLKIIKDK

DFLDNEENEDILEDIVLTLTLFEDREMIEERLKTYAHLFDDKVMKQLKRRRYTGWG

RLSRKLINGIRDKQSGKTILDFLKSDGFANRNFMQLIHDDSLTFKEDIQKAQVSGQG

DSLHEHIANLAGSPAIKKGILQTVKVVDELVKVMGRHKPENIVIEMARENQTTQKG

QKNSRERMKRIEEGIKELGSQILKEHPVENTQLQNEKLYLYYLQNGRDMYVDQEL

DINRLSDYDVDHIVPQSFLKDDSIDNKVLTRSDKNRGKSDNVPSEEVVKK

MKNYWRQLLNAKLITQRKFDNLTKAERGGLSELDKAGFIKRQLVETRQITKHVAQ

ILDSRMNTKYDENDKLIREVKVITLKSKLVSDFRKDFQFYKVREINNYHHAHDAYL

NAVVGTALIKKYPKLESEFVYGDYKVYDVRKMIAKSEQEIGKATAKYFFYSNIMN

FFKTEITLANGEIRKRPLIETNGETEIVWDKGRDFATVRKVLSMPQVNIVKKTEVQ

TGGFSKESILPKRNSDKLIARKKDWDPKKYGGFDSPTVAYSVLVVAKVEKGKSKK

LKSVKELLGITIMERSSFEKNPIDFLEAKGYKEVKKDLIIKLPKYSLFELENGRKRML

ASAGELQKGNELALPSKYVNFLYLASHYEKLKGSPEDNEQKQLFVEQHKHYLDEII

EQISEFSKRVILADANLDKVLSAYNKHRDKPIREQAENIIHLFTLTNLGAPAAFKYF

DTTIDRKRYTSTKEVLDATLIHQSITGLYETRIDLSQLGGDSRADPKKKRKV

Ub:Ser::Cas9

(SEQ ID NO: 50)

MQIFVKTLTGKTITLEVEPSDTIENVKAKIQDKEGIPPDQQRLIFAGKQLEDGRTLSD

YNIQKESTLHLVLRLRGGYDKKYSIGLDIGTNSVGWAVITDEYKVPSKKFKVLGNT

DRHSIKKNLIGALLFDSGETAEATRLKRTARRRYTRRKNRICYLQEIFSNEMAKVD

DSFFHRLEESFLVEEDKKHERHPIFGNIVDEVAYHEKYPTIYHLRKKLVDSTDKADL

RLIYLALAHMIKFRGHFLIEGDLNPDNSDVDKLFIQLVQTYNQLFEENPINASGVDA

KAILSARLSKSRRLENLIAQLPGEKKNGLFGNLIALSLGLTPNFKSNFDLAEDAKLQ

-continued

LSKDTYDDDLDNLLAQIGDQYADLFLAAKNLSDAILLSDILRVNTEITKAPLSASMI

KRYDEHHQDLTLLKALVRQQLPEKYKEIFFDQSKNGYAGYIDGGASQEEFYKFIKP

ILEKMDGTEELLVKLNREDLLRKQRTFDNGSIPHQIHLGELHAILRRQEDFYPFLKD

NREKIEKILTFRIPYYVGPLARGNSRFAWMTRKSEETITPWNFEEVVDKGASAQSFI

ERMTNFDKNLPNEKVLPKHSLLYEYFTVYNELTKVKYVTEGMRKPAFLSGEQKKA

IVDLLFKTNRKVTVKQLKEDYFKKIECFDSVEISGVEDRFNASLGTYHDLLKIIKDK

DFLDNEENEDILEDIVLTLTLFEDREMIEERLKTYAHLFDDKVMKQLKRRRYTGWG

RLSRKLINGIRDKQSGKTILDFLKSDGFANRNFMQLIHDDSLTFKEDIQKAQVSGQG

DSLHEHIANLAGSPAIKKGILQTVKVVDELVKVMGRHKPENIVIEMARENQTTQKG

QKNSRERMKRIEEGIKELGSQILKEHPVENTQLQNEKLYLYYLQNGRDMYVDQEL

DINRLSDYDVDHIVPQSFLKDDSIDNKVLTRSDKNRGKSDNVPSEEVVKK

MKNYWRQLLNAKLITQRKFDNLTKAERGGLSELDKAGFIKRQLVETRQITKHVAQ

ILDSRMNTKYDENDKLIREVKVITLKSKLVSDFRKDFQFYKVREINNYHHAHDAYL

NAVVGTALIKKYPKLESEFVYGDYKVYDVRKMIAKSEQEIGKATAKYFFYSNIMN

FFKTEITLANGEIRKRPLIETNGETGEIVWDKGRDFATVRKVLSMPQVNIVKKTEVQ

TGGFSKESILPKRNSDKLIARKKDWDPKKYGGFDSPTVAYSVLVVAKVEKGKSKK

LKSVKELLGITIMERSSFEKNPIDFLEAKGYKEVKKDLIIKLPKYSLFELENGRKRML

ASAGELQKGNELALPSKYVNFLYLASHYEKLKGSPEDNEQKQLFVEQHKHYLDEII

EQISEFSKRVILADANLDKVLSAYNKHRDKPIREQAENIIHLFTLTNLGAPAAFKYF

DTTIDRKRYTSTKEVLDATLIHQSITGLYETRIDLSQLGGDSRADPKKKRKV

Ub:Asn::Cas9
(SEQ ID NO: 51)
MQIFVKTLTGKTITLEVEPSDTIENVKAKIQDKEGIPPDQQRLIFAGKQLEDGRTLSD

YNIQKESTLHLVLRLRGGNDKKYSIGLDIGTNSVGWAVITDEYKVPSKKFKVLGNT

DRHSIKKNLIGALLFDSGETAEATRLKRTARRRYTRRKNRICYLQEIFSNEMAKVD

DSFFHRLEESFLVEEDKKHERHPIFGNIVDEVAYHEKYPTIYHLRKKLVDSTDKADL

RLIYLALAHMIKFRGHFLIEGDLNPDNSDVDKLFIQLVQTYNQLFEENPINASGVDA

KAILSARLSKSRRLENLIAQLPGEKKNGLFGNLIALSLGLTPNFKSNFDLAEDAKLQ

LSKDTYDDDLDNLLAQIGDQYADLFLAAKNLSDAILLSDILRVNTEITKAPLSASMI

KRYDEHHQDLTLLKALVRQQLPEKYKEIFFDQSKNGYAGYIDGGASQEEFYKFIKP

ILEKMDGTEELLVKLNREDLLRKQRTFDNGSIPHQIHLGELHAILRRQEDFYPFLKD

NREKIEKILTFRIPYYVGPLARGNSRFAWMTRKSEETITPWNFEEVVDKGASAQSFI

ERMTNFDKNLPNEKVLPKHSLLYEYFTVYNELTKVKYVTEGMRKPAFLSGEQKKA

IVDLLFKTNRKVTVKQLKEDYFKKIECFDSVEISGVEDRFNASLGTYHDLLKIIKDK

DFLDNEENEDILEDIVLTLTLFEDREMIEERLKTYAHLFDDKVMKQLKRRRYTGWG

RLSRKLINGIRDKQSGKTILDFLKSDGFANRNFMQLIHDDSLTFKEDIQKAQVSGQG

DSLHEHIANLAGSPAIKKGILQTVKVVDELVKVMGRHKPENIVIEMARENQTTQKG

QKNSRERMKRIEEGIKELGSQILKEHPVENTQLQNEKLYLYYLQNGRDMYVDQEL

DINRLSDYDVDHIVPQSFLKDDSIDNKVLTRSDKNRGKSDNVPSEEVVKK

MKNYWRQLLNAKLITQRKFDNLTKAERGGLSELDKAGFIKRQLVETRQITKHVAQ

ILDSRMNTKYDENDKLIREVKVITLKSKLVSDFRKDFQFYKVREINNYHHAHDAYL

NAVVGTALIKKYPKLESEFVYGDYKVYDVRKMIAKSEQEIGKATAKYFFYSNIMN

-continued

FFKTEITLANGEIRKRPLIETNGETGEIVWDKGRDFATVRKVLSMPQVNIVKKTEVQ

TGGFSKESILPKRNSDKLIARKKDWDPKKYGGFDSPTVAYSVLVVAKVEKGKSKK

LKSVKELLGITIMERSSFEKNPIDFLEAKGYKEVKKDLIIKLPKYSLFELENGRKRML

ASAGELQKGNELALPSKYVNFLYLASHYEKLKGSPEDNEQKQLFVEQHKHYLDEII

EQISEFSKRVILADANLDKVLSAYNKHRDKPIREQAENIIHLFTLTNLGAPAAFKYF

DTTIDRKRYTSTKEVLDATLIHQSITGLYETRIDLSQLGGDSRADPKKKRKV

Ub:Lys::Cas9

(SEQ ID NO: 52)

MQIFVKTLTGKTITLEVEPSDTIENVKAKIQDKEGIPPDQQRLIFAGKQLEDGRTLSD

YNIQKESTLHLVLRLRGGKDKKYSIGLDIGTNSVGWAVITDEYKVPSKKFKVLGNT

DRHSIKKNLIGALLFDSGETAEATRLKRTARRRYTRRKNRICYLQEIFSNEMAKVD

DSFFHRLEESFLVEEDKKHERHPIFGNIVDEVAYHEKYPTIYHLRKKLVDSTDKADL

RLIYLALAHMIKFRGHFLIEGDLNPDNSDVDKLFIQLVQTYNQLFEENPINASGVDA

KAILSARLSKSRRLENLIAQLPGEKKNGLFGNLIALSLGLTPNFKSNFDLAEDAKLQ

LSKDTYDDDLDNLLAQIGDQYADLFLAAKNLSDAILLSDILRVNTEITKAPLSASMI

KRYDEHHQDLTLLKALVRQQLPEKYKEIFFDQSKNGYAGYIDGGASQEEFYKFIKP

ILEKMDGTEELLVKLNREDLLRKQRTFDNGSIPHQIHLGELHAILRRQEDFYPFLKD

NREKIEKILTFRIPYYVGPLARGNSRFAWMTRKSEETITPWNFEEVVDKGASAQSFI

ERMTNFDKNLPNEKVLPKHSLLYEYFTVYNELTKVKYVTEGMRKPAFLSGEQKKA

IVDLLFKTNRKVTVKQLKEDYFKKIECFDSVEISGVEDRFNASLGTYHDLLKIIKDK

DFLDNEENEDILEDIVLTLTLFEDREMIEERLKTYAHLFDDKVMKQLKRRRYTGWG

RLSRKLINGIRDKQSGKTILDFLKSDGFANRNFMQLIHDDSLTFKEDIQKAQVSGQG

DSLHEHIANLAGSPAIKKGILQTVKVVDELVKVMGRHKPENIVIEMARENQTTQKG

QKNSRERMKRIEEGIKELGSQILKEHPVENTQLQNEKLYLYYLQNGRDMYVDQEL

DINRLSDYDVDHIVPQSFLKDDSIDNKVLTRSDKNRGKSDNVPSEEVVKK

MKNYWRQLLNAKLITQRKFDNLTKAERGGLSELDKAGFIKRQLVETRQITKHVAQ

ILDSRMNTKYDENDKLIREVKVITLKSKLVSDFRKDFQFYKVREINNYHHAHDAYL

NAVVGTALIKKYPKLESEFVYGDYKVYDVRKMIAKSEQEIGKATAKYFFYSNIMN

FFKTEITLANGEIRKRPLIETNGETGEIVWDKGRDFATVRKVLSMPQVNIVKKTEVQ

TGGFSKESILPKRNSDKLIARKKDWDPKKYGGFDSPTVAYSVLVVAKVEKGKSKK

LKSVKELLGITIMERSSFEKNPIDFLEAKGYKEVKKDLIIKLPKYSLFELENGRKRML

ASAGELQKGNELALPSKYVNFLYLASHYEKLKGSPEDNEQKQLFVEQHKHYLDEII

EQISEFSKRVILADANLDKVLSAYNKHRDKPIREQAENIIHLFTLTNLGAPAAFKYF

DTTIDRKRYTSTKEVLDATLIHQSITGLYETRIDLSQLGGDSRADPKKKRKV

Ub:Cys::Cas9

(SEQ ID NO: 53)

MQIFVKTLTGKTITLEVEPSDTIENVKAKIQDKEGIPPDQQRLIFAGKQLEDGRTLSD

YNIQKESTLHLVLRLRGGCDKKYSIGLDIGTNSVGWAVITDEYKVPSKKFKVLGNT

DRHSIKKNLIGALLFDSGETAEATRLKRTARRRYTRRKNRICYLQEIFSNEMAKVD

DSFFHRLEESFLVEEDKKHERHPIFGNIVDEVAYHEKYPTIYHLRKKLVDSTDKADL

RLIYLALAHMIKFRGHFLIEGDLNPDNSDVDKLFIQLVQTYNQLFEENPINASGVDA

KAILSARLSKSRRLENLIAQLPGEKKNGLFGNLIALSLGLTPNFKSNFDLAEDAKLQ

LSKDTYDDDLDNLLAQIGDQYADLFLAAKNLSDAILLSDILRVNTEITKAPLSASMI

```
KRYDEHHQDLTLLKALVRQQLPEKYKEIFFDQSKNGYAGYIDGGASQEEFYKFIKP

ILEKMDGTEELLVKLNREDLLRKQRTFDNGSIPHQIHLGELHAILRRQEDFYPFLKD

NREKIEKILTFRIPYYVGPLARGNSRFAWMTRKSEETITPWNFEEVVDKGASAQSFI

ERMTNFDKNLPNEKVLPKHSLLYEYFTVYNELTKVKYVTEGMRKPAFLSGEQKKA

IVDLLFKTNRKVTVKQLKEDYFKKIECFDSVEISGVEDRFNASLGTYHDLLKIIKDK

DFLDNEENEDILEDIVLTLTLFEDREMIEERLKTYAHLFDDKVMKQLKRRRYTGWG

RLSRKLINGIRDKQSGKTILDFLKSDGFANRNFMQLIHDDSLTFKEDIQKAQVSGQG

DSLHEHIANLAGSPAIKKGILQTVKVVDELVKVMGRHKPENIVIEMARENQTTQKG

QKNSRERMKRIEEGIKELGSQILKEHPVENTQLQNEKLYLYYLQNGRDMYVDQEL

DINRLSDYDVDHIVPQSFLKDDSIDNKVLTRSDKNRGKSDNVPSEEVVKK

MKNYWRQLLNAKLITQRKFDNLTKAERGGLSELDKAGFIKRQLVETRQITKHVAQ

ILDSRMNTKYDENDKLIREVKVITLKSKLVSDFRKDFQFYKVREINNYHHAHDAYL

NAVVGTALIKKYPKLESEFVYGDYKVYDVRKMIAKSEQEIGKATAKYFFYSNIMN

FFKTEITLANGEIRKRPLIETNGETGEIVWDKGRDFATVRKVLSMPQVNIVKKTEVQ

TGGFSKESILPKRNSDKLIARKKDWDPKKYGGFDSPTVAYSVLVVAKVEKGKSKK

LKSVKELLGITIMERSSFEKNPIDFLEAKGYKEVKKDLIIKLPKYSLFELENGRKRML

ASAGELQKGNELALPSKYVNFLYLASHYEKLKGSPEDNEQKQLFVEQHKHYLDEII

EQISEFSKRVILADANLDKVLSAYNKHRDKPIREQAENIIHLFTLTNLGAPAAFKYF

DTTIDRKRYTSTKEVLDATLIHQSITGLYETRIDLSQLGGDSRADPKKKRKV

Ub:Asp::Cas9
                                                     (SEQ ID NO: 54)
MQIFVKTLTGKTITLEVEPSDTIENVKAKIQDKEGIPPDQQRLIFAGKQLEDGRTLSD

YNIQKESTLHLVLRLRGGDDKKYSIGLDIGTNSVGWAVITDEYKVPSKKFKVLGNT

DRHSIKKNLIGALLFDSGETAEATRLKRTARRRYTRRKNRICYLQEIFSNEMAKVD

DSFFHRLEESFLVEEDKKHERHPIFGNIVDEVAYHEKYPTIYHLRKKLVDSTDKADL

RLIYLALAHMIKFRGHFLIEGDLNPDNSDVDKLFIQLVQTYNQLFEENPINASGVDA

KAILSARLSKSRRLENLIAQLPGEKKNGLFGNLIALSLGLTPNFKSNFDLAEDAKLQ

LSKDTYDDDLDNLLAQIGDQYADLFLAAKNLSDAILLSDILRVNTEITKAPLSASMI

KRYDEHHQDLTLLKALVRQQLPEKYKEIFFDQSKNGYAGYIDGGASQEEFYKFIKP

ILEKMDGTEELLVKLNREDLLRKQRTFDNGSIPHQIHLGELHAILRRQEDFYPFLKD

NREKIEKILTFRIPYYVGPLARGNSRFAWMTRKSEETITPWNFEEVVDKGASAQSFI

ERMTNFDKNLPNEKVLPKHSLLYEYFTVYNELTKVKYVTEGMRKPAFLSGEQKKA

IVDLLFKTNRKVTVKQLKEDYFKKIECFDSVEISGVEDRFNASLGTYHDLLKIIKDK

DFLDNEENEDILEDIVLTLTLFEDREMIEERLKTYAHLFDDKVMKQLKRRRYTGWG

RLSRKLINGIRDKQSGKTILDFLKSDGFANRNFMQLIHDDSLTFKEDIQKAQVSGQG

DSLHEHIANLAGSPAIKKGILQTVKVVDELVKVMGRHKPENIVIEMARENQTTQKG

QKNSRERMKRIEEGIKELGSQILKEHPVENTQLQNEKLYLYYLQNGRDMYVDQEL

DINRLSDYDVDHIVPQSFLKDDSIDNKVLTRSDKNRGKSDNVPSEEVVKK

MKNYWRQLLNAKLITQRKFDNLTKAERGGLSELDKAGFIKRQLVETRQITKHVAQ

ILDSRMNTKYDENDKLIREVKVITLKSKLVSDFRKDFQFYKVREINNYHHAHDAYL

NAVVGTALIKKYPKLESEFVYGDYKVYDVRKMIAKSEQEIGKATAKYFFYSNIMN

FFKTEITLANGEIRKRPLIETNGETGEIVWDKGRDFATVRKVLSMPQVNIVKKTEVQ
```

```
TGGFSKESILPKRNSDKLIARKKDWDPKKYGGFDSPTVAYSVLVVAKVEKGKSKK

LKSVKELLGITIMERSSFEKNPIDFLEAKGYKEVKKDLIIKLPKYSLFELENGRKRML

ASAGELQKGNELALPSKYVNFLYLASHYEKLKGSPEDNEQKLFVEQHKHYLDEII

EQISEFSKRVILADANLDKVLSAYNKHRDKPIREQAENIIHLFTLTNLGAPAAFKYF

DTTIDRKRYTSTKEVLDATLIHQSITGLYETRIDLSQLGGDSRADPKKKRKV
```

Ub:Phe::Cas9 (SEQ ID NO: 55)

```
MQIFVKTLTGKTITLEVEPSDTIENVKAKIQDKEGIPPDQQRLIFAGKQLEDGRTLSD

YNIQKESTLHLVLRLRGGFDKKYSIGLDIGTNSVGWAVITDEYKVPSKKFKVLGNT

DRHSIKKNLIGALLFDSGETAEATRLKRTARRRYTRRKNRICYLQEIFSNEMAKVD

DSFFHRLEESFLVEEDKKHERHPIFGNIVDEVAYHEKYPTIYHLRKKLVDSTDKADL

RLIYLALAHMIKFRGHFLIEGDLNPDNSDVDKLFIQLVQTYNQLFEENPINASGVDA

KAILSARLSKSRRLENLIAQLPGEKKNGLFGNLIALSLGLTPNFKSNFDLAEDAKLQ

LSKDTYDDDLDNLLAQIGDQYADLFLAAKNLSDAILLSDILRVNTEITKAPLSASMI

KRYDEHHQDLTLLKALVRQQLPEKYKEIFFDQSKNGYAGYIDGGASQEEFYKFIKP

ILEKMDGTEELLVKLNREDLLRKQRTFDNGSIPHQIHLGELHAILRRQEDFYPFLKD

NREKIEKILTFRIPYYVGPLARGNSRFAWMTRKSEETITPWNFEEVVDKGASAQSFI

ERMTNFDKNLPNEKVLPKHSLLYEYFTVYNELTKVKYVTEGMRKPAFLSGEQKKA

IVDLLFKTNRKVTVKQLKEDYFKKIECFDSVEISGVEDRFNASLGTYHDLLKIIKDK

DFLDNEENEDILEDIVLTLTLFEDREMIEERLKTYAHLFDDKVMKQLKRRRYTGWG

RLSRKLINGIRDKQSGKTILDFLKSDGFANRNFMQLIHDDSLTFKEDIQKAQVSGQG

DSLHEHIANLAGSPAIKKGILQTVKVVDELVKVMGRHKPENIVIEMARENQTTQKG

QKNSRERMKRIEEGIKELGSQILKEHPVENTQLQNEKLYLYYLQNGRDMYVDQEL

DINRLSDYDVDHIVPQSFLKDDSIDNKVLTRSDKNRGKSDNVPSEEVVKK

MKNYWRQLLNAKLITQRKFDNLTKAERGGLSELDKAGFIKRQLVETRQITKHVAQ

ILDSRMNTKYDENDKLIREVKVITLKSKLVSDFRKDFQFYKVREINNYHHAHDAYL

NAVVGTALIKKYPKLESEFVYGDYKVYDVRKMIAKSEQEIGKATAKYFFYSNIMN

FFKTEITLANGEIRKRPLIETNGETGEIVWDKGRDFATVRKVLSMPQVNIVKKTEVQ

TGGFSKESILPKRNSDKLIARKKDWDPKKYGGFDSPTVAYSVLVVAKVEKGKSKK

LKSVKELLGITIMERSSFEKNPIDFLEAKGYKEVKKDLIIKLPKYSLFELENGRKRML

ASAGELQKGNELALPSKYVNFLYLASHYEKLKGSPEDNEQKLFVEQHKHYLDEII

EQISEFSKRVILADANLDKVLSAYNKHRDKPIREQAENIIHLFTLTNLGAPAAFKYF

DTTIDRKRYTSTKEVLDATLIHQSITGLYETRIDLSQLGGDSRADPKKKRKV
```

Ub:Glu::Cas9 (SEQ ID NO: 56)

```
MQIFVKTLTGKTITLEVEPSDTIENVKAKIQDKEGIPPDQQRLIFAGKQLEDGRTLSD

YNIQKESTLHLVLRLRGGEDKKYSIGLDIGTNSVGWAVITDEYKVPSKKFKVLGNT

DRHSIKKNLIGALLFDSGETAEATRLKRTARRRYTRRKNRICYLQEIFSNEMAKVD

DSFFHRLEESFLVEEDKKHERHPIFGNIVDEVAYHEKYPTIYHLRKKLVDSTDKADL

RLIYLALAHMIKFRGHFLIEGDLNPDNSDVDKLFIQLVQTYNQLFEENPINASGVDA

KAILSARLSKSRRLENLIAQLPGEKKNGLFGNLIALSLGLTPNFKSNFDLAEDAKLQ

LSKDTYDDDLDNLLAQIGDQYADLFLAAKNLSDAILLSDILRVNTEITKAPLSASMI

KRYDEHHQDLTLLKALVRQQLPEKYKEIFFDQSKNGYAGYIDGGASQEEFYKFIKP
```

-continued

ILEKMDGTEELLVKLNREDLLRKQRTFDNGSIPHQIHLGELHAILRRQEDFYPFLKD

NREKIEKILTFRIPYYVGPLARGNSRFAWMTRKSEETITPWNFEEVVDKGASAQSFI

ERMTNFDKNLPNEKVLPKHSLLYEYFTVYNELTKVKYVTEGMRKPAFLSGEQKKA

IVDLLFKTNRKVTVKQLKEDYFKKIECFDSVEISGVEDRFNASLGTYHDLLKIIKDK

DFLDNEENEDILEDIVLTLTLFEDREMIEERLKTYAHLFDDKVMKQLKRRRYTGWG

RLSRKLINGIRDKQSGKTILDFLKSDGFANRNFMQLIHDDSLITKEDIQKAQVSGQG

DSLHEHIANLAGSPAIKKGILQTVKVVDELVKVMGRHKPENIVIEMARENQTTQKG

QKNSRERMKRIEEGIKELGSQILKEHPVENTQLQNEKLYLYYLQNGRDMYVDQEL

DINRLSDYDVDHIVPQSFLKDDSIDNKVLTRSDKNRGKSDNVPSEEVVKK

MKNYWRQLLNAKLITQRKFDNLTKAERGGLSELDKAGFIKRQLVETRQITKHVAQ

ILDSRMNTKYDENDKLIREVKVITLKSKLVSDFRKDFQFYKVREINNYHHAHDAYL

NAVVGTALIKKYPKLESEFVYGDYKVYDVRKMIAKSEQEIGKATAKYFFYSNIMN

FFKTEITLANGEIRKRPLIETNGETGEIVWDKGRDFATVRKVLSMPQVNIVKKTEVQ

TGGFSKESILPKRNSDKLIARKKDWDPKKYGGFDSPTVAYSVLVVAKVEKGKSKK

LKSVKELLGITIMERSSFEKNPIDFLEAKGYKEVKKDLIIKLPKYSLFELENGRKRML

ASAGELQKGNELALPSKYVNFLYLASHYEKLKGSPEDNEQKQLFVEQHKHYLDEII

EQISEFSKRVILADANLDKVLSAYNKHRDKPIREQAENIIHLFTLTNLGAPAAFKYF

DTTIDRKRYTSTKEVLDATLIHQSITGLYETRIDLSQLGGDSRADPKKKRKV

Ub:Arg::Cas9
(SEQ ID NO: 57)
MQIFVKTLTGKTITLEVEPSDTIENVKAKIQDKEGIPPDQQRLIFAGKQLEDGRTLSD

YNIQKESTLHLVLRLRGGRDKKYSIGLDIGTNSVGWAVITDEYKVPSKKFKVLGNT

DRHSIKKNLIGALLFDSGETAEATRLKRTARRRYTRRKNRICYLQEIFSNEMAKVD

DSFFHRLEESFLVEEDKKHERHPIFGNIVDEVAYHEKYPTIYHLRKKLVDSTDKADL

RLIYLALAHMIKFRGHFLIEGDLNPDNSDVDKLFIQLVQTYNQLFEENPINASGVDA

KAILSARLSKSRRLENLIAQLPGEKKNGLFGNLIALSLGLTPNFKSNFDLAEDAKLQ

LSKDTYDDDLDNLLAQIGDQYADLFLAAKNLSDAILLSDILRVNTEITKAPLSASMI

KRYDEHHQDLTLLKALVRQQLPEKYKEIFFDQSKNGYAGYIDGGASQEEFYKFIKP

ILEKMDGTEELLVKLNREDLLRKQRTFDNGSIPHQIHLGELHAILRRQEDFYPFLKD

NREKIEKILTFRIPYYVGPLARGNSRFAWMTRKSEETITPWNFEEVVDKGASAQSFI

ERMTNFDKNLPNEKVLPKHSLLYEYFTVYNELTKVKYVTEGMRKPAFLSGEQKKA

IVDLLFKTNRKVTVKQLKEDYFKKIECFDSVEISGVEDRFNASLGTYHDLLKIIKDK

DFLDNEENEDILEDIVLTLTLFEDREMIEERLKTYAHLFDDKVMKQLKRRRYTGWG

RLSRKLINGIRDKQSGKTILDFLKSDGFANRNFMQLIHDDSLTFKEDIQKAQVSGQG

DSLHEHIANLAGSPAIKKGILQTVKVVDELVKVMGRHKPENIVIEMARENQTTQKG

QKNSRERMKRIEEGIKELGSQILKEHPVENTQLQNEKLYLYYLQNGRDMYVDQEL

DINRLSDYDVDHIVPQSFLKDDSIDNKVLTRSDKNRGKSDNVPSEEVVKK

MKNYWRQLLNAKLITQRKFDNLTKAERGGLSELDKAGFIKRQLVETRQITKHVAQ

ILDSRMNTKYDENDKLIREVKVITLKSKLVSDFRKDFQFYKVREINNYHHAHDAYL

NAVVGTALIKKYPKLESEFVYGDYKVYDVRKMIAKSEQEIGKATAKYFFYSNIMN

FFKTEITLANGEIRKRPLIETNGETGEIVWDKGRDFATVRKVLSMPQVNIVKKTEVQ

TGGFSKESILPKRNSDKLIARKKDWDPKKYGGFDSPTVAYSVLVVAKVEKGKSKK

-continued

LKSVKELLGITIMERSSFEKNPIDFLEAKGYKEVKKDLIIKLPKYSLFELENGRKRML

ASAGELQKGNELALPSKYVNFLYLASHYEKLKGSPEDNEQKQLFVEQHKHYLDEII

EQISEFSKRVILADANLDKVLSAYNKHRDKPIREQAENIIHLFTLTNLGAPAAFKYF

DTTIDRKRYTSTKEVLDATLIHQSITGLYETRIDLSQLGGDSRADPKKKRKV

Ub:Gln::Cas9
(SEQ ID NO: 58)
MQIFVKTLTGKTITLEVEPSDTIENVKAKIQDKEGIPPDQQRLIFAGKQLEDGRTLSD

YNIQKESTLHLVLRLRGGQDKKYSIGLDIGTNSVGWAVITDEYKVPSKKFKVLGNT

DRHSIKKNLIGALLFDSGETAEATRLKRTARRRYTRRKNRICYLQEIFSNEMAKVD

DSFFHRLEESFLVEEDKKHERHPIFGNIVDEVAYHEKYPTIYHLRKKLVDSTDKADL

RLIYLALAHMIKFRGHFLIEGDLNPDNSDVDKLFIQLVQTYNQLFEENPINASGVDA

KAILSARLSKSRRLENLIAQLPGEKKNGLFGNLIALSLGLTPNFKSNFDLAEDAKLQ

LSKDTYDDDLDNLLAQIGDQYADLFLAAKNLSDAILLSDILRVNTEITKAPLSASMI

KRYDEHHQDLTLLKALVRQQLPEKYKEIFFDQSKNGYAGYIDGGASQEEFYKFIKP

ILEKMDGTEELLVKLNREDLLRKQRTFDNGSIPHQIHLGELHAILRRQEDFYPFLKD

NREKIEKILTFRIPYYVGPLARGNSRFAWMTRKSEETITPWNFEEVVDKGASAQSFI

ERMTNFDKNLPNEKVLPKHSLLYEYFTVYNELTKVKYVTEGMRKPAFLSGEQKKA

IVDLLFKTNRKVTVKQLKEDYFKKIECFDSVEISGVEDRFNASLGTYHDLLKIIKDK

DFLDNEENEDILEDIVLTLTLFEDREMIEERLKTYAHLFDDKVMKQLKRRRYTGWG

RLSRKLINGIRDKQSGKTILDFLKSDGFANRNFMQLIHDDSLTFKEDIQKAQVSGQG

DSLHEHIANLAGSPAIKKGILQTVKVVDELVKVMGRHKPENIVIEMARENQTTQKG

QKNSRERMKRIEEGIKELGSQILKEHPVENTQLQNEKLYLYYLQNGRDMYVDQEL

DINRLSDYDVDHIVPQSFLKDDSIDNKVLTRSDKNRGKSDNVPSEEVVKK

MKNYWRQLLNAKLITQRKFDNLTKAERGGLSELDKAGFIKRQLVETRQITKHVAQ

ILDSRMNTKYDENDKLIREVKVITLKSKLVSDFRKDFQFYKVREINNYHHAHDAYL

NAVVGTALIKKYPKLESEFVYGDYKVYDVRKMIAKSEQEIGKATAKYFFYSNIMN

FFKTEITLANGEIRKRPLIETNGETGEIVWDKGRDFATVRKVLSMPQVNIVKKTEVQ

TGGFSKESILPKRNSDKLIARKKDWDPKKYGGFDSPTVAYSVLVVAKVEKGKSKK

LKSVKELLGITIMERSSFEKNPIDFLEAKGYKEVKKDLIIKLPKYSLFELENGRKRML

ASAGELQKGNELALPSKYVNFLYLASHYEKLKGSPEDNEQKQLFVEQHKHYLDEII

EQISEFSKRVILADANLDKVLSAYNKHRDKPIREQAENIIHLFTLTNLGAPAAFKYF

DTTIDRKRYTSTKEVLDATLIHQSITGLYETRIDLSQLGGDSRADPKKKRKV

Ub(G76V)::Cas9
(SEQ ID NO: 59)
MQIFVKTLTGKTITLEVEPSDTIENVKAKIQDKEGIPPDQQRLIFAGKQLEDGRTLSD

YNIQKESTLHLVLRLRGVDKKYSIGLDIGTNSVGWAVITDEYKVPSKKFKVLGNTD

RHSIKKNLIGALLFDSGETAEATRLKRTARRRYTRRKNRICYLQEIFSNEMAKVDDS

FFHRLEESFLVEEDKKHERHPIFGNIVDEVAYHEKYPTIYHLRKKLVDSTDKADLRL

IYLALAHMIKFRGHFLIEGDLNPDNSDVDKLFIQLVQTYNQLFEENPINASGVDAKA

ILSARLSKSRRLENLIAQLPGEKKNGLFGNLIALSLGLTPNFKSNFDLAEDAKLQLSK

DTYDDDLDNLLAQIGDQYADLFLAAKNLSDAILLSDILRVNTEITKAPLSASMIKRY

DEHHQDLTLLKALVRQQLPEKYKEIFFDQSKNGYAGYIDGGASQEEFYKFIKPILEK

MDGTEELLVKLNREDLLRKQRTFDNGSIPHQIHLGELHAILRRQEDFYPFLKDNRE

KIEKILTFRIPYYVGPLARGNSRFAWMTRKSEETITPWNFEEVVDKGASAQSFTERM

TNFDKNLPNEKVLPKHSLLYEYFTVYNELTKVKYVTEGMRKPAFLSGEQKKAIVD

LLFKTNRKVTVKQLKEDYFKKIECFDSVEISGVEDRFNASLGTYHDLLKIIKDKDFL

DNEENEDILEDIVLTLTLFEDREMIEERLKTYAHLFDDKVMKQLKRRRYTGWGRLS

RKLINGIRDKQSGKTILDFLKSDGFANRNFMQLIHDDSLTFKEDIQKAQVSGQGDSL

HEHIANLAGSPAIKKGILQTVKVVDELVKVMGRHKPENIVIEMARENQTTQKGQK

NSRERMKRIEEGIKELGSQILKEHPVENTQLQNEKLYLYYLQNGRDMYVDQELDIN

RLSDYDVDHIVPQSFLKDDSIDNKVLTRSDKNRGKSDNVPSEEVVKK

MKNYWRQLLNAKLITQRKFDNLTKAERGGLSELDKAGFIKRQLVETRQITKHVAQ

ILDSRMNTKYDENDKLIREVKVITLKSKLVSDFRKDFQFYKVREINNYHHAHDAYL

NAVVGTALIKKYPKLESEFVYGDYKVYDVRKMIAKSEQEIGKATAKYFFYSNIMN

FFKTEITLANGEIRKRPLIETNGETGEIVWDKGRDFATVRKVLSMPQVNIVKKTEVQ

TGGFSKESILPKRNSDKLIARKKDWDPKKYGGFDSPTVAYSVLVVAKVEKGKSKK

LKSVKELLGITIMERSSFEKNPIDFLEAKGYKEVKKDLIIKLPKYSLFELENGRKRML

ASAGELQKGNELALPSKYVNFLYLASHYEKLKGSPEDNEQKQLFVEQHKHYLDEII

EQISEFSKRVILADANLDKVLSAYNKHRDKPIREQAENIIHLFTLTNLGAPAAFKYF

DTTIDRKRYTSTKEVLDATLIHQSITGLYETRIDLSQLGGDSRADPKKKRKV

DNA Sequences

Ub:
(SEQ ID NO: 60)
ACCACCTCTCAGACGCAGGACCAGGTGCAGGGTCGACTCCTTCTGGATGT

TGTAGTCAGAAAGAGTGCGGCCATCTTCCAGCTGCTTGCCTGCAAAGATG

AGCCTCTGCTGGTCGGGAGGGATGCCTTCTTTATCCTGGATCTTGGCCTT

CACATTTTCGATGGTGTCACTGGGCTCCACTTCCAGGGTGATGGTCTTGC

CGGTCAGGGTCTTCACGAAGATCTGCAT

Cas9:
(SEQ ID NO: 61)
GACAAGAAGTACTCCATTGGGCTCGATATCGGCACAAACAGCGTCGGCTG

GGCCGTCATTACGGACGAGTACAAGGTGCCGAGCAAAAAATTCAAAGTTC

TGGGCAATACCGATCGCCACAGCATAAAGAAGAACCTCATTGGCGCCCTC

CTGTTCGACTCCGGGGAGACGGCCGAAGCCACGCGGCTCAAAAGAACAGC

ACGGCGCAGATATACCCGCAGAAAGAATCGGATCTGCTACCTGCAGGAGA

TCTTTAGTAATGAGATGGCTAAGGTGGATGACTCTTTCTTCCATAGGCTG

GAGGAGTCCTTTTTGGTGGAGGAGGATAAAAAGCACGAGCGCCACCCAAT

CTTTGGCAATATCGTGGACGAGGTGGCGTACCATGAAAAGTACCCAACCA

TATATCATCTGAGGAAGAAGCTTGTAGACAGTACTGATAAGGCTGACTTG

CGGTTGATCTATCTCGCGCTGGCGCATATGATCAAATTTCGGGGACACTT

CCTCATCGAGGGGGACCTGAACCCAGACAACAGCGATGTCGACAAACTCT

TTATCCAACTGGTTCAGACTTACAATCAGCTTTTCGAAGAGAACCCGATC

AACGCATCCGGAGTTGACGCCAAAGCAATCCTGAGCGCTAGGCTGTCCAA

ATCCCGGCGGCTCGAAAACCTCATCGCACAGCTCCCTGGGGAGAAGAAGA

ACGGCCTGTTTGGTAATCTTATCGCCCTGTCACTCGGGCTGACCCCCAAC

TTTAAATCTAACTTCGACCTGGCCGAAGATGCCAAGCTTCAACTGAGCAA

AGACACCTACGATGATGATCTCGACAATCTGCTGGCCCAGATCGGCGACC

AGTACGCAGACCTTTTTTTGGCGGCAAAGAACCTGTCAGACGCCATTCTG

CTGAGTGATATTCTGCGAGTGAACACGGAGATCACCAAAGCTCCGCTGAG

CGCTAGTATGATCAAGCGCTATGATGAGCACCACCAAGACTTGACTTTGC

TGAAGGCCCTTGTCAGACAGCAACTGCCTGAGAAGTACAAGGAAATTTTC

TTCGATCAGTCTAAAAATGGCTACGCCGGATACATTGACGGCGGAGCAAG

CCAGGAGGAATTTTACAAATTTATTAAGCCCATCTTGGAAAAAATGGACG

GCACCGAGGAGCTGCTGGTAAAGCTTAACAGAGAAGATCTGTTGCGCAAA

CAGCGCACTTTCGACAATGGAAGCATCCCCCACCAGATTCACCTGGGCGA

ACTGCACGCTATCCTCAGGCGGCAAGAGGATTTCTACCCCTTTTTGAAAG

ATAACAGGGAAAGATTGAGAAAATCCTCACATTTCGGATACCCTACTAT

GTAGGCCCCCTCGCCCGGGGAAATTCCAGATTCGCGTGGATGACTCGCAA

ATCAGAAGAGACCATCACTCCCTGGAACTTGAGGAAGTCGTGGATAAGG

GGGCCTCTGCCCAGTCCTTCATCGAAAGGATGACTAACTTTGATAAAAAT

CTGCCTAACGAAAAGGTGCTTCCTAAACACTCTCTGCTGTACGAGTACTT

CACAGTTTATAACGAGCTCACCAAGGTCAAATACGTCACAGAAGGGATGA

GAAAGCCAGCATTCCTGTCTGGAGAGCAGAAGAAAGCTATCGTGGACCTC

CTCTTCAAGACGAACCGGAAAGTTACCGTGAAACAGCTCAAAGAAGACTA

TTTCAAAAAGATTGAATGTTTCGACTCTGTTGAAATCAGCGGAGTGGAGG

ATCGCTTCAACGCATCCCTGGGAACGTATCACGATCTCCTGAAAATCATT

-continued
```
AAAGACAAGGACTTCCTGGACAATGAGGAGAACGAGGACATTCTTGAGGA
CATTGTCCTCACCCTTACGTTGTTTGAAGATAGGGAGATGATTGAAGAAC
GCTTGAAAACTTACGCTCATCTCTTCGACGACAAAGTCATGAAACAGCTC
AAGAGGCGCCGATATACAGGATGGGGCGGCTGTCAAGAAAACTGATCAA
TGGGATCCGAGACAAGCAGAGTGGAAAGACAATCCTGGATTTTCTTAAGT
CCGATGGATTTGCCAACCGGAACTTCATGCAGTTGATCCATGATGACTCT
CTCACCTTTAAGGAGGACATCCAGAAAGCACAAGTTTCTGGCCAGGGGGA
CAGTCTTCACGAGCACATCGCTAATCTTGCAGGTAGCCCAGCTATCAAAA
AGGGAATACTGCAGACCGTTAAGGTCGTGGATGAACTCGTCAAAGTAATG
GGAAGGCATAAGCCCGAGAATATCGTTATCGAGATGGCCCGAGAGAACCA
AACTACCCAGAAGGGACAGAAGAACAGTAGGGAAAGGATGAAGAGGATTG
AAGAGGGTATAAAAGAACTGGGGTCCCAAATCCTTAAGGAACACCCAGTT
GAAAACACCCAGCTTCAGAATGAGAAGCTCTACCTGTACTACCTGCAGAA
CGGCAGGGACATGTACGTGGATCAGGAACTGGACATCAATCGGCTCTCCG
ACTACGACGTGGATCATATCGTGCCCCAGTCTTTTCTCAAAGATGATTCT
ATTGATAATAAAGTGTTGACAAGATCCGATAAAAATAGAGGGAAGAGTGA
TAACGTCCCCTCAGAAGAAGTTGTCAAGAAAATGAAAAATTATTGGCGGC
AGCTGCTGAACGCCAAACTGATCACACAACGGAAGTTCGATAATCTGACT
AAGGCTGAACGAGGTGGCCTGTCTGAGTTGGATAAAGCCGGCTTCATCAA
AAGGCAGCTTGTTGAGACACGCCAGATCACCAAGCACGTGGCCCAAATTC
TCGATTCACGCATGAACACCAAGTACGATGAAAATGACAAACTGATTCGA
GAGGTGAAAGTTATTACTCTGAAGTCTAAGCTGGTCTCAGATTTCAGAAA
GGACTTTCAGTTTTATAAGGTGAGAGAGATCAACAATTACCACCATGCGC
ATGATGCCTACCTGAATGCAGTGGTAGGCACTGCACTTATCAAAAAATAT
CCCAAGCTTGAATCTGAATTTGTTTACGGAGACTATAAAGTGTACGATGT
TAGGAAAATGATCGCAAAGTCTGAGCAGGAAATAGGCAAGGCCACCGCTA
AGTACTTCTTTTACAGCAATATTATGAATTTTTTCAAGACCGAGATTACA
CTGGCCAATGGAGAGATTCGGAAGCGACCACTTATCGAAACAAACGGAGA
AACAGGAGAAATCGTGTGGGACAAGGGTAGGGATTTCGCGACAGTCCGGA
AGGTCCTGTCCATGCCGCAGGTGAACATCGTTAAAAAGACCGAAGTACAG
ACCGGAGGCTTCTCCAAGGAAAGTATCCTCCCGAAAAGGAACAGCGACAA
GCTGATCGCACGCAAAAAAGATTGGGACCCCAAGAAATACGGCGGATTCG
ATTCTCCTACAGTCGCTTACAGTGTACTGGTTGTGGCCAAAGTGGAGAAA
GGGAAGTCTAAAAAACTCAAAAGCGTCAAGGAACTGCTGGGCATCACAAT
CATGGAGCGATCAAGCTTCGAAAAAAACCCCATCGACTTTCTCGAGGCGA
AAGGATATAAAGAGGTCAAAAAAGACCTCATCATTAAGCTTCCCAAGTAC
TCTCTCTTTGAGCTTGAAAACGGCCGGAAACGAATGCTCGCTAGTGCGGG
CGAGCTGCAGAAAGGTAACGAGCTGGCACTGCCCTCTAAATACGTTAATT
TCTTGTATCTGGCCAGCCACTATGAAAAGCTCAAAGGGTCTCCCGAAGAT
AATGAGCAGAAGCAGCTGTTCGTGGAACAACACAAACACTACCTTGATGA
GATCATCGAGCAAATAAGCGAATTCTCCAAAAGAGTGATCCTCGCCGACG
```

-continued
```
CTAACCTCGATAAGGTGCTTTCTGCTTACAATAAGCACAGGGATAAGCCC
ATCAGGGAGCAGGCAGAAAACATTATCCACTTGTTTACTCTGACCAACTT
GGGCGCGCCTGCAGCCTTCAAGTACTTCGACACCACCATAGACAGAAAGC
GGTACACCTCTACAAAGGAGGTCCTGGACGCCACACTGATTCATCAGTCA
ATTACGGGGCTCTATGAAACAAGAATCGACCTCTCTCAGCTCGGTGGAGA
CAGCAGGGCTGACCCCAAGAAGAAGAGGAAGGTG
```

Example 6

Use of a Bidirectional Promoter to Deliver an RNA-Directed Nuclease, Guide RNA, and HDR Templates Through a Single AAV Virus The delivery of RNA-directed nuclease, guide RNA, and HDR templates through a single AAV virus A revolutionary genome-editing technology known as CRISPR is transforming biological research and ushering in a new era for genetic medicine. Each cell in our body contains 3 billion base-pairs of DNA and even single changes—or mutations—can cause a wide variety of inherited or acquired diseases. Through a process akin to genome surgery, CRISPR technology allows researchers to target disease-associated mutations with unprecedented precision, treating diseases at their root cause.

Research labs across the world have shown that CRISPR can efficiently target disease mutations; however, until now the development of CRISPR-based therapeutics for human use has been hampered by delivery constraints. The preferred delivery choice for tissue-specific in vivo gene therapy is recombinant adeno-associated viruses (AAV). AAV has a notable history of safety, efficacy, and a lack of toxicity that is further illustrated by the increasing number of FDA approved trials using this approach—there have been 150 trials using AAV worldwide. These compact viruses can deliver materials with high efficiency and specificity to a wide variety of cell types, and while safe, their small size presents a significant obstacle for the packaging of CRISPR components.

Dominant diseases occur when people inherit one bad gene which then poisons the normal copy. While untreatable by gene-therapy technology, these mutations can be suppressed using CRISPR which disrupts the mutation and allows the other normal gene to work. We previously disclosed a method for the packaging of both CRISPR components into a single AAV virus using the compact H1 bidirectional promoter.

Recessive mutations, on the other hand, are the result of inheriting two bad copies of a gene. These diseases require delivering CRISPR as well as a long stretch of DNA surrounding the mutation (a template) so that the cell can edit out the mutations by copying in the correct sequence. While the vast majority of diseases fall into this category, no means exists to deliver CRISPR components and the template DNA via a single AAV virus exist due to the size limitations of AAV.

Historically, AAV served as a method to deliver templates for site-specific DNA change. Compared to other known methods, AAV templates are the most recombinogenic, although the rates were still low and on the order of less than 1 in 10⁴ prior to gene-editing methods. We know that DNA breaks are highly recombinogenic, and that co-delivery of CRISPR-Cas9 with an AAV template has the ability to recombine at a high frequency. We also know that ssDNA templates as small as 40-60nt are very effective HDr templates, as is dsDNA templates 200nt and bigger. Unfortunately, there are no means to deliver the CRISPR components and the HDR template in one AAV virus.

However, because the H1 bidirectional promoter system is so compact, we can deliver both the cutting (Cas9 and gRNA) and pasting (HDR template) elements through a single AAV virus. The therapeutic potential for this class of diseases is far larger both in terms of the numbers of diseases and people that can be treated.

Here, it was shown the AAV vector design for correcting mutations in vivo, using the H1 promoter to express an RNA-guided nuclease (Cas9), a guide RNA, and a donor template sequence. Two examples for mutation correction are illustrated for examples 1) using the SaCas9 nickase with two gRNAs and a template correction for the rd12 mutation (FIG. 25B) and 2) the SpCas9 correction of the rd10 mutation (FIG. 27).

Methods

Human embryonic kidney (HEK) cell line 293T (Life Technologies, Grand Island, N.Y.) was maintained at 37° C. with 5% $CO_2$/20% $O_2$ in Dulbecco's modified Eagle's Medium (DMEM) (Invitrogen) supplemented with 10% fetal bovine serum (Gibco, Life Technologies, Grand Island, N.Y.) and 2 mM GlutaMAX (Invitrogen).

Construct design. See FIG. 28. A construct was designed to using the mouse H1 promoter to express both SpCas9 and a gRNA. Two restrictions sites were incorporated before the flanking Not1 sites to allow for Gibson cloning of an HDR template: Kpn1 for left HDR, and Hpa1 for right HDR. For insertion after Kpn1 digestion, the following sequence 5'-GAGAGTGCACCATAGCGGCCGCGNNNGTACC-CACACAAAAAACCAACACACAG-3' (SEQ ID NO: 69), where N's represent the template region is used, or after Hpa1 digestion, the following sequence 5'-GGCACCGAGTCGGTGCTTTTTTGTTNNNNN-NAACGCGGCCGCCTAGAGTC GAC-3' (SEQ ID NO: 70), where N's represent the template region is used.

gRNAs (see Jaskula-Ranga, V., &. Zack, D. J. (2016). grID: A CRISPR-Cas9 guide RNA Database and Resource for Genome-Editing. *bioRxiv,* 097352) were generated by overlapping oligos that were annealed and amplified by PCR using two-step amplification Phusion Flash DNA polymerase (Thermo Fisher Scientific, Rockford, Ill.), and subsequently purified using Zymo DNA clean and concentrator columns. The purified PCR products were then resuspended in H2O and quantitated using a NanoDrop 1000 (Thermo Fisher Scientific). The gRNA-expressing constructs were generated using the Gibson Assembly (New England Biolabs, Ipswich, Mass.) (Gibson et al. (2009) *Nature Methods* 6:343-345) with slight modifications. The total reaction volume was reduced from 20 µl to 2 µl. Clones were verified by Sanger sequencing.

HEK293 cells were co-transfected with Cas9 (unmodified, or cell-cycle regulated versions) and the gRNA construct targeting rhodopsin. 48 hrs post transfection, genomic DNA was harvested and the sequence surrounding the target cut sites were amplified according to the primers listed in the Appendix. The PCR products were then purified and quantitated before performing the T7 Endo I assay. Briefly, 200 ng of PCR product was denatured and then slowly re-annealed to allow for the formation of heteroduplexes, T7 Endonuclease I was added to the PCR products and incubated at 37 C for 25 minutes to cleave heteroduplexes, the reaction was quenched in loading dye, and finally, the reaction was run on a 6% TBE PAGE gel to resolve the products. The gel was stained with SYBR-Gold, visualized, and quantitated using ImageJ. NHEJ frequencies were calculated using the binomial-derived equation:

$$1 - \sqrt{1 - \frac{(a+b)}{(a+b+c)}} \times 100;$$

where the values of "a" and "b" are equal to the integrated area of the cleaved fragments after background subtraction and "c" is equal to the integrated area of the un-cleaved PCR product after background subtraction.

Sequences

```
mSPA_HDR SpCas9 entry plasmid
                                       (SEQ ID NO: 62)
CCTGCTGTCTCCACCGAGCTGAGAGAGGTCGATTCTTGTTTCATAGAGCCCGT

AATTGACTGATGAATCAGTGTGGCGTCCAGGACCTCCTTTGTAGAGGTGTACCG

CTTTCTGTCTATGGTGGTGTCGAAGTACTTGAAGGCTGCAGGCGCGCCCAAGTT

GGTCAGAGTAAACAAGTGGATAATGTTTTCTGCCTGCTCCCTGATGGGCTTATC

CCTGTGCTTATTGTAAGCAGAAAGCACCTTATCGAGGTTAGCGTCGGCGAGGAT

CACTCTTTTGGAGAATTCGCTTATTTGCTCGATGATCTCATCAAGGTAGTGTTTG

TGTTGTTCCACGAACAGCTGCTTCTGCTCATTATCTTCGGGAGACCCTTTGAGCT

TTTCATAGTGGCTGGCCAGATACAAGAAATTAACGTATTTAGAGGGCAGTGCC

AGCTCGTTACCTTTCTGCAGCTCGCCCGCACTAGCGAGCATTCGTTTCCGGCCG

TTTTCAAGCTCAAAGAGAGTACTTGGGAAGCTTAATGATGAGGTCTTTTTTG

ACCTCTTTATATCCTTTCGCCTCGAGAAAGTCGATGGGTTTTTTCGAAGCTTG

ATCGCTCCATGATTGTGATGCCCAGCAGTTCCTTGACGCTTTTGAGTTTTTAGA

CTTCCCTTTCTCCACTTTGGCCACAACCAGTACACTGTAAGCGACTGTAGGAGA

ATCGAATCCGCCGTATTTCTTGGGGTCCCAATCTTTTTTGCGTGCGATCAGCTTG
```

-continued

```
TCGCTGTTCCTTTTCGGGAGGATACTTTCCTTGGAGAAGCCTCCGGTCTGTACTT

CGGTCTTTTTAACGATGTTCACCTGCGGCATGGACAGGACCTTCCGGACTGTCG

CGAAATCCCTACCCTTGTCCCACACGATTTCTCCTGTTTCTCCGTTTGTTTCGAT

AAGTGGTCGCTTCCGAATCTCTCCATTGGCCAGTGTAATCTCGGTCTTGAAAAA

ATTCATAATATTGCTGTAAAAGAAGTACTTAGCGGTGGCCTTGCCTATTTCCTG

CTCAGACTTTGCGATCATTTTCCTAACATCGTACACTTTATAGTCTCCGTAAACA

AATTCAGATTCAAGCTTGGGATATTTTTTGATAAGTGCAGTGCCTACCACTGCA

TTCAGGTAGGCATCATGCGCATGGTGGTAATTGTTGATCTCTCTCACCTTATAA

AACTGAAAGTCCTTTCTGAAATCTGAGACCAGCTTAGACTTCAGAGTAATAACT

TTCACCTCTCGAATCAGTTTGTCATTTTCATCGTACTTGGTGTTCATGCGTGAAT

CGAGAATTTGGGCCACGTGCTTGGTGATCTGGCGTGTCTCAACAAGCTGCCTTT

TGATGAAGCCGGCTTTATCCAACTCAGACAGGCCACCTCGTTCAGCCTTAGTCA

GATTATCGAACTTCCGTTGTGTGATCAGTTTGGCGTTCAGCAGCTGCCGCCAAT

AATTTTTCATTTTCTTGACAACTTCTTCTGAGGGGACGTTATCACTCTTCCCTCT

ATTTTTATCGGATCTTGTCAACACTTTATTATCAATAGAATCATCTTTGAGAAAA

GACTGGGGCACGATATGATCCACGTCGTAGTCGGAGAGCCGATTGATGTCCAG

TTCCTGATCCACGTACATGTCCCTGCCGTTCTGCAGGTAGTACAGGTAGAGCTT

CTCATTCTGAAGCTGGGTGTTTTCAACTGGGTGTTCCTTAAGGATTTGGGACCC

CAGTTCTTTTATACCCTCTTCAATCCTCTTCATCCTTTCCCTACTGTTCTTCTGTC

CCTTCTGGGTAGTTTGGTTCTCTCGGGCCATCTCGATAACGATATTCTCGGGCTT

ATGCCTTCCCATTACTTTGACGAGTTCATCCACGACCTTAACGGTCTGCAGTATT

CCCTTTTTGATAGCTGGGCTACCTGCAAGATTAGCGATGTGCTCGTGAAGACTG

TCCCCCTGGCCAGAAACTTGTGCTTTCTGGATGTCCTCCTTAAAGGTGAGAGAG

TCATCATGGATCAACTGCATGAAGTTCCGGTTGGCAAATCCATCGGACTTAAGA

AAATCCAGGATTGTCTTTCCACTCTGCTTGTCTCGGATCCCATTGATCAGTTTTC

TTGACAGCCGCCCCCATCCTGTATATCGGCGCCTCTTGAGCTGTTTCATGACTTT

GTCGTCGAAGAGATGAGCGTAAGTTTTCAAGCGTTCTTCAATCATCTCCCTATC

TTCAAACAACGTAAGGGTGAGGACAATGTCCTCAAGAATGTCCTCGTTCTCCTC

ATTGTCCAGGAAGTCCTTGTCTTTAATGATTTTCAGGAGATCGTGATACGTTCCC

AGGGATGCGTTGAAGCGATCCTCCACTCCGCTGATTTCAACAGAGTCGAAACAT

TCAATCTTTTTGAAATAGTCTTCTTTGAGCTGTTTCACGGTAACTTTCCGGTTCG

TCTTGAAGAGGAGGTCCACGATAGCTTTCTTCTGCTCTCCAGACAGGAATGCTG

GCTTTCTCATCCCTTCTGTGACGTATTTGACCTTGGTGAGCTCGTTATAAACTGT

GAAGTACTCGTACAGCAGAGAGTGTTTAGGAAGCACCTTTTCGTTAGGCAGATT

TTTATCAAAGTTAGTCATCCTTTCGATGAAGGACTGGGCAGAGGCCCCCTTATC

CACGACTTCCTCGAAGTTCCAGGGAGTGATGGTCTCTTCTGATTTGCGAGTCAT

CCACGCGAATCTGGAATTTCCCCGGGCGAGGGGGCCTACATAGTAGGGTATCC

GAAATGTGAGGATTTTCTCAATCTTTTCCCTGTTATCTTTCAAAAAGGGGTAGA

AATCCTCTTGCCGCCTGAGGATAGCGTGCAGTTCGCCCAGGTGAATCTGGTGGG

GGATGCTTCCATTGTCGAAAGTGCGCTGTTTGCGCAACAGATCTTCTCTGTTAA

GCTTTACCAGCAGCTCCTCGGTGCCGTCCATTTTTTCCAAGATGGGCTTAATAA
```

-continued

```
ATTTGTAAAATTCCTCCTGGCTTGCTCCGCCGTCAATGTATCCGGCGTAGCCATT

TTTAGACTGATCGAAGAAAATTTCCTTGTACTTCTCAGGCAGTTGCTGTCTGAC

AAGGGCCTTCAGCAAAGTCAAGTCTTGGTGGTGCTCATCATAGCGCTTGATCAT

ACTAGCGCTCAGCGGAGCTTTGGTGATCTCCGTGTTCACTCGCAGAATATCACT

CAGCAGAATGGCGTCTGACAGGTTCTTTGCCGCCAAAAAAAGGTCTGCGTACT

GGTCGCCGATCTGGGCCAGCAGATTGTCGAGATCATCATCGTAGGTGTCTTTGC

TCAGTTGAAGCTTGGCATCTTCGGCCAGGTCGAAGTTAGATTTAAAGTTGGGGG

TCAGCCCGAGTGACAGGGCGATAAGATTACCAAACAGGCCGTTCTTCTTCTCCC

CAGGGAGCTGTGCGATGAGGTTTTCGAGCCGCCGGGATTTGGACAGCCTAGCG

CTCAGGATTGCTTTGGCGTCAACTCCGGATGCGTTGATCGGGTTCTCTTCGAAA

AGCTGATTGTAAGTCTGAACCAGTTGGATAAAGAGTTTGTCGACATCGCTGTTG

TCTGGGTTCAGGTCCCCCTCGATGAGGAAGTGTCCCCGAAATTTGATCATATGC

GCCAGCGCGAGATAGATCAACCGCAAGTCAGCCTTATCAGTACTGTCTACAAG

CTTCTTCCTCAGATGATATATGGTTGGGT

ACTTTTCATGGTACGCCACCTCGTCCACGATATTGCCAAAGATTGGGTGGCGCT

CGTGCTTTTTATCCTCCTCCACCAAAAAGGACTCCTCCAGCCTATGGAAGAAAG

AGTCATCCACCTTAGCCATCTCATTACTAAAGATCTCCTGCAGGTAGCAGATCC

GATTCTTTCTGCGGGTATATCTGCGCCGTGCTGTTCTTTTGAGCCGCGTGGCTTC

GGCCGTCTCCCCGGAGTCGAACAGGAGGGCGCCAATGAGGTTCTTCTTTATGCT

GTGGCGATCGGTATTGCCCAGAACTTTGAATTTTTTGCTCGGCACCTTGTACTCG

TCCGTAATGACGGCCCAGCCGACGCTGTTTGTGCCGATATCGAGCCCAATGGAG

TACTTCTTGTCCATGGTGGCGGCTCTTGAAGGACGACGTCATCATCCCTTGCCC

GGATGCGCGGGCTTCTTGTCTAGCACAGGAGCCTGGGGTAGAGCGCATGCAAA

TTACGCGCTGTGCTTTGTGGGAAATCACCCTAAACGAAAAATTTATTCCTCTTTC

GAGCCTTATAGTGGCGGCCGGTCTACATCCTAGGTTTTAGAGCTAGAAATAGCA

AGTTAAAATAAGGCTAGTCCGTTATCAACTTGAAAAAGTGGCACCGAGTCGGT

GCTTTTTTGTTAACGCGGCCGCCTAGAGTCGACCTGCAGGCATGCAAGCTTGGC

GTAATCATGGTCATAGCTGTTTCCTGTGTGAAATTGTTATCCGCTCACAATTCCA

CACAACATACGAGCCGGAAGCATAAAGTGTAAAGCCTGGGGTGCCTAATGAGT

GAGCTAACTCACATTAATTGCGTTGCGCTCACTGCCCGCTTTCCAGTCGGGAAA

CCTGTCGTGCCAGCTGCATTAATGAATCGGCCAACGCGCGGGGAGAGGCGGTT

TGCGTATTGGGCGCTCTTCCGCTTCCTCGCTCACTGACTCGCTGCGCTCGGTCGT

TCGGCTGCGGCGAGCGGTATCAGCTCACTCAAAGGCGGTAATACGGTTATCCA

CAGAATCAGGGGATAACGCAGGAAAGAACATGTGAGCAAAAGGCCAGCAAAA

GGCCAGGAACCGTAAAAAGGCCGCGTTGCTGGCGTTTTTCCATAGGCTCCGCCC

CCCTGACGAGCATCACAAAAATCGACGCTCAAGTCAGAGGTGGCGAAACCCGA

CAGGACTATAAAGATACCAGGCGTTTCCCCCTGGAAGCTCCCTCGTGCGCTCTC

CTGTTCCGACCCTGCCGCTTACCGGATACCTGTCCGCCTTTCTCCCTTCGGGAAG

CGTGGCGCTTTCTCATAGCTCACGCTGTAGGTATCTCAGTTCGGTGTAGGTCGTT

CGCTCCAAGCTGGGCTGTGTGCACGAACCCCCCGTTCAGCCCGACCGCTGCGCC

TTATCCGGTAACTATCGTCTTGAGTCCAACCCGGTAAGACACGACTTATCGCCA
```

-continued

```
CTGGCAGCAGCCACTGGTAACAGGATTAGCAGAGCGAGGTATGTAGGCGGTGC

TACAGAGTTCTTGAAGTGGTGGCCTAACTACGGCTACACTAGAAGAACAGTATT

TGGTATCTGCGCTCTGCTGAAGCCAGTTACCTTCGGAAAAAGAGTTGGTAGCTC

TTGATCCGGCAAACAAACCACCGCTGGTAGCGGTGGTTTTTTTGTTTGCAA

GCAGCAGATTACGCGCAGAAAAAAAGGATCTCAAGAAGATCCTTTGATCTTTT

CTACGGGGTCTGACGCTCAGTGGAACGAAAACTCACGTTAAGGGATTTTGGTC

ATGAGATTATCAAAAGGATCTTCACCTAGATCCTTTTAAATTAAAAATGAAGT

TTTAAATCAATCTAAAGTATATATGAGTAAACTTGGTCTGACAGTTACCAATGC

TTAATCAGTGAGGCACCTATCTCAGCGATCTGTCTATTTCGTTCATCCATAGTTG

CCTGACTCCCCGTCGTGTAGATAACTACGATACGGGAGGGCTTACCATCTGGCC

CCAGTGCTGCAATGATACCGCGAGACCCACGCTCACCGGCTCCAGATTTATCAG

CAATAAACCAGCCAGCCGGAAGGGCCGAGCGCAGAAGTGGTCCTGCAACTTTA

TCCGCCTCCATCCAGTCTATTAATTGTTGCCGGGAAGCTAGAGTAAGTAGTTCG

CCAGTTAATAGTTTGCGCAACGTTGTTGCCATTGCTACAGGCATCGTGGTGTCA

CGCTCGTCGTTTGGTATGGCTTCATTCAGCTCCGGTTCCCAACGATCAAGGCGA

GTTACATGATCCCCCATGTTGTGCAAAAAAGCGGTTAGCTCCTTCGGTCCTCCG

ATCGTTGTCAGAAGTAAGTTGGCCGCAGTGTTATCACTCATGGTTATGGCAGCA

CTGCATAATTCTCTTACTGTCATGCCATCCGTAAGATGCTTTTCTGTGACTGGTG

AGTACTCAACCAAGTCATTCTGAGAATAGTGTATGCGGCGACCGAGTTGCTCTT

GCCCGGCGTCAATACGGGATAATACCGCGCCACATAGCAGAACTTTAAAAGTG

CTCATCATTGGAAAACGTTCTTCGGGGCGAAAACTCTCAAGGATCTTACCGCTG

TTGAGATCCAGTTCGATGTAACCCACTCGTGCACCCAACTGATCTTCAGCATCT

TTTACTTTCACCAGCGTTTCTGGGTGAGCAAAAACAGGAAG

GCAAAATGCCGCAAAAAAGGGAATAAGGGCGACACGGAAATGTTGAATACTC

ATACTCTTCCTTTTTCAATATTATTGAAGCATTTATCAGGGTTATTGTCTCATGA

GCGGATACATATTTGAATGTATTTAGAAAAATAAACAAATAGGGGTTCCGCGC

ACATTTCCCCGAAAAGTGCCACCTGACGTCTAAGAAACCATTATTATCATGACA

TTAACCTATAAAAATAGGCGTATCACGAGGCCCTTTCGTCTCGCGCGTTTCGGT

GATGACGGTGAAAACCTCTGACACATGCAGCTCCCGGAGACGGTCACAGCTTG

TCTGTAAGCGGATGCCGGGAGCAGACAAGCCCGTCAGGGCGCGTCAGCGGGTG

TTGGCGGGTGTCGGGGCTGGCTTAACTATGCGGCATCAGAGCAGATTGTACTGA

GAGTGCACCATAGCGGCCGCGGTACCCACACAAAAAACCAACACACAGATGTA

ATGAAAATAAAGATATTTTATT

TCACACCTTCCTCTTCTTCTTGGGGTCAGC
``` mSPA_HDR rd10(250)right
(SEQ ID NO: 63)
```
CTGCAGGCATGCAAGCTTGGCGTAATCATGGTCATAGCTGTTTCCTGTGTGAAA

TTGTTATCCGCTCACAATTCCACACAACATACGAGCCGGAAGCATAAAGTGTAA

AGCCTGGGGTGCCTAATGAGTGAGCTAACTCACATTAATTGCGTTGCGCTCACT

GCCCGCTTTCCAGTCGGGAAACCTGTCGTGCCAGCTGCATTAATGAATCGGCCA

ACGCGCGGGGAGAGGCGGTTTGCGTATTGGGCGC

TCTTCCGCTTCCTCGCTCACTGACTCGCTGCGCTCGGTCGTTCGGCTGCGGCGAG
```

-continued

```
CGGTATCAGCTCACTCAAAGGCGGTAATACGGTTATCCACAGAATCAGGGGAT

AACGCAGGAAAGAACATGTGAGCAAAAGGCCAGCAAAAGGCCAGGAACCGTA

AAAAGGCCGCGTTGCTGGCGTTTTTCCATAGGCTCCGCCCCCCTGACGAGCATC

ACAAAAATCGACGCTCAAGTCAGAGGTGGCGAAAC

CCGACAGGACTATAAAGATACCAGGCGTTTCCCCCTGGAAGCTCCCTCGTGCGC

TCTCCTGTTCCGACCCTGCCGCTTACCGGATACCTGTCCGCCTTTCTCCCTTCGG

GAAGCGTGGCGCTTTCTCATAGCTCACGCTGTAGGTATCTCAGTTCGGTGTAGG

TCGTTCGCTCCAAGCTGGGCTGTGTGCACGAACCCCCCGTTCAGCCCGACCGCT

GCGCCTTATCCGGTAACTATCGTCTTGAGTCCAACCCGGTAAGACACGACTTAT

CGCCACTGGCAGCAGCCACTGGTAACAGGATTAGCAGAGCGAGGTATGTAGGC

GGTGCTACAGAGTTCTTGAAGTGGTGGCCTAACTACGGCTACACTAGAAGAAC

AGTATTTGGTATCTGCGCTCTGCTGAAGCCAGTTACCTTCGGAAAAAGAGTTGG

TAGCTCTTGATCCGGCAAACAAACCACCGCTGGTAGCGGTGGTTTTTTTGTTTG

CAAGCAGCAGATTACGCGCAGAAAAAAAGGATCTCAAGAAGATCCTTTGATCT

TTTCTACGGGGTCTGACGCTCAGTGGAACGAAAACTCACGTTAAGGGATTTTGG

TCATGAGATTATCAAAAAGGATCTTCACCTAGATCCTTTTAAATTAAAAATGAA

GTTTTAAATCAATCTAAAGTATATATGAGTAAACTTGGTCTGACAGTTACCAAT

GCTTAATCAGTGAGGCACCTATCTCAGCGATCTGTCTATTTCGTTCATCCATAGT

TGCCTGACTCCCCGTCGTGTAGATAACTACGATACGGGAGGGCTTACCATCTGG

CCCCAGTGCTGCAATGATACCGCGAGACCCACGCTCACCGGCTCCAGATTTATC

AGCAATAAACCAGCCAGCCGGAAGGGCCGAGCGCAGAAGTGGTCCTGCAACTT

TATCCGCCTCCATCCAGTCTATTAATTGTTGCCGGGAAGCTAGAGTAAGTAGTT

CGCCAGTTAATAGTTTGCGCAACGTTGTTGCCATTGC

TACAGGCATCGTGGTGTCACGCTCGTCGTTTGGTATGGCTTCATTCAGCTCCGG

TTCCCAACGATCAAGGCGAGTTACATGATCCCCCATGTTGTGCAAAAAAGCGGT

TAGCTCCTTCGGTCCTCCGATCGTTGTCAGAAGTAAGTTGGCCGCAGTGTTATC

ACTCATGGTTATGGCAGCACTGCATAATTCTCTTACTGTCATGCCATCCGTAAG

ATGCTTTTCTGTGACTGGTGAGTACTCAACCAAGTCA

TTCTGAGAATAGTGTATGCGGCGACCGAGTTGCTCTTGCCCGGCGTCAATACGG

GATAATACCGCGCCACATAGCAGAACTTTAAAAGTGCTCATCATTGGAAAACG

TTCTTCGGGGCGAAAACTCTCAAGGATCTTACCGCTGTTGAGATCCAGTTCGAT

GTAACCCACTCGTGCACCCAACTGATCTTCAGCATCTTTTACTTTCACCAGCGTT

TCTGGGTGAGCAAAAACAGGAAGGCAAAATGCCGC

AAAAAAGGGAATAAGGGCGACACGGAAATGTTGAATACTCATACTCTTCCTTT

TTCAATATTATTGAAGCATTTATCAGGGTTATTGTCTCATGAGCGGATACATATT

TGAATGTATTTAGAAAAATAAACAAATAGGGGTTCCGCGCACATTTCCCCGAA

AAGTGCCACCTGACGTCTAAGAAACCATTATTATCATGACATTAACCTATAAAA

ATAGGCGTATCACGAGGCCCTTTCGTCTCGCGCGTTTCGGTGATGACGGTGAAA

ACCTCTGACACATGCAGCTCCCGGAGACGGTCACAGCTTGTCTGTAAGCGGATG

CCGGGAGCAGACAAGCCCGTCAGGGCGCGTCAGCGGGTGTTGGCGGGTGTCGG

GGCTGGCTTAACTATGCGGCATCAGAGCAGATTGTACTGAGAGTGCACCATAG
```

-continued
CGGCCGCGGTACCCACACAAAAAACCAACACACAGATGTAATGAAAATAAAG

ATATTTTATTTCACACCTTCCTCTTCTTCTTGGGGTCAGCCCTGCTGTCTCCACC

GAGCTGAGAGAGGTCGATTCTTGTTTCATAGAGCCCCGTAATTGACTGATGAAT

CAGTGTGGCGTCCAGGACCTCCTTTGTAGAGGTGTACCGCTTTCTGTCTATGGT

GGTGTCGAAGTACTTGAAGGCTGCAGGCGCGCCCAAGTTGGTCAGAGTAAACA

AGTGGATAATGTTTTCTGCCTGCTCCCTGATGGGCTTATCCCTGTGCTTATTGTA

AGCAGAAAGCACCTTATCGAGGTTAGCGTCGGCGAGGATCACTCTTTTGGAGA

ATTCGCTTATTTGCTCGATGATCTCATCAAGGTAGTGTTTGTGTTGTTCCACGAA

CAGCTGCTTCTGCTCATTATCTTCGGGAGACCCTTTGAGCTTTTCATAGTGGCTG

GCCAGATACAAGAAATTAACGTATTTAGAGGGCAGTGCCAGCTCGTTACCTTTC

TGCAGCTCGCCCGCACTAGCGAGCATTCGTTTCCGGCCGTTTTCAAGCTCAAAG

AGAGAGTACTTGGGAAGCTTAATGATGAGGTCTTTTTTGACCTCTTTATATCCTT

TCGCCTCGAGAAAGTCGATGGGGTTTTTTTCGAAGCTTGATCGCTCCATGATTG

TGATGCCCAGCAGTTCCTTGACGCTTTTGAGTTTTTTAGACTTCCCTTTCTCCAC

TTTGGCCACAACCAGTACACTGTAAGCGACTGTAGGAGAATCGAATCCGCCGT

ATTTCTTGGGGTCCCAATCTTTTT

TGCGTGCGATCAGCTTGTCGCTGTTCCTTTTCGGGAGGATACTTTCCTTGGAGA

AGCCTCCGGTCTGTACTTCGGTCTTTTTAACGATGTTCACCTGCGGCATGGACA

GGACCTTCCGGACTGTCGCGAAATCCCTACCCTTGTCCCACACGATTTCTCCTGT

TTCTCCGTTTGTTTCGATAAGTGGTCGCTTCCGAATCTCTCCATTGGCCAGTGTA

ATCTCGGTCTTGAAAAAATTCATAATATTGCTGTAA

AAGAAGTACTTAGCGGTGGCCTTGCCTATTTCCTGCTCAGACTTTGCGATCATTT

TCCTAACATCGTACACTTTATAGTCTCCGTAAACAAATTCAGATTCAAGCTTGG

GATATTTTTTGATAAGTGCAGTGCCTACCACTGCATTCAGGTAGGCATCATGCG

CATGGTGGTAATTGTTGATCTCTCTCACCTTATAAAACTGAAAGTCCTTTCTGAA

ATCTGAGACCAGCTTAGACTTCAGAGTAATAACTTTCACCTCTCGAATCAGTTT

GTCATTTTCATCGTACTTGGTGTTCATGCGTAATCGAGAATTTGGGCCACGTG

CTTGGTGATCTGGCGTGTCTCAACAAGCTGCCTTTTGATGAAGCCGGCTTTATC

CAACTCAGACAGGCCACCTCGTTCAGCCTTAGTCAGATTATCGAACTTCCGTTG

TGTGATCAGTTTGGCGTTCAGCAGCTGCCGCCAATAATTTTTCATTTCTTGACA

ACTTCTTCTGAGGGGACGTTATCACTCTTCCCTCTATTTTTATCGGATCTTGTCA

ACACTTTATTATCAATAGAATCATCTTTGAGAAAAGACTGGGGCACGATATGAT

CCACGTCGTAGTCGGAGAGCCGATTGATGTCCAGTTCCTGATCCACGTACATGT

CCCTGCCGTTCTGCAGGTAGTACAGGTAGAGCTTCTCATTCTGAAGCTGGGTGT

TTTCAACTGGGTGTTCCTTAAGGATTTGGGACCCCAGTTCTTTTATACCCTCTTC

AATCCTCTTCATCCTTTCCCTACTGTTCTTCTGTCCCTTCTGGGTAGTTTGGTTCT

CTCGGGCCATCTCGATAACGATATTCTCGGGCTTATGCCTTCCCATTACTTTGAC

GAGTTCATCCACGACCTTAACGGTCTGCAGTATTCCCTTTTTGATAGCTGGGCT

ACCTGCAAGATTAGCGATGTGCTCGTGAAGACTGTCCCCCTGGCCAGAAACTTG

TGCTTTCTGGATGTCCTCCTTAAAGGTGAGAGAGTCATCATGGATCAACTGCAT

GAAGTTCCGGTTGGCAAATCCATCGGACTTAAGAAAATCCAGGATTGTCTTTCC

-continued

```
ACTCTGCTTGTCTCGGATCCCATTGATCAGTTTTCTTGACAGCCGCCCCCATCCT
GTATATCGGCGCCTCTTGAGCTGTTTCATGACTTTGTCGTCGAAGAGATGAGCG
TAAGTTTTCAAGCGTTCTTCAATCATCTCCCTATCTTCAAACAACGTAAGGGTG
AGGACAATGTCCTCAAGAATGTCCTCGTTCTCCTCATTGTCCAGGAAGTCCTTG
TCTTTAATGATTTTCAGGAGATCGTGATACGTTCCCAGGGATGCGTTGAAGCGA
TCCTCCACTCCGCTGATTTCAACAGAGTCGAAACATTCAATCTTTTTGAAATAG
TCTTCTTTGAGCTGTTTCACGGTAACTTTCCGGTTCGTCTTGAAGAGGAGGTCCA
CGATAGCTTTCTTCTGCTCTCCAGACAGGAATGCTGGCTTTCTCATCCCTTCTGT
GACGTATTTGACCTTGGTGAGCTCGTTATAAACTGTGAAGTACTCGTACAGCAG
AGAGTGTTTAGGAAGCACCTTTTCGTTAGGCAGATTTTTATCAAAGTTAGTCAT
CCTTTCGATGAAGGACTGGGCAGAGGCCCCCTTATCCACGACTTCCTCGAAGTT
CCAGGGAGTGATGGTCTCTTCTGATTTGCGAGTCATCCACGCGAATCTGGAATT
TCCCCGGGCGAGGGGCCTACATAGTAGGGTATCCGAAATGTGAGGATTTTCTC
AATCTTTTCCCTGTTATCTTTCAAAAAGGGGTAGAAATCCTCTTGCCGCCTGAG
GATAGCGTGCAGTTCGCCCAGGTGAATCTGGTGGGGATGCTTCCATTGTCGAA
AGTGCGCTGTTTGCGCAACAGATCTTCTCTGTTAAGCTTTACCAGCAGCTCCTC
GGTGCCGTCCATTTTTTCCAAGATGGGCTTAATAAATTTGTAAAATTCCTCCTGG
CTTGCTCCGCCGTCAATGTATCCGGCGTAGCCATTTTTAGACTGATCGAAGAAA
ATTTCCTTGTACTTCTCAGGCAGTTGCTGTCTGACAAGGGCCTTCAGCAAAGTC
AAGTCTTGGTGGTGCTCATCATAGCGCTTGATCATACTAGCGCTCAGCGGAGCT
TTGGTGATCTCCGTGTTCACTCGCAGAATATCACTCAGCAGAATGGCGTCTGAC
AGGTTCTTTGCCGCCAAAAAAAGGTCTGCGTACTGGTCGCCGATCTGGGCCAGC
AGATTGTCGAGATCATCATCGTAGGTGTCTTTGCTCAGTTGAAGCTTGGCATCT
TCGGCCAGGTCGAAGTTAGATTTAAAGTTGGGGGTCAGCCCGAGTGACAGGGC
GATAAGATTACCAAACAGGCCGTTCTTCTTCTCCCCAGGGAGCTGTGCGATGAG
GTTTTCGAGCCGCCGGGATTTGGACAGCCTAGCGCTCAGGATTGCTTTGGCGTC
AACTCCGGATGCGTTGATCGGGTTCTCTTCGAAAAGCTGATTGTAAGTCTGAAC
CAGTTGGATAAAGAGTTTGTCGACATCGCTGTTGTCTGGGTTCAGGTCCCCCTC
GATGAGGAAGTGTCCCCGAAATTTGATCATATGCGCCAGCGCGAGATAGATCA
ACCGCAAGTCAGCCTTATCAGTACTGTCTACAAGCTTCTTCCTCAGATGATATA
TGGTTGGGTACTTTTCATGGTACGCCACCTCGTCCACGATATTGCCAAAGATTG
GGTGGCGCTCGTGCTTTTTATCCTCCTCCACCAAAAAGGACTCCTCCAGCCTAT
GGAAGAAAGAGTCATCCACCTTAGCCATCTCATTACTAAAGATCTCCTGCAGGT
AGCAGATCCGATTCTTTCTGCGGGTATATCTGCGCCGTGCTGTTCTTTTGAGCCG
CGTGGCTTCGGCCGTCTCCCCGGAGTCGAACAGGAGGGCGCCAATGAGGTTCTT
CTTTATGCTGTGGCGATCGGTATTGCCCAGAACTTTGAATTTTTTGCTCGGCACC
TTGTACTCGTCCGTAATGACGGCCCAGCCGACGCTGTTTGTGCCGATATCGAGC
CCAATGGAGTACTTCTTGTCCATGGTGGCGGCTCTTGAAGGACGACGTCATCAT
CCCTTGCCCGGATGCGCGGGCTTCTTGTCTAGCACAGGAGCCTGGGGTAGAGCG
CATGC

AAATTACGCGCTGTGCTTTGTGGGAAATCACCCTAAACGAAAAATTTATTCCTC
```

-continued

TTTCGAGCCTTATAGTGGCGGCCGGTCTACATCCTAGGTTTTAGAGCTAGAAAT

AGCAAGTTAAAATAAGGCTAGTCCGTTATCAACTTGAAAAAGTGGCACCGAGT

CGGTGCTTTTTTGTTGATATGGTGCTGTGTAGGCTCATATGTGGATCTCAGAACC

CACATGTACTCTGCTCCCCAGGTCTTGGTGCGCTTTCTATTCTCTGTCAGCAAAG

CCTATCGAAGAATCACCTACCACAACTGGCGCCACGGCTTCAATGTAGCCCAG

ACCATGTTTACCCTACTCATGGTACGTATGTAAATTGGATGGGCTAGATGAATC

AGAGGGCTGGGGCAAGGACCACAGCTAACTATCTTCTGGCCCAAGGAACGCGG

CCGCCTAGAGTCGAC mSPA_HDR rd10(250)left (SEQ ID NO: 64)

ATGTAATGAAAATAAAGATATTTTATTTCACACCTTCCTCTTCTTCTTGGGGTCA

GCCCTGCTGTCTCCACCGAGCTGAGAGAGGTCGATTCTTGTTTCATAGAGCCCC

GTAATTGACTGATGAATCAGTGTGGCGTCCAGGACCTCCTTTGTAGAGGTGTAC

CGCTTTCTGTCTATGGTGGTGTCGAAGTACTTGAAGGCTGCAGGCGCGCCCAAG

TTGGTCAGAGTAAACAAGTGGATAATGTTTTCTGCCTGCTCCCTGATGGGCTTA

TCCCTGTGCTTATTGTAAGCAGAAAGCACCTTATCGAGGTTAGCGTCGGCGAGG

ATCACTCTTTTGGAGAATTCGCTTATTTGCTCGATGATCTCATCAAGGTAGTGTT

TGTGTTGTTCCACGAACAGCTGCTTCTGCTCATTATCTTCGGGAGACCCTTTGAG

CTTTTCATAGTGGCTGGCCAGATACAAGAAATTAACGTATTTAGAGGGCAGTGC

CAGCTCGTTACCTTTCTGCAGCTCGCCCGCACTAGCGAGCATTCGTTTCCGGCC

GTTTTCAAGCTCAAAGAGAGAGTACTTGGGAAGCTTAATGATGAGGTCTTTTTT

GACCTCTTTATATCCTTTCGCCTCGAGAAAGTCGATGGGTTTTTTTCGAAGCTT

GATCGCTCCATGATTGTGATGCCCAGCAGTTCCTTGACGCTTTTGAGTTTTTTAG

ACTTCCCTTTCTCCACTTTGGCCACAACCAGTACACTGTAAGCGACTGTAGGAG

AATCGAATCCGCCGTATTTCTTGGGGTCCCAATCTTTTTTGCGTGCGATCAGCTT

GTCGCTGTTCCTTTTCGGGAGGATACTTTCCTTGGAGAAGCCTCCGGTCTGTACT

TCGGTCTTTTTAACGATGTTCACCTGCGGCATGGACAGGACCTTCCGGACTGTC

GCGAAATCCCTACCCTTGTCCCACACGATTTCTCCTGTTTCTCCGTTTGTTTCGA

TAAGTGGTCGCTTCCGAATCTCTCCATTGGCCAGTGTAATCTCGGTCTTGAAAA

AATTCATAATATTGCTGTAAAAGAAGTACTTAGCGGTGGCCTTGCCTATTTCCT

GCTCAGACTTTGCGATCATTTTCCTAACATCGTACACTTTATAGTCTCCGTAAAC

AAATTCAGATTCAAGCTTGGGATATTTTTTGATAAGTGCAGTGCCTACCACTGC

ATTCAGGTAGGCATCATGCGCATGGTGGTAATTGTTGATCTCTCTCACCTTATA

AAACTGAAAGTCCTTTCTGAAATCTGAGACCAGCTTAGACTTCAGAGTAATAAC

TTTCACCTCTCGAATCAGTTTGTCATTTTCATCGTACTTGGTGTTCATGCGTGAA

TCGAGAATTTGGGCCACGTGCTTGGTGATCTGGCGTGTCTCAACAAGCTGCCTT

TTGATGAAGCCGGCTTTATCCAACTCAGACAGGCCACCTCGTTCAGCCTTAGTC

AGATTATCGAACTTCCGTTGTGTGATCAGTTTGGCGTTCAGCAGCTGCCGCCAA

TAATTTTTCATTTCTTGACAACTTCTTCTGAGGGGACGTTATCACTCTTCCCTCT

ATTTTTATCGGATCTTGTCAACACTTTATTATCAATAGAATCATCTTTGAGAAAA

GACTGGGGCACGATATGATCCACGTCGTAGTCGGAGAGCCGATTGATGTCCAG

TTCCTGATCCACGTACATGTCCCTGCCGTTCTGCAGGTAGTACAGGTAGAGCTT

-continued

```
CTCATTCTGAAGCTGGGTGTTTTCAACTGGGTGTTCCTTAAGGATTTGGGACCC

CAGTTCTTTTATACCCTCTTCAATCCTCTTCATCCTTTCCCTACTGTTCTTCTGTC

CCTTCTGGGTAGTTTGGTTCTCTCGGGCCATCTCGATAACGATATTCTCGGGCTT

ATGCCTTCCCATTACTTTGACGAGTTCATCCACGACCTTAACGGTCTGCAGTATT

CCCTTTTTGATAGCTGGGCTACCTGCAAGATTAGCGATGTGCTCGTGAAGACTG

TCCCCCTGGCCAGAAACTTGTGCTTTCTGGATGTCCTCCTTAAAGGTGAGAGAG

TCATCATGGATCAACTGCATGAAGTTCCGGTTGGCAAATCCATCGGACTTAAGA

AAATCCAGGATTGTCTTTCCACTCTGCTTGTCTCGGATCCCATTGATCAGTTTTC

TTGACAGCCGCCCCCATCCTGTATATCGGCGCCTCTTGAGCTGTTTCATGACTTT

GTCGTCGAAGAGATGAGCGTAAGTTTTCAAGCGTTCTTCAATCATCTCCCTATC

TTCAAACAACGTAAGGGTGAGGACAATGTCCTCAAGAATGTCCTCGTTCTCCTC

ATTGTCCAGGAAGTCCTTGTCTTTAATGATTTTCAGGAGATCGTGATACGTTCCC

AGGGATGCGTTGAAGCGATCCTCCACTCCGCTGATTTCAACAGAGTCGAAACAT

TCAATCTTTTTGAAATAGTCTTCTTTGAGCTGTTTCACGGTAACTTTCCGGTTCG

TCTTGAAGAGGAGGTCCACGATAGCTTTCTTCTGCTCTCCAGACAGGAATGCTG

GCTTTCTCATCCCTTCTGTGACGTATTTGACCTTGGTGAGCTCGTTATAAACTGT

GAAGTACTCGTACAGCAGAGAGTGTTTAGGAAGCACCTTTTCGTTAGGCAGATT

TTTATCAAAGTTAGTCATCCTTTCGATGAAGGACTGGGCAGAGGCCCCCTTATC

CACGACTTCCTCGAAGTTCCAGGGAGTGATGGTCTCTTCTGATTTGCGAGTCAT

CCACGCGAATCTGGAATTTCCCCGGGCGAGGGGGCCTACATAGTAGGGTATCC

GAAATGTGAGGATTTTCTCAATCTTTTCCCTGTTATCTTTCAAAAAGGGGTAGA

AATCCTCTTGCCGCCTGAGGATAGCGTGCAGTTCGCCCAGGTGAATCTGGTGGG

GGATGCTTCCATTGTCGAAAGTGCGCTGTTTGCGCAACAGATCTTCTCTGTTAA

GCTTTACCAGCAGCTCCTCGGTGCCGTCCATTTTTTCCAAGATGGGCTTAATAA

ATTTGTAAAATTCCTCCTGGCTTGCTCCGCCGTCAATGTATCCGGCGTAGCCATT

TTTAGACTGATCGAAGAAAATTTCCTTGTACTTCTCAGGCAGTTGCTGTCTGAC

AAGGGCCTTCAGCAAAGTCAAGTCTTGGTGGTGCTCATCATAGCGCTTGATCAT

ACTAGCGCTCAGCGGAGCTTTGGTGATCTCCGTGTTCACTCGCAGAATATCACT

CAGCAGAATGGCGTCTGACAGGTTCTTTGCCGCCAAAAAAGGTCTGCGTACT

GGTCGCCGATCTGGGCCAGCAGATTGTCGAGATCATCATCGTAGGTGTCTTTGC

TCAGTTGAAGCTTGGCATCTTCGGCCAGGTCGAAGTTAGATTTAAAGTTGGGGG

TCAGCCCGAGTGACAGGGCGATAAGATTACCAAACAGGCCGTTCTTCTTCTCCC

CAGGGAGCTGTGCGATGAGGTTTTCGAGCCGCCGGGATTTGGACAGCCTAGCG

CTCAGGATTGCTTTGCGTCAACTCCGGATGCGTTGATCGGGTTCTCTTCGAAA

AGCTGATTGTAAGTCTGAACCAGTTGGATAAAGAGTTTGTCGACATCGCTGTTG

TCTGGGTTCAGGTCCCCCTCGATGAGGAAGTGTCCCCGAAATTTGATCATATGC

GCCAGCGCGAGATAGATCAACCGCAAGTCAGCCTTATCAGTACTGTCTACAAG

CTTCTTCCTCAGATGATATATGGTTGGGTACTTTTCATGGTACGCCACCTCGTCC

ACGATATTGCCAAAGATTGGGTGGCGCTCGTGCTTTTTATCCTCCTCCACCAAA

AAGGACTCCTCCAGCCTATGGAAGAAAGAGTCATCCACCTTAGCCATCTCATTA

CTAAAGATCTCCTGCAGGTAGCAGATCCGATTCTTTCTGCGGGTATATCTGCGC
```

-continued

```
CGTGCTGTTCTTTTGAGCCGCGTGGCTTCGGCCGTCTCCCCGGAGTCGAACAGG

AGGGCGCCAATGAGGTTCTTCTTTATGCTGTGGCGATCGGTATTGCCCAGAACT

TTGAATTTTTTGCTCGGCACCTTGTACTCGTCCGTAATGACGGCCCAGCCGACG

CTGTTTGTGCCGATATCGAGCCCAATGGAGTACTTCTTGTCCATGGTGGCGGCT

CTTGAAGGACGACGTCATCATCCCTTGCCCGGATGCGCGGGC

TTCTTGTCTAGCACAGGAGCCTGGGGTAGAGCGCATGCAAATTACGCGCTGTGC

TTTGTGGGAAATCACCCTAAACGAAAAATTTATTCCTCTTTCGAGCCTTATAGT

GGCGGCCGGTCTACATCCTAGGTTTTAGAGCTAGAAATAGCAAGTTAAAATAA

GGCTAGTCCGTTATCAACTTGAAAAAGTGGCACCGAGTCGGTGCTTTTTTGTTA

ACGCGGCCGCCTAGAGTCGACCTGCAGGCATGCAAGC

TTGGCGTAATCATGGTCATAGCTGTTTCCTGTGTGAAATTGTTATCCGCTCACAA

TTCCACACAACATACGAGCCGGAAGCATAAAGTGTAAAGCCTGGGGTGCCTAA

TGAGTGAGCTAACTCACATTAATTGCGTTGCGCTCACTGCCCGCTTTCCAGTCG

GGAAACCTGTCGTGCCAGCTGCATTAATGAATCGGCCAACGCGCGGGGAGAGG

CGGTTTGCGTATTGGGCGCTCTTCCGCTTCCTCGCT

CACTGACTCGCTGCGCTCGGTCGTTCGGCTGCGGCGAGCGGTATCAGCTCACTC

AAAGGCGGTAATACGGTTATCCACAGAATCAGGGGATAACGCAGGAAAGAAC

ATGTGAGCAAAAGGCCAGCAAAAGGCCAGGAACCGTAAAAAGGCCGCGTTGC

TGGCGTTTTTCCATAGGCTCCGCCCCCCTGACGAGCATCACAAAAATCGACGCT

CAAGTCAGAGGTGGCGAAACCCGACAGGACTATAAA

GATACCAGGCGTTTCCCCCTGGAAGCTCCCTCGTGCGCTCTCCTGTTCCGACCCT

GCCGCTTACCGGATACCTGTCCGCCTTTCTCCCTTCGGGAAGCGTGGCGCTTTCT

CATAGCTCACGCTGTAGGTATCTCAGTTCGGTGTAGGTCGTTCGCTCCAAGCTG

GGCTGTGTGCACGAACCCCCCGTTCAGCCCGACCGCTGCGCCTTATCCGGTAAC

TATCGTCTTGAGTCCAACCCGGTAAGACACGACTTATCGCCACTGGCAGCAGCC

ACTGGTAACAGGATTAGCAGAGCGAGGTATGTAGGCGGTGCTACAGAGTTCTT

GAAGTGGTGGCCTAACTACGGCTACACTAGAAGAACAGTATTTGGTATCTGCG

CTCTGCTGAAGCCAGTTACCTTCGGAAAAAGAGTTGGTAGCTCTTGATCCGGCA

AACAAACCACCGCTGGTAGCGGTGGTTTTTTTGTTTGCAAGCAGCAGATTACGC

GCAGAAAAAAAGGATCTCAAGAAGATCCTTTGATCTTTTCTACGGGGTCTGACG

CTCAGTGGAACGAAAACTCACGTTAAGGGATTTTGGTCATGAGATTATCAAAA

AGGATCTTCACCTAGATCCTTTTAAATTAAAAATGAAGTTTTAAATCAATCTAA

AGTATATATGAGTAAACTTGGTCTGACAGTTACCAATGCTTAATCAGTGAGGCA

CCTATCTCAGCGATCTGTCTATTTCGTTCATCCATAGTTGCCTGACTCCCCGTCGT

GTAGATAACTACGATACGGGAGGGCTTACCATCTGGCCCCAGTGCTGCAATGA

TACCGCGAGACCCACGCTCACCGGCTCCAGATTTATCAGCAATAAACCAGCCA

GCCGGAAGGGCCGAGCGCAGAAGTGGTCCTGCAACTTTATCCGCCTCCATCCA

GTCTATTAATTGTTGCCGGGAAGCTAGAGTAAGTAGTTCGCCAGTTAATAGTTT

GCGCAACGTTGTTGCCATTGCTACAGGCATCGTGGTGTCACGCTCGTCGTTTGG

TATGGCTTCATTCAGCTCCGGTTCCCAACGATCAAGGCGAGTTACATGATCCCC

CATGTTGTGCAAAAAAGCGGTTAGCTCCTTCGGTCCTCCGATCGTTGTCAGAAG
```

-continued

TAAGTTGGCCGCAGTGTTATCACTCATGGTTATGGCAGCACTGCATAATTCTCT

TACTGTCATGCCATCCGTAAGATGCTTTTCTGTGACTGGTGAGTACTCAACCAA

GTCATTCTGAGAATAGTGTATGCGGCGACCGAGTTGCTCTTGCCCGGCGTCAAT

ACGGGATAATACCGCGCCACATAGCAGAACTTTAAAAGTGCTCATCATTGGAA

AACGTTCTTCGGGGCGAAAACTCTCAAGGATCTTACCGCTGTTGAGATCCAGTT

CGATGTAACCCACTCGTGCACCCAACTGATCTTCAGCATCTTTTACTTTCACCAG

CGTTTCTGGGTGAGCAAAAACAGGAAGGCAAAATGCCGCAAAAAAGGGAATA

AGGGCGACACGGAAATGTTGAATACTCATACTCTTCCTTTTTCAATATTATTGA

AGCATTTATCAGGGTTATTGTCTCATGAGCGGATACATATTTGAATGTATTTAG

AAAAATAAACAAATAGGGGTTCCGCGCACATTTCCCCGAAAAGTGCCACCTGA

CGTCTAAGAAACCATTATTATCATGACATTAACCTATAAAAATAGGCGTATCAC

GAGGCCCTTTCGTCTCGCGCGTTTCGGTGATGACGGTGAAAACCTCTGACACAT

GCAGCTCCCGGAGACGGTCACAGCTTGTCTGTAAGCGGATGCCGGGAGCAGAC

AAGCCCGTCAGGGCGCGTCAGCGGGTGTTGGCGGGTGTCGGGGCTGGCTTAAC

TATGCGGCATCAGAGCAGATTGTACTGAGAGTGCACCATAGCGGCCGCGGTAC

GATATGGTGCTGTGTAGGCTCATATGTGGATCTCAGAACCCACATGTACTCTGC

TCCCCAGGTCTTGGTGCGCTTTCTATTCTCTGTCAGCAAAGCCTATCGAAGAAT

CACCTACCACAACTGGCGCCACGGCTTCAATGTAGCCCAGACCATGTTTACCCT

ACTCATGGTACGTATGTAAATTGGATGGGCTAGATGAATCAGAGGGCTGGGGC

AAGGACCACAGCTAACTATCTTCTGGCCCAAGGGTACCCACACAAAAAACCAA

CACACAG mSPA_HDR rd12(250)right (SEQ ID NO: 65)
CTGCAGGCATGCAAGCTTGGCGTAATCATGGTCATAGCTGTTTCCTGTGTGAAA

TTGTTATCCGCTCACAATTCCACACAACATACGAGCCGGAAGCATAAAGTGTAA

AGCCTGGGGTGCCTAATGAGTGAGCTAACTCACATTAATTGCGTTGCGCTCACT

GCCCGCTTTCCAGTCGGGAAACCTGTCGTGCCAGCTGCATTAATGAATCGGCCA

ACGCGCGGGGAGAGGCGGTTTGCGTATTGGGCGCTCTTCCGCTTCCTCGCTCAC

TGACTCGCTGCGCTCGGTCGTTCGGCTGCGGCGAGCGGTATCAGCTCACTCAAA

GGCGGTAATACGGTTATCCACAGAATCAGGGGATAACGCAGGAAAGAACATGT

GAGCAAAAGGCCAGCAAAAGGCCAGGAACCGTAAAAAGGCCGCGTTGCTGGC

GTTTTTCCATAGGCTCCGCCCCCCTGACGAGCATCACAAAAATCGACGCTCAAG

TCAGAGGTGGCGAAACCCGACAGGACTATAAAGATACCAGGCGTTTCCCCCTG

GAAGCTCCCTCGTGCGCTCTCCTGTTCCGACCCTGCCGCTTACCGGATACCTGTC

CGCCTTTCTCCCTTCGGGAAGCGTGGCGCTTTCTCATAGCTCACGCTGTAGGTAT

CTCAGTTCGGTGTAGGTCGTTCGCTCCAAGCTGGGCTGTGTGCACGAACCCCCC

GTTCAGCCCGACCGCTGCGCCTTATCCGGTAACTATCGTCTTGAGTCCAACCCG

GTAAGACACGACTTATCGCCACTGGCAGCAGCCACTGGTAACAGGATTAGCAG

AGCGAGGTATGTAGGCGGTGCTACAGAGTTCTTGAAGTGGTGGCCTAACTACG

GCTACACTAGAAGAACAGTATTTGGTATCTGCGCTCTGCTGAAGCCAGTTACCT

TCGGAAAAAGAGTTGGTAGCTCTTGATCCGGCAAACAAACCACCGCTGGTAGC

GGTGGTTTTTTTGTTTGCAAGCAGCAGATTACGCGCAGAAAAAAAGGATCTCAA

-continued

```
GAAGATCCTTTGATCTTTTCTACGGGGTCTGACGCTCAGTGGAACGAAAACTCA
CGTTAAGGGATTTTGGTCATGAGATTATCAAAAAGGATCTTCACCTAGATCCTT
TTAAATTAAAAATGAAGTTTTAAATCAATCTAAAGTATATATGAGTAAACTTGG
TCTGACAGTTACCAATGCTTAATCAGTGAGGCACCTATCTCAGCGATCTGTCTA
TTTCGTTCATCCATAGTTGCCTGACTCCCCGTCGTGTAGATAACTACGATACGG
GAGGGCTTACCATCTGGCCCCAGTGCTGCAATGATACCGCGAGACCCACGCTC
ACCGGCTCCAGATTTATCAGCAATAAACCAGCCAGCCGGAAGGGCCGAGCGCA
GAAGTGGTCCTGCAACTTTATCCGCCTCCATCCAGTCTATTAATTGTTGCCGGG
AAGCTAGAGTAAGTAGTTCGCCAGTTAATAGTTTGCGCAACGTTGTTGCCATTG
CTACAGGCATCGTGGTGTCACGCTCGTCGTTTGGTATGGCTTCATTCAGCTCCG
GTTCCCAACGATCAAGGCGAGTTACATGATCCCCCATGTTGTGCAAAAAAGCG
GTTAGCTCCTTCGGTCCTCCGATCGTTGTCAGAAGTAAGTTGGCCGCAGTGTTA
TCACTCATGGTTATGGCAGCACTGCATAATTCTCTTACTGTCATGCCATCCGTAA
GATGCTTTTCTGTGACTGGTGAGTACTCAACCAAGTCATTCTGAGAATAGTGTA
TGCGGCGACCGAGTTGCTCTTGCCCGGCGTCAATACGGGATAATACCGCGCCAC
ATAGCAGAACTTTAAAAGTGCTCATCATTGGAAAACGTTCTTCGGGGCGAAAA
CTCTCAAGGATCTTACCGCTGTTGAGATCCAGTTCGATGTAACCCACTCGTGCA
CCCAACTGATCTTCAGCATCTTTTACTTTCACCAGCGTTTCTGGGTGAGCAAAA
ACAGGAAGGCAAATGCCGCAAAAAAGGGAATAAGGGCGACACGGAAATGTT
GAATACTCATACTCTTCCTTTTTCAATATTATTGAAGCATTTATCAGGGTTATTG
TCTCATGAGCGGATACATATTTGAATGTATTTAGAAAAATAAACAAATAGGGG
TTCCGCGCACATTTCCCCGAAAAGTGCCACCTGACGTCTAAGAAACCATTATTA
TCATGACATTAACCTATAAAAATAGGCGTATCACGAGGCCCTTTCGTCTCGCGC
GTTTCGGTGATGACGGTGAAAACCTCTGACACATGCAGCTCCCGGAGACGGTC
ACAGCTTGTCTGTAAGCGGATGCCGGGAGCAGACAAGCCCGTCAGGGCGCGTC
AGCGGGTGTTGGCGGGTGTCGGGGCTGGCTTAACTATGCGGCATCAGAGCAGA
TTGTACTGAGAGTGCACCATAGCGGCCGCGGTACCCACACAAAAAACCAACAC
ACAGATGTAATGAAAATAAAGATATTTTATTTCACACCTTCCTCTTCTTCTTGGG
GTCAGCCCTGCTGTCTCCACCGAGCTGAGAGAGGTCGATTCTTGTTTCATAGAG
CCCCGTAATTGACTGATGAATCAGTGTGGCGTCCAGGACCTCCTTTGTAGAGGT
GTACCGCTTTCTGTCTATGGTGGTGTCGAAGTACTTGAAGGCTGCAGGCGCGCC
CAAGTTGGTCAGAGTAAACAAGTGGATAATGTTTTCTGCCTGCTCCCTGATGGG
CTTATCCCTGTGCTTATTGTAAGCAGAAAGCACCTTATCGAGGTTAGCGTCGGC
GAGGATCACTCTTTTGGAGAATTCGCTTATTTGCTCGATGATCTCATCAAGGTA
GTGTTTGTGTTGTTCCACGAACAGCTGCTTCTGCTCATTATCTTCGGGAGACCCT
TTGAGCTTTTCATAGTGGCTGGCCAGATACAAGAAATTAACGTATTTAGAGGGC
AGTGCCAGCTCGTTACCTTTCTGCAGCTCGCCCGCACTAGCGAGCATTCGTTTC
CGGCCGTTTTCAAGCTCAAAGAGAGAGTACTTGGGAAGCTTAATGATGAGGTC
TTTTTTGACCTCTTTATATCCTTTCGCCTCGAGAAAGTCGATGGGGTTTTTTCG
AAGCTTGATCGCTCCATGATTGTGATGCCCAGCAGTTCCTTGACGCTTTTGAGTT
TTTTAGACTTCCCTTTCTCCACTTTGGCCACAACCAGTACACTGTAAGCGACTGT
```

-continued

```
AGGAGAATCGAATCCGCCGTATTTCTTGGGGTCCCAATCTTTTTTGCGTGCGAT
CAGCTTGTCGCTGTTCCTTTTCGGGAGGATACTTTCCTTGGAGAAGCCTCCGGTC
TGTACTTCGGTCTTTTTAACGATGTTCACCTGCGGCATGGACAGGACCTTCCGG
ACTGTCGCGAAATCCCTACCCTTGTCCCACACGATTTCTCCTGTTTCTCCGTTTG
TTTCGATAAGTGGTCGCTTCCGAATCTCTCCATTGGCCAGTGTAATCTCGGTCTT
GAAAAAATTCATAATATTGCTGTAAAAGAAGTACTTAGCGGTGGCCTTGCCTAT
TTCCTGCTCAGACTTTGCGATCATTTTCCTAACATCGTACACTTTATAGTCTCCG
TAAACAAATTCAGATTCAAGCTTGGGATATTTTTTGATAAGTGCAGTGCCTACC
ACTGCATTCAGGTAGGCATCATGCGCATGGTGGTAATTGTTGATCTCTCTCACC
TTATAAAACTGAAAGTCCTTTCTGAAATCTGAGACCAGCTTAGACTTCAGAGTA
ATAACTTTCACCTCTCGAATCAGTTTGTCATTTTCATCGTACTTGGTGTTCATGC
GTGAATCGAGAATTTGGGCCACGTGCTTGGTGATCTGGCGTGTCTCAACAAGCT
GCCTTTTGATGAAGCCGGCTTTATCCAACTCAGACAGGCCACCTCGTTCAGCCT
TAGTCAGATTATCGAACTTCCGTTGTGTGATCAGTTTGGCGTTCAGCAGCTGCC
GCCAATAATTTTTCATTTTCTTGACAACTTCTTCTGAGGGGACGTTATCACTCTT
CCCTCTATTTTTATCGGATCTTGTCAACACTTTATTATCAATAGAATCATCTTTG
AGAAAAGACTGGGGCACGATATGATCCACGTCGTAGTCGGAGAGCCGATTGAT
GTCCAGTTCCTGATCCACGTACATGTCCCTGCCGTTCTGCAGGTAGTACAGGTA
GAGCTTCTCATTCTGAAGCTGGGTGTTTTCAACTGGGTGTTCCTTAAGGATTTGG
GACCCCAGTTCTTTTATACCCTCTTCAATCCTCTTCATCCTTTCCCTACTGTTCTT
CTGTCCCTTCTGGGTAGTTTGGTTCTCTCGGGCCATCTCGATAACGATATTCTCG
GGCTTATGCCTTCCCATTACTTTGACGAGTTCATCCACGACCTTAACGGTCTGCA
GTATTCCCTTTTTGATAGCTGGGCTACCTGCAAGATTAGCGATGTGCTCGTGAA
GACTGTCCCCCTGGCCAGAAACTTGTGCTTTCTGGATGTCCTCCTTAAAGGTGA
GAGAGTCATCATGGATCAACTGCATGAAGTTCCGGTTGGCAAATCCATCGGACT
TAAGAAAATCCAGGATTGTCTTTCCACTCTGCTTGTCTCGGATCCCATTGATCA
GTTTTCTTGACAGCCGCCCCCATCCTGTATATCGGCGCCTCTTGAGCTGTTTCAT
GACTTTGTCGTCGAAGAGATGAGCGTAAGTTTTCAAGCGTTCTTCAATCATCTC
CCTATCTTCAAACAACGTAAGGGTGAGGACAATGTCCTCAAGAATGTCCTCGTT
CTCCTCATTGTCCAGGAAGTCCTTGTCTTTAATGATTTTCAGGAGATCGTGATAC
GTTCCCAGGGATGCGTTGAAGCGATCCTCCACTCCGCTGATTTCAACAGAGTCG
AAACATTCAATCTTTTTGAAATAGTCTTCTTTGAGCTGTTTCACGGTAACTTTCC
GGTTCGTCTTGAAGAGGAGGTCCACGATAGCTTTCTTCTGCTCTCCAGACAGGA
ATGCTGGCTTTCTCATCCCTTCTGTGACGTATTTGACCTTGGTGAGCTCGTTATA
AACTGTGAAGTACTCGTACAGCAGAGAGTGTTTAGGAAGCACCTTTTCGTTAGG
CAGATTTTTATCAAAGTTAGTCATCCTTTCGATGAAGGACTGGGCAGAGGCCCC
CTTATCCACGACTTCCTCGAAGTTCCAGGGAGTGATGGTCTCTTCTGATTTGCG
AGTCATCCACGCGAATCTGGAATTTCCCCGGGCGAGGGGGCCTACATAGTAGG
GTATCCGAAATGTGAGGATTTTCTCAATCTTTTCCCTGTTATCTTTCAAAAAGGG
GTAGAAATCCTCTTGCCGCCTGAGGATAGCGTGCAGTTCGCCCAGGTGAATCTG
GTGGGGGATGCTTCCATTGTCGAAAGTGCGCTGTTTGCGCAACAGATCTTCTCT
```

-continued

```
GTTAAGCTTTACCAGCAGCTCCTCGGTGCCGTCCATTTTTTCCAAGATGGGCTTA

ATAAATTTGTAAAATTCCTCCTGGCTTGCTCCGCCGTCAATGTATCCGGCGTAG

CCATTTTTAGACTGATCGAAGAAAATTTCCTTGTACTTCTCAGGCAGTTGCTGTC

TGACAAGGGCCTTCAGCAAAGTCAAGTCTTGGTGGTGCTCATCATAGCGCTTGA

TCATACTAGCGCTCAGCGGAGCTTTGGTGATCTCCGTGTTCACTCGCAGAATAT

CACTCAGCAGAATGGCGTCTGACAGGTTCTTTGCCGCCAAAAAAGGTCTGCGT

ACTGGTCGCCGATCTGGGCCAGCAGATTGTCGAGATCATCATCGTAGGTGTCTT

TGCTCAGTTGAAGCTTGGCATCTTCGGCCAGGTCGAAGTTAGATTTAAAGTTGG

GGGTCAGCCCGAGTGACAGGGCGATAAGATTACCAAACAGGCCGTTCTTCTTCT

CCCCAGGGAGCTGTGCGATGAGGTTTTCGAGC

CGCCGGGATTTGGACAGCCTAGCGCTCAGGATTGCTTTGGCGTCAACTCCGGAT

GCGTTGATCGGGTTCTCTTCGAAAAGCTGATTGTAAGTCTGAACCAGTTGGATA

AAGAGTTTGTCGACATCGCTGTTGTCTGGGTTCAGGTCCCCCTCGATGAGGAAG

TGTCCCCGAAATTTGATCATATGCGCCAGCGCGAGATAGATCAACCGCAAGTC

AGCCTTATCAGTACTGTCTACAAGCTTCTTCCTCAG

ATGATATATGGTTGGGTACTTTTCATGGTACGCCACCTCGTCCACGATATTGCC

AAAGATTGGGTGGCGCTCGTGCTTTTTATCCTCCTCCACCAAAAAGGACTCCTC

CAGCCTATGGAAGAAAGAGTCATCCACCTTAGCCATCTCATTACTAAAGATCTC

CTGCAGGTAGCAGATCCGATTCTTTCTGCGGGTATATCTGCGCCGTGCTGTTCTT

TTGAGCCGCGTGGCTTCGGCCGTCTCCCCGGAGTCGAACAGGAGGGCGCCAAT

GAGGTTCTTCTTTATGCTGTGGCGATCGGTATTGCCCAGAACTTTGAATTTTTTG

CTCGGCACCTTGTACTCGTCCGTAATGACGGCCCAGCCGACGCTGTTTGTGCCG

ATATCGAGCCCAATGGAGTACTTCTTGTCCATGGTGGCGGCTCTTGAAGGACGA

CGTCATCATCCCTTGCCCGGATGCGCGGGCTTCTTGTCTAGCACAGGAGCCTGG

GGTAGAGCGCATGCAAATTACGCGCTGTGCTTTGTGGGAAATCACCCTAAACG

AAAAATTTATTCCTCTTTCGAGCCTTATAGTGGCGGCCGGTCTACATCCTAGGTT

TTAGAGCTAGAAATAGCAAGTTAAAATAAGGCTAGTCCGTTATCAACTTGAAA

AAGTGGCACCGAGTCGGTGCTTTTTTGTTGTTCTGTCTATAGGTAAGCTGACAA

ATAACAAATAGGCACATAGAAAATCTAGTAAGTAGTACCACCTGATATCTCAC

TTTGCTGCAGGCAGGATTCCCCTCTGGCTCACTGGCAGTCTCCTCCGGTGTGGG

CCAGGGCTCTTTGAAGTTGGATCTGAGCCTTTCTATCACCTGTTTGATGGACAA

GCCCTTTTGCACAAGTTTGACTTCAAGGAGGGCCATGTCACATACCACAGAAGG

TAAGTCCATGAACGCGGCCGCCTAGAGTCGAC mSPA_HDR rd12(250)left
                                             (SEQ ID NO: 66)
ATGTAATGAAAATAAAGATATTTTATTTCACACCTTCCTCTTCTTCTTGGGGTCA

GCCCTGCTGTCTCCACCGAGCTGAGAGAGGTCGATTCTTGTTTCATAGAGCCCC

GTAATTGACTGATGAATCAGTGTGGCGTCCAGGACCTCCTTTGTAGAGGTGTAC

CGCTTTCTGTCTATGGTGGTGTCGAAGTACTTGAAGGCTGCAGGCGCGCCCAAG

TTGGTCAGAGTAAACAAGTGGATAATGTTTTCTGCCTGCTCCCTGATGGGCTTA

TCCCTGTGCTTATTGTAAGCAGAAAGCACCTTATCGAGGTTAGCGTCGGCGAGG

ATCACTCTTTTGGAGAATTCGCTTATTTGCTCGATGATCTCATCAAGGTAGTGTT
```

-continued

```
TGTGTTGTTCCACGAACAGCTGCTTCTGCTCATTATCTTCGGGAGACCCTTTGAG

CTTTTCATAGTGGCTGGCCAGATACAAGAAATTAACGTATTTAGAGGGCAGTGC

CAGCTCGTTACCTTTCTGCAGCTCGCCCGCACTAGCGAGCATTCGTTTCCGGCC

GTTTTCAAGCTCAAAGAGAGAGTACTTGGGAAGCTTAATGATGAGGTCTTTTTT

GACCTCTTTATATCCTTTCGCCTCGAGAAAGTCGATGGGGTTTTTTCGAAGCTT

GATCGCTCCATGATTGTGATGCCCAGCAGTTCCTTGACGCTTTTGAGTTTTTAG

ACTTCCCTTTCTCCACTTTGGCCACAACCAGTACACTGTAAGCGACTGTAGGAG

AATCGAATCCGCCGTATTTCTTGGGGTCCCAATCTTTTTTGCGTGCGATCAGCTT

GTCGCTGTTCCTTTTCGGGAGGATACTTTCCTTGGAGAAGCCTCCGGTCTGTACT

TCGGTCTTTTTAACGATGTTCACCTGCGGCATGGACAGGACCTTCCGGACTGTC

GCGAAATCCCTACCCTTGTCCCACACGATTTCTCCTGTTTCTCCGTTTGTTTCGA

TAAGTGGTCGCTTCCGAATCTCTCCATTGGCCAGTGTAATCTCGGTCTTGAAAA

AATTCATAATATTGCTGTAAAAGAAGTACTTAGCGGTGGCCTTGCCTATTTCCT

GCTCAGACTTTGCGATCATTTTCCTAACATCGTACACTTTATAGTCTCCGTAAAC

AAATTCAGATTCAAGCTTGGGATATTTTTTGATAAGTGCAGTGCCTACCACTGC

ATTCAGGTAGGCATCATGCGCATGGTGGTAATTGTTGATCTCTCTCACCTTATA

AAACTGAAAGTCCTTTCTGAAATCTGAGACCAGCTTAGACTTCAGAGTAATAAC

TTTCACCTCTCGAATCAGTTTGTCATTTTCATCGTACTTGGTGTTCATGCGTGAA

TCGAGAATTTGGGCCACGTGCTTGGTGATCTGGCGTGTCTCAACAAGCTGCCTT

TTGATGAAGCCGGCTTTATCCAACTCAGACAGGCCACCTCGTTCAGCCTTAGTC

AGATTATCGAACTTCCGTTGTGTGATCAGTTTGGCGTTCAGCAGCTGCCGCCAA

TAATTTTTCATTTCTTGACAACTTCTTCTGAGGGGACGTTATCACTCTTCCCTCT

ATTTTTATCGGATCTTGTCAACACTTTATTATCAATAGAATCATCTTTGAGAAAA

GACTGGGGCACGATATGATCCACGTCGTAGTCGGAGAGCCGATTGATGTCCAG

TTCCTGATCCACGTACATGTCCCTGCCGTTCTGCAGGTAGTACAGGTAGAGCTT

CTCATTCTGAAGCTGGGTGTTTTCAACTGGGTGTTCCTTAAGGATTTGGGACCC

CAGTTCTTTTATACCCTCTTCAATCCTCTTCATCCTTTCCCTACTGTTCTTCTGTC

CCTTCTGGGTAGTTTGGTTCTCTCGGGCCATCTCGATAACGATATTCTCGGGCTT

ATGCCTTCCCATTACTTTGACGAGTTCATCCACGACCTTAACGGTCTGCAGTATT

CCCTTTTTGATAGCTGGGCTACCTGCAAGATTAGCGATGTGCTCGTGAAGACTG

TCCCCCTGGCCAGAAACTTGTGCTTTCTGGATGTCCTCCTTAAAGGTGAGAGAG

TCATCATGGATCAACTGCATGAAGTTCCGGTTGGCAAATCCATCGGACTTAAGA

AAATCCAGGATTGTCTTTCCACTCTGCTTGTCTCGGATCCCATTGATCAGTTTTC

TTGACAGCCGCCCCCATCCTGTATATCGGCGCCTCTTGAGCTGTTTCATGACTTT

GTCGTCGAAGAGATGAGCGTAAGTTTTCAAGCGTTCTTCAATCATCTCCCTATC

TTCAAACAACGTAAGGGTGAGGACAATGTCCTCAAGAATGTCCTCGTTCTCCTC

ATTGTCCAGGAAGTCCTTGTCTTTAATGATTTTCAGGAGATCGTGATACGTTCCC

AGGGATGCGTTGAAGCGATCCTCCACTCCGCTGATTTCAACAGAGTCGAAACAT

TCAATCTTTTTGAAATAGTCTTCTTTGAGCTGTTTCACGGTAACTTTCCGGTTCG

TCTTGAAGAGGAGGTCCACGATAGCTTTCTTCTGCTCTCCAGACAGGAATGCTG

GCTTTCTCATCCCTTCTGTGACGTATTTGACCTTGGTGAGCTCGTTATAAACTGT
```

-continued
GAAGTACTCGTACAGCAGAGAGTGTTTAGGAAGCACCTTTTCGTTAGGCAGATT

TTTATCAAAGTTAGTCATCCTTTCGATGAAGGACTGGGCAGAGGCCCCCTTATC

CACGACTTCCTCGAAGTTCCAGGGAGTGATGGTCTCTTCTGATTTGCGAGTCAT

CCACGCGAATCTGGAATTTCCCCGGGCGAGGGGCCTACATAGTAGGGTATCC

GAAATGTGAGGATTTTCTCAATCTTTTCCCTGTTATCTTTCAAAAAGGGGTAGA

AATCCTCTTGCCGCCTGAGGATAGCGTGCAGTTCGCCCAGGTGAATCTGGTGGG

GGATGCTTCCATTGTCGAAAGTGCGCTGTTTGCGCAACAGATCTTCTCTGTTAA

GCTTTACCAGCAGCTCCTCGGTGCCGTCCATTTTTTCCAAGATGGGCTTAATAA

ATTTGTAAAATTCCTCCTGGCTTGCTCCGCCGTCAATGTATCCGGCGTAGCCATT

TTTAGACTGATCGAAGAAAATTTCCTTGTACTTCTCAGGCAGTTGCTGTCTGAC

AAGGGCCTTCAGCAAAGTCAAGTCTTGGTGGTGCTCATCATAGCGCTTGATCAT

ACTAGCGCTCAGCGGAGCTTTGGTGATCTCCGTGTTCACTCGCAGAATATCACT

CAGCAGAATGGCGTCTGACAGGTTCTTTGCCGCCAAAAAAAGGTCTGCGTACT

GGTCGCCGATCTGGGCCAGCAGATTGTCGAGATCATCATCGTAGGTGTCTTTGC

TCAGTTGAAGCTTGGCATCTTCGGCCAGGTCGAAGTTAGATTTAAAGTTGGGGG

TCAGCCCGAGTGACAGGGCGATAAGATTACCAAACAGGCCGTTCTTCTTCTCCC

CAGGGAGCTGTGCGATGAGGTTTTCGAGCCGCCGGGATTTGGACAGCCTAGCG

CTCAGGATTGCTTTGGCGTCAACTCCGGATGCGTTGATCGGGTTCTCTTCGAAA

AGCTGATTGTAAGTCTGAACCAGTTGGATAAAGAGTTTGTCGACATCGCTGTTG

TCTGGGTTCAGGTCCCCCTCGATGAGGAAGTGTCCCCGAAATTTGATCATATGC

GCCAGCGCGAGATAGATCAACCGCAAGTCAGCCTTATCAGTACTGTCTACAAG

CTTCTTCCTCAGATGATATATGGTTGGGTACTTTTCATGGTACGCCACCTCGTCC

ACGATATTGCCAAAGATTGGGTGGCGCTCGTGCTTTTTATCCTCCTCCACCAAA

AAGGACTCCTCCAGCCTATGGAAGAAAGAGTCATCCACCTTAGCCATCTCATTA

CTAAAGATCTCCTGCAGGTAGCAGATCCGATTCTTTCTGCGGGTATATCTGCGC

CGTGCTGTTCTTTTGAGCCGCGTGGCTTCGGCCGTCTCCCCGGAGTCGAACAGG

AGGGCGCCAATGAGGTTCTTCTTTATGCTGTGGCGATCGGTATTGCCCAGAACT

TTGAATTTTTTGCTCGGCACCTTGTACTCGTCCGTAATGACGGCCCAGCCGACG

CTGTTTGTGCCGATATCGAGCCCAATGGAGTACTTCTTGTCCATGGTGGCGGCT

CTTGAAGGACGACGTCATCATCCCTTGCCCGGATGCGCGGGC

TTCTTGTCTAGCACAGGAGCCTGGGGTAGAGCGCATGCAAATTACGCGCTGTGC

TTTGTGGGAAATCACCCTAAACGAAAAATTTATTCCTCTTTCGAGCCTTATAGT

GGCGGCCGGTCTACATCCTAGGTTTTAGAGCTAGAAATAGCAAGTTAAAATAA

GGCTAGTCCGTTATCAACTTGAAAAAGTGGCACCGAGTCGGTGCTTTTTGTTA

ACGCGGCCGCCTAGAGTCGACCTGCAGGCATGCAAGC

TTGGCGTAATCATGGTCATAGCTGTTTCCTGTGTGAAATTGTTATCCGCTCACAA

TTCCACACAACATACGAGCCGGAAGCATAAAGTGTAAAGCCTGGGGTGCCTAA

TGAGTGAGCTAACTCACATTAATTGCGTTGCGCTCACTGCCCGCTTTCCAGTCG

GGAAACCTGTCGTGCCAGCTGCATTAATGAATCGGCCAACGCGCGGGGAGAGG

CGGTTTGCGTATTGGGCGCTCTTCCGCTTCCTCGCT

CACTGACTCGCTGCGCTCGGTCGTTCGGCTGCGGCGAGCGGTATCAGCTCACTC

-continued

```
AAAGGCGGTAATACGGTTATCCACAGAATCAGGGGATAACGCAGGAAAGAAC

ATGTGAGCAAAAGGCCAGCAAAAGGCCAGGAACCGTAAAAAGGCCGCGTTGC

TGGCGTTTTTCCATAGGCTCCGCCCCCCTGACGAGCATCACAAAAATCGACGCT

CAAGTCAGAGGTGGCGAAACCCGACAGGACTATAAA

GATACCAGGCGTTTCCCCCTGGAAGCTCCCTCGTGCGCTCTCCTGTTCCGACCCT

GCCGCTTACCGGATACCTGTCCGCCTTTCTCCCTTCGGGAAGCGTGGCGCTTTCT

CATAGCTCACGCTGTAGGTATCTCAGTTCGGTGTAGGTCGTTCGCTCCAAGCTG

GGCTGTGTGCACGAACCCCCCGTTCAGCCCGACCGCTGCGCCTTATCCGGTAAC

TATCGTCTTGAGTCCAACCCGGTAAGACACGACTTATCGCCACTGGCAGCAGCC

ACTGGTAACAGGATTAGCAGAGCGAGGTATGTAGGCGGTGCTACAGAGTTCTT

GAAGTGGTGGCCTAACTACGGCTACACTAGAAGAACAGTATTTGGTATCTGCG

CTCTGCTGAAGCCAGTTACCTTCGGAAAAAGAGTTGGTAGCTCTTGATCCGGCA

AACAAACCACCGCTGGTAGCGGTGGTTTTTTTGTTTGCAAGCAGCAGATTACGC

GCAGAAAAAAAGGATCTCAAGAAGATCCTTTGATCTTTTCTACGGGGTCTGACG

CTCAGTGGAACGAAAACTCACGTTAAGGGATTTTGGTCATGAGATTATCAAAA

AGGATCTTCACCTAGATCCTTTTAAATTAAAAATGAAGTTTTAAATCAATCTAA

AGTATATATGAGTAAACTTGGTCTGACAGTTACCAATGCTTAATCAGTGAGGCA

CCTATCTCAGCGATCTGTCTATTTCGTTCATCCATAGTTGCCTGACTCCCCGTCGT

GTAGATAACTACGATACGGGAGGGCTTACCATCTGGCCCCAGTGCTGCAATGA

TACCGCGAGACCCACGCTCACCGGCTCCAGATTTATCAGCAATAAACCAGCCA

GCCGGAAGGGCCGAGCGCAGAAGTGGTCCTGCAACTTTATCCGCCTCCATCCA

GTCTATTAATTGTTGCCGGGAAGCTAGAGTAAGTAGTTCGCCAGTTAATAGTTT

GCGCAACGTTGTTGCCATTGCTACAGGCATCGTGGTGTCACGCTCGTCGTTTGG

TATGGCTTCATTCAGCTCCGGTTCCCAACGATCAAGGCGAGTTACATGATCCCC

CATGTTGTGCAAAAAAGCGGTTAGCTCCTTCGGTCCTCCGATCGTTGTCAGAAG

TAAGTTGGCCGCAGTGTTATCACTCATGGTTATGGCAGCACTGCATAATTCTCT

TACTGTCATGCCATCCGTAAGATGCTTTTCTGTGACTGGTGAGTACTCAACCAA

GTCATTCTGAGAATAGTGTATGCGGCGACCGAGTTGCTCTTGCCCGGCGTCAAT

ACGGGATAATACCGCGCCACATAGCAGAACTTTAAAAGTGCTCATCATTGGAA

AACGTTCTTCGGGGCGAAAACTCTCAAGGATCTTACCGCTGTTGAGATCCAGTT

CGATGTAACCCACTCGTGCACCCAACTGATCTTCAGCATCTTTTACTTTCACCAG

CGTTTCTGGGTGAGCAAAAACAGGAAGGCAAAATGCCGCAAAAAAGGGAATA

AGGGCGACACGGAAATGTTGAATACTCATACTCTTCCTTTTTCAATATTATTGA

AGCATTTATCAGGGTTATTGTCTCATGAGCGGATACATATTTGAATGTATTTAG

AAAAATAAACAAATAGGGGTTCCGCGCACATTTCCCCGAAAAGTGCCACCTGA

CGTCTAAGAAACCATTATTATCATGACATTAACCTATAAAAATAGGCGTATCAC

GAGGCCCTTTCGTCTCGCGCGTTTCGGTGATGACGGTGAAAACCTCTGACACAT

GCAGCTCCCGGAGACGGTCACAGCTTGTCTGTAAGCGGATGCCGGGAGCAGAC

AAGCCCGTCAGGGCGCGTCAGCGGGTGTTGGCGGGTGTCGGGGCTGGCTTAAC

TATGCGGCATCAGAGCAGATTGTACTGAGAGTGCACCATAGCGGCCGCGGTTC

TGTCTATAGGTAAGCTGACAAATAACAAATAGGCACATAGAAAATCTAGTAAG
```

```
TAGTACCACCTGATATCTCACTTTGCT

GCAGGCAGGATTCCCCTCTGGCTCACTGGCAGTCTCCTCCGGTGTGGGCCAGGG

CTCTTTGAAGTTGGATCTGAGCCTTTCTATCACCTGTTTGATGGACAAGCCCTTT

TGCACAAGTTTGACTTCAAGGAGGGCCATGTCACATACCACAGAAGGTAAGTC

CATGGTACCCACACAAAAAACCAACACACAG
``` mSPA_HDR SaCas9 entry plasmid
(SEQ ID NO: 67)

```
GCTTGGCGTAATCATGGTCATAGCTGTTTCCTGTGTGAAATTGTTATCCGCTCAC

AATTCCACACAACATACGAGCCGGAAGCATAAAGTGTAAAGCCTGGGGTGCCT

AATGAGTGAGCTAACTCACATTAATTGCGTTGCGCTCACTGCCCGCTTTCCAGT

CGGGAAACCTGTCGTGCCAGCTGCATTAATGAATCGGCCAACGCGCGGGGAGA

GGCGGTTTGCGTATTGGGCGCTCTTCCGCTTCCTCGCTCACTGACTCGCTGCGCT

CGGTCGTTCGGCTGCGGCGAGCGGTATCAGCTCACTCAAAGGCGGTAATACGG

TTATCCACAGAATCAGGGGATAACGCAGGAAAGAACATGTGAGCAAAAGGCC

AGCAAAAGGCCAGGAACCGTAAAAAGGCCGCGTTGCTGGCGTTTTTCCATAGG

CTCCGCCCCCCTGACGAGCATCACAAAAATCGACGCTCAAGTCAGAGGTGGCG

AAACCCGACAGGACTATAAAGATACCAGGCGTTTCCCCCTGGAAGCTCCCTCGT

GCGCTCTCCTGTTCCGACCCTGCCGCTTACCGGATACCTGTCCGCCTTTCTCCCT

TCGGGAAGCGTGGCGCTTTCTCATAGCTCACGCTGTAGGTATCTCAGTTCGGTG

TAGGTCGTTCGCTCCAAGCTGGGCTGTGTGCACGAACCCCCCGTTCAGCCCGAC

CGCTGCGCCTTATCCGGTAACTATCGTCTTGAGTCCAACCCGGTAAGACACGAC

TTATCGCCACTGGCAGCAGCCACTGGTAACAGGATTAGCAGAGCGAGGTATGT

AGGCGGTGCTACAGAGTTCTTGAAGTGGTGGCCTAACTACGGCTACACTAGAA

GAACAGTATTTGGTATCTGCGCTCTGCTGAAGCCAGTTACCTTCGGAAAAAGAG

TTGGTAGCTCTTGATCCGGCAAACAAACCACCGCTGGTAGCGGTGGTTTTTTTG

TTTGCAAGCAGCAGATTACGCGCAGAAAAAAAGGATCTCAAGAAGATCCTTTG

ATCTTTTCTACGGGGTCTGACGCTCAGTGGAACGAAAACTCACGTTAAGGGATT

TTGGTCATGAGATTATCAAAAAGGATCTTCACCTAGATCCTTTTAAATTAAAAA

TGAAGTTTTAAATCAATCTAAAGTATATATGAGTAAACTTGGTCTGACAGTTAC

CAATGCTTAATCAGTGAGGCACCTATCTCAGCGATCTGTCTATTTCGTTCATCCA

TAGTTGCCTGACTCCCCGTCGTGTAGATAACTACGATACGGGAGGGCTTACCAT

CTGGCCCCAGTGCTGCAATGATACCGCGAGACCCACGCTCACCGGCTCCAGATT

TATCAGCAATAAACCAGCCAGCCGGAAGGGCCGAGCGCAGAAGTGGTCCTGCA

ACTTTATCCGCCTCCATCCAGTCTATTAATTGTTGCCGGGAAGCTAGAGTAAGT

AGTTCGCCAGTTAATAGTTTGCGCAACGTTGTTGCCATTGCTACAGGCATCGTG

GTGTCACGCTCGTCGTTTGGTATGGCTTCATTCAGCTCCGGTTCCCAACGATCA

AGGCGAGTTACATGATCCCCCATGTTGTGCAAAAAAGCGGTTAGCTCCTTCGGT

CCTCCGATCGTTGTCAGAAGTAAGTTGGCCGCAGTGTTATCACTCATGGTTATG

GCAGCACTGCATAATTCTCTTACTGTCATGCCATCCGTAAGATGCTTTTCTGTGA

CTGGTGAGTACTCAACCAAGTCATTCTGAGAATAGTGTATGCGGCGACCGAGTT

GCTCTTGCCCGGCGTCAATACGGGATAATACCGCGCCACATAGCAGAACTTTAA

AAGTGCTCATCATTGGAAAACGTTCTTCGGGGCGAAAACTCTCAAGGATCTTAC
```

-continued
```
CGCTGTTGAGATCCAGTTCGATGTAACCCACTCGTGCACCCAACTGATCTTCAG

CATCTTTTACTTTCACCAGCGTTTCTGGGTGAGCAAAAACAGGAAGGCAAAATG

CCGCAAAAAAGGGAATAAGGGCGACACGGAAATGTTGAATACTCATACTCTTC

CTTTTTCAATATTATTGAAGCATTTATCAGGGTTATTGTCTCATGAGCGGATACA

TATTTGAATGTATTTAGAAAAATAAACAAATAGGGGTTCCGCGCACATTTCCCC

GAAAAGTGCCACCTGACGTCTAAGAAACCATTATTATCATGACATTAACCTATA

AAAATAGGCGTATCACGAGGCCCTTTCGTCTCGCGCGTTTCGGTGATGACGGTG

AAAACCTCTGACACATGCAGCTCCCGGAGACGGTCACAGCTTGTCTGTAAGCG

GATGCCGGGAGCAGACAAGCCCGTCAGGGCGCGTCAGCGGGTGTTGGCGGGTG

TCGGGGCTGGCTTAACTATGCGGCATCAGAGCAGATTGTACTGAGAGTGCACC

ATAGCGGCCGCGGTACCCACACAAAAAACCAACACACAGATGTAATGAAAATA

AAGATATTTTATTAGGCTGATCAGCGAGCTCTAGGAATTCTTAGGATCCCTTTTT

CTTTTTTGCCTGGCCGGCCTTTTTCGTGGCCGCCGGCCTTTTGCCCTTTTTGATG

ATCTGAGGGTGCTTCTTAGATTTCACTTCATACAGGTTGCCCAGAATGTCTGTG

CTGTACTTCTTAATGCTCTGGGTCTTGGAGGCGATTGTCTTAATGATCCTGGGG

GGCCTCTTGTCGTTCATGTTTTCCAGGTACTCGCGGTAGGTGATGTCGATCATGT

TCACTTCGATCCGGTTCAGCAGGTCGTTGTTCACGCCGATCACTCTATACAGCT

CGCCGTTGATCTTGATCAGATCGTTGTTGTAGAAGGAGGCGATAAACTCGGCCT

GGTTGCTGATCTTCTTCAGCTTCTTAGCTTCCTCATAGCACTTGCTATTCACTTC

GTAGTAGTTTTCTTTTTTGATCACATCCAGATTCTTCACGGTCACGAACTTGTAC

ACGCCATTGTCCAGGTACACGTCGAATCTGTAGGGCTTCAGGGACAGCTTCACG

ACCTTGTTTCTGCTGTTGGGGTAGTCGTCGGTGATGTCCAGATGGGCGTTCAGT

TTGTTGCCGTAATACTTAATCTTCTTGATCACGGGGCCGTTGTCCTTTTTGGAGT

ACTTGGTCAGGTAGTTCCCGGTTTCCTCGTAGTACTTGTACAGGGGATTCTTCTC

GTCGCCGTACTGTTCCATAATCAGCTTCAGTTTCTGGTAGGTCTGGGGGTCGTG

GTGGTACATCAGCAGCTTTTCGGGGCTCTTGTTGATCAGCTTTTTCAGCTTGTCA

TTGTCCTTGTCGTACAGGCCGTTCAGATTGTTCACGATCAGGGTGTTGCCCTTGT

CGTCCTTCCGGGTGGAGTACAGGGTGTCGTTAATCAGCTCTCTATTAGGCTTCTT

GTCCACCCGGTGGCTGTACTTGTAGTCCTTGAAGTCCTTAATGTGCTTGATCTGG

TGGGGGGTGATGAAGATCTCTTTGTACTCCTGCTCGGTTTCGATCTCGGGCATG

CTCTCGGCCTGCTTTTCCTCGAACATCTGGTTTTCCATCACTTTTTTGGCCTTGTC

CAGTTTCTTCCACTCTTTGAAGATGAAATCGGCGTTGGCAATGATCAGGGCGTC

CTCGGCGTGGTGCTTGTACCCCTTGTTCCGCTCTTTCTTAAACTTCCACTTCCGC

CGCAGAAAGCTGGTGAAGCCGCCATTGATGGACTTCACTTTCACGTCCAGGTTG

TTCACTCTGAAGTAGCTCCGCAGCAGGTTCATCAGGCCTCTGGTGGCGTATCTG

GTATCCACCAGGTTCCGGTTGATGAAGTCTTTCTGCACGGAGAACCTGTTGATG

TCCCGTTCTTCCAGCAGATACTCTTTCTTGGTCTTGCTGATTCTGCCCTTGCCCTT

GGCCAGATTCAGGATGTGCTTCTTGAAGGTTTCGTAGCTGATCTTGCTGTCGCT

GCTGCTCAGGTACTGGAATGGGGTCCGGTTGCCCTTCTTGCTGTTTTCTTCCTGC

TTCACGAGCACCTTGTTGTTGAAGCTGTTGTCGAAGGACACGCTTCTGGGGATG

ATGTGGTCCACCTCATAGTTGAAGGGGTTGTTCAGCAGATCTTCCAGAGGGATG
```

-continued
```
GCTTCCAGGCTGTACAGGCACTTGCCTTCCTGCATGTCGTGCAGCTTGATCTTCT

CGATCAGGTACTTGGCGTTCTCTTTGCCGGTGGTCCGGATGATTTCCTCGATCCG

CTCGTTGGTCTGCCGGTTCCGCTTCTGCATCTCGTTGATCATTTTCTGGGCGTCC

TTGGAGTTCTTCTCGCGGGCCAGCTCGATAATGATGTCGTTGGGCAGGCCGTAC

TTCTTGATGATGGCGTTGATCACTTTGATGCTCTGGATGAAGCTTCTCTTCACGA

CGGGGCTCAGGATGAAGTCGTCCACCAGGGTGGTGGGGATCTCTTTCTGCTGGG

ACAGGTCCACCTTCTTGGGCACCAGCTTCAGCCGGTTGAAGATAGCGATCTGGT

TGTCGTTGGTGTGCCACAGCTCGTCCAGGATCAGGTTGATGGCCTTCAGGCTCA

GGTTGTGGGTGCCGGTATAGCCCTTCAGATTAGAGATCTGCTCGATCTCTTCCT

GGGTCAGCTCGGAGTTCAGATTGGTCAGTTCTTCCTGGATGTCCTCGCTGCTCT

GGTAGATGGTCAGGATCTTGGCAATCTGATCCAGCAGCTCGGCGTTCTCAATAA

TCTCTTTCCGGGCGGTAATGTCCTTGATGTCGTGGTACACCTTCAGGTTGGTGA

ACTCGGGCTTGCCGGTGCTGGTCACTCTGTAGCCCTTAATATCCTCTTCGTTCAC

GAGGATTTCTTTGGCGATCTGCTTCAGGGTGGGCTTCTTCTTCTGCTTGAACACG

TTCTCGATGATCTGGAACTTCTCGTAATATTCCAGCTTCTCGTTCTCGTCCCTGG

TGATCACGAGATTGTTCAGGTCGTTCAGGGCGTTGTACAGGTCGGCGTTGTAGG

CGTACTTCACGCTCCGCAGTTCCTCGGGGAAGTAGGTGCAGTGGCCCATCAGCA

TCTCGTACCATTCTTTGATGTCCTTCCAGCCGAAGGGGCTGCCCTCGCCAGGTC

CCTCATAGTAGGTCCGCCGGGTTTCCAGCAGGTCGATGTAGGTGTCGATGAAGC

TCTGGTCCAGCTGGTGGTAGGCCTTCTGCACCTTCAGCAGCTGTTTGGCTTCTTT

CACGTAGTCGCTGGTCTTGAATCTGTTGATGCTGCCCCGCACTTCGCCGTCTTTC

TTCAGCCGTTCCAGCTGCAGTTCGGCCACGTATTTCTCTTCCAGGGCCTTGCTGT

TCCGGCTGATCTGCTCTTTGGTGGACAGCTCGTTGCCGGTGTCCTCTTCCACCTC

GTTCACGTTGT

GCACGCCTCTTCTCTTGGCCAGGTGCAGCAGGGCGGCAGAGAACTCTTCCTCGC

TCAGCTTCTGGCTCAGGCCCTTCACTCTGGCCTCGTAGGGGTTGATGCCGCTCA

GCTCGCTGTGGTCGGTCAGCAGGTTGTAGTCGAACAGCAGCTTCTTCACTCTCT

GGATTCTATGCCGCCTCCGCCGCTTCAGCCTTCTGGCGCCTCTCTTGCTCCGCCT

GCCCTCGTTGTTTTCCACGTTGGCCTCTTTGAACAGCCGCACGCCGGCATCGAT

CACGTCCCGTGTCTCGTAGTCGATGATGCCGTAGCCCACGCTGGTGATGCCGAT

GTCCAGGCCCAGGATGTAGTTCCGCTTGGCTGCTGGGACTCCGTGGATACCGAC

CTTCCGCTTCTTCTTTGGGGCCATGTGGCGGCTCTTGAAGGACGACGTCATCAT

CCCTTGCCCGGATGCGCGGGCTTCTTGTCTAGCACAGGAGCCTGGGGTAGAGCG

CATGCAAATTACGCGCTGTGCTTTGTGGGAAATCACCCTAAACGAAAAATTTAT

TCCTCTTTCGAGCCTTATAGTGGCGGCCGGTCTACATCCTAGGTTTTAGTACTCT

GGAAACAGAATCTACTAAAACAAGGCAAAATGCCGTGTTTATCTCGTCAACTT

GTTGGCGAGATTTTTTGTTAACGCGGCCGCCTAGAGTCGACCTGCAGGCATGCAA
```

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

Although the foregoing subject matter has been described in some detail by way of illustration and example for purposes of clarity of understanding, it will be understood by those skilled in the art that certain changes and modifications can be practiced within the scope of the appended claims.

What is claimed is:

1. A non-naturally occurring CRISPR system comprising one or more vectors comprising: a bidirectional 7sk promoter, wherein
   a) one side of the bidirectional 7sk promoter is operably linked to at least one nucleotide sequence encoding a CRISPR guide RNA (gRNA), wherein the gRNA hybridizes with a target sequence of a DNA molecule or RNA molecule in a cell; and
   b) the other side of the bidirectional 7sk promoter is operably linked to a nucleotide sequence encoding a CRISPR enzyme,
wherein the gRNA targets and hybridizes with the target sequence and the CRISPR enzyme cleaves one or both strands of the DNA molecule or RNA molecule.

2. The system of claim 1, wherein the system is packaged into a single adeno-associated virus (AAV) particle.

3. The system of claim 1, wherein the system inactivates one or more gene products.

4. The system of claim 1, wherein the system excises at least one gene mutation.

5. The system of claim 1, herein the CRISPR enzyme is a SaCas9 nickase.

6. The system of claim 1, further comprising a donor template.

7. The system of claim 1, wherein the nucleotide sequence encoding the CRISPR enzyme is mutated to lack the ability to cleave one or both strands of the target polynucleotide.

8. The system of claim 1, wherein the bidirectional 7sk promoter further comprises at least one Kozak sequence.

9. The system of claim 1, further cot an RNA sequence that mediates cap-independent initiation of translation.

10. The system of claim 1, wherein the bidirectional 7sk promoter further comprises a GSTA4 5'UTR.

11. The system of claim 1, wherein the bidirectional 7sk promoter further comprises a beta globin 5' LTR.

12. The system of claim 1, wherein the bidirectional 7sk promoter comprises a nucleic acid sequence of any one of SEQ ID NOs: 3-8.

13. A non-naturally occurring CRISPR system comprising one or more vectors comprising:
   a) a 7sk2 promoter comprising the nucleic acid sequence of SEQ ID NO: 4 or SEQ ID NO: 7 operably linked to at least one nucleotide sequence encoding a CRISPR guide RNA (gRNA), wherein the gRNA hybridizes with a target sequence of a DNA molecule or RNA molecule in a cell; and
   b) a promoter operably linked to a nucleotide sequence encoding a CRISPR enzyme,
wherein components (a) and (h) are located on the same or different vectors of the system, wherein the gRNA targets and hybridizes with the target sequence and the CRISPR enzyme cleaves one or both strands of the DNA molecule or RNA molecule.

14. The system of claim 13, wherein the system is packaged into a single adeno-associated virus (AAV) particle.

15. The system of claim 13, wherein the system inactivates one or more gene products.

16. The system of claim 13, wherein the system excises at least one gene mutation.

17. The system of claim 13, wherein the CRISPR enzyme is a SaCas9 nickase.

18. The system of claim 13, further comprising a donor template.

19. The system of claim 13, wherein the nucleotide sequence encoding the CRISPR enzyme is mutated to lack the ability to cleave one or both strands of the target polynucleotide.

* * * * *